US011230721B2

(12) United States Patent
Cankar et al.

(10) Patent No.: US 11,230,721 B2
(45) Date of Patent: Jan. 25, 2022

(54) PRODUCTION OF A FLAVOUR COMPOUND IN A HOST CELL

(71) Applicant: Axxence Holding B.V., Lathum (NL)

(72) Inventors: Katarina Cankar, Wageningen (NL); Martinus Julius Beekwilder, Renkum (NL); Hendrik Jan Bosch, Wageningen (NL); Peter Hans van der Schaft, s-Hertogenbosch (NL); Wilhelmina Maria Johanna Weemen, Haps (NL)

(73) Assignee: Axxence Aromatic GmbH, Emmerich am Rhein (DE)

( * ) Notice: Subject to any disclaimer, the term of this patent is extended or adjusted under 35 U.S.C. 154(b) by 0 days.

(21) Appl. No.: 16/764,886

(22) PCT Filed: Nov. 19, 2018

(86) PCT No.: PCT/EP2018/081729

§ 371 (c)(1),
(2) Date: May 18, 2020

(87) PCT Pub. No.: WO2019/097049

PCT Pub. Date: May 23, 2019

(65) Prior Publication Data

US 2020/0392544 A1 Dec. 17, 2020

(30) Foreign Application Priority Data

Nov. 20, 2017 (EP) .................................... 17202546

(51) Int. Cl.

| | |
|---|---|
| ***C12N 1/20*** | (2006.01) |
| ***C12P 7/26*** | (2006.01) |
| ***C12P 7/02*** | (2006.01) |
| ***C12N 9/10*** | (2006.01) |
| ***C12N 9/88*** | (2006.01) |

(Continued)

(52) U.S. Cl.

CPC .................. *C12P 7/26* (2013.01); *C12N 1/20* (2013.01); *C12N 9/1029* (2013.01); *C12N 9/88* (2013.01); *C12N 9/93* (2013.01); *C12N 15/77* (2013.01); *C12P 7/02* (2013.01); *C12Y 203/01* (2013.01);

(Continued)

(58) Field of Classification Search

None

See application file for complete search history.

(56) References Cited

U.S. PATENT DOCUMENTS 3,787,287 A 1/1974 Hagino et al.
2020/0392544 A1* 12/2020 Cankar ................ C12N 9/1029

FOREIGN PATENT DOCUMENTS

CN 103865864 B 9/2016
EP 1226265 B1 7/2002

(Continued)

OTHER PUBLICATIONS

Guo et al., A bifunctional type III polyketide synthase from raspberry (*Rubus idaeus* L.) with both chalcone synthase and benzalacetone synthase activity, Journal of Plant Biochemistry and Biotechnology, vol. 26, No. 1, pp. 80-90, 2017 (Year: 2017).*

(Continued)

*Primary Examiner* — Richard C Ekstrom
(74) *Attorney, Agent, or Firm* — NLO; Catherine Shulz; Tamara Stegmann

(57) ABSTRACT

The present invention relates to the field of biotechnology; specifically the production of a flavor compound (raspberry ketone) in a host cell.

10 Claims, 18 Drawing Sheets

Specification includes a Sequence Listing.

(51) Int. Cl.
*C12N 9/00* (2006.01)
*C12N 15/77* (2006.01)

(52) U.S. Cl.
CPC ................ *C12Y 403/01023* (2013.01); *C12Y 602/01012* (2013.01)

(56) References Cited

FOREIGN PATENT DOCUMENTS

| | | | |
|---|---|---|---|
| GB | 2416769 | A | 2/2006 |
| GB | 2416770 | A | 2/2006 |
| WO | WO2006/089898 | A1 | 8/2006 |
| WO | WO2017/207950 | A1 | 12/2007 |
| WO | WO2011/140344 | A1 | 11/2011 |
| WO | WO2016/071505 | A1 | 5/2016 |
| WO | WO2016/189121 | A1 | 12/2016 |

OTHER PUBLICATIONS

Anonymous, EM_STD:AY219683, Mar. 24, 2003 URL:http://ibis.internal.epo.org/exam/dbfetch.j sp?id=EM_STD:AY219683.

Kirchner Oliver et al: Tools for genetic engineering in the amino acid-producing bacterium Corynebacterium glutamicum, Journal of Biotechnology, vol. 104, No. 1-3, Sep. 4, 2003, pp. 287-299, XP002371549, ISSN: 0168-1656, D0I.

Kyndt J A et al: Characterization of a bacterial tyrosine ammonia lyase, a biosynthetic enzyme for the photoactive yellow protein, FEBS LETT. Elsevier, Amsterdam, NL, vol. 512, No. 1-3, Feb. 13, 2002, pp. 240-244, XP004341386, ISSN: 0014-5793, DOI.

Silber M V et al: Identification of a 4-coumarate:CoA ligase gene family in the moss, *Physcomitrella patens*, Phytochemistry, Pergamon Press, GB, vol. 69, No. 13, Oct. 1, 2008, pp. 2449-2456, XP025535879, ISSN: 0031-9422,.

Danna Lee et al: Heterologous production of raspberry ketone in the wine yeast *Saccharomyces cerevisiae* via pathway engineering and synthetic enzyme fusion, Microbial Cell Factories, vol. 91, No. 1, Mar. 4, 2016 (Mar. 4, 2016), p. 365.

Jules Beekwilder et al: "Microbial production of natural raspberry ketone", Biotechnology Journal, vol. 2, No. 10, Oct. 1, 2007, pp. 1270-1279.

Berner, Martin, et al. "Genes and enzymes involved in caffeic acid biosynthesis in the actinomycete Saccharothrix espanaensis." Journal of bacteriology 188.7 (2006): 2666-2673.

Jendresen, Christian Bille, et al. "Highly active and specific tyrosine ammonia-lyases from diverse origins enable enhanced production of aromatic compounds in bacteria and *Saccharomyces cerevisiae*." Appl. Environ. Microbiol. 81.13 (2015): 4458-4476.

Lee, Diana, and Carl J. Douglas. "Two divergent members of a tobacco 4-coumarate: coenzyme A ligase (4CL) gene family (cDNA structure, gene inheritance and expression, and properties of recombinant proteins)." Plant Physiology 112.1 (1996): 193-205.

Ehlting, Jürgen, et al. "Three 4-coumarate: coenzyme A ligases in *Arabidopsis thaliana* represent two evolutionarily divergent classes in angiosperms." The plant journal 19.1 (1999): 9-20.

Fuganti, Claudio, and Gioia Zucchi. "Product distribution in the microbial biogeneration of raspberry ketone from 4-hydroxybenzalacetone." Journal of Molecular Catalysis B: Enzymatic 4.5-6 (1998): 289-293.

Zheng, Desen, and Geza Hrazdina. "Molecular and biochemical characterization of benzalacetone synthase and chaicone synthase genes and their proteins from raspberry (*Rubus idaeus* L.)." Archives of biochemistry and biophysics 470.2 (2008): 139-145.

Gibson, Daniel G., et al. "Enzymatic assembly of DNA molecules up to several hundred kilobases." Nature methods 6.5 (2009): 343-345.

Vandamme, Erick J., and Wim Soetaert. "Bioflavours and fragrances via fermentation and biocatalysis." Journal of Chemical Technology & Biotechnology: International Research in Process, Environmental & Clean Technology 77.12 (2002): 1323-1332.

Borejsza-Wysocki, Wlodzimierz, and Geza Hrazdina. "Aromatic polyketide synthases (purification, characterization, and antibody development to benzalacetone synthase from raspberry fruits)." Plant physiology 110.3 (1996): 791-799.

Koeduka, Takao, et al. "Characterization of raspberry ketone/zingerone synthase, catalyzing the alpha, beta-hydrogenation of phenylbutenones in raspberry fruits." Biochemical and biophysical research communications 412.1 (2011): 104-108.

Abe, Ikuro, et al. "Benzalacetone synthase: a novel polyketide synthase that plays a crucial role in the biosynthesis of phenylbutanones in Rheum palmatum." European Journal of Biochemistry 268.11 (2001): 3354-3359.

* cited by examiner

L-tyrosine 4-coumaric acid malonyl-CoA coumaroyl-CoA hydroxyphenylbutenone raspberry ketone

SEQUENCE LISTING

```
<160> NUMBER OF SEQ ID NOS: 117

<210> SEQ ID NO 1
<211> LENGTH: 531
<212> TYPE: PRT
<213> ORGANISM: Rhodobacter capsulatus
<220> FEATURE:
<223> OTHER INFORMATION: Tyrosine ammonia lyase enzyme from Rhodobacter
      capsulatus (RcTAL)

<400> SEQUENCE: 1

Met Thr Leu Gln Ser Gln Thr Ala Lys Asp Cys Leu Ala Leu Asp Gly
1               5                   10                  15

Ala Leu Thr Leu Val Gln Cys Glu Ala Ile Ala Thr His Arg Ser Arg
            20                  25                  30

Ile Ser Val Thr Pro Ala Leu Arg Glu Arg Cys Ala Arg Ala His Ala
        35                  40                  45

Arg Leu Glu His Ala Ile Ala Glu Gln Arg His Ile Tyr Gly Ile Thr
    50                  55                  60

Thr Gly Phe Gly Pro Leu Ala Asn Arg Leu Ile Gly Ala Asp Gln Gly
65                  70                  75                  80

Ala Glu Leu Gln Gln Asn Leu Ile Tyr His Leu Ala Thr Gly Val Gly
                85                  90                  95

Pro Lys Leu Ser Trp Ala Glu Ala Arg Ala Leu Met Leu Ala Arg Leu
            100                 105                 110

Asn Ser Ile Leu Gln Gly Ala Ser Gly Ala Ser Pro Glu Thr Ile Asp
        115                 120                 125

Arg Ile Val Ala Val Leu Asn Ala Gly Phe Ala Pro Glu Val Pro Ala
    130                 135                 140

Gln Gly Thr Val Gly Ala Ser Gly Asp Leu Thr Pro Leu Ala His Met
145                 150                 155                 160

Val Leu Ala Leu Gln Gly Arg Gly Arg Met Ile Asp Pro Ser Gly Arg
                165                 170                 175

Val Gln Glu Ala Gly Ala Val Met Asp Arg Leu Cys Gly Gly Pro Leu
            180                 185                 190
```

-continued

```
Thr Leu Ala Ala Arg Asp Gly Leu Ala Leu Val Asn Gly Thr Ser Ala
        195                 200                 205

Met Thr Ala Ile Ala Ala Leu Thr Gly Val Glu Ala Ala Arg Ala Ile
    210                 215                 220

Asp Ala Ala Leu Arg His Ser Ala Val Leu Met Glu Val Leu Ser Gly
225                 230                 235                 240

His Ala Glu Ala Trp His Pro Ala Phe Ala Glu Leu Arg Pro His Pro
                245                 250                 255

Gly Gln Leu Arg Ala Thr Glu Arg Leu Ala Gln Ala Leu Asp Gly Ala
            260                 265                 270

Gly Arg Val Cys Arg Thr Leu Thr Ala Ala Arg Arg Leu Thr Ala Ala
        275                 280                 285

Asp Leu Arg Pro Glu Asp His Pro Ala Gln Asp Ala Tyr Ser Leu Arg
    290                 295                 300

Val Val Pro Gln Leu Val Gly Ala Val Trp Asp Thr Leu Asp Trp His
305                 310                 315                 320

Asp Arg Val Val Thr Cys Glu Leu Asn Ser Val Thr Asp Asn Pro Ile
                325                 330                 335

Phe Pro Glu Gly Cys Ala Val Pro Ala Leu His Gly Gly Asn Phe Met
            340                 345                 350

Gly Val His Val Ala Leu Ala Ser Asp Ala Leu Asn Ala Ala Leu Val
        355                 360                 365

Thr Leu Ala Gly Leu Val Glu Arg Gln Ile Ala Arg Leu Thr Asp Glu
    370                 375                 380

Lys Leu Asn Lys Gly Leu Pro Ala Phe Leu His Gly Gly Gln Ala Gly
385                 390                 395                 400

Leu Gln Ser Gly Phe Met Gly Ala Gln Val Thr Ala Thr Ala Leu Leu
                405                 410                 415

Ala Glu Met Arg Ala Asn Ala Thr Pro Val Ser Val Gln Ser Leu Ser
            420                 425                 430

Thr Asn Gly Ala Asn Gln Asp Val Val Ser Met Gly Thr Ile Ala Ala
        435                 440                 445

Arg Arg Ala Arg Ala Gln Leu Leu Pro Leu Ser Gln Ile Gln Ala Ile
    450                 455                 460

Leu Ala Leu Ala Leu Ala Gln Ala Met Asp Leu Leu Asp Asp Pro Glu
465                 470                 475                 480

Gly Gln Ala Gly Trp Ser Leu Thr Ala Arg Asp Leu Arg Asp Arg Ile
                485                 490                 495

Arg Ala Val Ser Pro Gly Leu Arg Ala Asp Arg Pro Leu Ala Gly His
            500                 505                 510

Ile Glu Ala Val Ala Gln Gly Leu Arg His Pro Ser Ala Ala Ala Asp
        515                 520                 525

Pro Pro Ala
    530
```

<210> SEQ ID NO 2
<211> LENGTH: 1596
<212> TYPE: DNA
<213> ORGANISM: Rhodobacter capsulatus
<220> FEATURE:
<223> OTHER INFORMATION: Tyrosine ammonia lyase enzyme from Rhodobacter capsulatus (RcTAL) (codon optimised)

<400> SEQUENCE: 2

```
atgaccctgc aatcccagac tgcaaaggac tgcctggcgc tggatggtgc actgacactg      60
```

-continued

```
gttcagtgcg aagcaattgc cactcaccgc tcacggatct ccgtcacacc agcattgcgg    120

gaacgctgcg cccgcgcgca cgcacgtctg gagcacgcta tcgcagaaca gcgtcacatc    180

tatggtatca ccaccggctt cggaccactg gctaatcgcc tgatcggtgc agatcagggc    240

gccgaactcc agcagaacct catctaccac cttgctactg gcgtgggccc aaaactctcc    300

tgggctgaag cacgtgcact catgctggct cgtctcaact ccatccttca gggcgcatct    360

ggtgcatcac cagaaaccat cgaccgtatc gttgccgttc tgaacgctgg cttcgcccca    420

gaagtcccag ctcagggcac cgttggtgca tctggcgatc tgaccccact ggctcacatg    480

gtgctggcgc ttcagggtcg aggtcgtatg atcgatccat ccggccgtgt tcaggaagcc    540

ggcgcagtga tggatcgcct gtgcggtggc ccactgacct tggcagcccg tgacggtctg    600

gctctggtca acggtacttc cgctatgacc gcaatcgctg ctttgaccgg tgtggaggct    660

gcgcgcgcaa tcgacgccgc attgcgccac tccgctgtgc tcatggaggt tctctccggc    720

cacgctgagg cttggcaccc tgcatttgct gaactccgcc cacacccagg ccagctgcgc    780

gcaaccgaac gtctggccca ggctctcgat ggcgccggtc gcgtttgccg caccttgacc    840

gcggcccgtc gcctgaccgc agctgatctg cgccctgagg atcacccagc ccaggacgcc    900

tactccctgc gcgtggtgcc acagctggtt ggcgctgtct gggacaccct cgattggcac    960

gatcgcgtcg tgacctgcga actcaactct gtgaccgaca acccaatctt cccggaaggc   1020

tgcgctgttc cagcactgca cggcggcaac ttcatgggcg tgcacgtcgc actggcgtcg   1080

gacgccctga acgctgcatt ggttaccctg gcaggtctgg tggagcgcca gatcgcacgc   1140

cttactgatg agaagctgaa caagggactt ccggcattcc ttcacggtgg tcaggctggc   1200

cttcagtccg gcttcatggg cgcgcaggtc accgcaaccg cgctccttgc tgaaatgcgc   1260

gcaaacgcaa ccccggtgtc tgttcagtca ctgtctacca acggcgctaa ccaggatgtt   1320

gtcagcatgg gcaccatcgc tgcacgccgc gctcgcgcac agctgctccc actgtcccag   1380

attcaggcaa tcctggctct cgctctcgcc caggcaatgg atctgctgga tgatccagag   1440

ggccaggctg gctggtccct taccgcacgc gacctgcgcg atcgcatccg cgctgtctcg   1500

ccgggcctgc gcgcagatcg cccactggcc ggccacatcg aggcagtcgc tcagggtctg   1560

cgccaccctt ccgcagcagc tgatccacca gcataa                             1596
```

<210> SEQ ID NO 3
<211> LENGTH: 510
<212> TYPE: PRT
<213> ORGANISM: Saccharothrix espanaensis
<220> FEATURE:
<223> OTHER INFORMATION: Tyrosine ammonia lyase enzyme from Saccharothrix espanaensis (SeSam8)

<400> SEQUENCE: 3

```
Met Thr Gln Val Val Glu Arg Gln Ala Asp Arg Leu Ser Ser Arg Glu
1               5                   10                  15

Tyr Leu Ala Arg Val Val Arg Ser Ala Gly Trp Asp Ala Gly Leu Thr
            20                  25                  30

Ser Cys Thr Asp Glu Glu Ile Val Arg Met Gly Ala Ser Ala Arg Thr
        35                  40                  45

Ile Glu Glu Tyr Leu Lys Ser Asp Lys Pro Ile Tyr Gly Leu Thr Gln
    50                  55                  60

Gly Phe Gly Pro Leu Val Leu Phe Asp Ala Asp Ser Glu Leu Glu Gln
65                  70                  75                  80
```

-continued

```
Gly Gly Ser Leu Ile Ser His Leu Gly Thr Gly Gln Gly Ala Pro Leu
                85                  90                  95

Ala Pro Glu Val Ser Arg Leu Ile Leu Trp Leu Arg Ile Gln Asn Met
            100                 105                 110

Arg Lys Gly Tyr Ser Ala Val Ser Pro Val Phe Trp Gln Lys Leu Ala
        115                 120                 125

Asp Leu Trp Asn Lys Gly Phe Thr Pro Ala Ile Pro Arg His Gly Thr
    130                 135                 140

Val Ser Ala Ser Gly Asp Leu Gln Pro Leu Ala His Ala Ala Leu Ala
145                 150                 155                 160

Phe Thr Gly Val Gly Glu Ala Trp Thr Arg Asp Ala Asp Gly Arg Trp
                165                 170                 175

Ser Thr Val Pro Ala Val Asp Ala Leu Ala Ala Leu Gly Ala Glu Pro
            180                 185                 190

Phe Asp Trp Pro Val Arg Glu Ala Leu Ala Phe Val Asn Gly Thr Gly
        195                 200                 205

Ala Ser Leu Ala Val Ala Val Leu Asn His Arg Ser Ala Leu Arg Leu
    210                 215                 220

Val Arg Ala Cys Ala Val Leu Ser Ala Arg Leu Ala Thr Leu Leu Gly
225                 230                 235                 240

Ala Asn Pro Glu His Tyr Asp Val Gly His Gly Val Ala Arg Gly Gln
                245                 250                 255

Val Gly Gln Leu Thr Ala Ala Glu Trp Ile Arg Gln Gly Leu Pro Arg
            260                 265                 270

Gly Met Val Arg Asp Gly Ser Arg Pro Leu Gln Glu Pro Tyr Ser Leu
        275                 280                 285

Arg Cys Ala Pro Gln Val Leu Gly Ala Val Leu Asp Gln Leu Asp Gly
    290                 295                 300

Ala Gly Asp Val Leu Ala Arg Glu Val Asp Gly Cys Gln Asp Asn Pro
305                 310                 315                 320

Ile Thr Tyr Glu Gly Glu Leu Leu His Gly Gly Asn Phe His Ala Met
                325                 330                 335

Pro Val Gly Phe Ala Ser Asp Gln Ile Gly Leu Ala Met His Met Ala
            340                 345                 350

Ala Tyr Leu Ala Glu Arg Gln Leu Gly Leu Leu Val Ser Pro Val Thr
        355                 360                 365

Asn Gly Asp Leu Pro Pro Met Leu Thr Pro Arg Ala Gly Arg Gly Ala
    370                 375                 380

Gly Leu Ala Gly Val Gln Ile Ser Ala Thr Ser Phe Val Ser Arg Ile
385                 390                 395                 400

Arg Gln Leu Val Phe Pro Ala Ser Leu Thr Thr Leu Pro Thr Asn Gly
                405                 410                 415

Trp Asn Gln Asp His Val Pro Met Ala Leu Asn Gly Ala Asn Ser Val
            420                 425                 430

Phe Glu Ala Leu Glu Leu Gly Trp Leu Thr Val Gly Ser Leu Ala Val
        435                 440                 445

Gly Val Ala Gln Leu Ala Ala Met Thr Gly His Ala Ala Glu Gly Val
    450                 455                 460

Trp Ala Glu Leu Ala Gly Ile Cys Pro Pro Leu Asp Ala Asp Arg Pro
465                 470                 475                 480

Leu Gly Ala Glu Val Arg Ala Ala Arg Asp Leu Leu Ser Ala His Ala
                485                 490                 495

Asp Gln Leu Leu Val Asp Glu Ala Asp Gly Lys Asp Phe Gly
```

-continued 500 505 510

<210> SEQ ID NO 4
<211> LENGTH: 1533
<212> TYPE: DNA
<213> ORGANISM: Saccharothrix espanaensis
<220> FEATURE:
<223> OTHER INFORMATION: Tyrosine ammonia lyase enzyme from Saccharothrix espanaensis (SeSam8) (codon optimised)

<400> SEQUENCE: 4

```
atgacccagg tcgtggagcg ccaggctgat cgtctgtcca gccgcgagta cctggcacgc     60
gttgttcgtt ccgcaggctg ggacgcaggc ctcaccagct gcaccgatga agaaatcgtg    120
cgcatgggtg catccgcacg caccattgag gaatacctga agtctgataa gccgatctac    180
ggcctcaccc agggcttcgg tccactggtc ctgttcgatg cagattccga actggaacag    240
ggcggctctc tcatctccca tctgggcacc ggccagggtg caccgcttgc accggaagtg    300
tcccgcctga ttctgtggct ccgcatccaa aacatgcgca agggctattc ggctgtcagt    360
cctgtgttct ggcaaaaact ggccgacctc tggaacaagg gcttcacccc tgctatccct    420
cgccacggca ccgtgtccgc cagcggcgat ctccagcctc tggcacacgc tgccctggct    480
tttaccggcg tgggcgaggc atggacccgt gatgcagacg gccgttggtc caccgtgcca    540
gccgtggacg cattagcagc actgggtgca gagccgttcg attggccagt gcgcgaggct    600
ttggccttcg tgaacggtac gggcgcatca ctcgcggtgg cagttctcaa ccacagatcc    660
gctctccgtc tcgtacgagc atgtgcagtc ttgtctgccc gtttggctac cttgctagga    720
gctaatcctg aacactacga tgtcggccac ggagtcgcaa ggggacaagt tggccagctg    780
accgcggcgg aatggattcg gcagggacta ccacgcggca tggtccgaga cggttcgcgc    840
cctcttcaag aaccatacag cttgcgctgt gccccccagg tccttggcgc ggtgctggac    900
cagctggatg gtgcaggcga tgttctggcc cgcgaagtgg atggctgcca ggacaatcct    960
atcacctacg agggcgaact gctgcacggc ggtaacttcc acgctatgcc agtcggcttc   1020
gcatccgacc agatcggtct ggcgatgcac atggcagctt atctggctga acgccagctc   1080
ggcctgctgg tgagcccggt gaccaacggc gacctgccac caatgctgac cccacgcgct   1140
ggacgcggtg ccggcctggc gggcgttcag atctccgcaa cctccttcgt ctctcgcatc   1200
cgccagctgg tgttcccagc tagcctcacc accctcccaa ccaacggctg gaaccaggac   1260
catgtcccaa tggctctgaa cggcgcaaac agcgtgttcg aagctcttga actgggttgg   1320
ctgaccgtgg gtagcctggc agtcggcgtg gcccagctcg ctgcaatgac cggccacgca   1380
gctgagggcg tgtgggccga gttggcaggc atctgcccac cactggatgc tgaccgccca   1440
ctgggcgcgg aggtccgcgc tgctcgcgat ctcctctccg cacacgctga ccagctgctc   1500
gttgacgagg ctgatggcaa agacttcggc taa                                 1533
```

<210> SEQ ID NO 5
<211> LENGTH: 506
<212> TYPE: PRT
<213> ORGANISM: Flavobacterium johnsoniae
<220> FEATURE:
<223> OTHER INFORMATION: Tyrosine ammonia lyase enzyme from Flavobacterium johnsoniae (FjTAL)

<400> SEQUENCE: 5

```
Met Asn Thr Ile Asn Glu Tyr Leu Ser Leu Glu Glu Phe Glu Ala Ile
1               5                   10                  15
```

-continued

```
Ile Phe Gly Asn Gln Lys Val Thr Ile Ser Asp Val Val Val Asn Arg
            20                  25                  30

Val Asn Glu Ser Phe Asn Phe Leu Lys Glu Phe Ser Gly Asn Lys Val
        35                  40                  45

Ile Tyr Gly Val Asn Thr Gly Phe Gly Pro Met Ala Gln Tyr Arg Ile
    50                  55                  60

Lys Glu Ser Asp Gln Ile Gln Leu Gln Tyr Asn Leu Ile Arg Ser His
65                  70                  75                  80

Ser Ser Gly Thr Gly Lys Pro Leu Ser Pro Val Cys Ala Lys Ala Ala
                85                  90                  95

Ile Leu Ala Arg Leu Asn Thr Leu Ser Leu Gly Asn Ser Gly Val His
            100                 105                 110

Pro Ser Val Ile Asn Leu Met Ser Glu Leu Ile Asn Lys Asp Ile Thr
        115                 120                 125

Pro Leu Ile Phe Glu His Gly Gly Val Gly Ala Ser Gly Asp Leu Val
    130                 135                 140

Gln Leu Ser His Leu Ala Leu Val Leu Ile Gly Glu Gly Glu Val Phe
145                 150                 155                 160

Tyr Lys Gly Glu Arg Arg Pro Thr Pro Glu Val Phe Glu Ile Glu Gly
                165                 170                 175

Leu Lys Pro Ile Gln Val Glu Ile Arg Glu Gly Leu Ala Leu Ile Asn
            180                 185                 190

Gly Thr Ser Val Met Thr Gly Ile Gly Val Val Asn Val Tyr His Ala
        195                 200                 205

Lys Lys Leu Leu Asp Trp Ser Leu Lys Ser Ser Cys Ala Ile Asn Glu
    210                 215                 220

Leu Val Gln Ala Tyr Asp Asp His Phe Ser Ala Glu Leu Asn Gln Thr
225                 230                 235                 240

Lys Arg His Lys Gly Gln Gln Glu Ile Ala Leu Lys Met Arg Gln Asn
                245                 250                 255

Leu Ser Asp Ser Thr Leu Ile Arg Lys Arg Glu Asp His Leu Tyr Ser
            260                 265                 270

Gly Glu Asn Thr Glu Glu Ile Phe Lys Glu Lys Val Gln Glu Tyr Tyr
        275                 280                 285

Ser Leu Arg Cys Val Pro Gln Ile Leu Gly Pro Val Leu Glu Thr Ile
    290                 295                 300

Asn Asn Val Ala Ser Ile Leu Glu Asp Glu Phe Asn Ser Ala Asn Asp
305                 310                 315                 320

Asn Pro Ile Ile Asp Val Lys Asn Gln His Val Tyr His Gly Gly Asn
                325                 330                 335

Phe His Gly Asp Tyr Ile Ser Leu Glu Met Asp Lys Leu Lys Ile Val
            340                 345                 350

Ile Thr Lys Leu Thr Met Leu Ala Glu Arg Gln Leu Asn Tyr Leu Leu
        355                 360                 365

Asn Ser Lys Ile Asn Glu Leu Leu Pro Pro Phe Val Asn Leu Gly Thr
    370                 375                 380

Leu Gly Phe Asn Phe Gly Met Gln Gly Val Gln Phe Thr Ala Thr Ser
385                 390                 395                 400

Thr Thr Ala Glu Ser Gln Met Leu Ser Asn Pro Met Tyr Val His Ser
                405                 410                 415

Ile Pro Asn Asn Asn Asp Asn Gln Asp Ile Val Ser Met Gly Thr Asn
            420                 425                 430

Ser Ala Val Ile Thr Ser Lys Val Ile Glu Asn Ala Phe Glu Val Leu
```

-continued

```
        435                 440                 445

Ala Ile Glu Met Ile Thr Ile Val Gln Ala Ile Asp Tyr Leu Gly Gln
    450                 455                 460

Lys Asp Lys Ile Ser Ser Val Ser Lys Lys Trp Tyr Asp Glu Ile Arg
465                 470                 475                 480

Asn Ile Ile Pro Thr Phe Lys Glu Asp Gln Val Met Tyr Pro Phe Val
                485                 490                 495

Gln Lys Val Lys Asp His Leu Ile Asn Asn
            500                 505


<210> SEQ ID NO 6
<211> LENGTH: 1521
<212> TYPE: DNA
<213> ORGANISM: Flavobacterium johnsoniae;
<220> FEATURE:
<223> OTHER INFORMATION: Tyrosine ammonia lyase enzyme from
      Flavobacterium johnsoniae (FjTAL) (codon optimised)

<400> SEQUENCE: 6

atgaacacca tcaacgaata cctgtccctg gaagagttcg aagcgatcat cttcggtaac     60

cagaaggtta ccatctccga tgtggttgtg aaccgtgtta acgagtcctt caacttcctc    120

aaggagttct ccggcaacaa ggtcatctac ggtgtgaaca ccggcttcgg cccaatggca    180

caataccgta ttaaggaatc cgatcagatc cagcttcagt acaatctgat ccgttcccac    240

tcttcgggca ccggaaaacc actctcccca gtttgtgcta aggcagcaat cttggctcgc    300

ctgaacaccc tgtccctcgg taactccggc gtgcatccat ctgtcatcaa cctgatgtcg    360

gaactgatca acaaagacat taccccactc atcttcgagc acggtggcgt cggagcatcc    420

ggtgacctgg ttcagctttc tcacctggct ttggttctca tcggcgaagg cgaagtgttc    480

tacaagggtg aacgccgccc aactccagaa gttttcgaaa ttgagggctt gaagccaatc    540

caggttgaga tccgtgaggg cctcgccttg attaacggta ctagcgtgat gaccggtatt    600

ggagtggtca acgtgtacca cgcaaagaag ctgctggact ggtccctgaa gtcctcctgc    660

gccatcaatg aacttgttca ggcttacgat gatcacttca gcgcagagct gaaccagacg    720

aagcgccaca agggccagca ggaaatcgct ctgaagatgc gtcagaacct ctctgacagc    780

accctgatcc gcaagcgcga ggaccacctg tattccggcg aaaacaccga ggagattttc    840

aaggagaagg tgcaggagta ctactccctg cgctgcgttc cacagattct cggcccggtc    900

ctcgaaacta tcaataacgt cgcctccatc ctggaagatg agttcaactc cgctaacgat    960

aacccaatca tcgacgtgaa gaaccagcac gtgtaccatg gcggcaactt ccacggtgac   1020

tacatctctc tggaaatgga caagttgaaa atcgttatca ccaaactgac catgcttgca   1080

gaacgccagc ttaactatct tctcaactcc aagatcaacg aacttctgcc accattcgtg   1140

aacctcggca ccctgggttt caacttcggc atgcagggcg ttcagttcac cgcgacctcc   1200

accaccgcag aatctcagat gctgtccaac cctatgtacg ttcactccat tccaaacaac   1260

aacgataacc aggacatcgt ctccatgggc accaactccg cagtgatcac gtccaaggtt   1320

atcgagaacg ctttcgaagt cctggctatc gaaatgatca ccatcgttca ggccatcgat   1380

tacctcggcc agaaggataa gatctcctcc gtttccaaga agtggtacga tgaaatccgc   1440

aacattatcc ctaccttcaa ggaggatcag gttatgtacc cattcgtgca gaaggttaag   1500

gatcacctca tcaacaacta a                                             1521


<210> SEQ ID NO 7
```

<211> LENGTH: 542
<212> TYPE: PRT
<213> ORGANISM: Nicotiana tabacum
<220> FEATURE:
<221> NAME/KEY: misc_feature
<222> LOCATION: (287)..(287)
<223> OTHER INFORMATION: Xaa can be any naturally occurring amino acid
<220> FEATURE:
<223> OTHER INFORMATION: 4-coumarate-CoA ligase from Nicotiana tabacum
(Nt4CL)

<400> SEQUENCE: 7

```
Met Glu Lys Asp Thr Lys Gln Val Asp Ile Ile Phe Arg Ser Lys Leu
1               5                   10                  15

Pro Asp Ile Tyr Ile Pro Asn His Leu Pro Leu His Ser Tyr Cys Phe
            20                  25                  30

Glu Asn Ile Ser Glu Phe Ser Ser Arg Pro Cys Leu Ile Asn Gly Ala
        35                  40                  45

Asn Lys Gln Ile Tyr Thr Tyr Ala Asp Val Glu Leu Asn Ser Arg Lys
    50                  55                  60

Val Ala Ala Gly Leu His Lys Gln Gly Ile Gln Pro Lys Asp Thr Ile
65                  70                  75                  80

Met Ile Leu Leu Pro Asn Ser Pro Glu Phe Val Phe Ala Phe Ile Gly
                85                  90                  95

Ala Ser Tyr Leu Gly Ala Ile Ser Thr Met Ala Asn Pro Leu Phe Thr
            100                 105                 110

Pro Ala Glu Val Val Lys Gln Ala Glu Ala Ser Ser Ala Lys Ile Ile
        115                 120                 125

Val Thr Gln Ala Cys His Val Asn Lys Val Lys Asp Tyr Ala Phe Glu
    130                 135                 140

Asn Asp Val Lys Ile Ile Cys Ile Asp Ser Ala Pro Glu Gly Cys Leu
145                 150                 155                 160

His Phe Ser Val Leu Thr Gln Ala Asn Glu His Asp Ile Pro Glu Val
                165                 170                 175

Glu Ile Gln Pro Asp Asp Val Val Ala Leu Pro Tyr Ser Ser Gly Thr
            180                 185                 190

Thr Gly Leu Pro Lys Gly Val Met Leu Thr His Lys Gly Leu Val Thr
        195                 200                 205

Ser Val Ala Gln Gln Val Asp Gly Glu Asn Pro Asn Leu Tyr Ile His
    210                 215                 220

Ser Glu Asp Val Met Leu Cys Val Leu Pro Leu Phe His Ile Tyr Ser
225                 230                 235                 240

Leu Asn Ser Val Leu Leu Cys Gly Leu Arg Val Gly Ala Ala Ile Leu
                245                 250                 255

Ile Met Gln Lys Phe Asp Ile Val Ser Phe Leu Glu Leu Ile Gln Ser
            260                 265                 270

Tyr Lys Val Thr Ile Gly Pro Phe Val Pro Pro Ile Val Leu Xaa Ile
        275                 280                 285

Ala Lys Ser Pro Met Val Asp Asp Tyr Asp Leu Ser Ser Val Arg Thr
    290                 295                 300

Val Met Ser Gly Ala Ala Pro Leu Gly Lys Glu Leu Glu Asp Thr Val
305                 310                 315                 320

Arg Ala Lys Phe Pro Asn Ala Lys Leu Gly Gln Gly Tyr Gly Met Thr
                325                 330                 335

Glu Ala Gly Pro Val Leu Ala Met Cys Leu Ala Phe Ala Lys Glu Pro
            340                 345                 350
```

-continued

```
Phe Glu Ile Lys Ser Gly Ala Cys Gly Thr Val Val Arg Asn Ala Glu
        355                 360                 365

Met Lys Ile Val Asp Pro Lys Thr Gly Asn Ser Leu Pro Arg Asn Gln
    370                 375                 380

Ser Gly Glu Ile Cys Ile Arg Gly Asp Gln Ile Met Lys Gly Tyr Leu
385                 390                 395                 400

Asn Asp Pro Glu Ala Thr Ala Arg Thr Ile Asp Lys Glu Gly Trp Leu
                405                 410                 415

Tyr Thr Gly Asp Ile Gly Tyr Ile Asp Asp Asp Glu Leu Phe Ile
            420                 425                 430

Val Asp Arg Leu Lys Glu Leu Ile Lys Tyr Lys Gly Phe Gln Val Ala
        435                 440                 445

Pro Ala Glu Leu Glu Ala Leu Leu Leu Asn His Pro Asn Ile Ser Asp
    450                 455                 460

Ala Ala Val Val Pro Met Lys Asp Glu Gln Ala Gly Glu Val Pro Val
465                 470                 475                 480

Ala Phe Val Val Arg Ser Asn Gly Ser Thr Ile Thr Glu Asp Glu Val
                485                 490                 495

Lys Asp Phe Ile Ser Lys Gln Val Ile Phe Tyr Lys Arg Ile Lys Arg
            500                 505                 510

Val Phe Phe Val Asp Ala Ile Pro Lys Ser Pro Ser Gly Lys Ile Leu
        515                 520                 525

Arg Lys Asp Leu Arg Ala Lys Leu Ala Ala Gly Leu Pro Asn
    530                 535                 540
```

<210> SEQ ID NO 8
<211> LENGTH: 1629
<212> TYPE: DNA
<213> ORGANISM: Nicotiana tabacum
<220> FEATURE:
<223> OTHER INFORMATION: 4-coumarate-CoA ligase from Nicotiana tabacum (Nt4CL)

<400> SEQUENCE: 8

```
atggagaaag atacaaaaca ggttgacata attttccgat caaaactccc tgatatttac     60

atccctaacc atcttccttt acactcctac tgtttcgaaa acatttccga gttcagttct    120

cgtccttgtt taatcaatgg cgccaacaaa caaatttata cgtatgctga tgttgaactc    180

aattcaagaa aagttgctgc tggtcttcac aaacaaggga ttcaaccaaa ggatacaata    240

atgatcctat tgcctaactc cccagaattt gtgtttgctt tcattggtgc atcgtacctc    300

ggagctattt ctacaatggc caatcctttg tttactcctg ctgaggttgt gaagcaagcc    360

gaggcttcta gtgctaagat cattgtcaca caagcgtgtc atgttaacaa agtgaaagat    420

tatgcatttg agaatgatgt gaagatcata tgcatcgact cggcgccgga gggttgtctc    480

cacttctccg tgctaactca ggctaatgag cacgatattc ctgaggttga aattcaacct    540

gacgatgtgg tggcgttgcc atactcctcc gggacgacgg gattacctaa aggagtgatg    600

ttgacgcaca agggacttgt gacaagcgtc gcacaacaag tcgacggtga aaatccgaat    660

ttgtatatcc atagcgagga cgtgatgctt tgtgtcttgc ccttgttcca tatctattca    720

ctcaactccg ttttgctttg tggattaagg gtgggagcag cgattttgat tatgcagaaa    780

tttgatattg tttctttctt ggagttgata caaagttaca aggtgacaat agggccgttt    840

gtaccaccta ttgttttggy cattgctaag agtcctatgg ttgatgatta tgatctttca    900

tcagtaagaa ccgtcatgtc tggggctgca ccattaggaa aggagcttga agatactgtt    960
```

-continued

```
cgagccaaat ttcctaatgc taaacttggt cagggttatg gtatgacaga agctggacca   1020

gtgttggcta tgtgcttggc atttgcaaaa gaaccctttg aaataaaatc aggggcatgt   1080

ggaacagttg tgagaaatgc tgaaatgaaa attgtggatc ctaaaactgg taattctctt   1140

cccagaaatc aatctggaga aatttgcatt agaggagacc agatcatgaa aggctacctg   1200

aatgatccag aggccacagc aagaacaata gacaaagaag ggtggttata tactggtgac   1260

attggctaca ttgatgatga cgacgagctt ttcattgttg atcgattaaa ggaactgatc   1320

aaatacaaag gatttcaagt cgcacctgct gagctcgaag ctctccttct caaccatccc   1380

aacatttctg atgctgctgt tgtccccatg aaggacgagc aagcaggaga agttccagtg   1440

gcttttgttg ttagatccaa cggatccacc attactgaag atgaagtcaa agattttatt   1500

tcaaagcagg tgatatttta taagaggata aagcgggtat ttttcgtgga tgctattcct   1560

aaatctccat ctggcaaaat ccttcgaaaa gatttgagag ctaaactggc tgctgggctt   1620

ccaaattaa                                                           1629
```

```
<210> SEQ ID NO 9
<211> LENGTH: 561
<212> TYPE: PRT
<213> ORGANISM: Arabidopsis thaliana
<220> FEATURE:
<223> OTHER INFORMATION: 4-coumarate-CoA ligase from Arabidopsis
      thaliana (At4CL)

<400> SEQUENCE: 9

Met Ala Pro Gln Glu Gln Ala Val Ser Gln Val Met Glu Lys Gln Ser
1               5                   10                  15

Asn Asn Asn Asn Ser Asp Val Ile Phe Arg Ser Lys Leu Pro Asp Ile
            20                  25                  30

Tyr Ile Pro Asn His Leu Ser Leu His Asp Tyr Ile Phe Gln Asn Ile
        35                  40                  45

Ser Glu Phe Ala Thr Lys Pro Cys Leu Ile Asn Gly Pro Thr Gly His
    50                  55                  60

Val Tyr Thr Tyr Ser Asp Val His Val Ile Ser Arg Gln Ile Ala Ala
65                  70                  75                  80

Asn Phe His Lys Leu Gly Val Asn Gln Asn Asp Val Val Met Leu Leu
                85                  90                  95

Leu Pro Asn Cys Pro Glu Phe Val Leu Ser Phe Leu Ala Ala Ser Phe
            100                 105                 110

Arg Gly Ala Thr Ala Thr Ala Ala Asn Pro Phe Phe Thr Pro Ala Glu
        115                 120                 125

Ile Ala Lys Gln Ala Lys Ala Ser Asn Thr Lys Leu Ile Ile Thr Glu
    130                 135                 140

Ala Arg Tyr Val Asp Lys Ile Lys Pro Leu Gln Asn Asp Asp Gly Val
145                 150                 155                 160

Val Ile Val Cys Ile Asp Asp Asn Glu Ser Val Pro Ile Pro Glu Gly
                165                 170                 175

Cys Leu Arg Phe Thr Glu Leu Thr Gln Ser Thr Thr Glu Ala Ser Glu
            180                 185                 190

Val Ile Asp Ser Val Glu Ile Ser Pro Asp Asp Val Val Ala Leu Pro
        195                 200                 205

Tyr Ser Ser Gly Thr Thr Gly Leu Pro Lys Gly Val Met Leu Thr His
    210                 215                 220

Lys Gly Leu Val Thr Ser Val Ala Gln Gln Val Asp Gly Glu Asn Pro
225                 230                 235                 240
```

-continued

```
Asn Leu Tyr Phe His Ser Asp Asp Val Ile Leu Cys Val Leu Pro Met
                245                 250                 255

Phe His Ile Tyr Ala Leu Asn Ser Ile Met Leu Cys Gly Leu Arg Val
            260                 265                 270

Gly Ala Ala Ile Leu Ile Met Pro Lys Phe Glu Ile Asn Leu Leu Leu
        275                 280                 285

Glu Leu Ile Gln Arg Cys Lys Val Thr Val Ala Pro Met Val Pro Pro
    290                 295                 300

Ile Val Leu Ala Ile Ala Lys Ser Ser Glu Thr Glu Lys Tyr Asp Leu
305                 310                 315                 320

Ser Ser Ile Arg Val Val Lys Ser Gly Ala Ala Pro Leu Gly Lys Glu
                325                 330                 335

Leu Glu Asp Ala Val Asn Ala Lys Phe Pro Asn Ala Lys Leu Gly Gln
            340                 345                 350

Gly Tyr Gly Met Thr Glu Ala Gly Pro Val Leu Ala Met Ser Leu Gly
        355                 360                 365

Phe Ala Lys Glu Pro Phe Pro Val Lys Ser Gly Ala Cys Gly Thr Val
    370                 375                 380

Val Arg Asn Ala Glu Met Lys Ile Val Asp Pro Asp Thr Gly Asp Ser
385                 390                 395                 400

Leu Ser Arg Asn Gln Pro Gly Glu Ile Cys Ile Arg Gly His Gln Ile
                405                 410                 415

Met Lys Gly Tyr Leu Asn Asn Pro Ala Ala Thr Ala Glu Thr Ile Asp
            420                 425                 430

Lys Asp Gly Trp Leu His Thr Gly Asp Ile Gly Leu Ile Asp Asp Asp
        435                 440                 445

Asp Glu Leu Phe Ile Val Asp Arg Leu Lys Glu Leu Ile Lys Tyr Lys
    450                 455                 460

Gly Phe Gln Val Ala Pro Ala Glu Leu Glu Ala Leu Leu Ile Gly His
465                 470                 475                 480

Pro Asp Ile Thr Asp Val Ala Val Val Ala Met Lys Glu Glu Ala Ala
                485                 490                 495

Gly Glu Val Pro Val Ala Phe Val Val Lys Ser Lys Asp Ser Glu Leu
            500                 505                 510

Ser Glu Asp Asp Val Lys Gln Phe Val Ser Lys Gln Val Val Phe Tyr
        515                 520                 525

Lys Arg Ile Asn Lys Val Phe Phe Thr Glu Ser Ile Pro Lys Ala Pro
    530                 535                 540

Ser Gly Lys Ile Leu Arg Lys Asp Leu Arg Ala Lys Leu Ala Asn Gly
545                 550                 555                 560

Leu


<210> SEQ ID NO 10
<211> LENGTH: 1686
<212> TYPE: DNA
<213> ORGANISM: Arabidopsis thaliana
<220> FEATURE:
<223> OTHER INFORMATION: 4-coumarate-CoA ligase from Arabidopsis
      thaliana (At4CL) (codon optimised)

<400> SEQUENCE: 10

atggcaccac aggaacaggc agtctcccag gttatggaaa agcagtccaa caacaacaac      60

tccgatgtta tcttccgctc caagttgcct gacatctaca tcccaaacca tctgtccctg     120

cacgattaca ttttccagaa catctccgaa tttgctacta agccatgcct gatcaacggc     180
```

-continued ccaaccggtc acgtgtacac ctactctgac gtccacgtga tcagccgcca gatcgcagct 240
aacttccaca agctgggcgt gaaccagaac gacgtagtga tgctgctgct ccctaactgc 300
cctgagttcg tcctgtcctt cctggccgcc tccttccgcg gtgcaaccgc gaccgcggcc 360
aacccattct tcacgccagc agagatcgct aagcaggcta aggcttctaa caccaagctg 420
atcatcaccg aagcgcgcta cgtggacaag atcaagccac tccagaacga cgatggcgtt 480
gtgatcgtgt gcatcgacga caacgagtcc gttccaatcc cagagggctg tctgaggttc 540
accgagctga cccaatcgac caccgaagcg tccgaggtta tcgactccgt tgaaatctcc 600
cctgacgatg tcgtcgccct gccatactcc agcggcacca ccggcttgcc aaagggtgtg 660
atgctgaccc acaagggact cgttacctcc gtggcacagc aggtcgatgg tgaaaacccc 720
aacctgtact tccattccga tgacgtcatc ctgtgcgtcc tgccgatgtt ccacatctac 780
gctctgaact ccatcatgct gtgcggcctc cgcgtcggtg cagcaatcct gatcatgcca 840
aagttcgaaa tcaacctgct gctggagttg atccagcgct gcaaggtgac cgtggcaccc 900
atggtgcccc cgatcgtgct ggcaatcgcg aagtccagcg aaaccgaaaa gtacgacctg 960
tcatccatcc gcgtcgtcaa gtcgggcgcc gcaccactcg gcaaggagct ggaggacgct 1020
gtcaacgcta agttccctaa cgcgaagctc ggccagggct acggtatgac cgaggccggc 1080
ccagtcctgg ccatgtccct gggcttcgca aaggagccat tcccggtgaa gtccggcgca 1140
tgcggcaccg ttgtgcgcaa cgcagagatg aagatcgttg acccagatac cggtgactcc 1200
ctgtcccgta accagcccgg cgagatctgc atccgcggcc accagatcat gaagggctac 1260
ctgaacaacc ctgctgctac cgccgaaacc atcgataagg atggctggct ccacaccggc 1320
gacatcggtc tgatcgacga cgacgatgaa ctgttcatcg tcgatcgcct taaggagttg 1380
atcaagtaca agggcttcca ggtggccccc gcagaactgg aagcactgct catcggccac 1440
cctgatatca ccgatgtcgc cgtcgtggcc atgaaggagg aagcagcagg cgaagtgcca 1500
gtcgctttcg tggtgaagtc caaggattcc gagttgtccg aggatgatgt gaagcagttc 1560
gtgtccaagc aggtcgtgtt ctacaagcgc atcaacaagg tgttcttcac cgaatccatc 1620
ccaaaggcac catccggcaa gatcctgcgc aaggacctgc gcgctaagct ggctaacggc 1680
ctgtaa 1686

<210> SEQ ID NO 11
<211> LENGTH: 585
<212> TYPE: PRT
<213> ORGANISM: Physcomitrella patens
<220> FEATURE:
<223> OTHER INFORMATION: 4-coumarate-CoA ligase from Physcomitrella patens (Pp4CL)

<400> SEQUENCE: 11

Met Ser Pro Ser Leu Leu Pro Gln Pro Ile Val Ser Glu Ser Thr Gly
1 5 10 15

Glu Ser Val Met Lys Met Ser Leu Gln Ser Glu Val Arg Glu Ala Ser
20 25 30

Leu Ala Thr Gly Glu Asn Pro Glu Pro Phe Leu Leu Glu Thr Asp Ala
35 40 45

Glu Ser Gln Ile Met Glu Pro Val His Ala Glu Val His Asp Phe Ile
50 55 60

Tyr Arg Ser Lys Leu Pro Asp Ile Asp Ile Pro Asn His Met Pro Leu
65 70 75 80

-continued

```
Ala Asp Tyr Cys Leu Glu Lys Ser Ser Gln Trp Pro Asp Lys Val Cys
                85                  90                  95

Leu Ile Asp Gly Val Thr Gly Arg Glu His Arg Tyr Gly Glu Ile Glu
            100                 105                 110

Leu Ser Ser Arg Arg Val Ala Ala Gly Leu Asp Lys Ile Gly Val Lys
        115                 120                 125

Gln Gly Asp Val Ile Ala Leu Leu Leu Pro Asn Cys Ala Glu Phe Val
    130                 135                 140

Leu Val Phe Leu Gly Ala Ala Lys Arg Gly Ala Val Val Thr Thr Ala
145                 150                 155                 160

Asn Pro Phe Tyr Thr Ala Ala Glu Leu Glu Lys Gln Ile Glu Ala Ser
                165                 170                 175

Gly Ala Gly Ile Val Ile Thr Gln Ser Ser Tyr Ile Glu Lys Leu Ala
            180                 185                 190

Gly Leu Asn Val Gln Ile Ile Thr Val Asp Gln His Val Ala Asn Cys
        195                 200                 205

Met His Ile Ser Val Leu Leu Asn Ala Cys Glu Asp Glu Cys Pro Gln
    210                 215                 220

Val Arg Ile His Pro Asp Asp Leu Val Cys Leu Pro Tyr Ser Ser Gly
225                 230                 235                 240

Thr Thr Gly Leu Pro Lys Gly Val Met Leu Thr His Lys Ser Leu Val
                245                 250                 255

Ser Ser Val Ser Gln Gln Val Asp Gly Glu Ala Pro Asn Phe Asn Ile
            260                 265                 270

Thr Val Glu Asp Thr Leu Met Cys Val Leu Pro Met Phe His Ile Tyr
        275                 280                 285

Ser Leu Asn Ser Ile Leu Leu Cys Gly Leu Arg Val Gly Ala Thr Leu
    290                 295                 300

Val Ile Met Pro Lys Phe Glu Leu Pro Lys Leu Leu Asp Leu Ile Gln
305                 310                 315                 320

Arg His Lys Val Thr Met Gly Pro Phe Val Pro Pro Ile Val Leu Ala
                325                 330                 335

Ile Ala Lys Asn Pro Ile Val Glu Asn Tyr Asp Leu Ser Ser Met Arg
            340                 345                 350

Met Val Met Ser Gly Ala Ala Pro Leu Gly Arg Glu Leu Glu Asp Ala
        355                 360                 365

Phe Arg Ala Arg Leu Pro Asn Ala Val Leu Gly Gln Gly Tyr Gly Met
    370                 375                 380

Thr Glu Ala Gly Pro Val Leu Ala Met Cys Leu Ala Phe Ala Lys Thr
385                 390                 395                 400

Pro Phe Ser Val Lys Pro Gly Ser Cys Gly Thr Val Val Arg Asn Ala
                405                 410                 415

Glu Val Lys Ile Val Asp Thr Glu Thr Gly Met Ser Leu Pro Tyr Asn
            420                 425                 430

Gln Pro Gly Glu Ile Cys Ile Arg Gly Pro Gln Ile Met Lys Gly Tyr
        435                 440                 445

Leu Lys Asn Pro Glu Ala Thr Ala Asn Thr Ile Asp Lys Asp Gly Phe
    450                 455                 460

Leu His Thr Gly Asp Val Ala Phe Ile Asp Glu Asp Glu Glu Met Phe
465                 470                 475                 480

Ile Val Asp Arg Val Lys Glu Ile Ile Lys Phe Lys Gly Phe Gln Val
                485                 490                 495

Pro Pro Ala Glu Leu Glu Ala Leu Leu Leu Ser His Lys Glu Ile Gln
```

```
            500                 505                 510

Asp Ala Ala Val Val Ser Arg Lys Asp Asp Val Ala Gly Glu Val Pro
        515                 520                 525

Val Ala Phe Val Val Arg Ala Thr Ser Ser Thr Ile Thr Glu Asp Glu
    530                 535                 540

Val Lys Asp Tyr Ile Ala Lys Gln Val Val Phe Tyr Lys Lys Ile His
545                 550                 555                 560

Asn Val Tyr Phe Val Asp Ser Val Pro Lys Ser Pro Ser Gly Lys Ile
                565                 570                 575

Leu Arg Lys Asp Leu Arg Asn Lys Val
            580                 585


<210> SEQ ID NO 12
<211> LENGTH: 1758
<212> TYPE: DNA
<213> ORGANISM: Physcomitrella patens
<220> FEATURE:
<223> OTHER INFORMATION: 4-coumarate-CoA ligase from Physcomitrella
      patens (Pp4CL) (codon optimised)

<400> SEQUENCE: 12

atgtcaccat cgctccttcc ccagccaatc gtgtccgaat ccaccggtga atccgtgatg     60

aagatgtccc tccagtccga agtgcgcgaa gcatccctgg caaccggtga aaaccctgaa    120

ccattcctgc tggaaaccga tgctgaatcc cagatcatgg aacctgtgca cgctgaagtt    180

cacgatttca tctaccgttc taagctgcct gatatcgata tcccaaacca catgcctctg    240

gctgattact gcctggagaa gtcctcccag tggcctgata aggtgtgcct gatcgatggt    300

gtgaccggtc gcgaacaccg ctacggcgaa attgagctgt cctcccgccg cgtggcagca    360

ggccttgata agatcggcgt gaagcagggc gatgtcatcg cactgctctt gcctaactgc    420

gctgagttcg tcctggtgtt cctgggcgca gcgaagcgcg gcgccgttgt caccaccgct    480

aacccattct acaccgccgc cgagttggag aagcaaatcg aggcctccgg tgcgggcatt    540

gttatcactc agagcagcta catcgagaag ctcgcaggcc ttaacgtcca gatcatcacc    600

gttgatcagc acgtggctaa ttgcatgcac atctccgtgc tgctgaacgc atgcgaagat    660

gaatgccctc aggtgcgtat ccaccctgac gatctggtct gcctgccata ctcctccggc    720

accaccggct tgccaaaggg cgtgatgctg acccacaagt cccttgtgtc atccgtgtcc    780

caacaggtgg acggcgaagc accaaacttc aacatcactg tcgaggacac cctgatgtgc    840

gtgctgccca tgttccacat ctattccctc aactccatcc tgctgtgcgg cctccgtgtg    900

ggcgccaccc tcgttattat gccgaagttc gaactgccaa agctgttgga cctgatccag    960

cgtcacaagg tgaccatggg cccattcgtg ccgccaatcg tcctggccat cgcaaagaac   1020

ccaatcgtcg agaattacga tctctcctcc atgcgcatgg ttatgtccgg cgctgcacct   1080

ctgggtcggg agctggagga cgctttccgt gcccgcttgc caaacgccgt tctgggccag   1140

ggctacggga tgactgaagc cggcccagtc ctggctatgt gcctcgcatt cgcaaagacc   1200

ccattctccg tgaagccagg ctcctgcggc accgtggtgc gcaacgctga agtgaaaatc   1260

gtcgataccg aaaccggcat gtccctgcca tacaaccagc caggcgagat ctgcatccgc   1320

ggcccacaga tcatgaaggg ctacctgaag aacccagaag ctaccgctaa caccatcgat   1380

aaggatggct tcctgcacac cggcgatgtc gcattcatcg atgaggatga ggagatgttc   1440

atcgttgatc gcgtcaagga gatcatcaag ttcaagggct tccaggtgcc tcctgcggag   1500

ctggaagctc tcctgctgtc ccacaaggag atccaggacg ctgctgtcgt gtcccgtaag   1560
```

```
gatgacgtgg cgggcgaagt tccagtggca ttcgtggtcc gcgctaccag ctccaccatc   1620

accgaggatg aagtcaagga ttacatcgca aagcaggtcg ttttctacaa gaagatccac   1680

aacgtatact tcgtggattc cgtgccaaag tctccatccg gcaagatcct gcgtaaggat   1740

ctccgtaaca aggtgtaa                                                 1758
```

<210> SEQ ID NO 13
<211> LENGTH: 522
<212> TYPE: PRT
<213> ORGANISM: Streptomyces coelicolor
<220> FEATURE:
<223> OTHER INFORMATION: 4-coumarate-CoA ligase from Streptomyces coelicolor (Sc4CL)

<400> SEQUENCE: 13

```
Met Phe Arg Ser Glu Tyr Ala Asp Val Pro Pro Val Asp Leu Pro Ile
1               5                   10                  15

His Asp Ala Val Leu Gly Gly Ala Ala Ala Phe Gly Ser Thr Pro Ala
            20                  25                  30

Leu Ile Asp Gly Thr Asp Gly Thr Thr Leu Thr Tyr Glu Gln Val Asp
        35                  40                  45

Arg Phe His Arg Arg Val Ala Ala Ala Leu Ala Glu Thr Gly Val Arg
    50                  55                  60

Lys Gly Asp Val Leu Ala Leu His Ser Pro Asn Thr Val Ala Phe Pro
65                  70                  75                  80

Leu Ala Phe Tyr Ala Ala Thr Arg Ala Gly Ala Ser Val Thr Thr Val
                85                  90                  95

His Pro Leu Ala Thr Ala Glu Glu Phe Ala Lys Gln Leu Lys Asp Ser
            100                 105                 110

Ala Ala Arg Trp Ile Val Thr Val Ser Pro Leu Leu Ser Thr Ala Arg
        115                 120                 125

Arg Ala Ala Glu Leu Ala Gly Gly Val Gln Glu Ile Leu Val Cys Asp
    130                 135                 140

Ser Ala Pro Gly His Arg Ser Leu Val Asp Met Leu Ala Ser Thr Ala
145                 150                 155                 160

Pro Glu Pro Ser Val Ala Ile Asp Pro Ala Glu Asp Val Ala Ala Leu
                165                 170                 175

Pro Tyr Ser Ser Gly Thr Thr Gly Thr Pro Lys Gly Val Met Leu Thr
            180                 185                 190

His Arg Gln Ile Ala Thr Asn Leu Ala Gln Leu Glu Pro Ser Met Pro
        195                 200                 205

Ser Ala Pro Gly Asp Arg Val Leu Ala Val Leu Pro Phe Phe His Ile
    210                 215                 220

Tyr Gly Leu Thr Ala Leu Met Asn Ala Pro Leu Arg Leu Gly Ala Thr
225                 230                 235                 240

Val Val Val Leu Pro Arg Phe Asp Leu Glu Gln Phe Leu Ala Ala Ile
                245                 250                 255

Gln Asn His Arg Ile Thr Ser Leu Tyr Val Ala Pro Pro Ile Val Leu
            260                 265                 270

Ala Leu Ala Lys His Pro Leu Val Ala Asp Tyr Asp Leu Ser Ser Leu
        275                 280                 285

Arg Tyr Ile Val Ser Ala Ala Ala Pro Leu Asp Ala Arg Leu Ala Ala
    290                 295                 300

Ala Cys Ser Gln Arg Leu Gly Leu Pro Pro Val Gly Gln Ala Tyr Gly
305                 310                 315                 320
```

```
Met Thr Glu Leu Ser Pro Gly Thr His Val Val Pro Leu Asp Ala Met
                325                 330                 335

Ala Asp Ala Pro Pro Gly Thr Val Gly Arg Leu Ile Ala Gly Thr Glu
            340                 345                 350

Met Arg Ile Val Ser Leu Thr Asp Pro Gly Thr Asp Leu Pro Ala Gly
        355                 360                 365

Glu Ser Gly Glu Ile Leu Ile Arg Gly Pro Gln Ile Met Lys Gly Tyr
    370                 375                 380

Leu Gly Arg Pro Asp Ala Thr Ala Ala Met Ile Asp Glu Glu Gly Trp
385                 390                 395                 400

Leu His Thr Gly Asp Val Gly His Val Asp Ala Asp Gly Trp Leu Phe
                405                 410                 415

Val Val Asp Arg Val Lys Glu Leu Ile Lys Tyr Lys Gly Phe Gln Val
            420                 425                 430

Ala Pro Ala Glu Leu Glu Ala His Leu Leu Thr His Pro Gly Val Ala
        435                 440                 445

Asp Ala Ala Val Val Gly Ala Tyr Asp Asp Asp Gly Asn Glu Val Pro
    450                 455                 460

His Ala Phe Val Val Arg Gln Pro Ala Ala Pro Gly Leu Ala Glu Ser
465                 470                 475                 480

Glu Ile Met Met Tyr Val Ala Glu Arg Val Ala Pro Tyr Lys Arg Val
                485                 490                 495

Arg Arg Val Thr Phe Val Asp Ala Val Pro Arg Ala Ala Ser Gly Lys
            500                 505                 510

Ile Leu Arg Arg Gln Leu Arg Glu Pro Arg
        515                 520


<210> SEQ ID NO 14
<211> LENGTH: 1569
<212> TYPE: DNA
<213> ORGANISM: Streptomyces coelicolor
<220> FEATURE:
<223> OTHER INFORMATION: 4-coumarate-CoA ligase from Streptomyces
      coelicolor (Sc4CL) (codon optimised)

<400> SEQUENCE: 14

atgttccgtt ccgagtacgc agatgtgcct ccagtggacc tccctatcca cgatgctgtc     60

ctgggtggcg cggccgcatt cggcagcacc ccagctctga tcgatggcac cgatggcacc    120

accctgacct acgaacaggt cgatcgcttc caccgtcgcg tcgctgctgc tctggcggaa    180

accggcgtgc gcaagggcga tgtcctggcc ctgcactctc caaacaccgt tgctttccct    240

ctggcattct acgctgcaac ccgcgctggt gcatccgtga ccactgttca ccctctcgct    300

accgcagaag agtttgctaa gcagctgaag gattcggctg cacgttggat cgtcaccgtt    360

tccccactgc tgtccaccgc acgccgcgcc gcagagttgg caggcggcgt gcaggaaatt    420

ttggtctgcg attctgctcc aggtcaccgt tctctcgtcg atatgctggc tagcaccgca    480

cccgaaccat ccgtcgctat cgatccagca gaagatgtgg ctgcccttcc gtactcctct    540

ggcaccaccg gcaccccaaa gggtgtgatg ctgacccacc gccagattgc aaccaacctg    600

gctcagctgg aaccttccat gccatccgct ccaggtgacc gggtgctggc tgttctgcca    660

ttcttccaca tctacggctt gaccgcactc atgaacgctc ctttgcgcct gggtgctacc    720

gtggtggtgc tccctcgctt cgacctggag cagttccttg cagccatcca gaaccaccgt    780

atcaccagtt tgtacgtcgc ccccaccaatc gttttggcac tggctaagca ccctctggtg    840
```

-continued

```
gccgactatg acctttcctc cctccgttac atcgtgagcg ccgcggcacc gctcgacgcg    900

cgcctggcag ccgcttgttc ccagcgtctg ggcctgcccc cggtggggca agcgtacggt    960

atgaccgagc tgtctcctgg cacccacgtc gtgccgctcg atgcaatggc agatgcccca   1020

cccggcaccg tgggtcgcct gatagctggc accgagatgc gcatcgtgtc cctgaccgac   1080

ccaggcaccg acctgccggc aggcgaatcc ggcgaaatcc tgatccgcgg cccccagatt   1140

atgaagggct acctcggccg cccagatgct accgcagcaa tgatcgatga ggagggctgg   1200

ctgcacaccg gcgatgtggg ccacgtggac gctgatggtt ggttgttcgt cgtggatcgc   1260

gttaaggagc tgatcaagta caagggtttc caggttgctc ccgcggagct tgaagcacac   1320

ttgctcaccc acccaggtgt tgcagatgca gctgtcgtcg gcgcatacga cgacgacggt   1380

aacgaggtgc cgcacgcctt tgtggtccgc cagccggctg caccaggcct cgcggagtcc   1440

gaaatcatga tgtacgtggc tgaacgcgtt gctccataca agcgcgtgcg ccgcgtgacc   1500

ttcgtcgatg ccgtgccacg cgcagcatcc ggcaagatcc tgcgtcgcca gctgcgcgag   1560

ccacgctaa                                                           1569


<210> SEQ ID NO 15
<211> LENGTH: 383
<212> TYPE: PRT
<213> ORGANISM: Rubus idaeus
<220> FEATURE:
<223> OTHER INFORMATION: benzalacetone synthase from Rubus idaeus
      (RiPKS)

<400> SEQUENCE: 15

Met Val Thr Val Glu Glu Val Arg Lys Ala Gln Arg Ala Glu Gly Pro
1               5                   10                  15

Ala Thr Val Leu Ala Ile Gly Thr Ala Thr Pro Pro Asn Cys Val Gly
            20                  25                  30

Gln Ser Thr Tyr Pro Asp Tyr Tyr Phe Arg Ile Thr Asn Ser Glu His
        35                  40                  45

Lys Ile Glu Leu Lys Gln Lys Phe Gln Arg Met Cys Asp Lys Ser Met
    50                  55                  60

Ile Lys Lys Arg Tyr Met Tyr Leu Thr Glu Glu Ile Leu Lys Glu Asn
65                  70                  75                  80

Pro Ser Met Cys Glu Tyr Met Ala Pro Ser Leu Asp Ala Arg Gln Asp
                85                  90                  95

Met Val Ile Val Glu Ile Pro Lys Leu Gly Lys Glu Ala Ala Thr Lys
            100                 105                 110

Ala Ile Lys Glu Trp Gly Gln Pro Lys Ser Lys Ile Thr His Leu Val
        115                 120                 125

Phe Cys Thr Thr Ser Gly Val Asp Met Pro Gly Ala Asp Tyr Gln Leu
    130                 135                 140

Ile Lys Leu Phe Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Arg Gly Ala Arg Val Leu Val Val Cys Ser Glu
            180                 185                 190

Ile Thr Val Val Thr Phe Arg Gly Pro Ser Asp Thr His Leu Asp Cys
        195                 200                 205

Leu Val Gly Gln Ala Leu Phe Gly Asp Gly Val Ala Ser Ile Ile Val
    210                 215                 220
```

-continued

```
Gly Ala Asp Pro Leu Pro Glu Ile Glu Lys Pro Leu Phe Glu Leu Val
225                 230                 235                 240

Ser Ala Ala Gln Thr Ile Leu Pro Asp Ser Glu Gly Ala Ile Glu Gly
                245                 250                 255

His Leu Arg Glu Val Gly Leu Thr Phe His Leu Leu Glu Asn Val Pro
            260                 265                 270

Ala Leu Ile Ser Lys Asn Ile Glu Lys Ser Leu Asn Glu Thr Phe Lys
        275                 280                 285

Pro Leu Asp Ile Met Asp Trp Asn Ser Leu Phe Trp Ile Ala His Pro
    290                 295                 300

Gly Gly Pro Ala Ile Leu Asp Gln Val Glu Ala Lys Leu Gly Leu Lys
305                 310                 315                 320

Pro Glu Lys Leu Glu Ala Thr Gly His Ile Leu Ser Glu Tyr Gly Asn
                325                 330                 335

Met Ser Ser Ala Cys Val Leu Phe Ile Leu Asp Val Val Arg Arg Lys
            340                 345                 350

Ser Ala Ala Asn Gly Val Thr Thr Arg Ile Leu Ser Ile Gly Gln Ile
        355                 360                 365

Ser Lys Ser Leu Leu Ile Leu Ala Trp Phe Leu Phe Ser Leu Val
    370                 375                 380


<210> SEQ ID NO 16
<211> LENGTH: 1152
<212> TYPE: DNA
<213> ORGANISM: Rubus idaeus
<220> FEATURE:
<223> OTHER INFORMATION: benzalacetone synthase from Rubus idaeus
      (RiPKS) (codon optimised)

<400> SEQUENCE: 16

atggttaccg ttgaagaagt ccgcaaggct cagcgcgcag aaggccctgc aaccgttctg     60

gcaatcggca ccgcaacccc accaaactgc gtcggccagt ccacctaccc agattattat    120

ttccgtatca ccaactctga acacaagatt gaactgaagc agaagttcca gaggatgtgc    180

gataagtcca tgatcaagaa gcgttacatg taccttaccg aagagatcct gaaggagaac    240

ccatccatgt gcgagtacat ggctccatcc cttgatgctc gccaggacat ggtcatcgtg    300

gaaatcccaa agctgggcaa ggaagcagcc accaaggcaa tcaaggagtg gggccagccg    360

aagtcgaaga tcacccacct tgttttctgc accaccagcg gtgtggatat gcctggcgcc    420

gactaccagc tgatcaagct cttcggcctg cgcccatccg tcaagcgcct catgatgtac    480

cagcagggct gcttcgccgg cggcaccgtt ctgcgcctgg ctaaggatct ggcagaaaac    540

aaccgcggtg cccgcgttct cgtcgtgtgc tccgagatca ccgtggtcac cttccgcggc    600

ccatccgaca cccaccttga ctgtctggtt ggccaggcac tcttcggcga tggcgtggca    660

tccatcatcg tcggcgcaga tcctctccct gaaatcgaaa agccactttt cgaacttgtc    720

agcgcagcac agaccatcct gccagattct gagggcgcaa tcgagggcca cctccgcgag    780

gtgggtctta ccttccatct gctcgaaaac gtgccagcac tgatctccaa gaacatcgaa    840

aagtccctga acgaaacctt caagccactg gacatcatgg actggaactc cctgttctgg    900

atcgctcacc caggcggtcc ggctatcctg gatcaggtcg aggctaagct gggtctgaag    960

ccggagaagt tggaggctac cggccacatc ctgtccgaat acggcaacat gtcctccgca   1020

tgcgttctct tcatcctgga cgtggtgcgg cgcaagtccg cagccaacgg tgtgaccacc   1080

cgtatcctga gcatcggtca gatctccaag tccctgctga tcctggcatg gttcctcttc   1140
```

tccctggtgt aa 1152

<210> SEQ ID NO 17
<211> LENGTH: 384
<212> TYPE: PRT
<213> ORGANISM: Rheum palmatum
<220> FEATURE:
<223> OTHER INFORMATION: benzalacetone synthase from Rheum palmatum
(RpBAS)

<400> SEQUENCE: 17

Met Ala Thr Glu Glu Met Lys Lys Leu Ala Thr Val Met Ala Ile Gly
1 5 10 15

Thr Ala Asn Pro Pro Asn Cys Tyr Tyr Gln Ala Asp Phe Pro Asp Phe
20 25 30

Tyr Phe Arg Val Thr Asn Ser Asp His Leu Ile Asn Leu Lys Gln Lys
35 40 45

Phe Lys Arg Leu Cys Glu Asn Ser Arg Ile Glu Lys Arg Tyr Leu His
50 55 60

Val Thr Glu Glu Ile Leu Lys Glu Asn Pro Asn Ile Ala Ala Tyr Glu
65 70 75 80

Ala Thr Ser Leu Asn Val Arg His Lys Met Gln Val Lys Gly Val Ala
85 90 95

Glu Leu Gly Lys Glu Ala Ala Leu Lys Ala Ile Lys Glu Trp Gly Gln
100 105 110

Pro Lys Ser Lys Ile Thr His Leu Ile Val Cys Cys Leu Ala Gly Val
115 120 125

Asp Met Pro Gly Ala Asp Tyr Gln Leu Thr Lys Leu Leu Asp Leu Asp
130 135 140

Pro Ser Val Lys Arg Phe Met Phe Tyr His Leu Gly Cys Tyr Ala Gly
145 150 155 160

Gly Thr Val Leu Arg Leu Ala Lys Asp Ile Ala Glu Asn Asn Lys Gly
165 170 175

Ala Arg Val Leu Ile Val Cys Ser Glu Met Thr Thr Thr Cys Phe Arg
180 185 190

Gly Pro Ser Glu Thr His Leu Asp Ser Met Ile Gly Gln Ala Ile Leu
195 200 205

Gly Asp Gly Ala Ala Ala Val Ile Val Gly Ala Asp Pro Asp Leu Thr
210 215 220

Val Glu Arg Pro Ile Phe Glu Leu Val Ser Thr Ala Gln Thr Ile Val
225 230 235 240

Pro Glu Ser His Gly Ala Ile Glu Gly His Leu Leu Glu Ser Gly Leu
245 250 255

Ser Phe His Leu Tyr Lys Thr Val Pro Thr Leu Ile Ser Asn Asn Ile
260 265 270

Lys Thr Cys Leu Ser Asp Ala Phe Thr Pro Leu Asn Ile Ser Asp Trp
275 280 285

Asn Ser Leu Phe Trp Ile Ala His Pro Gly Gly Pro Ala Ile Leu Asp
290 295 300

Gln Val Thr Ala Lys Val Gly Leu Glu Lys Glu Lys Leu Lys Val Thr
305 310 315 320

Arg Gln Val Leu Lys Asp Tyr Gly Asn Met Ser Ser Ala Thr Val Phe
325 330 335

Phe Ile Met Asp Glu Met Arg Lys Lys Ser Leu Glu Asn Gly Gln Ala
340 345 350

-continued

```
Thr Thr Gly Glu Gly Leu Glu Trp Gly Val Leu Phe Gly Phe Gly Pro
        355                 360                 365

Gly Ile Thr Val Glu Thr Val Val Leu Arg Ser Val Pro Val Ile Ser
    370                 375                 380


<210> SEQ ID NO 18
<211> LENGTH: 1155
<212> TYPE: DNA
<213> ORGANISM: Rheum palmatum
<220> FEATURE:
<223> OTHER INFORMATION: benzalacetone synthase from Rheum palmatum
      (RpBAS) (codon optimised)

<400> SEQUENCE: 18

atggcaaccg aggagatgaa gaagctcgca accgtgatgg caatcggcac tgctaaccca      60

ccgaactgct attaccaagc tgattttccc gacttctact tccgcgtgac caactccgat     120

catctgatca acctgaagca gaagttcaag cgcctatgcg aaaactctcg catcgagaag     180

cgctacctcc acgtcaccga ggagatcctc aaggaaaacc caaacatcgc agcttacgag     240

gctactagcc tgaacgtgcg ccacaagatg caggtcaagg gcgtcgcaga actgggcaag     300

gaagctgctc tgaaggctat caaggaatgg ggccagccaa agtccaagat cacccacctg     360

atcgtctgct gcctggctgg cgtggatatg ccaggcgcag attaccagct cactaagctc     420

ctcgatctcg acccatccgt taagcgcttc atgttctacc acctgggttg ctacgccggt     480

ggcaccgtgc tccgcctggc taaggatatc gctgaaaaca acaagggcgc acgcgtgctg     540

atcgtgtgct ctgaaatgac caccacctgt ttccgcggcc cttcagaaac ccacctggac     600

tctatgatcg gccaggccat cctcggtgac ggtgccgcag ccgtgatcgt gggcgcggac     660

cctgatctga ccgtggagcg tccaatcttc gagctggtga gcacggctca gaccatcgtg     720

ccggagtccc acggcgccat cgagggccac ctcctggagt ctggcctgag cttccacctg     780

tacaagaccg tgccgaccct gatctccaac aacatcaaga cctgcctctc cgatgctttc     840

accccactga acatctccga ctggaacagc ctcttctgga tcgcacaccc aggcggcccg     900

gccatcctgg atcaggtgac cgctaaggtg ggcctggaaa aggaaaagct gaaggtgacc     960

cgccaggttc tgaaggatta cggcaacatg tcctccgcta ccgtgttctt catcatggat    1020

gaaatgcgta agaagtccct ggaaaacggc caggcaacca ccggcgaggg cctggaatgg    1080

ggcgtgctgt tcggcttcgg cccaggcatc accgtggaaa ccgtggtcct gcgctccgtc    1140

ccagtgatct cctaa                                                     1155


<210> SEQ ID NO 19
<211> LENGTH: 348
<212> TYPE: PRT
<213> ORGANISM: Rubus idaeus
<220> FEATURE:
<223> OTHER INFORMATION: benzalacetone reductase from Rubus idaeus
      (RiBAR)

<400> SEQUENCE: 19

Met Ala Ser Gly Gly Glu Met Gln Val Ser Asn Lys Gln Val Ile Phe
1               5                   10                  15

Arg Asp Tyr Val Thr Gly Phe Pro Lys Glu Ser Asp Met Glu Leu Thr
            20                  25                  30

Thr Arg Ser Ile Thr Leu Lys Leu Pro Gln Gly Ser Thr Gly Leu Leu
        35                  40                  45

Leu Lys Asn Leu Tyr Leu Ser Cys Asp Pro Tyr Met Arg Ala Arg Met
    50                  55                  60
```

```
Thr Asn His His Arg Leu Ser Tyr Val Asp Ser Phe Lys Pro Gly Ser
65                  70                  75                  80

Pro Ile Ile Gly Tyr Gly Val Ala Arg Val Leu Glu Ser Gly Asn Pro
                85                  90                  95

Lys Phe Asn Pro Gly Asp Leu Val Trp Gly Phe Thr Gly Trp Glu Glu
            100                 105                 110

Tyr Ser Val Ile Thr Ala Thr Glu Ser Leu Phe Lys Ile His Asn Thr
        115                 120                 125

Asp Val Pro Leu Ser Tyr Tyr Thr Gly Leu Leu Gly Met Pro Gly Met
    130                 135                 140

Thr Ala Tyr Ala Gly Phe Tyr Glu Ile Cys Ser Pro Lys Lys Gly Glu
145                 150                 155                 160

Thr Val Tyr Val Ser Ala Ala Ser Gly Ala Val Gly Gln Leu Val Gly
                165                 170                 175

Gln Phe Ala Lys Leu Thr Gly Cys Tyr Val Val Gly Ser Ala Gly Ser
            180                 185                 190

Lys Glu Lys Val Asp Leu Leu Lys Asn Lys Phe Gly Phe Asp Glu Ala
        195                 200                 205

Phe Asn Tyr Lys Glu Glu Ala Asp Leu Asp Ala Ala Leu Arg Arg Tyr
    210                 215                 220

Phe Pro Asp Gly Ile Asp Ile Tyr Phe Glu Asn Val Gly Gly Lys Met
225                 230                 235                 240

Leu Asp Ala Val Leu Pro Asn Met Arg Pro Lys Gly Arg Ile Ala Val
                245                 250                 255

Cys Gly Met Ile Ser Gln Tyr Asn Leu Glu Gln Pro Glu Gly Val Arg
            260                 265                 270

Asn Leu Met Ala Leu Ile Val Lys Gln Val Arg Met Glu Gly Phe Met
        275                 280                 285

Val Phe Ser Tyr Tyr His Leu Tyr Gly Lys Phe Leu Glu Thr Val Leu
    290                 295                 300

Pro Tyr Ile Lys Gln Gly Lys Ile Thr Tyr Val Glu Asp Val Val Asp
305                 310                 315                 320

Gly Leu Asp Asn Ala Pro Ala Ala Leu Ile Gly Leu Tyr Ser Gly Arg
                325                 330                 335

Asn Val Gly Lys Gln Val Val Val Val Ser Arg Glu
            340                 345
```

<210> SEQ ID NO 20
<211> LENGTH: 1047
<212> TYPE: DNA
<213> ORGANISM: Rubus idaeus
<220> FEATURE:
<223> OTHER INFORMATION: benzalacetone reductase from Rubus idaeus (RiBAR) (codon optimised)

<400> SEQUENCE: 20

```
atggcatccg gcggtgaaat gcaggtttcc aacaagcagg ttatcttccg tgattacgtt      60

accggcttcc caaaggaatc cgatatggaa ctcactaccc gctctatcac ccttaagtta     120

ccacaaggtt ctaccggcct gctcctgaag aacctgtacc tttcctgcga tccatatatg     180

cgcgcccgca tgaccaacca ccatcgtctg tcctacgttg attccttcaa gccaggtagc     240

ccaatcattg gttacggtgt agcacgcgtt ctggaatccg gtaatcctaa gtttaaccca     300

ggcgatcttg tttggggttt caccggttgg gaagaatact ctgtgatcac cgctactgaa     360

tccctgttca agatccataa caccgatgtg ccgctgtcct actacaccgg cctcctgggg     420
```

atgccaggca tgaccgcata cgctggcttc tacgagatct gtagccctaa gaagggcgaa 480
accgtctacg tgtccgctgc ctccggcgcg gttggccagc ttgtgggcca gttcgctaag 540
ctcaccggct gctacgtggt gggctctgcc ggctccaagg aaaaggtgga cctgctgaag 600
aacaagttcg gcttcgacga agcattcaac tacaaggagg aagcggacct ggacgctgcg 660
ctgcgtcggt acttccccga tggaattgat atttacttcg aaaacgtggg tggcaagatg 720
ctggacgctg tcctccccaa catgcgcccc aagggccgca tcgccgtctg cggcatgatc 780
tcccaataca accttgagca gccagagggc gtccgcaacc tgatggccct gatcgtcaag 840
caggtccgca tggaaggctt tatggtgttc tcctactacc acctgtacgg caagttcctg 900
gaaaccgtgc tcccatacat caagcagggc aagatcacct acgtggaaga tgtggtggat 960
ggcctggaca acgcaccagc agccctgatc ggcctgtact ccggccgcaa cgtgggcaag 1020
caggtcgtcg tggtgtcccg cgagtaa 1047

<210> SEQ ID NO 21
<211> LENGTH: 11497
<212> TYPE: DNA
<213> ORGANISM: Artificial Sequence
<220> FEATURE:
<223> OTHER INFORMATION: plasmid RiPKS-At4CL-RcTAL-pECXK (pECXK_A)

<400> SEQUENCE: 21
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380

-continued

```
tcagatctcc aagtccctgc tgatcctggc atggttcctc ttctccctgg tgtaaggatc   1440
taggaggatt atgagatggc accacaggaa caggcagtct cccaggttat ggaaaagcag   1500
tccaacaaca acaactccga tgttatcttc cgctccaagt tgcctgacat ctacatccca   1560
aaccatctgt ccctgcacga ttacattttc cagaacatct ccgaatttgc tactaagcca   1620
tgcctgatca acggcccaac cggtcacgtg tacacctact ctgacgtcca cgtgatcagc   1680
cgccagatcg cagctaactt ccacaagctg ggcgtgaacc agaacgacgt agtgatgctg   1740
ctgctcccta actgccctga gttcgtcctg tccttcctgg ccgcctcctt ccgcggtgca   1800
accgcgaccg cggccaaccc attcttcacg ccagcagaga tcgctaagca ggctaaggct   1860
tctaacacca agctgatcat caccgaagcg cgctacgtgg acaagatcaa gccactccag   1920
aacgacgatg gcgttgtgat cgtgtgcatc gacgacaacg agtccgttcc aatcccagag   1980
ggctgtctga ggttcaccga gctgacccaa tcgaccaccg aagcgtccga ggttatcgac   2040
tccgttgaaa tctcccctga cgatgtcgtc gccctgccat actccagcgg caccaccggc   2100
ttgccaaagg gtgtgatgct gacccacaag ggactcgtta cctccgtggc acagcaggtc   2160
gatggtgaaa accccaacct gtacttccat tccgatgacg tcatcctgtg cgtcctgccg   2220
atgttccaca tctacgctct gaactccatc atgctgtgcg gcctccgcgt cggtgcagca   2280
atcctgatca tgccaaagtt cgaaatcaac ctgctgctgg agttgatcca gcgctgcaag   2340
gtgaccgtgg cacccatggt gcccccgatc gtgctggcaa tcgcgaagtc cagcgaaacc   2400
gaaaagtacg acctgtcatc catccgcgtc gtcaagtcgg gcgccgcacc actcggcaag   2460
gagctggagg acgctgtcaa cgctaagttc cctaacgcga agctcggcca gggctacggt   2520
atgaccgagg ccggcccagt cctggccatg tccctgggct tcgcaaagga gccattcccg   2580
gtgaagtccg gcgcatgcgg caccgttgtg cgcaacgcag agatgaagat cgttgaccca   2640
gataccggtg actccctgtc ccgtaaccag cccggcgaga tctgcatccg cggccaccag   2700
atcatgaagg gctacctgaa caaccctgct gctaccgccg aaaccatcga taaggatggc   2760
tggctccaca ccggcgacat cggtctgatc gacgacgacg atgaactgtt catcgtcgat   2820
cgccttaagg agttgatcaa gtacaagggc ttccaggtgg cccccgcaga actggaagca   2880
ctgctcatcg gccaccctga tatcaccgat gtcgccgtcg tggccatgaa ggaggaagca   2940
gcaggcgaag tgccagtcgc tttcgtggtg aagtccaagg attccgagtt gtccgaggat   3000
gatgtgaagc agttcgtgtc caagcaggtc gtgttctaca agcgcatcaa caaggtgttc   3060
ttcaccgaat ccatcccaaa ggcaccatcc ggcaagatcc tgcgcaagga cctgcgcgct   3120
aagctggcta acggcctgta aggatctagg aggataaaga aatgaccctg caatcccaga   3180
ctgcaaagga ctgcctggcg ctggatggtg cactgacact ggttcagtgc gaagcaattg   3240
ccactcaccg ctcacggatc tccgtcacac cagcattgcg ggaacgctgc gcccgcgcgc   3300
acgcacgtct ggagcacgct atcgcagaac agcgtcacat ctatggtatc accaccggct   3360
tcggaccact ggctaatcgc ctgatcggtg cagatcaggg cgccgaactc cagcagaacc   3420
tcatctacca ccttgctact ggcgtgggcc caaaactctc ctgggctgaa gcacgtgcac   3480
tcatgctggc tcgtctcaac tccatccttc agggcgcatc tggtgcatca ccagaaacca   3540
tcgaccgtat cgttgccgtt ctgaacgctg gcttcgcccc agaagtccca gctcagggca   3600
ccgttggtgc atctggcgat ctgaccccac tggctcacat ggtgctggcg cttcagggtc   3660
gaggtcgtat gatcgatcca tccggccgtg ttcaggaagc cggcgcagtg atggatcgcc   3720
tgtgcggtgg cccactgacc ttggcagccc gtgacggtct ggctctggtc aacggtactt   3780
```

ccgctatgac cgcaatcgct gctttgaccg gtgtggaggc tgcgcgcgca atcgacgccg 3840
cattgcgcca ctccgctgtg ctcatggagg ttctctccgg ccacgctgag gcttggcacc 3900
ctgcatttgc tgaactccgc ccacacccag gccagctgcg cgcaaccgaa cgtctggccc 3960
aggctctcga tggcgccggt cgcgtttgcc gcaccttgac cgcggcccgt cgcctgaccg 4020
cagctgatct gcgccctgag gatcacccag cccaggacgc ctactccctg cgcgtggtgc 4080
cacagctggt tggcgctgtc tgggacaccc tcgattggca cgatcgcgtc gtgacctgcg 4140
aactcaactc tgtgaccgac aacccaatct tcccggaagg ctgcgctgtt ccagcactgc 4200
acggcggcaa cttcatgggc gtgcacgtcg cactggcgtc ggacgccctg aacgctgcat 4260
tggttaccct ggcaggtctg gtggagcgcc agatcgcacg ccttactgat gagaagctga 4320
acaagggact tccggcattc cttcacggtg gtcaggctgg ccttcagtcc ggcttcatgg 4380
gcgcgcaggt caccgcaacc gcgctccttg ctgaaatgcg cgcaaacgca accccggtgt 4440
ctgttcagtc actgtctacc aacggcgcta accaggatgt tgtcagcatg ggcaccatcg 4500
ctgcacgccg cgctcgcgca cagctgctcc cactgtccca gattcaggca atcctggctc 4560
tcgctctcgc ccaggcaatg gatctgctgg atgatccaga gggccaggct ggctggtccc 4620
ttaccgcacg cgacctgcgc gatcgcatcc gcgctgtctc gccgggcctg cgcgcagatc 4680
gcccactggc cggccacatc gaggcagtcg ctcagggtct gcgccaccct tccgcagcag 4740
ctgatccacc agcataactc tagagtcgac ctgcaggcat gcaagcttgg ctgttttggc 4800
ggatgagaga agattttcag cctgatacag attaaatcag aacgcagaag cggtctgata 4860
aaacagaatt tgcctggcgg cagtagcgcg gtggtcccac ctgaccccat gccgaactca 4920
gaagtgaaac gccgtagcgc cgatggtagt gtggggtctc cccatgcgag agtagggaac 4980
tgccaggcat caaataaaac gaaaggctca gtcgaaagac tgggcctttc gttttatctg 5040
ttgtttgtcg gtgaacgctc tcctgagtag gacaaatccg ccgggagcgg atttgaacgt 5100
tgcgaagcaa cggcccggag ggtggcgggc aggacgcccg ccataaactg ccaggcatca 5160
aattaagcag aaggccatcc tgacggatgg cctttttgcg tttctacaaa ctctttttgt 5220
ttatttttct aaatacattc aaatatgtat ccgctcatga attaattccg ctagatgacg 5280
tgcggcttcg acctcctggg cgtggcgctt gttggcgcgc tcgcggctgg ctgcggcacg 5340
acacgcgtct gagcagtatt ttgcgcgccg tcctcgtggg tcaggccggg gtgggatcag 5400
gccaccgcag taggcgcagc tgatgcgatc ctccactact gcgcgtcctc ctggcgctgc 5460
cgagcacgca gctcgtcggc cagctcttca aggtcggcca caagcgtttc taggtcgctc 5520
gcggcacttg cccagtcgcg tgatgctggc gcgtctgtcg tatcgagggc gcggaaaaat 5580
ccgatcaccg tttttaaatc gacggcggca tcgagtgcgt cggactccag cgcgacatcg 5640
gagagatcca ccgctgatgc ttcaggccag ttttggtact tcgtcgtgaa ggtcatgaca 5700
ccattataac gaacgttcgt taaaaattct agccccaatt ctgataattt cttccggcac 5760
tcctgcgaaa acctgcgaga cttcttgccc agaaaaaacg ccaagcgcag cggttaccgc 5820
actttttttc caggtgattt caccctgacc agcgaagcgg cactttagtg catgaggtgt 5880
gcccctggtt tcccctcttt ggagggttca acccaaaaaa gcacacaagc aaaaatgaaa 5940
atcatcatga gcaagttggt gcgaagcagc aacgcgctag ctccaaaaag gtctccagga 6000
tctcgaggag atttttgagg gggagggagt cgaggaagag ccagagcaga aggcggggaa 6060
ccgttctctg ccgacagcgt gagcccccct taaaaatcag gccggggagg aaccggggag 6120

```
ggatcagagc taggagcgag acaccctaaa ggggggggaac cgttttctgc tgacggtgtt   6180
tcgtttatta gttttcagcc cgtggatagc ggagggtgag ggcaagtgag agccagagca   6240
aggacgggac ccctaaaggg gggaaccgtt ttctgctgac ggtgtttcgt ttattagttt   6300
tcagcccgtg gacggccgcg tttagcttcc attccaagtg cctttctgac ttgttggatg   6360
cgcctttcac tgacacctag ttcgcctgca agctcacgag tcgagggatc agcaaccgat   6420
tgagaacggg catccaggat cgcagttttg acgcgaagtt cgagcaactc gcctgtcatt   6480
tctcggcgtt tgtttgcttc cgctaatcgc tgtcgcgtct cctgcgcata cttactttct   6540
gggtcagccc atctgcgtgc attcgatgta gctgcgcccc gtcgccccat cgtcgctaga   6600
gctttccgcc ctcggctgct ctgcgtttcc acccgacgag cagggacgac tggctggcct   6660
ttagccacgt agccgcgcac acgacgcgcc atcgtcaggc gatcacgcat ggcgggaaga   6720
tccggctccc ggccgtctgc accgaccgcc tgggcaacgt tgtacgccac ttcatacgcg   6780
tcgatgatct tggcatcttt taggcgctca ccagcagctt tgagctggta tcccacggtc   6840
aacgcgtggc gaaacgcggt ctcgtcgcgc gctcgctctg gatttgtcca gagcactcgc   6900
acgccgtcga tcaggtcgcc ggacgcgtcc agggcgctcg gcaggctcgc gtccaaaatc   6960
gctagcgcct tggcttctgc ggtggcgcgt tgtgccgctt caatgcgggc gcgtccgctg   7020
gaaaagtcct gctcaatgta ctttttcggc ttctgtgatc cggtcatcgt tcgagcaatc   7080
tccattaggt cggccagccg atccacacga tcatgctggc agtgccattt ataggctgtc   7140
ggatcgtctg agacgtgcag cggccaccgg ctcagcctat gcgaaaaagc ctggtcagcg   7200
ccgaaaacac gagtcatttc ttccgtcgtt gcagccagca ggcgcatatt tgggctggtt   7260
ttacctgctg cggcatacac cgggtcaatg agccagatga gctggcattt cccgctcagc   7320
ggattcacgc cgatccaagc cggcgctttt tctaggcgtg cccatttctc taaaatcgcg   7380
tagacctgcg ggtttacgtg ctcaatcttc ccgccggcct ggtggctggg cacatcgatg   7440
tcaagcacga tcaccgcggc atgttgcgcg tgcgtcagcg caacgtactg gcaccgcgtc   7500
agcgcttttg agccagcccg gtagagcttt ggttgggttt cgccggtatc cgggttttta   7560
atccaggcgc tcgcgaaatc tcttgtcttg ctgccctgga agctttcgcg tcccaggtga   7620
gcgagcagtt cgcggcgatc ttctgccgtc cagccgcgtg agccgcagcg catagcttcg   7680
gggtgggtgt cgaacagatc ggcggacaat ttccacgcgc tagctgtgac tgtgtcctgc   7740
ggatcggcta gagtcatgtc ttgagtgctt tctcccagct gatgactggg ggttagccga   7800
cgccctgtga gttcccgctc acggggcgtt caactttttc aggtatttgt gcagcttatc   7860
gtgttttctt cgtaaatgaa cgcttaacta ccttgttaaa cgtggcaaat aggcaggatt   7920
gatggggatc tagcttcacg ctgccgcaag cactcagggc gcaagggctg ctaaaggaag   7980
cggaacacgt agaaagccag tccgcagaaa cggtgctgac cccggatgaa tgtcagctac   8040
tgggctatct ggacaaggga aaacgcaagc gcaaagagaa agcaggtagc ttgcagtggg   8100
cttacatggc gatagctaga ctgggcggtt ttatggacag caagcgaacc ggaattgcca   8160
gctggggcgc cctctggtaa ggttgggaag ccctgcaaag taaactggat ggctttcttg   8220
ccgccaagga tctgatggcg caggggatca agatctgatc aagagacagg atgaggatcg   8280
tttcgcatga ttgaacaaga tggattgcac gcaggttctc cggccgcttg ggtggagagg   8340
ctattcggct atgactgggc acaacagaca atcggctgct ctgatgccgc cgtgttccgg   8400
ctgtcagcgc aggggcgccc ggttcttttt gtcaagaccg acctgtccgg tgccctgaat   8460
gaactccaag acgaggcagc gcggctatcg tggctggcca cgacgggcgt tccttgcgca   8520
```

gctgtgctcg acgttgtcac tgaagcggga agggactggc tgctattggg cgaagtgccg 8580
gggcaggatc tcctgtcatc tcaccttgct cctgccgaga aagtatccat catggctgat 8640
gcaatgcggc ggctgcatac gcttgatccg gctacctgcc cattcgacca ccaagcgaaa 8700
catcgcatcg agcgagcacg tactcggatg gaagccggtc ttgtcgatca ggatgatctg 8760
gacgaagagc atcaggggct cgcgccagcc gaactgttcg ccaggctcaa ggcgcggatg 8820
cccgacggcg aggatctcgt cgtgacccat ggcgatgcct gcttgccgaa tatcatggtg 8880
gaaaatggcc gcttttctgg attcatcgac tgtggccggc tgggtgtggc ggaccgctat 8940
caggacatag cgttggctac ccgtgatatt gctgaagagc ttggcggcga atgggctgac 9000
cgcttcctcg tgctttacgg tatcgccgct cccgattcgc agcgcatcgc cttctatcgc 9060
cttcttgacg agttcttctg agcgggactc tggggttcgc ggaatcatga ccaaaatccc 9120
ttaacgtgag ttttcgttcc actgagcgtc agaccccgta gaaaagatca aaggatcttc 9180
ttgagatcct ttttttctgc gcgtaatctg ctgcttgcaa acaaaaaaac caccgctacc 9240
agcggtggtt tgtttgccgg atcaagagct accaactctt tttccgaagg taactggctt 9300
cagcagagcg cagataccaa atactgtcct tctagtgtag ccgtagttag gccaccactt 9360
caagaactct gtagcaccgc ctacatacct cgctctgcta atcctgttac cagtggctgc 9420
tgccagtggc gataagtcgt gtcttaccgg gttggactca agacgatagt taccggataa 9480
ggcgcagcgg tcgggctgaa cggggggttc gtgcacacag cccagcttgg agcgaacgac 9540
ctacaccgaa ctgagatacc tacagcgtga gctatgagaa agcgccacgc ttcccgaagg 9600
gagaaaggcg gacaggtatc cggtaagcgg cagggtcgga acaggagagc gcacgaggga 9660
gcttccaggg ggaaacgcct ggtatcttta tagtcctgtc gggtttcgcc acctctgact 9720
tgagcgtcga tttttgtgat gctcgtcagg ggggcggagc ctatggaaaa acgccagcaa 9780
cgcggccttt ttacggttcc tggccttttg ctggcctttt gctcacatgt tctttcctgc 9840
gttatcccct gattctgtgg ataaccgtat taccgccttt gagtgagctg ataccgctcg 9900
ccgcagccga acgaccgagc gcagcgagtc agtgagcgag gaagcggaag agcgcctgat 9960
gcggtatttt ctccttacgc atctgtgcgg tatttcacac cgcatatggt gcactctcag 10020
tacaatctgc tctgatgccg catagttaag ccagtataca ctccgctatc gctacgtgac 10080
tgggtcatgg ctgcgccccg acacccgcca acacccgctg acgcgccctg acgggcttgt 10140
ctgctcccgg catccgctta cagacaagct gtgaccgtct ccgggagctg catgtgtcag 10200
aggttttcac cgtcatcacc gaaacgcgcg aggcagcaga tcaattcgcg cgcgaaggcg 10260
aagcggcatg catttacgtt gacaccatcg aatggtgcaa aacctttcgc ggtatggcat 10320
gatagcgccc ggaagagagt caattcaggg tggtgaatgt gaaaccagta acgttatacg 10380
atgtcgcaga gtatgccggt gtctcttatc agaccgtttc ccgcgtggtg aaccaggcca 10440
gccacgtttc tgcgaaaacg cgggaaaaag tggaagcggc gatggcggag ctgaattaca 10500
ttcccaaccg cgtggcacaa caactggcgg gcaaacagtc gttgctgatt ggcgttgcca 10560
cctccagtct ggccctgcac gcgccgtcgc aaattgtcgc ggcgattaaa tctcgcgccg 10620
atcaactggg tgccagcgtg gtggtgtcga tggtagaacg aagcggcgtc gaagcctgta 10680
aagcggcggt gcacaatctt ctcgcgcaac gcgtcagtgg gctgatcatt aactatccgc 10740
tggatgacca ggatgccatt gctgtggaag ctgcctgcac taatgttccg gcgttatttc 10800
ttgatgtctc tgaccagaca cccatcaaca gtattatttt ctcccatgaa gacggtacgc 10860

-continued gactgggcgt ggagcatctg gtcgcattgg gtcaccagca aatcgcgctg ttagcgggcc 10920
cattaagttc tgtctcggcg cgtctgcgtc tggctggctg gcataaatat ctcactcgca 10980
atcaaattca gccgatagcg gaacgggaag gcgactggag tgccatgtcc ggttttcaac 11040
aaaccatgca aatgctgaat gagggcatcg ttcccactgc gatgctggtt gccaacgatc 11100
agatggcgct gggcgcaatg cgcgccatta ccgagtccgg gctgcgcgtt ggtgcggata 11160
tctcggtagt gggatacgac gataccgaag acagctcatg ttatatcccg ccgtcaacca 11220
ccatcaaaca ggattttcgc ctgctggggc aaaccagcgt ggaccgcttg ctgcaactct 11280
ctcagggcca ggcggtgaag ggcaatcagc tgttgcccgt ctcactggtg aaaagaaaaa 11340
ccaccctggc gcccaatacg caaaccgcct ctccccgcgc gttggccgat tcattaatgc 11400
agctggcacg acaggtttcc cgactggaaa gcgggcagtg agcgcaacgc aattaatgtg 11460
agttagcgcg aattgatctg gtttgacagc ttatcat 11497

<210> SEQ ID NO 22
<211> LENGTH: 4494
<212> TYPE: DNA
<213> ORGANISM: Artificial Sequence
<220> FEATURE:
<223> OTHER INFORMATION: operon RiPKS-At4CL-RcTAL

<400> SEQUENCE: 22
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatggcacc 1200
acaggaacag gcagtctccc aggttatgga aaagcagtcc aacaacaaca actccgatgt 1260
tatcttccgc tccaagttgc ctgacatcta catcccaaac catctgtccc tgcacgatta 1320
cattttccag aacatctccg aatttgctac taagccatgc ctgatcaacg gcccaaccgg 1380
tcacgtgtac acctactctg acgtccacgt gatcagccgc cagatcgcag ctaacttcca 1440

-continued

```
caagctgggc gtgaaccaga acgacgtagt gatgctgctg ctccctaact gccctgagtt   1500
cgtcctgtcc ttcctggccg cctccttccg cggtgcaacc gcgaccgcgg ccaacccatt   1560
cttcacgcca gcagagatcg ctaagcaggc taaggcttct aacaccaagc tgatcatcac   1620
cgaagcgcgc tacgtggaca agatcaagcc actccagaac gacgatggcg ttgtgatcgt   1680
gtgcatcgac gacaacgagt ccgttccaat cccagagggc tgtctgaggt tcaccgagct   1740
gacccaatcg accaccgaag cgtccgaggt tatcgactcc gttgaaatct cccctgacga   1800
tgtcgtcgcc ctgccatact ccagcggcac caccggcttg ccaaagggtg tgatgctgac   1860
ccacaaggga ctcgttacct ccgtggcaca gcaggtcgat ggtgaaaacc ccaacctgta   1920
cttccattcc gatgacgtca tcctgtgcgt cctgccgatg ttccacatct acgctctgaa   1980
ctccatcatg ctgtgcggcc tccgcgtcgg tgcagcaatc ctgatcatgc caaagttcga   2040
aatcaacctg ctgctggagt tgatccagcg ctgcaaggtg accgtggcac ccatggtgcc   2100
cccgatcgtg ctggcaatcg cgaagtccag cgaaaccgaa aagtacgacc tgtcatccat   2160
ccgcgtcgtc aagtcgggcg ccgcaccact cggcaaggag ctggaggacg ctgtcaacgc   2220
taagttccct aacgcgaagc tcggccaggg ctacggtatg accgaggccg gcccagtcct   2280
ggccatgtcc ctgggcttcg caaaggagcc attcccggtg aagtccggcg catgcggcac   2340
cgttgtgcgc aacgcagaga tgaagatcgt tgacccagat accggtgact ccctgtcccg   2400
taaccagccc ggcgagatct gcatccgcgg ccaccagatc atgaagggct acctgaacaa   2460
ccctgctgct accgccgaaa ccatcgataa ggatggctgg ctccacaccg gcgacatcgg   2520
tctgatcgac gacgacgatg aactgttcat cgtcgatcgc cttaaggagt tgatcaagta   2580
caagggcttc caggtggccc ccgcagaact ggaagcactg ctcatcggcc accctgatat   2640
caccgatgtc gccgtcgtgg ccatgaagga ggaagcagca ggcgaagtgc cagtcgcttt   2700
cgtggtgaag tccaaggatt ccgagttgtc cgaggatgat gtgaagcagt tcgtgtccaa   2760
gcaggtcgtg ttctacaagc gcatcaacaa ggtgttcttc accgaatcca tcccaaaggc   2820
accatccggc aagatcctgc gcaaggacct gcgcgctaag ctggctaacg gcctgtaagg   2880
atctaggagg ataaagaaat gaccctgcaa tcccagactg caaaggactg cctggcgctg   2940
gatggtgcac tgacactggt tcagtgcgaa gcaattgcca ctcaccgctc acggatctcc   3000
gtcacaccag cattgcggga acgctgcgcc cgcgcgcacg cacgtctgga gcacgctatc   3060
gcagaacagc gtcacatcta tggtatcacc accggcttcg gaccactggc taatcgcctg   3120
atcggtgcag atcagggcgc cgaactccag cagaacctca tctaccacct tgctactggc   3180
gtgggcccaa aactctcctg ggctgaagca cgtgcactca tgctggctcg tctcaactcc   3240
atccttcagg gcgcatctgg tgcatcacca gaaaccatcg accgtatcgt tgccgttctg   3300
aacgctggct tcgccccaga agtcccagct cagggcaccg ttggtgcatc tggcgatctg   3360
accccactgg ctcacatggt gctggcgctt cagggtcgag gtcgtatgat cgatccatcc   3420
ggccgtgttc aggaagccgg cgcagtgatg gatcgcctgt gcggtggccc actgaccttg   3480
gcagcccgtg acggtctggc tctggtcaac ggtacttccg ctatgaccgc aatcgctgct   3540
ttgaccggtg tggaggctgc gcgcgcaatc gacgccgcat tgcgccactc cgctgtgctc   3600
atggaggttc tctccggcca cgctgaggct tggcaccctg catttgctga actccgccca   3660
cacccaggcc agctgcgcgc aaccgaacgt ctggcccagg ctctcgatgg cgccggtcgc   3720
gtttgccgca ccttgaccgc ggcccgtcgc ctgaccgcag ctgatctgcg ccctgaggat   3780
```

cacccagccc aggacgccta ctccctgcgc gtggtgccac agctggttgg cgctgtctgg 3840
gacaccctcg attggcacga tcgcgtcgtg acctgcgaac tcaactctgt gaccgacaac 3900
ccaatcttcc cggaaggctg cgctgttcca gcactgcacg gcggcaactt catgggcgtg 3960
cacgtcgcac tggcgtcgga cgccctgaac gctgcattgg ttaccctggc aggtctggtg 4020
gagcgccaga tcgcacgcct tactgatgag aagctgaaca agggacttcc ggcattcctt 4080
cacggtggtc aggctggcct tcagtccggc ttcatgggcg cgcaggtcac cgcaaccgcg 4140
ctccttgctg aaatgcgcgc aaacgcaacc ccggtgtctg ttcagtcact gtctaccaac 4200
ggcgctaacc aggatgttgt cagcatgggc accatcgctg cacgccgcgc tcgcgcacag 4260
ctgctcccac tgtcccagat tcaggcaatc ctggctctcg ctctcgccca ggcaatggat 4320
ctgctggatg atccagaggg ccaggctggc tggtccctta ccgcacgcga cctgcgcgat 4380
cgcatccgcg ctgtctcgcc gggcctgcgc gcagatcgcc cactggccgg ccacatcgag 4440
gcagtcgctc agggtctgcg ccacccttcc gcagcagctg atccaccagc ataa 4494

<210> SEQ ID NO 23
<211> LENGTH: 11422
<212> TYPE: DNA
<213> ORGANISM: Artificial Sequence
<220> FEATURE:
<223> OTHER INFORMATION: plasmid RiPKS-At4CL-FjTAL-pECXK (pECXK_B)

<400> SEQUENCE: 23
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380

-continued

```
tcagatctcc aagtccctgc tgatcctggc atggttcctc ttctccctgg tgtaaggatc   1440
taggaggatt atgagatggc accacaggaa caggcagtct cccaggttat ggaaaagcag   1500
tccaacaaca acaactccga tgttatcttc cgctccaagt tgcctgacat ctacatccca   1560
aaccatctgt ccctgcacga ttacattttc cagaacatct ccgaatttgc tactaagcca   1620
tgcctgatca acggcccaac cggtcacgtg tacacctact ctgacgtcca cgtgatcagc   1680
cgccagatcg cagctaactt ccacaagctg ggcgtgaacc agaacgacgt agtgatgctg   1740
ctgctcccta actgccctga gttcgtcctg tccttcctgg ccgcctcctt ccgcggtgca   1800
accgcgaccg cggccaaccc attcttcacg ccagcagaga tcgctaagca ggctaaggct   1860
tctaacacca agctgatcat caccgaagcg cgctacgtgg acaagatcaa gccactccag   1920
aacgacgatg gcgttgtgat cgtgtgcatc gacgacaacg agtccgttcc aatcccagag   1980
ggctgtctga ggttcaccga gctgacccaa tcgaccaccg aagcgtccga ggttatcgac   2040
tccgttgaaa tctcccctga cgatgtcgtc gccctgccat actccagcgg caccaccggc   2100
ttgccaaagg gtgtgatgct gacccacaag ggactcgtta cctccgtggc acagcaggtc   2160
gatggtgaaa accccaacct gtacttccat tccgatgacg tcatcctgtg cgtcctgccg   2220
atgttccaca tctacgctct gaactccatc atgctgtgcg gcctccgcgt cggtgcagca   2280
atcctgatca tgccaaagtt cgaaatcaac ctgctgctgg agttgatcca gcgctgcaag   2340
gtgaccgtgg cacccatggt gcccccgatc gtgctggcaa tcgcgaagtc cagcgaaacc   2400
gaaaagtacg acctgtcatc catccgcgtc gtcaagtcgg gcgccgcacc actcggcaag   2460
gagctggagg acgctgtcaa cgctaagttc cctaacgcga agctcggcca gggctacggt   2520
atgaccgagg ccggcccagt cctggccatg tccctgggct tcgcaaagga gccattcccg   2580
gtgaagtccg gcgcatgcgg caccgttgtg cgcaacgcag agatgaagat cgttgaccca   2640
gataccggtg actccctgtc ccgtaaccag cccggcgaga tctgcatccg cggccaccag   2700
atcatgaagg gctacctgaa caaccctgct gctaccgccg aaaccatcga taaggatggc   2760
tggctccaca ccggcgacat cggtctgatc gacgacgacg atgaactgtt catcgtcgat   2820
cgccttaagg agttgatcaa gtacaagggc ttccaggtgg cccccgcaga actggaagca   2880
ctgctcatcg gccaccctga tatcaccgat gtcgccgtcg tggccatgaa ggaggaagca   2940
gcaggcgaag tgccagtcgc tttcgtggtg aagtccaagg attccgagtt gtccgaggat   3000
gatgtgaagc agttcgtgtc caagcaggtc gtgttctaca agcgcatcaa caaggtgttc   3060
ttcaccgaat ccatcccaaa ggcaccatcc ggcaagatcc tgcgcaagga cctgcgcgct   3120
aagctggcta acggcctgta aggatctagg aggataaaga aatgaacacc atcaacgaat   3180
acctgtccct ggaagagttc gaagcgatca tcttcggtaa ccagaaggtt accatctccg   3240
atgtggttgt gaaccgtgtt aacgagtcct tcaacttcct caaggagttc tccggcaaca   3300
aggtcatcta cggtgtgaac accggcttcg gcccaatggc acaataccgt attaaggaat   3360
ccgatcagat ccagcttcag tacaatctga tccgttccca ctcttcgggc accggaaaac   3420
cactctcccc agtttgtgct aaggcagcaa tcttggctcg cctgaacacc ctgtccctcg   3480
gtaactccgg cgtgcatcca tctgtcatca acctgatgtc ggaactgatc aacaaagaca   3540
ttaccccact catcttcgag cacggtggcg tcggagcatc cggtgacctg gttcagcttt   3600
ctcacctggc tttggttctc atcggcgaag gcgaagtgtt ctacaagggt gaacgccgcc   3660
caactccaga agttttcgaa attgagggct tgaagccaat ccaggttgag atccgtgagg   3720
```

gcctcgcctt gattaacggt actagcgtga tgaccggtat tggagtggtc aacgtgtacc 3780
acgcaaagaa gctgctggac tggtccctga agtcctcctg cgccatcaat gaacttgttc 3840
aggcttacga tgatcacttc agcgcagagc tgaaccagac gaagcgccac aagggccagc 3900
aggaaatcgc tctgaagatg cgtcagaacc tctctgacag caccctgatc cgcaagcgcg 3960
aggaccacct gtattccggc gaaaacaccg aggagatttt caaggagaag gtgcaggagt 4020
actactccct gcgctgcgtt ccacagattc tcggcccggt cctcgaaact atcaataacg 4080
tcgcctccat cctggaagat gagttcaact ccgctaacga taacccaatc atcgacgtga 4140
agaaccagca cgtgtaccat ggcggcaact tccacggtga ctacatctct ctggaaatgg 4200
acaagttgaa aatcgttatc accaaactga ccatgcttgc agaacgccag cttaactatc 4260
ttctcaactc caagatcaac gaacttctgc caccattcgt gaacctcggc accctgggtt 4320
tcaacttcgg catgcagggc gttcagttca ccgcgacctc caccaccgca gaatctcaga 4380
tgctgtccaa ccctatgtac gttcactcca ttccaaacaa caacgataac caggacatcg 4440
tctccatggg caccaactcc gcagtgatca cgtccaaggt tatcgagaac gctttcgaag 4500
tcctggctat cgaaatgatc accatcgttc aggccatcga ttacctcggc cagaaggata 4560
agatctcctc cgtttccaag aagtggtacg atgaaatccg caacattatc cctaccttca 4620
aggaggatca ggttatgtac cccattcgtgc agaaggttaa ggatcacctc atcaacaact 4680
aactctagag tcgacctgca ggcatgcaag cttggctgtt ttggcggatg agagaagatt 4740
ttcagcctga tacagattaa atcagaacgc agaagcggtc tgataaaaca gaatttgcct 4800
ggcggcagta gcgcggtggt cccacctgac cccatgccga actcagaagt gaaacgccgt 4860
agcgccgatg gtagtgtggg gtctccccat gcgagagtag ggaactgcca ggcatcaaat 4920
aaaacgaaag gctcagtcga aagactgggc ctttcgtttt atctgttgtt tgtcggtgaa 4980
cgctctcctg agtaggacaa atccgccggg agcggatttg aacgttgcga agcaacggcc 5040
cggagggtgg cgggcaggac gcccgccata aactgccagg catcaaatta agcagaaggc 5100
catcctgacg gatggccttt ttgcgtttct acaaactctt tttgtttatt tttctaaata 5160
cattcaaata tgtatccgct catgaattaa ttccgctaga tgacgtgcgg cttcgacctc 5220
ctgggcgtgg cgcttgttgg cgcgctcgcg gctggctgcg gcacgacacg cgtctgagca 5280
gtattttgcg cgccgtcctc gtgggtcagg ccggggtggg atcaggccac cgcagtaggc 5340
gcagctgatg cgatcctcca ctactgcgcg tcctcctggc gctgccgagc acgcagctcg 5400
tcggccagct cttcaaggtc ggccacaagc gtttctaggt cgctcgcggc acttgcccag 5460
tcgcgtgatg ctggcgcgtc tgtcgtatcg agggcgcgga aaaatccgat caccgttttt 5520
aaatcgacgg cggcatcgag tgcgtcggac tccagcgcga catcggagag atccaccgct 5580
gatgcttcag gccagttttg gtacttcgtc gtgaaggtca tgacaccatt ataacgaacg 5640
ttcgttaaaa attctagccc caattctgat aatttcttcc ggcactcctg cgaaaacctg 5700
cgagacttct tgcccagaaa aaacgccaag cgcagcggtt accgcacttt ttttccaggt 5760
gatttcaccc tgaccagcga agcggcactt tagtgcatga ggtgtgcccc tggtttcccc 5820
tctttggagg gttcaaccca aaaaagcaca caagcaaaaa tgaaaatcat catgagcaag 5880
ttggtgcgaa gcagcaacgc gctagctcca aaaaggtctc caggatctcg aggagatttt 5940
tgagggggag ggagtcgagg aagagccaga gcagaaggcg gggaaccgtt ctctgccgac 6000
agcgtgagcc ccccttaaaa atcaggccgg ggaggaaccg gggagggatc agagctagga 6060
gcgagacacc ctaaaggggg ggaaccgttt tctgctgacg gtgtttcgtt tattagtttt 6120

-continued

```
cagcccgtgg atagcggagg gtgagggcaa gtgagagcca gagcaaggac gggaccccta   6180
aagggggggaa ccgttttctg ctgacggtgt ttcgtttatt agttttcagc ccgtggacgg   6240
ccgcgtttag cttccattcc aagtgccttt ctgacttgtt ggatgcgcct ttcactgaca   6300
cctagttcgc ctgcaagctc acgagtcgag ggatcagcaa ccgattgaga acgggcatcc   6360
aggatcgcag ttttgacgcg aagttcgagc aactcgcctg tcatttctcg gcgtttgttt   6420
gcttccgcta atcgctgtcg cgtctcctgc gcatacttac tttctgggtc agcccatctg   6480
cgtgcattcg atgtagctgc gccccgtcgc cccatcgtcg ctagagcttt ccgccctcgg   6540
ctgctctgcg tttccacccg acgagcaggg acgactggct ggcctttagc cacgtagccg   6600
cgcacacgac gcgccatcgt caggcgatca cgcatggcgg gaagatccgg ctcccggccg   6660
tctgcaccga ccgcctgggc aacgttgtac gccacttcat acgcgtcgat gatcttggca   6720
tcttttaggc gctcaccagc agctttgagc tggtatccca cggtcaacgc gtggcgaaac   6780
gcggtctcgt cgcgcgctcg ctctggattt gtccagagca ctcgcacgcc gtcgatcagg   6840
tcgccggacg cgtccagggc gctcggcagg ctcgcgtcca aaatcgctag cgccttggct   6900
tctgcggtgg cgcgttgtgc cgcttcaatg cgggcgcgtc cgctggaaaa gtcctgctca   6960
atgtactttt tcggcttctg tgatccggtc atcgttcgag caatctccat taggtcggcc   7020
agccgatcca cacgatcatg ctggcagtgc catttatagg ctgtcggatc gtctgagacg   7080
tgcagcggcc accggctcag cctatgcgaa aaagcctggt cagcgccgaa aacacgagtc   7140
atttcttccg tcgttgcagc cagcaggcgc atatttgggc tggttttacc tgctgcggca   7200
tacaccgggt caatgagcca gatgagctgg catttcccgc tcagcggatt cacgccgatc   7260
caagccggcg ctttttctag gcgtgcccat ttctctaaaa tcgcgtagac ctgcgggttt   7320
acgtgctcaa tcttcccgcc ggcctggtgg ctgggcacat cgatgtcaag cacgatcacc   7380
gcggcatgtt gcgcgtgcgt cagcgcaacg tactggcacc gcgtcagcgc ttttgagcca   7440
gcccggtaga gctttggttg ggtttcgccg gtatccgggt ttttaatcca ggcgctcgcg   7500
aaatctcttg tcttgctgcc ctggaagctt tcgcgtccca ggtgagcgag cagttcgcgg   7560
cgatcttctg ccgtccagcc gcgtgagccg cagcgcatag cttcggggtg ggtgtcgaac   7620
agatcggcgg acaatttcca cgcgctagct gtgactgtgt cctgcggatc ggctagagtc   7680
atgtcttgag tgctttctcc cagctgatga ctgggggtta gccgacgccc tgtgagttcc   7740
cgctcacggg gcgttcaact ttttcaggta tttgtgcagc ttatcgtgtt ttcttcgtaa   7800
atgaacgctt aactaccttg ttaaacgtgg caaataggca ggattgatgg ggatctagct   7860
tcacgctgcc gcaagcactc agggcgcaag ggctgctaaa ggaagcggaa cacgtagaaa   7920
gccagtccgc agaaacggtg ctgaccccgg atgaatgtca gctactgggc tatctggaca   7980
agggaaaacg caagcgcaaa gagaaagcag gtagcttgca gtgggcttac atggcgatag   8040
ctagactggg cggttttatg gacagcaagc gaaccggaat tgccagctgg ggcgccctct   8100
ggtaaggttg ggaagccctg caaagtaaac tggatggctt tcttgccgcc aaggatctga   8160
tggcgcaggg gatcaagatc tgatcaagag acaggatgag gatcgtttcg catgattgaa   8220
caagatggat tgcacgcagg ttctccggcc gcttgggtgg agaggctatt cggctatgac   8280
tgggcacaac agacaatcgg ctgctctgat gccgccgtgt tccggctgtc agcgcagggg   8340
cgcccggttc tttttgtcaa gaccgacctg tccggtgccc tgaatgaact ccaagacgag   8400
gcagcgcggc tatcgtggct ggccacgacg ggcgttcctt gcgcagctgt gctcgacgtt   8460
```

-continued gtcactgaag cgggaaggga ctggctgcta ttgggcgaag tgccggggca ggatctcctg 8520
tcatctcacc ttgctcctgc cgagaaagta tccatcatgg ctgatgcaat gcggcggctg 8580
catacgcttg atccggctac ctgcccattc gaccaccaag cgaaacatcg catcgagcga 8640
gcacgtactc ggatggaagc cggtcttgtc gatcaggatg atctggacga agagcatcag 8700
gggctcgcgc cagccgaact gttcgccagg ctcaaggcgc ggatgcccga cggcgaggat 8760
ctcgtcgtga cccatggcga tgcctgcttg ccgaatatca tggtggaaaa tggccgcttt 8820
tctggattca tcgactgtgg ccggctgggt gtggcggacc gctatcagga catagcgttg 8880
gctacccgtg atattgctga agagcttggc ggcgaatggg ctgaccgctt cctcgtgctt 8940
tacggtatcg ccgctcccga ttcgcagcgc atcgccttct atcgccttct tgacgagttc 9000
ttctgagcgg gactctgggg ttcgcggaat catgaccaaa atcccttaac gtgagttttc 9060
gttccactga gcgtcagacc ccgtagaaaa gatcaaagga tcttcttgag atcctttttt 9120
tctgcgcgta atctgctgct tgcaaacaaa aaaaccaccg ctaccagcgg tggtttgttt 9180
gccggatcaa gagctaccaa ctctttttcc gaaggtaact ggcttcagca gagcgcagat 9240
accaaatact gtccttctag tgtagccgta gttaggccac cacttcaaga actctgtagc 9300
accgcctaca tacctcgctc tgctaatcct gttaccagtg gctgctgcca gtggcgataa 9360
gtcgtgtctt accgggttgg actcaagacg atagttaccg gataaggcgc agcggtcggg 9420
ctgaacgggg ggttcgtgca cacagcccag cttggagcga acgacctaca ccgaactgag 9480
atacctacag cgtgagctat gagaaagcgc cacgcttccc gaagggagaa aggcggacag 9540
gtatccggta agcggcaggg tcggaacagg agagcgcacg agggagcttc caggggggaaa 9600 cgcctggtat ctttatagtc ctgtcgggtt tcgccacctc tgacttgagc gtcgattttt 9660
gtgatgctcg tcaggggggc ggagcctatg gaaaaacgcc agcaacgcgg cctttttacg 9720
gttcctggcc ttttgctggc cttttgctca catgttcttt cctgcgttat cccctgattc 9780
tgtggataac cgtattaccg cctttgagtg agctgatacc gctcgccgca gccgaacgac 9840
cgagcgcagc gagtcagtga gcgaggaagc ggaagagcgc ctgatgcggt attttctcct 9900
tacgcatctg tgcggtattt cacaccgcat atggtgcact ctcagtacaa tctgctctga 9960
tgccgcatag ttaagccagt atacactccg ctatcgctac gtgactgggt catggctgcg 10020
ccccgacacc cgccaacacc cgctgacgcg ccctgacggg cttgtctgct cccggcatcc 10080
gcttacagac aagctgtgac cgtctccggg agctgcatgt gtcagaggtt ttcaccgtca 10140
tcaccgaaac gcgcgaggca gcagatcaat tcgcgcgcga aggcgaagcg gcatgcattt 10200
acgttgacac catcgaatgg tgcaaaacct ttcgcggtat ggcatgatag cgcccggaag 10260
agagtcaatt cagggtggtg aatgtgaaac cagtaacgtt atacgatgtc gcagagtatg 10320
ccggtgtctc ttatcagacc gtttcccgcg tggtgaacca ggccagccac gtttctgcga 10380
aaacgcggga aaaagtggaa gcggcgatgg cggagctgaa ttacattccc aaccgcgtgg 10440
cacaacaact ggcgggcaaa cagtcgttgc tgattggcgt tgccacctcc agtctggccc 10500
tgcacgcgcc gtcgcaaatt gtcgcggcga ttaaatctcg cgccgatcaa ctgggtgcca 10560
gcgtggtggt gtcgatggta gaacgaagcg gcgtcgaagc ctgtaaagcg gcggtgcaca 10620
atcttctcgc gcaacgcgtc agtgggctga tcattaacta tccgctggat gaccaggatg 10680
ccattgctgt ggaagctgcc tgcactaatg ttccggcgtt atttcttgat gtctctgacc 10740
agacacccat caacagtatt attttctccc atgaagacgg tacgcgactg ggcgtggagc 10800
atctggtcgc attgggtcac cagcaaatcg cgctgttagc gggcccatta agttctgtct 10860

```
cggcgcgtct gcgtctggct ggctggcata aatatctcac tcgcaatcaa attcagccga  10920

tagcggaacg ggaaggcgac tggagtgcca tgtccggttt tcaacaaacc atgcaaatgc  10980

tgaatgaggg catcgttccc actgcgatgc tggttgccaa cgatcagatg gcgctgggcg  11040

caatgcgcgc cattaccgag tccgggctgc gcgttggtgc ggatatctcg gtagtgggat  11100

acgacgatac cgaagacagc tcatgttata tcccgccgtc aaccaccatc aaacaggatt  11160

ttcgcctgct ggggcaaacc agcgtggacc gcttgctgca actctctcag ggccaggcgg  11220

tgaagggcaa tcagctgttg cccgtctcac tggtgaaaag aaaaaccacc ctggcgccca  11280

atacgcaaac cgcctctccc cgcgcgttgg ccgattcatt aatgcagctg gcacgacagg  11340

tttcccgact ggaaagcggg cagtgagcgc aacgcaatta atgtgagtta gcgcgaattg  11400

atctggtttg acagcttatc at                                          11422
```

```
<210> SEQ ID NO 24
<211> LENGTH: 4419
<212> TYPE: DNA
<213> ORGANISM: Artificial Sequence
<220> FEATURE:
<223> OTHER INFORMATION: operon RiPKS-At4CL-FjTAL

<400> SEQUENCE: 24

ggatctagga gggagatcat atggttaccg ttgaagaagt ccgcaaggct cagcgcgcag     60

aaggccctgc aaccgttctg gcaatcggca ccgcaacccc accaaactgc gtcggccagt    120

ccacctaccc agattattat ttccgtatca ccaactctga acacaagatt gaactgaagc    180

agaagttcca gaggatgtgc gataagtcca tgatcaagaa gcgttacatg taccttaccg    240

aagagatcct gaaggagaac ccatccatgt gcgagtacat ggctccatcc cttgatgctc    300

gccaggacat ggtcatcgtg gaaatcccaa agctgggcaa ggaagcagcc accaaggcaa    360

tcaaggagtg gggccagccg aagtcgaaga tcacccacct tgttttctgc accaccagcg    420

gtgtggatat gcctggcgcc gactaccagc tgatcaagct cttcggcctg cgcccatccg    480

tcaagcgcct catgatgtac cagcagggct gcttcgccgg cggcaccgtt ctgcgcctgg    540

ctaaggatct ggcagaaaac aaccgcggtg cccgcgttct cgtcgtgtgc tccgagatca    600

ccgtggtcac cttccgcggc ccatccgaca cccaccttga ctgtctggtt ggccaggcac    660

tcttcggcga tggcgtggca tccatcatcg tcggcgcaga tcctctccct gaaatcgaaa    720

agccactttt cgaacttgtc agcgcagcac agaccatcct gccagattct gagggcgcaa    780

tcgagggcca cctccgcgag gtgggtctta ccttccatct gctcgaaaac gtgccagcac    840

tgatctccaa gaacatcgaa aagtccctga acgaaacctt caagccactg gacatcatgg    900

actggaactc cctgttctgg atcgctcacc caggcggtcc ggctatcctg gatcaggtcg    960

aggctaagct gggtctgaag ccggagaagt tggaggctac cggccacatc ctgtccgaat   1020

acggcaacat gtcctccgca tgcgttctct tcatcctgga cgtggtgcgg cgcaagtccg   1080

cagccaacgg tgtgaccacc cgtatcctga gcatcggtca gatctccaag tccctgctga   1140

tcctggcatg gttcctcttc tccctggtgt aaggatctag gaggattatg agatggcacc   1200

acaggaacag gcagtctccc aggttatgga aaagcagtcc aacaacaaca actccgatgt   1260

tatcttccgc tccaagttgc ctgacatcta catcccaaac catctgtccc tgcacgatta   1320

cattttccag aacatctccg aatttgctac taagccatgc ctgatcaacg gcccaaccgg   1380

tcacgtgtac acctactctg acgtccacgt gatcagccgc cagatcgcag ctaacttcca   1440
```

```
caagctgggc gtgaaccaga acgacgtagt gatgctgctg ctccctaact gccctgagtt   1500
cgtcctgtcc ttcctggccg cctccttccg cggtgcaacc gcgaccgcgg ccaacccatt   1560
cttcacgcca gcagagatcg ctaagcaggc taaggcttct aacaccaagc tgatcatcac   1620
cgaagcgcgc tacgtggaca agatcaagcc actccagaac gacgatggcg ttgtgatcgt   1680
gtgcatcgac gacaacgagt ccgttccaat cccagagggc tgtctgaggt tcaccgagct   1740
gacccaatcg accaccgaag cgtccgaggt tatcgactcc gttgaaatct cccctgacga   1800
tgtcgtcgcc ctgccatact ccagcggcac caccggcttg ccaaagggtg tgatgctgac   1860
ccacaaggga ctcgttacct ccgtggcaca gcaggtcgat ggtgaaaacc ccaacctgta   1920
cttccattcc gatgacgtca tcctgtgcgt cctgccgatg ttccacatct acgctctgaa   1980
ctccatcatg ctgtgcggcc tccgcgtcgg tgcagcaatc ctgatcatgc caaagttcga   2040
aatcaacctg ctgctggagt tgatccagcg ctgcaaggtg accgtggcac ccatggtgcc   2100
cccgatcgtg ctggcaatcg cgaagtccag cgaaaccgaa aagtacgacc tgtcatccat   2160
ccgcgtcgtc aagtcgggcg ccgcaccact cggcaaggag ctggaggacg ctgtcaacgc   2220
taagttccct aacgcgaagc tcggccaggg ctacggtatg accgaggccg gcccagtcct   2280
ggccatgtcc ctgggcttcg caaaggagcc attcccggtg aagtccggcg catgcggcac   2340
cgttgtgcgc aacgcagaga tgaagatcgt tgacccagat accggtgact ccctgtcccg   2400
taaccagccc ggcgagatct gcatccgcgg ccaccagatc atgaagggct acctgaacaa   2460
ccctgctgct accgccgaaa ccatcgataa ggatggctgg ctccacaccg gcgacatcgg   2520
tctgatcgac gacgacgatg aactgttcat cgtcgatcgc cttaaggagt tgatcaagta   2580
caagggcttc caggtggccc ccgcagaact ggaagcactg ctcatcggcc accctgatat   2640
caccgatgtc gccgtcgtgg ccatgaagga ggaagcagca ggcgaagtgc cagtcgcttt   2700
cgtggtgaag tccaaggatt ccgagttgtc cgaggatgat gtgaagcagt tcgtgtccaa   2760
gcaggtcgtg ttctacaagc gcatcaacaa ggtgttcttc accgaatcca tcccaaaggc   2820
accatccggc aagatcctgc gcaaggacct gcgcgctaag ctggctaacg gcctgtaagg   2880
atctaggagg ataaagaaat gaacaccatc aacgaatacc tgtccctgga agagttcgaa   2940
gcgatcatct tcggtaacca gaaggttacc atctccgatg tggttgtgaa ccgtgttaac   3000
gagtccttca acttcctcaa ggagttctcc ggcaacaagg tcatctacgg tgtgaacacc   3060
ggcttcggcc caatggcaca ataccgtatt aaggaatccg atcagatcca gcttcagtac   3120
aatctgatcc gttcccactc ttcgggcacc ggaaaaccac tctccccagt ttgtgctaag   3180
gcagcaatct tggctcgcct gaacaccctg tccctcggta actccggcgt gcatccatct   3240
gtcatcaacc tgatgtcgga actgatcaac aaagacatta ccccactcat cttcgagcac   3300
ggtggcgtcg gagcatccgg tgacctggtt cagctttctc acctggcttt ggttctcatc   3360
ggcgaaggcg aagtgttcta caagggtgaa cgccgcccaa ctccagaagt tttcgaaatt   3420
gagggcttga agccaatcca ggttgagatc cgtgagggcc tcgccttgat taacggtact   3480
agcgtgatga ccggtattgg agtggtcaac gtgtaccacg caaagaagct gctggactgg   3540
tccctgaagt cctcctgcgc catcaatgaa cttgttcagg cttacgatga tcacttcagc   3600
gcagagctga accagacgaa gcgccacaag ggccagcagg aaatcgctct gaagatgcgt   3660
cagaacctct ctgacagcac cctgatccgc aagcgcgagg accacctgta ttccggcgaa   3720
aacaccgagg agattttcaa ggagaaggtg caggagtact actccctgcg ctgcgttcca   3780
cagattctcg gcccggtcct cgaaactatc aataacgtcg cctccatcct ggaagatgag   3840
```

ttcaactccg ctaacgataa cccaatcatc gacgtgaaga accagcacgt gtaccatggc 3900
ggcaacttcc acggtgacta catctctctg gaaatggaca agttgaaaat cgttatcacc 3960
aaactgacca tgcttgcaga acgccagctt aactatcttc tcaactccaa gatcaacgaa 4020
cttctgccac cattcgtgaa cctcggcacc ctgggtttca acttcggcat gcagggcgtt 4080
cagttcaccg cgacctccac caccgcagaa tctcagatgc tgtccaaccc tatgtacgtt 4140
cactccattc caaacaacaa cgataaccag gacatcgtct ccatgggcac caactccgca 4200
gtgatcacgt ccaaggttat cgagaacgct ttcgaagtcc tggctatcga aatgatcacc 4260
atcgttcagg ccatcgatta cctcggccag aaggataaga tctcctccgt ttccaagaag 4320
tggtacgatg aaatccgcaa cattatccct accttcaagg aggatcaggt tatgtaccca 4380
ttcgtgcaga aggttaagga tcacctcatc aacaactaa 4419

<210> SEQ ID NO 25
<211> LENGTH: 11434
<212> TYPE: DNA
<213> ORGANISM: Artificial Sequence
<220> FEATURE:
<223> OTHER INFORMATION: plasmid RiPKS-At4CL-SeSam8-pECXK (pECXK_C)

<400> SEQUENCE: 25
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380
tcagatctcc aagtccctgc tgatcctggc atggttcctc ttctccctgg tgtaaggatc 1440

-continued taggaggatt atgagatggc accacaggaa caggcagtct cccaggttat ggaaaagcag 1500
tccaacaaca acaactccga tgttatcttc cgctccaagt tgcctgacat ctacatccca 1560
aaccatctgt ccctgcacga ttacattttc cagaacatct ccgaatttgc tactaagcca 1620
tgcctgatca acggcccaac cggtcacgtg tacacctact ctgacgtcca cgtgatcagc 1680
cgccagatcg cagctaactt ccacaagctg ggcgtgaacc agaacgacgt agtgatgctg 1740
ctgctcccta actgccctga gttcgtcctg tccttcctgg ccgcctcctt ccgcggtgca 1800
accgcgaccg cggccaaccc attcttcacg ccagcagaga tcgctaagca ggctaaggct 1860
tctaacacca agctgatcat caccgaagcg cgctacgtgg acaagatcaa gccactccag 1920
aacgacgatg gcgttgtgat cgtgtgcatc gacgacaacg agtccgttcc aatcccagag 1980
ggctgtctga ggttcaccga gctgacccaa tcgaccaccg aagcgtccga ggttatcgac 2040
tccgttgaaa tctcccctga cgatgtcgtc gccctgccat actccagcgg caccaccggc 2100
ttgccaaagg gtgtgatgct gacccacaag ggactcgtta cctccgtggc acagcaggtc 2160
gatggtgaaa accccaacct gtacttccat tccgatgacg tcatcctgtg cgtcctgccg 2220
atgttccaca tctacgctct gaactccatc atgctgtgcg gcctccgcgt cggtgcagca 2280
atcctgatca tgccaaagtt cgaaatcaac ctgctgctgg agttgatcca gcgctgcaag 2340
gtgaccgtgg cacccatggt gcccccgatc gtgctggcaa tcgcgaagtc cagcgaaacc 2400
gaaaagtacg acctgtcatc catccgcgtc gtcaagtcgg gcgccgcacc actcggcaag 2460
gagctggagg acgctgtcaa cgctaagttc cctaacgcga agctcggcca gggctacggt 2520
atgaccgagg ccggcccagt cctggccatg tccctgggct tcgcaaagga gccattcccg 2580
gtgaagtccg gcgcatgcgg caccgttgtg cgcaacgcag agatgaagat cgttgaccca 2640
gataccggtg actccctgtc ccgtaaccag cccggcgaga tctgcatccg cggccaccag 2700
atcatgaagg gctacctgaa caaccctgct gctaccgccg aaaccatcga taaggatggc 2760
tggctccaca ccggcgacat cggtctgatc gacgacgacg atgaactgtt catcgtcgat 2820
cgccttaagg agttgatcaa gtacaagggc ttccaggtgg cccccgcaga actggaagca 2880
ctgctcatcg gccaccctga tatcaccgat gtcgccgtcg tggccatgaa ggaggaagca 2940
gcaggcgaag tgccagtcgc tttcgtggtg aagtccaagg attccgagtt gtccgaggat 3000
gatgtgaagc agttcgtgtc caagcaggtc gtgttctaca agcgcatcaa caaggtgttc 3060
ttcaccgaat ccatcccaaa ggcaccatcc ggcaagatcc tgcgcaagga cctgcgcgct 3120
aagctggcta acggcctgta aggatctagg aggataaaga aatgacccag gtcgtggagc 3180
gccaggctga tcgtctgtcc agccgcgagt acctggcacg cgttgttcgt tccgcaggct 3240
gggacgcagg cctcaccagc tgcaccgatg aagaaatcgt gcgcatgggt gcatccgcac 3300
gcaccattga ggaatacctg aagtctgata agccgatcta cggcctcacc cagggcttcg 3360
gtccactggt cctgttcgat gcagattccg aactggaaca gggcggctct ctcatctccc 3420
atctgggcac cggccagggt gcaccgcttg caccggaagt gtcccgcctg attctgtggc 3480
tccgcatcca aaacatgcgc aagggctatt cggctgtcag tcctgtgttc tggcaaaaac 3540
tggccgacct ctggaacaag ggcttcaccc ctgctatccc tcgccacggc accgtgtccg 3600
ccagcggcga tctccagcct ctggcacacg ctgccctggc ttttaccggc gtgggcgagg 3660
catggacccg tgatgcagac ggccgttggt ccaccgtgcc agccgtggac gcattagcag 3720
cactgggtgc agagccgttc gattggccag tgcgcgaggc tttggccttc gtgaacggta 3780
cgggcgcatc actcgcggtg gcagttctca accacagatc cgctctccgt ctcgtacgag 3840

```
catgtgcagt cttgtctgcc cgtttggcta ccttgctagg agctaatcct gaacactacg   3900
atgtcggcca cggagtcgca aggggacaag ttggccagct gaccgcggcg gaatggattc   3960
ggcagggact accacgcggc atggtccgag acggttcgcg ccctcttcaa gaaccataca   4020
gcttgcgctg tgccccccag gtccttggcg cggtgctgga ccagctggat ggtgcaggcg   4080
atgttctggc ccgcgaagtg gatggctgcc aggacaatcc tatcacctac gagggcgaac   4140
tgctgcacgg cggtaacttc cacgctatgc cagtcggctt cgcatccgac cagatcggtc   4200
tggcgatgca catggcagct tatctggctg aacgccagct cggcctgctg gtgagcccgg   4260
tgaccaacgg cgacctgcca ccaatgctga ccccacgcgc tggacgcggt gccggcctgg   4320
cgggcgttca gatctccgca acctccttcg tctctcgcat ccgccagctg gtgttcccag   4380
ctagcctcac caccctccca accaacggct ggaaccagga ccatgtccca atggctctga   4440
acggcgcaaa cagcgtgttc gaagctcttg aactgggttg gctgaccgtg ggtagcctgg   4500
cagtcggcgt ggcccagctc gctgcaatga ccggccacgc agctgagggc gtgtgggccg   4560
agttggcagg catctgccca ccactggatg ctgaccgccc actgggcgcg gaggtccgcg   4620
ctgctcgcga tctcctctcc gcacacgctg accagctgct cgttgacgag gctgatggca   4680
aagacttcgg ctaactctag agtcgacctg caggcatgca agcttggctg ttttggcgga   4740
tgagagaaga ttttcagcct gatacagatt aaatcagaac gcagaagcgg tctgataaaa   4800
cagaatttgc ctggcggcag tagcgcggtg gtcccacctg accccatgcc gaactcagaa   4860
gtgaaacgcc gtagcgccga tggtagtgtg gggtctcccc atgcgagagt agggaactgc   4920
caggcatcaa ataaaacgaa aggctcagtc gaaagactgg gcctttcgtt ttatctgttg   4980
tttgtcggtg aacgctctcc tgagtaggac aaatccgccg ggagcggatt tgaacgttgc   5040
gaagcaacgg cccggagggt ggcgggcagg acgcccgcca taaactgcca ggcatcaaat   5100
taagcagaag gccatcctga cggatggcct ttttgcgttt ctacaaactc tttttgttta   5160
tttttctaaa tacattcaaa tatgtatccg ctcatgaatt aattccgcta gatgacgtgc   5220
ggcttcgacc tcctgggcgt ggcgcttgtt ggcgcgctcg cggctggctg cggcacgaca   5280
cgcgtctgag cagtattttg cgcgccgtcc tcgtgggtca ggccggggtg ggatcaggcc   5340
accgcagtag gcgcagctga tgcgatcctc cactactgcg cgtcctcctg gcgctgccga   5400
gcacgcagct cgtcggccag ctcttcaagg tcggccacaa gcgtttctag gtcgctcgcg   5460
gcacttgccc agtcgcgtga tgctggcgcg tctgtcgtat cgagggcgcg gaaaaatccg   5520
atcaccgttt ttaaatcgac ggcggcatcg agtgcgtcgg actccagcgc gacatcggag   5580
agatccaccg ctgatgcttc aggccagttt tggtacttcg tcgtgaaggt catgacacca   5640
ttataacgaa cgttcgttaa aaattctagc cccaattctg ataatttctt ccggcactcc   5700
tgcgaaaacc tgcgagactt cttgcccaga aaaaacgcca agcgcagcgg ttaccgcact   5760
ttttttccag gtgatttcac cctgaccagc gaagcggcac tttagtgcat gaggtgtgcc   5820
cctggtttcc cctctttgga gggttcaacc caaaaaagca cacaagcaaa aatgaaaatc   5880
atcatgagca agttggtgcg aagcagcaac gcgctagctc caaaaaggtc tccaggatct   5940
cgaggagatt tttgaggggg agggagtcga ggaagagcca gagcagaagg cggggaaccg   6000
ttctctgccg acagcgtgag cccccgttaa aaatcaggcc ggggaggaac cggggaggga   6060
tcagagctag gagcgagaca ccctaaaggg ggggaaccgt tttctgctga cggtgtttcg   6120
tttattagtt ttcagcccgt ggatagcgga gggtgagggc aagtgagagc cagagcaagg   6180
```

-continued

```
acgggacccc taaagggggg aaccgttttc tgctgacggt gtttcgttta ttagttttca   6240
gcccgtggac ggccgcgttt agcttccatt ccaagtgcct ttctgacttg ttggatgcgc   6300
ctttcactga cacctagttc gcctgcaagc tcacgagtcg agggatcagc aaccgattga   6360
gaacgggcat ccaggatcgc agttttgacg cgaagttcga gcaactcgcc tgtcatttct   6420
cggcgtttgt ttgcttccgc taatcgctgt cgcgtctcct gcgcatactt actttctggg   6480
tcagcccatc tgcgtgcatt cgatgtagct gcgccccgtc gccccatcgt cgctagagct   6540
ttccgccctc ggctgctctg cgtttccacc cgacgagcag ggacgactgg ctggccttta   6600
gccacgtagc cgcgcacacg acgcgccatc gtcaggcgat cacgcatggc gggaagatcc   6660
ggctcccggc cgtctgcacc gaccgcctgg gcaacgttgt acgccacttc atacgcgtcg   6720
atgatcttgg catcttttag gcgctcacca gcagctttga gctggtatcc cacggtcaac   6780
gcgtggcgaa acgcggtctc gtcgcgcgct cgctctggat ttgtccagag cactcgcacg   6840
ccgtcgatca ggtcgccgga cgcgtccagg gcgctcggca ggctcgcgtc caaaatcgct   6900
agcgccttgg cttctgcggt ggcgcgttgt gccgcttcaa tgcgggcgcg tccgctggaa   6960
aagtcctgct caatgtactt tttcggcttc tgtgatccgg tcatcgttcg agcaatctcc   7020
attaggtcgg ccagccgatc cacacgatca tgctggcagt gccatttata ggctgtcgga   7080
tcgtctgaga cgtgcagcgg ccaccggctc agcctatgcg aaaaagcctg gtcagcgccg   7140
aaaacacgag tcatttcttc cgtcgttgca gccagcaggc gcatatttgg gctggtttta   7200
cctgctgcgg catacaccgg gtcaatgagc cagatgagct ggcatttccc gctcagcgga   7260
ttcacgccga tccaagccgg cgctttttct aggcgtgccc atttctctaa aatcgcgtag   7320
acctgcgggt ttacgtgctc aatcttcccg ccggcctggt ggctgggcac atcgatgtca   7380
agcacgatca ccgcggcatg ttgcgcgtgc gtcagcgcaa cgtactggca ccgcgtcagc   7440
gcttttgagc cagcccggta gagctttggt tgggtttcgc cggtatccgg gtttttaatc   7500
caggcgctcg cgaaatctct tgtcttgctg ccctggaagc tttcgcgtcc caggtgagcg   7560
agcagttcgc ggcgatcttc tgccgtccag ccgcgtgagc cgcagcgcat agcttcgggg   7620
tgggtgtcga acagatcggc ggacaatttc cacgcgctag ctgtgactgt gtcctgcgga   7680
tcggctagag tcatgtcttg agtgctttct cccagctgat gactgggggt tagccgacgc   7740
cctgtgagtt cccgctcacg gggcgttcaa ctttttcagg tatttgtgca gcttatcgtg   7800
ttttcttcgt aaatgaacgc ttaactacct tgttaaacgt ggcaaatagg caggattgat   7860
ggggatctag cttcacgctg ccgcaagcac tcagggcgca agggctgcta aaggaagcgg   7920
aacacgtaga aagccagtcc gcagaaacgg tgctgacccc ggatgaatgt cagctactgg   7980
gctatctgga caagggaaaa cgcaagcgca aagagaaagc aggtagcttg cagtgggctt   8040
acatggcgat agctagactg ggcggtttta tggacagcaa gcgaaccgga attgccagct   8100
ggggcgccct ctggtaaggt tgggaagccc tgcaaagtaa actggatggc tttcttgccg   8160
ccaaggatct gatggcgcag gggatcaaga tctgatcaag agacaggatg aggatcgttt   8220
cgcatgattg aacaagatgg attgcacgca ggttctccgg ccgcttgggt ggagaggcta   8280
ttcggctatg actgggcaca acagacaatc ggctgctctg atgccgccgt gttccggctg   8340
tcagcgcagg ggcgcccggt tctttttgtc aagaccgacc tgtccggtgc cctgaatgaa   8400
ctccaagacg aggcagcgcg gctatcgtgg ctggccacga cgggcgttcc ttgcgcagct   8460
gtgctcgacg ttgtcactga agcgggaagg gactggctgc tattgggcga agtgccgggg   8520
caggatctcc tgtcatctca ccttgctcct gccgagaaag tatccatcat ggctgatgca   8580
```

atgcggcggc tgcatacgct tgatccggct acctgcccat tcgaccacca agcgaaacat 8640
cgcatcgagc gagcacgtac tcggatggaa gccggtcttg tcgatcagga tgatctggac 8700
gaagagcatc aggggctcgc gccagccgaa ctgttcgcca ggctcaaggc gcggatgccc 8760
gacggcgagg atctcgtcgt gacccatggc gatgcctgct tgccgaatat catggtggaa 8820
aatggccgct tttctggatt catcgactgt ggccggctgg gtgtggcgga ccgctatcag 8880
gacatagcgt tggctacccg tgatattgct gaagagcttg gcggcgaatg ggctgaccgc 8940
ttcctcgtgc tttacggtat cgccgctccc gattcgcagc gcatcgcctt ctatcgcctt 9000
cttgacgagt tcttctgagc gggactctgg ggttcgcgga atcatgacca aaatccctta 9060
acgtgagttt tcgttccact gagcgtcaga ccccgtagaa aagatcaaag gatcttcttg 9120
agatcctttt tttctgcgcg taatctgctg cttgcaaaca aaaaaaccac cgctaccagc 9180
ggtggtttgt ttgccggatc aagagctacc aactcttttt ccgaaggtaa ctggcttcag 9240
cagagcgcag ataccaaata ctgtccttct agtgtagccg tagttaggcc accacttcaa 9300
gaactctgta gcaccgccta catacctcgc tctgctaatc ctgttaccag tggctgctgc 9360
cagtggcgat aagtcgtgtc ttaccgggtt ggactcaaga cgatagttac cggataaggc 9420
gcagcggtcg ggctgaacgg ggggttcgtg cacacagccc agcttggagc gaacgaccta 9480
caccgaactg agatacctac agcgtgagct atgagaaagc gccacgcttc ccgaagggag 9540
aaaggcggac aggtatccgg taagcggcag ggtcggaaca ggagagcgca cgagggagct 9600
tccaggggga aacgcctggt atctttatag tcctgtcggg tttcgccacc tctgacttga 9660
gcgtcgattt ttgtgatgct cgtcaggggg gcggagccta tggaaaaacg ccagcaacgc 9720
ggccttttta cggttcctgg ccttttgctg gccttttgct cacatgttct ttcctgcgtt 9780
atcccctgat tctgtggata accgtattac cgcctttgag tgagctgata ccgctcgccg 9840
cagccgaacg accgagcgca gcgagtcagt gagcgaggaa gcggaagagc gcctgatgcg 9900
gtattttctc cttacgcatc tgtgcggtat ttcacaccgc atatggtgca ctctcagtac 9960
aatctgctct gatgccgcat agttaagcca gtatacactc cgctatcgct acgtgactgg 10020
gtcatggctg cgccccgaca cccgccaaca cccgctgacg cgccctgacg ggcttgtctg 10080
ctcccggcat ccgcttacag acaagctgtg accgtctccg ggagctgcat gtgtcagagg 10140
ttttcaccgt catcaccgaa acgcgcgagg cagcagatca attcgcgcgc gaaggcgaag 10200
cggcatgcat ttacgttgac accatcgaat ggtgcaaaac ctttcgcggt atggcatgat 10260
agcgcccgga agagagtcaa ttcagggtgg tgaatgtgaa accagtaacg ttatacgatg 10320
tcgcagagta tgccggtgtc tcttatcaga ccgtttcccg cgtggtgaac caggccagcc 10380
acgtttctgc gaaaacgcgg gaaaaagtgg aagcggcgat ggcggagctg aattacattc 10440
ccaaccgcgt ggcacaacaa ctggcgggca aacagtcgtt gctgattggc gttgccacct 10500
ccagtctggc cctgcacgcg ccgtcgcaaa ttgtcgcggc gattaaatct cgcgccgatc 10560
aactgggtgc cagcgtggtg gtgtcgatgg tagaacgaag cggcgtcgaa gcctgtaaag 10620
cggcggtgca caatcttctc gcgcaacgcg tcagtgggct gatcattaac tatccgctgg 10680
atgaccagga tgccattgct gtggaagctg cctgcactaa tgttccggcg ttatttcttg 10740
atgtctctga ccagacaccc atcaacagta ttattttctc ccatgaagac ggtacgcgac 10800
tgggcgtgga gcatctggtc gcattgggtc accagcaaat cgcgctgtta gcgggcccat 10860
taagttctgt ctcggcgcgt ctgcgtctgg ctggctggca taaatatctc actcgcaatc 10920
aaattcagcc gatagcggaa cgggaaggcg actggagtgc catgtccggt tttcaacaaa 10980
ccatgcaaat gctgaatgag ggcatcgttc ccactgcgat gctggttgcc aacgatcaga 11040
tggcgctggg cgcaatgcgc gccattaccg agtccgggct gcgcgttggt gcggatatct 11100
cggtagtggg atacgacgat accgaagaca gctcatgtta tatcccgccg tcaaccacca 11160
tcaaacagga ttttcgcctg ctggggcaaa ccagcgtgga ccgcttgctg caactctctc 11220
agggccaggc ggtgaagggc aatcagctgt tgcccgtctc actggtgaaa agaaaaacca 11280
ccctggcgcc caatacgcaa accgcctctc cccgcgcgtt ggccgattca ttaatgcagc 11340
tggcacgaca ggtttcccga ctggaaagcg ggcagtgagc gcaacgcaat taatgtgagt 11400
tagcgcgaat tgatctggtt tgacagctta tcat 11434

<210> SEQ ID NO 26
<211> LENGTH: 4431
<212> TYPE: DNA
<213> ORGANISM: Artificial Sequence
<220> FEATURE:
<223> OTHER INFORMATION: operon RiPKS-At4CL-SeSam8

<400> SEQUENCE: 26
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatggcacc 1200
acaggaacag gcagtctccc aggttatgga aaagcagtcc aacaacaaca actccgatgt 1260
tatcttccgc tccaagttgc ctgacatcta catcccaaac catctgtccc tgcacgatta 1320
cattttccag aacatctccg aatttgctac taagccatgc ctgatcaacg gcccaaccgg 1380
tcacgtgtac acctactctg acgtccacgt gatcagccgc cagatcgcag ctaacttcca 1440
caagctgggc gtgaaccaga acgacgtagt gatgctgctg ctccctaact gccctgagtt 1500
cgtcctgtcc ttcctggccg cctccttccg cggtgcaacc gcgaccgcgg ccaacccatt 1560

```
cttcacgcca gcagagatcg ctaagcaggc taaggcttct aacaccaagc tgatcatcac   1620
cgaagcgcgc tacgtggaca agatcaagcc actccagaac gacgatggcg ttgtgatcgt   1680
gtgcatcgac gacaacgagt ccgttccaat cccagagggc tgtctgaggt tcaccgagct   1740
gacccaatcg accaccgaag cgtccgaggt tatcgactcc gttgaaatct cccctgacga   1800
tgtcgtcgcc ctgccatact ccagcggcac caccggcttg ccaaagggtg tgatgctgac   1860
ccacaaggga ctcgttacct ccgtggcaca gcaggtcgat ggtgaaaacc ccaacctgta   1920
cttccattcc gatgacgtca tcctgtgcgt cctgccgatg ttccacatct acgctctgaa   1980
ctccatcatg ctgtgcggcc tccgcgtcgg tgcagcaatc ctgatcatgc caaagttcga   2040
aatcaacctg ctgctggagt tgatccagcg ctgcaaggtg accgtggcac ccatggtgcc   2100
cccgatcgtg ctggcaatcg cgaagtccag cgaaaccgaa aagtacgacc tgtcatccat   2160
ccgcgtcgtc aagtcgggcg ccgcaccact cggcaaggag ctggaggacg ctgtcaacgc   2220
taagttccct aacgcgaagc tcggccaggg ctacggtatg accgaggccg gcccagtcct   2280
ggccatgtcc ctgggcttcg caaaggagcc attcccggtg aagtccggcg catgcggcac   2340
cgttgtgcgc aacgcagaga tgaagatcgt tgacccagat accggtgact ccctgtcccg   2400
taaccagccc ggcgagatct gcatccgcgg ccaccagatc atgaagggct acctgaacaa   2460
ccctgctgct accgccgaaa ccatcgataa ggatggctgg ctccacaccg gcgacatcgg   2520
tctgatcgac gacgacgatg aactgttcat cgtcgatcgc cttaaggagt tgatcaagta   2580
caagggcttc caggtggccc ccgcagaact ggaagcactg ctcatcggcc accctgatat   2640
caccgatgtc gccgtcgtgg ccatgaagga ggaagcagca ggcgaagtgc cagtcgcttt   2700
cgtggtgaag tccaaggatt ccgagttgtc cgaggatgat gtgaagcagt tcgtgtccaa   2760
gcaggtcgtg ttctacaagc gcatcaacaa ggtgttcttc accgaatcca tcccaaaggc   2820
accatccggc aagatcctgc gcaaggacct gcgcgctaag ctggctaacg gcctgtaagg   2880
atctaggagg ataaagaaat gacccaggtc gtggagcgcc aggctgatcg tctgtccagc   2940
cgcgagtacc tggcacgcgt tgttcgttcc gcaggctggg acgcaggcct caccagctgc   3000
accgatgaag aaatcgtgcg catgggtgca tccgcacgca ccattgagga atacctgaag   3060
tctgataagc cgatctacgg cctcacccag ggcttcggtc cactggtcct gttcgatgca   3120
gattccgaac tggaacaggg cggctctctc atctcccatc tgggcaccgg ccagggtgca   3180
ccgcttgcac cggaagtgtc ccgcctgatt ctgtggctcc gcatccaaaa catgcgcaag   3240
ggctattcgg ctgtcagtcc tgtgttctgg caaaaactgg ccgacctctg gaacaagggc   3300
ttcacccctg ctatccctcg ccacggcacc gtgtccgcca gcggcgatct ccagcctctg   3360
gcacacgctg ccctggcttt taccggcgtg ggcgaggcat ggacccgtga tgcagacggc   3420
cgttggtcca ccgtgccagc cgtggacgca ttagcagcac tgggtgcaga gccgttcgat   3480
tggccagtgc gcgaggcttt ggccttcgtg aacggtacgg gcgcatcact cgcggtggca   3540
gttctcaacc acagatccgc tctccgtctc gtacgagcat gtgcagtctt gtctgcccgt   3600
ttggctacct tgctaggagc taatcctgaa cactacgatg tcggccacgg agtcgcaagg   3660
ggacaagttg gccagctgac cgcggcggaa tggattcggc agggactacc acgcggcatg   3720
gtccgagacg gttcgcgccc tcttcaagaa ccatacagct tgcgctgtgc cccccaggtc   3780
cttggcgcgg tgctggacca gctggatggt gcaggcgatg ttctggcccg cgaagtggat   3840
ggctgccagg acaatcctat cacctacgag ggcgaactgc tgcacggcgg taacttccac   3900
```

-continued

```
gctatgccag tcggcttcgc atccgaccag atcggtctgg cgatgcacat ggcagcttat   3960

ctggctgaac gccagctcgg cctgctggtg agcccggtga ccaacggcga cctgccacca   4020

atgctgaccc cacgcgctgg acgcggtgcc ggcctggcgg gcgttcagat ctccgcaacc   4080

tccttcgtct ctcgcatccg ccagctggtg ttcccagcta gcctcaccac cctcccaacc   4140

aacggctgga accaggacca tgtcccaatg gctctgaacg gcgcaaacag cgtgttcgaa   4200

gctcttgaac tgggttggct gaccgtgggt agcctggcag tcggcgtggc ccagctcgct   4260

gcaatgaccg gccacgcagc tgagggcgtg tgggccgagt tggcaggcat ctgcccacca   4320

ctggatgctg accgcccact gggcgcggag gtccgcgctg ctcgcgatct cctctccgca   4380

cacgctgacc agctgctcgt tgacgaggct gatggcaaag acttcggcta a            4431
```

<210> SEQ ID NO 27
<211> LENGTH: 11569
<212> TYPE: DNA
<213> ORGANISM: Artificial Sequence
<220> FEATURE:
<223> OTHER INFORMATION: plasmid RiPKS-Pp4CL-RcTAL-pECXK (pECXK_D)

<400> SEQUENCE: 27

```
cgactgcacg gtgcaccaat gcttctggcg tcaggcagcc atcggaagct gtggtatggc     60

tgtgcaggtc gtaaatcact gcataattcg tgtcgctcaa ggcgcactcc cgttctggat    120

aatgtttttt gcgccgacat cataacggtt ctggcaaata ttctgaaatg agctgttgac    180

aattaatcat ccggctcgta taatgtgtgg aattgtgagc ggataacaat ttcacacagg    240

aaacagacca tggaattcga gctggatcta ggagggagat catatggtta ccgttgaaga    300

agtccgcaag gctcagcgcg cagaaggccc tgcaaccgtt ctggcaatcg gcaccgcaac    360

cccaccaaac tgcgtcggcc agtccaccta cccagattat tatttccgta tcaccaactc    420

tgaacacaag attgaactga agcagaagtt ccagaggatg tgcgataagt ccatgatcaa    480

gaagcgttac atgtacctta ccgaagagat cctgaaggag aacccatcca tgtgcgagta    540

catggctcca tcccttgatg ctcgccagga catggtcatc gtggaaatcc caaagctggg    600

caaggaagca gccaccaagg caatcaagga gtggggccag ccgaagtcga agatcaccca    660

ccttgttttc tgcaccacca gcggtgtgga tatgcctggc gccgactacc agctgatcaa    720

gctcttcggc ctgcgcccat ccgtcaagcg cctcatgatg taccagcagg gctgcttcgc    780

cggcggcacc gttctgcgcc tggctaagga tctggcagaa aacaaccgcg gtgcccgcgt    840

tctcgtcgtg tgctccgaga tcaccgtggt caccttccgc ggcccatccg acacccacct    900

tgactgtctg gttggccagg cactcttcgg cgatggcgtg gcatccatca tcgtcggcgc    960

agatcctctc cctgaaatcg aaaagccact tttcgaactt gtcagcgcag cacagaccat   1020

cctgccagat tctgagggcg caatcgaggg ccacctccgc gaggtgggtc ttaccttcca   1080

tctgctcgaa aacgtgccag cactgatctc caagaacatc gaaaagtccc tgaacgaaac   1140

cttcaagcca ctggacatca tggactggaa ctccctgttc tggatcgctc acccaggcgg   1200

tccggctatc ctggatcagg tcgaggctaa gctgggtctg aagccggaga agttggaggc   1260

taccggccac atcctgtccg aatacggcaa catgtcctcc gcatgcgttc tcttcatcct   1320

ggacgtggtg cggcgcaagt ccgcagccaa cggtgtgacc acccgtatcc tgagcatcgg   1380

tcagatctcc aagtccctgc tgatcctggc atggttcctc ttctccctgg tgtaaggatc   1440

taggaggatt atgagatgtc accatcgctc cttccccagc caatcgtgtc cgaatccacc   1500

ggtgaatccg tgatgaagat gtccctccag tccgaagtgc gcgaagcatc cctggcaacc   1560
```

```
ggtgaaaacc ctgaaccatt cctgctggaa accgatgctg aatcccagat catggaacct   1620
gtgcacgctg aagttcacga tttcatctac cgttctaagc tgcctgatat cgatatccca   1680
aaccacatgc ctctggctga ttactgcctg gagaagtcct cccagtggcc tgataaggtg   1740
tgcctgatcg atggtgtgac cggtcgcgaa caccgctacg gcgaaattga gctgtcctcc   1800
cgccgcgtgg cagcaggcct tgataagatc ggcgtgaagc agggcgatgt catcgcactg   1860
ctcttgccta actgcgctga gttcgtcctg gtgttcctgg gcgcagcgaa gcgcggcgcc   1920
gttgtcacca ccgctaaccc attctacacc gccgccgagt tggagaagca aatcgaggcc   1980
tccggtgcgg gcattgttat cactcagagc agctacatcg agaagctcgc aggccttaac   2040
gtccagatca tcaccgttga tcagcacgtg gctaattgca tgcacatctc cgtgctgctg   2100
aacgcatgcg aagatgaatg ccctcaggtg cgtatccacc ctgacgatct ggtctgcctg   2160
ccatactcct ccggcaccac cggcttgcca aagggcgtga tgctgaccca caagtccctt   2220
gtgtcatccg tgtcccaaca ggtggacggc gaagcaccaa acttcaacat cactgtcgag   2280
gacaccctga tgtgcgtgct gcccatgttc cacatctatt ccctcaactc catcctgctg   2340
tgcggcctcc gtgtgggcgc caccctcgtt attatgccga agttcgaact gccaaagctg   2400
ttggacctga tccagcgtca caaggtgacc atgggcccat tcgtgccgcc aatcgtcctg   2460
gccatcgcaa agaacccaat cgtcgagaat tacgatctct cctccatgcg catggttatg   2520
tccggcgctg cacctctggg tcgggagctg gaggacgctt tccgtgcccg cttgccaaac   2580
gccgttctgg gccagggcta cgggatgact gaagccggcc cagtcctggc tatgtgcctc   2640
gcattcgcaa agaccccatt ctccgtgaag ccaggctcct gcggcaccgt ggtgcgcaac   2700
gctgaagtga aaatcgtcga taccgaaacc ggcatgtccc tgccatacaa ccagccaggc   2760
gagatctgca tccgcggccc acagatcatg aagggctacc tgaagaaccc agaagctacc   2820
gctaacacca tcgataagga tggcttcctg cacaccggcg atgtcgcatt catcgatgag   2880
gatgaggaga tgttcatcgt tgatcgcgtc aaggagatca tcaagttcaa gggcttccag   2940
gtgcctcctg cggagctgga agctctcctg ctgtcccaca aggagatcca ggacgctgct   3000
gtcgtgtccc gtaaggatga cgtggcgggc gaagttccag tggcattcgt ggtccgcgct   3060
accagctcca ccatcaccga ggatgaagtc aaggattaca tcgcaaagca ggtcgttttc   3120
tacaagaaga tccacaacgt atacttcgtg gattccgtgc caaagtctcc atccggcaag   3180
atcctgcgta aggatctccg taacaaggtg taaggatcta ggaggataaa gaaatgaccc   3240
tgcaatccca gactgcaaag gactgcctgg cgctggatgg tgcactgaca ctggttcagt   3300
gcgaagcaat tgccactcac cgctcacgga tctccgtcac accagcattg cgggaacgct   3360
gcgcccgcgc gcacgcacgt ctggagcacg ctatcgcaga acagcgtcac atctatggta   3420
tcaccaccgg cttcggacca ctggctaatc gcctgatcgg tgcagatcag ggcgccgaac   3480
tccagcagaa cctcatctac caccttgcta ctggcgtggg cccaaaactc tcctgggctg   3540
aagcacgtgc actcatgctg gctcgtctca actccatcct tcagggcgca tctggtgcat   3600
caccagaaac catcgaccgt atcgttgccg ttctgaacgc tggcttcgcc ccagaagtcc   3660
cagctcaggg caccgttggt gcatctggcg atctgacccc actggctcac atggtgctgg   3720
cgcttcaggg tcgaggtcgt atgatcgatc catccggccg tgttcaggaa gccggcgcag   3780
tgatggatcg cctgtgcggt ggcccactga ccttggcagc ccgtgacggt ctggctctgg   3840
tcaacggtac ttccgctatg accgcaatcg ctgctttgac cggtgtggag gctgcgcgcg   3900
```

-continued caatcgacgc cgcattgcgc cactccgctg tgctcatgga ggttctctcc ggccacgctg 3960
aggcttggca ccctgcattt gctgaactcc gcccacaccc aggccagctg cgcgcaaccg 4020
aacgtctggc ccaggctctc gatggcgccg gtcgcgtttg ccgcaccttg accgcggccc 4080
gtcgcctgac cgcagctgat ctgcgccctg aggatcaccc agcccaggac gcctactccc 4140
tgcgcgtggt gccacagctg gttggcgctg tctgggacac cctcgattgg cacgatcgcg 4200
tcgtgacctg cgaactcaac tctgtgaccg acaacccaat cttcccggaa ggctgcgctg 4260
ttccagcact gcacggcggc aacttcatgg gcgtgcacgt cgcactggcg tcggacgccc 4320
tgaacgctgc attggttacc ctggcaggtc tggtggagcg ccagatcgca cgccttactg 4380
atgagaagct gaacaaggga cttccggcat tccttcacgg tggtcaggct ggccttcagt 4440
ccggcttcat gggcgcgcag gtcaccgcaa ccgcgctcct tgctgaaatg cgcgcaaacg 4500
caaccccggt gtctgttcag tcactgtcta ccaacggcgc taaccaggat gttgtcagca 4560
tgggcaccat cgctgcacgc cgcgctcgcg cacagctgct cccactgtcc cagattcagg 4620
caatcctggc tctcgctctc gcccaggcaa tggatctgct ggatgatcca gagggccagg 4680
ctggctggtc ccttaccgca cgcgacctgc gcgatcgcat ccgcgctgtc tcgccgggcc 4740
tgcgcgcaga tcgcccactg gccggccaca tcgaggcagt cgctcagggt ctgcgccacc 4800
cttccgcagc agctgatcca ccagcataac tctagagtcg acctgcaggc atgcaagctt 4860
ggctgttttg gcggatgaga gaagattttc agcctgatac agattaaatc agaacgcaga 4920
agcggtctga taaaacagaa tttgcctggc ggcagtagcg cggtggtccc acctgacccc 4980
atgccgaact cagaagtgaa acgccgtagc gccgatggta gtgtggggtc tccccatgcg 5040
agagtaggga actgccaggc atcaaataaa acgaaaggct cagtcgaaag actgggcctt 5100
tcgttttatc tgttgtttgt cggtgaacgc tctcctgagt aggacaaatc cgccgggagc 5160
ggatttgaac gttgcgaagc aacggcccgg agggtggcgg gcaggacgcc cgccataaac 5220
tgccaggcat caaattaagc agaaggccat cctgacggat ggcctttttg cgtttctaca 5280
aactcttttt gtttattttt ctaaatacat tcaaatatgt atccgctcat gaattaattc 5340
cgctagatga cgtgcggctt cgacctcctg ggcgtggcgc ttgttggcgc gctcgcggct 5400
ggctgcggca cgacacgcgt ctgagcagta ttttgcgcgc cgtcctcgtg ggtcaggccg 5460
gggtgggatc aggccaccgc agtaggcgca gctgatgcga tcctccacta ctgcgcgtcc 5520
tcctggcgct gccgagcacg cagctcgtcg gccagctctt caaggtcggc cacaagcgtt 5580
tctaggtcgc tcgcggcact tgcccagtcg cgtgatgctg gcgcgtctgt cgtatcgagg 5640
gcgcggaaaa atccgatcac cgtttttaaa tcgacggcgg catcgagtgc gtcggactcc 5700
agcgcgacat cggagagatc caccgctgat gcttcaggcc agttttggta cttcgtcgtg 5760
aaggtcatga caccattata acgaacgttc gttaaaaatt ctagccccaa ttctgataat 5820
ttcttccggc actcctgcga aaacctgcga gacttcttgc ccagaaaaaa cgccaagcgc 5880
agcggttacc gcactttttt tccaggtgat ttcaccctga ccagcgaagc ggcactttag 5940
tgcatgaggt gtgcccctgg tttcccctct ttggagggtt caacccaaaa aagcacacaa 6000
gcaaaaatga aaatcatcat gagcaagttg gtgcgaagca gcaacgcgct agctccaaaa 6060
aggtctccag gatctcgagg agatttttga gggggaggga gtcgaggaag agccagagca 6120
gaaggcgggg aaccgttctc tgccgacagc gtgagccccc cttaaaaatc aggccgggga 6180
ggaaccgggg agggatcaga gctaggagcg agacacccta aaggggggga accgttttct 6240
gctgacggtg tttcgtttat tagttttcag cccgtggata gcggagggtg agggcaagtg 6300

-continued

```
agagccagag caaggacggg accccctaaag gggggaaccg ttttctgctg acggtgtttc   6360
gtttattagt tttcagcccg tggacggccg cgtttagctt ccattccaag tgcctttctg   6420
acttgttgga tgcgcctttc actgacacct agttcgcctg caagctcacg agtcgaggga   6480
tcagcaaccg attgagaacg ggcatccagg atcgcagttt tgacgcgaag ttcgagcaac   6540
tcgcctgtca tttctcggcg tttgtttgct tccgctaatc gctgtcgcgt ctcctgcgca   6600
tacttacttt ctgggtcagc ccatctgcgt gcattcgatg tagctgcgcc ccgtcgcccc   6660
atcgtcgcta gagctttccg ccctcggctg ctctgcgttt ccacccgacg agcagggacg   6720
actggctggc ctttagccac gtagccgcgc acacgacgcg ccatcgtcag gcgatcacgc   6780
atggcgggaa gatccggctc ccggccgtct gcaccgaccg cctgggcaac gttgtacgcc   6840
acttcatacg cgtcgatgat cttggcatct tttaggcgct caccagcagc tttgagctgg   6900
tatcccacgg tcaacgcgtg gcgaaacgcg gtctcgtcgc gcgctcgctc tggatttgtc   6960
cagagcactc gcacgccgtc gatcaggtcg ccggacgcgt ccagggcgct cggcaggctc   7020
gcgtccaaaa tcgctagcgc cttggcttct gcggtggcgc gttgtgccgc ttcaatgcgg   7080
gcgcgtccgc tggaaaagtc ctgctcaatg tactttttcg gcttctgtga tccggtcatc   7140
gttcgagcaa tctccattag gtcggccagc cgatccacac gatcatgctg gcagtgccat   7200
ttataggctg tcggatcgtc tgagacgtgc agcggccacc ggctcagcct atgcgaaaaa   7260
gcctggtcag cgccgaaaac acgagtcatt tcttccgtcg ttgcagccag caggcgcata   7320
tttgggctgg ttttacctgc tgcggcatac accgggtcaa tgagccagat gagctggcat   7380
ttcccgctca gcggattcac gccgatccaa gccggcgctt tttctaggcg tgcccatttc   7440
tctaaaatcg cgtagacctg cgggtttacg tgctcaatct tcccgccggc ctggtggctg   7500
ggcacatcga tgtcaagcac gatcaccgcg gcatgttgcg cgtgcgtcag cgcaacgtac   7560
tggcaccgcg tcagcgcttt tgagccagcc cggtagagct ttggttgggt ttcgccggta   7620
tccgggtttt taatccaggc gctcgcgaaa tctcttgtct tgctgccctg gaagctttcg   7680
cgtcccaggt gagcgagcag ttcgcggcga tcttctgccg tccagccgcg tgagccgcag   7740
cgcatagctt cggggtgggt gtcgaacaga tcggcggaca atttccacgc gctagctgtg   7800
actgtgtcct gcggatcggc tagagtcatg tcttgagtgc tttctcccag ctgatgactg   7860
ggggttagcc gacgccctgt gagttcccgc tcacggggcg ttcaactttt tcaggtattt   7920
gtgcagctta tcgtgttttc ttcgtaaatg aacgcttaac taccttgtta aacgtggcaa   7980
ataggcagga ttgatgggga tctagcttca cgctgccgca agcactcagg gcgcaagggc   8040
tgctaaagga agcggaacac gtagaaagcc agtccgcaga aacggtgctg accccggatg   8100
aatgtcagct actgggctat ctggacaagg gaaaacgcaa gcgcaaagag aaagcaggta   8160
gcttgcagtg ggcttacatg gcgatagcta gactgggcgg ttttatggac agcaagcgaa   8220
ccggaattgc cagctggggc gccctctggt aaggttggga agccctgcaa agtaaactgg   8280
atggctttct tgccgccaag gatctgatgg cgcaggggat caagatctga tcaagagaca   8340
ggatgaggat cgtttcgcat gattgaacaa gatggattgc acgcaggttc tccggccgct   8400
tgggtggaga ggctattcgg ctatgactgg gcacaacaga caatcggctg ctctgatgcc   8460
gccgtgttcc ggctgtcagc gcaggggcgc ccggttcttt ttgtcaagac cgacctgtcc   8520
ggtgccctga atgaactcca agacgaggca gcgcggctat cgtggctggc cacgacgggc   8580
gttccttgcg cagctgtgct cgacgttgtc actgaagcgg gaagggactg gctgctattg   8640
```

-continued

```
ggcgaagtgc cggggcagga tctcctgtca tctcaccttg ctcctgccga gaaagtatcc   8700
atcatggctg atgcaatgcg gcggctgcat acgcttgatc cggctacctg cccattcgac   8760
caccaagcga aacatcgcat cgagcgagca cgtactcgga tggaagccgg tcttgtcgat   8820
caggatgatc tggacgaaga gcatcagggg ctcgcgccag ccgaactgtt cgccaggctc   8880
aaggcgcgga tgcccgacgg cgaggatctc gtcgtgaccc atggcgatgc ctgcttgccg   8940
aatatcatgg tggaaaatgg ccgcttttct ggattcatcg actgtggccg gctgggtgtg   9000
gcggaccgct atcaggacat agcgttggct acccgtgata ttgctgaaga gcttggcggc   9060
gaatgggctg accgcttcct cgtgctttac ggtatcgccg ctcccgattc gcagcgcatc   9120
gccttctatc gccttcttga cgagttcttc tgagcgggac tctggggttc gcggaatcat   9180
gaccaaaatc ccttaacgtg agttttcgtt ccactgagcg tcagaccccg tagaaaagat   9240
caaaggatct tcttgagatc cttttttct gcgcgtaatc tgctgcttgc aaacaaaaaa   9300
accaccgcta ccagcggtgg tttgtttgcc ggatcaagag ctaccaactc tttttccgaa   9360
ggtaactggc ttcagcagag cgcagatacc aaatactgtc cttctagtgt agccgtagtt   9420
aggccaccac ttcaagaact ctgtagcacc gcctacatac ctcgctctgc taatcctgtt   9480
accagtggct gctgccagtg gcgataagtc gtgtcttacc gggttggact caagacgata   9540
gttaccggat aaggcgcagc ggtcgggctg aacggggggt tcgtgcacac agcccagctt   9600
ggagcgaacg acctacaccg aactgagata cctacagcgt gagctatgag aaagcgccac   9660
gcttcccgaa gggagaaagg cggacaggta tccggtaagc ggcagggtcg gaacaggaga   9720
gcgcacgagg gagcttccag ggggaaacgc ctggtatctt tatagtcctg tcgggtttcg   9780
ccacctctga cttgagcgtc gatttttgtg atgctcgtca ggggggcgga gcctatggaa   9840
aaacgccagc aacgcggcct ttttacggtt cctggccttt tgctggcctt ttgctcacat   9900
gttctttcct gcgttatccc ctgattctgt ggataaccgt attaccgcct ttgagtgagc   9960
tgataccgct cgccgcagcc gaacgaccga gcgcagcgag tcagtgagcg aggaagcgga  10020
agagcgcctg atgcggtatt ttctccttac gcatctgtgc ggtatttcac accgcatatg  10080
gtgcactctc agtacaatct gctctgatgc cgcatagtta agccagtata cactccgcta  10140
tcgctacgtg actgggtcat ggctgcgccc cgacacccgc caacacccgc tgacgcgccc  10200
tgacgggctt gtctgctccc ggcatccgct tacagacaag ctgtgaccgt ctccgggagc  10260
tgcatgtgtc agaggttttc accgtcatca ccgaaacgcg cgaggcagca gatcaattcg  10320
cgcgcgaagg cgaagcggca tgcatttacg ttgacaccat cgaatggtgc aaaacctttc  10380
gcggtatggc atgatagcgc ccggaagaga gtcaattcag ggtggtgaat gtgaaaccag  10440
taacgttata cgatgtcgca gagtatgccg gtgtctctta tcagaccgtt tcccgcgtgg  10500
tgaaccaggc cagccacgtt tctgcgaaaa cgcgggaaaa agtggaagcg gcgatggcgg  10560
agctgaatta cattcccaac cgcgtggcac aacaactggc gggcaaacag tcgttgctga  10620
ttggcgttgc cacctccagt ctggccctgc acgcgccgtc gcaaattgtc gcggcgatta  10680
aatctcgcgc cgatcaactg ggtgccagcg tggtggtgtc gatggtagaa cgaagcggcg  10740
tcgaagcctg taaagcggcg gtgcacaatc ttctcgcgca acgcgtcagt gggctgatca  10800
ttaactatcc gctggatgac caggatgcca ttgctgtgga agctgcctgc actaatgttc  10860
cggcgttatt tcttgatgtc tctgaccaga cacccatcaa cagtattatt ttctcccatg  10920
aagacggtac gcgactgggc gtggagcatc tggtcgcatt gggtcaccag caaatcgcgc  10980
tgttagcggg cccattaagt tctgtctcgg cgcgtctgcg tctggctggc tggcataaat  11040
```

atctcactcg caatcaaatt cagccgatag cggaacggga aggcgactgg agtgccatgt 11100
ccggttttca acaaaccatg caaatgctga atgagggcat cgttcccact gcgatgctgg 11160
ttgccaacga tcagatggcg ctgggcgcaa tgcgcgccat taccgagtcc gggctgcgcg 11220
ttggtgcgga tatctcggta gtgggatacg acgataccga agacagctca tgttatatcc 11280
cgccgtcaac caccatcaaa caggattttc gcctgctggg gcaaaccagc gtggaccgct 11340
tgctgcaact ctctcagggc caggcggtga agggcaatca gctgttgccc gtctcactgg 11400
tgaaaagaaa aaccaccctg gcgcccaata cgcaaaccgc ctctccccgc gcgttggccg 11460
attcattaat gcagctggca cgacaggttt cccgactgga aagcgggcag tgagcgcaac 11520
gcaattaatg tgagttagcg cgaattgatc tggtttgaca gcttatcat 11569

<210> SEQ ID NO 28
<211> LENGTH: 4566
<212> TYPE: DNA
<213> ORGANISM: Artificial Sequence
<220> FEATURE:
<223> OTHER INFORMATION: operon RiPKS-Pp4CL-RcTAL

<400> SEQUENCE: 28
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatgtcacc 1200
atcgctcctt ccccagccaa tcgtgtccga atccaccggt gaatccgtga tgaagatgtc 1260
cctccagtcc gaagtgcgcg aagcatccct ggcaaccggt gaaaaccctg aaccattcct 1320
gctggaaacc gatgctgaat cccagatcat ggaacctgtg cacgctgaag ttcacgattt 1380
catctaccgt tctaagctgc ctgatatcga tatcccaaac cacatgcctc tggctgatta 1440
ctgcctggag aagtcctccc agtggcctga taaggtgtgc ctgatcgatg gtgtgaccgg 1500

-continued

```
tcgcgaacac cgctacggcg aaattgagct gtcctcccgc cgcgtggcag caggccttga   1560
taagatcggc gtgaagcagg gcgatgtcat cgcactgctc ttgcctaact gcgctgagtt   1620
cgtcctggtg ttcctgggcg cagcgaagcg cggcgccgtt gtcaccaccg ctaacccatt   1680
ctacaccgcc gccgagttgg agaagcaaat cgaggcctcc ggtgcgggca ttgttatcac   1740
tcagagcagc tacatcgaga agctcgcagg ccttaacgtc cagatcatca ccgttgatca   1800
gcacgtggct aattgcatgc acatctccgt gctgctgaac gcatgcgaag atgaatgccc   1860
tcaggtgcgt atccaccctg acgatctggt ctgcctgcca tactcctccg gcaccaccgg   1920
cttgccaaag ggcgtgatgc tgacccacaa gtcccttgtg tcatccgtgt cccaacaggt   1980
ggacggcgaa gcaccaaact tcaacatcac tgtcgaggac accctgatgt gcgtgctgcc   2040
catgttccac atctattccc tcaactccat cctgctgtgc ggcctccgtg tgggcgccac   2100
cctcgttatt atgccgaagt tcgaactgcc aaagctgttg gacctgatcc agcgtcacaa   2160
ggtgaccatg ggcccattcg tgccgccaat cgtcctggcc atcgcaaaga acccaatcgt   2220
cgagaattac gatctctcct ccatgcgcat ggttatgtcc ggcgctgcac ctctgggtcg   2280
ggagctggag gacgctttcc gtgcccgctt gccaaacgcc gttctgggcc agggctacgg   2340
gatgactgaa gccggcccag tcctggctat gtgcctcgca ttcgcaaaga ccccattctc   2400
cgtgaagcca ggctcctgcg gcaccgtggt gcgcaacgct gaagtgaaaa tcgtcgatac   2460
cgaaaccggc atgtccctgc catacaacca gccaggcgag atctgcatcc gcggcccaca   2520
gatcatgaag ggctacctga agaacccaga agctaccgct aacaccatcg ataaggatgg   2580
cttcctgcac accggcgatg tcgcattcat cgatgaggat gaggagatgt tcatcgttga   2640
tcgcgtcaag gagatcatca agttcaaggg cttccaggtg cctcctgcgg agctggaagc   2700
tctcctgctg tcccacaagg agatccagga cgctgctgtc gtgtcccgta aggatgacgt   2760
ggcgggcgaa gttccagtgg cattcgtggt ccgcgctacc agctccacca tcaccgagga   2820
tgaagtcaag gattacatcg caaagcaggt cgttttctac aagaagatcc acaacgtata   2880
cttcgtggat tccgtgccaa agtctccatc cggcaagatc ctgcgtaagg atctccgtaa   2940
caaggtgtaa ggatctagga ggataaagaa atgaccctgc aatcccagac tgcaaaggac   3000
tgcctggcgc tggatggtgc actgacactg gttcagtgcg aagcaattgc cactcaccgc   3060
tcacggatct ccgtcacacc agcattgcgg gaacgctgcg cccgcgcgca cgcacgtctg   3120
gagcacgcta tcgcagaaca gcgtcacatc tatggtatca ccaccggctt cggaccactg   3180
gctaatcgcc tgatcggtgc agatcagggc gccgaactcc agcagaacct catctaccac   3240
cttgctactg gcgtgggccc aaaactctcc tgggctgaag cacgtgcact catgctggct   3300
cgtctcaact ccatccttca gggcgcatct ggtgcatcac cagaaaccat cgaccgtatc   3360
gttgccgttc tgaacgctgg cttcgcccca gaagtcccag ctcagggcac cgttggtgca   3420
tctggcgatc tgaccccact ggctcacatg gtgctggcgc ttcagggtcg aggtcgtatg   3480
atcgatccat ccggccgtgt tcaggaagcc ggcgcagtga tggatcgcct gtgcggtggc   3540
ccactgacct tggcagcccg tgacggtctg gctctggtca acggtacttc cgctatgacc   3600
gcaatcgctg ctttgaccgg tgtggaggct gcgcgcgcaa tcgacgccgc attgcgccac   3660
tccgctgtgc tcatggaggt tctctccggc cacgctgagg cttggcaccc tgcatttgct   3720
gaactccgcc cacacccagg ccagctgcgc gcaaccgaac gtctggccca ggctctcgat   3780
ggcgccggtc gcgtttgccg caccttgacc gcggcccgtc gcctgaccgc agctgatctg   3840
cgccctgagg atcacccagc ccaggacgcc tactccctgc gcgtggtgcc acagctggtt   3900
```

ggcgctgtct gggacaccct cgattggcac gatcgcgtcg tgacctgcga actcaactct 3960
gtgaccgaca acccaatctt cccggaaggc tgcgctgttc cagcactgca cggcggcaac 4020
ttcatgggcg tgcacgtcgc actggcgtcg gacgccctga acgctgcatt ggttaccctg 4080
gcaggtctgg tggagcgcca gatcgcacgc cttactgatg agaagctgaa caagggactt 4140
ccggcattcc ttcacggtgg tcaggctggc cttcagtccg gcttcatggg cgcgcaggtc 4200
accgcaaccg cgctccttgc tgaaatgcgc gcaaacgcaa ccccggtgtc tgttcagtca 4260
ctgtctacca acggcgctaa ccaggatgtt gtcagcatgg gcaccatcgc tgcacgccgc 4320
gctcgcgcac agctgctccc actgtcccag attcaggcaa tcctggctct cgctctcgcc 4380
caggcaatgg atctgctgga tgatccagag ggccaggctg gctggtccct taccgcacgc 4440
gacctgcgcg atcgcatccg cgctgtctcg ccgggcctgc gcgcagatcg cccactggcc 4500
ggccacatcg aggcagtcgc tcagggtctg cgccaccctt ccgcagcagc tgatccacca 4560
gcataa 4566

<210> SEQ ID NO 29
<211> LENGTH: 11494
<212> TYPE: DNA
<213> ORGANISM: Artificial Sequence
<220> FEATURE:
<223> OTHER INFORMATION: plasmid RiPKS-Pp4CL-FjTAL-pECXK (pECXK_E)

<400> SEQUENCE: 29
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320

-continued

```
ggacgtggtg cggcgcaagt ccgcagccaa cggtgtgacc acccgtatcc tgagcatcgg   1380
tcagatctcc aagtccctgc tgatcctggc atggttcctc ttctccctgg tgtaaggatc   1440
taggaggatt atgagatgtc accatcgctc cttccccagc caatcgtgtc cgaatccacc   1500
ggtgaatccg tgatgaagat gtccctccag tccgaagtgc gcgaagcatc cctggcaacc   1560
ggtgaaaacc ctgaaccatt cctgctggaa accgatgctg aatcccagat catggaacct   1620
gtgcacgctg aagttcacga tttcatctac cgttctaagc tgcctgatat cgatatccca   1680
aaccacatgc ctctggctga ttactgcctg gagaagtcct cccagtggcc tgataaggtg   1740
tgcctgatcg atggtgtgac cggtcgcgaa caccgctacg gcgaaattga gctgtcctcc   1800
cgccgcgtgg cagcaggcct tgataagatc ggcgtgaagc agggcgatgt catcgcactg   1860
ctcttgccta actgcgctga gttcgtcctg gtgttcctgg gcgcagcgaa gcgcggcgcc   1920
gttgtcacca ccgctaaccc attctacacc gccgccgagt tggagaagca aatcgaggcc   1980
tccggtgcgg gcattgttat cactcagagc agctacatcg agaagctcgc aggccttaac   2040
gtccagatca tcaccgttga tcagcacgtg gctaattgca tgcacatctc cgtgctgctg   2100
aacgcatgcg aagatgaatg ccctcaggtg cgtatccacc ctgacgatct ggtctgcctg   2160
ccatactcct ccggcaccac cggcttgcca aagggcgtga tgctgaccca caagtccctt   2220
gtgtcatccg tgtcccaaca ggtggacggc gaagcaccaa acttcaacat cactgtcgag   2280
gacaccctga tgtgcgtgct gcccatgttc cacatctatt ccctcaactc catcctgctg   2340
tgcggcctcc gtgtgggcgc caccctcgtt attatgccga agttcgaact gccaaagctg   2400
ttggacctga tccagcgtca caaggtgacc atgggcccat tcgtgccgcc aatcgtcctg   2460
gccatcgcaa agaacccaat cgtcgagaat tacgatctct cctccatgcg catggttatg   2520
tccggcgctg cacctctggg tcgggagctg gaggacgctt tccgtgcccg cttgccaaac   2580
gccgttctgg gccagggcta cggg atgact gaagccggcc cagtcctggc tatgtgcctc   2640
gcattcgcaa agaccccatt ctccgtgaag ccaggctcct gcggcaccgt ggtgcgcaac   2700
gctgaagtga aaatcgtcga taccgaaacc ggcatgtccc tgccatacaa ccagccaggc   2760
gagatctgca tccgcggccc acagatcatg aagggctacc tgaagaaccc agaagctacc   2820
gctaacacca tcgataagga tggcttcctg cacaccggcg atgtcgcatt catcgatgag   2880
gatgaggaga tgttcatcgt tgatcgcgtc aaggagatca tcaagttcaa gggcttccag   2940
gtgcctcctg cggagctgga agctctcctg ctgtcccaca aggagatcca ggacgctgct   3000
gtcgtgtccc gtaaggatga cgtggcgggc gaagttccag tggcattcgt ggtccgcgct   3060
accagctcca ccatcaccga ggatgaagtc aaggattaca tcgcaaagca ggtcgttttc   3120
tacaagaaga tccacaacgt atacttcgtg gattccgtgc caaagtctcc atccggcaag   3180
atcctgcgta aggatctccg taacaaggtg taaggatcta ggaggataaa gaaatgaaca   3240
ccatcaacga atacctgtcc ctggaagagt tcgaagcgat catcttcggt aaccagaagg   3300
ttaccatctc cgatgtggtt gtgaaccgtg ttaacgagtc cttcaacttc ctcaaggagt   3360
tctccggcaa caaggtcatc tacggtgtga acaccggctt cggcccaatg gcacaatacc   3420
gtattaagga atccgatcag atccagcttc agtacaatct gatccgttcc cactcttcgg   3480
gcaccggaaa accactctcc ccagtttgtg ctaaggcagc aatcttggct cgcctgaaca   3540
ccctgtccct cggtaactcc ggcgtgcatc catctgtcat caacctgatg tcggaactga   3600
tcaacaaaga cattacccca ctcatcttcg agcacggtgg cgtcggagca tccggtgacc   3660
tggttcagct ttctcacctg gctttggttc tcatcggcga aggcgaagtg ttctacaagg   3720
```

-continued

```
gtgaacgccg cccaactcca gaagttttcg aaattgaggg cttgaagcca atccaggttg   3780
agatccgtga gggcctcgcc ttgattaacg gtactagcgt gatgaccggt attggagtgg   3840
tcaacgtgta ccacgcaaag aagctgctgg actggtccct gaagtcctcc tgcgccatca   3900
atgaacttgt tcaggcttac gatgatcact tcagcgcaga gctgaaccag acgaagcgcc   3960
acaagggcca gcaggaaatc gctctgaaga tgcgtcagaa cctctctgac agcaccctga   4020
tccgcaagcg cgaggaccac ctgtattccg gcgaaaacac cgaggagatt ttcaaggaga   4080
aggtgcagga gtactactcc ctgcgctgcg ttccacagat tctcggcccg gtcctcgaaa   4140
ctatcaataa cgtcgcctcc atcctggaag atgagttcaa ctccgctaac gataacccaa   4200
tcatcgacgt gaagaaccag cacgtgtacc atggcggcaa cttccacggt gactacatct   4260
ctctggaaat ggacaagttg aaaatcgtta tcaccaaact gaccatgctt gcagaacgcc   4320
agcttaacta tcttctcaac tccaagatca acgaacttct gccaccattc gtgaacctcg   4380
gcaccctggg tttcaacttc ggcatgcagg gcgttcagtt caccgcgacc tccaccaccg   4440
cagaatctca gatgctgtcc aaccctatgt acgttcactc cattccaaac aacaacgata   4500
accaggacat cgtctccatg ggcaccaact ccgcagtgat cacgtccaag gttatcgaga   4560
acgctttcga agtcctggct atcgaaatga tcaccatcgt tcaggccatc gattacctcg   4620
gccagaagga taagatctcc tccgtttcca agaagtggta cgatgaaatc cgcaacatta   4680
tccctacctt caaggaggat caggttatgt acccattcgt gcagaaggtt aaggatcacc   4740
tcatcaacaa ctaactctag agtcgacctg caggcatgca agcttggctg ttttggcgga   4800
tgagagaaga ttttcagcct gatacagatt aaatcagaac gcagaagcgg tctgataaaa   4860
cagaatttgc ctggcggcag tagcgcggtg gtcccacctg accccatgcc gaactcagaa   4920
gtgaaacgcc gtagcgccga tggtagtgtg gggtctcccc atgcgagagt agggaactgc   4980
caggcatcaa ataaaacgaa aggctcagtc gaaagactgg gcctttcgtt ttatctgttg   5040
tttgtcggtg aacgctctcc tgagtaggac aaatccgccg ggagcggatt tgaacgttgc   5100
gaagcaacgg cccggagggt ggcgggcagg acgcccgcca taaactgcca ggcatcaaat   5160
taagcagaag gccatcctga cggatggcct ttttgcgttt ctacaaactc tttttgttta   5220
tttttctaaa tacattcaaa tatgtatccg ctcatgaatt aattccgcta gatgacgtgc   5280
ggcttcgacc tcctgggcgt ggcgcttgtt ggcgcgctcg cggctggctg cggcacgaca   5340
cgcgtctgag cagtattttg cgcgccgtcc tcgtgggtca ggccggggtg ggatcaggcc   5400
accgcagtag gcgcagctga tgcgatcctc cactactgcg cgtcctcctg gcgctgccga   5460
gcacgcagct cgtcggccag ctcttcaagg tcggccacaa gcgtttctag gtcgctcgcg   5520
gcacttgccc agtcgcgtga tgctggcgcg tctgtcgtat cgagggcgcg gaaaaatccg   5580
atcaccgttt ttaaatcgac ggcggcatcg agtgcgtcgg actccagcgc gacatcggag   5640
agatccaccg ctgatgcttc aggccagttt tggtacttcg tcgtgaaggt catgacacca   5700
ttataacgaa cgttcgttaa aaattctagc cccaattctg ataatttctt ccggcactcc   5760
tgcgaaaacc tgcgagactt cttgcccaga aaaaacgcca agcgcagcgg ttaccgcact   5820
ttttttccag gtgatttcac cctgaccagc gaagcggcac tttagtgcat gaggtgtgcc   5880
cctggtttcc cctctttgga gggttcaacc caaaaaagca cacaagcaaa aatgaaaatc   5940
atcatgagca agttggtgcg aagcagcaac gcgctagctc caaaaaggtc tccaggatct   6000
cgaggagatt tttgaggggg agggagtcga ggaagagcca gagcagaagg cggggaaccg   6060
```

-continued

```
ttctctgccg acagcgtgag ccccccttaa aaatcaggcc ggggaggaac cggggaggga   6120
tcagagctag gagcgagaca ccctaaaggg ggggaaccgt tttctgctga cggtgtttcg   6180
tttattagtt ttcagcccgt ggatagcgga gggtgagggc aagtgagagc cagagcaagg   6240
acgggacccc taaagggggg aaccgttttc tgctgacggt gtttcgttta ttagttttca   6300
gcccgtggac ggccgcgttt agcttccatt ccaagtgcct ttctgacttg ttggatgcgc   6360
ctttcactga cacctagttc gcctgcaagc tcacgagtcg agggatcagc aaccgattga   6420
gaacgggcat ccaggatcgc agttttgacg cgaagttcga gcaactcgcc tgtcatttct   6480
cggcgtttgt ttgcttccgc taatcgctgt cgcgtctcct gcgcatactt actttctggg   6540
tcagcccatc tgcgtgcatt cgatgtagct gcgccccgtc gccccatcgt cgctagagct   6600
ttccgccctc ggctgctctg cgtttccacc cgacgagcag ggacgactgg ctggccttta   6660
gccacgtagc cgcgcacacg acgcgccatc gtcaggcgat cacgcatggc gggaagatcc   6720
ggctcccggc cgtctgcacc gaccgcctgg gcaacgttgt acgccacttc atacgcgtcg   6780
atgatcttgg catcttttag gcgctcacca gcagctttga gctggtatcc cacggtcaac   6840
gcgtggcgaa acgcggtctc gtcgcgcgct cgctctggat ttgtccagag cactcgcacg   6900
ccgtcgatca ggtcgccgga cgcgtccagg gcgctcggca ggctcgcgtc caaaatcgct   6960
agcgccttgg cttctgcggt ggcgcgttgt gccgcttcaa tgcgggcgcg tccgctggaa   7020
aagtcctgct caatgtactt tttcggcttc tgtgatccgg tcatcgttcg agcaatctcc   7080
attaggtcgg ccagccgatc cacacgatca tgctggcagt gccatttata ggctgtcgga   7140
tcgtctgaga cgtgcagcgg ccaccggctc agcctatgcg aaaaagcctg gtcagcgccg   7200
aaaacacgag tcatttcttc cgtcgttgca gccagcaggc gcatatttgg gctggtttta   7260
cctgctgcgg catacaccgg gtcaatgagc cagatgagct ggcatttccc gctcagcgga   7320
ttcacgccga tccaagccgg cgctttttct aggcgtgccc atttctctaa aatcgcgtag   7380
acctgcgggt ttacgtgctc aatcttcccg ccggcctggt ggctgggcac atcgatgtca   7440
agcacgatca ccgcggcatg ttgcgcgtgc gtcagcgcaa cgtactggca ccgcgtcagc   7500
gcttttgagc cagcccggta gagctttggt tgggtttcgc cggtatccgg gtttttaatc   7560
caggcgctcg cgaaatctct tgtcttgctg ccctggaagc tttcgcgtcc caggtgagcg   7620
agcagttcgc ggcgatcttc tgccgtccag ccgcgtgagc cgcagcgcat agcttcgggg   7680
tgggtgtcga acagatcggc ggacaatttc cacgcgctag ctgtgactgt gtcctgcgga   7740
tcggctagag tcatgtcttg agtgctttct cccagctgat gactgggggt tagccgacgc   7800
cctgtgagtt cccgctcacg gggcgttcaa ctttttcagg tatttgtgca gcttatcgtg   7860
ttttcttcgt aaatgaacgc ttaactacct tgttaaacgt ggcaaatagg caggattgat   7920
ggggatctag cttcacgctg ccgcaagcac tcagggcgca agggctgcta aaggaagcgg   7980
aacacgtaga aagccagtcc gcagaaacgg tgctgacccc ggatgaatgt cagctactgg   8040
gctatctgga caagggaaaa cgcaagcgca aagagaaagc aggtagcttg cagtgggctt   8100
acatggcgat agctagactg ggcggtttta tggacagcaa gcgaaccgga attgccagct   8160
ggggcgccct ctggtaaggt tgggaagccc tgcaaagtaa actggatggc tttcttgccg   8220
ccaaggatct gatggcgcag gggatcaaga tctgatcaag agacaggatg aggatcgttt   8280
cgcatgattg aacaagatgg attgcacgca ggttctccgg ccgcttgggt ggagaggcta   8340
ttcggctatg actgggcaca acagacaatc ggctgctctg atgccgccgt gttccggctg   8400
tcagcgcagg ggcgcccggt tctttttgtc aagaccgacc tgtccggtgc cctgaatgaa   8460
```

-continued

```
ctccaagacg aggcagcgcg gctatcgtgg ctggccacga cgggcgttcc ttgcgcagct   8520
gtgctcgacg ttgtcactga agcgggaagg gactggctgc tattgggcga agtgccgggg   8580
caggatctcc tgtcatctca ccttgctcct gccgagaaag tatccatcat ggctgatgca   8640
atgcggcggc tgcatacgct tgatccggct acctgcccat tcgaccacca agcgaaacat   8700
cgcatcgagc gagcacgtac tcggatggaa gccggtcttg tcgatcagga tgatctggac   8760
gaagagcatc aggggctcgc gccagccgaa ctgttcgcca ggctcaaggc gcggatgccc   8820
gacggcgagg atctcgtcgt gacccatggc gatgcctgct tgccgaatat catggtggaa   8880
aatggccgct tttctggatt catcgactgt ggccggctgg gtgtggcgga ccgctatcag   8940
gacatagcgt tggctacccg tgatattgct gaagagcttg gcggcgaatg ggctgaccgc   9000
ttcctcgtgc tttacggtat cgccgctccc gattcgcagc gcatcgcctt ctatcgcctt   9060
cttgacgagt tcttctgagc gggactctgg ggttcgcgga atcatgacca aaatccctta   9120
acgtgagttt tcgttccact gagcgtcaga ccccgtagaa aagatcaaag gatcttcttg   9180
agatcctttt tttctgcgcg taatctgctg cttgcaaaca aaaaaaccac cgctaccagc   9240
ggtggtttgt ttgccggatc aagagctacc aactcttttt ccgaaggtaa ctggcttcag   9300
cagagcgcag ataccaaata ctgtccttct agtgtagccg tagttaggcc accacttcaa   9360
gaactctgta gcaccgccta catacctcgc tctgctaatc ctgttaccag tggctgctgc   9420
cagtggcgat aagtcgtgtc ttaccgggtt ggactcaaga cgatagttac cggataaggc   9480
gcagcggtcg ggctgaacgg ggggttcgtg cacacagccc agcttggagc gaacgaccta   9540
caccgaactg agatacctac agcgtgagct atgagaaagc gccacgcttc ccgaagggag   9600
aaaggcggac aggtatccgg taagcggcag ggtcggaaca ggagagcgca cgagggagct   9660
tccaggggga aacgcctggt atctttatag tcctgtcggg tttcgccacc tctgacttga   9720
gcgtcgattt ttgtgatgct cgtcaggggg gcggagccta tggaaaaacg ccagcaacgc   9780
ggccttttta cggttcctgg ccttttgctg gccttttgct cacatgttct ttcctgcgtt   9840
atcccctgat tctgtggata accgtattac cgcctttgag tgagctgata ccgctcgccg   9900
cagccgaacg accgagcgca gcgagtcagt gagcgaggaa gcggaagagc gcctgatgcg   9960
gtattttctc cttacgcatc tgtgcggtat ttcacaccgc atatggtgca ctctcagtac  10020
aatctgctct gatgccgcat agttaagcca gtatacactc cgctatcgct acgtgactgg  10080
gtcatggctg cgccccgaca cccgccaaca cccgctgacg cgccctgacg ggcttgtctg  10140
ctcccggcat ccgcttacag acaagctgtg accgtctccg ggagctgcat gtgtcagagg  10200
ttttcaccgt catcaccgaa acgcgcgagg cagcagatca attcgcgcgc gaaggcgaag  10260
cggcatgcat ttacgttgac accatcgaat ggtgcaaaac ctttcgcggt atggcatgat  10320
agcgcccgga agagagtcaa ttcagggtgg tgaatgtgaa accagtaacg ttatacgatg  10380
tcgcagagta tgccggtgtc tcttatcaga ccgtttcccg cgtggtgaac caggccagcc  10440
acgtttctgc gaaaacgcgg gaaaaagtgg aagcggcgat ggcggagctg aattacattc  10500
ccaaccgcgt ggcacaacaa ctggcgggca aacagtcgtt gctgattggc gttgccacct  10560
ccagtctggc cctgcacgcg ccgtcgcaaa ttgtcgcggc gattaaatct cgcgccgatc  10620
aactgggtgc cagcgtggtg gtgtcgatgg tagaacgaag cggcgtcgaa gcctgtaaag  10680
cggcggtgca caatcttctc gcgcaacgcg tcagtgggct gatcattaac tatccgctgg  10740
atgaccagga tgccattgct gtggaagctg cctgcactaa tgttccggcg ttatttcttg  10800
```

```
atgtctctga ccagacaccc atcaacagta ttattttctc ccatgaagac ggtacgcgac  10860

tgggcgtgga gcatctggtc gcattgggtc accagcaaat cgcgctgtta gcgggcccat  10920

taagttctgt ctcggcgcgt ctgcgtctgg ctggctggca taaatatctc actcgcaatc  10980

aaattcagcc gatagcggaa cgggaaggcg actggagtgc catgtccggt tttcaacaaa  11040

ccatgcaaat gctgaatgag ggcatcgttc ccactgcgat gctggttgcc aacgatcaga  11100

tggcgctggg cgcaatgcgc gccattaccg agtccgggct gcgcgttggt gcggatatct  11160

cggtagtggg atacgacgat accgaagaca gctcatgtta tatcccgccg tcaaccacca  11220

tcaaacagga ttttcgcctg ctggggcaaa ccagcgtgga ccgcttgctg caactctctc  11280

agggccaggc ggtgaagggc aatcagctgt tgcccgtctc actggtgaaa agaaaaacca  11340

ccctggcgcc caatacgcaa accgcctctc cccgcgcgtt ggccgattca ttaatgcagc  11400

tggcacgaca ggtttcccga ctggaaagcg ggcagtgagc gcaacgcaat taatgtgagt  11460

tagcgcgaat tgatctggtt tgacagctta tcat                              11494
```

<210> SEQ ID NO 30
<211> LENGTH: 4491
<212> TYPE: DNA
<213> ORGANISM: Artificial Sequence
<220> FEATURE:
<223> OTHER INFORMATION: operon RiPKS-Pp4CL-FjTAL

<400> SEQUENCE: 30

```
ggatctagga gggagatcat atggttaccg ttgaagaagt ccgcaaggct cagcgcgcag     60

aaggccctgc aaccgttctg gcaatcggca ccgcaacccc accaaactgc gtcggccagt    120

ccacctaccc agattattat ttccgtatca ccaactctga acacaagatt gaactgaagc    180

agaagttcca gaggatgtgc gataagtcca tgatcaagaa gcgttacatg taccttaccg    240

aagagatcct gaaggagaac ccatccatgt gcgagtacat ggctccatcc cttgatgctc    300

gccaggacat ggtcatcgtg gaaatcccaa agctgggcaa ggaagcagcc accaaggcaa    360

tcaaggagtg ggccagccg aagtcgaaga tcacccacct tgttttctgc accaccagcg     420

gtgtggatat gcctggcgcc gactaccagc tgatcaagct cttcggcctg cgcccatccg    480

tcaagcgcct catgatgtac cagcagggct gcttcgccgg cggcaccgtt ctgcgcctgg    540

ctaaggatct ggcagaaaac aaccgcggtg cccgcgttct cgtcgtgtgc tccgagatca    600

ccgtggtcac cttccgcggc ccatccgaca cccaccttga ctgtctggtt ggccaggcac    660

tcttcggcga tggcgtggca tccatcatcg tcggcgcaga tcctctccct gaaatcgaaa    720

agccactttt cgaacttgtc agcgcagcac agaccatcct gccagattct gagggcgcaa    780

tcgagggcca cctccgcgag gtgggtctta ccttccatct gctcgaaaac gtgccagcac    840

tgatctccaa gaacatcgaa aagtccctga acgaaacctt caagccactg gacatcatgg    900

actggaactc cctgttctgg atcgctcacc caggcggtcc ggctatcctg gatcaggtcg    960

aggctaagct gggtctgaag ccggagaagt tggaggctac cggccacatc ctgtccgaat   1020

acggcaacat gtcctccgca tgcgttctct tcatcctgga cgtggtgcgg cgcaagtccg   1080

cagccaacgg tgtgaccacc cgtatcctga gcatcggtca gatctccaag tccctgctga   1140

tcctggcatg gttcctcttc tccctggtgt aaggatctag gaggattatg agatgtcacc   1200

atcgctcctt ccccagccaa tcgtgtccga atccaccggt gaatccgtga tgaagatgtc   1260

cctccagtcc gaagtgcgcg aagcatccct ggcaaccggt gaaaaccctg aaccattcct   1320

gctggaaacc gatgctgaat cccagatcat ggaacctgtg cacgctgaag ttcacgattt   1380
```

-continued catctaccgt tctaagctgc ctgatatcga tatcccaaac cacatgcctc tggctgatta 1440
ctgcctggag aagtcctccc agtggcctga taaggtgtgc ctgatcgatg gtgtgaccgg 1500
tcgcgaacac cgctacggcg aaattgagct gtcctcccgc cgcgtggcag caggccttga 1560
taagatcggc gtgaagcagg gcgatgtcat cgcactgctc ttgcctaact gcgctgagtt 1620
cgtcctggtg ttcctgggcg cagcgaagcg cggcgccgtt gtcaccaccg ctaacccatt 1680
ctacaccgcc gccgagttgg agaagcaaat cgaggcctcc ggtgcgggca ttgttatcac 1740
tcagagcagc tacatcgaga agctcgcagg ccttaacgtc cagatcatca ccgttgatca 1800
gcacgtggct aattgcatgc acatctccgt gctgctgaac gcatgcgaag atgaatgccc 1860
tcaggtgcgt atccaccctg acgatctggt ctgcctgcca tactcctccg gcaccaccgg 1920
cttgccaaag ggcgtgatgc tgacccacaa gtcccttgtg tcatccgtgt cccaacaggt 1980
ggacggcgaa gcaccaaact tcaacatcac tgtcgaggac accctgatgt gcgtgctgcc 2040
catgttccac atctattccc tcaactccat cctgctgtgc ggcctccgtg tgggcgccac 2100
cctcgttatt atgccgaagt tcgaactgcc aaagctgttg gacctgatcc agcgtcacaa 2160
ggtgaccatg ggcccattcg tgccgccaat cgtcctggcc atcgcaaaga acccaatcgt 2220
cgagaattac gatctctcct ccatgcgcat ggttatgtcc ggcgctgcac ctctgggtcg 2280
ggagctggag gacgctttcc gtgcccgctt gccaaacgcc gttctgggcc agggctacgg 2340
gatgactgaa gccggcccag tcctggctat gtgcctcgca ttcgcaaaga ccccattctc 2400
cgtgaagcca ggctcctgcg gcaccgtggt gcgcaacgct gaagtgaaaa tcgtcgatac 2460
cgaaaccggc atgtccctgc catacaacca gccaggcgag atctgcatcc gcggcccaca 2520
gatcatgaag ggctacctga agaacccaga agctaccgct aacaccatcg ataaggatgg 2580
cttcctgcac accggcgatg tcgcattcat cgatgaggat gaggagatgt tcatcgttga 2640
tcgcgtcaag gagatcatca agttcaaggg cttccaggtg cctcctgcgg agctggaagc 2700
tctcctgctg tcccacaagg agatccagga cgctgctgtc gtgtcccgta aggatgacgt 2760
ggcgggcgaa gttccagtgg cattcgtggt ccgcgctacc agctccacca tcaccgagga 2820
tgaagtcaag gattacatcg caaagcaggt cgttttctac aagaagatcc acaacgtata 2880
cttcgtggat tccgtgccaa agtctccatc cggcaagatc ctgcgtaagg atctccgtaa 2940
caaggtgtaa ggatctagga ggataaagaa atgaacacca tcaacgaata cctgtccctg 3000
gaagagttcg aagcgatcat cttcggtaac cagaaggtta ccatctccga tgtggttgtg 3060
aaccgtgtta acgagtcctt caacttcctc aaggagttct ccggcaacaa ggtcatctac 3120
ggtgtgaaca ccggcttcgg cccaatggca caataccgta ttaaggaatc cgatcagatc 3180
cagcttcagt acaatctgat ccgttcccac tcttcgggca ccggaaaacc actctcccca 3240
gtttgtgcta aggcagcaat cttggctcgc ctgaacaccc tgtccctcgg taactccggc 3300
gtgcatccat ctgtcatcaa cctgatgtcg gaactgatca acaaagacat taccccactc 3360
atcttcgagc acggtggcgt cggagcatcc ggtgacctgg ttcagctttc tcacctggct 3420
ttggttctca tcggcgaagg cgaagtgttc tacaagggtg aacgccgccc aactccagaa 3480
gttttcgaaa ttgagggctt gaagccaatc caggttgaga tccgtgaggg cctcgccttg 3540
attaacggta ctagcgtgat gaccggtatt ggagtggtca acgtgtacca cgcaaagaag 3600
ctgctggact ggtccctgaa gtcctcctgc gccatcaatg aacttgttca ggcttacgat 3660
gatcacttca gcgcagagct gaaccagacg aagcgccaca agggccagca ggaaatcgct 3720

-continued

```
ctgaagatgc gtcagaacct ctctgacagc accctgatcc gcaagcgcga ggaccacctg   3780

tattccggcg aaaacaccga ggagattttc aaggagaagg tgcaggagta ctactccctg   3840

cgctgcgttc cacagattct cggcccggtc ctcgaaacta tcaataacgt cgcctccatc   3900

ctggaagatg agttcaactc cgctaacgat aacccaatca tcgacgtgaa gaaccagcac   3960

gtgtaccatg gcggcaactt ccacggtgac tacatctctc tggaaatgga caagttgaaa   4020

atcgttatca ccaaactgac catgcttgca gaacgccagc ttaactatct tctcaactcc   4080

aagatcaacg aacttctgcc accattcgtg aacctcggca ccctgggttt caacttcggc   4140

atgcagggcg ttcagttcac cgcgacctcc accaccgcag aatctcagat gctgtccaac   4200

cctatgtacg ttcactccat tccaaacaac aacgataacc aggacatcgt ctccatgggc   4260

accaactccg cagtgatcac gtccaaggtt atcgagaacg ctttcgaagt cctggctatc   4320

gaaatgatca ccatcgttca ggccatcgat tacctcggcc agaaggataa gatctcctcc   4380

gtttccaaga agtggtacga tgaaatccgc aacattatcc ctaccttcaa ggaggatcag   4440

gttatgtacc cattcgtgca gaaggttaag gatcacctca tcaacaacta a            4491
```

```
<210> SEQ ID NO 31
<211> LENGTH: 11506
<212> TYPE: DNA
<213> ORGANISM: Artificial Sequence
<220> FEATURE:
<223> OTHER INFORMATION: plasmid RiPKS-Pp4CL-SeSam8-pECXK (pECXK_F)

<400> SEQUENCE: 31
```

```
cgactgcacg gtgcaccaat gcttctggcg tcaggcagcc atcggaagct gtggtatggc     60

tgtgcaggtc gtaaatcact gcataattcg tgtcgctcaa ggcgcactcc cgttctggat    120

aatgtttttt gcgccgacat cataacggtt ctggcaaata ttctgaaatg agctgttgac    180

aattaatcat ccggctcgta taatgtgtgg aattgtgagc ggataacaat ttcacacagg    240

aaacagacca tggaattcga gctggatcta ggagggagat catatggtta ccgttgaaga    300

agtccgcaag gctcagcgcg cagaaggccc tgcaaccgtt ctggcaatcg gcaccgcaac    360

cccaccaaac tgcgtcggcc agtccaccta cccagattat tatttccgta tcaccaactc    420

tgaacacaag attgaactga agcagaagtt ccagaggatg tgcgataagt ccatgatcaa    480

gaagcgttac atgtacctta ccgaagagat cctgaaggag aacccatcca tgtgcgagta    540

catggctcca tcccttgatg ctcgccagga catggtcatc gtggaaatcc caaagctggg    600

caaggaagca gccaccaagg caatcaagga gtggggccag ccgaagtcga agatcaccca    660

ccttgttttc tgcaccacca gcggtgtgga tatgcctggc gccgactacc agctgatcaa    720

gctcttcggc ctgcgcccat ccgtcaagcg cctcatgatg taccagcagg gctgcttcgc    780

cggcggcacc gttctgcgcc tggctaagga tctggcagaa aacaaccgcg gtgcccgcgt    840

tctcgtcgtg tgctccgaga tcaccgtggt caccttccgc ggcccatccg acacccacct    900

tgactgtctg gttggccagg cactcttcgg cgatggcgtg gcatccatca tcgtcggcgc    960

agatcctctc cctgaaatcg aaaagccact tttcgaactt gtcagcgcag cacagaccat   1020

cctgccagat tctgagggcg caatcgaggg ccacctccgc gaggtgggtc ttaccttcca   1080

tctgctcgaa aacgtgccag cactgatctc caagaacatc gaaaagtccc tgaacgaaac   1140

cttcaagcca ctggacatca tggactggaa ctccctgttc tggatcgctc acccaggcgg   1200

tccggctatc ctggatcagg tcgaggctaa gctgggtctg aagccggaga agttggaggc   1260

taccggccac atcctgtccg aatacggcaa catgtcctcc gcatgcgttc tcttcatcct   1320
```

-continued

```
ggacgtggtg cggcgcaagt ccgcagccaa cggtgtgacc acccgtatcc tgagcatcgg   1380
tcagatctcc aagtccctgc tgatcctggc atggttcctc ttctccctgg tgtaaggatc   1440
taggaggatt atgagatgtc accatcgctc cttccccagc caatcgtgtc cgaatccacc   1500
ggtgaatccg tgatgaagat gtccctccag tccgaagtgc gcgaagcatc cctggcaacc   1560
ggtgaaaacc ctgaaccatt cctgctggaa accgatgctg aatcccagat catggaacct   1620
gtgcacgctg aagttcacga tttcatctac cgttctaagc tgcctgatat cgatatccca   1680
aaccacatgc ctctggctga ttactgcctg gagaagtcct cccagtggcc tgataaggtg   1740
tgcctgatcg atggtgtgac cggtcgcgaa caccgctacg gcgaaattga gctgtcctcc   1800
cgccgcgtgg cagcaggcct tgataagatc ggcgtgaagc agggcgatgt catcgcactg   1860
ctcttgccta actgcgctga gttcgtcctg gtgttcctgg gcgcagcgaa gcgcggcgcc   1920
gttgtcacca ccgctaaccc attctacacc gccgccgagt tggagaagca aatcgaggcc   1980
tccggtgcgg gcattgttat cactcagagc agctacatcg agaagctcgc aggccttaac   2040
gtccagatca tcaccgttga tcagcacgtg gctaattgca tgcacatctc cgtgctgctg   2100
aacgcatgcg aagatgaatg ccctcaggtg cgtatccacc ctgacgatct ggtctgcctg   2160
ccatactcct ccggcaccac cggcttgcca aagggcgtga tgctgaccca caagtccctt   2220
gtgtcatccg tgtcccaaca ggtggacggc gaagcaccaa acttcaacat cactgtcgag   2280
gacaccctga tgtgcgtgct gcccatgttc cacatctatt ccctcaactc catcctgctg   2340
tgcggcctcc gtgtgggcgc caccctcgtt attatgccga agttcgaact gccaaagctg   2400
ttggacctga tccagcgtca caaggtgacc atgggcccat tcgtgccgcc aatcgtcctg   2460
gccatcgcaa agaacccaat cgtcgagaat tacgatctct cctccatgcg catggttatg   2520
tccggcgctg cacctctggg tcgggagctg gaggacgctt tccgtgcccg cttgccaaac   2580
gccgttctgg gccagggcta cgggatgact gaagccggcc cagtcctggc tatgtgcctc   2640
gcattcgcaa agaccccatt ctccgtgaag ccaggctcct gcggcaccgt ggtgcgcaac   2700
gctgaagtga aaatcgtcga taccgaaacc ggcatgtccc tgccatacaa ccagccaggc   2760
gagatctgca tccgcggccc acagatcatg aagggctacc tgaagaaccc agaagctacc   2820
gctaacacca tcgataagga tggcttcctg cacaccggcg atgtcgcatt catcgatgag   2880
gatgaggaga tgttcatcgt tgatcgcgtc aaggagatca tcaagttcaa gggcttccag   2940
gtgcctcctg cggagctgga agctctcctg ctgtcccaca aggagatcca ggacgctgct   3000
gtcgtgtccc gtaaggatga cgtggcgggc gaagttccag tggcattcgt ggtccgcgct   3060
accagctcca ccatcaccga ggatgaagtc aaggattaca tcgcaaagca ggtcgttttc   3120
tacaagaaga tccacaacgt atacttcgtg gattccgtgc caaagtctcc atccggcaag   3180
atcctgcgta aggatctccg taacaaggtg taaggatcta ggaggataaa gaaatgaccc   3240
aggtcgtgga gcgccaggct gatcgtctgt ccagccgcga gtacctggca cgcgttgttc   3300
gttccgcagg ctgggacgca ggcctcacca gctgcaccga tgaagaaatc gtgcgcatgg   3360
gtgcatccgc acgcaccatt gaggaatacc tgaagtctga taagccgatc tacggcctca   3420
cccagggctt cggtccactg gtcctgttcg atgcagattc cgaactggaa cagggcggct   3480
ctctcatctc ccatctgggc accggccagg gtgcaccgct tgcaccggaa gtgtcccgcc   3540
tgattctgtg gctccgcatc caaaacatgc gcaagggcta ttcggctgtc agtcctgtgt   3600
tctggcaaaa actggccgac ctctggaaca agggcttcac ccctgctatc cctcgccacg   3660
```

-continued

```
gcaccgtgtc cgccagcggc gatctccagc ctctggcaca cgctgccctg gcttttaccg   3720
gcgtgggcga ggcatggacc cgtgatgcag acggccgttg gtccaccgtg ccagccgtgg   3780
acgcattagc agcactgggt gcagagccgt tcgattggcc agtgcgcgag gctttggcct   3840
tcgtgaacgg tacgggcgca tcactcgcgg tggcagttct caaccacaga tccgctctcc   3900
gtctcgtacg agcatgtgca gtcttgtctg cccgtttggc taccttgcta ggagctaatc   3960
ctgaacacta cgatgtcggc cacggagtcg caaggggaca agttggccag ctgaccgcgg   4020
cggaatggat tcggcaggga ctaccacgcg gcatggtccg agacggttcg cgccctcttc   4080
aagaaccata cagcttgcgc tgtgcccccc aggtccttgg cgcggtgctg gaccagctgg   4140
atggtgcagg cgatgttctg gcccgcgaag tggatggctg ccaggacaat cctatcacct   4200
acgagggcga actgctgcac ggcggtaact tccacgctat gccagtcggc ttcgcatccg   4260
accagatcgg tctggcgatg cacatggcag cttatctggc tgaacgccag ctcggcctgc   4320
tggtgagccc ggtgaccaac ggcgacctgc caccaatgct gaccccacgc gctggacgcg   4380
gtgccggcct ggcgggcgtt cagatctccg caacctcctt cgtctctcgc atccgccagc   4440
tggtgttccc agctagcctc accaccctcc caaccaacgg ctggaaccag gaccatgtcc   4500
caatggctct gaacggcgca aacagcgtgt tcgaagctct tgaactgggt tggctgaccg   4560
tgggtagcct ggcagtcggc gtggcccagc tcgctgcaat gaccggccac gcagctgagg   4620
gcgtgtgggc cgagttggca ggcatctgcc caccactgga tgctgaccgc ccactgggcg   4680
cggaggtccg cgctgctcgc gatctcctct ccgcacacgc tgaccagctg ctcgttgacg   4740
aggctgatgg caaagacttc ggctaactct agagtcgacc tgcaggcatg caagcttggc   4800
tgttttggcg gatgagagaa gattttcagc ctgatacaga ttaaatcaga acgcagaagc   4860
ggtctgataa aacagaattt gcctggcggc agtagcgcgg tggtcccacc tgaccccatg   4920
ccgaactcag aagtgaaacg ccgtagcgcc gatggtagtg tggggtctcc ccatgcgaga   4980
gtagggaact gccaggcatc aaataaaacg aaaggctcag tcgaaagact gggcctttcg   5040
ttttatctgt tgtttgtcgg tgaacgctct cctgagtagg acaaatccgc cgggagcgga   5100
tttgaacgtt gcgaagcaac ggcccggagg gtggcgggca ggacgcccgc cataaactgc   5160
caggcatcaa attaagcaga aggccatcct gacggatggc ctttttgcgt ttctacaaac   5220
tctttttgtt tatttttcta aatacattca aatatgtatc cgctcatgaa ttaattccgc   5280
tagatgacgt gcggcttcga cctcctgggc gtggcgcttg ttggcgcgct cgcggctggc   5340
tgcggcacga cacgcgtctg agcagtattt tgcgcgccgt cctcgtgggt caggccgggg   5400
tgggatcagg ccaccgcagt aggcgcagct gatgcgatcc tccactactg cgcgtcctcc   5460
tggcgctgcc gagcacgcag ctcgtcggcc agctcttcaa ggtcggccac aagcgtttct   5520
aggtcgctcg cggcacttgc ccagtcgcgt gatgctggcg cgtctgtcgt atcgagggcg   5580
cggaaaaatc cgatcaccgt ttttaaatcg acggcggcat cgagtgcgtc ggactccagc   5640
gcgacatcgg agagatccac cgctgatgct tcaggccagt tttggtactt cgtcgtgaag   5700
gtcatgacac cattataacg aacgttcgtt aaaaattcta gccccaattc tgataatttc   5760
ttccggcact cctgcgaaaa cctgcgagac ttcttgccca gaaaaaacgc caagcgcagc   5820
ggttaccgca ctttttttcc aggtgatttc accctgacca gcgaagcggc actttagtgc   5880
atgaggtgtg cccctggttt cccctctttg gagggttcaa cccaaaaaag cacacaagca   5940
aaaatgaaaa tcatcatgag caagttggtg cgaagcagca acgcgctagc tccaaaaagg   6000
tctccaggat ctcgaggaga tttttgaggg ggagggagtc gaggaagagc cagagcagaa   6060
```

```
ggcggggaac cgttctctgc cgacagcgtg agcccccctt aaaaatcagg ccggggagga   6120
accggggagg gatcagagct aggagcgaga caccctaaag ggggggaacc gttttctgct   6180
gacggtgttt cgtttattag ttttcagccc gtggatagcg gagggtgagg gcaagtgaga   6240
gccagagcaa ggacgggacc cctaaagggg ggaaccgttt tctgctgacg gtgtttcgtt   6300
tattagtttt cagcccgtgg acggccgcgt ttagcttcca ttccaagtgc ctttctgact   6360
tgttggatgc gcctttcact gacacctagt tcgcctgcaa gctcacgagt cgagggatca   6420
gcaaccgatt gagaacgggc atccaggatc gcagttttga cgcgaagttc gagcaactcg   6480
cctgtcattt ctcggcgttt gtttgcttcc gctaatcgct gtcgcgtctc ctgcgcatac   6540
ttactttctg ggtcagccca tctgcgtgca ttcgatgtag ctgcgccccg tcgccccatc   6600
gtcgctagag ctttccgccc tcggctgctc tgcgtttcca cccgacgagc agggacgact   6660
ggctggcctt tagccacgta gccgcgcaca cgacgcgcca tcgtcaggcg atcacgcatg   6720
gcgggaagat ccggctcccg gccgtctgca ccgaccgcct gggcaacgtt gtacgccact   6780
tcatacgcgt cgatgatctt ggcatctttt aggcgctcac cagcagcttt gagctggtat   6840
cccacggtca acgcgtggcg aaacgcggtc tcgtcgcgcg ctcgctctgg atttgtccag   6900
agcactcgca cgccgtcgat caggtcgccg gacgcgtcca gggcgctcgg caggctcgcg   6960
tccaaaatcg ctagcgcctt ggcttctgcg gtggcgcgtt gtgccgcttc aatgcgggcg   7020
cgtccgctgg aaaagtcctg ctcaatgtac tttttcggct tctgtgatcc ggtcatcgtt   7080
cgagcaatct ccattaggtc ggccagccga tccacacgat catgctggca gtgccattta   7140
taggctgtcg gatcgtctga gacgtgcagc ggccaccggc tcagcctatg cgaaaaagcc   7200
tggtcagcgc cgaaaacacg agtcatttct tccgtcgttg cagccagcag gcgcatattt   7260
gggctggttt tacctgctgc ggcatacacc gggtcaatga gccagatgag ctggcatttc   7320
ccgctcagcg gattcacgcc gatccaagcc ggcgcttttt ctaggcgtgc ccatttctct   7380
aaaatcgcgt agacctgcgg gtttacgtgc tcaatcttcc cgccggcctg gtggctgggc   7440
acatcgatgt caagcacgat caccgcggca tgttgcgcgt gcgtcagcgc aacgtactgg   7500
caccgcgtca gcgcttttga gccagcccgg tagagctttg gttgggtttc gccggtatcc   7560
gggtttttaa tccaggcgct cgcgaaatct cttgtcttgc tgccctggaa gctttcgcgt   7620
cccaggtgag cgagcagttc gcggcgatct tctgccgtcc agccgcgtga gccgcagcgc   7680
atagcttcgg ggtgggtgtc gaacagatcg gcggacaatt tccacgcgct agctgtgact   7740
gtgtcctgcg gatcggctag agtcatgtct tgagtgcttt ctcccagctg atgactgggg   7800
gttagccgac gccctgtgag ttcccgctca cggggcgttc aactttttca ggtatttgtg   7860
cagcttatcg tgtttcttc gtaaatgaac gcttaactac cttgttaaac gtggcaaata   7920
ggcaggattg atggggatct agcttcacgc tgccgcaagc actcagggcg caagggctgc   7980
taaaggaagc ggaacacgta gaaagccagt ccgcagaaac ggtgctgacc ccggatgaat   8040
gtcagctact gggctatctg gacaagggaa aacgcaagcg caaagagaaa gcaggtagct   8100
tgcagtgggc ttacatggcg atagctagac tgggcggttt tatggacagc aagcgaaccg   8160
gaattgccag ctggggcgcc ctctggtaag gttgggaagc cctgcaaagt aaactggatg   8220
gctttcttgc cgccaaggat ctgatggcgc aggggatcaa gatctgatca agagacagga   8280
tgaggatcgt ttcgcatgat tgaacaagat ggattgcacg caggttctcc ggccgcttgg   8340
gtggagaggc tattcggcta tgactgggca caacagacaa tcggctgctc tgatgccgcc   8400
```

gtgttccggc tgtcagcgca ggggcgcccg gttctttttg tcaagaccga cctgtccggt 8460
gccctgaatg aactccaaga cgaggcagcg cggctatcgt ggctggccac gacgggcgtt 8520
ccttgcgcag ctgtgctcga cgttgtcact gaagcgggaa gggactggct gctattgggc 8580
gaagtgccgg ggcaggatct cctgtcatct caccttgctc ctgccgagaa agtatccatc 8640
atggctgatg caatgcggcg gctgcatacg cttgatccgg ctacctgccc attcgaccac 8700
caagcgaaac atcgcatcga gcgagcacgt actcggatgg aagccggtct tgtcgatcag 8760
gatgatctgg acgaagagca tcaggggctc gcgccagccg aactgttcgc caggctcaag 8820
gcgcggatgc ccgacggcga ggatctcgtc gtgacccatg gcgatgcctg cttgccgaat 8880
atcatggtgg aaaatggccg cttttctgga ttcatcgact gtggccggct gggtgtggcg 8940
gaccgctatc aggacatagc gttggctacc cgtgatattg ctgaagagct tggcggcgaa 9000
tgggctgacc gcttcctcgt gctttacggt atcgccgctc ccgattcgca gcgcatcgcc 9060
ttctatcgcc ttcttgacga gttcttctga gcgggactct ggggttcgcg gaatcatgac 9120
caaaatccct taacgtgagt tttcgttcca ctgagcgtca gaccccgtag aaaagatcaa 9180
aggatcttct tgagatcctt tttttctgcg cgtaatctgc tgcttgcaaa caaaaaaacc 9240
accgctacca gcggtggttt gtttgccgga tcaagagcta ccaactcttt ttccgaaggt 9300
aactggcttc agcagagcgc agataccaaa tactgtcctt ctagtgtagc cgtagttagg 9360
ccaccacttc aagaactctg tagcaccgcc tacatacctc gctctgctaa tcctgttacc 9420
agtggctgct gccagtggcg ataagtcgtg tcttaccggg ttggactcaa gacgatagtt 9480
accggataag gcgcagcggt cgggctgaac ggggggttcg tgcacacagc ccagcttgga 9540
gcgaacgacc tacaccgaac tgagatacct acagcgtgag ctatgagaaa gcgccacgct 9600
tcccgaaggg agaaaggcgg acaggtatcc ggtaagcggc agggtcggaa caggagagcg 9660
cacgagggag cttccagggg gaaacgcctg gtatctttat agtcctgtcg ggtttcgcca 9720
cctctgactt gagcgtcgat ttttgtgatg ctcgtcaggg gggcggagcc tatggaaaaa 9780
cgccagcaac gcggcctttt tacggttcct ggccttttgc tggccttttg ctcacatgtt 9840
ctttcctgcg ttatcccctg attctgtgga taaccgtatt accgcctttg agtgagctga 9900
taccgctcgc cgcagccgaa cgaccgagcg cagcgagtca gtgagcgagg aagcggaaga 9960
gcgcctgatg cggtattttc tccttacgca tctgtgcggt atttcacacc gcatatggtg 10020
cactctcagt acaatctgct ctgatgccgc atagttaagc cagtatacac tccgctatcg 10080
ctacgtgact gggtcatggc tgcgccccga cacccgccaa cacccgctga cgcgccctga 10140
cgggcttgtc tgctcccggc atccgcttac agacaagctg tgaccgtctc cgggagctgc 10200
atgtgtcaga ggttttcacc gtcatcaccg aaacgcgcga ggcagcagat caattcgcgc 10260
gcgaaggcga agcggcatgc atttacgttg acaccatcga atggtgcaaa acctttcgcg 10320
gtatggcatg atagcgcccg gaagagagtc aattcagggt ggtgaatgtg aaaccagtaa 10380
cgttatacga tgtcgcagag tatgccggtg tctcttatca gaccgtttcc cgcgtggtga 10440
accaggccag ccacgtttct gcgaaaacgc gggaaaaagt ggaagcggcg atggcggagc 10500
tgaattacat tcccaaccgc gtggcacaac aactggcggg caaacagtcg ttgctgattg 10560
gcgttgccac ctccagtctg gccctgcacg cgccgtcgca aattgtcgcg gcgattaaat 10620
ctcgcgccga tcaactgggt gccagcgtgg tggtgtcgat ggtagaacga agcggcgtcg 10680
aagcctgtaa agcggcggtg cacaatcttc tcgcgcaacg cgtcagtggg ctgatcatta 10740
actatccgct ggatgaccag gatgccattg ctgtggaagc tgcctgcact aatgttccgg 10800
cgttatttct tgatgtctct gaccagacac ccatcaacag tattattttc tcccatgaag 10860
acggtacgcg actgggcgtg gagcatctgg tcgcattggg tcaccagcaa atcgcgctgt 10920
tagcgggccc attaagttct gtctcggcgc gtctgcgtct ggctggctgg cataaatatc 10980
tcactcgcaa tcaaattcag ccgatagcgg aacgggaagg cgactggagt gccatgtccg 11040
gttttcaaca aaccatgcaa atgctgaatg agggcatcgt tcccactgcg atgctggttg 11100
ccaacgatca gatggcgctg ggcgcaatgc gcgccattac cgagtccggg ctgcgcgttg 11160
gtgcggatat ctcggtagtg ggatacgacg ataccgaaga cagctcatgt tatatcccgc 11220
cgtcaaccac catcaaacag gattttcgcc tgctggggca aaccagcgtg gaccgcttgc 11280
tgcaactctc tcagggccag gcggtgaagg gcaatcagct gttgcccgtc tcactggtga 11340
aaagaaaaac caccctggcg cccaatacgc aaaccgcctc tccccgcgcg ttggccgatt 11400
cattaatgca gctggcacga caggtttccc gactggaaag cgggcagtga gcgcaacgca 11460
attaatgtga gttagcgcga attgatctgg tttgacagct tatcat 11506

<210> SEQ ID NO 32
<211> LENGTH: 4503
<212> TYPE: DNA
<213> ORGANISM: Artificial Sequence
<220> FEATURE:
<223> OTHER INFORMATION: operon RiPKS-Pp4CL-SeSam8

<400> SEQUENCE: 32
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatgtcacc 1200
atcgctcctt ccccagccaa tcgtgtccga atccaccggt gaatccgtga tgaagatgtc 1260
cctccagtcc gaagtgcgcg aagcatccct ggcaaccggt gaaaaccctg aaccattcct 1320

-continued

```
gctggaaacc gatgctgaat cccagatcat ggaacctgtg cacgctgaag ttcacgattt   1380
catctaccgt tctaagctgc ctgatatcga tatcccaaac cacatgcctc tggctgatta   1440
ctgcctggag aagtcctccc agtggcctga taaggtgtgc ctgatcgatg gtgtgaccgg   1500
tcgcgaacac cgctacggcg aaattgagct gtcctcccgc cgcgtggcag caggccttga   1560
taagatcggc gtgaagcagg gcgatgtcat cgcactgctc ttgcctaact gcgctgagtt   1620
cgtcctggtg ttcctgggcg cagcgaagcg cggcgccgtt gtcaccaccg ctaacccatt   1680
ctacaccgcc gccgagttgg agaagcaaat cgaggcctcc ggtgcgggca ttgttatcac   1740
tcagagcagc tacatcgaga agctcgcagg ccttaacgtc cagatcatca ccgttgatca   1800
gcacgtggct aattgcatgc acatctccgt gctgctgaac gcatgcgaag atgaatgccc   1860
tcaggtgcgt atccaccctg acgatctggt ctgcctgcca tactcctccg gcaccaccgg   1920
cttgccaaag ggcgtgatgc tgacccacaa gtcccttgtg tcatccgtgt cccaacaggt   1980
ggacggcgaa gcaccaaact tcaacatcac tgtcgaggac accctgatgt gcgtgctgcc   2040
catgttccac atctattccc tcaactccat cctgctgtgc ggcctccgtg tgggcgccac   2100
cctcgttatt atgccgaagt tcgaactgcc aaagctgttg gacctgatcc agcgtcacaa   2160
ggtgaccatg ggcccattcg tgccgccaat cgtcctggcc atcgcaaaga acccaatcgt   2220
cgagaattac gatctctcct ccatgcgcat ggttatgtcc ggcgctgcac ctctgggtcg   2280
ggagctggag gacgctttcc gtgcccgctt gccaaacgcc gttctgggcc agggctacgg   2340
gatgactgaa gccggcccag tcctggctat gtgcctcgca ttcgcaaaga ccccattctc   2400
cgtgaagcca ggctcctgcg gcaccgtggt gcgcaacgct gaagtgaaaa tcgtcgatac   2460
cgaaaccggc atgtccctgc catacaacca gccaggcgag atctgcatcc gcggcccaca   2520
gatcatgaag ggctacctga agaacccaga agctaccgct aacaccatcg ataaggatgg   2580
cttcctgcac accggcgatg tcgcattcat cgatgaggat gaggagatgt tcatcgttga   2640
tcgcgtcaag gagatcatca agttcaaggg cttccaggtg cctcctgcgg agctggaagc   2700
tctcctgctg tcccacaagg agatccagga cgctgctgtc gtgtcccgta aggatgacgt   2760
ggcgggcgaa gttccagtgg cattcgtggt ccgcgctacc agctccacca tcaccgagga   2820
tgaagtcaag gattacatcg caaagcaggt cgttttctac aagaagatcc acaacgtata   2880
cttcgtggat tccgtgccaa agtctccatc cggcaagatc ctgcgtaagg atctccgtaa   2940
caaggtgtaa ggatctagga ggataaagaa atgacccagg tcgtggagcg ccaggctgat   3000
cgtctgtcca gccgcgagta cctggcacgc gttgttcgtt ccgcaggctg ggacgcaggc   3060
ctcaccagct gcaccgatga agaaatcgtg cgcatgggtg catccgcacg caccattgag   3120
gaatacctga agtctgataa gccgatctac ggcctcaccc agggcttcgg tccactggtc   3180
ctgttcgatg cagattccga actggaacag ggcggctctc tcatctccca tctgggcacc   3240
ggccagggtg caccgcttgc accggaagtg tcccgcctga ttctgtggct ccgcatccaa   3300
aacatgcgca agggctattc ggctgtcagt cctgtgttct ggcaaaaact ggccgacctc   3360
tggaacaagg gcttcacccc tgctatccct cgccacggca ccgtgtccgc cagcggcgat   3420
ctccagcctc tggcacacgc tgccctggct tttaccggcg tgggcgaggc atggacccgt   3480
gatgcagacg gccgttggtc caccgtgcca gccgtggacg cattagcagc actgggtgca   3540
gagccgttcg attggccagt gcgcgaggct ttggccttcg tgaacggtac gggcgcatca   3600
ctcgcggtgg cagttctcaa ccacagatcc gctctccgtc tcgtacgagc atgtgcagtc   3660
ttgtctgccc gtttggctac cttgctagga gctaatcctg aacactacga tgtcggccac   3720
```

ggagtcgcaa ggggacaagt tggccagctg accgcggcgg aatggattcg gcagggacta 3780
ccacgcggca tggtccgaga cggttcgcgc cctcttcaag aaccatacag cttgcgctgt 3840
gccccccagg tccttggcgc ggtgctggac cagctggatg gtgcaggcga tgttctggcc 3900
cgcgaagtgg atggctgcca ggacaatcct atcacctacg agggcgaact gctgcacggc 3960
ggtaacttcc acgctatgcc agtcggcttc gcatccgacc agatcggtct ggcgatgcac 4020
atggcagctt atctggctga acgccagctc ggcctgctgg tgagcccggt gaccaacggc 4080
gacctgccac caatgctgac cccacgcgct ggacgcggtg ccggcctggc gggcgttcag 4140
atctccgcaa cctccttcgt ctctcgcatc cgccagctgg tgttcccagc tagcctcacc 4200
accctcccaa ccaacggctg gaaccaggac catgtcccaa tggctctgaa cggcgcaaac 4260
agcgtgttcg aagctcttga actgggttgg ctgaccgtgg gtagcctggc agtcggcgtg 4320
gcccagctcg ctgcaatgac cggccacgca gctgagggcg tgtgggccga gttggcaggc 4380
atctgcccac cactggatgc tgaccgccca ctgggcgcgg aggtccgcgc tgctcgcgat 4440
ctcctctccg cacacgctga ccagctgctc gttgacgagg ctgatggcaa agacttcggc 4500
taa 4503

<210> SEQ ID NO 33
<211> LENGTH: 11380
<212> TYPE: DNA
<213> ORGANISM: Artificial Sequence
<220> FEATURE:
<223> OTHER INFORMATION: plasmid RiPKS-Sc4CL-RcTAL-pECXK (pECXK_G)

<400> SEQUENCE: 33
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200

-continued

```
tccggctatc ctggatcagg tcgaggctaa gctgggtctg aagccggaga agttggaggc   1260
taccggccac atcctgtccg aatacggcaa catgtcctcc gcatgcgttc tcttcatcct   1320
ggacgtggtg cggcgcaagt ccgcagccaa cggtgtgacc acccgtatcc tgagcatcgg   1380
tcagatctcc aagtccctgc tgatcctggc atggttcctc ttctccctgg tgtaaggatc   1440
taggaggatt atgagatgtt ccgttccgag tacgcagatg tgcctccagt ggacctccct   1500
atccacgatg ctgtcctggg tggcgcggcc gcattcggca gcacccccagc tctgatcgat   1560
ggcaccgatg gcaccaccct gacctacgaa caggtcgatc gcttccaccg tcgcgtcgct   1620
gctgctctgg cggaaaccgg cgtgcgcaag ggcgatgtcc tggccctgca ctctccaaac   1680
accgttgctt tccctctggc attctacgct gcaacccgcg ctggtgcatc cgtgaccact   1740
gttcaccctc tcgctaccgc agaagagttt gctaagcagc tgaaggattc ggctgcacgt   1800
tggatcgtca ccgtttcccc actgctgtcc accgcacgcc gcgccgcaga gttggcaggc   1860
ggcgtgcagg aaattttggt ctgcgattct gctccaggtc accgttctct cgtcgatatg   1920
ctggctagca ccgcacccga accatccgtc gctatcgatc cagcagaaga tgtggctgcc   1980
cttccgtact cctctggcac caccggcacc ccaaagggtg tgatgctgac ccaccgccag   2040
attgcaacca acctggctca gctggaacct tccatgccat ccgctccagg tgaccgggtg   2100
ctggctgttc tgccattctt ccacatctac ggcttgaccg cactcatgaa cgctcctttg   2160
cgcctgggtg ctaccgtggt ggtgctccct cgcttcgacc tggagcagtt ccttgcagcc   2220
atccagaacc accgtatcac cagtttgtac gtcgccccac caatcgtttt ggcactggct   2280
aagcaccctc tggtggccga ctatgacctt tcctccctcc gttacatcgt gagcgccgcg   2340
gcaccgctcg acgcgcgcct ggcagccgct tgttcccagc gtctgggcct gcccccggtg   2400
gggcaagcgt acggtatgac cgagctgtct cctggcaccc acgtcgtgcc gctcgatgca   2460
atggcagatg ccccacccgg caccgtgggt cgcctgatag ctggcaccga gatgcgcatc   2520
gtgtccctga ccgacccagg caccgacctg ccggcaggcg aatccggcga aatcctgatc   2580
cgcggccccc agattatgaa gggctacctc ggccgcccag atgctaccgc agcaatgatc   2640
gatgaggagg gctggctgca caccggcgat gtgggccacg tggacgctga tggttggttg   2700
ttcgtcgtgg atcgcgttaa ggagctgatc aagtacaagg gtttccaggt tgctcccgcg   2760
gagcttgaag cacacttgct cacccaccca ggtgttgcag atgcagctgt cgtcggcgca   2820
tacgacgacg acggtaacga ggtgccgcac gcctttgtgg tccgccagcc ggctgcacca   2880
ggcctcgcgg agtccgaaat catgatgtac gtggctgaac gcgttgctcc atacaagcgc   2940
gtgcgccgcg tgaccttcgt cgatgccgtg ccacgcgcag catccggcaa gatcctgcgt   3000
cgccagctgc gcgagccacg ctaaggatct aggaggataa agaaatgacc ctgcaatccc   3060
agactgcaaa ggactgcctg gcgctggatg gtgcactgac actggttcag tgcgaagcaa   3120
ttgccactca ccgctcacgg atctccgtca caccagcatt gcgggaacgc tgcgcccgcg   3180
cgcacgcacg tctggagcac gctatcgcag aacagcgtca catctatggt atcaccaccg   3240
gcttcggacc actggctaat cgcctgatcg gtgcagatca gggcgccgaa ctccagcaga   3300
acctcatcta ccaccttgct actggcgtgg gcccaaaact ctcctgggct gaagcacgtg   3360
cactcatgct ggctcgtctc aactccatcc ttcagggcgc atctggtgca tcaccagaaa   3420
ccatcgaccg tatcgttgcc gttctgaacg ctggcttcgc cccagaagtc ccagctcagg   3480
gcaccgttgg tgcatctggc gatctgaccc cactggctca catggtgctg gcgcttcagg   3540
gtcgaggtcg tatgatcgat ccatccggcc gtgttcagga agccggcgca gtgatggatc   3600
```

```
gcctgtgcgg tggcccactg accttggcag cccgtgacgg tctggctctg gtcaacggta   3660
cttccgctat gaccgcaatc gctgctttga ccggtgtgga ggctgcgcgc gcaatcgacg   3720
ccgcattgcg ccactccgct gtgctcatgg aggttctctc cggccacgct gaggcttggc   3780
accctgcatt tgctgaactc cgcccacacc caggccagct gcgcgcaacc gaacgtctgg   3840
cccaggctct cgatggcgcc ggtcgcgttt gccgcacctt gaccgcggcc cgtcgcctga   3900
ccgcagctga tctgcgccct gaggatcacc cagcccagga cgcctactcc ctgcgcgtgg   3960
tgccacagct ggttggcgct gtctgggaca ccctcgattg gcacgatcgc gtcgtgacct   4020
gcgaactcaa ctctgtgacc gacaacccaa tcttcccgga aggctgcgct gttccagcac   4080
tgcacggcgg caacttcatg ggcgtgcacg tcgcactggc gtcggacgcc ctgaacgctg   4140
cattggttac cctggcaggt ctggtggagc gccagatcgc acgccttact gatgagaagc   4200
tgaacaaggg acttccggca ttccttcacg gtggtcaggc tggccttcag tccggcttca   4260
tgggcgcgca ggtcaccgca accgcgctcc ttgctgaaat gcgcgcaaac gcaaccccgg   4320
tgtctgttca gtcactgtct accaacggcg ctaaccagga tgttgtcagc atgggcacca   4380
tcgctgcacg ccgcgctcgc gcacagctgc tcccactgtc ccagattcag gcaatcctgg   4440
ctctcgctct cgcccaggca atggatctgc tggatgatcc agagggccag gctggctggt   4500
cccttaccgc acgcgacctg cgcgatcgca tccgcgctgt ctcgccgggc ctgcgcgcag   4560
atcgcccact ggccggccac atcgaggcag tcgctcaggg tctgcgccac ccttccgcag   4620
cagctgatcc accagcataa ctctagagtc gacctgcagg catgcaagct tggctgtttt   4680
ggcggatgag agaagatttt cagcctgata cagattaaat cagaacgcag aagcggtctg   4740
ataaaacaga atttgcctgg cggcagtagc gcggtggtcc cacctgaccc catgccgaac   4800
tcagaagtga aacgccgtag cgccgatggt agtgtggggt ctccccatgc gagagtaggg   4860
aactgccagg catcaaataa aacgaaaggc tcagtcgaaa gactgggcct ttcgttttat   4920
ctgttgtttg tcggtgaacg ctctcctgag taggacaaat ccgccgggag cggatttgaa   4980
cgttgcgaag caacggcccg gagggtggcg ggcaggacgc ccgccataaa ctgccaggca   5040
tcaaattaag cagaaggcca tcctgacgga tggccttttt gcgtttctac aaactctttt   5100
tgtttatttt tctaaataca ttcaaatatg tatccgctca tgaattaatt ccgctagatg   5160
acgtgcggct tcgacctcct gggcgtggcg cttgttggcg cgctcgcggc tggctgcggc   5220
acgacacgcg tctgagcagt attttgcgcg ccgtcctcgt gggtcaggcc ggggtgggat   5280
caggccaccg cagtaggcgc agctgatgcg atcctccact actgcgcgtc ctcctggcgc   5340
tgccgagcac gcagctcgtc ggccagctct tcaaggtcgg ccacaagcgt ttctaggtcg   5400
ctcgcggcac ttgcccagtc gcgtgatgct ggcgcgtctg tcgtatcgag ggcgcggaaa   5460
aatccgatca ccgtttttaa atcgacggcg gcatcgagtg cgtcggactc cagcgcgaca   5520
tcggagagat ccaccgctga tgcttcaggc cagttttggt acttcgtcgt gaaggtcatg   5580
acaccattat aacgaacgtt cgttaaaaat tctagcccca attctgataa tttcttccgg   5640
cactcctgcg aaaacctgcg agacttcttg cccagaaaaa acgccaagcg cagcggttac   5700
cgcacttttt ttccaggtga tttcaccctg accagcgaag cggcacttta gtgcatgagg   5760
tgtgcccctg gtttcccctc tttggagggt tcaacccaaa aaagcacaca agcaaaaatg   5820
aaaatcatca tgagcaagtt ggtgcgaagc agcaacgcgc tagctccaaa aaggtctcca   5880
ggatctcgag gagatttttg agggggaggg agtcgaggaa gagccagagc agaaggcggg   5940
```

-continued

```
gaaccgttct ctgccgacag cgtgagcccc ccttaaaaat caggccgggg aggaaccggg   6000
gagggatcag agctaggagc gagacaccct aaaggggggg aaccgttttc tgctgacggt   6060
gtttcgttta ttagttttca gcccgtggat agcggagggt gagggcaagt gagagccaga   6120
gcaaggacgg gacccctaaa ggggggaacc gttttctgct gacggtgttt cgtttattag   6180
ttttcagccc gtggacggcc gcgtttagct tccattccaa gtgcctttct gacttgttgg   6240
atgcgccttt cactgacacc tagttcgcct gcaagctcac gagtcgaggg atcagcaacc   6300
gattgagaac gggcatccag gatcgcagtt ttgacgcgaa gttcgagcaa ctcgcctgtc   6360
atttctcggc gtttgtttgc ttccgctaat cgctgtcgcg tctcctgcgc atacttactt   6420
tctgggtcag cccatctgcg tgcattcgat gtagctgcgc cccgtcgccc catcgtcgct   6480
agagctttcc gccctcggct gctctgcgtt tccacccgac gagcagggac gactggctgg   6540
cctttagcca cgtagccgcg cacacgacgc gccatcgtca ggcgatcacg catggcggga   6600
agatccggct cccggccgtc tgcaccgacc gcctgggcaa cgttgtacgc cacttcatac   6660
gcgtcgatga tcttggcatc ttttaggcgc tcaccagcag ctttgagctg gtatcccacg   6720
gtcaacgcgt ggcgaaacgc ggtctcgtcg cgcgctcgct ctggatttgt ccagagcact   6780
cgcacgccgt cgatcaggtc gccggacgcg tccagggcgc tcggcaggct cgcgtccaaa   6840
atcgctagcg ccttggcttc tgcggtggcg cgttgtgccg cttcaatgcg ggcgcgtccg   6900
ctggaaaagt cctgctcaat gtactttttc ggcttctgtg atccggtcat cgttcgagca   6960
atctccatta ggtcggccag ccgatccaca cgatcatgct ggcagtgcca tttataggct   7020
gtcggatcgt ctgagacgtg cagcggccac cggctcagcc tatgcgaaaa agcctggtca   7080
gcgccgaaaa cacgagtcat ttcttccgtc gttgcagcca gcaggcgcat atttgggctg   7140
gttttacctg ctgcggcata caccgggtca atgagccaga tgagctggca tttcccgctc   7200
agcggattca cgccgatcca agccggcgct tttctaggc gtgcccattt ctctaaaatc   7260
gcgtagacct gcgggtttac gtgctcaatc ttcccgccgg cctggtggct gggcacatcg   7320
atgtcaagca cgatcaccgc ggcatgttgc gcgtgcgtca gcgcaacgta ctggcaccgc   7380
gtcagcgctt ttgagccagc ccggtagagc tttggttggg tttcgccggt atccgggttt   7440
ttaatccagg cgctcgcgaa atctcttgtc ttgctgccct ggaagctttc gcgtcccagg   7500
tgagcgagca gttcgcggcg atcttctgcc gtccagccgc gtgagccgca gcgcatagct   7560
tcggggtggg tgtcgaacag atcggcggac aatttccacg cgctagctgt gactgtgtcc   7620
tgcggatcgg ctagagtcat gtcttgagtg ctttctccca gctgatgact gggggttagc   7680
cgacgccctg tgagttcccg ctcacggggc gttcaacttt ttcaggtatt tgtgcagctt   7740
atcgtgtttt cttcgtaaat gaacgcttaa ctaccttgtt aaacgtggca aataggcagg   7800
attgatgggg atctagcttc acgctgccgc aagcactcag ggcgcaaggg ctgctaaagg   7860
aagcggaaca cgtagaaagc cagtccgcag aaacggtgct gaccccggat gaatgtcagc   7920
tactgggcta tctggacaag ggaaaacgca agcgcaaaga gaaagcaggt agcttgcagt   7980
gggcttacat ggcgatagct agactgggcg gttttatgga cagcaagcga accggaattg   8040
ccagctgggg cgccctctgg taaggttggg aagccctgca aagtaaactg gatggctttc   8100
ttgccgccaa ggatctgatg gcgcagggga tcaagatctg atcaagagac aggatgagga   8160
tcgtttcgca tgattgaaca agatggattg cacgcaggtt ctccggccgc ttgggtggag   8220
aggctattcg gctatgactg ggcacaacag acaatcggct gctctgatgc cgccgtgttc   8280
cggctgtcag cgcaggggcg cccggttctt tttgtcaaga ccgacctgtc cggtgccctg   8340
```

```
aatgaactcc aagacgaggc agcgcggcta tcgtggctgg ccacgacggg cgttccttgc   8400
gcagctgtgc tcgacgttgt cactgaagcg ggaagggact ggctgctatt gggcgaagtg   8460
ccggggcagg atctcctgtc atctcacctt gctcctgccg agaaagtatc catcatggct   8520
gatgcaatgc ggcggctgca tacgcttgat ccggctacct gcccattcga ccaccaagcg   8580
aaacatcgca tcgagcgagc acgtactcgg atggaagccg gtcttgtcga tcaggatgat   8640
ctggacgaag agcatcaggg gctcgcgcca gccgaactgt tcgccaggct caaggcgcgg   8700
atgcccgacg gcgaggatct cgtcgtgacc catggcgatg cctgcttgcc gaatatcatg   8760
gtggaaaatg gccgcttttc tggattcatc gactgtggcc ggctgggtgt ggcggaccgc   8820
tatcaggaca tagcgttggc tacccgtgat attgctgaag agcttggcgg cgaatgggct   8880
gaccgcttcc tcgtgcttta cggtatcgcc gctcccgatt cgcagcgcat cgccttctat   8940
cgccttcttg acgagttctt ctgagcggga ctctggggtt cgcggaatca tgaccaaaat   9000
cccttaacgt gagttttcgt tccactgagc gtcagacccc gtagaaaaga tcaaaggatc   9060
ttcttgagat cctttttttc tgcgcgtaat ctgctgcttg caaacaaaaa aaccaccgct   9120
accagcggtg gtttgtttgc cggatcaaga gctaccaact ctttttccga aggtaactgg   9180
cttcagcaga gcgcagatac caaatactgt ccttctagtg tagccgtagt taggccacca   9240
cttcaagaac tctgtagcac cgcctacata cctcgctctg ctaatcctgt taccagtggc   9300
tgctgccagt ggcgataagt cgtgtcttac cgggttggac tcaagacgat agttaccgga   9360
taaggcgcag cggtcgggct gaacgggggg ttcgtgcaca cagcccagct tggagcgaac   9420
gacctacacc gaactgagat acctacagcg tgagctatga gaaagcgcca cgcttcccga   9480
agggagaaag gcggacaggt atccggtaag cggcagggtc ggaacaggag agcgcacgag   9540
ggagcttcca gggggaaacg cctggtatct ttatagtcct gtcgggtttc gccacctctg   9600
acttgagcgt cgatttttgt gatgctcgtc aggggggcgg agcctatgga aaaacgccag   9660
caacgcggcc tttttacggt tcctggcctt ttgctggcct tttgctcaca tgttctttcc   9720
tgcgttatcc cctgattctg tggataaccg tattaccgcc tttgagtgag ctgataccgc   9780
tcgccgcagc cgaacgaccg agcgcagcga gtcagtgagc gaggaagcgg aagagcgcct   9840
gatgcggtat tttctcctta cgcatctgtg cggtatttca caccgcatat ggtgcactct   9900
cagtacaatc tgctctgatg ccgcatagtt aagccagtat acactccgct atcgctacgt   9960
gactgggtca tggctgcgcc ccgacacccg ccaacacccg ctgacgcgcc ctgacgggct  10020
tgtctgctcc cggcatccgc ttacagacaa gctgtgaccg tctccgggag ctgcatgtgt  10080
cagaggtttt caccgtcatc accgaaacgc gcgaggcagc agatcaattc gcgcgcgaag  10140
gcgaagcggc atgcatttac gttgacacca tcgaatggtg caaaaccttt cgcggtatgg  10200
catgatagcg cccggaagag agtcaattca gggtggtgaa tgtgaaacca gtaacgttat  10260
acgatgtcgc agagtatgcc ggtgtctctt atcagaccgt ttcccgcgtg gtgaaccagg  10320
ccagccacgt ttctgcgaaa acgcgggaaa aagtggaagc ggcgatggcg gagctgaatt  10380
acattcccaa ccgcgtggca caacaactgg cgggcaaaca gtcgttgctg attggcgttg  10440
ccacctccag tctggccctg cacgcgccgt cgcaaattgt cgcggcgatt aaatctcgcg  10500
ccgatcaact gggtgccagc gtggtggtgt cgatggtaga acgaagcggc gtcgaagcct  10560
gtaaagcggc ggtgcacaat cttctcgcgc aacgcgtcag tgggctgatc attaactatc  10620
cgctggatga ccaggatgcc attgctgtgg aagctgcctg cactaatgtt ccggcgttat  10680
```

ttcttgatgt ctctgaccag acacccatca acagtattat tttctcccat gaagacggta 10740
cgcgactggg cgtggagcat ctggtcgcat tgggtcacca gcaaatcgcg ctgttagcgg 10800
gcccattaag ttctgtctcg gcgcgtctgc gtctggctgg ctggcataaa tatctcactc 10860
gcaatcaaat tcagccgata gcggaacggg aaggcgactg gagtgccatg tccggttttc 10920
aacaaaccat gcaaatgctg aatgagggca tcgttcccac tgcgatgctg gttgccaacg 10980
atcagatggc gctgggcgca atgcgcgcca ttaccgagtc cgggctgcgc gttggtgcgg 11040
atatctcggt agtgggatac gacgataccg aagacagctc atgttatatc ccgccgtcaa 11100
ccaccatcaa acaggatttt cgcctgctgg ggcaaaccag cgtggaccgc ttgctgcaac 11160
tctctcaggg ccaggcggtg aagggcaatc agctgttgcc cgtctcactg gtgaaaagaa 11220
aaaccaccct ggcgcccaat acgcaaaccg cctctccccg cgcgttggcc gattcattaa 11280
tgcagctggc acgacaggtt tcccgactgg aaagcgggca gtgagcgcaa cgcaattaat 11340
gtgagttagc gcgaattgat ctggtttgac agcttatcat 11380

<210> SEQ ID NO 34
<211> LENGTH: 4377
<212> TYPE: DNA
<213> ORGANISM: Artificial Sequence
<220> FEATURE:
<223> OTHER INFORMATION: operon RiPKS-Sc4CL-RcTAL

<400> SEQUENCE: 34
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatgttccg 1200
ttccgagtac gcagatgtgc ctccagtgga cctccctatc cacgatgctg tcctgggtgg 1260
cgcggccgca ttcggcagca ccccagctct gatcgatggc accgatggca ccaccctgac 1320
ctacgaacag gtcgatcgct tccaccgtcg cgtcgctgct gctctggcgg aaaccggcgt 1380

```
gcgcaagggc gatgtcctgg ccctgcactc tccaaacacc gttgctttcc ctctggcatt   1440
ctacgctgca acccgcgctg gtgcatccgt gaccactgtt caccctctcg ctaccgcaga   1500
agagtttgct aagcagctga aggattcggc tgcacgttgg atcgtcaccg tttccccact   1560
gctgtccacc gcacgccgcg ccgcagagtt ggcaggcggc gtgcaggaaa ttttggtctg   1620
cgattctgct ccaggtcacc gttctctcgt cgatatgctg gctagcaccg cacccgaacc   1680
atccgtcgct atcgatccag cagaagatgt ggctgccctt ccgtactcct ctggcaccac   1740
cggcacccca aagggtgtga tgctgaccca ccgccagatt gcaaccaacc tggctcagct   1800
ggaaccttcc atgccatccg ctccaggtga ccgggtgctg gctgttctgc cattcttcca   1860
catctacggc ttgaccgcac tcatgaacgc tcctttgcgc ctgggtgcta ccgtggtggt   1920
gctccctcgc ttcgacctgg agcagttcct tgcagccatc cagaaccacc gtatcaccag   1980
tttgtacgtc gccccaccaa tcgttttggc actggctaag caccctctgg tggccgacta   2040
tgacctttcc tccctccgtt acatcgtgag cgccgcggca ccgctcgacg cgcgcctggc   2100
agccgcttgt tcccagcgtc tgggcctgcc cccggtgggg caagcgtacg gtatgaccga   2160
gctgtctcct ggcacccacg tcgtgccgct cgatgcaatg gcagatgccc cacccggcac   2220
cgtgggtcgc ctgatagctg gcaccgagat gcgcatcgtg tccctgaccg acccaggcac   2280
cgacctgccg gcaggcgaat ccggcgaaat cctgatccgc ggcccccaga ttatgaaggg   2340
ctacctcggc cgcccagatg ctaccgcagc aatgatcgat gaggagggct ggctgcacac   2400
cggcgatgtg ggccacgtgg acgctgatgg ttggttgttc gtcgtggatc gcgttaagga   2460
gctgatcaag tacaagggtt tccaggttgc tcccgcggag cttgaagcac acttgctcac   2520
ccacccaggt gttgcagatg cagctgtcgt cggcgcatac gacgacgacg gtaacgaggt   2580
gccgcacgcc tttgtggtcc gccagccggc tgcaccaggc ctcgcggagt ccgaaatcat   2640
gatgtacgtg gctgaacgcg ttgctccata caagcgcgtg cgccgcgtga ccttcgtcga   2700
tgccgtgcca cgcgcagcat ccggcaagat cctgcgtcgc cagctgcgcg agccacgcta   2760
aggatctagg aggataaaga aatgaccctg caatcccaga ctgcaaagga ctgcctggcg   2820
ctggatggtg cactgacact ggttcagtgc gaagcaattg ccactcaccg ctcacggatc   2880
tccgtcacac cagcattgcg ggaacgctgc gcccgcgcgc acgcacgtct ggagcacgct   2940
atcgcagaac agcgtcacat ctatggtatc accaccggct tcggaccact ggctaatcgc   3000
ctgatcggtg cagatcaggg cgccgaactc cagcagaacc tcatctacca ccttgctact   3060
ggcgtgggcc caaaactctc ctgggctgaa gcacgtgcac tcatgctggc tcgtctcaac   3120
tccatccttc agggcgcatc tggtgcatca ccagaaacca tcgaccgtat cgttgccgtt   3180
ctgaacgctg gcttcgcccc agaagtccca gctcagggca ccgttggtgc atctggcgat   3240
ctgaccccac tggctcacat ggtgctggcg cttcagggtc gaggtcgtat gatcgatcca   3300
tccggccgtg ttcaggaagc cggcgcagtg atggatcgcc tgtgcggtgg cccactgacc   3360
ttggcagccc gtgacggtct ggctctggtc aacggtactt ccgctatgac cgcaatcgct   3420
gctttgaccg gtgtggaggc tgcgcgcgca atcgacgccg cattgcgcca ctccgctgtg   3480
ctcatggagg ttctctccgg ccacgctgag gcttggcacc ctgcatttgc tgaactccgc   3540
ccacacccag gccagctgcg cgcaaccgaa cgtctggccc aggctctcga tggcgccggt   3600
cgcgtttgcc gcaccttgac cgcggcccgt cgcctgaccg cagctgatct gcgccctgag   3660
gatcacccag cccaggacgc ctactccctg cgcgtggtgc cacagctggt tggcgctgtc   3720
```

-continued tgggacaccc tcgattggca cgatcgcgtc gtgacctgcg aactcaactc tgtgaccgac 3780
aacccaatct tcccggaagg ctgcgctgtt ccagcactgc acggcggcaa cttcatgggc 3840
gtgcacgtcg cactggcgtc ggacgccctg aacgctgcat tggttaccct ggcaggtctg 3900
gtggagcgcc agatcgcacg ccttactgat gagaagctga acaagggact tccggcattc 3960
cttcacggtg gtcaggctgg ccttcagtcc ggcttcatgg gcgcgcaggt caccgcaacc 4020
gcgctccttg ctgaaatgcg cgcaaacgca accccggtgt ctgttcagtc actgtctacc 4080
aacggcgcta accaggatgt tgtcagcatg ggcaccatcg ctgcacgccg cgctcgcgca 4140
cagctgctcc cactgtccca gattcaggca atcctggctc tcgctctcgc ccaggcaatg 4200
gatctgctgg atgatccaga gggccaggct ggctggtccc ttaccgcacg cgacctgcgc 4260
gatcgcatcc gcgctgtctc gccgggcctg cgcgcagatc gcccactggc cggccacatc 4320
gaggcagtcg ctcagggtct gcgccaccct tccgcagcag ctgatccacc agcataa 4377

<210> SEQ ID NO 35
<211> LENGTH: 11305
<212> TYPE: DNA
<213> ORGANISM: Artificial Sequence
<220> FEATURE:
<223> OTHER INFORMATION: plasmid RiPKS-Sc4CL-FjTAL-pECXK (pECXK_H)

<400> SEQUENCE: 35
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380
tcagatctcc aagtccctgc tgatcctggc atggttcctc ttctccctgg tgtaaggatc 1440

-continued

```
taggaggatt atgagatgtt ccgttccgag tacgcagatg tgcctccagt ggacctccct   1500
atccacgatg ctgtcctggg tggcgcggcc gcattcggca gcaccccagc tctgatcgat   1560
ggcaccgatg gcaccaccct gacctacgaa caggtcgatc gcttccaccg tcgcgtcgct   1620
gctgctctgg cggaaaccgg cgtgcgcaag ggcgatgtcc tggccctgca ctctccaaac   1680
accgttgctt tccctctggc attctacgct gcaacccgcg ctggtgcatc cgtgaccact   1740
gttcaccctc tcgctaccgc agaagagttt gctaagcagc tgaaggattc ggctgcacgt   1800
tggatcgtca ccgtttcccc actgctgtcc accgcacgcc gcgccgcaga gttggcaggc   1860
ggcgtgcagg aaattttggt ctgcgattct gctccaggtc accgttctct cgtcgatatg   1920
ctggctagca ccgcacccga accatccgtc gctatcgatc cagcagaaga tgtggctgcc   1980
cttccgtact cctctggcac caccggcacc ccaaagggtg tgatgctgac ccaccgccag   2040
attgcaacca acctggctca gctggaacct tccatgccat ccgctccagg tgaccgggtg   2100
ctggctgttc tgccattctt ccacatctac ggcttgaccg cactcatgaa cgctcctttg   2160
cgcctgggtg ctaccgtggt ggtgctccct cgcttcgacc tggagcagtt ccttgcagcc   2220
atccagaacc accgtatcac cagtttgtac gtcgccccac caatcgtttt ggcactggct   2280
aagcaccctc tggtggccga ctatgacctt tcctccctcc gttacatcgt gagcgccgcg   2340
gcaccgctcg acgcgcgcct ggcagccgct tgttcccagc gtctgggcct gcccccggtg   2400
gggcaagcgt acggtatgac cgagctgtct cctggcaccc acgtcgtgcc gctcgatgca   2460
atggcagatg ccccacccgg caccgtgggt cgcctgatag ctggcaccga gatgcgcatc   2520
gtgtccctga ccgacccagg caccgacctg ccggcaggcg aatccggcga aatcctgatc   2580
cgcggccccc agattatgaa gggctacctc ggccgcccag atgctaccgc agcaatgatc   2640
gatgaggagg gctggctgca caccggcgat gtgggccacg tggacgctga tggttggttg   2700
ttcgtcgtgg atcgcgttaa ggagctgatc aagtacaagg gtttccaggt tgctcccgcg   2760
gagcttgaag cacacttgct cacccaccca ggtgttgcag atgcagctgt cgtcggcgca   2820
tacgacgacg acggtaacga ggtgccgcac gcctttgtgg tccgccagcc ggctgcacca   2880
ggcctcgcgg agtccgaaat catgatgtac gtggctgaac gcgttgctcc atacaagcgc   2940
gtgcgccgcg tgaccttcgt cgatgccgtg ccacgcgcag catccggcaa gatcctgcgt   3000
cgccagctgc gcgagccacg ctaaggatct aggaggataa agaaatgaac accatcaacg   3060
aatacctgtc cctggaagag ttcgaagcga tcatcttcgg taaccagaag gttaccatct   3120
ccgatgtggt tgtgaaccgt gttaacgagt ccttcaactt cctcaaggag ttctccggca   3180
acaaggtcat ctacggtgtg aacaccggct tcggcccaat ggcacaatac cgtattaagg   3240
aatccgatca gatccagctt cagtacaatc tgatccgttc ccactcttcg ggcaccggaa   3300
aaccactctc cccagtttgt gctaaggcag caatcttggc tcgcctgaac accctgtccc   3360
tcggtaactc cggcgtgcat ccatctgtca tcaacctgat gtcggaactg atcaacaaag   3420
acattacccc actcatcttc gagcacggtg gcgtcggagc atccggtgac ctggttcagc   3480
tttctcacct ggctttggtt ctcatcggcg aaggcgaagt gttctacaag ggtgaacgcc   3540
gcccaactcc agaagttttc gaaattgagg gcttgaagcc aatccaggtt gagatccgtg   3600
agggcctcgc cttgattaac ggtactagcg tgatgaccgg tattggagtg gtcaacgtgt   3660
accacgcaaa gaagctgctg gactggtccc tgaagtcctc ctgcgccatc aatgaacttg   3720
ttcaggctta cgatgatcac ttcagcgcag agctgaacca gacgaagcgc cacaagggcc   3780
```

-continued

```
agcaggaaat cgctctgaag atgcgtcaga acctctctga cagcaccctg atccgcaagc   3840
gcgaggacca cctgtattcc ggcgaaaaca ccgaggagat tttcaaggag aaggtgcagg   3900
agtactactc cctgcgctgc gttccacaga ttctcggccc ggtcctcgaa actatcaata   3960
acgtcgcctc catcctggaa gatgagttca actccgctaa cgataaccca atcatcgacg   4020
tgaagaacca gcacgtgtac catggcggca acttccacgg tgactacatc tctctggaaa   4080
tggacaagtt gaaaatcgtt atcaccaaac tgaccatgct tgcagaacgc cagcttaact   4140
atcttctcaa ctccaagatc aacgaacttc tgccaccatt cgtgaacctc ggcaccctgg   4200
gtttcaactt cggcatgcag ggcgttcagt tcaccgcgac ctccaccacc gcagaatctc   4260
agatgctgtc caaccctatg tacgttcact ccattccaaa caacaacgat aaccaggaca   4320
tcgtctccat gggcaccaac tccgcagtga tcacgtccaa ggttatcgag aacgctttcg   4380
aagtcctggc tatcgaaatg atcaccatcg ttcaggccat cgattacctc ggccagaagg   4440
ataagatctc ctccgtttcc aagaagtggt acgatgaaat ccgcaacatt atccctacct   4500
tcaaggagga tcaggttatg tacccattcg tgcagaaggt taaggatcac ctcatcaaca   4560
actaactcta gagtcgacct gcaggcatgc aagcttggct gttttggcgg atgagagaag   4620
attttcagcc tgatacagat taaatcagaa cgcagaagcg gtctgataaa acagaatttg   4680
cctggcggca gtagcgcggt ggtcccacct gaccccatgc cgaactcaga agtgaaacgc   4740
cgtagcgccg atggtagtgt ggggtctccc catgcgagag tagggaactg ccaggcatca   4800
aataaaacga aaggctcagt cgaaagactg ggcctttcgt tttatctgtt gtttgtcggt   4860
gaacgctctc ctgagtagga caaatccgcc gggagcggat ttgaacgttg cgaagcaacg   4920
gcccggaggg tggcgggcag gacgcccgcc ataaactgcc aggcatcaaa ttaagcagaa   4980
ggccatcctg acggatggcc tttttgcgtt tctacaaact ctttttgttt atttttctaa   5040
atacattcaa atatgtatcc gctcatgaat taattccgct agatgacgtg cggcttcgac   5100
ctcctgggcg tggcgcttgt tggcgcgctc gcggctggct gcggcacgac acgcgtctga   5160
gcagtatttt gcgcgccgtc ctcgtgggtc aggccggggt gggatcaggc caccgcagta   5220
ggcgcagctg atgcgatcct ccactactgc gcgtcctcct ggcgctgccg agcacgcagc   5280
tcgtcggcca gctcttcaag gtcggccaca agcgtttcta ggtcgctcgc ggcacttgcc   5340
cagtcgcgtg atgctggcgc gtctgtcgta tcgagggcgc ggaaaaatcc gatcaccgtt   5400
tttaaatcga cggcggcatc gagtgcgtcg gactccagcg cgacatcgga gagatccacc   5460
gctgatgctt caggccagtt ttggtacttc gtcgtgaagg tcatgacacc attataacga   5520
acgttcgtta aaaattctag ccccaattct gataatttct tccggcactc ctgcgaaaac   5580
ctgcgagact tcttgcccag aaaaaacgcc aagcgcagcg gttaccgcac tttttttcca   5640
ggtgatttca ccctgaccag cgaagcggca ctttagtgca tgaggtgtgc ccctggtttc   5700
ccctctttgg agggttcaac ccaaaaaagc acacaagcaa aaatgaaaat catcatgagc   5760
aagttggtgc gaagcagcaa cgcgctagct ccaaaaaggt ctccaggatc tcgaggagat   5820
ttttgagggg gagggagtcg aggaagagcc agagcagaag gcggggaacc gttctctgcc   5880
gacagcgtga gcccccctta aaaatcaggc cggggaggaa ccggggaggg atcagagcta   5940
ggagcgagac accctaaagg gggggaaccg ttttctgctg acggtgtttc gtttattagt   6000
tttcagcccg tggatagcgg agggtgaggg caagtgagag ccagagcaag gacgggaccc   6060
ctaaaggggg gaaccgtttt ctgctgacgg tgtttcgttt attagttttc agcccgtgga   6120
cggccgcgtt tagcttccat tccaagtgcc tttctgactt gttggatgcg cctttcactg   6180
```

-continued

```
acacctagtt cgcctgcaag ctcacgagtc gagggatcag caaccgattg agaacgggca   6240
tccaggatcg cagttttgac gcgaagttcg agcaactcgc ctgtcatttc tcggcgtttg   6300
tttgcttccg ctaatcgctg tcgcgtctcc tgcgcatact tactttctgg gtcagcccat   6360
ctgcgtgcat tcgatgtagc tgcgccccgt cgccccatcg tcgctagagc tttccgccct   6420
cggctgctct gcgtttccac ccgacgagca gggacgactg gctggccttt agccacgtag   6480
ccgcgcacac gacgcgccat cgtcaggcga tcacgcatgg cgggaagatc cggctcccgg   6540
ccgtctgcac cgaccgcctg ggcaacgttg tacgccactt catacgcgtc gatgatcttg   6600
gcatctttta ggcgctcacc agcagctttg agctggtatc ccacggtcaa cgcgtggcga   6660
aacgcggtct cgtcgcgcgc tcgctctgga tttgtccaga gcactcgcac gccgtcgatc   6720
aggtcgccgg acgcgtccag ggcgctcggc aggctcgcgt ccaaaatcgc tagcgccttg   6780
gcttctgcgg tggcgcgttg tgccgcttca atgcgggcgc gtccgctgga aaagtcctgc   6840
tcaatgtact tttcggctt ctgtgatccg gtcatcgttc gagcaatctc cattaggtcg   6900
gccagccgat ccacacgatc atgctggcag tgccatttat aggctgtcgg atcgtctgag   6960
acgtgcagcg gccaccggct cagcctatgc gaaaaagcct ggtcagcgcc gaaaacacga   7020
gtcatttctt ccgtcgttgc agccagcagg cgcatatttg ggctggtttt acctgctgcg   7080
gcatacaccg ggtcaatgag ccagatgagc tggcatttcc cgctcagcgg attcacgccg   7140
atccaagccg gcgctttttc taggcgtgcc catttctcta aaatcgcgta gacctgcggg   7200
tttacgtgct caatcttccc gccggcctgg tggctgggca catcgatgtc aagcacgatc   7260
accgcggcat gttgcgcgtg cgtcagcgca acgtactggc accgcgtcag cgcttttgag   7320
ccagcccggt agagctttgg ttgggtttcg ccggtatccg ggtttttaat ccaggcgctc   7380
gcgaaatctc ttgtcttgct gccctggaag ctttcgcgtc ccaggtgagc gagcagttcg   7440
cggcgatctt ctgccgtcca gccgcgtgag ccgcagcgca tagcttcggg gtgggtgtcg   7500
aacagatcgg cggacaattt ccacgcgcta gctgtgactg tgtcctgcgg atcggctaga   7560
gtcatgtctt gagtgctttc tcccagctga tgactggggg ttagccgacg ccctgtgagt   7620
tcccgctcac ggggcgttca actttttcag gtatttgtgc agcttatcgt gttttcttcg   7680
taaatgaacg cttaactacc ttgttaaacg tggcaaatag gcaggattga tggggatcta   7740
gcttcacgct gccgcaagca ctcagggcgc aagggctgct aaaggaagcg gaacacgtag   7800
aaagccagtc cgcagaaacg gtgctgaccc cggatgaatg tcagctactg ggctatctgg   7860
acaagggaaa acgcaagcgc aaagagaaag caggtagctt gcagtgggct tacatggcga   7920
tagctagact gggcggtttt atggacagca agcgaaccgg aattgccagc tggggcgccc   7980
tctggtaagg ttgggaagcc ctgcaaagta aactggatgg ctttcttgcc gccaaggatc   8040
tgatggcgca ggggatcaag atctgatcaa gagacaggat gaggatcgtt tcgcatgatt   8100
gaacaagatg gattgcacgc aggttctccg gccgcttggg tggagaggct attcggctat   8160
gactgggcac aacagacaat cggctgctct gatgccgccg tgttccggct gtcagcgcag   8220
gggcgcccgg ttctttttgt caagaccgac ctgtccggtg ccctgaatga actccaagac   8280
gaggcagcgc ggctatcgtg gctggccacg acgggcgttc cttgcgcagc tgtgctcgac   8340
gttgtcactg aagcgggaag ggactggctg ctattgggcg aagtgccggg gcaggatctc   8400
ctgtcatctc accttgctcc tgccgagaaa gtatccatca tggctgatgc aatgcggcgg   8460
ctgcatacgc ttgatccggc tacctgccca ttcgaccacc aagcgaaaca tcgcatcgag   8520
```

-continued

```
cgagcacgta ctcggatgga agccggtctt gtcgatcagg atgatctgga cgaagagcat   8580
caggggctcg cgccagccga actgttcgcc aggctcaagg cgcggatgcc cgacggcgag   8640
gatctcgtcg tgacccatgg cgatgcctgc ttgccgaata tcatggtgga aaatggccgc   8700
ttttctggat tcatcgactg tggccggctg ggtgtggcgg accgctatca ggacatagcg   8760
ttggctaccc gtgatattgc tgaagagctt ggcggcgaat gggctgaccg cttcctcgtg   8820
ctttacggta tcgccgctcc cgattcgcag cgcatcgcct tctatcgcct tcttgacgag   8880
ttcttctgag cgggactctg gggttcgcgg aatcatgacc aaaatccctt aacgtgagtt   8940
ttcgttccac tgagcgtcag accccgtaga aaagatcaaa ggatcttctt gagatccttt   9000
ttttctgcgc gtaatctgct gcttgcaaac aaaaaaacca ccgctaccag cggtggtttg   9060
tttgccggat caagagctac caactctttt tccgaaggta actggcttca gcagagcgca   9120
gataccaaat actgtccttc tagtgtagcc gtagttaggc caccacttca agaactctgt   9180
agcaccgcct acatacctcg ctctgctaat cctgttacca gtggctgctg ccagtggcga   9240
taagtcgtgt cttaccgggt tggactcaag acgatagtta ccggataagg cgcagcggtc   9300
gggctgaacg gggggttcgt gcacacagcc cagcttggag cgaacgacct acaccgaact   9360
gagataccta cagcgtgagc tatgagaaag cgccacgctt cccgaaggga gaaaggcgga   9420
caggtatccg gtaagcggca gggtcggaac aggagagcgc acgagggagc ttccaggggg   9480
aaacgcctgg tatctttata gtcctgtcgg gtttcgccac ctctgacttg agcgtcgatt   9540
tttgtgatgc tcgtcagggg ggcggagcct atggaaaaac gccagcaacg cggccttttt   9600
acggttcctg gccttttgct ggccttttgc tcacatgttc tttcctgcgt tatcccctga   9660
ttctgtggat aaccgtatta ccgcctttga gtgagctgat accgctcgcc gcagccgaac   9720
gaccgagcgc agcgagtcag tgagcgagga agcggaagag cgcctgatgc ggtattttct   9780
ccttacgcat ctgtgcggta tttcacaccg catatggtgc actctcagta caatctgctc   9840
tgatgccgca tagttaagcc agtatacact ccgctatcgc tacgtgactg ggtcatggct   9900
gcgccccgac acccgccaac acccgctgac gcgccctgac gggcttgtct gctcccggca   9960
tccgcttaca gacaagctgt gaccgtctcc gggagctgca tgtgtcagag gttttcaccg  10020
tcatcaccga aacgcgcgag gcagcagatc aattcgcgcg cgaaggcgaa gcggcatgca  10080
tttacgttga caccatcgaa tggtgcaaaa cctttcgcgg tatggcatga tagcgcccgg  10140
aagagagtca attcagggtg gtgaatgtga aaccagtaac gttatacgat gtcgcagagt  10200
atgccggtgt ctcttatcag accgtttccc gcgtggtgaa ccaggccagc cacgtttctg  10260
cgaaaacgcg ggaaaaagtg gaagcggcga tggcggagct gaattacatt cccaaccgcg  10320
tggcacaaca actggcgggc aaacagtcgt tgctgattgg cgttgccacc tccagtctgg  10380
ccctgcacgc gccgtcgcaa attgtcgcgg cgattaaatc tcgcgccgat caactgggtg  10440
ccagcgtggt ggtgtcgatg gtagaacgaa gcggcgtcga agcctgtaaa gcggcggtgc  10500
acaatcttct cgcgcaacgc gtcagtgggc tgatcattaa ctatccgctg gatgaccagg  10560
atgccattgc tgtggaagct gcctgcacta atgttccggc gttatttctt gatgtctctg  10620
accagacacc catcaacagt attattttct cccatgaaga cggtacgcga ctgggcgtgg  10680
agcatctggt cgcattgggt caccagcaaa tcgcgctgtt agcgggccca ttaagttctg  10740
tctcggcgcg tctgcgtctg gctggctggc ataaatatct cactcgcaat caaattcagc  10800
cgatagcgga acgggaaggc gactggagtg ccatgtccgg ttttcaacaa accatgcaaa  10860
tgctgaatga gggcatcgtt cccactgcga tgctggttgc caacgatcag atggcgctgg  10920
```

gcgcaatgcg cgccattacc gagtccgggc tgcgcgttgg tgcggatatc tcggtagtgg 10980
gatacgacga taccgaagac agctcatgtt atatcccgcc gtcaaccacc atcaaacagg 11040
attttcgcct gctggggcaa accagcgtgg accgcttgct gcaactctct cagggccagg 11100
cggtgaaggg caatcagctg ttgcccgtct cactggtgaa aagaaaaacc accctggcgc 11160
ccaatacgca aaccgcctct ccccgcgcgt tggccgattc attaatgcag ctggcacgac 11220
aggtttcccg actggaaagc gggcagtgag cgcaacgcaa ttaatgtgag ttagcgcgaa 11280
ttgatctggt ttgacagctt atcat 11305

<210> SEQ ID NO 36
<211> LENGTH: 4302
<212> TYPE: DNA
<213> ORGANISM: Artificial Sequence
<220> FEATURE:
<223> OTHER INFORMATION: operon RiPKS-Sc4CL-FjTAL

<400> SEQUENCE: 36
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatgttccg 1200
ttccgagtac gcagatgtgc ctccagtgga cctccctatc cacgatgctg tcctgggtgg 1260
cgcggccgca ttcggcagca ccccagctct gatcgatggc accgatggca ccaccctgac 1320
ctacgaacag gtcgatcgct tccaccgtcg cgtcgctgct gctctggcgg aaaccggcgt 1380
gcgcaagggc gatgtcctgg ccctgcactc tccaaacacc gttgctttcc ctctggcatt 1440
ctacgctgca acccgcgctg gtgcatccgt gaccactgtt caccctctcg ctaccgcaga 1500
agagtttgct aagcagctga aggattcggc tgcacgttgg atcgtcaccg tttccccact 1560
gctgtccacc gcacgccgcg ccgcagagtt ggcaggcggc gtgcaggaaa ttttggtctg 1620

-continued

```
cgattctgct ccaggtcacc gttctctcgt cgatatgctg gctagcaccg cacccgaacc   1680
atccgtcgct atcgatccag cagaagatgt ggctgccctt ccgtactcct ctggcaccac   1740
cggcacccca aagggtgtga tgctgaccca ccgccagatt gcaaccaacc tggctcagct   1800
ggaaccttcc atgccatccg ctccaggtga ccgggtgctg gctgttctgc cattcttcca   1860
catctacggc ttgaccgcac tcatgaacgc tcctttgcgc ctgggtgcta ccgtggtggt   1920
gctccctcgc ttcgacctgg agcagttcct tgcagccatc cagaaccacc gtatcaccag   1980
tttgtacgtc gccccaccaa tcgttttggc actggctaag caccctctgg tggccgacta   2040
tgacctttcc tccctccgtt acatcgtgag cgccgcggca ccgctcgacg cgcgcctggc   2100
agccgcttgt tcccagcgtc tgggcctgcc cccggtgggg caagcgtacg gtatgaccga   2160
gctgtctcct ggcacccacg tcgtgccgct cgatgcaatg gcagatgccc cacccggcac   2220
cgtgggtcgc ctgatagctg gcaccgagat gcgcatcgtg tccctgaccg acccaggcac   2280
cgacctgccg gcaggcgaat ccggcgaaat cctgatccgc ggcccccaga ttatgaaggg   2340
ctacctcggc cgcccagatg ctaccgcagc aatgatcgat gaggagggct ggctgcacac   2400
cggcgatgtg ggccacgtgg acgctgatgg ttggttgttc gtcgtggatc gcgttaagga   2460
gctgatcaag tacaagggtt tccaggttgc tcccgcggag cttgaagcac acttgctcac   2520
ccacccaggt gttgcagatg cagctgtcgt cggcgcatac gacgacgacg gtaacgaggt   2580
gccgcacgcc tttgtggtcc gccagccggc tgcaccaggc ctcgcggagt ccgaaatcat   2640
gatgtacgtg gctgaacgcg ttgctccata caagcgcgtg cgccgcgtga ccttcgtcga   2700
tgccgtgcca cgcgcagcat ccggcaagat cctgcgtcgc cagctgcgcg agccacgcta   2760
aggatctagg aggataaaga aatgaacacc atcaacgaat acctgtccct ggaagagttc   2820
gaagcgatca tcttcggtaa ccagaaggtt accatctccg atgtggttgt gaaccgtgtt   2880
aacgagtcct tcaacttcct caaggagttc tccggcaaca aggtcatcta cggtgtgaac   2940
accggcttcg gcccaatggc acaataccgt attaaggaat ccgatcagat ccagcttcag   3000
tacaatctga tccgttccca ctcttcgggc accggaaaac cactctcccc agtttgtgct   3060
aaggcagcaa tcttggctcg cctgaacacc ctgtccctcg gtaactccgg cgtgcatcca   3120
tctgtcatca acctgatgtc ggaactgatc aacaaagaca ttaccccact catcttcgag   3180
cacggtggcg tcggagcatc cggtgacctg gttcagcttt ctcacctggc tttggttctc   3240
atcggcgaag gcgaagtgtt ctacaagggt gaacgccgcc caactccaga agttttcgaa   3300
attgagggct tgaagccaat ccaggttgag atccgtgagg gcctcgcctt gattaacggt   3360
actagcgtga tgaccggtat tggagtggtc aacgtgtacc acgcaaagaa gctgctggac   3420
tggtccctga agtcctcctg cgccatcaat gaacttgttc aggcttacga tgatcacttc   3480
agcgcagagc tgaaccagac gaagcgccac aagggccagc aggaaatcgc tctgaagatg   3540
cgtcagaacc tctctgacag caccctgatc cgcaagcgcg aggaccacct gtattccggc   3600
gaaaacaccg aggagatttt caaggagaag gtgcaggagt actactccct gcgctgcgtt   3660
ccacagattc tcggcccggt cctcgaaact atcaataacg tcgcctccat cctggaagat   3720
gagttcaact ccgctaacga taacccaatc atcgacgtga agaaccagca cgtgtaccat   3780
ggcggcaact tccacggtga ctacatctct ctggaaatgg acaagttgaa aatcgttatc   3840
accaaactga ccatgcttgc agaacgccag cttaactatc ttctcaactc caagatcaac   3900
gaacttctgc caccattcgt gaacctcggc accctgggtt tcaacttcgg catgcagggc   3960
gttcagttca ccgcgacctc caccaccgca gaatctcaga tgctgtccaa ccctatgtac   4020
```

gttcactcca ttccaaacaa caacgataac caggacatcg tctccatggg caccaactcc 4080
gcagtgatca cgtccaaggt tatcgagaac gctttcgaag tcctggctat cgaaatgatc 4140
accatcgttc aggccatcga ttacctcggc cagaaggata agatctcctc cgtttccaag 4200
aagtggtacg atgaaatccg caacattatc cctaccttca aggaggatca ggttatgtac 4260
ccattcgtgc agaaggttaa ggatcacctc atcaacaact aa 4302

<210> SEQ ID NO 37
<211> LENGTH: 11317
<212> TYPE: DNA
<213> ORGANISM: Artificial Sequence
<220> FEATURE:
<223> OTHER INFORMATION: plasmid RiPKS-Sc4CL-SeSam8-pECXK (pECXK_I)

<400> SEQUENCE: 37
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380
tcagatctcc aagtccctgc tgatcctggc atggttcctc ttctccctgg tgtaaggatc 1440
taggaggatt atgagatgtt ccgttccgag tacgcagatg tgcctccagt ggacctccct 1500
atccacgatg ctgtcctggg tggcgcggcc gcattcggca gcaccccagc tctgatcgat 1560
ggcaccgatg gcaccaccct gacctacgaa caggtcgatc gcttccaccg tcgcgtcgct 1620
gctgctctgg cggaaaccgg cgtgcgcaag ggcgatgtcc tggccctgca ctctccaaac 1680
accgttgctt tccctctggc attctacgct gcaacccgcg ctggtgcatc cgtgaccact 1740

-continued

```
gttcaccctc tcgctaccgc agaagagttt gctaagcagc tgaaggattc ggctgcacgt   1800
tggatcgtca ccgtttcccc actgctgtcc accgcacgcc gcgccgcaga gttggcaggc   1860
ggcgtgcagg aaattttggt ctgcgattct gctccaggtc accgttctct cgtcgatatg   1920
ctggctagca ccgcacccga accatccgtc gctatcgatc cagcagaaga tgtggctgcc   1980
cttccgtact cctctggcac caccggcacc ccaaagggtg tgatgctgac ccaccgccag   2040
attgcaacca acctggctca gctggaacct tccatgccat ccgctccagg tgaccgggtg   2100
ctggctgttc tgccattctt ccacatctac ggcttgaccg cactcatgaa cgctcctttg   2160
cgcctgggtg ctaccgtggt ggtgctccct cgcttcgacc tggagcagtt ccttgcagcc   2220
atccagaacc accgtatcac cagtttgtac gtcgccccac caatcgtttt ggcactggct   2280
aagcaccctc tggtggccga ctatgacctt tcctccctcc gttacatcgt gagcgccgcg   2340
gcaccgctcg acgcgcgcct ggcagccgct tgttcccagc gtctgggcct gccccccggtg   2400
gggcaagcgt acggtatgac cgagctgtct cctggcaccc acgtcgtgcc gctcgatgca   2460
atggcagatg ccccacccgg caccgtgggt cgcctgatag ctggcaccga gatgcgcatc   2520
gtgtccctga ccgacccagg caccgacctg ccggcaggcg aatccggcga aatcctgatc   2580
cgcggccccc agattatgaa gggctacctc ggccgcccag atgctaccgc agcaatgatc   2640
gatgaggagg gctggctgca caccggcgat gtgggccacg tggacgctga tggttggttg   2700
ttcgtcgtgg atcgcgttaa ggagctgatc aagtacaagg gtttccaggt tgctcccgcg   2760
gagcttgaag cacacttgct cacccaccca ggtgttgcag atgcagctgt cgtcggcgca   2820
tacgacgacg acggtaacga ggtgccgcac gcctttgtgg tccgccagcc ggctgcacca   2880
ggcctcgcgg agtccgaaat catgatgtac gtggctgaac gcgttgctcc atacaagcgc   2940
gtgcgccgcg tgaccttcgt cgatgccgtg ccacgcgcag catccggcaa gatcctgcgt   3000
cgccagctgc gcgagccacg ctaaggatct aggaggataa agaaatgacc caggtcgtgg   3060
agcgccaggc tgatcgtctg tccagccgcg agtacctggc acgcgttgtt cgttccgcag   3120
gctgggacgc aggcctcacc agctgcaccg atgaagaaat cgtgcgcatg ggtgcatccg   3180
cacgcaccat tgaggaatac ctgaagtctg ataagccgat ctacggcctc acccagggct   3240
tcggtccact ggtcctgttc gatgcagatt ccgaactgga acagggcggc tctctcatct   3300
cccatctggg caccggccag ggtgcaccgc ttgcaccgga agtgtcccgc ctgattctgt   3360
ggctccgcat ccaaaacatg cgcaagggct attcggctgt cagtcctgtg ttctggcaaa   3420
aactggccga cctctggaac aagggcttca cccctgctat ccctcgccac ggcaccgtgt   3480
ccgccagcgg cgatctccag cctctggcac acgctgccct ggcttttacc ggcgtgggcg   3540
aggcatggac ccgtgatgca gacggccgtt ggtccaccgt gccagccgtg gacgcattag   3600
cagcactggg tgcagagccg ttcgattggc cagtgcgcga ggctttggcc ttcgtgaacg   3660
gtacgggcgc atcactcgcg gtggcagttc tcaaccacag atccgctctc cgtctcgtac   3720
gagcatgtgc agtcttgtct gcccgtttgg ctaccttgct aggagctaat cctgaacact   3780
acgatgtcgg ccacggagtc gcaaggggac aagttggcca gctgaccgcg gcggaatgga   3840
ttcggcaggg actaccacgc ggcatggtcc gagacggttc gcgccctctt caagaaccat   3900
acagcttgcg ctgtgccccc caggtccttg gcgcggtgct ggaccagctg gatggtgcag   3960
gcgatgttct ggcccgcgaa gtggatggct gccaggacaa tcctatcacc tacgagggcg   4020
aactgctgca cggcggtaac ttccacgcta tgccagtcgg cttcgcatcc gaccagatcg   4080
gtctggcgat gcacatggca gcttatctgg ctgaacgcca gctcggcctg ctggtgagcc   4140
```

-continued

```
cggtgaccaa cggcgacctg ccaccaatgc tgaccccacg cgctggacgc ggtgccggcc   4200
tggcgggcgt tcagatctcc gcaacctcct tcgtctctcg catccgccag ctggtgttcc   4260
cagctagcct caccaccctc ccaaccaacg gctggaacca ggaccatgtc ccaatggctc   4320
tgaacggcgc aaacagcgtg ttcgaagctc ttgaactggg ttggctgacc gtgggtagcc   4380
tggcagtcgg cgtggcccag ctcgctgcaa tgaccggcca cgcagctgag ggcgtgtggg   4440
ccgagttggc aggcatctgc ccaccactgg atgctgaccg cccactgggc gcggaggtcc   4500
gcgctgctcg cgatctcctc tccgcacacg ctgaccagct gctcgttgac gaggctgatg   4560
gcaaagactt cggctaactc tagagtcgac ctgcaggcat gcaagcttgg ctgttttggc   4620
ggatgagaga agattttcag cctgatacag attaaatcag aacgcagaag cggtctgata   4680
aaacagaatt tgcctggcgg cagtagcgcg gtggtcccac ctgaccccat gccgaactca   4740
gaagtgaaac gccgtagcgc cgatggtagt gtggggtctc cccatgcgag agtagggaac   4800
tgccaggcat caaataaaac gaaaggctca gtcgaaagac tgggcctttc gttttatctg   4860
ttgtttgtcg gtgaacgctc tcctgagtag gacaaatccg ccgggagcgg atttgaacgt   4920
tgcgaagcaa cggcccggag ggtggcgggc aggacgcccg ccataaactg ccaggcatca   4980
aattaagcag aaggccatcc tgacggatgg cctttttgcg tttctacaaa ctctttttgt   5040
ttatttttct aaatacattc aaatatgtat ccgctcatga attaattccg ctagatgacg   5100
tgcggcttcg acctcctggg cgtggcgctt gttggcgcgc tcgcggctgg ctgcggcacg   5160
acacgcgtct gagcagtatt ttgcgcgccg tcctcgtggg tcaggccggg gtgggatcag   5220
gccaccgcag taggcgcagc tgatgcgatc ctccactact gcgcgtcctc ctggcgctgc   5280
cgagcacgca gctcgtcggc cagctcttca aggtcggcca caagcgtttc taggtcgctc   5340
gcggcacttg cccagtcgcg tgatgctggc gcgtctgtcg tatcgagggc gcggaaaaat   5400
ccgatcaccg tttttaaatc gacggcggca tcgagtgcgt cggactccag cgcgacatcg   5460
gagagatcca ccgctgatgc ttcaggccag ttttggtact tcgtcgtgaa ggtcatgaca   5520
ccattataac gaacgttcgt taaaaattct agccccaatt ctgataattt cttccggcac   5580
tcctgcgaaa acctgcgaga cttcttgccc agaaaaaacg ccaagcgcag cggttaccgc   5640
acttttttc caggtgattt caccctgacc agcgaagcgg cactttagtg catgaggtgt   5700
gcccctggtt tcccctcttt ggagggttca acccaaaaaa gcacacaagc aaaaatgaaa   5760
atcatcatga gcaagttggt gcgaagcagc aacgcgctag ctccaaaaag gtctccagga   5820
tctcgaggag atttttgagg gggagggagt cgaggaagag ccagagcaga aggcggggaa   5880
ccgttctctg ccgacagcgt gagccccccct taaaaatcag gccggggagg aaccggggag   5940
ggatcagagc taggagcgag acaccctaaa gggggggaac cgttttctgc tgacggtgtt   6000
tcgtttatta gttttcagcc cgtggatagc ggagggtgag ggcaagtgag agccagagca   6060
aggacgggac ccctaaaggg gggaaccgtt ttctgctgac ggtgtttcgt ttattagttt   6120
tcagcccgtg gacggccgcg tttagcttcc attccaagtg cctttctgac ttgttggatg   6180
cgcctttcac tgacacctag ttcgcctgca agctcacgag tcgagggatc agcaaccgat   6240
tgagaacggg catccaggat cgcagttttg acgcgaagtt cgagcaactc gcctgtcatt   6300
tctcggcgtt tgtttgcttc cgctaatcgc tgtcgcgtct cctgcgcata cttactttct   6360
gggtcagccc atctgcgtgc attcgatgta gctgcgcccc gtcgccccat cgtcgctaga   6420
gctttccgcc ctcggctgct ctgcgtttcc acccgacgag cagggacgac tggctggcct   6480
```

-continued

```
ttagccacgt agccgcgcac acgacgcgcc atcgtcaggc gatcacgcat ggcgggaaga   6540
tccggctccc ggccgtctgc accgaccgcc tgggcaacgt tgtacgccac ttcatacgcg   6600
tcgatgatct tggcatcttt taggcgctca ccagcagctt tgagctggta tcccacggtc   6660
aacgcgtggc gaaacgcggt ctcgtcgcgc gctcgctctg gatttgtcca gagcactcgc   6720
acgccgtcga tcaggtcgcc ggacgcgtcc agggcgctcg gcaggctcgc gtccaaaatc   6780
gctagcgcct tggcttctgc ggtggcgcgt tgtgccgctt caatgcgggc gcgtccgctg   6840
gaaaagtcct gctcaatgta ctttttcggc ttctgtgatc cggtcatcgt tcgagcaatc   6900
tccattaggt cggccagccg atccacacga tcatgctggc agtgccattt ataggctgtc   6960
ggatcgtctg agacgtgcag cggccaccgg ctcagcctat gcgaaaaagc ctggtcagcg   7020
ccgaaaacac gagtcatttc ttccgtcgtt gcagccagca ggcgcatatt tgggctggtt   7080
ttacctgctg cggcatacac cgggtcaatg agccagatga gctggcattt cccgctcagc   7140
ggattcacgc cgatccaagc cggcgctttt tctaggcgtg cccatttctc taaaatcgcg   7200
tagacctgcg ggtttacgtg ctcaatcttc ccgccggcct ggtggctggg cacatcgatg   7260
tcaagcacga tcaccgcggc atgttgcgcg tgcgtcagcg caacgtactg gcaccgcgtc   7320
agcgcttttg agccagcccg gtagagcttt ggttgggttt cgccggtatc cgggttttta   7380
atccaggcgc tcgcgaaatc tcttgtcttg ctgccctgga agctttcgcg tcccaggtga   7440
gcgagcagtt cgcggcgatc ttctgccgtc cagccgcgtg agccgcagcg catagcttcg   7500
gggtgggtgt cgaacagatc ggcggacaat ttccacgcgc tagctgtgac tgtgtcctgc   7560
ggatcggcta gagtcatgtc ttgagtgctt tctcccagct gatgactggg ggttagccga   7620
cgccctgtga gttcccgctc acggggcgtt caacttttc aggtatttgt gcagcttatc    7680
gtgttttctt cgtaaatgaa cgcttaacta ccttgttaaa cgtggcaaat aggcaggatt   7740
gatggggatc tagcttcacg ctgccgcaag cactcagggc gcaagggctg ctaaaggaag   7800
cggaacacgt agaaagccag tccgcagaaa cggtgctgac cccggatgaa tgtcagctac   7860
tgggctatct ggacaaggga aaacgcaagc gcaaagagaa agcaggtagc ttgcagtggg   7920
cttacatggc gatagctaga ctgggcggtt ttatggacag caagcgaacc ggaattgcca   7980
gctggggcgc cctctggtaa ggttgggaag ccctgcaaag taaactggat ggctttcttg   8040
ccgccaagga tctgatggcg caggggatca agatctgatc aagagacagg atgaggatcg   8100
tttcgcatga ttgaacaaga tggattgcac gcaggttctc cggccgcttg ggtggagagg   8160
ctattcggct atgactgggc acaacagaca atcggctgct ctgatgccgc cgtgttccgg   8220
ctgtcagcgc aggggcgccc ggttcttttt gtcaagaccg acctgtccgg tgccctgaat   8280
gaactccaag acgaggcagc gcggctatcg tggctggcca cgacgggcgt tccttgcgca   8340
gctgtgctcg acgttgtcac tgaagcggga agggactggc tgctattggg cgaagtgccg   8400
gggcaggatc tcctgtcatc tcaccttgct cctgccgaga aagtatccat catggctgat   8460
gcaatgcggc ggctgcatac gcttgatccg gctacctgcc cattcgacca ccaagcgaaa   8520
catcgcatcg agcgagcacg tactcggatg gaagccggtc ttgtcgatca ggatgatctg   8580
gacgaagagc atcaggggct cgcgccagcc gaactgttcg ccaggctcaa ggcgcggatg   8640
cccgacggcg aggatctcgt cgtgacccat ggcgatgcct gcttgccgaa tatcatggtg   8700
gaaaatggcc gcttttctgg attcatcgac tgtggccggc tgggtgtggc ggaccgctat   8760
caggacatag cgttggctac ccgtgatatt gctgaagagc ttggcggcga atgggctgac   8820
cgcttcctcg tgctttacgg tatcgccgct cccgattcgc agcgcatcgc cttctatcgc   8880
```

cttcttgacg agttcttctg agcgggactc tggggttcgc ggaatcatga ccaaaatccc 8940
ttaacgtgag ttttcgttcc actgagcgtc agaccccgta gaaaagatca aaggatcttc 9000
ttgagatcct ttttttctgc gcgtaatctg ctgcttgcaa acaaaaaaac caccgctacc 9060
agcggtggtt tgtttgccgg atcaagagct accaactctt tttccgaagg taactggctt 9120
cagcagagcg cagataccaa atactgtcct tctagtgtag ccgtagttag gccaccactt 9180
caagaactct gtagcaccgc ctacatacct cgctctgcta atcctgttac cagtggctgc 9240
tgccagtggc gataagtcgt gtcttaccgg gttggactca agacgatagt taccggataa 9300
ggcgcagcgg tcgggctgaa cggggggttc gtgcacacag cccagcttgg agcgaacgac 9360
ctacaccgaa ctgagatacc tacagcgtga gctatgagaa agcgccacgc ttcccgaagg 9420
gagaaaggcg gacaggtatc cggtaagcgg cagggtcgga acaggagagc gcacgaggga 9480
gcttccaggg ggaaacgcct ggtatcttta tagtcctgtc gggtttcgcc acctctgact 9540
tgagcgtcga tttttgtgat gctcgtcagg ggggcggagc ctatggaaaa acgccagcaa 9600
cgcggccttt ttacggttcc tggccttttg ctggcctttt gctcacatgt tctttcctgc 9660
gttatcccct gattctgtgg ataaccgtat taccgccttt gagtgagctg ataccgctcg 9720
ccgcagccga acgaccgagc gcagcgagtc agtgagcgag gaagcggaag agcgcctgat 9780
gcggtatttt ctccttacgc atctgtgcgg tatttcacac cgcatatggt gcactctcag 9840
tacaatctgc tctgatgccg catagttaag ccagtataca ctccgctatc gctacgtgac 9900
tgggtcatgg ctgcgccccg acacccgcca acacccgctg acgcgccctg acgggcttgt 9960
ctgctcccgg catccgctta cagacaagct gtgaccgtct ccgggagctg catgtgtcag 10020
aggttttcac cgtcatcacc gaaacgcgcg aggcagcaga tcaattcgcg cgcgaaggcg 10080
aagcggcatg catttacgtt gacaccatcg aatggtgcaa aacctttcgc ggtatggcat 10140
gatagcgccc ggaagagagt caattcaggg tggtgaatgt gaaaccagta acgttatacg 10200
atgtcgcaga gtatgccggt gtctcttatc agaccgtttc ccgcgtggtg aaccaggcca 10260
gccacgtttc tgcgaaaacg cgggaaaaag tggaagcggc gatggcggag ctgaattaca 10320
ttcccaaccg cgtggcacaa caactggcgg gcaaacagtc gttgctgatt ggcgttgcca 10380
cctccagtct ggccctgcac gcgccgtcgc aaattgtcgc ggcgattaaa tctcgcgccg 10440
atcaactggg tgccagcgtg gtggtgtcga tggtagaacg aagcggcgtc gaagcctgta 10500
aagcggcggt gcacaatctt ctcgcgcaac gcgtcagtgg gctgatcatt aactatccgc 10560
tggatgacca ggatgccatt gctgtggaag ctgcctgcac taatgttccg gcgttatttc 10620
ttgatgtctc tgaccagaca cccatcaaca gtattatttt ctcccatgaa gacggtacgc 10680
gactgggcgt ggagcatctg gtcgcattgg gtcaccagca aatcgcgctg ttagcgggcc 10740
cattaagttc tgtctcggcg cgtctgcgtc tggctggctg gcataaatat ctcactcgca 10800
atcaaattca gccgatagcg gaacgggaag gcgactggag tgccatgtcc ggttttcaac 10860
aaaccatgca aatgctgaat gagggcatcg ttcccactgc gatgctggtt gccaacgatc 10920
agatggcgct gggcgcaatg cgcgccatta ccgagtccgg gctgcgcgtt ggtgcggata 10980
tctcggtagt gggatacgac gataccgaag acagctcatg ttatatcccg ccgtcaacca 11040
ccatcaaaca ggattttcgc ctgctggggc aaaccagcgt ggaccgcttg ctgcaactct 11100
ctcagggcca ggcggtgaag ggcaatcagc tgttgcccgt ctcactggtg aaaagaaaaa 11160
ccaccctggc gcccaatacg caaaccgcct ctccccgcgc gttggccgat tcattaatgc 11220
agctggcacg acaggtttcc cgactggaaa gcgggcagtg agcgcaacgc aattaatgtg 11280
agttagcgcg aattgatctg gtttgacagc ttatcat 11317

<210> SEQ ID NO 38
<211> LENGTH: 4314
<212> TYPE: DNA
<213> ORGANISM: Artificial Sequence
<220> FEATURE:
<223> OTHER INFORMATION: operon RiPKS-Sc4CL-SeSam8

<400> SEQUENCE: 38
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatgttccg 1200
ttccgagtac gcagatgtgc ctccagtgga cctccctatc cacgatgctg tcctgggtgg 1260
cgcggccgca ttcggcagca ccccagctct gatcgatggc accgatggca ccaccctgac 1320
ctacgaacag gtcgatcgct tccaccgtcg cgtcgctgct gctctggcgg aaaccggcgt 1380
gcgcaagggc gatgtcctgg ccctgcactc tccaaacacc gttgctttcc ctctggcatt 1440
ctacgctgca acccgcgctg gtgcatccgt gaccactgtt caccctctcg ctaccgcaga 1500
agagtttgct aagcagctga aggattcggc tgcacgttgg atcgtcaccg tttccccact 1560
gctgtccacc gcacgccgcg ccgcagagtt ggcaggcggc gtgcaggaaa ttttggtctg 1620
cgattctgct ccaggtcacc gttctctcgt cgatatgctg gctagcaccg cacccgaacc 1680
atccgtcgct atcgatccag cagaagatgt ggctgccctt ccgtactcct ctggcaccac 1740
cggcacccca aagggtgtga tgctgaccca ccgccagatt gcaaccaacc tggctcagct 1800
ggaaccttcc atgccatccg ctccaggtga ccgggtgctg gctgttctgc cattcttcca 1860
catctacggc ttgaccgcac tcatgaacgc tcctttgcgc ctgggtgcta ccgtggtggt 1920
gctccctcgc ttcgacctgg agcagttcct tgcagccatc cagaaccacc gtatcaccag 1980

-continued

```
tttgtacgtc gccccaccaa tcgttttggc actggctaag caccctctgg tggccgacta   2040
tgacctttcc tccctccgtt acatcgtgag cgccgcggca ccgctcgacg cgcgcctggc   2100
agccgcttgt tcccagcgtc tgggcctgcc cccggtgggg caagcgtacg gtatgaccga   2160
gctgtctcct ggcacccacg tcgtgccgct cgatgcaatg gcagatgccc cacccggcac   2220
cgtgggtcgc ctgatagctg gcaccgagat gcgcatcgtg tccctgaccg acccaggcac   2280
cgacctgccg gcaggcgaat ccggcgaaat cctgatccgc ggcccccaga ttatgaaggg   2340
ctacctcggc cgcccagatg ctaccgcagc aatgatcgat gaggagggct ggctgcacac   2400
cggcgatgtg ggccacgtgg acgctgatgg ttggttgttc gtcgtggatc gcgttaagga   2460
gctgatcaag tacaagggtt tccaggttgc tcccgcggag cttgaagcac acttgctcac   2520
ccacccaggt gttgcagatg cagctgtcgt cggcgcatac gacgacgacg gtaacgaggt   2580
gccgcacgcc tttgtggtcc gccagccggc tgcaccaggc ctcgcggagt ccgaaatcat   2640
gatgtacgtg gctgaacgcg ttgctccata caagcgcgtg cgccgcgtga ccttcgtcga   2700
tgccgtgcca cgcgcagcat ccggcaagat cctgcgtcgc cagctgcgcg agccacgcta   2760
aggatctagg aggataaaga aatgacccag gtcgtggagc gccaggctga tcgtctgtcc   2820
agccgcgagt acctggcacg cgttgttcgt tccgcaggct gggacgcagg cctcaccagc   2880
tgcaccgatg aagaaatcgt gcgcatgggt gcatccgcac gcaccattga ggaatacctg   2940
aagtctgata agccgatcta cggcctcacc cagggcttcg gtccactggt cctgttcgat   3000
gcagattccg aactggaaca gggcggctct ctcatctccc atctgggcac cggccagggt   3060
gcaccgcttg caccggaagt gtcccgcctg attctgtggc tccgcatcca aaacatgcgc   3120
aagggctatt cggctgtcag tcctgtgttc tggcaaaaac tggccgacct ctggaacaag   3180
ggcttcaccc ctgctatccc tcgccacggc accgtgtccg ccagcggcga tctccagcct   3240
ctggcacacg ctgccctggc ttttaccggc gtgggcgagg catggacccg tgatgcagac   3300
ggccgttggt ccaccgtgcc agccgtggac gcattagcag cactgggtgc agagccgttc   3360
gattggccag tgcgcgaggc tttggccttc gtgaacggta cgggcgcatc actcgcggtg   3420
gcagttctca accacagatc cgctctccgt ctcgtacgag catgtgcagt cttgtctgcc   3480
cgtttggcta ccttgctagg agctaatcct gaacactacg atgtcggcca cggagtcgca   3540
aggggacaag ttggccagct gaccgcggcg gaatggattc ggcagggact accacgcggc   3600
atggtccgag acggttcgcg ccctcttcaa gaaccataca gcttgcgctg tgccccccag   3660
gtccttggcg cggtgctgga ccagctggat ggtgcaggcg atgttctggc ccgcgaagtg   3720
gatggctgcc aggacaatcc tatcacctac gagggcgaac tgctgcacgg cggtaacttc   3780
cacgctatgc cagtcggctt cgcatccgac cagatcggtc tggcgatgca catggcagct   3840
tatctggctg aacgccagct cggcctgctg gtgagcccgg tgaccaacgg cgacctgcca   3900
ccaatgctga ccccacgcgc tggacgcggt gccggcctgg cgggcgttca gatctccgca   3960
acctccttcg tctctcgcat ccgccagctg gtgttcccag ctagcctcac caccctccca   4020
accaacggct ggaaccagga ccatgtccca atggctctga acggcgcaaa cagcgtgttc   4080
gaagctcttg aactgggttg gctgaccgtg ggtagcctgg cagtcggcgt ggcccagctc   4140
gctgcaatga ccggccacgc agctgagggc gtgtgggccg agttggcagg catctgccca   4200
ccactggatg ctgaccgccc actgggcgcg gaggtccgcg ctgctcgcga tctcctctcc   4260
gcacacgctg accagctgct cgttgacgag gctgatggca aagacttcgg ctaa         4314
```

<210> SEQ ID NO 39
<211> LENGTH: 11440
<212> TYPE: DNA
<213> ORGANISM: Artificial Sequence
<220> FEATURE:
<223> OTHER INFORMATION: plasmid RiPKS-Nt4CL-RcTAL-pECXK (pECXK_J)

<400> SEQUENCE: 39
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380
tcagatctcc aagtccctgc tgatcctggc atggttcctc ttctccctgg tgtaaggatc 1440
taggaggatt atgagatgga gaaagataca aaacaggttg acataatttt ccgatcaaaa 1500
ctccctgata tttacatccc taaccatctt cctttacact cctactgttt cgaaaacatt 1560
tccgagttca gttctcgtcc ttgtttaatc aatggcgcca acaaacaaat ttatacgtat 1620
gctgatgttg aactcaattc aagaaaagtt gctgctggtc ttcacaaaca agggattcaa 1680
ccaaaggata caataatgat cctattgcct aactccccag aatttgtgtt tgctttcatt 1740
ggtgcatcgt acctcggagc tatttctaca atggccaatc ctttgtttac tcctgctgag 1800
gttgtgaagc aagccgaggc ttctagtgct aagatcattg tcacacaagc gtgtcatgtt 1860
aacaaagtga aagattatgc atttgagaat gatgtgaaga tcatatgcat cgactcggcg 1920
ccggagggtt gtctccactt ctccgtgcta actcaggcta atgagcacga tattcctgag 1980
gttgaaattc aacctgacga tgtggtggcg ttgccatact cctccgggac gacgggatta 2040
cctaaaggag tgatgttgac gcacaaggga cttgtgacaa gcgtcgcaca acaagtcgac 2100

-continued

```
ggtgaaaatc cgaatttgta tatccatagc gaggacgtga tgctttgtgt cttgcccttg   2160
ttccatatct attcactcaa ctccgttttg ctttgtggat taagggtggg agcagcgatt   2220
ttgattatgc agaaatttga tattgtttct ttcttggagt tgatacaaag ttacaaggtg   2280
acaatagggc cgtttgtacc acctattgtt ttggycattg ctaagagtcc tatggttgat   2340
gattatgatc tttcatcagt aagaaccgtc atgtctgggg ctgcaccatt aggaaaggag   2400
cttgaagata ctgttcgagc caaatttcct aatgctaaac ttggtcaggg ttatggtatg   2460
acagaagctg gaccagtgtt ggctatgtgc ttggcatttg caaaagaacc ctttgaaata   2520
aaatcagggg catgtggaac agttgtgaga aatgctgaaa tgaaaattgt ggatcctaaa   2580
actggtaatt ctcttcccag aaatcaatct ggagaaattt gcattagagg agaccagatc   2640
atgaaaggct acctgaatga tccagaggcc acagcaagaa caatagacaa agaagggtgg   2700
ttatatactg gtgacattgg ctacattgat gatgacgacg agcttttcat tgttgatcga   2760
ttaaaggaac tgatcaaata caaaggattt caagtcgcac ctgctgagct cgaagctctc   2820
cttctcaacc atcccaacat ttctgatgct gctgttgtcc ccatgaagga cgagcaagca   2880
ggagaagttc cagtggcttt tgttgttaga tccaacggat ccaccattac tgaagatgaa   2940
gtcaaagatt ttatttcaaa gcaggtgata ttttataaga ggataaagcg ggtatttttc   3000
gtggatgcta ttcctaaatc tccatctggc aaaatccttc gaaaagattt gagagctaaa   3060
ctggctgctg ggcttccaaa ttaaggatct aggaggataa agaaatgacc ctgcaatccc   3120
agactgcaaa ggactgcctg gcgctggatg gtgcactgac actggttcag tgcgaagcaa   3180
ttgccactca ccgctcacgg atctccgtca caccagcatt gcgggaacgc tgcgcccgcg   3240
cgcacgcacg tctggagcac gctatcgcag aacagcgtca catctatggt atcaccaccg   3300
gcttcggacc actggctaat cgcctgatcg gtgcagatca gggcgccgaa ctccagcaga   3360
acctcatcta ccaccttgct actggcgtgg gcccaaaact ctcctgggct gaagcacgtg   3420
cactcatgct ggctcgtctc aactccatcc ttcagggcgc atctggtgca tcaccagaaa   3480
ccatcgaccg tatcgttgcc gttctgaacg ctggcttcgc cccagaagtc ccagctcagg   3540
gcaccgttgg tgcatctggc gatctgaccc cactggctca catggtgctg gcgcttcagg   3600
gtcgaggtcg tatgatcgat ccatccggcc gtgttcagga agccggcgca gtgatggatc   3660
gcctgtgcgg tggcccactg accttggcag cccgtgacgg tctggctctg gtcaacggta   3720
cttccgctat gaccgcaatc gctgctttga ccggtgtgga ggctgcgcgc gcaatcgacg   3780
ccgcattgcg ccactccgct gtgctcatgg aggttctctc cggccacgct gaggcttggc   3840
accctgcatt tgctgaactc cgcccacacc caggccagct gcgcgcaacc gaacgtctgg   3900
cccaggctct cgatggcgcc ggtcgcgttt gccgcacctt gaccgcggcc cgtcgcctga   3960
ccgcagctga tctgcgccct gaggatcacc cagcccagga cgcctactcc ctgcgcgtgg   4020
tgccacagct ggttggcgct gtctgggaca ccctcgattg gcacgatcgc gtcgtgacct   4080
gcgaactcaa ctctgtgacc gacaacccaa tcttcccgga aggctgcgct gttccagcac   4140
tgcacggcgg caacttcatg ggcgtgcacg tcgcactggc gtcggacgcc ctgaacgctg   4200
cattggttac cctggcaggt ctggtggagc gccagatcgc acgccttact gatgagaagc   4260
tgaacaaggg acttccggca ttccttcacg gtggtcaggc tggccttcag tccggcttca   4320
tgggcgcgca ggtcaccgca accgcgctcc ttgctgaaat gcgcgcaaac gcaaccccgg   4380
tgtctgttca gtcactgtct accaacggcg ctaaccagga tgttgtcagc atgggcacca   4440
```

```
tcgctgcacg ccgcgctcgc gcacagctgc tcccactgtc ccagattcag gcaatcctgg   4500
ctctcgctct cgcccaggca atggatctgc tggatgatcc agagggccag gctggctggt   4560
cccttaccgc acgcgacctg cgcgatcgca tccgcgctgt ctcgccgggc ctgcgcgcag   4620
atcgcccact ggccggccac atcgaggcag tcgctcaggg tctgcgccac ccttccgcag   4680
cagctgatcc accagcataa ctctagagtc gacctgcagg catgcaagct tggctgtttt   4740
ggcggatgag agaagatttt cagcctgata cagattaaat cagaacgcag aagcggtctg   4800
ataaaacaga atttgcctgg cggcagtagc gcggtggtcc cacctgaccc catgccgaac   4860
tcagaagtga aacgccgtag cgccgatggt agtgtggggt ctccccatgc gagagtaggg   4920
aactgccagg catcaaataa aacgaaaggc tcagtcgaaa gactgggcct ttcgttttat   4980
ctgttgtttg tcggtgaacg ctctcctgag taggacaaat ccgccgggag cggatttgaa   5040
cgttgcgaag caacggcccg gagggtggcg ggcaggacgc ccgccataaa ctgccaggca   5100
tcaaattaag cagaaggcca tcctgacgga tggccttttt gcgtttctac aaactctttt   5160
tgtttatttt tctaaataca ttcaaatatg tatccgctca tgaattaatt ccgctagatg   5220
acgtgcggct tcgacctcct gggcgtggcg cttgttggcg cgctcgcggc tggctgcggc   5280
acgacacgcg tctgagcagt attttgcgcg ccgtcctcgt gggtcaggcc ggggtgggat   5340
caggccaccg cagtaggcgc agctgatgcg atcctccact actgcgcgtc ctcctggcgc   5400
tgccgagcac gcagctcgtc ggccagctct tcaaggtcgg ccacaagcgt ttctaggtcg   5460
ctcgcggcac ttgcccagtc gcgtgatgct ggcgcgtctg tcgtatcgag ggcgcggaaa   5520
aatccgatca ccgtttttaa atcgacggcg gcatcgagtg cgtcggactc cagcgcgaca   5580
tcggagagat ccaccgctga tgcttcaggc cagttttggt acttcgtcgt gaaggtcatg   5640
acaccattat aacgaacgtt cgttaaaaat tctagcccca attctgataa tttcttccgg   5700
cactcctgcg aaaacctgcg agacttcttg cccagaaaaa acgccaagcg cagcggttac   5760
cgcacttttt ttccaggtga tttcaccctg accagcgaag cggcacttta gtgcatgagg   5820
tgtgcccctg gtttcccctc tttggagggt tcaacccaaa aaagcacaca agcaaaaatg   5880
aaaatcatca tgagcaagtt ggtgcgaagc agcaacgcgc tagctccaaa aaggtctcca   5940
ggatctcgag gagatttttg agggggaggg agtcgaggaa gagccagagc agaaggcggg   6000
gaaccgttct ctgccgacag cgtgagcccc ccttaaaaat caggccgggg aggaaccggg   6060
gagggatcag agctaggagc gagacaccct aaaggggggg aaccgttttc tgctgacggt   6120
gtttcgttta ttagttttca gcccgtggat agcggagggt gagggcaagt gagagccaga   6180
gcaaggacgg gacccctaaa ggggggaacc gttttctgct gacggtgttt cgtttattag   6240
ttttcagccc gtggacggcc gcgtttagct tccattccaa gtgcctttct gacttgttgg   6300
atgcgccttt cactgacacc tagttcgcct gcaagctcac gagtcgaggg atcagcaacc   6360
gattgagaac gggcatccag gatcgcagtt ttgacgcgaa gttcgagcaa ctcgcctgtc   6420
atttctcggc gtttgtttgc ttccgctaat cgctgtcgcg tctcctgcgc atacttactt   6480
tctgggtcag cccatctgcg tgcattcgat gtagctgcgc cccgtcgccc catcgtcgct   6540
agagctttcc gccctcggct gctctgcgtt tccacccgac gagcagggac gactggctgg   6600
cctttagcca cgtagccgcg cacacgacgc gccatcgtca ggcgatcacg catggcggga   6660
agatccggct cccggccgtc tgcaccgacc gcctgggcaa cgttgtacgc cacttcatac   6720
gcgtcgatga tcttggcatc ttttaggcgc tcaccagcag ctttgagctg gtatcccacg   6780
gtcaacgcgt ggcgaaacgc ggtctcgtcg cgcgctcgct ctggatttgt ccagagcact   6840
```

cgcacgccgt cgatcaggtc gccggacgcg tccagggcgc tcggcaggct cgcgtccaaa 6900
atcgctagcg ccttggcttc tgcggtggcg cgttgtgccg cttcaatgcg ggcgcgtccg 6960
ctggaaaagt cctgctcaat gtactttttc ggcttctgtg atccggtcat cgttcgagca 7020
atctccatta ggtcggccag ccgatccaca cgatcatgct ggcagtgcca tttataggct 7080
gtcggatcgt ctgagacgtg cagcggccac cggctcagcc tatgcgaaaa agcctggtca 7140
gcgccgaaaa cacgagtcat ttcttccgtc gttgcagcca gcaggcgcat atttgggctg 7200
gttttacctg ctgcggcata caccgggtca atgagccaga tgagctggca tttcccgctc 7260
agcggattca cgccgatcca agccggcgct ttttctaggc gtgcccattt ctctaaaatc 7320
gcgtagacct gcgggtttac gtgctcaatc ttcccgccgg cctggtggct gggcacatcg 7380
atgtcaagca cgatcaccgc ggcatgttgc gcgtgcgtca gcgcaacgta ctggcaccgc 7440
gtcagcgctt ttgagccagc ccggtagagc tttggttggg tttcgccggt atccgggttt 7500
ttaatccagg cgctcgcgaa atctcttgtc ttgctgccct ggaagctttc gcgtcccagg 7560
tgagcgagca gttcgcggcg atcttctgcc gtccagccgc gtgagccgca gcgcatagct 7620
tcggggtggg tgtcgaacag atcggcggac aatttccacg cgctagctgt gactgtgtcc 7680
tgcggatcgg ctagagtcat gtcttgagtg ctttctccca gctgatgact gggggttagc 7740
cgacgccctg tgagttcccg ctcacggggc gttcaacttt ttcaggtatt tgtgcagctt 7800
atcgtgtttt cttcgtaaat gaacgcttaa ctaccttgtt aaacgtggca aataggcagg 7860
attgatgggg atctagcttc acgctgccgc aagcactcag ggcgcaaggg ctgctaaagg 7920
aagcggaaca cgtagaaagc cagtccgcag aaacggtgct gaccccggat gaatgtcagc 7980
tactgggcta tctggacaag ggaaaacgca agcgcaaaga gaaagcaggt agcttgcagt 8040
gggcttacat ggcgatagct agactgggcg gttttatgga cagcaagcga accggaattg 8100
ccagctgggg cgccctctgg taaggttggg aagccctgca aagtaaactg gatggctttc 8160
ttgccgccaa ggatctgatg gcgcagggga tcaagatctg atcaagagac aggatgagga 8220
tcgtttcgca tgattgaaca agatggattg cacgcaggtt ctccggccgc ttgggtggag 8280
aggctattcg gctatgactg ggcacaacag acaatcggct gctctgatgc cgccgtgttc 8340
cggctgtcag cgcaggggcg cccggttctt tttgtcaaga ccgacctgtc cggtgccctg 8400
aatgaactcc aagacgaggc agcgcggcta tcgtggctgg ccacgacggg cgttccttgc 8460
gcagctgtgc tcgacgttgt cactgaagcg ggaagggact ggctgctatt gggcgaagtg 8520
ccggggcagg atctcctgtc atctcacctt gctcctgccg agaaagtatc catcatggct 8580
gatgcaatgc ggcggctgca tacgcttgat ccggctacct gcccattcga ccaccaagcg 8640
aaacatcgca tcgagcgagc acgtactcgg atggaagccg gtcttgtcga tcaggatgat 8700
ctggacgaag agcatcaggg gctcgcgcca gccgaactgt tcgccaggct caaggcgcgg 8760
atgcccgacg gcgaggatct cgtcgtgacc catggcgatg cctgcttgcc gaatatcatg 8820
gtggaaaatg gccgcttttc tggattcatc gactgtggcc ggctgggtgt ggcggaccgc 8880
tatcaggaca tagcgttggc tacccgtgat attgctgaag agcttggcgg cgaatgggct 8940
gaccgcttcc tcgtgcttta cggtatcgcc gctcccgatt cgcagcgcat cgccttctat 9000
cgccttcttg acgagttctt ctgagcggga ctctggggtt cgcggaatca tgaccaaaat 9060
cccttaacgt gagttttcgt tccactgagc gtcagacccc gtagaaaaga tcaaaggatc 9120
ttcttgagat cctttttttc tgcgcgtaat ctgctgcttg caaacaaaaa aaccaccgct 9180
accagcggtg gtttgtttgc cggatcaaga gctaccaact ctttttccga aggtaactgg 9240
cttcagcaga gcgcagatac caaatactgt ccttctagtg tagccgtagt taggccacca 9300
cttcaagaac tctgtagcac cgcctacata cctcgctctg ctaatcctgt taccagtggc 9360
tgctgccagt ggcgataagt cgtgtcttac cgggttggac tcaagacgat agttaccgga 9420
taaggcgcag cggtcgggct gaacgggggg ttcgtgcaca cagcccagct tggagcgaac 9480
gacctacacc gaactgagat acctacagcg tgagctatga gaaagcgcca cgcttcccga 9540
agggagaaag gcggacaggt atccggtaag cggcagggtc ggaacaggag agcgcacgag 9600
ggagcttcca gggggaaacg cctggtatct ttatagtcct gtcgggtttc gccacctctg 9660
acttgagcgt cgatttttgt gatgctcgtc aggggggcgg agcctatgga aaaacgccag 9720
caacgcggcc tttttacggt tcctggcctt ttgctggcct tttgctcaca tgttctttcc 9780
tgcgttatcc cctgattctg tggataaccg tattaccgcc tttgagtgag ctgataccgc 9840
tcgccgcagc cgaacgaccg agcgcagcga gtcagtgagc gaggaagcgg aagagcgcct 9900
gatgcggtat tttctcctta cgcatctgtg cggtatttca caccgcatat ggtgcactct 9960
cagtacaatc tgctctgatg ccgcatagtt aagccagtat acactccgct atcgctacgt 10020
gactgggtca tggctgcgcc ccgacacccg ccaacacccg ctgacgcgcc ctgacgggct 10080
tgtctgctcc cggcatccgc ttacagacaa gctgtgaccg tctccgggag ctgcatgtgt 10140
cagaggtttt caccgtcatc accgaaacgc gcgaggcagc agatcaattc gcgcgcgaag 10200
gcgaagcggc atgcatttac gttgacacca tcgaatggtg caaaaccttt cgcggtatgg 10260
catgatagcg cccggaagag agtcaattca gggtggtgaa tgtgaaacca gtaacgttat 10320
acgatgtcgc agagtatgcc ggtgtctctt atcagaccgt ttcccgcgtg gtgaaccagg 10380
ccagccacgt ttctgcgaaa acgcgggaaa aagtggaagc ggcgatggcg gagctgaatt 10440
acattcccaa ccgcgtggca caacaactgg cgggcaaaca gtcgttgctg attggcgttg 10500
ccacctccag tctggccctg cacgcgccgt cgcaaattgt cgcggcgatt aaatctcgcg 10560
ccgatcaact gggtgccagc gtggtggtgt cgatggtaga acgaagcggc gtcgaagcct 10620
gtaaagcggc ggtgcacaat cttctcgcgc aacgcgtcag tgggctgatc attaactatc 10680
cgctggatga ccaggatgcc attgctgtgg aagctgcctg cactaatgtt ccggcgttat 10740
ttcttgatgt ctctgaccag acacccatca acagtattat tttctcccat gaagacggta 10800
cgcgactggg cgtggagcat ctggtcgcat tgggtcacca gcaaatcgcg ctgttagcgg 10860
gcccattaag ttctgtctcg gcgcgtctgc gtctggctgg ctggcataaa tatctcactc 10920
gcaatcaaat tcagccgata gcggaacggg aaggcgactg gagtgccatg tccggttttc 10980
aacaaaccat gcaaatgctg aatgagggca tcgttcccac tgcgatgctg gttgccaacg 11040
atcagatggc gctgggcgca atgcgcgcca ttaccgagtc cgggctgcgc gttggtgcgg 11100
atatctcggt agtgggatac gacgataccg aagacagctc atgttatatc ccgccgtcaa 11160
ccaccatcaa acaggatttt cgcctgctgg ggcaaaccag cgtggaccgc ttgctgcaac 11220
tctctcaggg ccaggcggtg aagggcaatc agctgttgcc cgtctcactg gtgaaaagaa 11280
aaaccaccct ggcgcccaat acgcaaaccg cctctccccg cgcgttggcc gattcattaa 11340
tgcagctggc acgacaggtt tcccgactgg aaagcgggca gtgagcgcaa cgcaattaat 11400
gtgagttagc gcgaattgat ctggtttgac agcttatcat 11440

<210> SEQ ID NO 40
<211> LENGTH: 4437

<212> TYPE: DNA
<213> ORGANISM: Artificial Sequence
<220> FEATURE:
<223> OTHER INFORMATION: operon RiPKS-Nt4CL-RcTAL

<400> SEQUENCE: 40
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180
agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatggagaa 1200
agatacaaaa caggttgaca taattttccg atcaaaactc cctgatattt acatccctaa 1260
ccatcttcct ttacactcct actgtttcga aaacatttcc gagttcagtt ctcgtccttg 1320
tttaatcaat ggcgccaaca aacaaattta tacgtatgct gatgttgaac tcaattcaag 1380
aaaagttgct gctggtcttc acaaacaagg gattcaacca aaggatacaa taatgatcct 1440
attgcctaac tccccagaat ttgtgtttgc tttcattggt gcatcgtacc tcggagctat 1500
ttctacaatg gccaatcctt tgtttactcc tgctgaggtt gtgaagcaag ccgaggcttc 1560
tagtgctaag atcattgtca cacaagcgtg tcatgttaac aaagtgaaag attatgcatt 1620
tgagaatgat gtgaagatca tatgcatcga ctcggcgccg gagggttgtc tccacttctc 1680
cgtgctaact caggctaatg agcacgatat tcctgaggtt gaaattcaac ctgacgatgt 1740
ggtggcgttg ccatactcct ccgggacgac gggattacct aaaggagtga tgttgacgca 1800
caagggactt gtgacaagcg tcgcacaaca agtcgacggt gaaaatccga atttgtatat 1860
ccatagcgag gacgtgatgc tttgtgtctt gcccttgttc catatctatt cactcaactc 1920
cgttttgctt tgtggattaa gggtgggagc agcgattttg attatgcaga aatttgatat 1980
tgtttctttc ttggagttga tacaaagtta caaggtgaca atagggccgt ttgtaccacc 2040
tattgttttg gycattgcta agagtcctat ggttgatgat tatgatcttt catcagtaag 2100
aaccgtcatg tctggggctg caccattagg aaaggagctt gaagatactg ttcgagccaa 2160

```
atttcctaat gctaaacttg gtcagggtta tggtatgaca gaagctggac cagtgttggc   2220
tatgtgcttg gcatttgcaa aagaaccctt tgaaataaaa tcaggggcat gtggaacagt   2280
tgtgagaaat gctgaaatga aaattgtgga tcctaaaact ggtaattctc ttcccagaaa   2340
tcaatctgga gaaatttgca ttagaggaga ccagatcatg aaaggctacc tgaatgatcc   2400
agaggccaca gcaagaacaa tagacaaaga agggtggtta tatactggtg acattggcta   2460
cattgatgat gacgacgagc ttttcattgt tgatcgatta aaggaactga tcaaatacaa   2520
aggatttcaa gtcgcacctg ctgagctcga agctctcctt ctcaaccatc ccaacatttc   2580
tgatgctgct gttgtcccca tgaaggacga gcaagcagga gaagttccag tggcttttgt   2640
tgttagatcc aacggatcca ccattactga agatgaagtc aaagatttta tttcaaagca   2700
ggtgatattt tataagagga taaagcgggt atttttcgtg gatgctattc ctaaatctcc   2760
atctggcaaa atccttcgaa aagatttgag agctaaactg gctgctgggc ttccaaatta   2820
aggatctagg aggataaaga aatgaccctg caatcccaga ctgcaaagga ctgcctggcg   2880
ctggatggtg cactgacact ggttcagtgc gaagcaattg ccactcaccg ctcacggatc   2940
tccgtcacac cagcattgcg ggaacgctgc gcccgcgcgc acgcacgtct ggagcacgct   3000
atcgcagaac agcgtcacat ctatggtatc accaccggct tcggaccact ggctaatcgc   3060
ctgatcggtg cagatcaggg cgccgaactc cagcagaacc tcatctacca ccttgctact   3120
ggcgtgggcc caaaactctc ctgggctgaa gcacgtgcac tcatgctggc tcgtctcaac   3180
tccatccttc agggcgcatc tggtgcatca ccagaaacca tcgaccgtat cgttgccgtt   3240
ctgaacgctg gcttcgcccc agaagtccca gctcagggca ccgttggtgc atctggcgat   3300
ctgaccccac tggctcacat ggtgctggcg cttcagggtc gaggtcgtat gatcgatcca   3360
tccggccgtg ttcaggaagc cggcgcagtg atggatcgcc tgtgcggtgg cccactgacc   3420
ttggcagccc gtgacggtct ggctctggtc aacggtactt ccgctatgac cgcaatcgct   3480
gctttgaccg gtgtggaggc tgcgcgcgca atcgacgccg cattgcgcca ctccgctgtg   3540
ctcatggagg ttctctccgg ccacgctgag gcttggcacc ctgcatttgc tgaactccgc   3600
ccacacccag gccagctgcg cgcaaccgaa cgtctggccc aggctctcga tggcgccggt   3660
cgcgtttgcc gcaccttgac cgcggcccgt cgcctgaccg cagctgatct gcgccctgag   3720
gatcacccag cccaggacgc ctactccctg cgcgtggtgc cacagctggt tggcgctgtc   3780
tgggacaccc tcgattggca cgatcgcgtc gtgacctgcg aactcaactc tgtgaccgac   3840
aacccaatct tcccggaagg ctgcgctgtt ccagcactgc acggcggcaa cttcatgggc   3900
gtgcacgtcg cactggcgtc ggacgccctg aacgctgcat tggttaccct ggcaggtctg   3960
gtggagcgcc agatcgcacg ccttactgat gagaagctga acaagggact tccggcattc   4020
cttcacggtg gtcaggctgg ccttcagtcc ggcttcatgg gcgcgcaggt caccgcaacc   4080
gcgctccttg ctgaaatgcg cgcaaacgca accccggtgt ctgttcagtc actgtctacc   4140
aacggcgcta accaggatgt tgtcagcatg ggcaccatcg ctgcacgccg cgctcgcgca   4200
cagctgctcc cactgtccca gattcaggca atcctggctc tcgctctcgc ccaggcaatg   4260
gatctgctgg atgatccaga gggccaggct ggctggtccc ttaccgcacg cgacctgcgc   4320
gatcgcatcc gcgctgtctc gccgggcctg cgcgcagatc gcccactggc cggccacatc   4380
gaggcagtcg ctcagggtct gcgccaccct tccgcagcag ctgatccacc agcataa      4437
```

<210> SEQ ID NO 41
<211> LENGTH: 11365

<212> TYPE: DNA
<213> ORGANISM: Artificial Sequence
<220> FEATURE:
<223> OTHER INFORMATION: plasmid RiPKS-Nt4CL-FjTAL-pECXK (pECXK_K)

<400> SEQUENCE: 41
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggtta ccgttgaaga 300
agtccgcaag gctcagcgcg cagaaggccc tgcaaccgtt ctggcaatcg gcaccgcaac 360
cccaccaaac tgcgtcggcc agtccaccta cccagattat tatttccgta tcaccaactc 420
tgaacacaag attgaactga agcagaagtt ccagaggatg tgcgataagt ccatgatcaa 480
gaagcgttac atgtacctta ccgaagagat cctgaaggag aacccatcca tgtgcgagta 540
catggctcca tcccttgatg ctcgccagga catggtcatc gtggaaatcc caaagctggg 600
caaggaagca gccaccaagg caatcaagga gtggggccag ccgaagtcga agatcaccca 660
ccttgttttc tgcaccacca gcggtgtgga tatgcctggc gccgactacc agctgatcaa 720
gctcttcggc ctgcgcccat ccgtcaagcg cctcatgatg taccagcagg gctgcttcgc 780
cggcggcacc gttctgcgcc tggctaagga tctggcagaa aacaaccgcg gtgcccgcgt 840
tctcgtcgtg tgctccgaga tcaccgtggt caccttccgc ggcccatccg acacccacct 900
tgactgtctg gttggccagg cactcttcgg cgatggcgtg gcatccatca tcgtcggcgc 960
agatcctctc cctgaaatcg aaaagccact tttcgaactt gtcagcgcag cacagaccat 1020
cctgccagat tctgagggcg caatcgaggg ccacctccgc gaggtgggtc ttaccttcca 1080
tctgctcgaa aacgtgccag cactgatctc caagaacatc gaaaagtccc tgaacgaaac 1140
cttcaagcca ctggacatca tggactggaa ctccctgttc tggatcgctc acccaggcgg 1200
tccggctatc ctggatcagg tcgaggctaa gctgggtctg aagccggaga agttggaggc 1260
taccggccac atcctgtccg aatacggcaa catgtcctcc gcatgcgttc tcttcatcct 1320
ggacgtggtg cggcgcaagt ccgcagccaa cggtgtgacc acccgtatcc tgagcatcgg 1380
tcagatctcc aagtccctgc tgatcctggc atggttcctc ttctccctgg tgtaaggatc 1440
taggaggatt atgagatgga gaaagataca aaacaggttg acataatttt ccgatcaaaa 1500
ctccctgata tttacatccc taaccatctt cctttacact cctactgttt cgaaaacatt 1560
tccgagttca gttctcgtcc ttgtttaatc aatggcgcca acaaacaaat ttatacgtat 1620
gctgatgttg aactcaattc aagaaaagtt gctgctggtc ttcacaaaca agggattcaa 1680
ccaaaggata caataatgat cctattgcct aactccccag aatttgtgtt tgctttcatt 1740
ggtgcatcgt acctcggagc tatttctaca atggccaatc ctttgtttac tcctgctgag 1800
gttgtgaagc aagccgaggc ttctagtgct aagatcattg tcacacaagc gtgtcatgtt 1860
aacaaagtga aagattatgc atttgagaat gatgtgaaga tcatatgcat cgactcggcg 1920
ccggagggtt gtctccactt ctccgtgcta actcaggcta atgagcacga tattcctgag 1980
gttgaaattc aacctgacga tgtggtggcg ttgccatact cctccgggac gacgggatta 2040
cctaaaggag tgatgttgac gcacaaggga cttgtgacaa gcgtcgcaca acaagtcgac 2100
ggtgaaaatc cgaatttgta tatccatagc gaggacgtga tgctttgtgt cttgcccttg 2160
ttccatatct attcactcaa ctccgttttg ctttgtggat taagggtggg agcagcgatt 2220
ttgattatgc agaaatttga tattgtttct ttcttggagt tgatacaaag ttacaaggtg 2280
acaatagggc cgtttgtacc acctattgtt ttggycattg ctaagagtcc tatggttgat 2340
gattatgatc tttcatcagt aagaaccgtc atgtctgggg ctgcaccatt aggaaaggag 2400
cttgaagata ctgttcgagc caaatttcct aatgctaaac ttggtcaggg ttatggtatg 2460
acagaagctg gaccagtgtt ggctatgtgc ttggcatttg caaaagaacc ctttgaaata 2520
aaatcagggg catgtggaac agttgtgaga aatgctgaaa tgaaaattgt ggatcctaaa 2580
actggtaatt ctcttcccag aaatcaatct ggagaaattt gcattagagg agaccagatc 2640
atgaaaggct acctgaatga tccagaggcc acagcaagaa caatagacaa agaagggtgg 2700
ttatatactg gtgacattgg ctacattgat gatgacgacg agcttttcat tgttgatcga 2760
ttaaaggaac tgatcaaata caaaggattt caagtcgcac ctgctgagct cgaagctctc 2820
cttctcaacc atcccaacat ttctgatgct gctgttgtcc ccatgaagga cgagcaagca 2880
ggagaagttc cagtggcttt tgttgttaga tccaacggat ccaccattac tgaagatgaa 2940
gtcaaagatt ttatttcaaa gcaggtgata ttttataaga ggataaagcg ggtatttttc 3000
gtggatgcta ttcctaaatc tccatctggc aaaatccttc gaaaagattt gagagctaaa 3060
ctggctgctg ggcttccaaa ttaaggatct aggaggataa agaaatgaac accatcaacg 3120
aatacctgtc cctggaagag ttcgaagcga tcatcttcgg taaccagaag gttaccatct 3180
ccgatgtggt tgtgaaccgt gttaacgagt ccttcaactt cctcaaggag ttctccggca 3240
acaaggtcat ctacggtgtg aacaccggct tcggcccaat ggcacaatac cgtattaagg 3300
aatccgatca gatccagctt cagtacaatc tgatccgttc ccactcttcg ggcaccggaa 3360
aaccactctc cccagtttgt gctaaggcag caatcttggc tcgcctgaac accctgtccc 3420
tcggtaactc cggcgtgcat ccatctgtca tcaacctgat gtcggaactg atcaacaaag 3480
acattacccc actcatcttc gagcacggtg gcgtcggagc atccggtgac ctggttcagc 3540
tttctcacct ggctttggtt ctcatcggcg aaggcgaagt gttctacaag ggtgaacgcc 3600
gcccaactcc agaagttttc gaaattgagg gcttgaagcc aatccaggtt gagatccgtg 3660
agggcctcgc cttgattaac ggtactagcg tgatgaccgg tattggagtg gtcaacgtgt 3720
accacgcaaa gaagctgctg gactggtccc tgaagtcctc ctgcgccatc aatgaacttg 3780
ttcaggctta cgatgatcac ttcagcgcag agctgaacca gacgaagcgc cacaagggcc 3840
agcaggaaat cgctctgaag atgcgtcaga acctctctga cagcaccctg atccgcaagc 3900
gcgaggacca cctgtattcc ggcgaaaaca ccgaggagat tttcaaggag aaggtgcagg 3960
agtactactc cctgcgctgc gttccacaga ttctcggccc ggtcctcgaa actatcaata 4020
acgtcgcctc catcctggaa gatgagttca actccgctaa cgataaccca atcatcgacg 4080
tgaagaacca gcacgtgtac catggcggca acttccacgg tgactacatc tctctggaaa 4140
tggacaagtt gaaaatcgtt atcaccaaac tgaccatgct tgcagaacgc cagcttaact 4200
atcttctcaa ctccaagatc aacgaacttc tgccaccatt cgtgaacctc ggcaccctgg 4260
gtttcaactt cggcatgcag ggcgttcagt tcaccgcgac ctccaccacc gcagaatctc 4320
agatgctgtc caaccctatg tacgttcact ccattccaaa caacaacgat aaccaggaca 4380
tcgtctccat gggcaccaac tccgcagtga tcacgtccaa ggttatcgag aacgctttcg 4440
aagtcctggc tatcgaaatg atcaccatcg ttcaggccat cgattacctc ggccagaagg 4500
ataagatctc ctccgtttcc aagaagtggt acgatgaaat ccgcaacatt atccctacct 4560

```
tcaaggagga tcaggttatg tacccattcg tgcagaaggt taaggatcac ctcatcaaca   4620
actaactcta gagtcgacct gcaggcatgc aagcttggct gttttggcgg atgagagaag   4680
attttcagcc tgatacagat taaatcagaa cgcagaagcg gtctgataaa acagaatttg   4740
cctggcggca gtagcgcggt ggtcccacct gaccccatgc cgaactcaga agtgaaacgc   4800
cgtagcgccg atggtagtgt ggggtctccc catgcgagag tagggaactg ccaggcatca   4860
aataaaacga aaggctcagt cgaaagactg ggcctttcgt tttatctgtt gtttgtcggt   4920
gaacgctctc ctgagtagga caaatccgcc gggagcggat ttgaacgttg cgaagcaacg   4980
gcccggaggg tggcgggcag gacgcccgcc ataaactgcc aggcatcaaa ttaagcagaa   5040
ggccatcctg acggatggcc tttttgcgtt tctacaaact ctttttgttt atttttctaa   5100
atacattcaa atatgtatcc gctcatgaat taattccgct agatgacgtg cggcttcgac   5160
ctcctgggcg tggcgcttgt tggcgcgctc gcggctggct gcggcacgac acgcgtctga   5220
gcagtatttt gcgcgccgtc ctcgtgggtc aggccggggt gggatcaggc caccgcagta   5280
ggcgcagctg atgcgatcct ccactactgc gcgtcctcct ggcgctgccg agcacgcagc   5340
tcgtcggcca gctcttcaag gtcggccaca agcgtttcta ggtcgctcgc ggcacttgcc   5400
cagtcgcgtg atgctggcgc gtctgtcgta tcgagggcgc ggaaaaatcc gatcaccgtt   5460
tttaaatcga cggcggcatc gagtgcgtcg gactccagcg cgacatcgga gagatccacc   5520
gctgatgctt caggccagtt ttggtacttc gtcgtgaagg tcatgacacc attataacga   5580
acgttcgtta aaaattctag ccccaattct gataatttct tccggcactc ctgcgaaaac   5640
ctgcgagact tcttgcccag aaaaaacgcc aagcgcagcg gttaccgcac tttttttcca   5700
ggtgatttca ccctgaccag cgaagcggca ctttagtgca tgaggtgtgc ccctggtttc   5760
ccctctttgg agggttcaac ccaaaaaagc acacaagcaa aaatgaaaat catcatgagc   5820
aagttggtgc gaagcagcaa cgcgctagct ccaaaaaggt ctccaggatc tcgaggagat   5880
ttttgagggg gagggagtcg aggaagagcc agagcagaag gcggggaacc gttctctgcc   5940
gacagcgtga gcccccctta aaaatcaggc cggggaggaa ccggggaggg atcagagcta   6000
ggagcgagac accctaaagg gggggaaccg ttttctgctg acggtgtttc gtttattagt   6060
tttcagcccg tggatagcgg agggtgaggg caagtgagag ccagagcaag gacgggaccc   6120
ctaaaggggg gaaccgtttt ctgctgacgg tgtttcgttt attagttttc agcccgtgga   6180
cggccgcgtt tagcttccat tccaagtgcc tttctgactt gttggatgcg cctttcactg   6240
acacctagtt cgcctgcaag ctcacgagtc gagggatcag caaccgattg agaacgggca   6300
tccaggatcg cagttttgac gcgaagttcg agcaactcgc ctgtcatttc tcggcgtttg   6360
tttgcttccg ctaatcgctg tcgcgtctcc tgcgcatact tactttctgg gtcagcccat   6420
ctgcgtgcat tcgatgtagc tgcgccccgt cgccccatcg tcgctagagc tttccgccct   6480
cggctgctct gcgtttccac ccgacgagca gggacgactg gctggccttt agccacgtag   6540
ccgcgcacac gacgcgccat cgtcaggcga tcacgcatgg cgggaagatc cggctcccgg   6600
ccgtctgcac cgaccgcctg ggcaacgttg tacgccactt catacgcgtc gatgatcttg   6660
gcatctttta ggcgctcacc agcagctttg agctggtatc ccacggtcaa cgcgtggcga   6720
aacgcggtct cgtcgcgcgc tcgctctgga tttgtccaga gcactcgcac gccgtcgatc   6780
aggtcgccgg acgcgtccag ggcgctcggc aggctcgcgt ccaaaatcgc tagcgccttg   6840
gcttctgcgg tggcgcgttg tgccgcttca atgcgggcgc gtccgctgga aaagtcctgc   6900
```

-continued tcaatgtact ttttcggctt ctgtgatccg gtcatcgttc gagcaatctc cattaggtcg 6960
gccagccgat ccacacgatc atgctggcag tgccatttat aggctgtcgg atcgtctgag 7020
acgtgcagcg gccaccggct cagcctatgc gaaaaagcct ggtcagcgcc gaaaacacga 7080
gtcatttctt ccgtcgttgc agccagcagg cgcatatttg ggctggtttt acctgctgcg 7140
gcatacaccg ggtcaatgag ccagatgagc tggcatttcc cgctcagcgg attcacgccg 7200
atccaagccg gcgctttttc taggcgtgcc catttctcta aaatcgcgta gacctgcggg 7260
tttacgtgct caatcttccc gccggcctgg tggctgggca catcgatgtc aagcacgatc 7320
accgcggcat gttgcgcgtg cgtcagcgca acgtactggc accgcgtcag cgcttttgag 7380
ccagcccggt agagctttgg ttgggtttcg ccggtatccg ggttttttaat ccaggcgctc 7440 gcgaaatctc ttgtcttgct gccctggaag ctttcgcgtc ccaggtgagc gagcagttcg 7500
cggcgatctt ctgccgtcca gccgcgtgag ccgcagcgca tagcttcggg gtgggtgtcg 7560
aacagatcgg cggacaattt ccacgcgcta gctgtgactg tgtcctgcgg atcggctaga 7620
gtcatgtctt gagtgctttc tcccagctga tgactggggg ttagccgacg ccctgtgagt 7680
tcccgctcac ggggcgttca actttttcag gtatttgtgc agcttatcgt gttttcttcg 7740
taaatgaacg cttaactacc ttgttaaacg tggcaaatag gcaggattga tggggatcta 7800
gcttcacgct gccgcaagca ctcagggcgc aagggctgct aaaggaagcg gaacacgtag 7860
aaagccagtc cgcagaaacg gtgctgaccc cggatgaatg tcagctactg ggctatctgg 7920
acaagggaaa acgcaagcgc aaagagaaag caggtagctt gcagtgggct tacatggcga 7980
tagctagact gggcggtttt atggacagca agcgaaccgg aattgccagc tggggcgccc 8040
tctggtaagg ttgggaagcc ctgcaaagta aactggatgg ctttcttgcc gccaaggatc 8100
tgatggcgca ggggatcaag atctgatcaa gagacaggat gaggatcgtt tcgcatgatt 8160
gaacaagatg gattgcacgc aggttctccg gccgcttggg tggagaggct attcggctat 8220
gactgggcac aacagacaat cggctgctct gatgccgccg tgttccggct gtcagcgcag 8280
gggcgcccgg ttctttttgt caagaccgac ctgtccggtg ccctgaatga actccaagac 8340
gaggcagcgc ggctatcgtg gctggccacg acgggcgttc cttgcgcagc tgtgctcgac 8400
gttgtcactg aagcgggaag ggactggctg ctattgggcg aagtgccggg gcaggatctc 8460
ctgtcatctc accttgctcc tgccgagaaa gtatccatca tggctgatgc aatgcggcgg 8520
ctgcatacgc ttgatccggc tacctgccca ttcgaccacc aagcgaaaca tcgcatcgag 8580
cgagcacgta ctcggatgga agccggtctt gtcgatcagg atgatctgga cgaagagcat 8640
caggggctcg cgccagccga actgttcgcc aggctcaagg cgcggatgcc cgacggcgag 8700
gatctcgtcg tgacccatgg cgatgcctgc ttgccgaata tcatggtgga aaatggccgc 8760
ttttctggat tcatcgactg tggccggctg ggtgtggcgg accgctatca ggacatagcg 8820
ttggctaccc gtgatattgc tgaagagctt ggcggcgaat gggctgaccg cttcctcgtg 8880
ctttacggta tcgccgctcc cgattcgcag cgcatcgcct tctatcgcct tcttgacgag 8940
ttcttctgag cgggactctg gggttcgcgg aatcatgacc aaaatccctt aacgtgagtt 9000
ttcgttccac tgagcgtcag accccgtaga aaagatcaaa ggatcttctt gagatccttt 9060
ttttctgcgc gtaatctgct gcttgcaaac aaaaaaacca ccgctaccag cggtggtttg 9120
tttgccggat caagagctac caactctttt tccgaaggta actggcttca gcagagcgca 9180
gataccaaat actgtccttc tagtgtagcc gtagttaggc caccacttca agaactctgt 9240
agcaccgcct acatacctcg ctctgctaat cctgttacca gtggctgctg ccagtggcga 9300

-continued

```
taagtcgtgt cttaccgggt tggactcaag acgatagtta ccggataagg cgcagcggtc   9360
gggctgaacg gggggttcgt gcacacagcc cagcttggag cgaacgacct acaccgaact   9420
gagataccta cagcgtgagc tatgagaaag cgccacgctt cccgaaggga gaaaggcgga   9480
caggtatccg gtaagcggca gggtcggaac aggagagcgc acgagggagc ttccaggggg   9540
aaacgcctgg tatctttata gtcctgtcgg gtttcgccac ctctgacttg agcgtcgatt   9600
tttgtgatgc tcgtcagggg ggcggagcct atggaaaaac gccagcaacg cggccttttt   9660
acggttcctg gccttttgct ggccttttgc tcacatgttc tttcctgcgt tatcccctga   9720
ttctgtggat aaccgtatta ccgcctttga gtgagctgat accgctcgcc gcagccgaac   9780
gaccgagcgc agcgagtcag tgagcgagga agcggaagag cgcctgatgc ggtattttct   9840
ccttacgcat ctgtgcggta tttcacaccg catatggtgc actctcagta caatctgctc   9900
tgatgccgca tagttaagcc agtatacact ccgctatcgc tacgtgactg ggtcatggct   9960
gcgccccgac acccgccaac acccgctgac gcgccctgac gggcttgtct gctcccggca  10020
tccgcttaca gacaagctgt gaccgtctcc gggagctgca tgtgtcagag gttttcaccg  10080
tcatcaccga aacgcgcgag gcagcagatc aattcgcgcg cgaaggcgaa gcggcatgca  10140
tttacgttga caccatcgaa tggtgcaaaa cctttcgcgg tatggcatga tagcgcccgg  10200
aagagagtca attcagggtg gtgaatgtga aaccagtaac gttatacgat gtcgcagagt  10260
atgccggtgt ctcttatcag accgtttccc gcgtggtgaa ccaggccagc cacgtttctg  10320
cgaaaacgcg ggaaaaagtg gaagcggcga tggcggagct gaattacatt cccaaccgcg  10380
tggcacaaca actggcgggc aaacagtcgt tgctgattgg cgttgccacc tccagtctgg  10440
ccctgcacgc gccgtcgcaa attgtcgcgg cgattaaatc tcgcgccgat caactgggtg  10500
ccagcgtggt ggtgtcgatg gtagaacgaa gcggcgtcga agcctgtaaa gcggcggtgc  10560
acaatcttct cgcgcaacgc gtcagtgggc tgatcattaa ctatccgctg gatgaccagg  10620
atgccattgc tgtggaagct gcctgcacta atgttccggc gttatttctt gatgtctctg  10680
accagacacc catcaacagt attattttct cccatgaaga cggtacgcga ctgggcgtgg  10740
agcatctggt cgcattgggt caccagcaaa tcgcgctgtt agcgggccca ttaagttctg  10800
tctcggcgcg tctgcgtctg gctggctggc ataaatatct cactcgcaat caaattcagc  10860
cgatagcgga acgggaaggc gactggagtg ccatgtccgg ttttcaacaa accatgcaaa  10920
tgctgaatga gggcatcgtt cccactgcga tgctggttgc caacgatcag atggcgctgg  10980
gcgcaatgcg cgccattacc gagtccgggc tgcgcgttgg tgcggatatc tcggtagtgg  11040
gatacgacga taccgaagac agctcatgtt atatcccgcc gtcaaccacc atcaaacagg  11100
attttcgcct gctggggcaa accagcgtgg accgcttgct gcaactctct cagggccagg  11160
cggtgaaggg caatcagctg ttgcccgtct cactggtgaa aagaaaaacc accctggcgc  11220
ccaatacgca aaccgcctct ccccgcgcgt tggccgattc attaatgcag ctggcacgac  11280
aggtttcccg actggaaagc gggcagtgag cgcaacgcaa ttaatgtgag ttagcgcgaa  11340
ttgatctggt ttgacagctt atcat                                        11365
```

<210> SEQ ID NO 42
<211> LENGTH: 4362
<212> TYPE: DNA
<213> ORGANISM: Artificial Sequence
<220> FEATURE:
<223> OTHER INFORMATION: operon RiPKS-Nt4CL-FjTAL -continued

<400> SEQUENCE: 42

```
ggatctagga gggagatcat atggttaccg ttgaagaagt ccgcaaggct cagcgcgcag     60
aaggccctgc aaccgttctg gcaatcggca ccgcaacccc accaaactgc gtcggccagt    120
ccacctaccc agattattat ttccgtatca ccaactctga acacaagatt gaactgaagc    180
agaagttcca gaggatgtgc gataagtcca tgatcaagaa gcgttacatg taccttaccg    240
aagagatcct gaaggagaac ccatccatgt gcgagtacat ggctccatcc cttgatgctc    300
gccaggacat ggtcatcgtg gaaatcccaa agctgggcaa ggaagcagcc accaaggcaa    360
tcaaggagtg ggccagccg aagtcgaaga tcacccacct tgttttctgc accaccagcg    420
gtgtggatat gcctggcgcc gactaccagc tgatcaagct cttcggcctg cgcccatccg    480
tcaagcgcct catgatgtac cagcagggct gcttcgccgg cggcaccgtt ctgcgcctgg    540
ctaaggatct ggcagaaaac aaccgcggtg cccgcgttct cgtcgtgtgc tccgagatca    600
ccgtggtcac cttccgcggc ccatccgaca cccaccttga ctgtctggtt ggccaggcac    660
tcttcggcga tggcgtggca tccatcatcg tcggcgcaga tcctctccct gaaatcgaaa    720
agccactttt cgaacttgtc agcgcagcac agaccatcct gccagattct gagggcgcaa    780
tcgagggcca cctccgcgag gtgggtctta ccttccatct gctcgaaaac gtgccagcac    840
tgatctccaa gaacatcgaa aagtccctga acgaaacctt caagccactg gacatcatgg    900
actggaactc cctgttctgg atcgctcacc caggcggtcc ggctatcctg gatcaggtcg    960
aggctaagct gggtctgaag ccggagaagt tggaggctac cggccacatc ctgtccgaat   1020
acggcaacat gtcctccgca tgcgttctct tcatcctgga cgtggtgcgg cgcaagtccg   1080
cagccaacgg tgtgaccacc cgtatcctga gcatcggtca gatctccaag tccctgctga   1140
tcctggcatg gttcctcttc tccctggtgt aaggatctag gaggattatg agatggagaa   1200
agatacaaaa caggttgaca taattttccg atcaaaactc cctgatattt acatccctaa   1260
ccatcttcct ttacactcct actgtttcga aaacatttcc gagttcagtt ctcgtccttg   1320
tttaatcaat ggcgccaaca aacaaattta tacgtatgct gatgttgaac tcaattcaag   1380
aaaagttgct gctggtcttc acaaacaagg gattcaacca aaggatacaa taatgatcct   1440
attgcctaac tccccagaat ttgtgtttgc tttcattggt gcatcgtacc tcggagctat   1500
ttctacaatg gccaatcctt tgtttactcc tgctgaggtt gtgaagcaag ccgaggcttc   1560
tagtgctaag atcattgtca cacaagcgtg tcatgttaac aaagtgaaag attatgcatt   1620
tgagaatgat gtgaagatca tatgcatcga ctcggcgccg gagggttgtc tccacttctc   1680
cgtgctaact caggctaatg agcacgatat tcctgaggtt gaaattcaac ctgacgatgt   1740
ggtggcgttg ccatactcct ccgggacgac gggattacct aaaggagtga tgttgacgca   1800
caagggactt gtgacaagcg tcgcacaaca agtcgacggt gaaaatccga atttgtatat   1860
ccatagcgag gacgtgatgc tttgtgtctt gcccttgttc catatctatt cactcaactc   1920
cgttttgctt tgtggattaa gggtgggagc agcgattttg attatgcaga aatttgatat   1980
tgtttctttc ttggagttga tacaaagtta caaggtgaca atagggccgt ttgtaccacc   2040
tattgttttg gycattgcta agagtcctat ggttgatgat tatgatcttt catcagtaag   2100
aaccgtcatg tctggggctg caccattagg aaaggagctt gaagatactg ttcgagccaa   2160
atttcctaat gctaaacttg gtcagggtta tggtatgaca gaagctggac cagtgttggc   2220
tatgtgcttg gcatttgcaa aagaaccctt tgaaataaaa tcaggggcat gtggaacagt   2280
tgtgagaaat gctgaaatga aaattgtgga tcctaaaact ggtaattctc ttcccagaaa   2340
```

```
tcaatctgga gaaatttgca ttagaggaga ccagatcatg aaaggctacc tgaatgatcc   2400

agaggccaca gcaagaacaa tagacaaaga agggtggtta tatactggtg acattggcta   2460

cattgatgat gacgacgagc ttttcattgt tgatcgatta aaggaactga tcaaatacaa   2520

aggatttcaa gtcgcacctg ctgagctcga agctctcctt ctcaaccatc ccaacatttc   2580

tgatgctgct gttgtcccca tgaaggacga gcaagcagga gaagttccag tggcttttgt   2640

tgttagatcc aacggatcca ccattactga agatgaagtc aaagatttta tttcaaagca   2700

ggtgatattt tataagagga taaagcgggt atttttcgtg gatgctattc ctaaatctcc   2760

atctggcaaa atccttcgaa aagatttgag agctaaactg gctgctgggc ttccaaatta   2820

aggatctagg aggataaaga aatgaacacc atcaacgaat acctgtccct ggaagagttc   2880

gaagcgatca tcttcggtaa ccagaaggtt accatctccg atgtggttgt gaaccgtgtt   2940

aacgagtcct tcaacttcct caaggagttc tccggcaaca aggtcatcta cggtgtgaac   3000

accggcttcg gcccaatggc acaataccgt attaaggaat ccgatcagat ccagcttcag   3060

tacaatctga tccgttccca ctcttcgggc accggaaaac cactctcccc agtttgtgct   3120

aaggcagcaa tcttggctcg cctgaacacc ctgtccctcg gtaactccgg cgtgcatcca   3180

tctgtcatca acctgatgtc ggaactgatc aacaaagaca ttaccccact catcttcgag   3240

cacggtggcg tcggagcatc cggtgacctg gttcagcttt ctcacctggc tttggttctc   3300

atcggcgaag gcgaagtgtt ctacaagggt gaacgccgcc caactccaga agttttcgaa   3360

attgagggct tgaagccaat ccaggttgag atccgtgagg gcctcgcctt gattaacggt   3420

actagcgtga tgaccggtat tggagtggtc aacgtgtacc acgcaaagaa gctgctggac   3480

tggtccctga agtcctcctg cgccatcaat gaacttgttc aggcttacga tgatcacttc   3540

agcgcagagc tgaaccagac gaagcgccac aagggccagc aggaaatcgc tctgaagatg   3600

cgtcagaacc tctctgacag caccctgatc cgcaagcgcg aggaccacct gtattccggc   3660

gaaaacaccg aggagatttt caaggagaag gtgcaggagt actactccct gcgctgcgtt   3720

ccacagattc tcggcccggt cctcgaaact atcaataacg tcgcctccat cctggaagat   3780

gagttcaact ccgctaacga taacccaatc atcgacgtga agaaccagca cgtgtaccat   3840

ggcggcaact tccacggtga ctacatctct ctggaaatgg acaagttgaa aatcgttatc   3900

accaaactga ccatgcttgc agaacgccag cttaactatc ttctcaactc caagatcaac   3960

gaacttctgc caccattcgt gaacctcggc accctgggtt tcaacttcgg catgcagggc   4020

gttcagttca ccgcgacctc caccaccgca gaatctcaga tgctgtccaa ccctatgtac   4080

gttcactcca ttccaaacaa caacgataac caggacatcg tctccatggg caccaactcc   4140

gcagtgatca cgtccaaggt tatcgagaac gctttcgaag tcctggctat cgaaatgatc   4200

accatcgttc aggccatcga ttacctcggc cagaaggata agatctcctc cgtttccaag   4260

aagtggtacg atgaaatccg caacattatc cctaccttca aggaggatca ggttatgtac   4320

ccattcgtgc agaaggttaa ggatcacctc atcaacaact aa                      4362
```

<210> SEQ ID NO 43
<211> LENGTH: 11377
<212> TYPE: DNA
<213> ORGANISM: Artificial Sequence
<220> FEATURE:
<223> OTHER INFORMATION: plasmid RiPKS-Nt4CL-SeSam8-pECXK (pECXK_L)

<400> SEQUENCE: 43

-continued

```
cgactgcacg gtgcaccaat gcttctggcg tcaggcagcc atcggaagct gtggtatggc     60
tgtgcaggtc gtaaatcact gcataattcg tgtcgctcaa ggcgcactcc cgttctggat    120
aatgtttttt gcgccgacat cataacggtt ctggcaaata ttctgaaatg agctgttgac    180
aattaatcat ccggctcgta taatgtgtgg aattgtgagc ggataacaat ttcacacagg    240
aaacagacca tggaattcga gctggatcta ggagggagat catatggtta ccgttgaaga    300
agtccgcaag gctcagcgcg cagaaggccc tgcaaccgtt ctggcaatcg gcaccgcaac    360
cccaccaaac tgcgtcggcc agtccaccta cccagattat tatttccgta tcaccaactc    420
tgaacacaag attgaactga agcagaagtt ccagaggatg tgcgataagt ccatgatcaa    480
gaagcgttac atgtacctta ccgaagagat cctgaaggag aacccatcca tgtgcgagta    540
catggctcca tcccttgatg ctcgccagga catggtcatc gtggaaatcc caaagctggg    600
caaggaagca gccaccaagg caatcaagga gtggggccag ccgaagtcga agatcaccca    660
ccttgttttc tgcaccacca gcggtgtgga tatgcctggc gccgactacc agctgatcaa    720
gctcttcggc ctgcgcccat ccgtcaagcg cctcatgatg taccagcagg gctgcttcgc    780
cggcggcacc gttctgcgcc tggctaagga tctggcagaa aacaaccgcg gtgcccgcgt    840
tctcgtcgtg tgctccgaga tcaccgtggt caccttccgc ggcccatccg acacccacct    900
tgactgtctg gttggccagg cactcttcgg cgatggcgtg gcatccatca tcgtcggcgc    960
agatcctctc cctgaaatcg aaaagccact tttcgaactt gtcagcgcag cacagaccat   1020
cctgccagat tctgagggcg caatcgaggg ccacctccgc gaggtgggtc ttaccttcca   1080
tctgctcgaa aacgtgccag cactgatctc caagaacatc gaaaagtccc tgaacgaaac   1140
cttcaagcca ctggacatca tggactggaa ctccctgttc tggatcgctc acccaggcgg   1200
tccggctatc ctggatcagg tcgaggctaa gctgggtctg aagccggaga agttggaggc   1260
taccggccac atcctgtccg aatacggcaa catgtcctcc gcatgcgttc tcttcatcct   1320
ggacgtggtg cggcgcaagt ccgcagccaa cggtgtgacc acccgtatcc tgagcatcgg   1380
tcagatctcc aagtccctgc tgatcctggc atggttcctc ttctccctgg tgtaaggatc   1440
taggaggatt atgagatgga gaaagataca aaacaggttg acataatttt ccgatcaaaa   1500
ctccctgata tttacatccc taaccatctt cctttacact cctactgttt cgaaaacatt   1560
tccgagttca gttctcgtcc ttgtttaatc aatggcgcca acaaacaaat ttatacgtat   1620
gctgatgttg aactcaattc aagaaaagtt gctgctggtc ttcacaaaca agggattcaa   1680
ccaaaggata caataatgat cctattgcct aactccccag aatttgtgtt tgctttcatt   1740
ggtgcatcgt acctcggagc tatttctaca atggccaatc ctttgtttac tcctgctgag   1800
gttgtgaagc aagccgaggc ttctagtgct aagatcattg tcacacaagc gtgtcatgtt   1860
aacaaagtga aagattatgc atttgagaat gatgtgaaga tcatatgcat cgactcggcg   1920
ccggagggtt gtctccactt ctccgtgcta actcaggcta atgagcacga tattcctgag   1980
gttgaaattc aacctgacga tgtggtggcg ttgccatact cctccgggac gacgggatta   2040
cctaaaggag tgatgttgac gcacaaggga cttgtgacaa gcgtcgcaca acaagtcgac   2100
ggtgaaaatc cgaatttgta tatccatagc gaggacgtga tgctttgtgt cttgcccttg   2160
ttccatatct attcactcaa ctccgttttg ctttgtggat taagggtggg agcagcgatt   2220
ttgattatgc agaaatttga tattgtttct ttcttggagt tgatacaaag ttacaaggtg   2280
acaatagggc cgtttgtacc acctattgtt ttggycattg ctaagagtcc tatggttgat   2340
gattatgatc tttcatcagt aagaaccgtc atgtctgggg ctgcaccatt aggaaaggag   2400
```

cttgaagata ctgttcgagc caaatttcct aatgctaaac ttggtcaggg ttatggtatg 2460
acagaagctg gaccagtgtt ggctatgtgc ttggcatttg caaaagaacc ctttgaaata 2520
aaatcagggg catgtggaac agttgtgaga aatgctgaaa tgaaaattgt ggatcctaaa 2580
actggtaatt ctcttcccag aaatcaatct ggagaaattt gcattagagg agaccagatc 2640
atgaaaggct acctgaatga tccagaggcc acagcaagaa caatagacaa agaagggtgg 2700
ttatatactg gtgacattgg ctacattgat gatgacgacg agcttttcat tgttgatcga 2760
ttaaaggaac tgatcaaata caaaggattt caagtcgcac ctgctgagct cgaagctctc 2820
cttctcaacc atcccaacat ttctgatgct gctgttgtcc ccatgaagga cgagcaagca 2880
ggagaagttc cagtggcttt tgttgttaga tccaacggat ccaccattac tgaagatgaa 2940
gtcaaagatt ttatttcaaa gcaggtgata ttttataaga ggataaagcg ggtatttttc 3000
gtggatgcta ttcctaaatc tccatctggc aaaatccttc gaaaagattt gagagctaaa 3060
ctggctgctg ggcttccaaa ttaaggatct aggaggataa agaaatgacc caggtcgtgg 3120
agcgccaggc tgatcgtctg tccagccgcg agtacctggc acgcgttgtt cgttccgcag 3180
gctgggacgc aggcctcacc agctgcaccg atgaagaaat cgtgcgcatg ggtgcatccg 3240
cacgcaccat tgaggaatac ctgaagtctg ataagccgat ctacggcctc acccagggct 3300
tcggtccact ggtcctgttc gatgcagatt ccgaactgga acagggcggc tctctcatct 3360
cccatctggg caccggccag ggtgcaccgc ttgcaccgga agtgtcccgc ctgattctgt 3420
ggctccgcat ccaaaacatg cgcaagggct attcggctgt cagtcctgtg ttctggcaaa 3480
aactggccga cctctggaac aagggcttca cccctgctat ccctcgccac ggcaccgtgt 3540
ccgccagcgg cgatctccag cctctggcac acgctgccct ggcttttacc ggcgtgggcg 3600
aggcatggac ccgtgatgca gacggccgtt ggtccaccgt gccagccgtg gacgcattag 3660
cagcactggg tgcagagccg ttcgattggc cagtgcgcga ggctttggcc ttcgtgaacg 3720
gtacgggcgc atcactcgcg gtggcagttc tcaaccacag atccgctctc cgtctcgtac 3780
gagcatgtgc agtcttgtct gcccgtttgg ctaccttgct aggagctaat cctgaacact 3840
acgatgtcgg ccacggagtc gcaaggggac aagttggcca gctgaccgcg gcggaatgga 3900
ttcggcaggg actaccacgc ggcatggtcc gagacggttc gcgccctctt caagaaccat 3960
acagcttgcg ctgtgccccc caggtccttg gcgcggtgct ggaccagctg gatggtgcag 4020
gcgatgttct ggcccgcgaa gtggatggct gccaggacaa tcctatcacc tacgagggcg 4080
aactgctgca cggcggtaac ttccacgcta tgccagtcgg cttcgcatcc gaccagatcg 4140
gtctggcgat gcacatggca gcttatctgg ctgaacgcca gctcggcctg ctggtgagcc 4200
cggtgaccaa cggcgacctg ccaccaatgc tgaccccacg cgctggacgc ggtgccggcc 4260
tggcgggcgt tcagatctcc gcaacctcct tcgtctctcg catccgccag ctggtgttcc 4320
cagctagcct caccaccctc ccaaccaacg gctggaacca ggaccatgtc ccaatggctc 4380
tgaacggcgc aaacagcgtg ttcgaagctc ttgaactggg ttggctgacc gtgggtagcc 4440
tggcagtcgg cgtggcccag ctcgctgcaa tgaccggcca cgcagctgag ggcgtgtggg 4500
ccgagttggc aggcatctgc ccaccactgg atgctgaccg cccactgggc gcggaggtcc 4560
gcgctgctcg cgatctcctc tccgcacacg ctgaccagct gctcgttgac gaggctgatg 4620
gcaaagactt cggctaactc tagagtcgac ctgcaggcat gcaagcttgg ctgttttggc 4680
ggatgagaga agattttcag cctgatacag attaaatcag aacgcagaag cggtctgata 4740

-continued

```
aaacagaatt tgcctggcgg cagtagcgcg gtggtcccac ctgaccccat gccgaactca   4800
gaagtgaaac gccgtagcgc cgatggtagt gtggggtctc cccatgcgag agtagggaac   4860
tgccaggcat caaataaaac gaaaggctca gtcgaaagac tgggcctttc gttttatctg   4920
ttgtttgtcg gtgaacgctc tcctgagtag gacaaatccg ccgggagcgg atttgaacgt   4980
tgcgaagcaa cggcccggag ggtggcgggc aggacgcccg ccataaactg ccaggcatca   5040
aattaagcag aaggccatcc tgacggatgg cctttttgcg tttctacaaa ctctttttgt   5100
ttatttttct aaatacattc aaatatgtat ccgctcatga attaattccg ctagatgacg   5160
tgcggcttcg acctcctggg cgtggcgctt gttggcgcgc tcgcggctgg ctgcggcacg   5220
acacgcgtct gagcagtatt ttgcgcgccg tcctcgtggg tcaggccggg gtgggatcag   5280
gccaccgcag taggcgcagc tgatgcgatc ctccactact gcgcgtcctc ctggcgctgc   5340
cgagcacgca gctcgtcggc cagctcttca aggtcggcca caagcgtttc taggtcgctc   5400
gcggcacttg cccagtcgcg tgatgctggc gcgtctgtcg tatcgagggc gcggaaaaat   5460
ccgatcaccg tttttaaatc gacggcggca tcgagtgcgt cggactccag cgcgacatcg   5520
gagagatcca ccgctgatgc ttcaggccag ttttggtact tcgtcgtgaa ggtcatgaca   5580
ccattataac gaacgttcgt taaaaattct agccccaatt ctgataattt cttccggcac   5640
tcctgcgaaa acctgcgaga cttcttgccc agaaaaaacg ccaagcgcag cggttaccgc   5700
acttttttc caggtgattt caccctgacc agcgaagcgg cactttagtg catgaggtgt   5760
gcccctggtt tcccctcttt ggagggttca acccaaaaaa gcacacaagc aaaaatgaaa   5820
atcatcatga gcaagttggt gcgaagcagc aacgcgctag ctccaaaaag gtctccagga   5880
tctcgaggag atttttgagg gggagggagt cgaggaagag ccagagcaga aggcggggaa   5940
ccgttctctg ccgacagcgt gagcccccct taaaaatcag gccggggagg aaccggggag   6000
ggatcagagc taggagcgag acaccctaaa ggggggggaac cgttttctgc tgacggtgtt   6060
tcgtttatta gttttcagcc cgtggatagc ggagggtgag ggcaagtgag agccagagca   6120
aggacgggac ccctaaaggg gggaaccgtt ttctgctgac ggtgtttcgt ttattagttt   6180
tcagcccgtg gacggccgcg tttagcttcc attccaagtg cctttctgac ttgttggatg   6240
cgcctttcac tgacacctag ttcgcctgca agctcacgag tcgagggatc agcaaccgat   6300
tgagaacggg catccaggat cgcagttttg acgcgaagtt cgagcaactc gcctgtcatt   6360
tctcggcgtt tgtttgcttc cgctaatcgc tgtcgcgtct cctgcgcata cttactttct   6420
gggtcagccc atctgcgtgc attcgatgta gctgcgcccc gtcgccccat cgtcgctaga   6480
gctttccgcc ctcggctgct ctgcgtttcc acccgacgag cagggacgac tggctggcct   6540
ttagccacgt agccgcgcac acgacgcgcc atcgtcaggc gatcacgcat ggcgggaaga   6600
tccggctccc ggccgtctgc accgaccgcc tgggcaacgt tgtacgccac ttcatacgcg   6660
tcgatgatct tggcatcttt taggcgctca ccagcagctt tgagctggta tcccacggtc   6720
aacgcgtggc gaaacgcggt ctcgtcgcgc gctcgctctg gatttgtcca gagcactcgc   6780
acgccgtcga tcaggtcgcc ggacgcgtcc agggcgctcg gcaggctcgc gtccaaaatc   6840
gctagcgcct tggcttctgc ggtggcgcgt tgtgccgctt caatgcgggc gcgtccgctg   6900
gaaaagtcct gctcaatgta ctttttcggc ttctgtgatc cggtcatcgt tcgagcaatc   6960
tccattaggt cggccagccg atccacacga tcatgctggc agtgccattt ataggctgtc   7020
ggatcgtctg agacgtgcag cggccaccgg ctcagcctat gcgaaaaagc ctggtcagcg   7080
ccgaaaacac gagtcatttc ttccgtcgtt gcagccagca ggcgcatatt tgggctggtt   7140
```

-continued

```
ttacctgctg cggcatacac cgggtcaatg agccagatga gctggcattt cccgctcagc   7200
ggattcacgc cgatccaagc cggcgctttt tctaggcgtg cccatttctc taaaatcgcg   7260
tagacctgcg ggtttacgtg ctcaatcttc ccgccggcct ggtggctggg cacatcgatg   7320
tcaagcacga tcaccgcggc atgttgcgcg tgcgtcagcg caacgtactg gcaccgcgtc   7380
agcgcttttg agccagcccg gtagagcttt ggttgggttt cgccggtatc cgggttttta   7440
atccaggcgc tcgcgaaatc tcttgtcttg ctgccctgga agctttcgcg tcccaggtga   7500
gcgagcagtt cgcggcgatc ttctgccgtc cagccgcgtg agccgcagcg catagcttcg   7560
gggtgggtgt cgaacagatc ggcggacaat ttccacgcgc tagctgtgac tgtgtcctgc   7620
ggatcggcta gagtcatgtc ttgagtgctt tctcccagct gatgactggg ggttagccga   7680
cgccctgtga gttcccgctc acggggcgtt caactttttc aggtatttgt gcagcttatc   7740
gtgttttctt cgtaaatgaa cgcttaacta ccttgttaaa cgtggcaaat aggcaggatt   7800
gatggggatc tagcttcacg ctgccgcaag cactcagggc gcaagggctg ctaaaggaag   7860
cggaacacgt agaaagccag tccgcagaaa cggtgctgac cccggatgaa tgtcagctac   7920
tgggctatct ggacaaggga aaacgcaagc gcaaagagaa agcaggtagc ttgcagtggg   7980
cttacatggc gatagctaga ctgggcggtt ttatggacag caagcgaacc ggaattgcca   8040
gctggggcgc cctctggtaa ggttgggaag ccctgcaaag taaactggat ggctttcttg   8100
ccgccaagga tctgatggcg caggggatca agatctgatc aagagacagg atgaggatcg   8160
tttcgcatga ttgaacaaga tggattgcac gcaggttctc cggccgcttg ggtggagagg   8220
ctattcggct atgactgggc acaacagaca atcggctgct ctgatgccgc cgtgttccgg   8280
ctgtcagcgc aggggcgccc ggttcttttt gtcaagaccg acctgtccgg tgccctgaat   8340
gaactccaag acgaggcagc gcggctatcg tggctggcca cgacgggcgt tccttgcgca   8400
gctgtgctcg acgttgtcac tgaagcggga agggactggc tgctattggg cgaagtgccg   8460
gggcaggatc tcctgtcatc tcaccttgct cctgccgaga aagtatccat catggctgat   8520
gcaatgcggc ggctgcatac gcttgatccg gctacctgcc cattcgacca ccaagcgaaa   8580
catcgcatcg agcgagcacg tactcggatg gaagccggtc ttgtcgatca ggatgatctg   8640
gacgaagagc atcaggggct cgcgccagcc gaactgttcg ccaggctcaa ggcgcggatg   8700
cccgacggcg aggatctcgt cgtgacccat ggcgatgcct gcttgccgaa tatcatggtg   8760
gaaaatggcc gcttttctgg attcatcgac tgtggccggc tgggtgtggc ggaccgctat   8820
caggacatag cgttggctac ccgtgatatt gctgaagagc ttggcggcga atgggctgac   8880
cgcttcctcg tgctttacgg tatcgccgct cccgattcgc agcgcatcgc cttctatcgc   8940
cttcttgacg agttcttctg agcgggactc tggggttcgc ggaatcatga ccaaaatccc   9000
ttaacgtgag ttttcgttcc actgagcgtc agaccccgta gaaaagatca aaggatcttc   9060
ttgagatcct ttttttctgc gcgtaatctg ctgcttgcaa acaaaaaaac caccgctacc   9120
agcggtggtt tgtttgccgg atcaagagct accaactctt tttccgaagg taactggctt   9180
cagcagagcg cagataccaa atactgtcct tctagtgtag ccgtagttag gccaccactt   9240
caagaactct gtagcaccgc ctacatacct cgctctgcta atcctgttac cagtggctgc   9300
tgccagtggc gataagtcgt gtcttaccgg gttggactca agacgatagt taccggataa   9360
ggcgcagcgg tcgggctgaa cggggggttc gtgcacacag cccagcttgg agcgaacgac   9420
ctacaccgaa ctgagatacc tacagcgtga gctatgagaa agcgccacgc ttcccgaagg   9480
```

-continued gagaaaggcg gacaggtatc cggtaagcgg cagggtcgga acaggagagc gcacgaggga 9540
gcttccaggg ggaaacgcct ggtatcttta tagtcctgtc gggtttcgcc acctctgact 9600
tgagcgtcga tttttgtgat gctcgtcagg ggggcggagc ctatggaaaa acgccagcaa 9660
cgcggccttt ttacggttcc tggccttttg ctggcctttt gctcacatgt tctttcctgc 9720
gttatcccct gattctgtgg ataaccgtat taccgccttt gagtgagctg ataccgctcg 9780
ccgcagccga acgaccgagc gcagcgagtc agtgagcgag gaagcggaag agcgcctgat 9840
gcggtatttt ctccttacgc atctgtgcgg tatttcacac cgcatatggt gcactctcag 9900
tacaatctgc tctgatgccg catagttaag ccagtataca ctccgctatc gctacgtgac 9960
tgggtcatgg ctgcgccccg acacccgcca acacccgctg acgcgccctg acgggcttgt 10020
ctgctcccgg catccgctta cagacaagct gtgaccgtct ccgggagctg catgtgtcag 10080
aggttttcac cgtcatcacc gaaacgcgcg aggcagcaga tcaattcgcg cgcgaaggcg 10140
aagcggcatg catttacgtt gacaccatcg aatggtgcaa aacctttcgc ggtatggcat 10200
gatagcgccc ggaagagagt caattcaggg tggtgaatgt gaaaccagta acgttatacg 10260
atgtcgcaga gtatgccggt gtctcttatc agaccgtttc ccgcgtggtg aaccaggcca 10320
gccacgtttc tgcgaaaacg cgggaaaaag tggaagcggc gatggcggag ctgaattaca 10380
ttcccaaccg cgtggcacaa caactggcgg gcaaacagtc gttgctgatt ggcgttgcca 10440
cctccagtct ggccctgcac gcgccgtcgc aaattgtcgc ggcgattaaa tctcgcgccg 10500
atcaactggg tgccagcgtg gtggtgtcga tggtagaacg aagcggcgtc gaagcctgta 10560
aagcggcggt gcacaatctt ctcgcgcaac gcgtcagtgg gctgatcatt aactatccgc 10620
tggatgacca ggatgccatt gctgtggaag ctgcctgcac taatgttccg gcgttatttc 10680
ttgatgtctc tgaccagaca cccatcaaca gtattatttt ctcccatgaa gacggtacgc 10740
gactgggcgt ggagcatctg gtcgcattgg gtcaccagca aatcgcgctg ttagcgggcc 10800
cattaagttc tgtctcggcg cgtctgcgtc tggctggctg gcataaatat ctcactcgca 10860
atcaaattca gccgatagcg gaacgggaag gcgactggag tgccatgtcc ggttttcaac 10920
aaaccatgca aatgctgaat gagggcatcg ttcccactgc gatgctggtt gccaacgatc 10980
agatggcgct gggcgcaatg cgcgccatta ccgagtccgg gctgcgcgtt ggtgcggata 11040
tctcggtagt gggatacgac gataccgaag acagctcatg ttatatcccg ccgtcaacca 11100
ccatcaaaca ggattttcgc ctgctggggc aaaccagcgt ggaccgcttg ctgcaactct 11160
ctcagggcca ggcggtgaag ggcaatcagc tgttgcccgt ctcactggtg aaaagaaaaa 11220
ccaccctggc gcccaatacg caaaccgcct ctccccgcgc gttggccgat tcattaatgc 11280
agctggcacg acaggtttcc cgactggaaa gcgggcagtg agcgcaacgc aattaatgtg 11340
agttagcgcg aattgatctg gtttgacagc ttatcat 11377

<210> SEQ ID NO 44
<211> LENGTH: 4374
<212> TYPE: DNA
<213> ORGANISM: Artificial Sequence
<220> FEATURE:
<223> OTHER INFORMATION: operon RiPKS-Nt4CL-SeSam8

<400> SEQUENCE: 44
ggatctagga gggagatcat atggttaccg ttgaagaagt ccgcaaggct cagcgcgcag 60
aaggccctgc aaccgttctg gcaatcggca ccgcaacccc accaaactgc gtcggccagt 120
ccacctaccc agattattat ttccgtatca ccaactctga acacaagatt gaactgaagc 180

-continued agaagttcca gaggatgtgc gataagtcca tgatcaagaa gcgttacatg taccttaccg 240
aagagatcct gaaggagaac ccatccatgt gcgagtacat ggctccatcc cttgatgctc 300
gccaggacat ggtcatcgtg gaaatcccaa agctgggcaa ggaagcagcc accaaggcaa 360
tcaaggagtg gggccagccg aagtcgaaga tcacccacct tgttttctgc accaccagcg 420
gtgtggatat gcctggcgcc gactaccagc tgatcaagct cttcggcctg cgcccatccg 480
tcaagcgcct catgatgtac cagcagggct gcttcgccgg cggcaccgtt ctgcgcctgg 540
ctaaggatct ggcagaaaac aaccgcggtg cccgcgttct cgtcgtgtgc tccgagatca 600
ccgtggtcac cttccgcggc ccatccgaca cccaccttga ctgtctggtt ggccaggcac 660
tcttcggcga tggcgtggca tccatcatcg tcggcgcaga tcctctccct gaaatcgaaa 720
agccactttt cgaacttgtc agcgcagcac agaccatcct gccagattct gagggcgcaa 780
tcgagggcca cctccgcgag gtgggtctta ccttccatct gctcgaaaac gtgccagcac 840
tgatctccaa gaacatcgaa aagtccctga acgaaacctt caagccactg gacatcatgg 900
actggaactc cctgttctgg atcgctcacc caggcggtcc ggctatcctg gatcaggtcg 960
aggctaagct gggtctgaag ccggagaagt tggaggctac cggccacatc ctgtccgaat 1020
acggcaacat gtcctccgca tgcgttctct tcatcctgga cgtggtgcgg cgcaagtccg 1080
cagccaacgg tgtgaccacc cgtatcctga gcatcggtca gatctccaag tccctgctga 1140
tcctggcatg gttcctcttc tccctggtgt aaggatctag gaggattatg agatggagaa 1200
agatacaaaa caggttgaca taattttccg atcaaaactc cctgatattt acatccctaa 1260
ccatcttcct ttacactcct actgtttcga aaacatttcc gagttcagtt ctcgtccttg 1320
tttaatcaat ggcgccaaca aacaaattta tacgtatgct gatgttgaac tcaattcaag 1380
aaaagttgct gctggtcttc acaaacaagg gattcaacca aaggatacaa taatgatcct 1440
attgcctaac tccccagaat ttgtgtttgc tttcattggt gcatcgtacc tcggagctat 1500
ttctacaatg gccaatcctt tgtttactcc tgctgaggtt gtgaagcaag ccgaggcttc 1560
tagtgctaag atcattgtca cacaagcgtg tcatgttaac aaagtgaaag attatgcatt 1620
tgagaatgat gtgaagatca tatgcatcga ctcggcgccg gagggttgtc tccacttctc 1680
cgtgctaact caggctaatg agcacgatat tcctgaggtt gaaattcaac ctgacgatgt 1740
ggtggcgttg ccatactcct ccgggacgac gggattacct aaaggagtga tgttgacgca 1800
caagggactt gtgacaagcg tcgcacaaca agtcgacggt gaaaatccga atttgtatat 1860
ccatagcgag gacgtgatgc tttgtgtctt gcccttgttc catatctatt cactcaactc 1920
cgttttgctt tgtggattaa gggtgggagc agcgattttg attatgcaga aatttgatat 1980
tgtttctttc ttggagttga tacaaagtta caaggtgaca atagggccgt ttgtaccacc 2040
tattgttttg gycattgcta agagtcctat ggttgatgat tatgatcttt catcagtaag 2100
aaccgtcatg tctggggctg caccattagg aaaggagctt gaagatactg ttcgagccaa 2160
atttcctaat gctaaacttg gtcagggtta tggtatgaca gaagctggac cagtgttggc 2220
tatgtgcttg gcatttgcaa aagaaccctt tgaaataaaa tcaggggcat gtggaacagt 2280
tgtgagaaat gctgaaatga aaattgtgga tcctaaaact ggtaattctc ttcccagaaa 2340
tcaatctgga gaaatttgca ttagaggaga ccagatcatg aaaggctacc tgaatgatcc 2400
agaggccaca gcaagaacaa tagacaaaga agggtggtta tatactggtg acattggcta 2460
cattgatgat gacgacgagc ttttcattgt tgatcgatta aaggaactga tcaaatacaa 2520
aggatttcaa gtcgcacctg ctgagctcga agctctcctt ctcaaccatc ccaacatttc 2580
tgatgctgct gttgtcccca tgaaggacga gcaagcagga gaagttccag tggcttttgt 2640
tgttagatcc aacggatcca ccattactga agatgaagtc aaagatttta tttcaaagca 2700
ggtgatattt tataagagga taaagcgggt atttttcgtg gatgctattc ctaaatctcc 2760
atctggcaaa atccttcgaa aagatttgag agctaaactg gctgctgggc ttccaaatta 2820
aggatctagg aggataaaga aatgacccag gtcgtggagc gccaggctga tcgtctgtcc 2880
agccgcgagt acctggcacg cgttgttcgt tccgcaggct gggacgcagg cctcaccagc 2940
tgcaccgatg aagaaatcgt gcgcatgggt gcatccgcac gcaccattga ggaatacctg 3000
aagtctgata agccgatcta cggcctcacc cagggcttcg gtccactggt cctgttcgat 3060
gcagattccg aactggaaca gggcggctct ctcatctccc atctgggcac cggccagggt 3120
gcaccgcttg caccggaagt gtcccgcctg attctgtggc tccgcatcca aaacatgcgc 3180
aagggctatt cggctgtcag tcctgtgttc tggcaaaaac tggccgacct ctggaacaag 3240
ggcttcaccc ctgctatccc tcgccacggc accgtgtccg ccagcggcga tctccagcct 3300
ctggcacacg ctgccctggc ttttaccggc gtgggcgagg catggacccg tgatgcagac 3360
ggccgttggt ccaccgtgcc agccgtggac gcattagcag cactgggtgc agagccgttc 3420
gattggccag tgcgcgaggc tttggccttc gtgaacggta cgggcgcatc actcgcggtg 3480
gcagttctca accacagatc cgctctccgt ctcgtacgag catgtgcagt cttgtctgcc 3540
cgtttggcta ccttgctagg agctaatcct gaacactacg atgtcggcca cggagtcgca 3600
aggggacaag ttggccagct gaccgcggcg gaatggattc ggcagggact accacgcggc 3660
atggtccgag acggttcgcg ccctcttcaa gaaccataca gcttgcgctg tgccccccag 3720
gtccttggcg cggtgctgga ccagctggat ggtgcaggcg atgttctggc ccgcgaagtg 3780
gatggctgcc aggacaatcc tatcacctac gagggcgaac tgctgcacgg cggtaacttc 3840
cacgctatgc cagtcggctt cgcatccgac cagatcggtc tggcgatgca catggcagct 3900
tatctggctg aacgccagct cggcctgctg gtgagcccgg tgaccaacgg cgacctgcca 3960
ccaatgctga ccccacgcgc tggacgcggt gccggcctgg cgggcgttca gatctccgca 4020
acctccttcg tctctcgcat ccgccagctg gtgttcccag ctagcctcac caccctccca 4080
accaacggct ggaaccagga ccatgtccca atggctctga acggcgcaaa cagcgtgttc 4140
gaagctcttg aactgggttg gctgaccgtg ggtagcctgg cagtcggcgt ggcccagctc 4200
gctgcaatga ccggccacgc agctgagggc gtgtgggccg agttggcagg catctgccca 4260
ccactggatg ctgaccgccc actgggcgcg gaggtccgcg ctgctcgcga tctcctctcc 4320
gcacacgctg accagctgct cgttgacgag gctgatggca aagacttcgg ctaa 4374

<210> SEQ ID NO 45
<211> LENGTH: 11500
<212> TYPE: DNA
<213> ORGANISM: Artificial Sequence
<220> FEATURE:
<223> OTHER INFORMATION: plasmid RpBAS-At4CL-RcTAL-pECXK (pECXK_M)

<400> SEQUENCE: 45
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240

-continued

```
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat ggcaccacag gaacaggcag tctcccaggt tatggaaaag   1500
cagtccaaca acaacaactc cgatgttatc ttccgctcca agttgcctga catctacatc   1560
ccaaaccatc tgtccctgca cgattacatt ttccagaaca tctccgaatt tgctactaag   1620
ccatgcctga tcaacggccc aaccggtcac gtgtacacct actctgacgt ccacgtgatc   1680
agccgccaga tcgcagctaa cttccacaag ctgggcgtga accagaacga cgtagtgatg   1740
ctgctgctcc ctaactgccc tgagttcgtc ctgtccttcc tggccgcctc cttccgcggt   1800
gcaaccgcga ccgcggccaa cccattcttc acgccagcag agatcgctaa gcaggctaag   1860
gcttctaaca ccaagctgat catcaccgaa gcgcgctacg tggacaagat caagccactc   1920
cagaacgacg atggcgttgt gatcgtgtgc atcgacgaca acgagtccgt tccaatccca   1980
gagggctgtc tgaggttcac cgagctgacc caatcgacca ccgaagcgtc cgaggttatc   2040
gactccgttg aaatctcccc tgacgatgtc gtcgccctgc catactccag cggcaccacc   2100
ggcttgccaa agggtgtgat gctgacccac aagggactcg ttacctccgt ggcacagcag   2160
gtcgatggtg aaaaccccaa cctgtacttc cattccgatg acgtcatcct gtgcgtcctg   2220
ccgatgttcc acatctacgc tctgaactcc atcatgctgt gcggcctccg cgtcggtgca   2280
gcaatcctga tcatgccaaa gttcgaaatc aacctgctgc tggagttgat ccagcgctgc   2340
aaggtgaccg tggcacccat ggtgccccccg atcgtgctgg caatcgcgaa gtccagcgaa   2400
accgaaaagt acgacctgtc atccatccgc gtcgtcaagt cgggcgccgc accactcggc   2460
aaggagctgg aggacgctgt caacgctaag ttccctaacg cgaagctcgg ccagggctac   2520
ggtatgaccg aggccggccc agtcctggcc atgtccctgg gcttcgcaaa ggagccattc   2580
```

-continued

```
ccggtgaagt ccggcgcatg cggcaccgtt gtgcgcaacg cagagatgaa gatcgttgac   2640
ccagataccg gtgactccct gtcccgtaac cagcccggcg agatctgcat ccgcggccac   2700
cagatcatga agggctacct gaacaaccct gctgctaccg ccgaaaccat cgataaggat   2760
ggctggctcc acaccggcga catcggtctg atcgacgacg acgatgaact gttcatcgtc   2820
gatcgcctta aggagttgat caagtacaag ggcttccagg tggcccccgc agaactggaa   2880
gcactgctca tcggccaccc tgatatcacc gatgtcgccg tcgtggccat gaaggaggaa   2940
gcagcaggcg aagtgccagt cgctttcgtg gtgaagtcca aggattccga gttgtccgag   3000
gatgatgtga agcagttcgt gtccaagcag gtcgtgttct acaagcgcat caacaaggtg   3060
ttcttcaccg aatccatccc aaaggcacca tccggcaaga tcctgcgcaa ggacctgcgc   3120
gctaagctgg ctaacggcct gtaaggatct aggaggataa agaaatgacc ctgcaatccc   3180
agactgcaaa ggactgcctg gcgctggatg gtgcactgac actggttcag tgcgaagcaa   3240
ttgccactca ccgctcacgg atctccgtca caccagcatt gcgggaacgc tgcgcccgcg   3300
cgcacgcacg tctggagcac gctatcgcag aacagcgtca catctatggt atcaccaccg   3360
gcttcggacc actggctaat cgcctgatcg gtgcagatca gggcgccgaa ctccagcaga   3420
acctcatcta ccaccttgct actggcgtgg gcccaaaact ctcctgggct gaagcacgtg   3480
cactcatgct ggctcgtctc aactccatcc ttcagggcgc atctggtgca tcaccagaaa   3540
ccatcgaccg tatcgttgcc gttctgaacg ctggcttcgc cccagaagtc ccagctcagg   3600
gcaccgttgg tgcatctggc gatctgaccc cactggctca catggtgctg gcgcttcagg   3660
gtcgaggtcg tatgatcgat ccatccggcc gtgttcagga agccggcgca gtgatggatc   3720
gcctgtgcgg tggcccactg accttggcag cccgtgacgg tctggctctg gtcaacggta   3780
cttccgctat gaccgcaatc gctgctttga ccggtgtgga ggctgcgcgc gcaatcgacg   3840
ccgcattgcg ccactccgct gtgctcatgg aggttctctc cggccacgct gaggcttggc   3900
accctgcatt tgctgaactc cgcccacacc caggccagct gcgcgcaacc gaacgtctgg   3960
cccaggctct cgatggcgcc ggtcgcgttt gccgcacctt gaccgcggcc cgtcgcctga   4020
ccgcagctga tctgcgccct gaggatcacc cagcccagga cgcctactcc ctgcgcgtgg   4080
tgccacagct ggttggcgct gtctgggaca ccctcgattg gcacgatcgc gtcgtgacct   4140
gcgaactcaa ctctgtgacc gacaacccaa tcttcccgga aggctgcgct gttccagcac   4200
tgcacggcgg caacttcatg ggcgtgcacg tcgcactggc gtcggacgcc ctgaacgctg   4260
cattggttac cctggcaggt ctggtggagc gccagatcgc acgccttact gatgagaagc   4320
tgaacaaggg acttccggca ttccttcacg gtggtcaggc tggccttcag tccggcttca   4380
tgggcgcgca ggtcaccgca accgcgctcc ttgctgaaat gcgcgcaaac gcaaccccgg   4440
tgtctgttca gtcactgtct accaacggcg ctaaccagga tgttgtcagc atgggcacca   4500
tcgctgcacg ccgcgctcgc gcacagctgc tcccactgtc ccagattcag gcaatcctgg   4560
ctctcgctct cgcccaggca atggatctgc tggatgatcc agagggccag gctggctggt   4620
cccttaccgc acgcgacctg cgcgatcgca tccgcgctgt ctcgccgggc ctgcgcgcag   4680
atcgcccact ggccggccac atcgaggcag tcgctcaggg tctgcgccac ccttccgcag   4740
cagctgatcc accagcataa ctctagagtc gacctgcagg catgcaagct tggctgtttt   4800
ggcggatgag agaagatttt cagcctgata cagattaaat cagaacgcag aagcggtctg   4860
ataaaacaga atttgcctgg cggcagtagc gcggtggtcc cacctgaccc catgccgaac   4920
tcagaagtga aacgccgtag cgccgatggt agtgtggggt ctccccatgc gagagtaggg   4980
```

```
aactgccagg catcaaataa aacgaaaggc tcagtcgaaa gactgggcct ttcgttttat   5040
ctgttgtttg tcggtgaacg ctctcctgag taggacaaat ccgccgggag cggatttgaa   5100
cgttgcgaag caacggcccg gagggtggcg ggcaggacgc ccgccataaa ctgccaggca   5160
tcaaattaag cagaaggcca tcctgacgga tggccttttt gcgtttctac aaactctttt   5220
tgtttatttt tctaaataca ttcaaatatg tatccgctca tgaattaatt ccgctagatg   5280
acgtgcggct tcgacctcct gggcgtggcg cttgttggcg cgctcgcggc tggctgcggc   5340
acgacacgcg tctgagcagt attttgcgcg ccgtcctcgt gggtcaggcc ggggtgggat   5400
caggccaccg cagtaggcgc agctgatgcg atcctccact actgcgcgtc ctcctggcgc   5460
tgccgagcac gcagctcgtc ggccagctct tcaaggtcgg ccacaagcgt ttctaggtcg   5520
ctcgcggcac ttgcccagtc gcgtgatgct ggcgcgtctg tcgtatcgag ggcgcggaaa   5580
aatccgatca ccgtttttaa atcgacggcg gcatcgagtg cgtcggactc cagcgcgaca   5640
tcggagagat ccaccgctga tgcttcaggc cagttttggt acttcgtcgt gaaggtcatg   5700
acaccattat aacgaacgtt cgttaaaaat tctagcccca attctgataa tttcttccgg   5760
cactcctgcg aaaacctgcg agacttcttg cccagaaaaa acgccaagcg cagcggttac   5820
cgcacttttt ttccaggtga tttcaccctg accagcgaag cggcacttta gtgcatgagg   5880
tgtgcccctg gtttcccctc tttggagggt tcaacccaaa aaagcacaca agcaaaaatg   5940
aaaatcatca tgagcaagtt ggtgcgaagc agcaacgcgc tagctccaaa aaggtctcca   6000
ggatctcgag gagatttttg agggggaggg agtcgaggaa gagccagagc agaaggcggg   6060
gaaccgttct ctgccgacag cgtgagcccc ccttaaaaat caggccgggg aggaaccggg   6120
gagggatcag agctaggagc gagacaccct aaaggggggg aaccgttttc tgctgacggt   6180
gtttcgttta ttagttttca gcccgtggat agcggagggt gagggcaagt gagagccaga   6240
gcaaggacgg gacccctaaa ggggggaacc gttttctgct gacggtgttt cgtttattag   6300
ttttcagccc gtggacggcc gcgtttagct tccattccaa gtgcctttct gacttgttgg   6360
atgcgccttt cactgacacc tagttcgcct gcaagctcac gagtcgaggg atcagcaacc   6420
gattgagaac gggcatccag gatcgcagtt ttgacgcgaa gttcgagcaa ctcgcctgtc   6480
atttctcggc gtttgtttgc ttccgctaat cgctgtcgcg tctcctgcgc atacttactt   6540
tctgggtcag cccatctgcg tgcattcgat gtagctgcgc cccgtcgccc catcgtcgct   6600
agagctttcc gccctcggct gctctgcgtt tccacccgac gagcagggac gactggctgg   6660
cctttagcca cgtagccgcg cacacgacgc gccatcgtca ggcgatcacg catggcggga   6720
agatccggct cccggccgtc tgcaccgacc gcctgggcaa cgttgtacgc cacttcatac   6780
gcgtcgatga tcttggcatc ttttaggcgc tcaccagcag ctttgagctg gtatcccacg   6840
gtcaacgcgt ggcgaaacgc ggtctcgtcg cgcgctcgct ctggatttgt ccagagcact   6900
cgcacgccgt cgatcaggtc gccggacgcg tccagggcgc tcggcaggct cgcgtccaaa   6960
atcgctagcg ccttggcttc tgcggtggcg cgttgtgccg cttcaatgcg ggcgcgtccg   7020
ctggaaaagt cctgctcaat gtactttttc ggcttctgtg atccggtcat cgttcgagca   7080
atctccatta ggtcggccag ccgatccaca cgatcatgct ggcagtgcca tttataggct   7140
gtcggatcgt ctgagacgtg cagcggccac cggctcagcc tatgcgaaaa agcctggtca   7200
gcgccgaaaa cacgagtcat ttcttccgtc gttgcagcca gcaggcgcat atttgggctg   7260
gttttacctg ctgcggcata caccgggtca atgagccaga tgagctggca tttcccgctc   7320
```

```
agcggattca cgccgatcca agccggcgct ttttctaggc gtgcccattt ctctaaaatc   7380
gcgtagacct gcgggtttac gtgctcaatc ttcccgccgg cctggtggct gggcacatcg   7440
atgtcaagca cgatcaccgc ggcatgttgc gcgtgcgtca gcgcaacgta ctggcaccgc   7500
gtcagcgctt ttgagccagc ccggtagagc tttggttggg tttcgccggt atccgggttt   7560
ttaatccagg cgctcgcgaa atctcttgtc ttgctgccct ggaagctttc gcgtcccagg   7620
tgagcgagca gttcgcggcg atcttctgcc gtccagccgc gtgagccgca gcgcatagct   7680
tcggggtggg tgtcgaacag atcggcggac aatttccacg cgctagctgt gactgtgtcc   7740
tgcggatcgg ctagagtcat gtcttgagtg ctttctccca gctgatgact gggggttagc   7800
cgacgccctg tgagttcccg ctcacggggc gttcaacttt ttcaggtatt tgtgcagctt   7860
atcgtgtttt cttcgtaaat gaacgcttaa ctaccttgtt aaacgtggca aataggcagg   7920
attgatgggg atctagcttc acgctgccgc aagcactcag ggcgcaaggg ctgctaaagg   7980
aagcggaaca cgtagaaagc cagtccgcag aaacggtgct gaccccggat gaatgtcagc   8040
tactgggcta tctggacaag ggaaaacgca agcgcaaaga gaaagcaggt agcttgcagt   8100
gggcttacat ggcgatagct agactgggcg gttttatgga cagcaagcga accggaattg   8160
ccagctgggg cgccctctgg taaggttggg aagccctgca aagtaaactg gatggctttc   8220
ttgccgccaa ggatctgatg gcgcagggga tcaagatctg atcaagagac aggatgagga   8280
tcgtttcgca tgattgaaca agatggattg cacgcaggtt ctccggccgc ttgggtggag   8340
aggctattcg gctatgactg ggcacaacag acaatcggct gctctgatgc cgccgtgttc   8400
cggctgtcag cgcaggggcg cccggttctt tttgtcaaga ccgacctgtc cggtgccctg   8460
aatgaactcc aagacgaggc agcgcggcta tcgtggctgg ccacgacggg cgttccttgc   8520
gcagctgtgc tcgacgttgt cactgaagcg ggaagggact ggctgctatt gggcgaagtg   8580
ccggggcagg atctcctgtc atctcacctt gctcctgccg agaaagtatc catcatggct   8640
gatgcaatgc ggcggctgca tacgcttgat ccggctacct gcccattcga ccaccaagcg   8700
aaacatcgca tcgagcgagc acgtactcgg atggaagccg gtcttgtcga tcaggatgat   8760
ctggacgaag agcatcaggg gctcgcgcca gccgaactgt tcgccaggct caaggcgcgg   8820
atgcccgacg gcgaggatct cgtcgtgacc catggcgatg cctgcttgcc gaatatcatg   8880
gtggaaaatg gccgcttttc tggattcatc gactgtggcc ggctgggtgt ggcggaccgc   8940
tatcaggaca tagcgttggc tacccgtgat attgctgaag agcttggcgg cgaatgggct   9000
gaccgcttcc tcgtgcttta cggtatcgcc gctcccgatt cgcagcgcat cgccttctat   9060
cgccttcttg acgagttctt ctgagcggga ctctggggtt cgcggaatca tgaccaaaat   9120
cccttaacgt gagttttcgt tccactgagc gtcagacccc gtagaaaaga tcaaaggatc   9180
ttcttgagat cctttttttc tgcgcgtaat ctgctgcttg caaacaaaaa aaccaccgct   9240
accagcggtg gtttgtttgc cggatcaaga gctaccaact ctttttccga aggtaactgg   9300
cttcagcaga gcgcagatac caaatactgt ccttctagtg tagccgtagt taggccacca   9360
cttcaagaac tctgtagcac cgcctacata cctcgctctg ctaatcctgt taccagtggc   9420
tgctgccagt ggcgataagt cgtgtcttac cgggttggac tcaagacgat agttaccgga   9480
taaggcgcag cggtcgggct gaacgggggg ttcgtgcaca cagcccagct tggagcgaac   9540
gacctacacc gaactgagat acctacagcg tgagctatga gaaagcgcca cgcttcccga   9600
agggagaaag gcggacaggt atccggtaag cggcagggtc ggaacaggag agcgcacgag   9660
ggagcttcca gggggaaacg cctggtatct ttatagtcct gtcgggtttc gccacctctg   9720
```

acttgagcgt cgatttttgt gatgctcgtc aggggggcgg agcctatgga aaaacgccag 9780
caacgcggcc tttttacggt tcctggcctt ttgctggcct tttgctcaca tgttctttcc 9840
tgcgttatcc cctgattctg tggataaccg tattaccgcc tttgagtgag ctgataccgc 9900
tcgccgcagc cgaacgaccg agcgcagcga gtcagtgagc gaggaagcgg aagagcgcct 9960
gatgcggtat tttctcctta cgcatctgtg cggtatttca caccgcatat ggtgcactct 10020
cagtacaatc tgctctgatg ccgcatagtt aagccagtat acactccgct atcgctacgt 10080
gactgggtca tggctgcgcc ccgacacccg ccaacacccg ctgacgcgcc ctgacgggct 10140
tgtctgctcc cggcatccgc ttacagacaa gctgtgaccg tctccgggag ctgcatgtgt 10200
cagaggtttt caccgtcatc accgaaacgc gcgaggcagc agatcaattc gcgcgcgaag 10260
gcgaagcggc atgcatttac gttgacacca tcgaatggtg caaaaccttt cgcggtatgg 10320
catgatagcg cccggaagag agtcaattca gggtggtgaa tgtgaaacca gtaacgttat 10380
acgatgtcgc agagtatgcc ggtgtctctt atcagaccgt ttcccgcgtg gtgaaccagg 10440
ccagccacgt ttctgcgaaa acgcgggaaa aagtggaagc ggcgatggcg gagctgaatt 10500
acattcccaa ccgcgtggca caacaactgg cgggcaaaca gtcgttgctg attggcgttg 10560
ccacctccag tctggccctg cacgcgccgt cgcaaattgt cgcggcgatt aaatctcgcg 10620
ccgatcaact gggtgccagc gtggtggtgt cgatggtaga acgaagcggc gtcgaagcct 10680
gtaaagcggc ggtgcacaat cttctcgcgc aacgcgtcag tgggctgatc attaactatc 10740
cgctggatga ccaggatgcc attgctgtgg aagctgcctg cactaatgtt ccggcgttat 10800
ttcttgatgt ctctgaccag acacccatca acagtattat tttctcccat gaagacggta 10860
cgcgactggg cgtggagcat ctggtcgcat tgggtcacca gcaaatcgcg ctgttagcgg 10920
gcccattaag ttctgtctcg gcgcgtctgc gtctggctgg ctggcataaa tatctcactc 10980
gcaatcaaat tcagccgata gcggaacggg aaggcgactg gagtgccatg tccggttttc 11040
aacaaaccat gcaaatgctg aatgagggca tcgttcccac tgcgatgctg gttgccaacg 11100
atcagatggc gctgggcgca atgcgcgcca ttaccgagtc cgggctgcgc gttggtgcgg 11160
atatctcggt agtgggatac gacgataccg aagacagctc atgttatatc ccgccgtcaa 11220
ccaccatcaa acaggatttt cgcctgctgg ggcaaaccag cgtggaccgc ttgctgcaac 11280
tctctcaggg ccaggcggtg aagggcaatc agctgttgcc cgtctcactg gtgaaaagaa 11340
aaaccaccct ggcgcccaat acgcaaaccg cctctccccg cgcgttggcc gattcattaa 11400
tgcagctggc acgacaggtt tcccgactgg aaagcgggca gtgagcgcaa cgcaattaat 11460
gtgagttagc gcgaattgat ctggtttgac agcttatcat 11500

<210> SEQ ID NO 46
<211> LENGTH: 4497
<212> TYPE: DNA
<213> ORGANISM: Artificial Sequence
<220> FEATURE:
<223> OTHER INFORMATION: operon RpBAS-At4CL-RcTAL

<400> SEQUENCE: 46
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240

-continued

```
caaacatcgc agcttacgag gctactagcc tgaacgtgcg ccacaagatg caggtcaagg    300
gcgtcgcaga actgggcaag gaagctgctc tgaaggctat caaggaatgg ggccagccaa    360
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatggc   1200
accacaggaa caggcagtct cccaggttat ggaaaagcag tccaacaaca acaactccga   1260
tgttatcttc cgctccaagt tgcctgacat ctacatccca aaccatctgt ccctgcacga   1320
ttacattttc cagaacatct ccgaatttgc tactaagcca tgcctgatca acggcccaac   1380
cggtcacgtg tacacctact ctgacgtcca cgtgatcagc cgccagatcg cagctaactt   1440
ccacaagctg ggcgtgaacc agaacgacgt agtgatgctg ctgctcccta actgccctga   1500
gttcgtcctg tccttcctgg ccgcctcctt ccgcggtgca accgcgaccg cggccaaccc   1560
attcttcacg ccagcagaga tcgctaagca ggctaaggct tctaacacca agctgatcat   1620
caccgaagcg cgctacgtgg acaagatcaa gccactccag aacgacgatg gcgttgtgat   1680
cgtgtgcatc gacgacaacg agtccgttcc aatcccagag ggctgtctga ggttcaccga   1740
gctgacccaa tcgaccaccg aagcgtccga ggttatcgac tccgttgaaa tctcccctga   1800
cgatgtcgtc gccctgccat actccagcgg caccaccggc ttgccaaagg gtgtgatgct   1860
gacccacaag ggactcgtta cctccgtggc acagcaggtc gatggtgaaa accccaacct   1920
gtacttccat tccgatgacg tcatcctgtg cgtcctgccg atgttccaca tctacgctct   1980
gaactccatc atgctgtgcg gcctccgcgt cggtgcagca atcctgatca tgccaaagtt   2040
cgaaatcaac ctgctgctgg agttgatcca gcgctgcaag gtgaccgtgg cacccatggt   2100
gcccccgatc gtgctggcaa tcgcgaagtc cagcgaaacc gaaaagtacg acctgtcatc   2160
catccgcgtc gtcaagtcgg gcgccgcacc actcggcaag gagctggagg acgctgtcaa   2220
cgctaagttc cctaacgcga agctcggcca gggctacggt atgaccgagg ccggcccagt   2280
cctggccatg tccctgggct tcgcaaagga gccattcccg gtgaagtccg gcgcatgcgg   2340
caccgttgtg cgcaacgcag agatgaagat cgttgaccca gataccggtg actccctgtc   2400
ccgtaaccag cccggcgaga tctgcatccg cggccaccag atcatgaagg gctacctgaa   2460
caaccctgct gctaccgccg aaaccatcga taaggatggc tggctccaca ccggcgacat   2520
cggtctgatc gacgacgacg atgaactgtt catcgtcgat cgccttaagg agttgatcaa   2580
gtacaagggc ttccaggtgg cccccgcaga actggaagca ctgctcatcg gccaccctga   2640
```

tatcaccgat gtcgccgtcg tggccatgaa ggaggaagca gcaggcgaag tgccagtcgc 2700
tttcgtggtg aagtccaagg attccgagtt gtccgaggat gatgtgaagc agttcgtgtc 2760
caagcaggtc gtgttctaca agcgcatcaa caaggtgttc ttcaccgaat ccatcccaaa 2820
ggcaccatcc ggcaagatcc tgcgcaagga cctgcgcgct aagctggcta acggcctgta 2880
aggatctagg aggataaaga aatgaccctg caatcccaga ctgcaaagga ctgcctggcg 2940
ctggatggtg cactgacact ggttcagtgc gaagcaattg ccactcaccg ctcacggatc 3000
tccgtcacac cagcattgcg ggaacgctgc gcccgcgcgc acgcacgtct ggagcacgct 3060
atcgcagaac agcgtcacat ctatggtatc accaccggct tcggaccact ggctaatcgc 3120
ctgatcggtg cagatcaggg cgccgaactc cagcagaacc tcatctacca ccttgctact 3180
ggcgtgggcc caaaactctc ctgggctgaa gcacgtgcac tcatgctggc tcgtctcaac 3240
tccatccttc agggcgcatc tggtgcatca ccagaaacca tcgaccgtat cgttgccgtt 3300
ctgaacgctg gcttcgcccc agaagtccca gctcagggca ccgttggtgc atctggcgat 3360
ctgaccccac tggctcacat ggtgctggcg cttcagggtc gaggtcgtat gatcgatcca 3420
tccggccgtg ttcaggaagc cggcgcagtg atggatcgcc tgtgcggtgg cccactgacc 3480
ttggcagccc gtgacggtct ggctctggtc aacggtactt ccgctatgac cgcaatcgct 3540
gctttgaccg gtgtggaggc tgcgcgcgca atcgacgccg cattgcgcca ctccgctgtg 3600
ctcatggagg ttctctccgg ccacgctgag gcttggcacc ctgcatttgc tgaactccgc 3660
ccacacccag gccagctgcg cgcaaccgaa cgtctggccc aggctctcga tggcgccggt 3720
cgcgtttgcc gcaccttgac cgcggcccgt cgcctgaccg cagctgatct gcgccctgag 3780
gatcacccag cccaggacgc ctactccctg cgcgtggtgc cacagctggt tggcgctgtc 3840
tgggacaccc tcgattggca cgatcgcgtc gtgacctgcg aactcaactc tgtgaccgac 3900
aacccaatct tcccggaagg ctgcgctgtt ccagcactgc acggcggcaa cttcatgggc 3960
gtgcacgtcg cactggcgtc ggacgccctg aacgctgcat tggttaccct ggcaggtctg 4020
gtggagcgcc agatcgcacg ccttactgat gagaagctga acaagggact tccggcattc 4080
cttcacggtg gtcaggctgg ccttcagtcc ggcttcatgg gcgcgcaggt caccgcaacc 4140
gcgctccttg ctgaaatgcg cgcaaacgca accccggtgt ctgttcagtc actgtctacc 4200
aacggcgcta accaggatgt tgtcagcatg ggcaccatcg ctgcacgccg cgctcgcgca 4260
cagctgctcc cactgtccca gattcaggca atcctggctc tcgctctcgc ccaggcaatg 4320
gatctgctgg atgatccaga gggccaggct ggctggtccc ttaccgcacg cgacctgcgc 4380
gatcgcatcc gcgctgtctc gccgggcctg cgcgcagatc gcccactggc cggccacatc 4440
gaggcagtcg ctcagggtct gcgccaccct tccgcagcag ctgatccacc agcataa 4497

<210> SEQ ID NO 47
<211> LENGTH: 11425
<212> TYPE: DNA
<213> ORGANISM: Artificial Sequence
<220> FEATURE:
<223> OTHER INFORMATION: plasmid RpBAS-At4CL-FjTAL-pECXK (pECXK_N)

<400> SEQUENCE: 47
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180

-continued

```
aattaatcat ccggctcgta taatgtgtgg aattgtgagc ggataacaat ttcacacagg    240
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcacccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat ggcaccacag gaacaggcag tctcccaggt tatggaaaag   1500
cagtccaaca acaacaactc cgatgttatc ttccgctcca agttgcctga catctacatc   1560
ccaaaccatc tgtccctgca cgattacatt ttccagaaca tctccgaatt tgctactaag   1620
ccatgcctga tcaacggccc aaccggtcac gtgtacacct actctgacgt ccacgtgatc   1680
agccgccaga tcgcagctaa cttccacaag ctgggcgtga accagaacga cgtagtgatg   1740
ctgctgctcc ctaactgccc tgagttcgtc ctgtccttcc tggccgcctc cttccgcggt   1800
gcaaccgcga ccgcggccaa cccattcttc acgccagcag agatcgctaa gcaggctaag   1860
gcttctaaca ccaagctgat catcaccgaa gcgcgctacg tggacaagat caagccactc   1920
cagaacgacg atggcgttgt gatcgtgtgc atcgacgaca acgagtccgt tccaatccca   1980
gagggctgtc tgaggttcac cgagctgacc caatcgacca ccgaagcgtc cgaggttatc   2040
gactccgttg aaatctcccc tgacgatgtc gtcgccctgc catactccag cggcaccacc   2100
ggcttgccaa agggtgtgat gctgacccac aagggactcg ttacctccgt ggcacagcag   2160
gtcgatggtg aaaaccccaa cctgtacttc cattccgatg acgtcatcct gtgcgtcctg   2220
ccgatgttcc acatctacgc tctgaactcc atcatgctgt gcggcctccg cgtcggtgca   2280
gcaatcctga tcatgccaaa gttcgaaatc aacctgctgc tggagttgat ccagcgctgc   2340
aaggtgaccg tggcacccat ggtgccccg atcgtgctgg caatcgcgaa gtccagcgaa    2400
accgaaaagt acgacctgtc atccatccgc gtcgtcaagt cgggcgccgc accactcggc   2460
aaggagctgg aggacgctgt caacgctaag ttccctaacg cgaagctcgg ccagggctac   2520
ggtatgaccg aggccggccc agtcctggcc atgtccctgg gcttcgcaaa ggagccattc   2580
```

```
ccggtgaagt ccggcgcatg cggcaccgtt gtgcgcaacg cagagatgaa gatcgttgac   2640
ccagataccg gtgactccct gtcccgtaac cagcccggcg agatctgcat ccgcggccac   2700
cagatcatga agggctacct gaacaaccct gctgctaccg ccgaaaccat cgataaggat   2760
ggctggctcc acaccggcga catcggtctg atcgacgacg acgatgaact gttcatcgtc   2820
gatcgcctta aggagttgat caagtacaag ggcttccagg tggcccccgc agaactggaa   2880
gcactgctca tcggccaccc tgatatcacc gatgtcgccg tcgtggccat gaaggaggaa   2940
gcagcaggcg aagtgccagt cgctttcgtg gtgaagtcca aggattccga gttgtccgag   3000
gatgatgtga agcagttcgt gtccaagcag gtcgtgttct acaagcgcat caacaaggtg   3060
ttcttcaccg aatccatccc aaaggcacca tccggcaaga tcctgcgcaa ggacctgcgc   3120
gctaagctgg ctaacggcct gtaaggatct aggaggataa agaaatgaac accatcaacg   3180
aatacctgtc cctggaagag ttcgaagcga tcatcttcgg taaccagaag gttaccatct   3240
ccgatgtggt tgtgaaccgt gttaacgagt ccttcaactt cctcaaggag ttctccggca   3300
acaaggtcat ctacggtgtg aacaccggct tcggcccaat ggcacaatac cgtattaagg   3360
aatccgatca gatccagctt cagtacaatc tgatccgttc ccactcttcg ggcaccggaa   3420
aaccactctc cccagtttgt gctaaggcag caatcttggc tcgcctgaac accctgtccc   3480
tcggtaactc cggcgtgcat ccatctgtca tcaacctgat gtcggaactg atcaacaaag   3540
acattacccc actcatcttc gagcacggtg gcgtcggagc atccggtgac ctggttcagc   3600
tttctcacct ggctttggtt ctcatcggcg aaggcgaagt gttctacaag ggtgaacgcc   3660
gcccaactcc agaagttttc gaaattgagg gcttgaagcc aatccaggtt gagatccgtg   3720
agggcctcgc cttgattaac ggtactagcg tgatgaccgg tattggagtg gtcaacgtgt   3780
accacgcaaa gaagctgctg gactggtccc tgaagtcctc ctgcgccatc aatgaacttg   3840
ttcaggctta cgatgatcac ttcagcgcag agctgaacca gacgaagcgc cacaagggcc   3900
agcaggaaat cgctctgaag atgcgtcaga acctctctga cagcaccctg atccgcaagc   3960
gcgaggacca cctgtattcc ggcgaaaaca ccgaggagat tttcaaggag aaggtgcagg   4020
agtactactc cctgcgctgc gttccacaga ttctcggccc ggtcctcgaa actatcaata   4080
acgtcgcctc catcctggaa gatgagttca actccgctaa cgataaccca atcatcgacg   4140
tgaagaacca gcacgtgtac catggcggca acttccacgg tgactacatc tctctggaaa   4200
tggacaagtt gaaaatcgtt atcaccaaac tgaccatgct tgcagaacgc cagcttaact   4260
atcttctcaa ctccaagatc aacgaacttc tgccaccatt cgtgaacctc ggcaccctgg   4320
gtttcaactt cggcatgcag ggcgttcagt tcaccgcgac ctccaccacc gcagaatctc   4380
agatgctgtc caaccctatg tacgttcact ccattccaaa caacaacgat aaccaggaca   4440
tcgtctccat gggcaccaac tccgcagtga tcacgtccaa ggttatcgag aacgctttcg   4500
aagtcctggc tatcgaaatg atcaccatcg ttcaggccat cgattacctc ggccagaagg   4560
ataagatctc ctccgtttcc aagaagtggt acgatgaaat ccgcaacatt atccctacct   4620
tcaaggagga tcaggttatg tacccattcg tgcagaaggt taaggatcac ctcatcaaca   4680
actaactcta gagtcgacct gcaggcatgc aagcttggct gttttggcgg atgagagaag   4740
attttcagcc tgatacagat taaatcagaa cgcagaagcg gtctgataaa acagaatttg   4800
cctggcggca gtagcgcggt ggtcccacct gaccccatgc cgaactcaga agtgaaacgc   4860
cgtagcgccg atggtagtgt ggggtctccc catgcgagag tagggaactg ccaggcatca   4920
```

-continued

```
aataaaacga aaggctcagt cgaaagactg ggcctttcgt tttatctgtt gtttgtcggt   4980
gaacgctctc ctgagtagga caaatccgcc gggagcggat ttgaacgttg cgaagcaacg   5040
gcccggaggg tggcgggcag gacgcccgcc ataaactgcc aggcatcaaa ttaagcagaa   5100
ggccatcctg acggatggcc tttttgcgtt tctacaaact ctttttgttt atttttctaa   5160
atacattcaa atatgtatcc gctcatgaat taattccgct agatgacgtg cggcttcgac   5220
ctcctgggcg tggcgcttgt tggcgcgctc gcggctggct gcggcacgac acgcgtctga   5280
gcagtatttt gcgcgccgtc ctcgtgggtc aggccggggt gggatcaggc caccgcagta   5340
ggcgcagctg atgcgatcct ccactactgc gcgtcctcct ggcgctgccg agcacgcagc   5400
tcgtcggcca gctcttcaag gtcggccaca agcgtttcta ggtcgctcgc ggcacttgcc   5460
cagtcgcgtg atgctggcgc gtctgtcgta tcgagggcgc ggaaaaatcc gatcaccgtt   5520
tttaaatcga cggcggcatc gagtgcgtcg gactccagcg cgacatcgga gagatccacc   5580
gctgatgctt caggccagtt ttggtacttc gtcgtgaagg tcatgacacc attataacga   5640
acgttcgtta aaaattctag ccccaattct gataatttct tccggcactc ctgcgaaaac   5700
ctgcgagact tcttgcccag aaaaaacgcc aagcgcagcg gttaccgcac tttttttcca   5760
ggtgatttca ccctgaccag cgaagcggca ctttagtgca tgaggtgtgc ccctggtttc   5820
ccctctttgg agggttcaac ccaaaaaagc acacaagcaa aaatgaaaat catcatgagc   5880
aagttggtgc gaagcagcaa cgcgctagct ccaaaaaggt ctccaggatc tcgaggagat   5940
ttttgagggg gagggagtcg aggaagagcc agagcagaag gcggggaacc gttctctgcc   6000
gacagcgtga gcccccctta aaaatcaggc cggggaggaa ccggggaggg atcagagcta   6060
ggagcgagac accctaaagg gggggaaccg ttttctgctg acggtgtttc gtttattagt   6120
tttcagcccg tggatagcgg agggtgaggg caagtgagag ccagagcaag gacgggaccc   6180
ctaaaggggg gaaccgtttt ctgctgacgg tgtttcgttt attagttttc agcccgtgga   6240
cggccgcgtt tagcttccat tccaagtgcc tttctgactt gttggatgcg cctttcactg   6300
acacctagtt cgcctgcaag ctcacgagtc gagggatcag caaccgattg agaacgggca   6360
tccaggatcg cagttttgac gcgaagttcg agcaactcgc ctgtcatttc tcggcgtttg   6420
tttgcttccg ctaatcgctg tcgcgtctcc tgcgcatact tactttctgg gtcagcccat   6480
ctgcgtgcat tcgatgtagc tgcgccccgt cgcccccatcg tcgctagagc tttccgccct   6540
cggctgctct gcgtttccac ccgacgagca gggacgactg gctggccttt agccacgtag   6600
ccgcgcacac gacgcgccat cgtcaggcga tcacgcatgg cgggaagatc cggctcccgg   6660
ccgtctgcac cgaccgcctg ggcaacgttg tacgccactt catacgcgtc gatgatcttg   6720
gcatctttta ggcgctcacc agcagctttg agctggtatc ccacggtcaa cgcgtggcga   6780
aacgcggtct cgtcgcgcgc tcgctctgga tttgtccaga gcactcgcac gccgtcgatc   6840
aggtcgccgg acgcgtccag ggcgctcggc aggctcgcgt ccaaaatcgc tagcgccttg   6900
gcttctgcgg tggcgcgttg tgccgcttca atgcgggcgc gtccgctgga aaagtcctgc   6960
tcaatgtact ttttcggctt ctgtgatccg gtcatcgttc gagcaatctc cattaggtcg   7020
gccagccgat ccacacgatc atgctggcag tgccatttat aggctgtcgg atcgtctgag   7080
acgtgcagcg gccaccggct cagcctatgc gaaaaagcct ggtcagcgcc gaaaacacga   7140
gtcatttctt ccgtcgttgc agccagcagg cgcatatttg ggctggtttt acctgctgcg   7200
gcatacaccg ggtcaatgag ccagatgagc tggcatttcc cgctcagcgg attcacgccg   7260
atccaagccg gcgctttttc taggcgtgcc catttctcta aaatcgcgta gacctgcggg   7320
```

```
tttacgtgct caatcttccc gccggcctgg tggctgggca catcgatgtc aagcacgatc   7380

accgcggcat gttgcgcgtg cgtcagcgca acgtactggc accgcgtcag cgcttttgag   7440

ccagcccggt agagctttgg ttgggtttcg ccggtatccg ggtttttaat ccaggcgctc   7500

gcgaaatctc ttgtcttgct gccctggaag ctttcgcgtc ccaggtgagc gagcagttcg   7560

cggcgatctt ctgccgtcca gccgcgtgag ccgcagcgca tagcttcggg gtgggtgtcg   7620

aacagatcgg cggacaattt ccacgcgcta gctgtgactg tgtcctgcgg atcggctaga   7680

gtcatgtctt gagtgctttc tcccagctga tgactggggg ttagccgacg ccctgtgagt   7740

tcccgctcac ggggcgttca actttttcag gtatttgtgc agcttatcgt gttttcttcg   7800

taaatgaacg cttaactacc ttgttaaacg tggcaaatag gcaggattga tggggatcta   7860

gcttcacgct gccgcaagca ctcagggcgc aagggctgct aaaggaagcg gaacacgtag   7920

aaagccagtc cgcagaaacg gtgctgaccc cggatgaatg tcagctactg ggctatctgg   7980

acaagggaaa acgcaagcgc aaagagaaag caggtagctt gcagtgggct tacatggcga   8040

tagctagact gggcggtttt atggacagca agcgaaccgg aattgccagc tggggcgccc   8100

tctggtaagg ttgggaagcc ctgcaaagta aactggatgg ctttcttgcc gccaaggatc   8160

tgatggcgca ggggatcaag atctgatcaa gagacaggat gaggatcgtt tcgcatgatt   8220

gaacaagatg gattgcacgc aggttctccg gccgcttggg tggagaggct attcggctat   8280

gactgggcac aacagacaat cggctgctct gatgccgccg tgttccggct gtcagcgcag   8340

gggcgcccgg ttctttttgt caagaccgac ctgtccggtg ccctgaatga actccaagac   8400

gaggcagcgc ggctatcgtg gctggccacg acgggcgttc cttgcgcagc tgtgctcgac   8460

gttgtcactg aagcgggaag ggactggctg ctattgggcg aagtgccggg gcaggatctc   8520

ctgtcatctc accttgctcc tgccgagaaa gtatccatca tggctgatgc aatgcggcgg   8580

ctgcatacgc ttgatccggc tacctgccca ttcgaccacc aagcgaaaca tcgcatcgag   8640

cgagcacgta ctcggatgga agccggtctt gtcgatcagg atgatctgga cgaagagcat   8700

caggggctcg cgccagccga actgttcgcc aggctcaagg cgcggatgcc cgacggcgag   8760

gatctcgtcg tgacccatgg cgatgcctgc ttgccgaata tcatggtgga aaatggccgc   8820

ttttctggat tcatcgactg tggccggctg ggtgtggcgg accgctatca ggacatagcg   8880

ttggctaccc gtgatattgc tgaagagctt ggcggcgaat gggctgaccg cttcctcgtg   8940

ctttacggta tcgccgctcc cgattcgcag cgcatcgcct tctatcgcct tcttgacgag   9000

ttcttctgag cgggactctg gggttcgcgg aatcatgacc aaaatccctt aacgtgagtt   9060

ttcgttccac tgagcgtcag accccgtaga aaagatcaaa ggatcttctt gagatccttt   9120

ttttctgcgc gtaatctgct gcttgcaaac aaaaaaacca ccgctaccag cggtggtttg   9180

tttgccggat caagagctac caactctttt tccgaaggta actggcttca gcagagcgca   9240

gataccaaat actgtccttc tagtgtagcc gtagttaggc caccacttca agaactctgt   9300

agcaccgcct acatacctcg ctctgctaat cctgttacca gtggctgctg ccagtggcga   9360

taagtcgtgt cttaccgggt tggactcaag acgatagtta ccggataagg cgcagcggtc   9420

gggctgaacg gggggttcgt gcacacagcc cagcttggag cgaacgacct acaccgaact   9480

gagataccta cagcgtgagc tatgagaaag cgccacgctt cccgaaggga gaaaggcgga   9540

caggtatccg gtaagcggca gggtcggaac aggagagcgc acgagggagc ttccaggggg   9600

aaacgcctgg tatctttata gtcctgtcgg gtttcgccac ctctgacttg agcgtcgatt   9660
```

tttgtgatgc tcgtcagggg ggcggagcct atggaaaaac gccagcaacg cggccttttt 9720
acggttcctg gccttttgct ggccttttgc tcacatgttc tttcctgcgt tatcccctga 9780
ttctgtggat aaccgtatta ccgcctttga gtgagctgat accgctcgcc gcagccgaac 9840
gaccgagcgc agcgagtcag tgagcgagga agcggaagag cgcctgatgc ggtattttct 9900
ccttacgcat ctgtgcggta tttcacaccg catatggtgc actctcagta caatctgctc 9960
tgatgccgca tagttaagcc agtatacact ccgctatcgc tacgtgactg ggtcatggct 10020
gcgccccgac acccgccaac acccgctgac gcgccctgac gggcttgtct gctcccggca 10080
tccgcttaca gacaagctgt gaccgtctcc gggagctgca tgtgtcagag gttttcaccg 10140
tcatcaccga aacgcgcgag gcagcagatc aattcgcgcg cgaaggcgaa gcggcatgca 10200
tttacgttga caccatcgaa tggtgcaaaa cctttcgcgg tatggcatga tagcgcccgg 10260
aagagagtca attcagggtg gtgaatgtga aaccagtaac gttatacgat gtcgcagagt 10320
atgccggtgt ctcttatcag accgtttccc gcgtggtgaa ccaggccagc cacgtttctg 10380
cgaaaacgcg ggaaaaagtg gaagcggcga tggcggagct gaattacatt cccaaccgcg 10440
tggcacaaca actggcgggc aaacagtcgt tgctgattgg cgttgccacc tccagtctgg 10500
ccctgcacgc gccgtcgcaa attgtcgcgg cgattaaatc tcgcgccgat caactgggtg 10560
ccagcgtggt ggtgtcgatg gtagaacgaa gcggcgtcga agcctgtaaa gcggcggtgc 10620
acaatcttct cgcgcaacgc gtcagtgggc tgatcattaa ctatccgctg gatgaccagg 10680
atgccattgc tgtggaagct gcctgcacta atgttccggc gttatttctt gatgtctctg 10740
accagacacc catcaacagt attattttct cccatgaaga cggtacgcga ctgggcgtgg 10800
agcatctggt cgcattgggt caccagcaaa tcgcgctgtt agcgggccca ttaagttctg 10860
tctcggcgcg tctgcgtctg gctggctggc ataaatatct cactcgcaat caaattcagc 10920
cgatagcgga acgggaaggc gactggagtg ccatgtccgg ttttcaacaa accatgcaaa 10980
tgctgaatga gggcatcgtt cccactgcga tgctggttgc caacgatcag atggcgctgg 11040
gcgcaatgcg cgccattacc gagtccgggc tgcgcgttgg tgcggatatc tcggtagtgg 11100
gatacgacga taccgaagac agctcatgtt atatcccgcc gtcaaccacc atcaaacagg 11160
attttcgcct gctggggcaa accagcgtgg accgcttgct gcaactctct cagggccagg 11220
cggtgaaggg caatcagctg ttgcccgtct cactggtgaa aagaaaaacc accctggcgc 11280
ccaatacgca aaccgcctct ccccgcgcgt tggccgattc attaatgcag ctggcacgac 11340
aggtttcccg actggaaagc gggcagtgag cgcaacgcaa ttaatgtgag ttagcgcgaa 11400
ttgatctggt ttgacagctt atcat 11425

<210> SEQ ID NO 48
<211> LENGTH: 4422
<212> TYPE: DNA
<213> ORGANISM: Artificial Sequence
<220> FEATURE:
<223> OTHER INFORMATION: operon RpBAS-At4CL-FjTAL

<400> SEQUENCE: 48
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300

-continued gcgtcgcaga actgggcaag gaagctgctc tgaaggctat caaggaatgg ggccagccaa 360
agtccaagat cacccacctg atcgtctgct gcctggctgg cgtggatatg ccaggcgcag 420
attaccagct cactaagctc ctcgatctcg acccatccgt taagcgcttc atgttctacc 480
acctgggttg ctacgccggt ggcaccgtgc tccgcctggc taaggatatc gctgaaaaca 540
acaagggcgc acgcgtgctg atcgtgtgct ctgaaatgac caccacctgt ttccgcggcc 600
cttcagaaac ccacctggac tctatgatcg gccaggccat cctcggtgac ggtgccgcag 660
ccgtgatcgt gggcgcggac cctgatctga ccgtggagcg tccaatcttc gagctggtga 720
gcacggctca gaccatcgtg ccggagtccc acggcgccat cgagggccac ctcctggagt 780
ctggcctgag cttccacctg tacaagaccg tgccgaccct gatctccaac aacatcaaga 840
cctgcctctc cgatgctttc accccactga acatctccga ctggaacagc ctcttctgga 900
tcgcacaccc aggcggcccg gccatcctgg atcaggtgac cgctaaggtg ggcctggaaa 960
aggaaaagct gaaggtgacc cgccaggttc tgaaggatta cggcaacatg tcctccgcta 1020
ccgtgttctt catcatggat gaaatgcgta agaagtccct ggaaaacggc caggcaacca 1080
ccggcgaggg cctggaatgg ggcgtgctgt tcggcttcgg cccaggcatc accgtggaaa 1140
ccgtggtcct gcgctccgtc ccagtgatct cctaaggatc taggaggatt atgagatggc 1200
accacaggaa caggcagtct cccaggttat ggaaaagcag tccaacaaca acaactccga 1260
tgttatcttc cgctccaagt tgcctgacat ctacatccca aaccatctgt ccctgcacga 1320
ttacattttc cagaacatct ccgaatttgc tactaagcca tgcctgatca acggcccaac 1380
cggtcacgtg tacacctact ctgacgtcca cgtgatcagc cgccagatcg cagctaactt 1440
ccacaagctg ggcgtgaacc agaacgacgt agtgatgctg ctgctcccta actgccctga 1500
gttcgtcctg tccttcctgg ccgcctcctt ccgcggtgca accgcgaccg cggccaaccc 1560
attcttcacg ccagcagaga tcgctaagca ggctaaggct tctaacacca agctgatcat 1620
caccgaagcg cgctacgtgg acaagatcaa gccactccag aacgacgatg gcgttgtgat 1680
cgtgtgcatc gacgacaacg agtccgttcc aatcccagag ggctgtctga ggttcaccga 1740
gctgacccaa tcgaccaccg aagcgtccga ggttatcgac tccgttgaaa tctcccctga 1800
cgatgtcgtc gccctgccat actccagcgg caccaccggc ttgccaaagg gtgtgatgct 1860
gacccacaag ggactcgtta cctccgtggc acagcaggtc gatggtgaaa accccaacct 1920
gtacttccat tccgatgacg tcatcctgtg cgtcctgccg atgttccaca tctacgctct 1980
gaactccatc atgctgtgcg gcctccgcgt cggtgcagca atcctgatca tgccaaagtt 2040
cgaaatcaac ctgctgctgg agttgatcca gcgctgcaag gtgaccgtgg cacccatggt 2100
gcccccgatc gtgctggcaa tcgcgaagtc cagcgaaacc gaaaagtacg acctgtcatc 2160
catccgcgtc gtcaagtcgg gcgccgcacc actcggcaag gagctggagg acgctgtcaa 2220
cgctaagttc cctaacgcga agctcggcca gggctacggt atgaccgagg ccggcccagt 2280
cctggccatg tccctgggct tcgcaaagga gccattcccg gtgaagtccg gcgcatgcgg 2340
caccgttgtg cgcaacgcag agatgaagat cgttgaccca gataccggtg actccctgtc 2400
ccgtaaccag cccggcgaga tctgcatccg cggccaccag atcatgaagg gctacctgaa 2460
caaccctgct gctaccgccg aaaccatcga taaggatggc tggctccaca ccggcgacat 2520
cggtctgatc gacgacgacg atgaactgtt catcgtcgat cgccttaagg agttgatcaa 2580
gtacaagggc ttccaggtgg cccccgcaga actggaagca ctgctcatcg gccaccctga 2640

```
tatcaccgat gtcgccgtcg tggccatgaa ggaggaagca gcaggcgaag tgccagtcgc   2700
tttcgtggtg aagtccaagg attccgagtt gtccgaggat gatgtgaagc agttcgtgtc   2760
caagcaggtc gtgttctaca agcgcatcaa caaggtgttc ttcaccgaat ccatcccaaa   2820
ggcaccatcc ggcaagatcc tgcgcaagga cctgcgcgct aagctggcta acggcctgta   2880
aggatctagg aggataaaga aatgaacacc atcaacgaat acctgtccct ggaagagttc   2940
gaagcgatca tcttcggtaa ccagaaggtt accatctccg atgtggttgt gaaccgtgtt   3000
aacgagtcct tcaacttcct caaggagttc tccggcaaca aggtcatcta cggtgtgaac   3060
accggcttcg gcccaatggc acaataccgt attaaggaat ccgatcagat ccagcttcag   3120
tacaatctga tccgttccca ctcttcgggc accggaaaac cactctcccc agtttgtgct   3180
aaggcagcaa tcttggctcg cctgaacacc ctgtccctcg gtaactccgg cgtgcatcca   3240
tctgtcatca acctgatgtc ggaactgatc aacaaagaca ttaccccact catcttcgag   3300
cacggtggcg tcggagcatc cggtgacctg gttcagcttt ctcacctggc tttggttctc   3360
atcggcgaag gcgaagtgtt ctacaagggt gaacgccgcc caactccaga agtttttcgaa   3420
attgagggct tgaagccaat ccaggttgag atccgtgagg gcctcgcctt gattaacggt   3480
actagcgtga tgaccggtat tggagtggtc aacgtgtacc acgcaaagaa gctgctggac   3540
tggtccctga agtcctcctg cgccatcaat gaacttgttc aggcttacga tgatcacttc   3600
agcgcagagc tgaaccagac gaagcgccac aagggccagc aggaaatcgc tctgaagatg   3660
cgtcagaacc tctctgacag caccctgatc cgcaagcgcg aggaccacct gtattccggc   3720
gaaaacaccg aggagatttt caaggagaag gtgcaggagt actactccct gcgctgcgtt   3780
ccacagattc tcggcccggt cctcgaaact atcaataacg tcgcctccat cctggaagat   3840
gagttcaact ccgctaacga taacccaatc atcgacgtga agaaccagca cgtgtaccat   3900
ggcggcaact tccacggtga ctacatctct ctggaaatgg acaagttgaa aatcgttatc   3960
accaaactga ccatgcttgc agaacgccag cttaactatc ttctcaactc caagatcaac   4020
gaacttctgc caccattcgt gaacctcggc accctgggtt tcaacttcgg catgcagggc   4080
gttcagttca ccgcgacctc caccaccgca gaatctcaga tgctgtccaa ccctatgtac   4140
gttcactcca ttccaaacaa caacgataac caggacatcg tctccatggg caccaactcc   4200
gcagtgatca cgtccaaggt tatcgagaac gctttcgaag tcctggctat cgaaatgatc   4260
accatcgttc aggccatcga ttacctcggc cagaaggata agatctcctc cgtttccaag   4320
aagtggtacg atgaaatccg caacattatc cctaccttca aggaggatca ggttatgtac   4380
ccattcgtgc agaaggttaa ggatcacctc atcaacaact aa                      4422
```

<210> SEQ ID NO 49
<211> LENGTH: 11437
<212> TYPE: DNA
<213> ORGANISM: Artificial Sequence
<220> FEATURE:
<223> OTHER INFORMATION: plasmid RpBAS-At4CL-SeSam8-pECXK (pECXK_O)

<400> SEQUENCE: 49

```
cgactgcacg gtgcaccaat gcttctggcg tcaggcagcc atcggaagct gtggtatggc     60
tgtgcaggtc gtaaatcact gcataattcg tgtcgctcaa ggcgcactcc cgttctggat    120
aatgtttttt gcgccgacat cataacggtt ctggcaaata ttctgaaatg agctgttgac    180
aattaatcat ccggctcgta taatgtgtgg aattgtgagc ggataacaat ttcacacagg    240
aaacagacca tggaattcga gctggatcta ggagggagat catatggcaa ccgaggagat    300
```

-continued

```
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat ggcaccacag gaacaggcag tctcccaggt tatggaaaag   1500
cagtccaaca acaacaactc cgatgttatc ttccgctcca agttgcctga catctacatc   1560
ccaaaccatc tgtccctgca cgattacatt ttccagaaca tctccgaatt tgctactaag   1620
ccatgcctga tcaacggccc aaccggtcac gtgtacacct actctgacgt ccacgtgatc   1680
agccgccaga tcgcagctaa cttccacaag ctgggcgtga accagaacga cgtagtgatg   1740
ctgctgctcc ctaactgccc tgagttcgtc ctgtccttcc tggccgcctc cttccgcggt   1800
gcaaccgcga ccgcggccaa cccattcttc acgccagcag agatcgctaa gcaggctaag   1860
gcttctaaca ccaagctgat catcaccgaa gcgcgctacg tggacaagat caagccactc   1920
cagaacgacg atggcgttgt gatcgtgtgc atcgacgaca acgagtccgt tccaatccca   1980
gagggctgtc tgaggttcac cgagctgacc caatcgacca ccgaagcgtc cgaggttatc   2040
gactccgttg aaatctcccc tgacgatgtc gtcgccctgc catactccag cggcaccacc   2100
ggcttgccaa agggtgtgat gctgacccac aagggactcg ttacctccgt ggcacagcag   2160
gtcgatggtg aaaaccccaa cctgtacttc cattccgatg acgtcatcct gtgcgtcctg   2220
ccgatgttcc acatctacgc tctgaactcc atcatgctgt gcggcctccg cgtcggtgca   2280
gcaatcctga tcatgccaaa gttcgaaatc aacctgctgc tggagttgat ccagcgctgc   2340
aaggtgaccg tggcacccat ggtgccccccg atcgtgctgg caatcgcgaa gtccagcgaa   2400
accgaaaagt acgacctgtc atccatccgc gtcgtcaagt cgggcgccgc accactcggc   2460
aaggagctgg aggacgctgt caacgctaag ttccctaacg cgaagctcgg ccagggctac   2520
ggtatgaccg aggccggccc agtcctggcc atgtccctgg gcttcgcaaa ggagccattc   2580
ccggtgaagt ccggcgcatg cggcaccgtt gtgcgcaacg cagagatgaa gatcgttgac   2640
```

-continued

```
ccagataccg gtgactccct gtcccgtaac cagcccggcg agatctgcat ccgcggccac   2700
cagatcatga agggctacct gaacaaccct gctgctaccg ccgaaaccat cgataaggat   2760
ggctggctcc acaccggcga catcggtctg atcgacgacg acgatgaact gttcatcgtc   2820
gatcgcctta aggagttgat caagtacaag ggcttccagg tggcccccgc agaactggaa   2880
gcactgctca tcggccaccc tgatatcacc gatgtcgccg tcgtggccat gaaggaggaa   2940
gcagcaggcg aagtgccagt cgctttcgtg gtgaagtcca aggattccga gttgtccgag   3000
gatgatgtga agcagttcgt gtccaagcag gtcgtgttct acaagcgcat caacaaggtg   3060
ttcttcaccg aatccatccc aaaggcacca tccggcaaga tcctgcgcaa ggacctgcgc   3120
gctaagctgg ctaacggcct gtaaggatct aggaggataa agaaatgacc caggtcgtgg   3180
agcgccaggc tgatcgtctg tccagccgcg agtacctggc acgcgttgtt cgttccgcag   3240
gctgggacgc aggcctcacc agctgcaccg atgaagaaat cgtgcgcatg ggtgcatccg   3300
cacgcaccat tgaggaatac ctgaagtctg ataagccgat ctacggcctc acccagggct   3360
tcggtccact ggtcctgttc gatgcagatt ccgaactgga acagggcggc tctctcatct   3420
cccatctggg caccggccag ggtgcaccgc ttgcaccgga agtgtcccgc ctgattctgt   3480
ggctccgcat ccaaaacatg cgcaagggct attcggctgt cagtcctgtg ttctggcaaa   3540
aactggccga cctctggaac aagggcttca cccctgctat ccctcgccac ggcaccgtgt   3600
ccgccagcgg cgatctccag cctctggcac acgctgccct ggcttttacc ggcgtgggcg   3660
aggcatggac ccgtgatgca gacggccgtt ggtccaccgt gccagccgtg gacgcattag   3720
cagcactggg tgcagagccg ttcgattggc cagtgcgcga ggctttggcc ttcgtgaacg   3780
gtacgggcgc atcactcgcg gtggcagttc tcaaccacag atccgctctc cgtctcgtac   3840
gagcatgtgc agtcttgtct gcccgtttgg ctaccttgct aggagctaat cctgaacact   3900
acgatgtcgg ccacggagtc gcaaggggac aagttggcca gctgaccgcg gcggaatgga   3960
ttcggcaggg actaccacgc ggcatggtcc gagacggttc gcgccctctt caagaaccat   4020
acagcttgcg ctgtgccccc caggtccttg gcgcggtgct ggaccagctg gatggtgcag   4080
gcgatgttct ggcccgcgaa gtggatggct gccaggacaa tcctatcacc tacgagggcg   4140
aactgctgca cggcggtaac ttccacgcta tgccagtcgg cttcgcatcc gaccagatcg   4200
gtctggcgat gcacatggca gcttatctgg ctgaacgcca gctcggcctg ctggtgagcc   4260
cggtgaccaa cggcgacctg ccaccaatgc tgaccccacg cgctggacgc ggtgccggcc   4320
tggcgggcgt tcagatctcc gcaacctcct tcgtctctcg catccgccag ctggtgttcc   4380
cagctagcct caccaccctc ccaaccaacg gctggaacca ggaccatgtc ccaatggctc   4440
tgaacggcgc aaacagcgtg ttcgaagctc ttgaactggg ttggctgacc gtgggtagcc   4500
tggcagtcgg cgtggcccag ctcgctgcaa tgaccggcca cgcagctgag ggcgtgtggg   4560
ccgagttggc aggcatctgc ccaccactgg atgctgaccg cccactgggc gcggaggtcc   4620
gcgctgctcg cgatctcctc tccgcacacg ctgaccagct gctcgttgac gaggctgatg   4680
gcaaagactt cggctaactc tagagtcgac ctgcaggcat gcaagcttgg ctgttttggc   4740
ggatgagaga agattttcag cctgatacag attaaatcag aacgcagaag cggtctgata   4800
aaacagaatt tgcctggcgg cagtagcgcg gtggtcccac ctgaccccat gccgaactca   4860
gaagtgaaac gccgtagcgc cgatggtagt gtggggtctc cccatgcgag agtagggaac   4920
tgccaggcat caaataaaac gaaaggctca gtcgaaagac tgggcctttc gttttatctg   4980
ttgtttgtcg gtgaacgctc tcctgagtag gacaaatccg ccgggagcgg atttgaacgt   5040
```

-continued tgcgaagcaa cggcccggag ggtggcgggc aggacgcccg ccataaactg ccaggcatca 5100
aattaagcag aaggccatcc tgacggatgg cctttttgcg tttctacaaa ctctttttgt 5160
ttatttttct aaatacattc aaatatgtat ccgctcatga attaattccg ctagatgacg 5220
tgcggcttcg acctcctggg cgtggcgctt gttggcgcgc tcgcggctgg ctgcggcacg 5280
acacgcgtct gagcagtatt ttgcgcgccg tcctcgtggg tcaggccggg gtgggatcag 5340
gccaccgcag taggcgcagc tgatgcgatc ctccactact gcgcgtcctc ctggcgctgc 5400
cgagcacgca gctcgtcggc cagctcttca aggtcggcca caagcgtttc taggtcgctc 5460
gcggcacttg cccagtcgcg tgatgctggc gcgtctgtcg tatcgagggc gcggaaaaat 5520
ccgatcaccg tttttaaatc gacggcggca tcgagtgcgt cggactccag cgcgacatcg 5580
gagagatcca ccgctgatgc ttcaggccag ttttggtact tcgtcgtgaa ggtcatgaca 5640
ccattataac gaacgttcgt taaaaattct agccccaatt ctgataattt cttccggcac 5700
tcctgcgaaa acctgcgaga cttcttgccc agaaaaaacg ccaagcgcag cggttaccgc 5760
actttttttc caggtgattt caccctgacc agcgaagcgg cactttagtg catgaggtgt 5820
gcccctggtt tcccctcttt ggagggttca acccaaaaaa gcacacaagc aaaaatgaaa 5880
atcatcatga gcaagttggt gcgaagcagc aacgcgctag ctccaaaaag gtctccagga 5940
tctcgaggag atttttgagg gggagggagt cgaggaagag ccagagcaga aggcggggaa 6000
ccgttctctg ccgacagcgt gagcccccct taaaaatcag gccggggagg aaccggggag 6060
ggatcagagc taggagcgag acaccctaaa ggggggggaac cgttttctgc tgacggtgtt 6120
tcgtttatta gttttcagcc cgtggatagc ggagggtgag ggcaagtgag agccagagca 6180
aggacgggac ccctaaaggg gggaaccgtt ttctgctgac ggtgtttcgt ttattagttt 6240
tcagcccgtg gacggccgcg tttagcttcc attccaagtg cctttctgac ttgttggatg 6300
cgcctttcac tgacacctag ttcgcctgca agctcacgag tcgagggatc agcaaccgat 6360
tgagaacggg catccaggat cgcagttttg acgcgaagtt cgagcaactc gcctgtcatt 6420
tctcggcgtt tgtttgcttc cgctaatcgc tgtcgcgtct cctgcgcata cttactttct 6480
gggtcagccc atctgcgtgc attcgatgta gctgcgcccc gtcgccccat cgtcgctaga 6540
gctttccgcc ctcggctgct ctgcgtttcc acccgacgag cagggacgac tggctggcct 6600
ttagccacgt agccgcgcac acgacgcgcc atcgtcaggc gatcacgcat ggcgggaaga 6660
tccggctccc ggccgtctgc accgaccgcc tgggcaacgt tgtacgccac ttcatacgcg 6720
tcgatgatct tggcatcttt taggcgctca ccagcagctt tgagctggta tcccacggtc 6780
aacgcgtggc gaaacgcggt ctcgtcgcgc gctcgctctg gatttgtcca gagcactcgc 6840
acgccgtcga tcaggtcgcc ggacgcgtcc agggcgctcg gcaggctcgc gtccaaaatc 6900
gctagcgcct tggcttctgc ggtggcgcgt tgtgccgctt caatgcgggc gcgtccgctg 6960
gaaaagtcct gctcaatgta ctttttcggc ttctgtgatc cggtcatcgt tcgagcaatc 7020
tccattaggt cggccagccg atccacacga tcatgctggc agtgccattt ataggctgtc 7080
ggatcgtctg agacgtgcag cggccaccgg ctcagcctat gcgaaaaagc ctggtcagcg 7140
ccgaaaacac gagtcatttc ttccgtcgtt gcagccagca ggcgcatatt tgggctggtt 7200
ttacctgctg cggcatacac cgggtcaatg agccagatga gctggcattt cccgctcagc 7260
ggattcacgc cgatccaagc cggcgctttt tctaggcgtg cccatttctc taaaatcgcg 7320
tagacctgcg ggtttacgtg ctcaatcttc ccgccggcct ggtggctggg cacatcgatg 7380
tcaagcacga tcaccgcggc atgttgcgcg tgcgtcagcg caacgtactg gcaccgcgtc 7440
agcgcttttg agccagcccg gtagagcttt ggttgggttt cgccggtatc cgggttttta 7500
atccaggcgc tcgcgaaatc tcttgtcttg ctgccctgga agctttcgcg tcccaggtga 7560
gcgagcagtt cgcggcgatc ttctgccgtc cagccgcgtg agccgcagcg catagcttcg 7620
gggtgggtgt cgaacagatc ggcggacaat ttccacgcgc tagctgtgac tgtgtcctgc 7680
ggatcggcta gagtcatgtc ttgagtgctt tctcccagct gatgactggg ggttagccga 7740
cgccctgtga gttcccgctc acggggcgtt caactttttc aggtatttgt gcagcttatc 7800
gtgttttctt cgtaaatgaa cgcttaacta ccttgttaaa cgtggcaaat aggcaggatt 7860
gatggggatc tagcttcacg ctgccgcaag cactcagggc gcaagggctg ctaaaggaag 7920
cggaacacgt agaaagccag tccgcagaaa cggtgctgac cccggatgaa tgtcagctac 7980
tgggctatct ggacaaggga aaacgcaagc gcaaagagaa agcaggtagc ttgcagtggg 8040
cttacatggc gatagctaga ctgggcggtt ttatggacag caagcgaacc ggaattgcca 8100
gctggggcgc cctctggtaa ggttgggaag ccctgcaaag taaactggat ggctttcttg 8160
ccgccaagga tctgatggcg caggggatca agatctgatc aagagacagg atgaggatcg 8220
tttcgcatga ttgaacaaga tggattgcac gcaggttctc cggccgcttg ggtggagagg 8280
ctattcggct atgactgggc acaacagaca atcggctgct ctgatgccgc cgtgttccgg 8340
ctgtcagcgc aggggcgccc ggttcttttt gtcaagaccg acctgtccgg tgccctgaat 8400
gaactccaag acgaggcagc gcggctatcg tggctggcca cgacgggcgt tccttgcgca 8460
gctgtgctcg acgttgtcac tgaagcggga agggactggc tgctattggg cgaagtgccg 8520
gggcaggatc tcctgtcatc tcaccttgct cctgccgaga aagtatccat catggctgat 8580
gcaatgcggc ggctgcatac gcttgatccg gctacctgcc cattcgacca ccaagcgaaa 8640
catcgcatcg agcgagcacg tactcggatg gaagccggtc ttgtcgatca ggatgatctg 8700
gacgaagagc atcaggggct cgcgccagcc gaactgttcg ccaggctcaa ggcgcggatg 8760
cccgacggcg aggatctcgt cgtgacccat ggcgatgcct gcttgccgaa tatcatggtg 8820
gaaaatggcc gcttttctgg attcatcgac tgtggccggc tgggtgtggc ggaccgctat 8880
caggacatag cgttggctac ccgtgatatt gctgaagagc ttggcggcga atgggctgac 8940
cgcttcctcg tgctttacgg tatcgccgct cccgattcgc agcgcatcgc cttctatcgc 9000
cttcttgacg agttcttctg agcgggactc tggggttcgc ggaatcatga ccaaaatccc 9060
ttaacgtgag ttttcgttcc actgagcgtc agaccccgta gaaaagatca aaggatcttc 9120
ttgagatcct ttttttctgc gcgtaatctg ctgcttgcaa acaaaaaaac caccgctacc 9180
agcggtggtt tgtttgccgg atcaagagct accaactctt tttccgaagg taactggctt 9240
cagcagagcg cagataccaa atactgtcct tctagtgtag ccgtagttag gccaccactt 9300
caagaactct gtagcaccgc ctacatacct cgctctgcta atcctgttac cagtggctgc 9360
tgccagtggc gataagtcgt gtcttaccgg gttggactca agacgatagt taccggataa 9420
ggcgcagcgg tcgggctgaa cggggggttc gtgcacacag cccagcttgg agcgaacgac 9480
ctacaccgaa ctgagatacc tacagcgtga gctatgagaa agcgccacgc ttcccgaagg 9540
gagaaaggcg gacaggtatc cggtaagcgg cagggtcgga acaggagagc gcacgaggga 9600
gcttccaggg ggaaacgcct ggtatcttta tagtcctgtc gggtttcgcc acctctgact 9660
tgagcgtcga tttttgtgat gctcgtcagg ggggcggagc ctatggaaaa acgccagcaa 9720
cgcggccttt ttacggttcc tggccttttg ctggcctttt gctcacatgt tctttcctgc 9780
gttatcccct gattctgtgg ataaccgtat taccgccttt gagtgagctg ataccgctcg 9840
ccgcagccga acgaccgagc gcagcgagtc agtgagcgag gaagcggaag agcgcctgat 9900
gcggtatttt ctccttacgc atctgtgcgg tatttcacac cgcatatggt gcactctcag 9960
tacaatctgc tctgatgccg catagttaag ccagtataca ctccgctatc gctacgtgac 10020
tgggtcatgg ctgcgccccg acacccgcca acacccgctg acgcgccctg acgggcttgt 10080
ctgctcccgg catccgctta cagacaagct gtgaccgtct ccgggagctg catgtgtcag 10140
aggttttcac cgtcatcacc gaaacgcgcg aggcagcaga tcaattcgcg cgcgaaggcg 10200
aagcggcatg catttacgtt gacaccatcg aatggtgcaa aacctttcgc ggtatggcat 10260
gatagcgccc ggaagagagt caattcaggg tggtgaatgt gaaaccagta acgttatacg 10320
atgtcgcaga gtatgccggt gtctcttatc agaccgtttc ccgcgtggtg aaccaggcca 10380
gccacgtttc tgcgaaaacg cgggaaaaag tggaagcggc gatggcggag ctgaattaca 10440
ttcccaaccg cgtggcacaa caactggcgg gcaaacagtc gttgctgatt ggcgttgcca 10500
cctccagtct ggccctgcac gcgccgtcgc aaattgtcgc ggcgattaaa tctcgcgccg 10560
atcaactggg tgccagcgtg gtggtgtcga tggtagaacg aagcggcgtc gaagcctgta 10620
aagcggcggt gcacaatctt ctcgcgcaac gcgtcagtgg gctgatcatt aactatccgc 10680
tggatgacca ggatgccatt gctgtggaag ctgcctgcac taatgttccg gcgttatttc 10740
ttgatgtctc tgaccagaca cccatcaaca gtattatttt ctcccatgaa gacggtacgc 10800
gactgggcgt ggagcatctg gtcgcattgg gtcaccagca aatcgcgctg ttagcgggcc 10860
cattaagttc tgtctcggcg cgtctgcgtc tggctggctg gcataaatat ctcactcgca 10920
atcaaattca gccgatagcg gaacgggaag gcgactggag tgccatgtcc ggttttcaac 10980
aaaccatgca aatgctgaat gagggcatcg ttcccactgc gatgctggtt gccaacgatc 11040
agatggcgct gggcgcaatg cgcgccatta ccgagtccgg gctgcgcgtt ggtgcggata 11100
tctcggtagt gggatacgac gataccgaag acagctcatg ttatatcccg ccgtcaacca 11160
ccatcaaaca ggattttcgc ctgctggggc aaaccagcgt ggaccgcttg ctgcaactct 11220
ctcagggcca ggcggtgaag ggcaatcagc tgttgcccgt ctcactggtg aaaagaaaaa 11280
ccaccctggc gcccaatacg caaaccgcct ctccccgcgc gttggccgat tcattaatgc 11340
agctggcacg acaggtttcc cgactggaaa gcgggcagtg agcgcaacgc aattaatgtg 11400
agttagcgcg aattgatctg gtttgacagc ttatcat 11437

<210> SEQ ID NO 50
<211> LENGTH: 4434
<212> TYPE: DNA
<213> ORGANISM: Artificial Sequence
<220> FEATURE:
<223> OTHER INFORMATION: operon RpBAS-At4CL-SeSam8

<400> SEQUENCE: 50
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300
gcgtcgcaga actgggcaag gaagctgctc tgaaggctat caaggaatgg ggccagccaa 360

-continued

```
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatggc   1200
accacaggaa caggcagtct cccaggttat ggaaaagcag tccaacaaca acaactccga   1260
tgttatcttc cgctccaagt tgcctgacat ctacatccca aaccatctgt ccctgcacga   1320
ttacattttc cagaacatct ccgaatttgc tactaagcca tgcctgatca acggcccaac   1380
cggtcacgtg tacacctact ctgacgtcca cgtgatcagc cgccagatcg cagctaactt   1440
ccacaagctg ggcgtgaacc agaacgacgt agtgatgctg ctgctcccta actgccctga   1500
gttcgtcctg tccttcctgg ccgcctcctt ccgcggtgca accgcgaccg cggccaaccc   1560
attcttcacg ccagcagaga tcgctaagca ggctaaggct tctaacacca agctgatcat   1620
caccgaagcg cgctacgtgg acaagatcaa gccactccag aacgacgatg gcgttgtgat   1680
cgtgtgcatc gacgacaacg agtccgttcc aatcccagag ggctgtctga ggttcaccga   1740
gctgacccaa tcgaccaccg aagcgtccga ggttatcgac tccgttgaaa tctcccctga   1800
cgatgtcgtc gccctgccat actccagcgg caccaccggc ttgccaaagg gtgtgatgct   1860
gacccacaag ggactcgtta cctccgtggc acagcaggtc gatggtgaaa accccaacct   1920
gtacttccat tccgatgacg tcatcctgtg cgtcctgccg atgttccaca tctacgctct   1980
gaactccatc atgctgtgcg gcctccgcgt cggtgcagca atcctgatca tgccaaagtt   2040
cgaaatcaac ctgctgctgg agttgatcca gcgctgcaag gtgaccgtgg cacccatggt   2100
gcccccgatc gtgctggcaa tcgcgaagtc cagcgaaacc gaaaagtacg acctgtcatc   2160
catccgcgtc gtcaagtcgg gcgccgcacc actcggcaag gagctggagg acgctgtcaa   2220
cgctaagttc cctaacgcga agctcggcca gggctacggt atgaccgagg ccggcccagt   2280
cctggccatg tccctgggct tcgcaaagga gccattcccg gtgaagtccg gcgcatgcgg   2340
caccgttgtg cgcaacgcag agatgaagat cgttgaccca gataccggtg actccctgtc   2400
ccgtaaccag cccggcgaga tctgcatccg cggccaccag atcatgaagg gctacctgaa   2460
caaccctgct gctaccgccg aaaccatcga taaggatggc tggctccaca ccggcgacat   2520
cggtctgatc gacgacgacg atgaactgtt catcgtcgat cgccttaagg agttgatcaa   2580
gtacaagggc ttccaggtgg cccccgcaga actggaagca ctgctcatcg gccaccctga   2640
tatcaccgat gtcgccgtcg tggccatgaa ggaggaagca gcaggcgaag tgccagtcgc   2700
tttcgtggtg aagtccaagg attccgagtt gtccgaggat gatgtgaagc agttcgtgtc   2760
```

caagcaggtc gtgttctaca agcgcatcaa caaggtgttc ttcaccgaat ccatcccaaa 2820
ggcaccatcc ggcaagatcc tgcgcaagga cctgcgcgct aagctggcta acggcctgta 2880
aggatctagg aggataaaga aatgacccag gtcgtggagc gccaggctga tcgtctgtcc 2940
agccgcgagt acctggcacg cgttgttcgt tccgcaggct gggacgcagg cctcaccagc 3000
tgcaccgatg aagaaatcgt gcgcatgggt gcatccgcac gcaccattga ggaatacctg 3060
aagtctgata agccgatcta cggcctcacc cagggcttcg gtccactggt cctgttcgat 3120
gcagattccg aactggaaca gggcggctct ctcatctccc atctgggcac cggccagggt 3180
gcaccgcttg caccggaagt gtcccgcctg attctgtggc tccgcatcca aaacatgcgc 3240
aagggctatt cggctgtcag tcctgtgttc tggcaaaaac tggccgacct ctggaacaag 3300
ggcttcaccc ctgctatccc tcgccacggc accgtgtccg ccagcggcga tctccagcct 3360
ctggcacacg ctgccctggc ttttaccggc gtgggcgagg catggacccg tgatgcagac 3420
ggccgttggt ccaccgtgcc agccgtggac gcattagcag cactgggtgc agagccgttc 3480
gattggccag tgcgcgaggc tttggccttc gtgaacggta cgggcgcatc actcgcggtg 3540
gcagttctca accacagatc cgctctccgt ctcgtacgag catgtgcagt cttgtctgcc 3600
cgtttggcta ccttgctagg agctaatcct gaacactacg atgtcggcca cggagtcgca 3660
aggggacaag ttggccagct gaccgcggcg gaatggattc ggcagggact accacgcggc 3720
atggtccgag acggttcgcg ccctcttcaa gaaccataca gcttgcgctg tgccccccag 3780
gtccttggcg cggtgctgga ccagctggat ggtgcaggcg atgttctggc ccgcgaagtg 3840
gatggctgcc aggacaatcc tatcacctac gagggcgaac tgctgcacgg cggtaacttc 3900
cacgctatgc cagtcggctt cgcatccgac cagatcggtc tggcgatgca catggcagct 3960
tatctggctg aacgccagct cggcctgctg gtgagcccgg tgaccaacgg cgacctgcca 4020
ccaatgctga ccccacgcgc tggacgcggt gccggcctgg cgggcgttca gatctccgca 4080
acctccttcg tctctcgcat ccgccagctg gtgttcccag ctagcctcac caccctccca 4140
accaacggct ggaaccagga ccatgtccca atggctctga acggcgcaaa cagcgtgttc 4200
gaagctcttg aactgggttg gctgaccgtg ggtagcctgg cagtcggcgt ggcccagctc 4260
gctgcaatga ccggccacgc agctgagggc gtgtgggccg agttggcagg catctgccca 4320
ccactggatg ctgaccgccc actgggcgcg gaggtccgcg ctgctcgcga tctcctctcc 4380
gcacacgctg accagctgct cgttgacgag gctgatggca aagacttcgg ctaa 4434

<210> SEQ ID NO 51
<211> LENGTH: 11572
<212> TYPE: DNA
<213> ORGANISM: Artificial Sequence
<220> FEATURE:
<223> OTHER INFORMATION: plasmid RpBAS-Pp4CL-RcTAL-pECXK (pECXK_P)

<400> SEQUENCE: 51
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360

-continued

```
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gtcaccatcg ctccttcccc agccaatcgt gtccgaatcc   1500
accggtgaat ccgtgatgaa gatgtccctc cagtccgaag tgcgcgaagc atccctggca   1560
accggtgaaa accctgaacc attcctgctg gaaaccgatg ctgaatccca gatcatggaa   1620
cctgtgcacg ctgaagttca cgatttcatc taccgttcta agctgcctga tatcgatatc   1680
ccaaaccaca tgcctctggc tgattactgc ctggagaagt cctcccagtg gcctgataag   1740
gtgtgcctga tcgatggtgt gaccggtcgc gaacaccgct acggcgaaat tgagctgtcc   1800
tcccgccgcg tggcagcagg ccttgataag atcggcgtga agcagggcga tgtcatcgca   1860
ctgctcttgc ctaactgcgc tgagttcgtc ctggtgttcc tgggcgcagc gaagcgcggc   1920
gccgttgtca ccaccgctaa cccattctac accgccgccg agttggagaa gcaaatcgag   1980
gcctccggtg cgggcattgt tatcactcag agcagctaca tcgagaagct cgcaggcctt   2040
aacgtccaga tcatcaccgt tgatcagcac gtggctaatt gcatgcacat ctccgtgctg   2100
ctgaacgcat gcgaagatga atgccctcag gtgcgtatcc accctgacga tctggtctgc   2160
ctgccatact cctccggcac caccggcttg ccaaagggcg tgatgctgac ccacaagtcc   2220
cttgtgtcat ccgtgtccca acaggtggac ggcgaagcac caaacttcaa catcactgtc   2280
gaggacaccc tgatgtgcgt gctgcccatg ttccacatct attccctcaa ctccatcctg   2340
ctgtgcggcc tccgtgtggg cgccaccctc gttattatgc cgaagttcga actgccaaag   2400
ctgttggacc tgatccagcg tcacaaggtg accatgggcc cattcgtgcc gccaatcgtc   2460
ctggccatcg caaagaaccc aatcgtcgag aattacgatc tctcctccat gcgcatggtt   2520
atgtccggcg ctgcacctct gggtcgggag ctggaggacg ctttccgtgc ccgcttgcca   2580
aacgccgttc tgggccaggg ctacgggatg actgaagccg gcccagtcct ggctatgtgc   2640
ctcgcattcg caaagacccc attctccgtg aagccaggct cctgcggcac cgtggtgcgc   2700
aacgctgaag tgaaaatcgt cgataccgaa accggcatgt ccctgccata caaccagcca   2760
```

ggcgagatct gcatccgcgg cccacagatc atgaagggct acctgaagaa cccagaagct 2820
accgctaaca ccatcgataa ggatggcttc ctgcacaccg gcgatgtcgc attcatcgat 2880
gaggatgagg agatgttcat cgttgatcgc gtcaaggaga tcatcaagtt caagggcttc 2940
caggtgcctc ctgcggagct ggaagctctc ctgctgtccc acaaggagat ccaggacgct 3000
gctgtcgtgt cccgtaagga tgacgtggcg ggcgaagttc cagtggcatt cgtggtccgc 3060
gctaccagct ccaccatcac cgaggatgaa gtcaaggatt acatcgcaaa gcaggtcgtt 3120
ttctacaaga agatccacaa cgtatacttc gtggattccg tgccaaagtc tccatccggc 3180
aagatcctgc gtaaggatct ccgtaacaag gtgtaaggat ctaggaggat aaagaaatga 3240
ccctgcaatc ccagactgca aaggactgcc tggcgctgga tggtgcactg acactggttc 3300
agtgcgaagc aattgccact caccgctcac ggatctccgt cacaccagca ttgcgggaac 3360
gctgcgcccg cgcgcacgca cgtctggagc acgctatcgc agaacagcgt cacatctatg 3420
gtatcaccac cggcttcgga ccactggcta atcgcctgat cggtgcagat cagggcgccg 3480
aactccagca gaacctcatc taccaccttg ctactggcgt gggcccaaaa ctctcctggg 3540
ctgaagcacg tgcactcatg ctggctcgtc tcaactccat ccttcagggc gcatctggtg 3600
catcaccaga aaccatcgac cgtatcgttg ccgttctgaa cgctggcttc gccccagaag 3660
tcccagctca gggcaccgtt ggtgcatctg gcgatctgac ccccactggct cacatggtgc 3720
tggcgcttca gggtcgaggt cgtatgatcg atccatccgg ccgtgttcag gaagccggcg 3780
cagtgatgga tcgcctgtgc ggtggcccac tgaccttggc agcccgtgac ggtctggctc 3840
tggtcaacgg tacttccgct atgaccgcaa tcgctgcttt gaccggtgtg gaggctgcgc 3900
gcgcaatcga cgccgcattg cgccactccg ctgtgctcat ggaggttctc tccggccacg 3960
ctgaggcttg gcaccctgca tttgctgaac tccgcccaca cccaggccag ctgcgcgcaa 4020
ccgaacgtct ggcccaggct ctcgatggcg ccggtcgcgt ttgccgcacc ttgaccgcgg 4080
cccgtcgcct gaccgcagct gatctgcgcc ctgaggatca cccagcccag gacgcctact 4140
ccctgcgcgt ggtgccacag ctggttggcg ctgtctggga caccctcgat tggcacgatc 4200
gcgtcgtgac ctgcgaactc aactctgtga ccgacaaccc aatcttcccg gaaggctgcg 4260
ctgttccagc actgcacggc ggcaacttca tgggcgtgca cgtcgcactg gcgtcggacg 4320
ccctgaacgc tgcattggtt accctggcag gtctggtgga gcgccagatc gcacgcctta 4380
ctgatgagaa gctgaacaag ggacttccgg cattccttca cggtggtcag gctggccttc 4440
agtccggctt catgggcgcg caggtcaccg caaccgcgct ccttgctgaa atgcgcgcaa 4500
acgcaacccc ggtgtctgtt cagtcactgt ctaccaacgg cgctaaccag gatgttgtca 4560
gcatgggcac catcgctgca cgccgcgctc gcgcacagct gctcccactg tcccagattc 4620
aggcaatcct ggctctcgct ctcgcccagg caatggatct gctggatgat ccagagggcc 4680
aggctggctg gtcccttacc gcacgcgacc tgcgcgatcg catccgcgct gtctcgccgg 4740
gcctgcgcgc agatcgccca ctggccggcc acatcgaggc agtcgctcag ggtctgcgcc 4800
acccttccgc agcagctgat ccaccagcat aactctagag tcgacctgca ggcatgcaag 4860
cttggctgtt ttggcggatg agagaagatt ttcagcctga tacagattaa atcagaacgc 4920
agaagcggtc tgataaaaca gaatttgcct ggcggcagta gcgcggtggt cccacctgac 4980
cccatgccga actcagaagt gaaacgccgt agcgccgatg gtagtgtggg gtctccccat 5040
gcgagagtag ggaactgcca ggcatcaaat aaaacgaaag gctcagtcga aagactgggc 5100

-continued

```
ctttcgtttt atctgttgtt tgtcggtgaa cgctctcctg agtaggacaa atccgccggg   5160
agcggatttg aacgttgcga agcaacggcc cggagggtgg cgggcaggac gcccgccata   5220
aactgccagg catcaaatta agcagaaggc catcctgacg gatggccttt ttgcgtttct   5280
acaaactctt tttgtttatt tttctaaata cattcaaata tgtatccgct catgaattaa   5340
ttccgctaga tgacgtgcgg cttcgacctc ctgggcgtgg cgcttgttgg cgcgctcgcg   5400
gctggctgcg gcacgacacg cgtctgagca gtattttgcg cgccgtcctc gtgggtcagg   5460
ccggggtggg atcaggccac cgcagtaggc gcagctgatg cgatcctcca ctactgcgcg   5520
tcctcctggc gctgccgagc acgcagctcg tcggccagct cttcaaggtc ggccacaagc   5580
gtttctaggt cgctcgcggc acttgcccag tcgcgtgatg ctggcgcgtc tgtcgtatcg   5640
agggcgcgga aaaatccgat caccgttttt aaatcgacgg cggcatcgag tgcgtcggac   5700
tccagcgcga catcggagag atccaccgct gatgcttcag gccagttttg gtacttcgtc   5760
gtgaaggtca tgacaccatt ataacgaacg ttcgttaaaa attctagccc caattctgat   5820
aatttcttcc ggcactcctg cgaaaacctg cgagacttct tgcccagaaa aaacgccaag   5880
cgcagcggtt accgcacttt ttttccaggt gatttcaccc tgaccagcga agcggcactt   5940
tagtgcatga ggtgtgcccc tggtttcccc tctttggagg gttcaaccca aaaaagcaca   6000
caagcaaaaa tgaaaatcat catgagcaag ttggtgcgaa gcagcaacgc gctagctcca   6060
aaaaggtctc caggatctcg aggagatttt tgagggggag ggagtcgagg aagagccaga   6120
gcagaaggcg gggaaccgtt ctctgccgac agcgtgagcc ccccttaaaa atcaggccgg   6180
ggaggaaccg gggagggatc agagctagga gcgagacacc ctaaaggggg ggaaccgttt   6240
tctgctgacg gtgtttcgtt tattagtttt cagcccgtgg atagcggagg gtgagggcaa   6300
gtgagagcca gagcaaggac gggacccccta aagggggaa ccgttttctg ctgacggtgt   6360
ttcgtttatt agttttcagc ccgtggacgg ccgcgtttag cttccattcc aagtgccttt   6420
ctgacttgtt ggatgcgcct ttcactgaca cctagttcgc ctgcaagctc acgagtcgag   6480
ggatcagcaa ccgattgaga acgggcatcc aggatcgcag ttttgacgcg aagttcgagc   6540
aactcgcctg tcatttctcg gcgtttgttt gcttccgcta atcgctgtcg cgtctcctgc   6600
gcatacttac tttctgggtc agcccatctg cgtgcattcg atgtagctgc gccccgtcgc   6660
cccatcgtcg ctagagcttt ccgccctcgg ctgctctgcg tttccacccg acgagcaggg   6720
acgactggct ggcctttagc cacgtagccg cgcacacgac gcgccatcgt caggcgatca   6780
cgcatggcgg gaagatccgg ctcccggccg tctgcaccga ccgcctgggc aacgttgtac   6840
gccacttcat acgcgtcgat gatcttggca tcttttaggc gctcaccagc agctttgagc   6900
tggtatccca cggtcaacgc gtggcgaaac gcggtctcgt cgcgcgctcg ctctggattt   6960
gtccagagca ctcgcacgcc gtcgatcagg tcgccggacg cgtccagggc gctcggcagg   7020
ctcgcgtcca aaatcgctag cgccttggct tctgcggtgg cgcgttgtgc cgcttcaatg   7080
cgggcgcgtc cgctggaaaa gtcctgctca atgtactttt tcggcttctg tgatccggtc   7140
atcgttcgag caatctccat taggtcggcc agccgatcca cacgatcatg ctggcagtgc   7200
catttatagg ctgtcggatc gtctgagacg tgcagcggcc accggctcag cctatgcgaa   7260
aaagcctggt cagcgccgaa aacacgagtc atttcttccg tcgttgcagc cagcaggcgc   7320
atatttgggc tggttttacc tgctgcggca tacaccgggt caatgagcca gatgagctgg   7380
catttcccgc tcagcggatt cacgccgatc caagccggcg ctttttctag gcgtgcccat   7440
ttctctaaaa tcgcgtagac ctgcgggttt acgtgctcaa tcttcccgcc ggcctggtgg   7500
```

ctgggcacat cgatgtcaag cacgatcacc gcggcatgtt gcgcgtgcgt cagcgcaacg 7560
tactggcacc gcgtcagcgc ttttgagcca gcccggtaga gctttggttg ggtttcgccg 7620
gtatccgggt ttttaatcca ggcgctcgcg aaatctcttg tcttgctgcc ctggaagctt 7680
tcgcgtccca ggtgagcgag cagttcgcgg cgatcttctg ccgtccagcc gcgtgagccg 7740
cagcgcatag cttcggggtg ggtgtcgaac agatcggcgg acaatttcca cgcgctagct 7800
gtgactgtgt cctgcggatc ggctagagtc atgtcttgag tgctttctcc cagctgatga 7860
ctgggggtta gccgacgccc tgtgagttcc cgctcacggg gcgttcaact ttttcaggta 7920
tttgtgcagc ttatcgtgtt ttcttcgtaa atgaacgctt aactaccttg ttaaacgtgg 7980
caaataggca ggattgatgg ggatctagct tcacgctgcc gcaagcactc agggcgcaag 8040
ggctgctaaa ggaagcggaa cacgtagaaa gccagtccgc agaaacggtg ctgaccccgg 8100
atgaatgtca gctactgggc tatctggaca agggaaaacg caagcgcaaa gagaaagcag 8160
gtagcttgca gtgggcttac atggcgatag ctagactggg cggttttatg gacagcaagc 8220
gaaccggaat tgccagctgg ggcgccctct ggtaaggttg ggaagccctg caaagtaaac 8280
tggatggctt tcttgccgcc aaggatctga tggcgcaggg gatcaagatc tgatcaagag 8340
acaggatgag gatcgtttcg catgattgaa caagatggat tgcacgcagg ttctccggcc 8400
gcttgggtgg agaggctatt cggctatgac tgggcacaac agacaatcgg ctgctctgat 8460
gccgccgtgt tccggctgtc agcgcagggg cgcccggttc tttttgtcaa gaccgacctg 8520
tccggtgccc tgaatgaact ccaagacgag gcagcgcggc tatcgtggct ggccacgacg 8580
ggcgttcctt gcgcagctgt gctcgacgtt gtcactgaag cgggaaggga ctggctgcta 8640
ttgggcgaag tgccggggca ggatctcctg tcatctcacc ttgctcctgc cgagaaagta 8700
tccatcatgg ctgatgcaat gcggcggctg catacgcttg atccggctac ctgcccattc 8760
gaccaccaag cgaaacatcg catcgagcga gcacgtactc ggatggaagc cggtcttgtc 8820
gatcaggatg atctggacga agagcatcag gggctcgcgc cagccgaact gttcgccagg 8880
ctcaaggcgc ggatgcccga cggcgaggat ctcgtcgtga cccatggcga tgcctgcttg 8940
ccgaatatca tggtggaaaa tggccgcttt tctggattca tcgactgtgg ccggctgggt 9000
gtggcggacc gctatcagga catagcgttg gctacccgtg atattgctga agagcttggc 9060
ggcgaatggg ctgaccgctt cctcgtgctt tacggtatcg ccgctcccga ttcgcagcgc 9120
atcgccttct atcgccttct tgacgagttc ttctgagcgg gactctgggg ttcgcggaat 9180
catgaccaaa atcccttaac gtgagttttc gttccactga gcgtcagacc ccgtagaaaa 9240
gatcaaagga tcttcttgag atcctttttt tctgcgcgta atctgctgct tgcaaacaaa 9300
aaaaccaccg ctaccagcgg tggtttgttt gccggatcaa gagctaccaa ctctttttcc 9360
gaaggtaact ggcttcagca gagcgcagat accaaatact gtccttctag tgtagccgta 9420
gttaggccac cacttcaaga actctgtagc accgcctaca tacctcgctc tgctaatcct 9480
gttaccagtg gctgctgcca gtggcgataa gtcgtgtctt accgggttgg actcaagacg 9540
atagttaccg gataaggcgc agcggtcggg ctgaacgggg ggttcgtgca cacagcccag 9600
cttggagcga acgacctaca ccgaactgag atacctacag cgtgagctat gagaaagcgc 9660
cacgcttccc gaagggagaa aggcggacag gtatccggta agcggcaggg tcggaacagg 9720
agagcgcacg agggagcttc cagggggaaa cgcctggtat ctttatagtc ctgtcgggtt 9780
tcgccacctc tgacttgagc gtcgattttt gtgatgctcg tcaggggggc ggagcctatg 9840

-continued gaaaaacgcc agcaacgcgg cctttttacg gttcctggcc ttttgctggc cttttgctca 9900
catgttcttt cctgcgttat cccctgattc tgtggataac cgtattaccg cctttgagtg 9960
agctgatacc gctcgccgca gccgaacgac cgagcgcagc gagtcagtga gcgaggaagc 10020
ggaagagcgc ctgatgcggt attttctcct tacgcatctg tgcggtattt cacaccgcat 10080
atggtgcact ctcagtacaa tctgctctga tgccgcatag ttaagccagt atacactccg 10140
ctatcgctac gtgactgggt catggctgcg ccccgacacc cgccaacacc cgctgacgcg 10200
ccctgacggg cttgtctgct cccggcatcc gcttacagac aagctgtgac cgtctccggg 10260
agctgcatgt gtcagaggtt ttcaccgtca tcaccgaaac gcgcgaggca gcagatcaat 10320
tcgcgcgcga aggcgaagcg gcatgcattt acgttgacac catcgaatgg tgcaaaacct 10380
ttcgcggtat ggcatgatag cgcccggaag agagtcaatt cagggtggtg aatgtgaaac 10440
cagtaacgtt atacgatgtc gcagagtatg ccggtgtctc ttatcagacc gtttcccgcg 10500
tggtgaacca ggccagccac gtttctgcga aaacgcggga aaaagtggaa gcggcgatgg 10560
cggagctgaa ttacattccc aaccgcgtgg cacaacaact ggcgggcaaa cagtcgttgc 10620
tgattggcgt tgccacctcc agtctggccc tgcacgcgcc gtcgcaaatt gtcgcggcga 10680
ttaaatctcg cgccgatcaa ctgggtgcca gcgtggtggt gtcgatggta gaacgaagcg 10740
gcgtcgaagc ctgtaaagcg gcggtgcaca atcttctcgc gcaacgcgtc agtgggctga 10800
tcattaacta tccgctggat gaccaggatg ccattgctgt ggaagctgcc tgcactaatg 10860
ttccggcgtt atttcttgat gtctctgacc agacacccat caacagtatt attttctccc 10920
atgaagacgg tacgcgactg ggcgtggagc atctggtcgc attgggtcac cagcaaatcg 10980
cgctgttagc gggcccatta agttctgtct cggcgcgtct gcgtctggct ggctggcata 11040
aatatctcac tcgcaatcaa attcagccga tagcggaacg ggaaggcgac tggagtgcca 11100
tgtccggttt tcaacaaacc atgcaaatgc tgaatgaggg catcgttccc actgcgatgc 11160
tggttgccaa cgatcagatg gcgctgggcg caatgcgcgc cattaccgag tccgggctgc 11220
gcgttggtgc ggatatctcg gtagtgggat acgacgatac cgaagacagc tcatgttata 11280
tcccgccgtc aaccaccatc aaacaggatt ttcgcctgct ggggcaaacc agcgtggacc 11340
gcttgctgca actctctcag ggccaggcgg tgaagggcaa tcagctgttg cccgtctcac 11400
tggtgaaaag aaaaaccacc ctggcgccca atacgcaaac cgcctctccc cgcgcgttgg 11460
ccgattcatt aatgcagctg gcacgacagg tttcccgact ggaaagcggg cagtgagcgc 11520
aacgcaatta atgtgagtta gcgcgaattg atctggtttg acagcttatc at 11572

<210> SEQ ID NO 52
<211> LENGTH: 4569
<212> TYPE: DNA
<213> ORGANISM: Artificial Sequence
<220> FEATURE:
<223> OTHER INFORMATION: operon RpBAS-Pp4CL-RcTAL

<400> SEQUENCE: 52
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300
gcgtcgcaga actgggcaag gaagctgctc tgaaggctat caaggaatgg ggccagccaa 360

```
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtc   1200
accatcgctc cttccccagc caatcgtgtc cgaatccacc ggtgaatccg tgatgaagat   1260
gtccctccag tccgaagtgc gcgaagcatc cctggcaacc ggtgaaaacc ctgaaccatt   1320
cctgctggaa accgatgctg aatcccagat catggaacct gtgcacgctg aagttcacga   1380
tttcatctac cgttctaagc tgcctgatat cgatatccca aaccacatgc ctctggctga   1440
ttactgcctg gagaagtcct cccagtggcc tgataaggtg tgcctgatcg atggtgtgac   1500
cggtcgcgaa caccgctacg gcgaaattga gctgtcctcc cgccgcgtgg cagcaggcct   1560
tgataagatc ggcgtgaagc agggcgatgt catcgcactg ctcttgccta actgcgctga   1620
gttcgtcctg gtgttcctgg gcgcagcgaa gcgcggcgcc gttgtcacca ccgctaaccc   1680
attctacacc gccgccgagt tggagaagca aatcgaggcc tccggtgcgg gcattgttat   1740
cactcagagc agctacatcg agaagctcgc aggccttaac gtccagatca tcaccgttga   1800
tcagcacgtg gctaattgca tgcacatctc cgtgctgctg aacgcatgcg aagatgaatg   1860
ccctcaggtg cgtatccacc ctgacgatct ggtctgcctg ccatactcct ccggcaccac   1920
cggcttgcca aagggcgtga tgctgaccca caagtccctt gtgtcatccg tgtcccaaca   1980
ggtggacggc gaagcaccaa acttcaacat cactgtcgag gacaccctga tgtgcgtgct   2040
gcccatgttc cacatctatt ccctcaactc catcctgctg tgcggcctcc gtgtgggcgc   2100
caccctcgtt attatgccga agttcgaact gccaaagctg ttggacctga tccagcgtca   2160
caaggtgacc atgggcccat tcgtgccgcc aatcgtcctg gccatcgcaa agaacccaat   2220
cgtcgagaat tacgatctct cctccatgcg catggttatg tccggcgctg cacctctggg   2280
tcgggagctg gaggacgctt tccgtgcccg cttgccaaac gccgttctgg gccagggcta   2340
cgggatgact gaagccggcc cagtcctggc tatgtgcctc gcattcgcaa agaccccatt   2400
ctccgtgaag ccaggctcct gcggcaccgt ggtgcgcaac gctgaagtga aaatcgtcga   2460
taccgaaacc ggcatgtccc tgccatacaa ccagccaggc gagatctgca tccgcggccc   2520
acagatcatg aagggctacc tgaagaaccc agaagctacc gctaacacca tcgataagga   2580
tggcttcctg cacaccggcg atgtcgcatt catcgatgag gatgaggaga tgttcatcgt   2640
tgatcgcgtc aaggagatca tcaagttcaa gggcttccag gtgcctcctg cggagctgga   2700
```

agctctcctg ctgtcccaca aggagatcca ggacgctgct gtcgtgtccc gtaaggatga 2760
cgtggcgggc gaagttccag tggcattcgt ggtccgcgct accagctcca ccatcaccga 2820
ggatgaagtc aaggattaca tcgcaaagca ggtcgttttc tacaagaaga tccacaacgt 2880
atacttcgtg gattccgtgc caaagtctcc atccggcaag atcctgcgta aggatctccg 2940
taacaaggtg taaggatcta ggaggataaa gaaatgaccc tgcaatccca gactgcaaag 3000
gactgcctgg cgctggatgg tgcactgaca ctggttcagt gcgaagcaat tgccactcac 3060
cgctcacgga tctccgtcac accagcattg cgggaacgct gcgcccgcgc gcacgcacgt 3120
ctggagcacg ctatcgcaga acagcgtcac atctatggta tcaccaccgg cttcggacca 3180
ctggctaatc gcctgatcgg tgcagatcag ggcgccgaac tccagcagaa cctcatctac 3240
caccttgcta ctggcgtggg cccaaaactc tcctgggctg aagcacgtgc actcatgctg 3300
gctcgtctca actccatcct tcagggcgca tctggtgcat caccagaaac catcgaccgt 3360
atcgttgccg ttctgaacgc tggcttcgcc ccagaagtcc cagctcaggg caccgttggt 3420
gcatctggcg atctgacccc actggctcac atggtgctgg cgcttcaggg tcgaggtcgt 3480
atgatcgatc catccggccg tgttcaggaa gccggcgcag tgatggatcg cctgtgcggt 3540
ggcccactga ccttggcagc ccgtgacggt ctggctctgg tcaacggtac ttccgctatg 3600
accgcaatcg ctgctttgac cggtgtggag gctgcgcgcg caatcgacgc cgcattgcgc 3660
cactccgctg tgctcatgga ggttctctcc ggccacgctg aggcttggca ccctgcattt 3720
gctgaactcc gcccacaccc aggccagctg cgcgcaaccg aacgtctggc ccaggctctc 3780
gatggcgccg gtcgcgtttg ccgcaccttg accgcggccc gtcgcctgac cgcagctgat 3840
ctgcgccctg aggatcaccc agcccaggac gcctactccc tgcgcgtggt gccacagctg 3900
gttggcgctg tctgggacac cctcgattgg cacgatcgcg tcgtgacctg cgaactcaac 3960
tctgtgaccg acaacccaat cttcccggaa ggctgcgctg ttccagcact gcacggcggc 4020
aacttcatgg gcgtgcacgt cgcactggcg tcggacgccc tgaacgctgc attggttacc 4080
ctggcaggtc tggtggagcg ccagatcgca cgccttactg atgagaagct gaacaaggga 4140
cttccggcat tccttcacgg tggtcaggct ggccttcagt ccggcttcat gggcgcgcag 4200
gtcaccgcaa ccgcgctcct tgctgaaatg cgcgcaaacg caaccccggt gtctgttcag 4260
tcactgtcta ccaacggcgc taaccaggat gttgtcagca tgggcaccat cgctgcacgc 4320
cgcgctcgcg cacagctgct cccactgtcc cagattcagg caatcctggc tctcgctctc 4380
gcccaggcaa tggatctgct ggatgatcca gagggccagg ctggctggtc ccttaccgca 4440
cgcgacctgc gcgatcgcat ccgcgctgtc tcgccgggcc tgcgcgcaga tcgcccactg 4500
gccggccaca tcgaggcagt cgctcagggt ctgcgccacc cttccgcagc agctgatcca 4560
ccagcataa 4569

<210> SEQ ID NO 53
<211> LENGTH: 11497
<212> TYPE: DNA
<213> ORGANISM: Artificial Sequence
<220> FEATURE:
<223> OTHER INFORMATION: plasmid RpBAS-Pp4CL-FjTAL-pECXK (pECXK_Q)

<400> SEQUENCE: 53
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180

-continued

```
aattaatcat ccggctcgta taatgtgtgg aattgtgagc ggataacaat ttcacacagg    240
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gtcaccatcg ctccttcccc agccaatcgt gtccgaatcc   1500
accggtgaat ccgtgatgaa gatgtccctc cagtccgaag tgcgcgaagc atccctggca   1560
accggtgaaa accctgaacc attcctgctg gaaaccgatg ctgaatccca gatcatggaa   1620
cctgtgcacg ctgaagttca cgatttcatc taccgttcta agctgcctga tatcgatatc   1680
ccaaaccaca tgcctctggc tgattactgc ctggagaagt cctcccagtg gcctgataag   1740
gtgtgcctga tcgatggtgt gaccggtcgc gaacaccgct acggcgaaat tgagctgtcc   1800
tcccgccgcg tggcagcagg ccttgataag atcggcgtga agcagggcga tgtcatcgca   1860
ctgctcttgc ctaactgcgc tgagttcgtc ctggtgttcc tgggcgcagc gaagcgcggc   1920
gccgttgtca ccaccgctaa cccattctac accgccgccg agttggagaa gcaaatcgag   1980
gcctccggtg cgggcattgt tatcactcag agcagctaca tcgagaagct cgcaggcctt   2040
aacgtccaga tcatcaccgt tgatcagcac gtggctaatt gcatgcacat ctccgtgctg   2100
ctgaacgcat gcgaagatga atgccctcag gtgcgtatcc accctgacga tctggtctgc   2160
ctgccatact cctccggcac caccggcttg ccaaagggcg tgatgctgac ccacaagtcc   2220
cttgtgtcat ccgtgtccca acaggtggac ggcgaagcac caaacttcaa catcactgtc   2280
gaggacaccc tgatgtgcgt gctgcccatg ttccacatct attccctcaa ctccatcctg   2340
ctgtgcggcc tccgtgtggg cgccaccctc gttattatgc cgaagttcga actgccaaag   2400
ctgttggacc tgatccagcg tcacaaggtg accatgggcc cattcgtgcc gccaatcgtc   2460
ctggccatcg caaagaaccc aatcgtcgag aattacgatc tctcctccat gcgcatggtt   2520
```

atgtccggcg ctgcacctct gggtcgggag ctggaggacg ctttccgtgc ccgcttgcca 2580
aacgccgttc tgggccaggg ctacgggatg actgaagccg gcccagtcct ggctatgtgc 2640
ctcgcattcg caaagacccc attctccgtg aagccaggct cctgcggcac cgtggtgcgc 2700
aacgctgaag tgaaaatcgt cgataccgaa accggcatgt ccctgccata caaccagcca 2760
ggcgagatct gcatccgcgg cccacagatc atgaagggct acctgaagaa cccagaagct 2820
accgctaaca ccatcgataa ggatggcttc ctgcacaccg gcgatgtcgc attcatcgat 2880
gaggatgagg agatgttcat cgttgatcgc gtcaaggaga tcatcaagtt caagggcttc 2940
caggtgcctc ctgcggagct ggaagctctc ctgctgtccc acaaggagat ccaggacgct 3000
gctgtcgtgt cccgtaagga tgacgtggcg ggcgaagttc cagtggcatt cgtggtccgc 3060
gctaccagct ccaccatcac cgaggatgaa gtcaaggatt acatcgcaaa gcaggtcgtt 3120
ttctacaaga agatccacaa cgtatacttc gtggattccg tgccaaagtc tccatccggc 3180
aagatcctgc gtaaggatct ccgtaacaag gtgtaaggat ctaggaggat aaagaaatga 3240
acaccatcaa cgaatacctg tccctggaag agttcgaagc gatcatcttc ggtaaccaga 3300
aggttaccat ctccgatgtg gttgtgaacc gtgttaacga gtccttcaac ttcctcaagg 3360
agttctccgg caacaaggtc atctacggtg tgaacaccgg cttcggccca atggcacaat 3420
accgtattaa ggaatccgat cagatccagc ttcagtacaa tctgatccgt tcccactctt 3480
cgggcaccgg aaaaccactc tccccagttt gtgctaaggc agcaatcttg gctcgcctga 3540
acaccctgtc cctcggtaac tccggcgtgc atccatctgt catcaacctg atgtcggaac 3600
tgatcaacaa agacattacc ccactcatct tcgagcacgg tggcgtcgga gcatccggtg 3660
acctggttca gctttctcac ctggctttgg ttctcatcgg cgaaggcgaa gtgttctaca 3720
agggtgaacg ccgcccaact ccagaagttt tcgaaattga gggcttgaag ccaatccagg 3780
ttgagatccg tgagggcctc gccttgatta acggtactag cgtgatgacc ggtattggag 3840
tggtcaacgt gtaccacgca aagaagctgc tggactggtc cctgaagtcc tcctgcgcca 3900
tcaatgaact tgttcaggct tacgatgatc acttcagcgc agagctgaac cagacgaagc 3960
gccacaaggg ccagcaggaa atcgctctga agatgcgtca gaacctctct gacagcaccc 4020
tgatccgcaa gcgcgaggac cacctgtatt ccggcgaaaa caccgaggag attttcaagg 4080
agaaggtgca ggagtactac tccctgcgct gcgttccaca gattctcggc ccggtcctcg 4140
aaactatcaa taacgtcgcc tccatcctgg aagatgagtt caactccgct aacgataacc 4200
caatcatcga cgtgaagaac cagcacgtgt accatggcgg caacttccac ggtgactaca 4260
tctctctgga aatggacaag ttgaaaatcg ttatcaccaa actgaccatg cttgcagaac 4320
gccagcttaa ctatcttctc aactccaaga tcaacgaact tctgccacca ttcgtgaacc 4380
tcggcaccct gggtttcaac ttcggcatgc agggcgttca gttcaccgcg acctccacca 4440
ccgcagaatc tcagatgctg tccaacccta tgtacgttca ctccattcca aacaacaacg 4500
ataaccagga catcgtctcc atgggcacca actccgcagt gatcacgtcc aaggttatcg 4560
agaacgcttt cgaagtcctg gctatcgaaa tgatcaccat cgttcaggcc atcgattacc 4620
tcggccagaa ggataagatc tcctccgttt ccaagaagtg gtacgatgaa atccgcaaca 4680
ttatccctac cttcaaggag gatcaggtta tgtacccatt cgtgcagaag gttaaggatc 4740
acctcatcaa caactaactc tagagtcgac ctgcaggcat gcaagcttgg ctgttttggc 4800
ggatgagaga agattttcag cctgatacag attaaatcag aacgcagaag cggtctgata 4860
aaacagaatt tgcctggcgg cagtagcgcg gtggtcccac ctgaccccat gccgaactca 4920
gaagtgaaac gccgtagcgc cgatggtagt gtggggtctc cccatgcgag agtagggaac 4980
tgccaggcat caaataaaac gaaaggctca gtcgaaagac tgggcctttc gttttatctg 5040
ttgtttgtcg gtgaacgctc tcctgagtag gacaaatccg ccgggagcgg atttgaacgt 5100
tgcgaagcaa cggcccggag ggtggcgggc aggacgcccg ccataaactg ccaggcatca 5160
aattaagcag aaggccatcc tgacggatgg cctttttgcg tttctacaaa ctctttttgt 5220
ttatttttct aaatacattc aaatatgtat ccgctcatga attaattccg ctagatgacg 5280
tgcggcttcg acctcctggg cgtggcgctt gttggcgcgc tcgcggctgg ctgcggcacg 5340
acacgcgtct gagcagtatt ttgcgcgccg tcctcgtggg tcaggccggg gtgggatcag 5400
gccaccgcag taggcgcagc tgatgcgatc ctccactact gcgcgtcctc ctggcgctgc 5460
cgagcacgca gctcgtcggc cagctcttca aggtcggcca caagcgtttc taggtcgctc 5520
gcggcacttg cccagtcgcg tgatgctggc gcgtctgtcg tatcgagggc gcggaaaaat 5580
ccgatcaccg tttttaaatc gacggcggca tcgagtgcgt cggactccag cgcgacatcg 5640
gagagatcca ccgctgatgc ttcaggccag ttttggtact tcgtcgtgaa ggtcatgaca 5700
ccattataac gaacgttcgt taaaaattct agccccaatt ctgataattt cttccggcac 5760
tcctgcgaaa acctgcgaga cttcttgccc agaaaaaacg ccaagcgcag cggttaccgc 5820
actttttttc caggtgattt caccctgacc agcgaagcgg cactttagtg catgaggtgt 5880
gcccctggtt tcccctcttt ggagggttca acccaaaaaa gcacacaagc aaaaatgaaa 5940
atcatcatga gcaagttggt gcgaagcagc aacgcgctag ctccaaaaag gtctccagga 6000
tctcgaggag atttttgagg gggagggagt cgaggaagag ccagagcaga aggcggggaa 6060
ccgttctctg ccgacagcgt gagcccccct taaaaatcag gccggggagg aaccggggag 6120
ggatcagagc taggagcgag acaccctaaa ggggggggaac cgttttctgc tgacggtgtt 6180
tcgtttatta gttttcagcc cgtggatagc ggagggtgag ggcaagtgag agccagagca 6240
aggacgggac ccctaaaggg gggaaccgtt ttctgctgac ggtgtttcgt ttattagttt 6300
tcagcccgtg gacggccgcg tttagcttcc attccaagtg cctttctgac ttgttggatg 6360
cgcctttcac tgacacctag ttcgcctgca agctcacgag tcgagggatc agcaaccgat 6420
tgagaacggg catccaggat cgcagttttg acgcgaagtt cgagcaactc gcctgtcatt 6480
tctcggcgtt tgtttgcttc cgctaatcgc tgtcgcgtct cctgcgcata cttactttct 6540
gggtcagccc atctgcgtgc attcgatgta gctgcgcccc gtcgccccat cgtcgctaga 6600
gctttccgcc ctcggctgct ctgcgtttcc acccgacgag cagggacgac tggctggcct 6660
ttagccacgt agccgcgcac acgacgcgcc atcgtcaggc gatcacgcat ggcgggaaga 6720
tccggctccc ggccgtctgc accgaccgcc tgggcaacgt tgtacgccac ttcatacgcg 6780
tcgatgatct tggcatcttt taggcgctca ccagcagctt tgagctggta tcccacggtc 6840
aacgcgtggc gaaacgcggt ctcgtcgcgc gctcgctctg gatttgtcca gagcactcgc 6900
acgccgtcga tcaggtcgcc ggacgcgtcc agggcgctcg gcaggctcgc gtccaaaatc 6960
gctagcgcct tggcttctgc ggtggcgcgt tgtgccgctt caatgcgggc gcgtccgctg 7020
gaaaagtcct gctcaatgta ctttttcggc ttctgtgatc cggtcatcgt tcgagcaatc 7080
tccattaggt cggccagccg atccacacga tcatgctggc agtgccattt ataggctgtc 7140
ggatcgtctg agacgtgcag cggccaccgg ctcagcctat gcgaaaaagc ctggtcagcg 7200
ccgaaaacac gagtcatttc ttccgtcgtt gcagccagca ggcgcatatt tgggctggtt 7260

-continued

```
ttacctgctg cggcatacac cgggtcaatg agccagatga gctggcattt cccgctcagc   7320
ggattcacgc cgatccaagc cggcgctttt tctaggcgtg cccatttctc taaaatcgcg   7380
tagacctgcg ggtttacgtg ctcaatcttc ccgccggcct ggtggctggg cacatcgatg   7440
tcaagcacga tcaccgcggc atgttgcgcg tgcgtcagcg caacgtactg gcaccgcgtc   7500
agcgcttttg agccagcccg gtagagcttt ggttgggttt cgccggtatc cgggtttta   7560
atccaggcgc tcgcgaaatc tcttgtcttg ctgccctgga agctttcgcg tcccaggtga   7620
gcgagcagtt cgcggcgatc ttctgccgtc cagccgcgtg agccgcagcg catagcttcg   7680
gggtgggtgt cgaacagatc ggcggacaat ttccacgcgc tagctgtgac tgtgtcctgc   7740
ggatcggcta gagtcatgtc ttgagtgctt tctcccagct gatgactggg ggttagccga   7800
cgccctgtga gttcccgctc acggggcgtt caacttttc aggtatttgt gcagcttatc   7860
gtgttttctt cgtaaatgaa cgcttaacta ccttgttaaa cgtggcaaat aggcaggatt   7920
gatggggatc tagcttcacg ctgccgcaag cactcagggc gcaagggctg ctaaaggaag   7980
cggaacacgt agaaagccag tccgcagaaa cggtgctgac cccggatgaa tgtcagctac   8040
tgggctatct ggacaaggga aaacgcaagc gcaaagagaa agcaggtagc ttgcagtggg   8100
cttacatggc gatagctaga ctgggcggtt ttatggacag caagcgaacc ggaattgcca   8160
gctggggcgc cctctggtaa ggttgggaag ccctgcaaag taaactggat ggctttcttg   8220
ccgccaagga tctgatggcg caggggatca agatctgatc aagagacagg atgaggatcg   8280
tttcgcatga ttgaacaaga tggattgcac gcaggttctc cggccgcttg ggtggagagg   8340
ctattcggct atgactgggc acaacagaca atcggctgct ctgatgccgc cgtgttccgg   8400
ctgtcagcgc aggggcgccc ggttcttttt gtcaagaccg acctgtccgg tgccctgaat   8460
gaactccaag acgaggcagc gcggctatcg tggctggcca cgacgggcgt tccttgcgca   8520
gctgtgctcg acgttgtcac tgaagcggga agggactggc tgctattggg cgaagtgccg   8580
gggcaggatc tcctgtcatc tcaccttgct cctgccgaga aagtatccat catggctgat   8640
gcaatgcggc ggctgcatac gcttgatccg gctacctgcc cattcgacca ccaagcgaaa   8700
catcgcatcg agcgagcacg tactcggatg gaagccggtc ttgtcgatca ggatgatctg   8760
gacgaagagc atcaggggct cgcgccagcc gaactgttcg ccaggctcaa ggcgcggatg   8820
cccgacggcg aggatctcgt cgtgacccat ggcgatgcct gcttgccgaa tatcatggtg   8880
gaaaatggcc gcttttctgg attcatcgac tgtggccggc tgggtgtggc ggaccgctat   8940
caggacatag cgttggctac ccgtgatatt gctgaagagc ttggcggcga atgggctgac   9000
cgcttcctcg tgctttacgg tatcgccgct cccgattcgc agcgcatcgc cttctatcgc   9060
cttcttgacg agttcttctg agcgggactc tggggttcgc ggaatcatga ccaaaatccc   9120
ttaacgtgag ttttcgttcc actgagcgtc agaccccgta gaaaagatca aaggatcttc   9180
ttgagatcct ttttttctgc gcgtaatctg ctgcttgcaa acaaaaaaac caccgctacc   9240
agcggtggtt tgtttgccgg atcaagagct accaactctt tttccgaagg taactggctt   9300
cagcagagcg cagataccaa atactgtcct tctagtgtag ccgtagttag gccaccactt   9360
caagaactct gtagcaccgc ctacatacct cgctctgcta atcctgttac cagtggctgc   9420
tgccagtggc gataagtcgt gtcttaccgg gttggactca agacgatagt taccggataa   9480
ggcgcagcgg tcgggctgaa cggggggttc gtgcacacag cccagcttgg agcgaacgac   9540
ctacaccgaa ctgagatacc tacagcgtga gctatgagaa agcgccacgc ttcccgaagg   9600
gagaaaggcg gacaggtatc cggtaagcgg cagggtcgga acaggagagc gcacgaggga   9660
```

```
gcttccaggg ggaaacgcct ggtatcttta tagtcctgtc gggtttcgcc acctctgact   9720

tgagcgtcga tttttgtgat gctcgtcagg ggggcggagc ctatggaaaa acgccagcaa   9780

cgcggccttt ttacggttcc tggccttttg ctggcctttt gctcacatgt tctttcctgc   9840

gttatcccct gattctgtgg ataaccgtat taccgccttt gagtgagctg ataccgctcg   9900

ccgcagccga acgaccgagc gcagcgagtc agtgagcgag gaagcggaag agcgcctgat   9960

gcggtatttt ctccttacgc atctgtgcgg tatttcacac cgcatatggt gcactctcag  10020

tacaatctgc tctgatgccg catagttaag ccagtataca ctccgctatc gctacgtgac  10080

tgggtcatgg ctgcgccccg acacccgcca acacccgctg acgcgccctg acgggcttgt  10140

ctgctcccgg catccgctta cagacaagct gtgaccgtct ccgggagctg catgtgtcag  10200

aggttttcac cgtcatcacc gaaacgcgcg aggcagcaga tcaattcgcg cgcgaaggcg  10260

aagcggcatg catttacgtt gacaccatcg aatggtgcaa aacctttcgc ggtatggcat  10320

gatagcgccc ggaagagagt caattcaggg tggtgaatgt gaaaccagta acgttatacg  10380

atgtcgcaga gtatgccggt gtctcttatc agaccgtttc ccgcgtggtg aaccaggcca  10440

gccacgtttc tgcgaaaacg cgggaaaaag tggaagcggc gatggcggag ctgaattaca  10500

ttcccaaccg cgtggcacaa caactggcgg gcaaacagtc gttgctgatt ggcgttgcca  10560

cctccagtct ggccctgcac gcgccgtcgc aaattgtcgc ggcgattaaa tctcgcgccg  10620

atcaactggg tgccagcgtg gtggtgtcga tggtagaacg aagcggcgtc gaagcctgta  10680

aagcggcggt gcacaatctt ctcgcgcaac gcgtcagtgg gctgatcatt aactatccgc  10740

tggatgacca ggatgccatt gctgtggaag ctgcctgcac taatgttccg gcgttatttc  10800

ttgatgtctc tgaccagaca cccatcaaca gtattatttt ctcccatgaa gacggtacgc  10860

gactgggcgt ggagcatctg gtcgcattgg gtcaccagca aatcgcgctg ttagcgggcc  10920

cattaagttc tgtctcggcg cgtctgcgtc tggctggctg gcataaatat ctcactcgca  10980

atcaaattca gccgatagcg gaacgggaag gcgactggag tgccatgtcc ggttttcaac  11040

aaaccatgca aatgctgaat gagggcatcg ttcccactgc gatgctggtt gccaacgatc  11100

agatggcgct gggcgcaatg cgcgccatta ccgagtccgg gctgcgcgtt ggtgcggata  11160

tctcggtagt gggatacgac gataccgaag acagctcatg ttatatcccg ccgtcaacca  11220

ccatcaaaca ggattttcgc ctgctggggc aaaccagcgt ggaccgcttg ctgcaactct  11280

ctcagggcca ggcggtgaag ggcaatcagc tgttgcccgt ctcactggtg aaaagaaaaa  11340

ccaccctggc gcccaatacg caaaccgcct ctccccgcgc gttggccgat tcattaatgc  11400

agctggcacg acaggtttcc cgactggaaa gcgggcagtg agcgcaacgc aattaatgtg  11460

agttagcgcg aattgatctg gtttgacagc ttatcat                          11497
```

<210> SEQ ID NO 54
<211> LENGTH: 4494
<212> TYPE: DNA
<213> ORGANISM: Artificial Sequence
<220> FEATURE:
<223> OTHER INFORMATION: operon RpBAS-Pp4CL-FjTAL

<400> SEQUENCE: 54

```
ggatctagga gggagatcat atggcaaccg aggagatgaa gaagctcgca accgtgatgg     60

caatcggcac tgctaaccca ccgaactgct attaccaagc tgattttccc gacttctact    120

tccgcgtgac caactccgat catctgatca acctgaagca gaagttcaag cgcctatgcg    180
```

-continued

```
aaaactctcg catcgagaag cgctacctcc acgtcaccga ggagatcctc aaggaaaacc    240
caaacatcgc agcttacgag gctactagcc tgaacgtgcg ccacaagatg caggtcaagg    300
gcgtcgcaga actgggcaag gaagctgctc tgaaggctat caaggaatgg ggccagccaa    360
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtc   1200
accatcgctc cttccccagc caatcgtgtc cgaatccacc ggtgaatccg tgatgaagat   1260
gtccctccag tccgaagtgc gcgaagcatc cctggcaacc ggtgaaaacc ctgaaccatt   1320
cctgctggaa accgatgctg aatcccagat catggaacct gtgcacgctg aagttcacga   1380
tttcatctac cgttctaagc tgcctgatat cgatatccca aaccacatgc ctctggctga   1440
ttactgcctg gagaagtcct cccagtggcc tgataaggtg tgcctgatcg atggtgtgac   1500
cggtcgcgaa caccgctacg gcgaaattga gctgtcctcc cgccgcgtgg cagcaggcct   1560
tgataaagatc ggcgtgaagc agggcgatgt catcgcactg ctcttgccta actgcgctga   1620
gttcgtcctg gtgttcctgg gcgcagcgaa gcgcggcgcc gttgtcacca ccgctaaccc   1680
attctacacc gccgccgagt tggagaagca aatcgaggcc tccggtgcgg gcattgttat   1740
cactcagagc agctacatcg agaagctcgc aggccttaac gtccagatca tcaccgttga   1800
tcagcacgtg gctaattgca tgcacatctc cgtgctgctg aacgcatgcg aagatgaatg   1860
ccctcaggtg cgtatccacc ctgacgatct ggtctgcctg ccatactcct ccggcaccac   1920
cggcttgcca aagggcgtga tgctgaccca caagtccctt gtgtcatccg tgtcccaaca   1980
ggtggacggc gaagcaccaa acttcaacat cactgtcgag gacaccctga tgtgcgtgct   2040
gcccatgttc cacatctatt ccctcaactc catcctgctg tgcggcctcc gtgtgggcgc   2100
caccctcgtt attatgccga agttcgaact gccaaagctg ttggacctga tccagcgtca   2160
caaggtgacc atgggcccat tcgtgccgcc aatcgtcctg gccatcgcaa agaacccaat   2220
cgtcgagaat tacgatctct cctccatgcg catggttatg tccggcgctg cacctctggg   2280
tcgggagctg gaggacgctt tccgtgcccg cttgccaaac gccgttctgg gccagggcta   2340
cgggatgact gaagccggcc cagtcctggc tatgtgcctc gcattcgcaa agaccccatt   2400
ctccgtgaag ccaggctcct gcggcaccgt ggtgcgcaac gctgaagtga aaatcgtcga   2460
taccgaaacc ggcatgtccc tgccatacaa ccagccaggc gagatctgca tccgcggccc   2520
acagatcatg aagggctacc tgaagaaccc agaagctacc gctaacacca tcgataagga   2580
```

tggcttcctg cacaccggcg atgtcgcatt catcgatgag gatgaggaga tgttcatcgt 2640
tgatcgcgtc aaggagatca tcaagttcaa gggcttccag gtgcctcctg cggagctgga 2700
agctctcctg ctgtcccaca aggagatcca ggacgctgct gtcgtgtccc gtaaggatga 2760
cgtggcgggc gaagttccag tggcattcgt ggtccgcgct accagctcca ccatcaccga 2820
ggatgaagtc aaggattaca tcgcaaagca ggtcgttttc tacaagaaga tccacaacgt 2880
atacttcgtg gattccgtgc caaagtctcc atccggcaag atcctgcgta aggatctccg 2940
taacaaggtg taaggatcta ggaggataaa gaaatgaaca ccatcaacga atacctgtcc 3000
ctggaagagt tcgaagcgat catcttcggt aaccagaagg ttaccatctc cgatgtggtt 3060
gtgaaccgtg ttaacgagtc cttcaacttc ctcaaggagt tctccggcaa caaggtcatc 3120
tacggtgtga acaccggctt cggcccaatg gcacaatacc gtattaagga atccgatcag 3180
atccagcttc agtacaatct gatccgttcc cactcttcgg gcaccggaaa accactctcc 3240
ccagtttgtg ctaaggcagc aatcttggct cgcctgaaca ccctgtccct cggtaactcc 3300
ggcgtgcatc catctgtcat caacctgatg tcggaactga tcaacaaaga cattacccca 3360
ctcatcttcg agcacggtgg cgtcggagca tccggtgacc tggttcagct ttctcacctg 3420
gctttggttc tcatcggcga aggcgaagtg ttctacaagg gtgaacgccg cccaactcca 3480
gaagttttcg aaattgaggg cttgaagcca atccaggttg agatccgtga gggcctcgcc 3540
ttgattaacg gtactagcgt gatgaccggt attggagtgg tcaacgtgta ccacgcaaag 3600
aagctgctgg actggtccct gaagtcctcc tgcgccatca atgaacttgt tcaggcttac 3660
gatgatcact tcagcgcaga gctgaaccag acgaagcgcc acaagggcca gcaggaaatc 3720
gctctgaaga tgcgtcagaa cctctctgac agcaccctga tccgcaagcg cgaggaccac 3780
ctgtattccg gcgaaaacac cgaggagatt ttcaaggaga aggtgcagga gtactactcc 3840
ctgcgctgcg ttccacagat tctcggcccg gtcctcgaaa ctatcaataa cgtcgcctcc 3900
atcctggaag atgagttcaa ctccgctaac gataacccaa tcatcgacgt gaagaaccag 3960
cacgtgtacc atggcggcaa cttccacggt gactacatct ctctggaaat ggacaagttg 4020
aaaatcgtta tcaccaaact gaccatgctt gcagaacgcc agcttaacta tcttctcaac 4080
tccaagatca acgaacttct gccaccattc gtgaacctcg gcaccctggg tttcaacttc 4140
ggcatgcagg gcgttcagtt caccgcgacc tccaccaccg cagaatctca gatgctgtcc 4200
aaccctatgt acgttcactc cattccaaac aacaacgata accaggacat cgtctccatg 4260
ggcaccaact ccgcagtgat cacgtccaag gttatcgaga acgctttcga agtcctggct 4320
atcgaaatga tcaccatcgt tcaggccatc gattacctcg gccagaagga taagatctcc 4380
tccgtttcca agaagtggta cgatgaaatc cgcaacatta tccctacctt caaggaggat 4440
caggttatgt acccattcgt gcagaaggtt aaggatcacc tcatcaacaa ctaa 4494

<210> SEQ ID NO 55
<211> LENGTH: 11509
<212> TYPE: DNA
<213> ORGANISM: Artificial Sequence
<220> FEATURE:
<223> OTHER INFORMATION: plasmid RpBAS-Pp4CL-SeSam8-pECXK (pECXK_R)

<400> SEQUENCE: 55
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120

-continued

```
aatgtttttt gcgccgacat cataacggtt ctggcaaata ttctgaaatg agctgttgac    180
aattaatcat ccggctcgta taatgtgtgg aattgtgagc ggataacaat ttcacacagg    240
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gtcaccatcg ctccttcccc agccaatcgt gtccgaatcc   1500
accggtgaat ccgtgatgaa gatgtccctc cagtccgaag tgcgcgaagc atccctggca   1560
accggtgaaa accctgaacc attcctgctg gaaaccgatg ctgaatccca gatcatggaa   1620
cctgtgcacg ctgaagttca cgatttcatc taccgttcta agctgcctga tatcgatatc   1680
ccaaaccaca tgcctctggc tgattactgc ctggagaagt cctcccagtg gcctgataag   1740
gtgtgcctga tcgatggtgt gaccggtcgc gaacaccgct acggcgaaat tgagctgtcc   1800
tcccgccgcg tggcagcagg ccttgataag atcggcgtga agcagggcga tgtcatcgca   1860
ctgctcttgc ctaactgcgc tgagttcgtc ctggtgttcc tgggcgcagc gaagcgcggc   1920
gccgttgtca ccaccgctaa cccattctac accgccgccg agttggagaa gcaaatcgag   1980
gcctccggtg cgggcattgt tatcactcag agcagctaca tcgagaagct cgcaggcctt   2040
aacgtccaga tcatcaccgt tgatcagcac gtggctaatt gcatgcacat ctccgtgctg   2100
ctgaacgcat gcgaagatga atgccctcag gtgcgtatcc accctgacga tctggtctgc   2160
ctgccatact cctccggcac caccggcttg ccaaagggcg tgatgctgac ccacaagtcc   2220
cttgtgtcat ccgtgtccca acaggtggac ggcgaagcac caaacttcaa catcactgtc   2280
gaggacaccc tgatgtgcgt gctgcccatg ttccacatct attccctcaa ctccatcctg   2340
ctgtgcggcc tccgtgtggg cgccaccctc gttattatgc cgaagttcga actgccaaag   2400
ctgttggacc tgatccagcg tcacaaggtg accatgggcc cattcgtgcc gccaatcgtc   2460
ctggccatcg caaagaaccc aatcgtcgag aattacgatc tctcctccat gcgcatggtt   2520
```

atgtccggcg ctgcacctct gggtcgggag ctggaggacg ctttccgtgc ccgcttgcca 2580
aacgccgttc tgggccaggg ctacgggatg actgaagccg gcccagtcct ggctatgtgc 2640
ctcgcattcg caaagacccc attctccgtg aagccaggct cctgcggcac cgtggtgcgc 2700
aacgctgaag tgaaaatcgt cgataccgaa accggcatgt ccctgccata caaccagcca 2760
ggcgagatct gcatccgcgg cccacagatc atgaagggct acctgaagaa cccagaagct 2820
accgctaaca ccatcgataa ggatggcttc ctgcacaccg gcgatgtcgc attcatcgat 2880
gaggatgagg agatgttcat cgttgatcgc gtcaaggaga tcatcaagtt caagggcttc 2940
caggtgcctc ctgcggagct ggaagctctc ctgctgtccc acaaggagat ccaggacgct 3000
gctgtcgtgt cccgtaagga tgacgtggcg ggcgaagttc cagtggcatt cgtggtccgc 3060
gctaccagct ccaccatcac cgaggatgaa gtcaaggatt acatcgcaaa gcaggtcgtt 3120
ttctacaaga agatccacaa cgtatacttc gtggattccg tgccaaagtc tccatccggc 3180
aagatcctgc gtaaggatct ccgtaacaag gtgtaaggat ctaggaggat aaagaaatga 3240
cccaggtcgt ggagcgccag gctgatcgtc tgtccagccg cgagtacctg gcacgcgttg 3300
ttcgttccgc aggctgggac gcaggcctca ccagctgcac cgatgaagaa atcgtgcgca 3360
tgggtgcatc cgcacgcacc attgaggaat acctgaagtc tgataagccg atctacggcc 3420
tcacccaggg cttcggtcca ctggtcctgt tcgatgcaga ttccgaactg gaacagggcg 3480
gctctctcat ctcccatctg ggcaccggcc agggtgcacc gcttgcaccg gaagtgtccc 3540
gcctgattct gtggctccgc atccaaaaca tgcgcaaggg ctattcggct gtcagtcctg 3600
tgttctggca aaaactggcc gacctctgga acaagggctt caccccctgct atccctcgcc 3660
acggcaccgt gtccgccagc ggcgatctcc agcctctggc acacgctgcc ctggctttta 3720
ccggcgtggg cgaggcatgg acccgtgatg cagacggccg ttggtccacc gtgccagccg 3780
tggacgcatt agcagcactg ggtgcagagc cgttcgattg gccagtgcgc gaggctttgg 3840
ccttcgtgaa cggtacgggc gcatcactcg cggtggcagt tctcaaccac agatccgctc 3900
tccgtctcgt acgagcatgt gcagtcttgt ctgcccgttt ggctaccttg ctaggagcta 3960
atcctgaaca ctacgatgtc ggccacggag tcgcaagggg acaagttggc cagctgaccg 4020
cggcggaatg gattcggcag ggactaccac gcggcatggt ccgagacggt tcgcgccctc 4080
ttcaagaacc atacagcttg cgctgtgccc cccaggtcct tggcgcggtg ctggaccagc 4140
tggatggtgc aggcgatgtt ctggcccgcg aagtggatgg ctgccaggac aatcctatca 4200
cctacgaggg cgaactgctg cacggcggta acttccacgc tatgccagtc ggcttcgcat 4260
ccgaccagat cggtctggcg atgcacatgg cagcttatct ggctgaacgc cagctcggcc 4320
tgctggtgag cccggtgacc aacggcgacc tgccaccaat gctgacccca cgcgctggac 4380
gcggtgccgg cctggcgggc gttcagatct ccgcaacctc cttcgtctct cgcatccgcc 4440
agctggtgtt cccagctagc ctcaccaccc tcccaaccaa cggctggaac caggaccatg 4500
tcccaatggc tctgaacggc gcaaacagcg tgttcgaagc tcttgaactg ggttggctga 4560
ccgtgggtag cctggcagtc ggcgtggccc agctcgctgc aatgaccggc cacgcagctg 4620
agggcgtgtg ggccgagttg gcaggcatct gcccaccact ggatgctgac cgcccactgg 4680
gcgcggaggt ccgcgctgct cgcgatctcc tctccgcaca cgctgaccag ctgctcgttg 4740
acgaggctga tggcaaagac ttcggctaac tctagagtcg acctgcaggc atgcaagctt 4800
ggctgttttg gcggatgaga gaagattttc agcctgatac agattaaatc agaacgcaga 4860

-continued

```
agcggtctga taaaacagaa tttgcctggc ggcagtagcg cggtggtccc acctgacccc   4920
atgccgaact cagaagtgaa acgccgtagc gccgatggta gtgtggggtc tccccatgcg   4980
agagtaggga actgccaggc atcaaataaa acgaaaggct cagtcgaaag actgggcctt   5040
tcgttttatc tgttgtttgt cggtgaacgc tctcctgagt aggacaaatc cgccgggagc   5100
ggatttgaac gttgcgaagc aacggcccgg agggtggcgg gcaggacgcc cgccataaac   5160
tgccaggcat caaattaagc agaaggccat cctgacggat ggcctttttg cgtttctaca   5220
aactcttttt gtttattttt ctaaatacat tcaaatatgt atccgctcat gaattaattc   5280
cgctagatga cgtgcggctt cgacctcctg ggcgtggcgc ttgttggcgc gctcgcggct   5340
ggctgcggca cgacacgcgt ctgagcagta ttttgcgcgc cgtcctcgtg ggtcaggccg   5400
gggtgggatc aggccaccgc agtaggcgca gctgatgcga tcctccacta ctgcgcgtcc   5460
tcctggcgct gccgagcacg cagctcgtcg gccagctctt caaggtcggc cacaagcgtt   5520
tctaggtcgc tcgcggcact tgcccagtcg cgtgatgctg gcgcgtctgt cgtatcgagg   5580
gcgcggaaaa atccgatcac cgtttttaaa tcgacggcgg catcgagtgc gtcggactcc   5640
agcgcgacat cggagagatc caccgctgat gcttcaggcc agttttggta cttcgtcgtg   5700
aaggtcatga caccattata acgaacgttc gttaaaaatt ctagccccaa ttctgataat   5760
ttcttccggc actcctgcga aaacctgcga gacttcttgc ccagaaaaaa cgccaagcgc   5820
agcggttacc gcactttttt tccaggtgat ttcaccctga ccagcgaagc ggcactttag   5880
tgcatgaggt gtgcccctgg tttcccctct ttggagggtt caacccaaaa aagcacacaa   5940
gcaaaaatga aaatcatcat gagcaagttg gtgcgaagca gcaacgcgct agctccaaaa   6000
aggtctccag gatctcgagg agatttttga gggggaggga gtcgaggaag agccagagca   6060
gaaggcgggg aaccgttctc tgccgacagc gtgagccccc cttaaaaatc aggccgggga   6120
ggaaccgggg agggatcaga gctaggagcg agacacccta aaggggggga accgttttct   6180
gctgacggtg tttcgtttat tagttttcag cccgtggata gcggagggtg agggcaagtg   6240
agagccagag caaggacggg accccctaaag gggggaaccg ttttctgctg acggtgtttc   6300
gtttattagt tttcagcccg tggacggccg cgtttagctt ccattccaag tgcctttctg   6360
acttgttgga tgcgcctttc actgacacct agttcgcctg caagctcacg agtcgaggga   6420
tcagcaaccg attgagaacg ggcatccagg atcgcagttt tgacgcgaag ttcgagcaac   6480
tcgcctgtca tttctcggcg tttgtttgct tccgctaatc gctgtcgcgt ctcctgcgca   6540
tacttacttt ctgggtcagc ccatctgcgt gcattcgatg tagctgcgcc ccgtcgcccc   6600
atcgtcgcta gagctttccg ccctcggctg ctctgcgttt ccacccgacg agcagggacg   6660
actggctggc ctttagccac gtagccgcgc acacgacgcg ccatcgtcag gcgatcacgc   6720
atggcgggaa gatccggctc ccggccgtct gcaccgaccg cctgggcaac gttgtacgcc   6780
acttcatacg cgtcgatgat cttggcatct tttaggcgct caccagcagc tttgagctgg   6840
tatcccacgg tcaacgcgtg gcgaaacgcg gtctcgtcgc gcgctcgctc tggatttgtc   6900
cagagcactc gcacgccgtc gatcaggtcg ccggacgcgt ccagggcgct cggcaggctc   6960
gcgtccaaaa tcgctagcgc cttggcttct gcggtggcgc gttgtgccgc ttcaatgcgg   7020
gcgcgtccgc tggaaaagtc ctgctcaatg tacttttttcg gcttctgtga tccggtcatc   7080
gttcgagcaa tctccattag gtcggccagc cgatccacac gatcatgctg gcagtgccat   7140
ttataggctg tcggatcgtc tgagacgtgc agcggccacc ggctcagcct atgcgaaaaa   7200
gcctggtcag cgccgaaaac acgagtcatt tcttccgtcg ttgcagccag caggcgcata   7260
```

-continued

```
tttgggctgg ttttacctgc tgcggcatac accgggtcaa tgagccagat gagctggcat   7320
ttcccgctca gcggattcac gccgatccaa gccggcgctt tttctaggcg tgcccatttc   7380
tctaaaatcg cgtagacctg cgggtttacg tgctcaatct tcccgccggc ctggtggctg   7440
ggcacatcga tgtcaagcac gatcaccgcg gcatgttgcg cgtgcgtcag cgcaacgtac   7500
tggcaccgcg tcagcgcttt tgagccagcc cggtagagct ttggttgggt ttcgccggta   7560
tccgggtttt taatccaggc gctcgcgaaa tctcttgtct tgctgccctg gaagctttcg   7620
cgtcccaggt gagcgagcag ttcgcggcga tcttctgccg tccagccgcg tgagccgcag   7680
cgcatagctt cggggtgggt gtcgaacaga tcggcggaca atttccacgc gctagctgtg   7740
actgtgtcct gcggatcggc tagagtcatg tcttgagtgc tttctcccag ctgatgactg   7800
ggggttagcc gacgccctgt gagttcccgc tcacggggcg ttcaactttt tcaggtattt   7860
gtgcagctta tcgtgttttc ttcgtaaatg aacgcttaac taccttgtta aacgtggcaa   7920
ataggcagga ttgatgggga tctagcttca cgctgccgca agcactcagg gcgcaagggc   7980
tgctaaagga agcggaacac gtagaaagcc agtccgcaga aacggtgctg accccggatg   8040
aatgtcagct actgggctat ctggacaagg gaaaacgcaa gcgcaaagag aaagcaggta   8100
gcttgcagtg ggcttacatg gcgatagcta gactgggcgg ttttatggac agcaagcgaa   8160
ccggaattgc cagctggggc gccctctggt aaggttggga agccctgcaa agtaaactgg   8220
atggctttct tgccgccaag gatctgatgg cgcaggggat caagatctga tcaagagaca   8280
ggatgaggat cgtttcgcat gattgaacaa gatggattgc acgcaggttc tccggccgct   8340
tgggtggaga ggctattcgg ctatgactgg gcacaacaga caatcggctg ctctgatgcc   8400
gccgtgttcc ggctgtcagc gcaggggcgc ccggttcttt ttgtcaagac cgacctgtcc   8460
ggtgccctga atgaactcca agacgaggca gcgcggctat cgtggctggc cacgacgggc   8520
gttccttgcg cagctgtgct cgacgttgtc actgaagcgg gaagggactg gctgctattg   8580
ggcgaagtgc cggggcagga tctcctgtca tctcaccttg ctcctgccga gaaagtatcc   8640
atcatggctg atgcaatgcg gcggctgcat acgcttgatc cggctacctg cccattcgac   8700
caccaagcga aacatcgcat cgagcgagca cgtactcgga tggaagccgg tcttgtcgat   8760
caggatgatc tggacgaaga gcatcagggg ctcgcgccag ccgaactgtt cgccaggctc   8820
aaggcgcgga tgcccgacgg cgaggatctc gtcgtgaccc atggcgatgc ctgcttgccg   8880
aatatcatgg tggaaaatgg ccgcttttct ggattcatcg actgtggccg gctgggtgtg   8940
gcggaccgct atcaggacat agcgttggct acccgtgata ttgctgaaga gcttggcggc   9000
gaatgggctg accgcttcct cgtgctttac ggtatcgccg ctcccgattc gcagcgcatc   9060
gccttctatc gccttcttga cgagttcttc tgagcgggac tctggggttc gcggaatcat   9120
gaccaaaatc ccttaacgtg agttttcgtt ccactgagcg tcagaccccg tagaaaagat   9180
caaaggatct tcttgagatc cttttttttct gcgcgtaatc tgctgcttgc aaacaaaaaa   9240
accaccgcta ccagcggtgg tttgtttgcc ggatcaagag ctaccaactc tttttccgaa   9300
ggtaactggc ttcagcagag cgcagatacc aaatactgtc cttctagtgt agccgtagtt   9360
aggccaccac ttcaagaact ctgtagcacc gcctacatac ctcgctctgc taatcctgtt   9420
accagtggct gctgccagtg gcgataagtc gtgtcttacc gggttggact caagacgata   9480
gttaccggat aaggcgcagc ggtcgggctg aacggggggt tcgtgcacac agcccagctt   9540
ggagcgaacg acctacaccg aactgagata cctacagcgt gagctatgag aaagcgccac   9600
```

gcttcccgaa gggagaaagg cggacaggta tccggtaagc ggcagggtcg gaacaggaga 9660
gcgcacgagg gagcttccag ggggaaacgc ctggtatctt tatagtcctg tcgggtttcg 9720
ccacctctga cttgagcgtc gatttttgtg atgctcgtca ggggggcgga gcctatggaa 9780
aaacgccagc aacgcggcct ttttacggtt cctggccttt tgctggcctt ttgctcacat 9840
gttctttcct gcgttatccc ctgattctgt ggataaccgt attaccgcct ttgagtgagc 9900
tgataccgct cgccgcagcc gaacgaccga gcgcagcgag tcagtgagcg aggaagcgga 9960
agagcgcctg atgcggtatt ttctccttac gcatctgtgc ggtatttcac accgcatatg 10020
gtgcactctc agtacaatct gctctgatgc cgcatagtta agccagtata cactccgcta 10080
tcgctacgtg actgggtcat ggctgcgccc cgacacccgc caacacccgc tgacgcgccc 10140
tgacgggctt gtctgctccc ggcatccgct tacagacaag ctgtgaccgt ctccgggagc 10200
tgcatgtgtc agaggttttc accgtcatca ccgaaacgcg cgaggcagca gatcaattcg 10260
cgcgcgaagg cgaagcggca tgcatttacg ttgacaccat cgaatggtgc aaaacctttc 10320
gcggtatggc atgatagcgc ccggaagaga gtcaattcag ggtggtgaat gtgaaaccag 10380
taacgttata cgatgtcgca gagtatgccg gtgtctctta tcagaccgtt tcccgcgtgg 10440
tgaaccaggc cagccacgtt tctgcgaaaa cgcgggaaaa agtggaagcg gcgatggcgg 10500
agctgaatta cattcccaac cgcgtggcac aacaactggc gggcaaacag tcgttgctga 10560
ttggcgttgc cacctccagt ctggccctgc acgcgccgtc gcaaattgtc gcggcgatta 10620
aatctcgcgc cgatcaactg ggtgccagcg tggtggtgtc gatggtagaa cgaagcggcg 10680
tcgaagcctg taaagcggcg gtgcacaatc ttctcgcgca acgcgtcagt gggctgatca 10740
ttaactatcc gctggatgac caggatgcca ttgctgtgga agctgcctgc actaatgttc 10800
cggcgttatt tcttgatgtc tctgaccaga cacccatcaa cagtattatt ttctcccatg 10860
aagacggtac gcgactgggc gtggagcatc tggtcgcatt gggtcaccag caaatcgcgc 10920
tgttagcggg cccattaagt tctgtctcgg cgcgtctgcg tctggctggc tggcataaat 10980
atctcactcg caatcaaatt cagccgatag cggaacggga aggcgactgg agtgccatgt 11040
ccggttttca acaaaccatg caaatgctga atgagggcat cgttcccact gcgatgctgg 11100
ttgccaacga tcagatggcg ctgggcgcaa tgcgcgccat taccgagtcc gggctgcgcg 11160
ttggtgcgga tatctcggta gtgggatacg acgataccga agacagctca tgttatatcc 11220
cgccgtcaac caccatcaaa caggattttc gcctgctggg gcaaaccagc gtggaccgct 11280
tgctgcaact ctctcagggc caggcggtga agggcaatca gctgttgccc gtctcactgg 11340
tgaaaagaaa aaccaccctg gcgcccaata cgcaaaccgc ctctccccgc gcgttggccg 11400
attcattaat gcagctggca cgacaggttt cccgactgga aagcgggcag tgagcgcaac 11460
gcaattaatg tgagttagcg cgaattgatc tggtttgaca gcttatcat 11509

<210> SEQ ID NO 56
<211> LENGTH: 4506
<212> TYPE: DNA
<213> ORGANISM: Artificial Sequence
<220> FEATURE:
<223> OTHER INFORMATION: operon RpBAS-Pp4CL-SeSam8

<400> SEQUENCE: 56
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180

```
aaaactctcg catcgagaag cgctacctcc acgtcaccga ggagatcctc aaggaaaacc    240
caaacatcgc agcttacgag gctactagcc tgaacgtgcg ccacaagatg caggtcaagg    300
gcgtcgcaga actgggcaag gaagctgctc tgaaggctat caaggaatgg ggccagccaa    360
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtc   1200
accatcgctc cttccccagc caatcgtgtc cgaatccacc ggtgaatccg tgatgaagat   1260
gtccctccag tccgaagtgc gcgaagcatc cctggcaacc ggtgaaaacc ctgaaccatt   1320
cctgctggaa accgatgctg aatcccagat catggaacct gtgcacgctg aagttcacga   1380
tttcatctac cgttctaagc tgcctgatat cgatatccca aaccacatgc ctctggctga   1440
ttactgcctg gagaagtcct cccagtggcc tgataaggtg tgcctgatcg atggtgtgac   1500
cggtcgcgaa caccgctacg gcgaaattga gctgtcctcc cgccgcgtgg cagcaggcct   1560
tgataagatc ggcgtgaagc agggcgatgt catcgcactg ctcttgccta actgcgctga   1620
gttcgtcctg gtgttcctgg gcgcagcgaa gcgcggcgcc gttgtcacca ccgctaaccc   1680
attctacacc gccgccgagt tggagaagca aatcgaggcc tccggtgcgg gcattgttat   1740
cactcagagc agctacatcg agaagctcgc aggccttaac gtccagatca tcaccgttga   1800
tcagcacgtg gctaattgca tgcacatctc cgtgctgctg aacgcatgcg aagatgaatg   1860
ccctcaggtg cgtatccacc ctgacgatct ggtctgcctg ccatactcct ccggcaccac   1920
cggcttgcca aagggcgtga tgctgaccca caagtccctt gtgtcatccg tgtcccaaca   1980
ggtggacggc gaagcaccaa acttcaacat cactgtcgag gacaccctga tgtgcgtgct   2040
gcccatgttc cacatctatt ccctcaactc catcctgctg tgcggcctcc gtgtgggcgc   2100
caccctcgtt attatgccga agttcgaact gccaaagctg ttggacctga tccagcgtca   2160
caaggtgacc atgggcccat tcgtgccgcc aatcgtcctg gccatcgcaa agaacccaat   2220
cgtcgagaat tacgatctct cctccatgcg catggttatg tccggcgctg cacctctggg   2280
tcgggagctg gaggacgctt tccgtgcccg cttgccaaac gccgttctgg gccagggcta   2340
cgggatgact gaagccggcc cagtcctggc tatgtgcctc gcattcgcaa agaccccatt   2400
ctccgtgaag ccaggctcct gcggcaccgt ggtgcgcaac gctgaagtga aaatcgtcga   2460
taccgaaacc ggcatgtccc tgccatacaa ccagccaggc gagatctgca tccgcggccc   2520
```

acagatcatg aagggctacc tgaagaaccc agaagctacc gctaacacca tcgataagga 2580
tggcttcctg cacaccggcg atgtcgcatt catcgatgag gatgaggaga tgttcatcgt 2640
tgatcgcgtc aaggagatca tcaagttcaa gggcttccag gtgcctcctg cggagctgga 2700
agctctcctg ctgtcccaca aggagatcca ggacgctgct gtcgtgtccc gtaaggatga 2760
cgtggcgggc gaagttccag tggcattcgt ggtccgcgct accagctcca ccatcaccga 2820
ggatgaagtc aaggattaca tcgcaaagca ggtcgttttc tacaagaaga tccacaacgt 2880
atacttcgtg gattccgtgc caaagtctcc atccggcaag atcctgcgta aggatctccg 2940
taacaaggtg taaggatcta ggaggataaa gaaatgaccc aggtcgtgga gcgccaggct 3000
gatcgtctgt ccagccgcga gtacctggca cgcgttgttc gttccgcagg ctgggacgca 3060
ggcctcacca gctgcaccga tgaagaaatc gtgcgcatgg gtgcatccgc acgcaccatt 3120
gaggaatacc tgaagtctga taagccgatc tacggcctca cccagggctt cggtccactg 3180
gtcctgttcg atgcagattc cgaactggaa cagggcggct ctctcatctc ccatctgggc 3240
accggccagg gtgcaccgct tgcaccggaa gtgtcccgcc tgattctgtg gctccgcatc 3300
caaaacatgc gcaagggcta ttcggctgtc agtcctgtgt tctggcaaaa actggccgac 3360
ctctggaaca agggcttcac ccctgctatc cctcgccacg gcaccgtgtc cgccagcggc 3420
gatctccagc ctctggcaca cgctgccctg gcttttaccg gcgtgggcga ggcatggacc 3480
cgtgatgcag acggccgttg gtccaccgtg ccagccgtgg acgcattagc agcactgggt 3540
gcagagccgt tcgattggcc agtgcgcgag gctttggcct tcgtgaacgg tacgggcgca 3600
tcactcgcgg tggcagttct caaccacaga tccgctctcc gtctcgtacg agcatgtgca 3660
gtcttgtctg cccgtttggc taccttgcta ggagctaatc ctgaacacta cgatgtcggc 3720
cacggagtcg caaggggaca agttggccag ctgaccgcgg cggaatggat tcggcaggga 3780
ctaccacgcg gcatggtccg agacggttcg cgccctcttc aagaaccata cagcttgcgc 3840
tgtgcccccc aggtccttgg cgcggtgctg gaccagctgg atggtgcagg cgatgttctg 3900
gcccgcgaag tggatggctg ccaggacaat cctatcacct acgagggcga actgctgcac 3960
ggcggtaact tccacgctat gccagtcggc ttcgcatccg accagatcgg tctggcgatg 4020
cacatggcag cttatctggc tgaacgccag ctcggcctgc tggtgagccc ggtgaccaac 4080
ggcgacctgc caccaatgct gaccccacgc gctggacgcg gtgccggcct ggcgggcgtt 4140
cagatctccg caacctcctt cgtctctcgc atccgccagc tggtgttccc agctagcctc 4200
accaccctcc caaccaacgg ctggaaccag gaccatgtcc caatggctct gaacggcgca 4260
aacagcgtgt tcgaagctct tgaactgggt tggctgaccg tgggtagcct ggcagtcggc 4320
gtggcccagc tcgctgcaat gaccggccac gcagctgagg gcgtgtgggc cgagttggca 4380
ggcatctgcc caccactgga tgctgaccgc ccactgggcg cggaggtccg cgctgctcgc 4440
gatctcctct ccgcacacgc tgaccagctg ctcgttgacg aggctgatgg caaagacttc 4500
ggctaa 4506

<210> SEQ ID NO 57
<211> LENGTH: 11383
<212> TYPE: DNA
<213> ORGANISM: Artificial Sequence
<220> FEATURE:
<223> OTHER INFORMATION: plasmid RpBAS-Sc4CL-RcTAL-pECXK (pECXK_S)

<400> SEQUENCE: 57
cgactgcacg gtgcaccaat gcttctggcg tcaggcagcc atcggaagct gtggtatggc 60

```
tgtgcaggtc gtaaatcact gcataattcg tgtcgctcaa ggcgcactcc cgttctggat    120
aatgtttttt gcgccgacat cataacggtt ctggcaaata ttctgaaatg agctgttgac    180
aattaatcat ccggctcgta taatgtgtgg aattgtgagc ggataacaat ttcacacagg    240
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gttccgttcc gagtacgcag atgtgcctcc agtggacctc   1500
cctatccacg atgctgtcct gggtggcgcg gccgcattcg gcagcacccc agctctgatc   1560
gatggcaccg atggcaccac cctgacctac gaacaggtcg atcgcttcca ccgtcgcgtc   1620
gctgctgctc tggcggaaac cggcgtgcgc aagggcgatg tcctggccct gcactctcca   1680
aacaccgttg ctttccctct ggcattctac gctgcaaccc gcgctggtgc atccgtgacc   1740
actgttcacc ctctcgctac cgcagaagag tttgctaagc agctgaagga ttcggctgca   1800
cgttggatcg tcaccgtttc cccactgctg tccaccgcac gccgcgccgc agagttggca   1860
ggcggcgtgc aggaaatttt ggtctgcgat tctgctccag gtcaccgttc tctcgtcgat   1920
atgctggcta gcaccgcacc cgaaccatcc gtcgctatcg atccagcaga agatgtggct   1980
gcccttccgt actcctctgg caccaccggc accccaaagg gtgtgatgct gacccaccgc   2040
cagattgcaa ccaacctggc tcagctggaa ccttccatgc catccgctcc aggtgaccgg   2100
gtgctggctg ttctgccatt cttccacatc tacggcttga ccgcactcat gaacgctcct   2160
ttgcgcctgg gtgctaccgt ggtggtgctc cctcgcttcg acctggagca gttccttgca   2220
gccatccaga accaccgtat caccagtttg tacgtcgccc caccaatcgt tttggcactg   2280
gctaagcacc ctctggtggc cgactatgac ctttcctccc tccgttacat cgtgagcgcc   2340
gcggcaccgc tcgacgcgcg cctggcagcc gcttgttccc agcgtctggg cctgcccccg   2400
```

-continued

```
gtggggcaag cgtacggtat gaccgagctg tctcctggca cccacgtcgt gccgctcgat   2460
gcaatggcag atgccccacc cggcaccgtg ggtcgcctga tagctggcac cgagatgcgc   2520
atcgtgtccc tgaccgaccc aggcaccgac ctgccggcag gcgaatccgg cgaaatcctg   2580
atccgcggcc cccagattat gaagggctac ctcggccgcc cagatgctac cgcagcaatg   2640
atcgatgagg agggctggct gcacaccggc gatgtgggcc acgtggacgc tgatggttgg   2700
ttgttcgtcg tggatcgcgt taaggagctg atcaagtaca agggtttcca ggttgctccc   2760
gcggagcttg aagcacactt gctcacccac ccaggtgttg cagatgcagc tgtcgtcggc   2820
gcatacgacg acgacggtaa cgaggtgccg cacgcctttg tggtccgcca gccggctgca   2880
ccaggcctcg cggagtccga aatcatgatg tacgtggctg aacgcgttgc tccatacaag   2940
cgcgtgcgcc gcgtgacctt cgtcgatgcc gtgccacgcg cagcatccgg caagatcctg   3000
cgtcgccagc tgcgcgagcc acgctaagga tctaggagga taaagaaatg accctgcaat   3060
cccagactgc aaaggactgc ctggcgctgg atggtgcact gacactggtt cagtgcgaag   3120
caattgccac tcaccgctca cggatctccg tcacaccagc attgcgggaa cgctgcgccc   3180
gcgcgcacgc acgtctggag cacgctatcg cagaacagcg tcacatctat ggtatcacca   3240
ccggcttcgg accactggct aatcgcctga tcggtgcaga tcagggcgcc gaactccagc   3300
agaacctcat ctaccacctt gctactggcg tgggcccaaa actctcctgg gctgaagcac   3360
gtgcactcat gctggctcgt ctcaactcca tccttcaggg cgcatctggt gcatcaccag   3420
aaaccatcga ccgtatcgtt gccgttctga acgctggctt cgccccagaa gtcccagctc   3480
agggcaccgt tggtgcatct ggcgatctga ccccactggc tcacatggtg ctggcgcttc   3540
agggtcgagg tcgtatgatc gatccatccg gccgtgttca ggaagccggc gcagtgatgg   3600
atcgcctgtg cggtggccca ctgaccttgg cagcccgtga cggtctggct ctggtcaacg   3660
gtacttccgc tatgaccgca atcgctgctt tgaccggtgt ggaggctgcg cgcgcaatcg   3720
acgccgcatt gcgccactcc gctgtgctca tggaggttct ctccggccac gctgaggctt   3780
ggcaccctgc atttgctgaa ctccgcccac acccaggcca gctgcgcgca accgaacgtc   3840
tggcccaggc tctcgatggc gccggtcgcg tttgccgcac cttgaccgcg gcccgtcgcc   3900
tgaccgcagc tgatctgcgc cctgaggatc acccagccca ggacgcctac tccctgcgcg   3960
tggtgccaca gctggttggc gctgtctggg acaccctcga ttggcacgat cgcgtcgtga   4020
cctgcgaact caactctgtg accgacaacc caatcttccc ggaaggctgc gctgttccag   4080
cactgcacgg cggcaacttc atgggcgtgc acgtcgcact ggcgtcggac gccctgaacg   4140
ctgcattggt taccctggca ggtctggtgg agcgccagat cgcacgcctt actgatgaga   4200
agctgaacaa gggacttccg gcattccttc acggtggtca ggctggcctt cagtccggct   4260
tcatgggcgc gcaggtcacc gcaaccgcgc tccttgctga aatgcgcgca aacgcaaccc   4320
cggtgtctgt tcagtcactg tctaccaacg gcgctaacca ggatgttgtc agcatgggca   4380
ccatcgctgc acgccgcgct cgcgcacagc tgctcccact gtcccagatt caggcaatcc   4440
tggctctcgc tctcgcccag gcaatggatc tgctggatga tccagagggc caggctggct   4500
ggtcccttac cgcacgcgac ctgcgcgatc gcatccgcgc tgtctcgccg ggcctgcgcg   4560
cagatcgccc actggccggc cacatcgagg cagtcgctca gggtctgcgc cacccttccg   4620
cagcagctga tccaccagca taactctaga gtcgacctgc aggcatgcaa gcttggctgt   4680
tttggcggat gagagaagat tttcagcctg atacagatta aatcagaacg cagaagcggt   4740
ctgataaaac agaatttgcc tggcggcagt agcgcggtgg tcccacctga ccccatgccg   4800
```

-continued aactcagaag tgaaacgccg tagcgccgat ggtagtgtgg ggtctcccca tgcgagagta 4860
gggaactgcc aggcatcaaa taaaacgaaa ggctcagtcg aaagactggg cctttcgttt 4920
tatctgttgt ttgtcggtga acgctctcct gagtaggaca aatccgccgg gagcggattt 4980
gaacgttgcg aagcaacggc ccggagggtg gcgggcagga cgcccgccat aaactgccag 5040
gcatcaaatt aagcagaagg ccatcctgac ggatggcctt tttgcgtttc tacaaactct 5100
ttttgtttat ttttctaaat acattcaaat atgtatccgc tcatgaatta attccgctag 5160
atgacgtgcg gcttcgacct cctgggcgtg gcgcttgttg gcgcgctcgc ggctggctgc 5220
ggcacgacac gcgtctgagc agtattttgc gcgccgtcct cgtgggtcag gccggggtgg 5280
gatcaggcca ccgcagtagg cgcagctgat gcgatcctcc actactgcgc gtcctcctgg 5340
cgctgccgag cacgcagctc gtcggccagc tcttcaaggt cggccacaag cgtttctagg 5400
tcgctcgcgg cacttgccca gtcgcgtgat gctggcgcgt ctgtcgtatc gagggcgcgg 5460
aaaaatccga tcaccgtttt taaatcgacg gcggcatcga gtgcgtcgga ctccagcgcg 5520
acatcggaga gatccaccgc tgatgcttca ggccagtttt ggtacttcgt cgtgaaggtc 5580
atgacaccat tataacgaac gttcgttaaa aattctagcc ccaattctga taatttcttc 5640
cggcactcct gcgaaaacct gcgagacttc ttgcccagaa aaaacgccaa gcgcagcggt 5700
taccgcactt tttttccagg tgatttcacc ctgaccagcg aagcggcact ttagtgcatg 5760
aggtgtgccc ctggtttccc ctctttggag ggttcaaccc aaaaaagcac acaagcaaaa 5820
atgaaaatca tcatgagcaa gttggtgcga agcagcaacg cgctagctcc aaaaaggtct 5880
ccaggatctc gaggagattt ttgaggggga gggagtcgag gaagagccag agcagaaggc 5940
ggggaaccgt tctctgccga cagcgtgagc ccccccttaaa aatcaggccg gggaggaacc 6000
ggggagggat cagagctagg agcgagacac cctaaagggg gggaaccgtt ttctgctgac 6060
ggtgtttcgt ttattagttt tcagcccgtg gatagcggag ggtgagggca agtgagagcc 6120
agagcaagga cgggacccct aaagggggga accgttttct gctgacggtg tttcgtttat 6180
tagttttcag cccgtggacg gccgcgttta gcttccattc caagtgcctt tctgacttgt 6240
tggatgcgcc tttcactgac acctagttcg cctgcaagct cacgagtcga gggatcagca 6300
accgattgag aacgggcatc caggatcgca gttttgacgc gaagttcgag caactcgcct 6360
gtcatttctc ggcgtttgtt tgcttccgct aatcgctgtc gcgtctcctg cgcatactta 6420
ctttctgggt cagcccatct gcgtgcattc gatgtagctg cgccccgtcg ccccatcgtc 6480
gctagagctt tccgccctcg gctgctctgc gtttccaccc gacgagcagg gacgactggc 6540
tggcctttag ccacgtagcc gcgcacacga cgcgccatcg tcaggcgatc acgcatggcg 6600
ggaagatccg gctcccggcc gtctgcaccg accgcctggg caacgttgta cgccacttca 6660
tacgcgtcga tgatcttggc atcttttagg cgctcaccag cagctttgag ctggtatccc 6720
acggtcaacg cgtggcgaaa cgcggtctcg tcgcgcgctc gctctggatt tgtccagagc 6780
actcgcacgc cgtcgatcag gtcgccggac gcgtccaggg cgctcggcag gctcgcgtcc 6840
aaaatcgcta gcgccttggc ttctgcggtg gcgcgttgtg ccgcttcaat gcgggcgcgt 6900
ccgctggaaa agtcctgctc aatgtacttt ttcggcttct gtgatccggt catcgttcga 6960
gcaatctcca ttaggtcggc cagccgatcc acacgatcat gctggcagtg ccatttatag 7020
gctgtcggat cgtctgagac gtgcagcggc caccggctca gcctatgcga aaaagcctgg 7080
tcagcgccga aaacacgagt catttcttcc gtcgttgcag ccagcaggcg catatttggg 7140

-continued

```
ctggttttac ctgctgcggc atacaccggg tcaatgagcc agatgagctg gcatttcccg   7200
ctcagcggat tcacgccgat ccaagccggc gctttttcta ggcgtgccca tttctctaaa   7260
atcgcgtaga cctgcgggtt tacgtgctca atcttcccgc cggcctggtg gctgggcaca   7320
tcgatgtcaa gcacgatcac cgcggcatgt tgcgcgtgcg tcagcgcaac gtactggcac   7380
cgcgtcagcg cttttgagcc agcccggtag agctttggtt gggtttcgcc ggtatccggg   7440
tttttaatcc aggcgctcgc gaaatctctt gtcttgctgc cctggaagct ttcgcgtccc   7500
aggtgagcga gcagttcgcg gcgatcttct gccgtccagc cgcgtgagcc gcagcgcata   7560
gcttcggggt gggtgtcgaa cagatcggcg gacaatttcc acgcgctagc tgtgactgtg   7620
tcctgcggat cggctagagt catgtcttga gtgctttctc ccagctgatg actgggggtt   7680
agccgacgcc ctgtgagttc ccgctcacgg ggcgttcaac tttttcaggt atttgtgcag   7740
cttatcgtgt tttcttcgta aatgaacgct taactacctt gttaaacgtg gcaaataggc   7800
aggattgatg gggatctagc ttcacgctgc cgcaagcact cagggcgcaa gggctgctaa   7860
aggaagcgga acacgtagaa agccagtccg cagaaacggt gctgaccccg gatgaatgtc   7920
agctactggg ctatctggac aagggaaaac gcaagcgcaa agagaaagca ggtagcttgc   7980
agtgggctta catggcgata gctagactgg gcggttttat ggacagcaag cgaaccggaa   8040
ttgccagctg gggcgccctc tggtaaggtt gggaagccct gcaaagtaaa ctggatggct   8100
ttcttgccgc caaggatctg atggcgcagg ggatcaagat ctgatcaaga gacaggatga   8160
ggatcgtttc gcatgattga acaagatgga ttgcacgcag gttctccggc cgcttgggtg   8220
gagaggctat tcggctatga ctgggcacaa cagacaatcg gctgctctga tgccgccgtg   8280
ttccggctgt cagcgcaggg gcgcccggtt ctttttgtca agaccgacct gtccggtgcc   8340
ctgaatgaac tccaagacga ggcagcgcgg ctatcgtggc tggccacgac gggcgttcct   8400
tgcgcagctg tgctcgacgt tgtcactgaa gcgggaaggg actggctgct attgggcgaa   8460
gtgccggggc aggatctcct gtcatctcac cttgctcctg ccgagaaagt atccatcatg   8520
gctgatgcaa tgcggcggct gcatacgctt gatccggcta cctgcccatt cgaccaccaa   8580
gcgaaacatc gcatcgagcg agcacgtact cggatggaag ccggtcttgt cgatcaggat   8640
gatctggacg aagagcatca ggggctcgcg ccagccgaac tgttcgccag gctcaaggcg   8700
cggatgcccg acggcgagga tctcgtcgtg acccatggcg atgcctgctt gccgaatatc   8760
atggtggaaa atggccgctt ttctggattc atcgactgtg gccggctggg tgtggcggac   8820
cgctatcagg acatagcgtt ggctacccgt gatattgctg aagagcttgg cggcgaatgg   8880
gctgaccgct tcctcgtgct ttacggtatc gccgctcccg attcgcagcg catcgccttc   8940
tatcgccttc ttgacgagtt cttctgagcg ggactctggg gttcgcggaa tcatgaccaa   9000
aatcccttaa cgtgagtttt cgttccactg agcgtcagac cccgtagaaa agatcaaagg   9060
atcttcttga gatccttttt ttctgcgcgt aatctgctgc ttgcaaacaa aaaaaccacc   9120
gctaccagcg gtggtttgtt tgccggatca agagctacca actctttttc cgaaggtaac   9180
tggcttcagc agagcgcaga taccaaatac tgtccttcta gtgtagccgt agttaggcca   9240
ccacttcaag aactctgtag caccgcctac atacctcgct ctgctaatcc tgttaccagt   9300
ggctgctgcc agtggcgata agtcgtgtct taccgggttg gactcaagac gatagttacc   9360
ggataaggcg cagcggtcgg gctgaacggg gggttcgtgc acacagccca gcttggagcg   9420
aacgacctac accgaactga gatacctaca gcgtgagcta tgagaaagcg ccacgcttcc   9480
cgaagggaga aaggcggaca ggtatccggt aagcggcagg gtcggaacag gagagcgcac   9540
```

```
gagggagctt ccagggggaa acgcctggta tctttatagt cctgtcgggt ttcgccacct   9600
ctgacttgag cgtcgatttt tgtgatgctc gtcagggggg cggagcctat ggaaaaacgc   9660
cagcaacgcg gcctttttac ggttcctggc cttttgctgg ccttttgctc acatgttctt   9720
tcctgcgtta tcccctgatt ctgtggataa ccgtattacc gcctttgagt gagctgatac   9780
cgctcgccgc agccgaacga ccgagcgcag cgagtcagtg agcgaggaag cggaagagcg   9840
cctgatgcgg tattttctcc ttacgcatct gtgcggtatt tcacaccgca tatggtgcac   9900
tctcagtaca atctgctctg atgccgcata gttaagccag tatacactcc gctatcgcta   9960
cgtgactggg tcatggctgc gccccgacac ccgccaacac ccgctgacgc gccctgacgg  10020
gcttgtctgc tcccggcatc cgcttacaga caagctgtga ccgtctccgg gagctgcatg  10080
tgtcagaggt tttcaccgtc atcaccgaaa cgcgcgaggc agcagatcaa ttcgcgcgcg  10140
aaggcgaagc ggcatgcatt tacgttgaca ccatcgaatg gtgcaaaacc tttcgcggta  10200
tggcatgata gcgcccggaa gagagtcaat tcagggtggt gaatgtgaaa ccagtaacgt  10260
tatacgatgt cgcagagtat gccggtgtct cttatcagac cgtttcccgc gtggtgaacc  10320
aggccagcca cgtttctgcg aaaacgcggg aaaaagtgga agcggcgatg gcggagctga  10380
attacattcc caaccgcgtg gcacaacaac tggcgggcaa acagtcgttg ctgattggcg  10440
ttgccacctc cagtctggcc ctgcacgcgc cgtcgcaaat tgtcgcggcg attaaatctc  10500
gcgccgatca actgggtgcc agcgtggtgg tgtcgatggt agaacgaagc ggcgtcgaag  10560
cctgtaaagc ggcggtgcac aatcttctcg cgcaacgcgt cagtgggctg atcattaact  10620
atccgctgga tgaccaggat gccattgctg tggaagctgc ctgcactaat gttccggcgt  10680
tatttcttga tgtctctgac cagacaccca tcaacagtat tattttctcc catgaagacg  10740
gtacgcgact gggcgtggag catctggtcg cattgggtca ccagcaaatc gcgctgttag  10800
cgggcccatt aagttctgtc tcggcgcgtc tgcgtctggc tggctggcat aaatatctca  10860
ctcgcaatca aattcagccg atagcggaac gggaaggcga ctggagtgcc atgtccggtt  10920
ttcaacaaac catgcaaatg ctgaatgagg gcatcgttcc cactgcgatg ctggttgcca  10980
acgatcagat ggcgctgggc gcaatgcgcg ccattaccga gtccgggctg cgcgttggtg  11040
cggatatctc ggtagtggga tacgacgata ccgaagacag ctcatgttat atcccgccgt  11100
caaccaccat caaacaggat tttcgcctgc tggggcaaac cagcgtggac cgcttgctgc  11160
aactctctca gggccaggcg gtgaagggca atcagctgtt gcccgtctca ctggtgaaaa  11220
gaaaaaccac cctggcgccc aatacgcaaa ccgcctctcc ccgcgcgttg gccgattcat  11280
taatgcagct ggcacgacag gtttcccgac tggaaagcgg gcagtgagcg caacgcaatt  11340
aatgtgagtt agcgcgaatt gatctggttt gacagcttat cat                    11383
```

<210> SEQ ID NO 58
<211> LENGTH: 4380
<212> TYPE: DNA
<213> ORGANISM: Artificial Sequence
<220> FEATURE:
<223> OTHER INFORMATION: operon RpBAS-Sc4CL-RcTAL

<400> SEQUENCE: 58

```
ggatctagga gggagatcat atggcaaccg aggagatgaa gaagctcgca accgtgatgg     60
caatcggcac tgctaaccca ccgaactgct attaccaagc tgattttccc gacttctact    120
tccgcgtgac caactccgat catctgatca acctgaagca gaagttcaag cgcctatgcg    180
```

```
aaaactctcg catcgagaag cgctacctcc acgtcaccga ggagatcctc aaggaaaacc    240
caaacatcgc agcttacgag gctactagcc tgaacgtgcg ccacaagatg caggtcaagg    300
gcgtcgcaga actgggcaag gaagctgctc tgaaggctat caaggaatgg ggccagccaa    360
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtt   1200
ccgttccgag tacgcagatg tgcctccagt ggacctccct atccacgatg ctgtcctggg   1260
tggcgcggcc gcattcggca gcaccccagc tctgatcgat ggcaccgatg gcaccaccct   1320
gacctacgaa caggtcgatc gcttccaccg tcgcgtcgct gctgctctgg cggaaaccgg   1380
cgtgcgcaag ggcgatgtcc tggccctgca ctctccaaac accgttgctt tccctctggc   1440
attctacgct gcaacccgcg ctggtgcatc cgtgaccact gttcaccctc tcgctaccgc   1500
agaagagttt gctaagcagc tgaaggattc ggctgcacgt tggatcgtca ccgtttcccc   1560
actgctgtcc accgcacgcc gcgccgcaga gttggcaggc ggcgtgcagg aaattttggt   1620
ctgcgattct gctccaggtc accgttctct cgtcgatatg ctggctagca ccgcacccga   1680
accatccgtc gctatcgatc cagcagaaga tgtggctgcc cttccgtact cctctggcac   1740
caccggcacc ccaaagggtg tgatgctgac ccaccgccag attgcaacca acctggctca   1800
gctggaacct tccatgccat ccgctccagg tgaccgggtg ctggctgttc tgccattctt   1860
ccacatctac ggcttgaccg cactcatgaa cgctcctttg cgcctgggtg ctaccgtggt   1920
ggtgctccct cgcttcgacc tggagcagtt ccttgcagcc atccagaacc accgtatcac   1980
cagtttgtac gtcgccccac caatcgtttt ggcactggct aagcaccctc tggtggccga   2040
ctatgacctt tcctccctcc gttacatcgt gagcgccgcg gcaccgctcg acgcgcgcct   2100
ggcagccgct tgttcccagc gtctgggcct gcccccggtg gggcaagcgt acggtatgac   2160
cgagctgtct cctggcaccc acgtcgtgcc gctcgatgca atggcagatg ccccacccgg   2220
caccgtgggt cgcctgatag ctggcaccga gatgcgcatc gtgtccctga ccgacccagg   2280
caccgacctg ccggcaggcg aatccggcga aatcctgatc cgcggccccc agattatgaa   2340
gggctacctc ggccgcccag atgctaccgc agcaatgatc gatgaggagg gctggctgca   2400
caccggcgat gtgggccacg tggacgctga tggttggttg ttcgtcgtgg atcgcgttaa   2460
ggagctgatc aagtacaagg gtttccaggt tgctcccgcg gagcttgaag cacacttgct   2520
cacccaccca ggtgttgcag atgcagctgt cgtcggcgca tacgacgacg acggtaacga   2580
```

ggtgccgcac gcctttgtgg tccgccagcc ggctgcacca ggcctcgcgg agtccgaaat 2640
catgatgtac gtggctgaac gcgttgctcc atacaagcgc gtgcgccgcg tgaccttcgt 2700
cgatgccgtg ccacgcgcag catccggcaa gatcctgcgt cgccagctgc gcgagccacg 2760
ctaaggatct aggaggataa agaaatgacc ctgcaatccc agactgcaaa ggactgcctg 2820
gcgctggatg gtgcactgac actggttcag tgcgaagcaa ttgccactca ccgctcacgg 2880
atctccgtca caccagcatt gcgggaacgc tgcgcccgcg cgcacgcacg tctggagcac 2940
gctatcgcag aacagcgtca catctatggt atcaccaccg gcttcggacc actggctaat 3000
cgcctgatcg gtgcagatca gggcgccgaa ctccagcaga acctcatcta ccaccttgct 3060
actggcgtgg gcccaaaact ctcctgggct gaagcacgtg cactcatgct ggctcgtctc 3120
aactccatcc ttcagggcgc atctggtgca tcaccagaaa ccatcgaccg tatcgttgcc 3180
gttctgaacg ctggcttcgc cccagaagtc ccagctcagg gcaccgttgg tgcatctggc 3240
gatctgaccc cactggctca catggtgctg gcgcttcagg gtcgaggtcg tatgatcgat 3300
ccatccggcc gtgttcagga agccggcgca gtgatggatc gcctgtgcgg tggcccactg 3360
accttggcag cccgtgacgg tctggctctg gtcaacggta cttccgctat gaccgcaatc 3420
gctgctttga ccggtgtgga ggctgcgcgc gcaatcgacg ccgcattgcg ccactccgct 3480
gtgctcatgg aggttctctc cggccacgct gaggcttggc accctgcatt tgctgaactc 3540
cgcccacacc caggccagct gcgcgcaacc gaacgtctgg cccaggctct cgatggcgcc 3600
ggtcgcgttt gccgcacctt gaccgcggcc cgtcgcctga ccgcagctga tctgcgccct 3660
gaggatcacc cagcccagga cgcctactcc ctgcgcgtgg tgccacagct ggttggcgct 3720
gtctgggaca ccctcgattg gcacgatcgc gtcgtgacct gcgaactcaa ctctgtgacc 3780
gacaacccaa tcttcccgga aggctgcgct gttccagcac tgcacggcgg caacttcatg 3840
ggcgtgcacg tcgcactggc gtcggacgcc ctgaacgctg cattggttac cctggcaggt 3900
ctggtggagc gccagatcgc acgccttact gatgagaagc tgaacaaggg acttccggca 3960
ttccttcacg gtggtcaggc tggccttcag tccggcttca tgggcgcgca ggtcaccgca 4020
accgcgctcc ttgctgaaat gcgcgcaaac gcaaccccgg tgtctgttca gtcactgtct 4080
accaacggcg ctaaccagga tgttgtcagc atgggcacca tcgctgcacg ccgcgctcgc 4140
gcacagctgc tcccactgtc ccagattcag gcaatcctgg ctctcgctct cgcccaggca 4200
atggatctgc tggatgatcc agagggccag gctggctggt cccttaccgc acgcgacctg 4260
cgcgatcgca tccgcgctgt ctcgccgggc ctgcgcgcag atcgcccact ggccggccac 4320
atcgaggcag tcgctcaggg tctgcgccac ccttccgcag cagctgatcc accagcataa 4380

<210> SEQ ID NO 59
<211> LENGTH: 11308
<212> TYPE: DNA
<213> ORGANISM: Artificial Sequence
<220> FEATURE:
<223> OTHER INFORMATION: plasmid RpBAS-Sc4CL-FjTAL-pECXK (pECXK_T)

<400> SEQUENCE: 59
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240

-continued

```
aaacagacca tggaattcga gctggatcta ggagggagat catatggcaa ccgaggagat    300
gaagaagctc gcaaccgtga tggcaatcgg cactgctaac ccaccgaact gctattacca    360
agctgatttt cccgacttct acttccgcgt gaccaactcc gatcatctga tcaacctgaa    420
gcagaagttc aagcgcctat gcgaaaactc tcgcatcgag aagcgctacc tccacgtcac    480
cgaggagatc ctcaaggaaa acccaaacat cgcagcttac gaggctacta gcctgaacgt    540
gcgccacaag atgcaggtca agggcgtcgc agaactgggc aaggaagctg ctctgaaggc    600
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gttccgttcc gagtacgcag atgtgcctcc agtggacctc   1500
cctatccacg atgctgtcct gggtggcgcg gccgcattcg gcagcacccc agctctgatc   1560
gatggcaccg atggcaccac cctgacctac gaacaggtcg atcgcttcca ccgtcgcgtc   1620
gctgctgctc tggcggaaac cggcgtgcgc aagggcgatg tcctggccct gcactctcca   1680
aacaccgttg ctttccctct ggcattctac gctgcaaccc gcgctggtgc atccgtgacc   1740
actgttcacc ctctcgctac cgcagaagag tttgctaagc agctgaagga ttcggctgca   1800
cgttggatcg tcaccgtttc cccactgctg tccaccgcac gccgcgccgc agagttggca   1860
ggcggcgtgc aggaaatttt ggtctgcgat tctgctccag gtcaccgttc tctcgtcgat   1920
atgctggcta gcaccgcacc cgaaccatcc gtcgctatcg atccagcaga agatgtggct   1980
gcccttccgt actcctctgg caccaccggc accccaaagg gtgtgatgct gacccaccgc   2040
cagattgcaa ccaacctggc tcagctggaa ccttccatgc catccgctcc aggtgaccgg   2100
gtgctggctg ttctgccatt cttccacatc tacggcttga ccgcactcat gaacgctcct   2160
ttgcgcctgg gtgctaccgt ggtggtgctc cctcgcttcg acctggagca gttccttgca   2220
gccatccaga accaccgtat caccagtttg tacgtcgccc caccaatcgt tttggcactg   2280
gctaagcacc ctctggtggc cgactatgac ctttcctccc tccgttacat cgtgagcgcc   2340
gcggcaccgc tcgacgcgcg cctggcagcc gcttgttccc agcgtctggg cctgccccccg   2400
gtggggcaag cgtacggtat gaccgagctg tctcctggca cccacgtcgt gccgctcgat   2460
gcaatggcag atgccccacc cggcaccgtg ggtcgcctga tagctggcac cgagatgcgc   2520
atcgtgtccc tgaccgaccc aggcaccgac ctgccggcag gcgaatccgg cgaaatcctg   2580
atccgcggcc cccagattat gaagggctac ctcggccgcc cagatgctac cgcagcaatg   2640
```

```
atcgatgagg agggctggct gcacaccggc gatgtgggcc acgtggacgc tgatggttgg   2700
ttgttcgtcg tggatcgcgt taaggagctg atcaagtaca agggtttcca ggttgctccc   2760
gcggagcttg aagcacactt gctcacccac ccaggtgttg cagatgcagc tgtcgtcggc   2820
gcatacgacg acgacggtaa cgaggtgccg cacgcctttg tggtccgcca gccggctgca   2880
ccaggcctcg cggagtccga aatcatgatg tacgtggctg aacgcgttgc tccatacaag   2940
cgcgtgcgcc gcgtgacctt cgtcgatgcc gtgccacgcg cagcatccgg caagatcctg   3000
cgtcgccagc tgcgcgagcc acgctaagga tctaggagga taaagaaatg aacaccatca   3060
acgaatacct gtccctggaa gagttcgaag cgatcatctt cggtaaccag aaggttacca   3120
tctccgatgt ggttgtgaac cgtgttaacg agtccttcaa cttcctcaag gagttctccg   3180
gcaacaaggt catctacggt gtgaacaccg gcttcggccc aatggcacaa taccgtatta   3240
aggaatccga tcagatccag cttcagtaca atctgatccg ttcccactct tcgggcaccg   3300
gaaaaccact ctccccagtt tgtgctaagg cagcaatctt ggctcgcctg aacaccctgt   3360
ccctcggtaa ctccggcgtg catccatctg tcatcaacct gatgtcggaa ctgatcaaca   3420
aagacattac cccactcatc ttcgagcacg gtggcgtcgg agcatccggt gacctggttc   3480
agctttctca cctggctttg gttctcatcg gcgaaggcga agtgttctac aagggtgaac   3540
gccgcccaac tccagaagtt ttcgaaattg agggcttgaa gccaatccag gttgagatcc   3600
gtgagggcct cgccttgatt aacggtacta gcgtgatgac cggtattgga gtggtcaacg   3660
tgtaccacgc aaagaagctg ctggactggt ccctgaagtc ctcctgcgcc atcaatgaac   3720
ttgttcaggc ttacgatgat cacttcagcg cagagctgaa ccagacgaag cgccacaagg   3780
gccagcagga aatcgctctg aagatgcgtc agaacctctc tgacagcacc ctgatccgca   3840
agcgcgagga ccacctgtat tccggcgaaa acaccgagga gattttcaag gagaaggtgc   3900
aggagtacta ctccctgcgc tgcgttccac agattctcgg cccggtcctc gaaactatca   3960
ataacgtcgc ctccatcctg gaagatgagt tcaactccgc taacgataac ccaatcatcg   4020
acgtgaagaa ccagcacgtg taccatggcg gcaacttcca cggtgactac atctctctgg   4080
aaatggacaa gttgaaaatc gttatcacca aactgaccat gcttgcagaa cgccagctta   4140
actatcttct caactccaag atcaacgaac ttctgccacc attcgtgaac ctcggcaccc   4200
tgggtttcaa cttcggcatg cagggcgttc agttcaccgc gacctccacc accgcagaat   4260
ctcagatgct gtccaaccct atgtacgttc actccattcc aaacaacaac gataaccagg   4320
acatcgtctc catgggcacc aactccgcag tgatcacgtc caaggttatc gagaacgctt   4380
tcgaagtcct ggctatcgaa atgatcacca tcgttcaggc catcgattac ctcggccaga   4440
aggataagat ctcctccgtt tccaagaagt ggtacgatga aatccgcaac attatcccta   4500
ccttcaagga ggatcaggtt atgtacccat tcgtgcagaa ggttaaggat cacctcatca   4560
acaactaact ctagagtcga cctgcaggca tgcaagcttg gctgttttgg cggatgagag   4620
aagattttca gcctgataca gattaaatca gaacgcagaa gcggtctgat aaaacagaat   4680
ttgcctggcg gcagtagcgc ggtggtccca cctgacccca tgccgaactc agaagtgaaa   4740
cgccgtagcg ccgatggtag tgtggggtct ccccatgcga gagtagggaa ctgccaggca   4800
tcaaataaaa cgaaaggctc agtcgaaaga ctgggccttt cgttttatct gttgtttgtc   4860
ggtgaacgct ctcctgagta ggacaaatcc gccgggagcg gatttgaacg ttgcgaagca   4920
acggcccgga gggtggcggg caggacgccc gccataaact gccaggcatc aaattaagca   4980
```

-continued

```
gaaggccatc ctgacggatg gcctttttgc gtttctacaa actctttttg tttatttttc   5040
taaatacatt caaatatgta tccgctcatg aattaattcc gctagatgac gtgcggcttc   5100
gacctcctgg gcgtggcgct tgttggcgcg ctcgcggctg gctgcggcac gacacgcgtc   5160
tgagcagtat tttgcgcgcc gtcctcgtgg gtcaggccgg ggtgggatca ggccaccgca   5220
gtaggcgcag ctgatgcgat cctccactac tgcgcgtcct cctggcgctg ccgagcacgc   5280
agctcgtcgg ccagctcttc aaggtcggcc acaagcgttt ctaggtcgct cgcggcactt   5340
gcccagtcgc gtgatgctgg cgcgtctgtc gtatcgaggg cgcggaaaaa tccgatcacc   5400
gtttttaaat cgacggcggc atcgagtgcg tcggactcca gcgcgacatc ggagagatcc   5460
accgctgatg cttcaggcca gttttggtac ttcgtcgtga aggtcatgac accattataa   5520
cgaacgttcg ttaaaaattc tagccccaat tctgataatt tcttccggca ctcctgcgaa   5580
aacctgcgag acttcttgcc cagaaaaaac gccaagcgca gcggttaccg cacttttttt   5640
ccaggtgatt tcaccctgac cagcgaagcg gcactttagt gcatgaggtg tgcccctggt   5700
ttcccctctt tggagggttc aacccaaaaa agcacacaag caaaaatgaa aatcatcatg   5760
agcaagttgg tgcgaagcag caacgcgcta gctccaaaaa ggtctccagg atctcgagga   5820
gatttttgag gggagggag tcgaggaaga gccagagcag aaggcgggga accgttctct   5880
gccgacagcg tgagcccccc ttaaaaatca ggccggggag gaaccgggga gggatcagag   5940
ctaggagcga gacaccctaa aggggggga ccgttttctg ctgacggtgt ttcgtttatt   6000
agttttcagc ccgtggatag cggagggtga gggcaagtga gagccagagc aaggacggga   6060
cccctaaagg ggggaaccgt tttctgctga cggtgtttcg tttattagtt ttcagcccgt   6120
ggacggccgc gtttagcttc cattccaagt gcctttctga cttgttggat gcgcctttca   6180
ctgacaccta gttcgcctgc aagctcacga gtcgagggat cagcaaccga ttgagaacgg   6240
gcatccagga tcgcagtttt gacgcgaagt tcgagcaact cgcctgtcat ttctcggcgt   6300
ttgtttgctt ccgctaatcg ctgtcgcgtc tcctgcgcat acttactttc tgggtcagcc   6360
catctgcgtg cattcgatgt agctgcgccc cgtcgcccca tcgtcgctag agctttccgc   6420
cctcggctgc tctgcgtttc cacccgacga gcagggacga ctggctggcc tttagccacg   6480
tagccgcgca cacgacgcgc catcgtcagg cgatcacgca tggcgggaag atccggctcc   6540
cggccgtctg caccgaccgc ctgggcaacg ttgtacgcca cttcatacgc gtcgatgatc   6600
ttggcatctt ttaggcgctc accagcagct ttgagctggt atcccacggt caacgcgtgg   6660
cgaaacgcgg tctcgtcgcg cgctcgctct ggatttgtcc agagcactcg cacgccgtcg   6720
atcaggtcgc cggacgcgtc cagggcgctc ggcaggctcg cgtccaaaat cgctagcgcc   6780
ttggcttctg cggtggcgcg ttgtgccgct tcaatgcggg cgcgtccgct ggaaaagtcc   6840
tgctcaatgt actttttcgg cttctgtgat ccggtcatcg ttcgagcaat ctccattagg   6900
tcggccagcc gatccacacg atcatgctgg cagtgccatt tataggctgt cggatcgtct   6960
gagacgtgca gcggccaccg gctcagccta tgcgaaaaag cctggtcagc gccgaaaaca   7020
cgagtcattt cttccgtcgt tgcagccagc aggcgcatat ttgggctggt tttacctgct   7080
gcggcataca ccgggtcaat gagccagatg agctggcatt tcccgctcag cggattcacg   7140
ccgatccaag ccggcgcttt ttctaggcgt gcccatttct ctaaaatcgc gtagacctgc   7200
gggtttacgt gctcaatctt cccgccggcc tggtggctgg gcacatcgat gtcaagcacg   7260
atcaccgcgg catgttgcgc gtgcgtcagc gcaacgtact ggcaccgcgt cagcgctttt   7320
gagccagccc ggtagagctt tggttgggtt tcgccggtat ccgggttttt aatccaggcg   7380
```

-continued

```
ctcgcgaaat ctcttgtctt gctgccctgg aagctttcgc gtcccaggtg agcgagcagt   7440
tcgcggcgat cttctgccgt ccagccgcgt gagccgcagc gcatagcttc ggggtgggtg   7500
tcgaacagat cggcggacaa tttccacgcg ctagctgtga ctgtgtcctg cggatcggct   7560
agagtcatgt cttgagtgct ttctcccagc tgatgactgg gggttagccg acgccctgtg   7620
agttcccgct cacggggcgt tcaacttttt caggtatttg tgcagcttat cgtgttttct   7680
tcgtaaatga acgcttaact accttgttaa acgtggcaaa taggcaggat tgatggggat   7740
ctagcttcac gctgccgcaa gcactcaggg cgcaagggct gctaaaggaa gcggaacacg   7800
tagaaagcca gtccgcagaa acggtgctga ccccggatga atgtcagcta ctgggctatc   7860
tggacaaggg aaaacgcaag cgcaaagaga aagcaggtag cttgcagtgg gcttacatgg   7920
cgatagctag actgggcggt tttatggaca gcaagcgaac cggaattgcc agctggggcg   7980
ccctctggta aggttgggaa gccctgcaaa gtaaactgga tggctttctt gccgccaagg   8040
atctgatggc gcaggggatc aagatctgat caagagacag gatgaggatc gtttcgcatg   8100
attgaacaag atggattgca cgcaggttct ccggccgctt gggtggagag gctattcggc   8160
tatgactggg cacaacagac aatcggctgc tctgatgccg ccgtgttccg gctgtcagcg   8220
caggggcgcc cggttctttt tgtcaagacc gacctgtccg gtgccctgaa tgaactccaa   8280
gacgaggcag cgcggctatc gtggctggcc acgacgggcg ttccttgcgc agctgtgctc   8340
gacgttgtca ctgaagcggg aagggactgg ctgctattgg gcgaagtgcc ggggcaggat   8400
ctcctgtcat ctcaccttgc tcctgccgag aaagtatcca tcatggctga tgcaatgcgg   8460
cggctgcata cgcttgatcc ggctacctgc ccattcgacc accaagcgaa acatcgcatc   8520
gagcgagcac gtactcggat ggaagccggt cttgtcgatc aggatgatct ggacgaagag   8580
catcaggggc tcgcgccagc cgaactgttc gccaggctca aggcgcggat gcccgacggc   8640
gaggatctcg tcgtgaccca tggcgatgcc tgcttgccga atatcatggt ggaaaatggc   8700
cgcttttctg gattcatcga ctgtggccgg ctgggtgtgg cggaccgcta tcaggacata   8760
gcgttggcta cccgtgatat tgctgaagag cttggcggcg aatgggctga ccgcttcctc   8820
gtgctttacg gtatcgccgc tcccgattcg cagcgcatcg ccttctatcg ccttcttgac   8880
gagttcttct gagcgggact ctggggttcg cggaatcatg accaaaatcc cttaacgtga   8940
gttttcgttc cactgagcgt cagaccccgt agaaaagatc aaaggatctt cttgagatcc   9000
tttttttctg cgcgtaatct gctgcttgca aacaaaaaaa ccaccgctac cagcggtggt   9060
ttgtttgccg gatcaagagc taccaactct ttttccgaag gtaactggct tcagcagagc   9120
gcagatacca aatactgtcc ttctagtgta gccgtagtta ggccaccact tcaagaactc   9180
tgtagcaccg cctacatacc tcgctctgct aatcctgtta ccagtggctg ctgccagtgg   9240
cgataagtcg tgtcttaccg ggttggactc aagacgatag ttaccggata aggcgcagcg   9300
gtcgggctga acggggggtt cgtgcacaca gcccagcttg gagcgaacga cctacaccga   9360
actgagatac ctacagcgtg agctatgaga aagcgccacg cttcccgaag ggagaaaggc   9420
ggacaggtat ccggtaagcg gcagggtcgg aacaggagag cgcacgaggg agcttccagg   9480
gggaaacgcc tggtatcttt atagtcctgt cgggtttcgc cacctctgac ttgagcgtcg   9540
atttttgtga tgctcgtcag gggggcggag cctatggaaa aacgccagca acgcggcctt   9600
tttacggttc ctggcctttt gctggccttt tgctcacatg ttctttcctg cgttatcccc   9660
tgattctgtg gataaccgta ttaccgcctt tgagtgagct gataccgctc gccgcagccg   9720
```

-continued

```
aacgaccgag cgcagcgagt cagtgagcga ggaagcggaa gagcgcctga tgcggtattt   9780

tctccttacg catctgtgcg gtatttcaca ccgcatatgg tgcactctca gtacaatctg   9840

ctctgatgcc gcatagttaa gccagtatac actccgctat cgctacgtga ctgggtcatg   9900

gctgcgcccc gacacccgcc aacacccgct gacgcgccct gacgggcttg tctgctcccg   9960

gcatccgctt acagacaagc tgtgaccgtc tccgggagct gcatgtgtca gaggttttca  10020

ccgtcatcac cgaaacgcgc gaggcagcag atcaattcgc gcgcgaaggc gaagcggcat  10080

gcatttacgt tgacaccatc gaatggtgca aaacctttcg cggtatggca tgatagcgcc  10140

cggaagagag tcaattcagg gtggtgaatg tgaaaccagt aacgttatac gatgtcgcag  10200

agtatgccgg tgtctcttat cagaccgttt cccgcgtggt gaaccaggcc agccacgttt  10260

ctgcgaaaac gcgggaaaaa gtggaagcgg cgatggcgga gctgaattac attcccaacc  10320

gcgtggcaca acaactggcg ggcaaacagt cgttgctgat tggcgttgcc acctccagtc  10380

tggccctgca cgcgccgtcg caaattgtcg cggcgattaa atctcgcgcc gatcaactgg  10440

gtgccagcgt ggtggtgtcg atggtagaac gaagcggcgt cgaagcctgt aaagcggcgg  10500

tgcacaatct tctcgcgcaa cgcgtcagtg ggctgatcat taactatccg ctggatgacc  10560

aggatgccat tgctgtggaa gctgcctgca ctaatgttcc ggcgttattt cttgatgtct  10620

ctgaccagac acccatcaac agtattattt tctcccatga agacggtacg cgactgggcg  10680

tggagcatct ggtcgcattg ggtcaccagc aaatcgcgct gttagcgggc ccattaagtt  10740

ctgtctcggc gcgtctgcgt ctggctggct ggcataaata tctcactcgc aatcaaattc  10800

agccgatagc ggaacgggaa ggcgactgga gtgccatgtc cggttttcaa caaaccatgc  10860

aaatgctgaa tgagggcatc gttcccactg cgatgctggt tgccaacgat cagatggcgc  10920

tgggcgcaat gcgcgccatt accgagtccg ggctgcgcgt tggtgcggat atctcggtag  10980

tgggatacga cgataccgaa gacagctcat gttatatccc gccgtcaacc accatcaaac  11040

aggattttcg cctgctgggg caaaccagcg tggaccgctt gctgcaactc tctcagggcc  11100

aggcggtgaa gggcaatcag ctgttgcccg tctcactggt gaaaagaaaa accaccctgg  11160

cgcccaatac gcaaaccgcc tctccccgcg cgttggccga ttcattaatg cagctggcac  11220

gacaggtttc ccgactggaa agcgggcagt gagcgcaacg caattaatgt gagttagcgc  11280

gaattgatct ggtttgacag cttatcat                                     11308
```

<210> SEQ ID NO 60
<211> LENGTH: 4305
<212> TYPE: DNA
<213> ORGANISM: Artificial Sequence
<220> FEATURE:
<223> OTHER INFORMATION: operon RpBAS-Sc4CL-FjTAL

<400> SEQUENCE: 60

```
ggatctagga gggagatcat atggcaaccg aggagatgaa gaagctcgca accgtgatgg     60

caatcggcac tgctaaccca ccgaactgct attaccaagc tgattttccc gacttctact    120

tccgcgtgac caactccgat catctgatca acctgaagca gaagttcaag cgcctatgcg    180

aaaactctcg catcgagaag cgctacctcc acgtcaccga ggagatcctc aaggaaaacc    240

caaacatcgc agcttacgag gctactagcc tgaacgtgcg ccacaagatg caggtcaagg    300

gcgtcgcaga actgggcaag gaagctgctc tgaaggctat caaggaatgg ggccagccaa    360

agtccaagat cacccacctg atcgtctgct gcctggctgg cgtggatatg ccaggcgcag    420

attaccagct cactaagctc ctcgatctcg acccatccgt taagcgcttc atgttctacc    480
```

-continued

```
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtt   1200
ccgttccgag tacgcagatg tgcctccagt ggacctccct atccacgatg ctgtcctggg   1260
tggcgcggcc gcattcggca gcaccccagc tctgatcgat ggcaccgatg gcaccaccct   1320
gacctacgaa caggtcgatc gcttccaccg tcgcgtcgct gctgctctgg cggaaaccgg   1380
cgtgcgcaag ggcgatgtcc tggccctgca ctctccaaac accgttgctt tccctctggc   1440
attctacgct gcaacccgcg ctggtgcatc cgtgaccact gttcaccctc tcgctaccgc   1500
agaagagttt gctaagcagc tgaaggattc ggctgcacgt tggatcgtca ccgtttcccc   1560
actgctgtcc accgcacgcc gcgccgcaga gttggcaggc ggcgtgcagg aaattttggt   1620
ctgcgattct gctccaggtc accgttctct cgtcgatatg ctggctagca ccgcacccga   1680
accatccgtc gctatcgatc cagcagaaga tgtggctgcc cttccgtact cctctggcac   1740
caccggcacc ccaaagggtg tgatgctgac ccaccgccag attgcaacca acctggctca   1800
gctggaacct tccatgccat ccgctccagg tgaccgggtg ctggctgttc tgccattctt   1860
ccacatctac ggcttgaccg cactcatgaa cgctcctttg cgcctgggtg ctaccgtggt   1920
ggtgctccct cgcttcgacc tggagcagtt ccttgcagcc atccagaacc accgtatcac   1980
cagtttgtac gtcgccccac caatcgtttt ggcactggct aagcaccctc tggtggccga   2040
ctatgacctt tcctccctcc gttacatcgt gagcgccgcg gcaccgctcg acgcgcgcct   2100
ggcagccgct tgttcccagc gtctgggcct gcccccggtg ggcaagcgt acggtatgac    2160
cgagctgtct cctggcaccc acgtcgtgcc gctcgatgca atggcagatg ccccacccgg   2220
caccgtgggt cgcctgatag ctggcaccga gatgcgcatc gtgtccctga ccgacccagg   2280
caccgacctg ccggcaggcg aatccggcga aatcctgatc cgcggccccc agattatgaa   2340
gggctacctc ggccgcccag atgctaccgc agcaatgatc gatgaggagg gctggctgca   2400
caccggcgat gtgggccacg tggacgctga tggttggttg ttcgtcgtgg atcgcgttaa   2460
ggagctgatc aagtacaagg gtttccaggt tgctcccgcg gagcttgaag cacacttgct   2520
cacccaccca ggtgttgcag atgcagctgt cgtcggcgca tacgacgacg acggtaacga   2580
ggtgccgcac gcctttgtgg tccgccagcc ggctgcacca ggcctcgcgg agtccgaaat   2640
catgatgtac gtggctgaac gcgttgctcc atacaagcgc gtgcgccgcg tgaccttcgt   2700
cgatgccgtg ccacgcgcag catccggcaa gatcctgcgt cgccagctgc gcgagccacg   2760
ctaaggatct aggaggataa agaaatgaac accatcaacg aatacctgtc cctggaagag   2820
```

ttcgaagcga tcatcttcgg taaccagaag gttaccatct ccgatgtggt tgtgaaccgt 2880
gttaacgagt ccttcaactt cctcaaggag ttctccggca acaaggtcat ctacggtgtg 2940
aacaccggct tcggcccaat ggcacaatac cgtattaagg aatccgatca gatccagctt 3000
cagtacaatc tgatccgttc ccactcttcg ggcaccggaa aaccactctc cccagtttgt 3060
gctaaggcag caatcttggc tcgcctgaac accctgtccc tcggtaactc cggcgtgcat 3120
ccatctgtca tcaacctgat gtcggaactg atcaacaaag acattacccc actcatcttc 3180
gagcacggtg gcgtcggagc atccggtgac ctggttcagc tttctcacct ggctttggtt 3240
ctcatcggcg aaggcgaagt gttctacaag ggtgaacgcc gcccaactcc agaagttttc 3300
gaaattgagg gcttgaagcc aatccaggtt gagatccgtg agggcctcgc cttgattaac 3360
ggtactagcg tgatgaccgg tattggagtg gtcaacgtgt accacgcaaa gaagctgctg 3420
gactggtccc tgaagtcctc ctgcgccatc aatgaacttg ttcaggctta cgatgatcac 3480
ttcagcgcag agctgaacca gacgaagcgc cacaagggcc agcaggaaat cgctctgaag 3540
atgcgtcaga acctctctga cagcaccctg atccgcaagc gcgaggacca cctgtattcc 3600
ggcgaaaaca ccgaggagat tttcaaggag aaggtgcagg agtactactc cctgcgctgc 3660
gttccacaga ttctcggccc ggtcctcgaa actatcaata acgtcgcctc catcctggaa 3720
gatgagttca actccgctaa cgataaccca atcatcgacg tgaagaacca gcacgtgtac 3780
catggcggca acttccacgg tgactacatc tctctggaaa tggacaagtt gaaaatcgtt 3840
atcaccaaac tgaccatgct tgcagaacgc cagcttaact atcttctcaa ctccaagatc 3900
aacgaacttc tgccaccatt cgtgaacctc ggcaccctgg gtttcaactt cggcatgcag 3960
ggcgttcagt tcaccgcgac ctccaccacc gcagaatctc agatgctgtc caaccctatg 4020
tacgttcact ccattccaaa caacaacgat aaccaggaca tcgtctccat gggcaccaac 4080
tccgcagtga tcacgtccaa ggttatcgag aacgctttcg aagtcctggc tatcgaaatg 4140
atcaccatcg ttcaggccat cgattacctc ggccagaagg ataagatctc ctccgtttcc 4200
aagaagtggt acgatgaaat ccgcaacatt atccctacct tcaaggagga tcaggttatg 4260
tacccattcg tgcagaaggt taaggatcac ctcatcaaca actaa 4305

<210> SEQ ID NO 61
<211> LENGTH: 11320
<212> TYPE: DNA
<213> ORGANISM: Artificial Sequence
<220> FEATURE:
<223> OTHER INFORMATION: plasmid RpBAS-Sc4CL-SeSam8-pECXK (pECXK_U)

<400> SEQUENCE: 61
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360
agctgatttt cccgacttct acttccgcgt gaccaactcc gatcatctga tcaacctgaa 420
gcagaagttc aagcgcctat gcgaaaactc tcgcatcgag aagcgctacc tccacgtcac 480
cgaggagatc ctcaaggaaa acccaaacat cgcagcttac gaggctacta gcctgaacgt 540
gcgccacaag atgcaggtca agggcgtcgc agaactgggc aaggaagctg ctctgaaggc 600

-continued

```
tatcaaggaa tggggccagc caaagtccaa gatcacccac ctgatcgtct gctgcctggc    660
tggcgtggat atgccaggcg cagattacca gctcactaag ctcctcgatc tcgacccatc    720
cgttaagcgc ttcatgttct accacctggg ttgctacgcc ggtggcaccg tgctccgcct    780
ggctaaggat atcgctgaaa acaacaaggg cgcacgcgtg ctgatcgtgt gctctgaaat    840
gaccaccacc tgtttccgcg gcccttcaga aacccacctg gactctatga tcggccaggc    900
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat gttccgttcc gagtacgcag atgtgcctcc agtggacctc   1500
cctatccacg atgctgtcct gggtggcgcg gccgcattcg gcagcacccc agctctgatc   1560
gatggcaccg atggcaccac cctgacctac gaacaggtcg atcgcttcca ccgtcgcgtc   1620
gctgctgctc tggcggaaac cggcgtgcgc aagggcgatg tcctggccct gcactctcca   1680
aacaccgttg ctttccctct ggcattctac gctgcaaccc gcgctggtgc atccgtgacc   1740
actgttcacc ctctcgctac cgcagaagag tttgctaagc agctgaagga ttcggctgca   1800
cgttggatcg tcaccgtttc cccactgctg tccaccgcac gccgcgccgc agagttggca   1860
ggcggcgtgc aggaaatttt ggtctgcgat tctgctccag gtcaccgttc tctcgtcgat   1920
atgctggcta gcaccgcacc cgaaccatcc gtcgctatcg atccagcaga agatgtggct   1980
gcccttccgt actcctctgg caccaccggc accccaaagg gtgtgatgct gacccaccgc   2040
cagattgcaa ccaacctggc tcagctggaa ccttccatgc catccgctcc aggtgaccgg   2100
gtgctggctg ttctgccatt cttccacatc tacggcttga ccgcactcat gaacgctcct   2160
ttgcgcctgg gtgctaccgt ggtggtgctc cctcgcttcg acctggagca gttccttgca   2220
gccatccaga accaccgtat caccagtttg tacgtcgccc caccaatcgt tttggcactg   2280
gctaagcacc ctctggtggc cgactatgac ctttcctccc tccgttacat cgtgagcgcc   2340
gcggcaccgc tcgacgcgcg cctggcagcc gcttgttccc agcgtctggg cctgcccccg   2400
gtggggcaag cgtacggtat gaccgagctg tctcctggca cccacgtcgt gccgctcgat   2460
gcaatggcag atgccccacc cggcaccgtg ggtcgcctga tagctggcac cgagatgcgc   2520
atcgtgtccc tgaccgaccc aggcaccgac ctgccggcag gcgaatccgg cgaaatcctg   2580
atccgcggcc cccagattat gaagggctac ctcggccgcc cagatgctac cgcagcaatg   2640
atcgatgagg agggctggct gcacaccggc gatgtgggcc acgtggacgc tgatggttgg   2700
ttgttcgtcg tggatcgcgt taaggagctg atcaagtaca agggtttcca ggttgctccc   2760
gcggagcttg aagcacactt gctcacccac ccaggtgttg cagatgcagc tgtcgtcggc   2820
gcatacgacg acgacggtaa cgaggtgccg cacgcctttg tggtccgcca gccggctgca   2880
ccaggcctcg cggagtccga aatcatgatg tacgtggctg aacgcgttgc tccatacaag   2940
```

-continued cgcgtgcgcc gcgtgacctt cgtcgatgcc gtgccacgcg cagcatccgg caagatcctg 3000
cgtcgccagc tgcgcgagcc acgctaagga tctaggagga taaagaaatg acccaggtcg 3060
tggagcgcca ggctgatcgt ctgtccagcc gcgagtacct ggcacgcgtt gttcgttccg 3120
caggctggga cgcaggcctc accagctgca ccgatgaaga aatcgtgcgc atgggtgcat 3180
ccgcacgcac cattgaggaa tacctgaagt ctgataagcc gatctacggc ctcacccagg 3240
gcttcggtcc actggtcctg ttcgatgcag attccgaact ggaacagggc ggctctctca 3300
tctcccatct gggcaccggc cagggtgcac cgcttgcacc ggaagtgtcc cgcctgattc 3360
tgtggctccg catccaaaac atgcgcaagg gctattcggc tgtcagtcct gtgttctggc 3420
aaaaactggc cgacctctgg aacaagggct tcacccctgc tatccctcgc cacggcaccg 3480
tgtccgccag cggcgatctc cagcctctgg cacacgctgc cctggctttt accggcgtgg 3540
gcgaggcatg gacccgtgat gcagacggcc gttggtccac cgtgccagcc gtggacgcat 3600
tagcagcact gggtgcagag ccgttcgatt ggccagtgcg cgaggctttg gccttcgtga 3660
acggtacggg cgcatcactc gcggtggcag ttctcaacca cagatccgct ctccgtctcg 3720
tacgagcatg tgcagtcttg tctgcccgtt tggctacctt gctaggagct aatcctgaac 3780
actacgatgt cggccacgga gtcgcaaggg gacaagttgg ccagctgacc gcggcggaat 3840
ggattcggca gggactacca cgcggcatgg tccgagacgg ttcgcgccct cttcaagaac 3900
catacagctt gcgctgtgcc ccccaggtcc ttggcgcggt gctggaccag ctggatggtg 3960
caggcgatgt tctggcccgc gaagtggatg gctgccagga caatcctatc acctacgagg 4020
gcgaactgct gcacggcggt aacttccacg ctatgccagt cggcttcgca tccgaccaga 4080
tcggtctggc gatgcacatg gcagcttatc tggctgaacg ccagctcggc ctgctggtga 4140
gcccggtgac caacggcgac ctgccaccaa tgctgacccc acgcgctgga cgcggtgccg 4200
gcctggcggg cgttcagatc tccgcaacct ccttcgtctc tcgcatccgc cagctggtgt 4260
tcccagctag cctcaccacc ctcccaacca acggctggaa ccaggaccat gtcccaatgg 4320
ctctgaacgg cgcaaacagc gtgttcgaag ctcttgaact gggttggctg accgtgggta 4380
gcctggcagt cggcgtggcc cagctcgctg caatgaccgg ccacgcagct gagggcgtgt 4440
gggccgagtt ggcaggcatc tgcccaccac tggatgctga ccgcccactg ggcgcggagg 4500
tccgcgctgc tcgcgatctc ctctccgcac acgctgacca gctgctcgtt gacgaggctg 4560
atggcaaaga cttcggctaa ctctagagtc gacctgcagg catgcaagct tggctgtttt 4620
ggcggatgag agaagatttt cagcctgata cagattaaat cagaacgcag aagcggtctg 4680
ataaaacaga atttgcctgg cggcagtagc gcggtggtcc cacctgaccc catgccgaac 4740
tcagaagtga aacgccgtag cgccgatggt agtgtggggt ctccccatgc gagagtaggg 4800
aactgccagg catcaaataa aacgaaaggc tcagtcgaaa gactgggcct ttcgttttat 4860
ctgttgtttg tcggtgaacg ctctcctgag taggacaaat ccgccgggag cggatttgaa 4920
cgttgcgaag caacggcccg gagggtggcg ggcaggacgc ccgccataaa ctgccaggca 4980
tcaaattaag cagaaggcca tcctgacgga tggccttttt gcgtttctac aaactctttt 5040
tgtttatttt tctaaataca ttcaaatatg tatccgctca tgaattaatt ccgctagatg 5100
acgtgcggct tcgacctcct gggcgtggcg cttgttggcg cgctcgcggc tggctgcggc 5160
acgacacgcg tctgagcagt attttgcgcg ccgtcctcgt gggtcaggcc ggggtgggat 5220
caggccaccg cagtaggcgc agctgatgcg atcctccact actgcgcgtc ctcctggcgc 5280
tgccgagcac gcagctcgtc ggccagctct tcaaggtcgg ccacaagcgt ttctaggtcg 5340
ctcgcggcac ttgcccagtc gcgtgatgct ggcgcgtctg tcgtatcgag ggcgcggaaa 5400
aatccgatca ccgtttttaa atcgacggcg gcatcgagtg cgtcggactc cagcgcgaca 5460
tcggagagat ccaccgctga tgcttcaggc cagttttggt acttcgtcgt gaaggtcatg 5520
acaccattat aacgaacgtt cgttaaaaat tctagcccca attctgataa tttcttccgg 5580
cactcctgcg aaaacctgcg agacttcttg cccagaaaaa acgccaagcg cagcggttac 5640
cgcacttttt ttccaggtga tttcaccctg accagcgaag cggcacttta gtgcatgagg 5700
tgtgcccctg gtttcccctc tttggagggt tcaacccaaa aaagcacaca agcaaaaatg 5760
aaaatcatca tgagcaagtt ggtgcgaagc agcaacgcgc tagctccaaa aaggtctcca 5820
ggatctcgag gagatttttg agggggaggg agtcgaggaa gagccagagc agaaggcggg 5880
gaaccgttct ctgccgacag cgtgagcccc ccttaaaaat caggccgggg aggaaccggg 5940
gagggatcag agctaggagc gagacaccct aaaggggggg aaccgttttc tgctgacggt 6000
gtttcgttta ttagttttca gcccgtggat agcggagggt gagggcaagt gagagccaga 6060
gcaaggacgg gacccctaaa ggggggaacc gttttctgct gacggtgttt cgtttattag 6120
ttttcagccc gtggacggcc gcgtttagct tccattccaa gtgcctttct gacttgttgg 6180
atgcgccttt cactgacacc tagttcgcct gcaagctcac gagtcgaggg atcagcaacc 6240
gattgagaac gggcatccag gatcgcagtt ttgacgcgaa gttcgagcaa ctcgcctgtc 6300
atttctcggc gtttgtttgc ttccgctaat cgctgtcgcg tctcctgcgc atacttactt 6360
tctgggtcag cccatctgcg tgcattcgat gtagctgcgc cccgtcgccc catcgtcgct 6420
agagctttcc gccctcggct gctctgcgtt tccacccgac gagcagggac gactggctgg 6480
cctttagcca cgtagccgcg cacacgacgc gccatcgtca ggcgatcacg catggcggga 6540
agatccggct cccggccgtc tgcaccgacc gcctgggcaa cgttgtacgc cacttcatac 6600
gcgtcgatga tcttggcatc ttttaggcgc tcaccagcag ctttgagctg gtatcccacg 6660
gtcaacgcgt ggcgaaacgc ggtctcgtcg cgcgctcgct ctggatttgt ccagagcact 6720
cgcacgccgt cgatcaggtc gccggacgcg tccagggcgc tcggcaggct cgcgtccaaa 6780
atcgctagcg ccttggcttc tgcggtggcg cgttgtgccg cttcaatgcg ggcgcgtccg 6840
ctggaaaagt cctgctcaat gtactttttc ggcttctgtg atccggtcat cgttcgagca 6900
atctccatta ggtcggccag ccgatccaca cgatcatgct ggcagtgcca tttataggct 6960
gtcggatcgt ctgagacgtg cagcggccac cggctcagcc tatgcgaaaa agcctggtca 7020
gcgccgaaaa cacgagtcat ttcttccgtc gttgcagcca gcaggcgcat atttgggctg 7080
gttttacctg ctgcggcata caccgggtca atgagccaga tgagctggca tttcccgctc 7140
agcggattca cgccgatcca agccggcgct tttctaggc gtgcccattt ctctaaaatc 7200
gcgtagacct gcgggtttac gtgctcaatc ttcccgccgg cctggtggct gggcacatcg 7260
atgtcaagca cgatcaccgc ggcatgttgc gcgtgcgtca gcgcaacgta ctggcaccgc 7320
gtcagcgctt ttgagccagc ccggtagagc tttggttggg tttcgccggt atccgggttt 7380
ttaatccagg cgctcgcgaa atctcttgtc ttgctgccct ggaagctttc gcgtcccagg 7440
tgagcgagca gttcgcggcg atcttctgcc gtccagccgc gtgagccgca gcgcatagct 7500
tcggggtggg tgtcgaacag atcggcggac aatttccacg cgctagctgt gactgtgtcc 7560
tgcggatcgg ctagagtcat gtcttgagtg ctttctccca gctgatgact gggggttagc 7620
cgacgccctg tgagttcccg ctcacggggc gttcaacttt ttcaggtatt tgtgcagctt 7680

-continued

```
atcgtgtttt cttcgtaaat gaacgcttaa ctaccttgtt aaacgtggca aataggcagg   7740
attgatgggg atctagcttc acgctgccgc aagcactcag ggcgcaaggg ctgctaaagg   7800
aagcggaaca cgtagaaagc cagtccgcag aaacggtgct gaccccggat gaatgtcagc   7860
tactgggcta tctggacaag ggaaaacgca agcgcaaaga gaaagcaggt agcttgcagt   7920
gggcttacat ggcgatagct agactgggcg gttttatgga cagcaagcga accggaattg   7980
ccagctgggg cgccctctgg taaggttggg aagccctgca aagtaaactg gatggctttc   8040
ttgccgccaa ggatctgatg gcgcagggga tcaagatctg atcaagagac aggatgagga   8100
tcgtttcgca tgattgaaca agatggattg cacgcaggtt ctccggccgc ttgggtggag   8160
aggctattcg gctatgactg ggcacaacag acaatcggct gctctgatgc cgccgtgttc   8220
cggctgtcag cgcaggggcg cccggttctt tttgtcaaga ccgacctgtc cggtgccctg   8280
aatgaactcc aagacgaggc agcgcggcta tcgtggctgg ccacgacggg cgttccttgc   8340
gcagctgtgc tcgacgttgt cactgaagcg ggaagggact ggctgctatt gggcgaagtg   8400
ccggggcagg atctcctgtc atctcacctt gctcctgccg agaaagtatc catcatggct   8460
gatgcaatgc ggcggctgca tacgcttgat ccggctacct gcccattcga ccaccaagcg   8520
aaacatcgca tcgagcgagc acgtactcgg atggaagccg gtcttgtcga tcaggatgat   8580
ctggacgaag agcatcaggg gctcgcgcca gccgaactgt tcgccaggct caaggcgcgg   8640
atgcccgacg gcgaggatct cgtcgtgacc catggcgatg cctgcttgcc gaatatcatg   8700
gtggaaaatg gccgcttttc tggattcatc gactgtggcc ggctgggtgt ggcggaccgc   8760
tatcaggaca tagcgttggc tacccgtgat attgctgaag agcttggcgg cgaatgggct   8820
gaccgcttcc tcgtgcttta cggtatcgcc gctcccgatt cgcagcgcat cgccttctat   8880
cgccttcttg acgagttctt ctgagcggga ctctggggtt cgcggaatca tgaccaaaat   8940
cccttaacgt gagttttcgt tccactgagc gtcagacccc gtagaaaaga tcaaaggatc   9000
ttcttgagat cctttttttc tgcgcgtaat ctgctgcttg caaacaaaaa aaccaccgct   9060
accagcggtg gtttgtttgc cggatcaaga gctaccaact ctttttccga aggtaactgg   9120
cttcagcaga gcgcagatac caaatactgt ccttctagtg tagccgtagt taggccacca   9180
cttcaagaac tctgtagcac cgcctacata cctcgctctg ctaatcctgt taccagtggc   9240
tgctgccagt ggcgataagt cgtgtcttac cgggttggac tcaagacgat agttaccgga   9300
taaggcgcag cggtcgggct gaacgggggg ttcgtgcaca cagcccagct tggagcgaac   9360
gacctacacc gaactgagat acctacagcg tgagctatga gaaagcgcca cgcttcccga   9420
agggagaaag gcggacaggt atccggtaag cggcagggtc ggaacaggag agcgcacgag   9480
ggagcttcca gggggaaacg cctggtatct ttatagtcct gtcgggtttc gccacctctg   9540
acttgagcgt cgatttttgt gatgctcgtc aggggggcgg agcctatgga aaaacgccag   9600
caacgcggcc tttttacggt tcctggcctt ttgctggcct tttgctcaca tgttctttcc   9660
tgcgttatcc cctgattctg tggataaccg tattaccgcc tttgagtgag ctgataccgc   9720
tcgccgcagc cgaacgaccg agcgcagcga gtcagtgagc gaggaagcgg aagagcgcct   9780
gatgcggtat tttctcctta cgcatctgtg cggtatttca caccgcatat ggtgcactct   9840
cagtacaatc tgctctgatg ccgcatagtt aagccagtat acactccgct atcgctacgt   9900
gactgggtca tggctgcgcc ccgacacccg ccaacacccg ctgacgcgcc ctgacgggct   9960
tgtctgctcc cggcatccgc ttacagacaa gctgtgaccg tctccgggag ctgcatgtgt  10020
cagaggtttt caccgtcatc accgaaacgc gcgaggcagc agatcaattc gcgcgcgaag  10080
```

```
gcgaagcggc atgcatttac gttgacacca tcgaatggtg caaaaccttt cgcggtatgg  10140
catgatagcg cccggaagag agtcaattca gggtggtgaa tgtgaaacca gtaacgttat  10200
acgatgtcgc agagtatgcc ggtgtctctt atcagaccgt ttcccgcgtg gtgaaccagg  10260
ccagccacgt ttctgcgaaa acgcgggaaa aagtggaagc ggcgatggcg gagctgaatt  10320
acattcccaa ccgcgtggca caacaactgg cgggcaaaca gtcgttgctg attggcgttg  10380
ccacctccag tctggccctg cacgcgccgt cgcaaattgt cgcggcgatt aaatctcgcg  10440
ccgatcaact gggtgccagc gtggtggtgt cgatggtaga acgaagcggc gtcgaagcct  10500
gtaaagcggc ggtgcacaat cttctcgcgc aacgcgtcag tgggctgatc attaactatc  10560
cgctggatga ccaggatgcc attgctgtgg aagctgcctg cactaatgtt ccggcgttat  10620
ttcttgatgt ctctgaccag acacccatca acagtattat tttctcccat gaagacggta  10680
cgcgactggg cgtggagcat ctggtcgcat tgggtcacca gcaaatcgcg ctgttagcgg  10740
gcccattaag ttctgtctcg gcgcgtctgc gtctggctgg ctggcataaa tatctcactc  10800
gcaatcaaat tcagccgata gcggaacggg aaggcgactg gagtgccatg tccggttttc  10860
aacaaaccat gcaaatgctg aatgagggca tcgttcccac tgcgatgctg gttgccaacg  10920
atcagatggc gctgggcgca atgcgcgcca ttaccgagtc cgggctgcgc gttggtgcgg  10980
atatctcggt agtgggatac gacgataccg aagacagctc atgttatatc ccgccgtcaa  11040
ccaccatcaa acaggatttt cgcctgctgg ggcaaaccag cgtggaccgc ttgctgcaac  11100
tctctcaggg ccaggcggtg aagggcaatc agctgttgcc cgtctcactg gtgaaaagaa  11160
aaaccaccct ggcgcccaat acgcaaaccg cctctccccg cgcgttggcc gattcattaa  11220
tgcagctggc acgacaggtt tcccgactgg aaagcgggca gtgagcgcaa cgcaattaat  11280
gtgagttagc gcgaattgat ctggtttgac agcttatcat                        11320
```

<210> SEQ ID NO 62
<211> LENGTH: 4317
<212> TYPE: DNA
<213> ORGANISM: Artificial Sequence
<220> FEATURE:
<223> OTHER INFORMATION: operon RpBAS-Sc4CL-SeSam8

<400> SEQUENCE: 62

```
ggatctagga gggagatcat atggcaaccg aggagatgaa gaagctcgca accgtgatgg     60
caatcggcac tgctaaccca ccgaactgct attaccaagc tgattttccc gacttctact    120
tccgcgtgac caactccgat catctgatca acctgaagca gaagttcaag cgcctatgcg    180
aaaactctcg catcgagaag cgctacctcc acgtcaccga ggagatcctc aaggaaaacc    240
caaacatcgc agcttacgag gctactagcc tgaacgtgcg ccacaagatg caggtcaagg    300
gcgtcgcaga actgggcaag gaagctgctc tgaaggctat caaggaatgg ggccagccaa    360
agtccaagat cacccacctg atcgtctgct gcctggctgg cgtggatatg ccaggcgcag    420
attaccagct cactaagctc ctcgatctcg acccatccgt taagcgcttc atgttctacc    480
acctgggttg ctacgccggt ggcaccgtgc tccgcctggc taaggatatc gctgaaaaca    540
acaagggcgc acgcgtgctg atcgtgtgct ctgaaatgac caccacctgt ttccgcggcc    600
cttcagaaac ccacctggac tctatgatcg gccaggccat cctcggtgac ggtgccgcag    660
ccgtgatcgt gggcgcggac cctgatctga ccgtggagcg tccaatcttc gagctggtga    720
gcacggctca gaccatcgtg ccggagtccc acggcgccat cgagggccac ctcctggagt    780
```

-continued

```
ctggcctgag cttccacctg tacaagaccg tgccgaccct gatctccaac aacatcaaga    840
cctgcctctc cgatgctttc accccactga acatctccga ctggaacagc ctcttctgga    900
tcgcacaccc aggcggcccg gccatcctgg atcaggtgac cgctaaggtg ggcctggaaa    960
aggaaaagct gaaggtgacc cgccaggttc tgaaggatta cggcaacatg tcctccgcta   1020
ccgtgttctt catcatggat gaaatgcgta agaagtccct ggaaaacggc caggcaacca   1080
ccggcgaggg cctggaatgg ggcgtgctgt tcggcttcgg cccaggcatc accgtggaaa   1140
ccgtggtcct gcgctccgtc ccagtgatct cctaaggatc taggaggatt atgagatgtt   1200
ccgttccgag tacgcagatg tgcctccagt ggacctccct atccacgatg ctgtcctggg   1260
tggcgcggcc gcattcggca gcaccccagc tctgatcgat ggcaccgatg gcaccaccct   1320
gacctacgaa caggtcgatc gcttccaccg tcgcgtcgct gctgctctgg cggaaaccgg   1380
cgtgcgcaag ggcgatgtcc tggccctgca ctctccaaac accgttgctt tccctctggc   1440
attctacgct gcaacccgcg ctggtgcatc cgtgaccact gttcaccctc tcgctaccgc   1500
agaagagttt gctaagcagc tgaaggattc ggctgcacgt tggatcgtca ccgtttcccc   1560
actgctgtcc accgcacgcc gcgccgcaga gttggcaggc ggcgtgcagg aaattttggt   1620
ctgcgattct gctccaggtc accgttctct cgtcgatatg ctggctagca ccgcacccga   1680
accatccgtc gctatcgatc cagcagaaga tgtggctgcc cttccgtact cctctggcac   1740
caccggcacc ccaaagggtg tgatgctgac ccaccgccag attgcaacca acctggctca   1800
gctggaacct tccatgccat ccgctccagg tgaccgggtg ctggctgttc tgccattctt   1860
ccacatctac ggcttgaccg cactcatgaa cgctcctttg cgcctgggtg ctaccgtggt   1920
ggtgctccct cgcttcgacc tggagcagtt ccttgcagcc atccagaacc accgtatcac   1980
cagtttgtac gtcgccccac caatcgtttt ggcactggct aagcaccctc tggtggccga   2040
ctatgacctt tcctccctcc gttacatcgt gagcgccgcg gcaccgctcg acgcgcgcct   2100
ggcagccgct tgttcccagc gtctgggcct gcccccggtg gggcaagcgt acggtatgac   2160
cgagctgtct cctggcaccc acgtcgtgcc gctcgatgca atggcagatg ccccacccgg   2220
caccgtgggt cgcctgatag ctggcaccga gatgcgcatc gtgtccctga ccgacccagg   2280
caccgacctg ccggcaggcg aatccggcga aatcctgatc cgcggccccc agattatgaa   2340
gggctacctc ggccgcccag atgctaccgc agcaatgatc gatgaggagg gctggctgca   2400
caccggcgat gtgggccacg tggacgctga tggttggttg ttcgtcgtgg atcgcgttaa   2460
ggagctgatc aagtacaagg gtttccaggt tgctcccgcg gagcttgaag cacacttgct   2520
cacccaccca ggtgttgcag atgcagctgt cgtcggcgca tacgacgacg acggtaacga   2580
ggtgccgcac gcctttgtgg tccgccagcc ggctgcacca ggcctcgcgg agtccgaaat   2640
catgatgtac gtggctgaac gcgttgctcc atacaagcgc gtgcgccgcg tgaccttcgt   2700
cgatgccgtg ccacgcgcag catccggcaa gatcctgcgt cgccagctgc gcgagccacg   2760
ctaaggatct aggaggataa agaaatgacc caggtcgtgg agcgccaggc tgatcgtctg   2820
tccagccgcg agtacctggc acgcgttgtt cgttccgcag gctgggacgc aggcctcacc   2880
agctgcaccg atgaagaaat cgtgcgcatg ggtgcatccg cacgcaccat tgaggaatac   2940
ctgaagtctg ataagccgat ctacggcctc acccagggct tcggtccact ggtcctgttc   3000
gatgcagatt ccgaactgga acagggcggc tctctcatct cccatctggg caccggccag   3060
ggtgcaccgc ttgcaccgga agtgtcccgc ctgattctgt ggctccgcat ccaaaacatg   3120
cgcaagggct attcggctgt cagtcctgtg ttctggcaaa aactggccga cctctggaac   3180
```

aagggcttca cccctgctat ccctcgccac ggcaccgtgt ccgccagcgg cgatctccag 3240
cctctggcac acgctgccct ggcttttacc ggcgtgggcg aggcatggac ccgtgatgca 3300
gacggccgtt ggtccaccgt gccagccgtg gacgcattag cagcactggg tgcagagccg 3360
ttcgattggc cagtgcgcga ggctttggcc ttcgtgaacg gtacgggcgc atcactcgcg 3420
gtggcagttc tcaaccacag atccgctctc cgtctcgtac gagcatgtgc agtcttgtct 3480
gcccgtttgg ctaccttgct aggagctaat cctgaacact acgatgtcgg ccacggagtc 3540
gcaaggggac aagttggcca gctgaccgcg gcggaatgga ttcggcaggg actaccacgc 3600
ggcatggtcc gagacggttc gcgccctctt caagaaccat acagcttgcg ctgtgccccc 3660
caggtccttg gcgcggtgct ggaccagctg gatggtgcag gcgatgttct ggcccgcgaa 3720
gtggatggct gccaggacaa tcctatcacc tacgagggcg aactgctgca cggcggtaac 3780
ttccacgcta tgccagtcgg cttcgcatcc gaccagatcg gtctggcgat gcacatggca 3840
gcttatctgg ctgaacgcca gctcggcctg ctggtgagcc cggtgaccaa cggcgacctg 3900
ccaccaatgc tgaccccacg cgctggacgc ggtgccggcc tggcgggcgt tcagatctcc 3960
gcaacctcct tcgtctctcg catccgccag ctggtgttcc cagctagcct caccaccctc 4020
ccaaccaacg gctggaacca ggaccatgtc ccaatggctc tgaacggcgc aaacagcgtg 4080
ttcgaagctc ttgaactggg ttggctgacc gtgggtagcc tggcagtcgg cgtggcccag 4140
ctcgctgcaa tgaccggcca cgcagctgag ggcgtgtggg ccgagttggc aggcatctgc 4200
ccaccactgg atgctgaccg cccactgggc gcggaggtcc gcgctgctcg cgatctcctc 4260
tccgcacacg ctgaccagct gctcgttgac gaggctgatg gcaaagactt cggctaa 4317

<210> SEQ ID NO 63
<211> LENGTH: 11443
<212> TYPE: DNA
<213> ORGANISM: Artificial Sequence
<220> FEATURE:
<223> OTHER INFORMATION: plasmid RpBAS-Nt4CL-RcTAL-pECXK (pECXK_V)

<400> SEQUENCE: 63
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360
agctgatttt cccgacttct acttccgcgt gaccaactcc gatcatctga tcaacctgaa 420
gcagaagttc aagcgcctat gcgaaaactc tcgcatcgag aagcgctacc tccacgtcac 480
cgaggagatc ctcaaggaaa acccaaacat cgcagcttac gaggctacta gcctgaacgt 540
gcgccacaag atgcaggtca agggcgtcgc agaactgggc aaggaagctg ctctgaaggc 600
tatcaaggaa tggggccagc caaagtccaa gatcacccac ctgatcgtct gctgcctggc 660
tggcgtggat atgccaggcg cagattacca gctcactaag ctcctcgatc tcgacccatc 720
cgttaagcgc ttcatgttct accacctggg ttgctacgcc ggtggcaccg tgctccgcct 780
ggctaaggat atcgctgaaa acaacaaggg cgcacgcgtg ctgatcgtgt gctctgaaat 840
gaccaccacc tgtttccgcg gcccttcaga aacccacctg gactctatga tcggccaggc 900

```
catcctcggt gacggtgccg cagccgtgat cgtgggcgcg gaccctgatc tgaccgtgga    960
gcgtccaatc ttcgagctgg tgagcacggc tcagaccatc gtgccggagt cccacggcgc   1020
catcgagggc cacctcctgg agtctggcct gagcttccac ctgtacaaga ccgtgccgac   1080
cctgatctcc aacaacatca agacctgcct ctccgatgct ttcaccccac tgaacatctc   1140
cgactggaac agcctcttct ggatcgcaca cccaggcggc ccggccatcc tggatcaggt   1200
gaccgctaag gtgggcctgg aaaaggaaaa gctgaaggtg acccgccagg ttctgaagga   1260
ttacggcaac atgtcctccg ctaccgtgtt cttcatcatg gatgaaatgc gtaagaagtc   1320
cctggaaaac ggccaggcaa ccaccggcga gggcctggaa tggggcgtgc tgttcggctt   1380
cggcccaggc atcaccgtgg aaaccgtggt cctgcgctcc gtcccagtga tctcctaagg   1440
atctaggagg attatgagat ggagaaagat acaaaacagg ttgacataat tttccgatca   1500
aaactccctg atatttacat ccctaaccat cttcctttac actcctactg tttcgaaaac   1560
atttccgagt tcagttctcg tccttgttta atcaatggcg ccaacaaaca aatttatacg   1620
tatgctgatg ttgaactcaa ttcaagaaaa gttgctgctg gtcttcacaa acaagggatt   1680
caaccaaagg atacaataat gatcctattg cctaactccc cagaatttgt gtttgctttc   1740
attggtgcat cgtacctcgg agctatttct acaatggcca atcctttgtt tactcctgct   1800
gaggttgtga agcaagccga ggcttctagt gctaagatca ttgtcacaca agcgtgtcat   1860
gttaacaaag tgaaagatta tgcatttgag aatgatgtga agatcatatg catcgactcg   1920
gcgccggagg gttgtctcca cttctccgtg ctaactcagg ctaatgagca cgatattcct   1980
gaggttgaaa ttcaacctga cgatgtggtg gcgttgccat actcctccgg gacgacggga   2040
ttacctaaag gagtgatgtt gacgcacaag ggacttgtga caagcgtcgc acaacaagtc   2100
gacggtgaaa atccgaattt gtatatccat agcgaggacg tgatgctttg tgtcttgccc   2160
ttgttccata tctattcact caactccgtt ttgctttgtg gattaagggt gggagcagcg   2220
attttgatta tgcagaaatt tgatattgtt tctttcttgg agttgataca aagttacaag   2280
gtgacaatag ggccgtttgt accacctatt gttttggyca ttgctaagag tcctatggtt   2340
gatgattatg atctttcatc agtaagaacc gtcatgtctg gggctgcacc attaggaaag   2400
gagcttgaag atactgttcg agccaaattt cctaatgcta aacttggtca gggttatggt   2460
atgacagaag ctggaccagt gttggctatg tgcttggcat ttgcaaaaga accctttgaa   2520
ataaaatcag gggcatgtgg aacagttgtg agaaatgctg aaatgaaaat tgtggatcct   2580
aaaactggta attctcttcc cagaaatcaa tctggagaaa tttgcattag aggagaccag   2640
atcatgaaag gctacctgaa tgatccagag gccacagcaa gaacaataga caaagaaggg   2700
tggttatata ctggtgacat tggctacatt gatgatgacg acgagctttt cattgttgat   2760
cgattaaagg aactgatcaa atacaaagga tttcaagtcg cacctgctga gctcgaagct   2820
ctccttctca accatcccaa catttctgat gctgctgttg tccccatgaa ggacgagcaa   2880
gcaggagaag ttccagtggc ttttgttgtt agatccaacg gatccaccat tactgaagat   2940
gaagtcaaag attttatttc aaagcaggtg atattttata agaggataaa gcgggtattt   3000
ttcgtggatg ctattcctaa atctccatct ggcaaaatcc ttcgaaaaga tttgagagct   3060
aaactggctg ctgggcttcc aaattaagga tctaggagga taaagaaatg accctgcaat   3120
cccagactgc aaaggactgc ctggcgctgg atggtgcact gacactggtt cagtgcgaag   3180
caattgccac tcaccgctca cggatctccg tcacaccagc attgcgggaa cgctgcgccc   3240
gcgcgcacgc acgtctggag cacgctatcg cagaacagcg tcacatctat ggtatcacca   3300
```

-continued ccggcttcgg accactggct aatcgcctga tcggtgcaga tcagggcgcc gaactccagc 3360
agaacctcat ctaccacctt gctactggcg tgggcccaaa actctcctgg gctgaagcac 3420
gtgcactcat gctggctcgt ctcaactcca tccttcaggg cgcatctggt gcatcaccag 3480
aaaccatcga ccgtatcgtt gccgttctga acgctggctt cgccccagaa gtcccagctc 3540
agggcaccgt tggtgcatct ggcgatctga ccccactggc tcacatggtg ctggcgcttc 3600
agggtcgagg tcgtatgatc gatccatccg gccgtgttca ggaagccggc gcagtgatgg 3660
atcgcctgtg cggtggccca ctgaccttgg cagcccgtga cggtctggct ctggtcaacg 3720
gtacttccgc tatgaccgca atcgctgctt tgaccggtgt ggaggctgcg cgcgcaatcg 3780
acgccgcatt gcgccactcc gctgtgctca tggaggttct ctccggccac gctgaggctt 3840
ggcaccctgc atttgctgaa ctccgcccac acccaggcca gctgcgcgca accgaacgtc 3900
tggcccaggc tctcgatggc gccggtcgcg tttgccgcac cttgaccgcg gcccgtcgcc 3960
tgaccgcagc tgatctgcgc cctgaggatc acccagccca ggacgcctac tccctgcgcg 4020
tggtgccaca gctggttggc gctgtctggg acaccctcga ttggcacgat cgcgtcgtga 4080
cctgcgaact caactctgtg accgacaacc caatcttccc ggaaggctgc gctgttccag 4140
cactgcacgg cggcaacttc atgggcgtgc acgtcgcact ggcgtcggac gccctgaacg 4200
ctgcattggt taccctggca ggtctggtgg agcgccagat cgcacgcctt actgatgaga 4260
agctgaacaa gggacttccg gcattccttc acggtggtca ggctggcctt cagtccggct 4320
tcatgggcgc gcaggtcacc gcaaccgcgc tccttgctga aatgcgcgca aacgcaaccc 4380
cggtgtctgt tcagtcactg tctaccaacg gcgctaacca ggatgttgtc agcatgggca 4440
ccatcgctgc acgccgcgct cgcgcacagc tgctcccact gtcccagatt caggcaatcc 4500
tggctctcgc tctcgcccag gcaatggatc tgctggatga tccagagggc caggctggct 4560
ggtcccttac cgcacgcgac ctgcgcgatc gcatccgcgc tgtctcgccg ggcctgcgcg 4620
cagatcgccc actggccggc cacatcgagg cagtcgctca gggtctgcgc cacccttccg 4680
cagcagctga tccaccagca taactctaga gtcgacctgc aggcatgcaa gcttggctgt 4740
tttggcggat gagagaagat tttcagcctg atacagatta aatcagaacg cagaagcggt 4800
ctgataaaac agaatttgcc tggcggcagt agcgcggtgg tcccacctga ccccatgccg 4860
aactcagaag tgaaacgccg tagcgccgat ggtagtgtgg ggtctcccca tgcgagagta 4920
gggaactgcc aggcatcaaa taaaacgaaa ggctcagtcg aaagactggg cctttcgttt 4980
tatctgttgt ttgtcggtga acgctctcct gagtaggaca aatccgccgg gagcggattt 5040
gaacgttgcg aagcaacggc ccggagggtg gcgggcagga cgcccgccat aaactgccag 5100
gcatcaaatt aagcagaagg ccatcctgac ggatggcctt tttgcgtttc tacaaactct 5160
ttttgtttat ttttctaaat acattcaaat atgtatccgc tcatgaatta attccgctag 5220
atgacgtgcg gcttcgacct cctgggcgtg gcgcttgttg gcgcgctcgc ggctggctgc 5280
ggcacgacac gcgtctgagc agtattttgc gcgccgtcct cgtgggtcag gccggggtgg 5340
gatcaggcca ccgcagtagg cgcagctgat gcgatcctcc actactgcgc gtcctcctgg 5400
cgctgccgag cacgcagctc gtcggccagc tcttcaaggt cggccacaag cgtttctagg 5460
tcgctcgcgg cacttgccca gtcgcgtgat gctggcgcgt ctgtcgtatc gagggcgcgg 5520
aaaaatccga tcaccgtttt taaatcgacg gcggcatcga gtgcgtcgga ctccagcgcg 5580
acatcggaga gatccaccgc tgatgcttca ggccagtttt ggtacttcgt cgtgaaggtc 5640

```
atgacaccat tataacgaac gttcgttaaa aattctagcc ccaattctga taatttcttc   5700
cggcactcct gcgaaaacct gcgagacttc ttgcccagaa aaaacgccaa gcgcagcggt   5760
taccgcactt tttttccagg tgatttcacc ctgaccagcg aagcggcact ttagtgcatg   5820
aggtgtgccc ctggtttccc ctctttggag ggttcaaccc aaaaaagcac acaagcaaaa   5880
atgaaaatca tcatgagcaa gttggtgcga agcagcaacg cgctagctcc aaaaaggtct   5940
ccaggatctc gaggagattt ttgaggggga gggagtcgag gaagagccag agcagaaggc   6000
ggggaaccgt tctctgccga cagcgtgagc ccccccttaaa aatcaggccg gggaggaacc   6060
ggggagggat cagagctagg agcgagacac cctaaagggg gggaaccgtt ttctgctgac   6120
ggtgtttcgt ttattagttt tcagcccgtg gatagcggag ggtgagggca agtgagagcc   6180
agagcaagga cgggacccct aaaggggga accgttttct gctgacggtg tttcgtttat   6240
tagttttcag cccgtggacg gccgcgttta gcttccattc caagtgcctt tctgacttgt   6300
tggatgcgcc tttcactgac acctagttcg cctgcaagct cacgagtcga gggatcagca   6360
accgattgag aacgggcatc caggatcgca gttttgacgc gaagttcgag caactcgcct   6420
gtcatttctc ggcgtttgtt tgcttccgct aatcgctgtc gcgtctcctg cgcatactta   6480
ctttctgggt cagcccatct gcgtgcattc gatgtagctg cgccccgtcg ccccatcgtc   6540
gctagagctt tccgccctcg gctgctctgc gtttccaccc gacgagcagg gacgactggc   6600
tggcctttag ccacgtagcc gcgcacacga cgcgccatcg tcaggcgatc acgcatggcg   6660
ggaagatccg gctcccggcc gtctgcaccg accgcctggg caacgttgta cgccacttca   6720
tacgcgtcga tgatcttggc atcttttagg cgctcaccag cagctttgag ctggtatccc   6780
acggtcaacg cgtggcgaaa cgcggtctcg tcgcgcgctc gctctggatt tgtccagagc   6840
actcgcacgc cgtcgatcag gtcgccggac gcgtccaggg cgctcggcag gctcgcgtcc   6900
aaaatcgcta gcgccttggc ttctgcggtg gcgcgttgtg ccgcttcaat gcgggcgcgt   6960
ccgctggaaa agtcctgctc aatgtacttt ttcggcttct gtgatccggt catcgttcga   7020
gcaatctcca ttaggtcggc cagccgatcc acacgatcat gctggcagtg ccatttatag   7080
gctgtcggat cgtctgagac gtgcagcggc caccggctca gcctatgcga aaaagcctgg   7140
tcagcgccga aaacacgagt catttcttcc gtcgttgcag ccagcaggcg catatttggg   7200
ctggttttac ctgctgcggc atacaccggg tcaatgagcc agatgagctg gcatttcccg   7260
ctcagcggat tcacgccgat ccaagccggc gctttttcta ggcgtgccca tttctctaaa   7320
atcgcgtaga cctgcgggtt tacgtgctca atcttcccgc cggcctggtg gctgggcaca   7380
tcgatgtcaa gcacgatcac cgcggcatgt tgcgcgtgcg tcagcgcaac gtactggcac   7440
cgcgtcagcg cttttgagcc agcccggtag agctttggtt gggtttcgcc ggtatccggg   7500
tttttaatcc aggcgctcgc gaaatctctt gtcttgctgc cctggaagct ttcgcgtccc   7560
aggtgagcga gcagttcgcg gcgatcttct gccgtccagc cgcgtgagcc gcagcgcata   7620
gcttcggggt gggtgtcgaa cagatcggcg gacaatttcc acgcgctagc tgtgactgtg   7680
tcctgcggat cggctagagt catgtcttga gtgctttctc ccagctgatg actgggggtt   7740
agccgacgcc ctgtgagttc ccgctcacgg ggcgttcaac tttttcaggt atttgtgcag   7800
cttatcgtgt tttcttcgta aatgaacgct taactacctt gttaaacgtg gcaaataggc   7860
aggattgatg ggatctagc ttcacgctgc cgcaagcact cagggcgcaa gggctgctaa   7920
aggaagcgga acacgtagaa agccagtccg cagaaacggt gctgaccccg gatgaatgtc   7980
agctactggg ctatctggac aagggaaaac gcaagcgcaa agagaaagca ggtagcttgc   8040
```

-continued

```
agtgggctta catggcgata gctagactgg gcggttttat ggacagcaag cgaaccggaa   8100
ttgccagctg gggcgccctc tggtaaggtt gggaagccct gcaaagtaaa ctggatggct   8160
ttcttgccgc caaggatctg atggcgcagg ggatcaagat ctgatcaaga gacaggatga   8220
ggatcgtttc gcatgattga acaagatgga ttgcacgcag gttctccggc cgcttgggtg   8280
gagaggctat tcggctatga ctgggcacaa cagacaatcg gctgctctga tgccgccgtg   8340
ttccggctgt cagcgcaggg gcgcccggtt ctttttgtca agaccgacct gtccggtgcc   8400
ctgaatgaac tccaagacga ggcagcgcgg ctatcgtggc tggccacgac gggcgttcct   8460
tgcgcagctg tgctcgacgt tgtcactgaa gcgggaaggg actggctgct attgggcgaa   8520
gtgccggggc aggatctcct gtcatctcac cttgctcctg ccgagaaagt atccatcatg   8580
gctgatgcaa tgcggcggct gcatacgctt gatccggcta cctgcccatt cgaccaccaa   8640
gcgaaacatc gcatcgagcg agcacgtact cggatggaag ccggtcttgt cgatcaggat   8700
gatctggacg aagagcatca ggggctcgcg ccagccgaac tgttcgccag gctcaaggcg   8760
cggatgcccg acggcgagga tctcgtcgtg acccatggcg atgcctgctt gccgaatatc   8820
atggtggaaa atggccgctt ttctggattc atcgactgtg gccggctggg tgtggcggac   8880
cgctatcagg acatagcgtt ggctacccgt gatattgctg aagagcttgg cggcgaatgg   8940
gctgaccgct tcctcgtgct ttacggtatc gccgctcccg attcgcagcg catcgccttc   9000
tatcgccttc ttgacgagtt cttctgagcg ggactctggg gttcgcggaa tcatgaccaa   9060
aatcccttaa cgtgagtttt cgttccactg agcgtcagac cccgtagaaa agatcaaagg   9120
atcttcttga gatccttttt ttctgcgcgt aatctgctgc ttgcaaacaa aaaaaccacc   9180
gctaccagcg gtggtttgtt tgccggatca agagctacca actctttttc cgaaggtaac   9240
tggcttcagc agagcgcaga taccaaatac tgtccttcta gtgtagccgt agttaggcca   9300
ccacttcaag aactctgtag caccgcctac atacctcgct ctgctaatcc tgttaccagt   9360
ggctgctgcc agtggcgata agtcgtgtct taccgggttg gactcaagac gatagttacc   9420
ggataaggcg cagcggtcgg gctgaacggg gggttcgtgc acacagccca gcttggagcg   9480
aacgacctac accgaactga gatacctaca gcgtgagcta tgagaaagcg ccacgcttcc   9540
cgaagggaga aaggcggaca ggtatccggt aagcggcagg gtcggaacag gagagcgcac   9600
gagggagctt ccagggggaa acgcctggta tctttatagt cctgtcgggt ttcgccacct   9660
ctgacttgag cgtcgatttt tgtgatgctc gtcagggggg cggagcctat ggaaaaacgc   9720
cagcaacgcg gcctttttac ggttcctggc cttttgctgg ccttttgctc acatgttctt   9780
tcctgcgtta tcccctgatt ctgtggataa ccgtattacc gcctttgagt gagctgatac   9840
cgctcgccgc agccgaacga ccgagcgcag cgagtcagtg agcgaggaag cggaagagcg   9900
cctgatgcgg tattttctcc ttacgcatct gtgcggtatt tcacaccgca tatggtgcac   9960
tctcagtaca atctgctctg atgccgcata gttaagccag tatacactcc gctatcgcta  10020
cgtgactggg tcatggctgc gccccgacac ccgccaacac ccgctgacgc gccctgacgg  10080
gcttgtctgc tcccggcatc cgcttacaga caagctgtga ccgtctccgg gagctgcatg  10140
tgtcagaggt tttcaccgtc atcaccgaaa cgcgcgaggc agcagatcaa ttcgcgcgcg  10200
aaggcgaagc ggcatgcatt tacgttgaca ccatcgaatg gtgcaaaacc tttcgcggta  10260
tggcatgata gcgcccggaa gagagtcaat tcagggtggt gaatgtgaaa ccagtaacgt  10320
tatacgatgt cgcagagtat gccggtgtct cttatcagac cgtttcccgc gtggtgaacc  10380
```

aggccagcca cgtttctgcg aaaacgcggg aaaaagtgga agcggcgatg gcggagctga 10440
attacattcc caaccgcgtg gcacaacaac tggcgggcaa acagtcgttg ctgattggcg 10500
ttgccacctc cagtctggcc ctgcacgcgc cgtcgcaaat tgtcgcggcg attaaatctc 10560
gcgccgatca actgggtgcc agcgtggtgg tgtcgatggt agaacgaagc ggcgtcgaag 10620
cctgtaaagc ggcggtgcac aatcttctcg cgcaacgcgt cagtgggctg atcattaact 10680
atccgctgga tgaccaggat gccattgctg tggaagctgc ctgcactaat gttccggcgt 10740
tatttcttga tgtctctgac cagacaccca tcaacagtat tattttctcc catgaagacg 10800
gtacgcgact gggcgtggag catctggtcg cattgggtca ccagcaaatc gcgctgttag 10860
cgggcccatt aagttctgtc tcggcgcgtc tgcgtctggc tggctggcat aaatatctca 10920
ctcgcaatca aattcagccg atagcggaac gggaaggcga ctggagtgcc atgtccggtt 10980
ttcaacaaac catgcaaatg ctgaatgagg gcatcgttcc cactgcgatg ctggttgcca 11040
acgatcagat ggcgctgggc gcaatgcgcg ccattaccga gtccgggctg cgcgttggtg 11100
cggatatctc ggtagtggga tacgacgata ccgaagacag ctcatgttat atcccgccgt 11160
caaccaccat caaacaggat tttcgcctgc tggggcaaac cagcgtggac cgcttgctgc 11220
aactctctca gggccaggcg gtgaagggca atcagctgtt gcccgtctca ctggtgaaaa 11280
gaaaaaccac cctggcgccc aatacgcaaa ccgcctctcc ccgcgcgttg gccgattcat 11340
taatgcagct ggcacgacag gtttcccgac tggaaagcgg gcagtgagcg caacgcaatt 11400
aatgtgagtt agcgcgaatt gatctggttt gacagcttat cat 11443

<210> SEQ ID NO 64
<211> LENGTH: 4440
<212> TYPE: DNA
<213> ORGANISM: Artificial Sequence
<220> FEATURE:
<223> OTHER INFORMATION: operon RpBAS-Nt4CL-RcTAL

<400> SEQUENCE: 64
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300
gcgtcgcaga actgggcaag gaagctgctc tgaaggctat caaggaatgg ggccagccaa 360
agtccaagat cacccacctg atcgtctgct gcctggctgg cgtggatatg ccaggcgcag 420
attaccagct cactaagctc ctcgatctcg acccatccgt taagcgcttc atgttctacc 480
acctgggttg ctacgccggt ggcaccgtgc tccgcctggc taaggatatc gctgaaaaca 540
acaagggcgc acgcgtgctg atcgtgtgct ctgaaatgac caccacctgt ttccgcggcc 600
cttcagaaac ccacctggac tctatgatcg gccaggccat cctcggtgac ggtgccgcag 660
ccgtgatcgt gggcgcggac cctgatctga ccgtggagcg tccaatcttc gagctggtga 720
gcacggctca gaccatcgtg ccggagtccc acggcgccat cgagggccac ctcctggagt 780
ctggcctgag cttccacctg tacaagaccg tgccgaccct gatctccaac aacatcaaga 840
cctgcctctc cgatgctttc accccactga acatctccga ctggaacagc ctcttctgga 900
tcgcacaccc aggcggcccg gccatcctgg atcaggtgac cgctaaggtg ggcctggaaa 960
aggaaaagct gaaggtgacc cgccaggttc tgaaggatta cggcaacatg tcctccgcta 1020
ccgtgttctt catcatggat gaaatgcgta agaagtccct ggaaaacggc caggcaacca 1080
ccggcgaggg cctggaatgg ggcgtgctgt tcggcttcgg cccaggcatc accgtggaaa 1140
ccgtggtcct gcgctccgtc ccagtgatct cctaaggatc taggaggatt atgagatgga 1200
gaaagataca aaacaggttg acataatttt ccgatcaaaa ctccctgata tttacatccc 1260
taaccatctt cctttacact cctactgttt cgaaaacatt tccgagttca gttctcgtcc 1320
ttgtttaatc aatggcgcca acaaacaaat ttatacgtat gctgatgttg aactcaattc 1380
aagaaaagtt gctgctggtc ttcacaaaca agggattcaa ccaaaggata caataatgat 1440
cctattgcct aactccccag aatttgtgtt tgctttcatt ggtgcatcgt acctcggagc 1500
tatttctaca atggccaatc ctttgtttac tcctgctgag gttgtgaagc aagccgaggc 1560
ttctagtgct aagatcattg tcacacaagc gtgtcatgtt aacaaagtga aagattatgc 1620
atttgagaat gatgtgaaga tcatatgcat cgactcggcg ccggagggtt gtctccactt 1680
ctccgtgcta actcaggcta atgagcacga tattcctgag gttgaaattc aacctgacga 1740
tgtggtggcg ttgccatact cctccgggac gacgggatta cctaaaggag tgatgttgac 1800
gcacaaggga cttgtgacaa gcgtcgcaca acaagtcgac ggtgaaaatc cgaatttgta 1860
tatccatagc gaggacgtga tgctttgtgt cttgcccttg ttccatatct attcactcaa 1920
ctccgttttg ctttgtggat taagggtggg agcagcgatt ttgattatgc agaaatttga 1980
tattgtttct ttcttggagt tgatacaaag ttacaaggtg acaatagggc cgtttgtacc 2040
acctattgtt ttggycattg ctaagagtcc tatggttgat gattatgatc tttcatcagt 2100
aagaaccgtc atgtctgggg ctgcaccatt aggaaaggag cttgaagata ctgttcgagc 2160
caaatttcct aatgctaaac ttggtcaggg ttatggtatg acagaagctg gaccagtgtt 2220
ggctatgtgc ttggcatttg caaaagaacc ctttgaaata aaatcagggg catgtggaac 2280
agttgtgaga aatgctgaaa tgaaaattgt ggatcctaaa actggtaatt ctcttcccag 2340
aaatcaatct ggagaaattt gcattagagg agaccagatc atgaaaggct acctgaatga 2400
tccagaggcc acagcaagaa caatagacaa agaagggtgg ttatatactg gtgacattgg 2460
ctacattgat gatgacgacg agcttttcat tgttgatcga ttaaaggaac tgatcaaata 2520
caaaggattt caagtcgcac ctgctgagct cgaagctctc cttctcaacc atcccaacat 2580
ttctgatgct gctgttgtcc ccatgaagga cgagcaagca ggagaagttc cagtggcttt 2640
tgttgttaga tccaacggat ccaccattac tgaagatgaa gtcaaagatt ttatttcaaa 2700
gcaggtgata ttttataaga ggataaagcg ggtatttttc gtggatgcta ttcctaaatc 2760
tccatctggc aaaatccttc gaaaagattt gagagctaaa ctggctgctg ggcttccaaa 2820
ttaaggatct aggaggataa agaaatgacc ctgcaatccc agactgcaaa ggactgcctg 2880
gcgctggatg gtgcactgac actggttcag tgcgaagcaa ttgccactca ccgctcacgg 2940
atctccgtca caccagcatt gcgggaacgc tgcgcccgcg cgcacgcacg tctggagcac 3000
gctatcgcag aacagcgtca catctatggt atcaccaccg gcttcggacc actggctaat 3060
cgcctgatcg gtgcagatca gggcgccgaa ctccagcaga acctcatcta ccaccttgct 3120
actggcgtgg gcccaaaact ctcctgggct gaagcacgtg cactcatgct ggctcgtctc 3180
aactccatcc ttcagggcgc atctggtgca tcaccagaaa ccatcgaccg tatcgttgcc 3240
gttctgaacg ctggcttcgc cccagaagtc ccagctcagg gcaccgttgg tgcatctggc 3300
gatctgaccc cactggctca catggtgctg gcgcttcagg gtcgaggtcg tatgatcgat 3360
ccatccggcc gtgttcagga agccggcgca gtgatggatc gcctgtgcgg tggcccactg 3420
accttggcag cccgtgacgg tctggctctg gtcaacggta cttccgctat gaccgcaatc 3480
gctgctttga ccggtgtgga ggctgcgcgc gcaatcgacg ccgcattgcg ccactccgct 3540
gtgctcatgg aggttctctc cggccacgct gaggcttggc accctgcatt tgctgaactc 3600
cgcccacacc caggccagct gcgcgcaacc gaacgtctgg cccaggctct cgatggcgcc 3660
ggtcgcgttt gccgcacctt gaccgcggcc cgtcgcctga ccgcagctga tctgcgccct 3720
gaggatcacc cagcccagga cgcctactcc ctgcgcgtgg tgccacagct ggttggcgct 3780
gtctgggaca ccctcgattg gcacgatcgc gtcgtgacct gcgaactcaa ctctgtgacc 3840
gacaacccaa tcttcccgga aggctgcgct gttccagcac tgcacggcgg caacttcatg 3900
ggcgtgcacg tcgcactggc gtcggacgcc ctgaacgctg cattggttac cctggcaggt 3960
ctggtggagc gccagatcgc acgccttact gatgagaagc tgaacaaggg acttccggca 4020
ttccttcacg gtggtcaggc tggccttcag tccggcttca tgggcgcgca ggtcaccgca 4080
accgcgctcc ttgctgaaat gcgcgcaaac gcaaccccgg tgtctgttca gtcactgtct 4140
accaacggcg ctaaccagga tgttgtcagc atgggcacca tcgctgcacg ccgcgctcgc 4200
gcacagctgc tcccactgtc ccagattcag gcaatcctgg ctctcgctct cgcccaggca 4260
atggatctgc tggatgatcc agagggccag gctggctggt cccttaccgc acgcgacctg 4320
cgcgatcgca tccgcgctgt ctcgccgggc ctgcgcgcag atcgcccact ggccggccac 4380
atcgaggcag tcgctcaggg tctgcgccac ccttccgcag cagctgatcc accagcataa 4440

<210> SEQ ID NO 65
<211> LENGTH: 11368
<212> TYPE: DNA
<213> ORGANISM: Artificial Sequence
<220> FEATURE:
<223> OTHER INFORMATION: plasmid RpBAS-Nt4CL-FjTAL-pECXK (pECXK_W)

<400> SEQUENCE: 65
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360
agctgatttt cccgacttct acttccgcgt gaccaactcc gatcatctga tcaacctgaa 420
gcagaagttc aagcgcctat gcgaaaactc tcgcatcgag aagcgctacc tccacgtcac 480
cgaggagatc ctcaaggaaa acccaaacat cgcagcttac gaggctacta gcctgaacgt 540
gcgccacaag atgcaggtca agggcgtcgc agaactgggc aaggaagctg ctctgaaggc 600
tatcaaggaa tggggccagc caaagtccaa gatcacccac ctgatcgtct gctgcctggc 660
tggcgtggat atgccaggcg cagattacca gctcactaag ctcctcgatc tcgacccatc 720
cgttaagcgc ttcatgttct accacctggg ttgctacgcc ggtggcaccg tgctccgcct 780
ggctaaggat atcgctgaaa acaacaaggg cgcacgcgtg ctgatcgtgt gctctgaaat 840
gaccaccacc tgtttccgcg gcccttcaga aacccacctg gactctatga tcggccaggc 900
catcctcggt gacggtgccg cagccgtgat cgtgggcgcg gaccctgatc tgaccgtgga 960
gcgtccaatc ttcgagctgg tgagcacggc tcagaccatc gtgccggagt cccacggcgc 1020
catcgagggc cacctcctgg agtctggcct gagcttccac ctgtacaaga ccgtgccgac 1080
cctgatctcc aacaacatca agacctgcct ctccgatgct ttcaccccac tgaacatctc 1140
cgactggaac agcctcttct ggatcgcaca cccaggcggc ccggccatcc tggatcaggt 1200
gaccgctaag gtgggcctgg aaaaggaaaa gctgaaggtg acccgccagg ttctgaagga 1260
ttacggcaac atgtcctccg ctaccgtgtt cttcatcatg gatgaaatgc gtaagaagtc 1320
cctggaaaac ggccaggcaa ccaccggcga gggcctggaa tggggcgtgc tgttcggctt 1380
cggcccaggc atcaccgtgg aaaccgtggt cctgcgctcc gtcccagtga tctcctaagg 1440
atctaggagg attatgagat ggagaaagat acaaaacagg ttgacataat tttccgatca 1500
aaactccctg atatttacat ccctaaccat cttcctttac actcctactg tttcgaaaac 1560
atttccgagt tcagttctcg tccttgttta atcaatggcg ccaacaaaca aatttatacg 1620
tatgctgatg ttgaactcaa ttcaagaaaa gttgctgctg gtcttcacaa acaagggatt 1680
caaccaaagg atacaataat gatcctattg cctaactccc cagaatttgt gtttgctttc 1740
attggtgcat cgtacctcgg agctatttct acaatggcca atcctttgtt tactcctgct 1800
gaggttgtga agcaagccga ggcttctagt gctaagatca ttgtcacaca agcgtgtcat 1860
gttaacaaag tgaaagatta tgcatttgag aatgatgtga agatcatatg catcgactcg 1920
gcgccggagg gttgtctcca cttctccgtg ctaactcagg ctaatgagca cgatattcct 1980
gaggttgaaa ttcaacctga cgatgtggtg gcgttgccat actcctccgg gacgacggga 2040
ttacctaaag gagtgatgtt gacgcacaag ggacttgtga caagcgtcgc acaacaagtc 2100
gacggtgaaa atccgaattt gtatatccat agcgaggacg tgatgctttg tgtcttgccc 2160
ttgttccata tctattcact caactccgtt ttgctttgtg gattaagggt gggagcagcg 2220
attttgatta tgcagaaatt tgatattgtt tctttcttgg agttgataca aagttacaag 2280
gtgacaatag ggccgtttgt accacctatt gttttggyca ttgctaagag tcctatggtt 2340
gatgattatg atctttcatc agtaagaacc gtcatgtctg gggctgcacc attaggaaag 2400
gagcttgaag atactgttcg agccaaattt cctaatgcta aacttggtca gggttatggt 2460
atgacagaag ctggaccagt gttggctatg tgcttggcat ttgcaaaaga accctttgaa 2520
ataaaatcag ggcatgtgg aacagttgtg agaaatgctg aaatgaaaat tgtggatcct 2580
aaaactggta attctcttcc cagaaatcaa tctggagaaa tttgcattag aggagaccag 2640
atcatgaaag gctacctgaa tgatccagag gccacagcaa gaacaataga caaagaaggg 2700
tggttatata ctggtgacat tggctacatt gatgatgacg acgagctttt cattgttgat 2760
cgattaaagg aactgatcaa atacaaagga tttcaagtcg cacctgctga gctcgaagct 2820
ctccttctca accatcccaa catttctgat gctgctgttg tccccatgaa ggacgagcaa 2880
gcaggagaag ttccagtggc ttttgttgtt agatccaacg gatccaccat tactgaagat 2940
gaagtcaaag attttatttc aaagcaggtg atattttata agaggataaa gcgggtattt 3000
ttcgtggatg ctattcctaa atctccatct ggcaaaatcc ttcgaaaaga tttgagagct 3060
aaactggctg ctgggcttcc aaattaagga tctaggagga taaagaaatg aacaccatca 3120
acgaatacct gtccctggaa gagttcgaag cgatcatctt cggtaaccag aaggttacca 3180
tctccgatgt ggttgtgaac cgtgttaacg agtccttcaa cttcctcaag gagttctccg 3240
gcaacaaggt catctacggt gtgaacaccg gcttcggccc aatggcacaa taccgtatta 3300
aggaatccga tcagatccag cttcagtaca atctgatccg ttcccactct tcgggcaccg 3360

-continued

```
gaaaaccact ctccccagtt tgtgctaagg cagcaatctt ggctcgcctg aacaccctgt   3420
ccctcggtaa ctccggcgtg catccatctg tcatcaacct gatgtcggaa ctgatcaaca   3480
aagacattac cccactcatc ttcgagcacg gtggcgtcgg agcatccggt gacctggttc   3540
agctttctca cctggctttg gttctcatcg gcgaaggcga agtgttctac aagggtgaac   3600
gccgcccaac tccagaagtt ttcgaaattg agggcttgaa gccaatccag gttgagatcc   3660
gtgagggcct cgccttgatt aacggtacta gcgtgatgac cggtattgga gtggtcaacg   3720
tgtaccacgc aaagaagctg ctggactggt ccctgaagtc ctcctgcgcc atcaatgaac   3780
ttgttcaggc ttacgatgat cacttcagcg cagagctgaa ccagacgaag cgccacaagg   3840
gccagcagga aatcgctctg aagatgcgtc agaacctctc tgacagcacc ctgatccgca   3900
agcgcgagga ccacctgtat tccggcgaaa acaccgagga gattttcaag gagaaggtgc   3960
aggagtacta ctccctgcgc tgcgttccac agattctcgg cccggtcctc gaaactatca   4020
ataacgtcgc ctccatcctg gaagatgagt tcaactccgc taacgataac ccaatcatcg   4080
acgtgaagaa ccagcacgtg taccatggcg gcaacttcca cggtgactac atctctctgg   4140
aaatggacaa gttgaaaatc gttatcacca aactgaccat gcttgcagaa cgccagctta   4200
actatcttct caactccaag atcaacgaac ttctgccacc attcgtgaac ctcggcaccc   4260
tgggtttcaa cttcggcatg cagggcgttc agttcaccgc gacctccacc accgcagaat   4320
ctcagatgct gtccaaccct atgtacgttc actccattcc aaacaacaac gataaccagg   4380
acatcgtctc catgggcacc aactccgcag tgatcacgtc caaggttatc gagaacgctt   4440
tcgaagtcct ggctatcgaa atgatcacca tcgttcaggc catcgattac ctcggccaga   4500
aggataagat ctcctccgtt tccaagaagt ggtacgatga aatccgcaac attatcccta   4560
ccttcaagga ggatcaggtt atgtacccat tcgtgcagaa ggttaaggat cacctcatca   4620
acaactaact ctagagtcga cctgcaggca tgcaagcttg gctgttttgg cggatgagag   4680
aagattttca gcctgataca gattaaatca gaacgcagaa gcggtctgat aaaacagaat   4740
ttgcctggcg gcagtagcgc ggtggtccca cctgacccca tgccgaactc agaagtgaaa   4800
cgccgtagcg ccgatggtag tgtggggtct ccccatgcga gagtagggaa ctgccaggca   4860
tcaaataaaa cgaaaggctc agtcgaaaga ctgggccttt cgttttatct gttgtttgtc   4920
ggtgaacgct ctcctgagta ggacaaatcc gccgggagcg gatttgaacg ttgcgaagca   4980
acggcccgga gggtggcggg caggacgccc gccataaact gccaggcatc aaattaagca   5040
gaaggccatc ctgacggatg gcctttttgc gtttctacaa actctttttg tttatttttc   5100
taaatacatt caaatatgta tccgctcatg aattaattcc gctagatgac gtgcggcttc   5160
gacctcctgg gcgtggcgct tgttggcgcg ctcgcggctg gctgcggcac gacacgcgtc   5220
tgagcagtat tttgcgcgcc gtcctcgtgg gtcaggccgg ggtgggatca ggccaccgca   5280
gtaggcgcag ctgatgcgat cctccactac tgcgcgtcct cctggcgctg ccgagcacgc   5340
agctcgtcgg ccagctcttc aaggtcggcc acaagcgttt ctaggtcgct cgcggcactt   5400
gcccagtcgc gtgatgctgg cgcgtctgtc gtatcgaggg cgcggaaaaa tccgatcacc   5460
gtttttaaat cgacggcggc atcgagtgcg tcggactcca gcgcgacatc ggagagatcc   5520
accgctgatg cttcaggcca gttttggtac ttcgtcgtga aggtcatgac accattataa   5580
cgaacgttcg ttaaaaattc tagccccaat tctgataatt tcttccggca ctcctgcgaa   5640
aacctgcgag acttcttgcc cagaaaaaac gccaagcgca gcggttaccg cacttttttt   5700
ccaggtgatt tcaccctgac cagcgaagcg gcactttagt gcatgaggtg tgcccctggt   5760
```

ttcccctctt tggagggttc aacccaaaaa agcacacaag caaaaatgaa aatcatcatg 5820
agcaagttgg tgcgaagcag caacgcgcta gctccaaaaa ggtctccagg atctcgagga 5880
gatttttgag ggggagggag tcgaggaaga gccagagcag aaggcgggga accgttctct 5940
gccgacagcg tgagcccccc ttaaaaatca ggccggggag gaaccgggga gggatcagag 6000
ctaggagcga gacaccctaa aggggggga ccgttttctg ctgacggtgt ttcgtttatt 6060
agttttcagc ccgtggatag cggagggtga gggcaagtga gagccagagc aaggacggga 6120
cccctaaagg ggggaaccgt tttctgctga cggtgtttcg tttattagtt ttcagcccgt 6180
ggacggccgc gtttagcttc cattccaagt gcctttctga cttgttggat gcgcctttca 6240
ctgacaccta gttcgcctgc aagctcacga gtcgagggat cagcaaccga ttgagaacgg 6300
gcatccagga tcgcagtttt gacgcgaagt tcgagcaact cgcctgtcat ttctcggcgt 6360
ttgtttgctt ccgctaatcg ctgtcgcgtc tcctgcgcat acttactttc tgggtcagcc 6420
catctgcgtg cattcgatgt agctgcgccc cgtcgcccca tcgtcgctag agctttccgc 6480
cctcggctgc tctgcgtttc cacccgacga gcagggacga ctggctggcc tttagccacg 6540
tagccgcgca cacgacgcgc catcgtcagg cgatcacgca tggcgggaag atccggctcc 6600
cggccgtctg caccgaccgc ctgggcaacg ttgtacgcca cttcatacgc gtcgatgatc 6660
ttggcatctt ttaggcgctc accagcagct ttgagctggt atcccacggt caacgcgtgg 6720
cgaaacgcgg tctcgtcgcg cgctcgctct ggatttgtcc agagcactcg cacgccgtcg 6780
atcaggtcgc cggacgcgtc cagggcgctc ggcaggctcg cgtccaaaat cgctagcgcc 6840
ttggcttctg cggtggcgcg ttgtgccgct tcaatgcggg cgcgtccgct ggaaaagtcc 6900
tgctcaatgt actttttcgg cttctgtgat ccggtcatcg ttcgagcaat ctccattagg 6960
tcggccagcc gatccacacg atcatgctgg cagtgccatt tataggctgt cggatcgtct 7020
gagacgtgca gcggccaccg gctcagccta tgcgaaaaag cctggtcagc gccgaaaaca 7080
cgagtcattt cttccgtcgt tgcagccagc aggcgcatat ttgggctggt tttacctgct 7140
gcggcataca ccgggtcaat gagccagatg agctggcatt tcccgctcag cggattcacg 7200
ccgatccaag ccggcgcttt ttctaggcgt gcccatttct ctaaaatcgc gtagacctgc 7260
gggtttacgt gctcaatctt cccgccggcc tggtggctgg gcacatcgat gtcaagcacg 7320
atcaccgcgg catgttgcgc gtgcgtcagc gcaacgtact ggcaccgcgt cagcgctttt 7380
gagccagccc ggtagagctt tggttgggtt tcgccggtat ccgggttttt aatccaggcg 7440
ctcgcgaaat ctcttgtctt gctgccctgg aagctttcgc gtcccaggtg agcgagcagt 7500
tcgcggcgat cttctgccgt ccagccgcgt gagccgcagc gcatagcttc ggggtgggtg 7560
tcgaacagat cggcggacaa tttccacgcg ctagctgtga ctgtgtcctg cggatcggct 7620
agagtcatgt cttgagtgct ttctcccagc tgatgactgg gggttagccg acgccctgtg 7680
agttcccgct cacggggcgt tcaacttttt caggtatttg tgcagcttat cgtgttttct 7740
tcgtaaatga acgcttaact accttgttaa acgtggcaaa taggcaggat tgatggggat 7800
ctagcttcac gctgccgcaa gcactcaggg cgcaagggct gctaaaggaa gcggaacacg 7860
tagaaagcca gtccgcagaa acggtgctga ccccggatga atgtcagcta ctgggctatc 7920
tggacaaggg aaaacgcaag cgcaaagaga aagcaggtag cttgcagtgg gcttacatgg 7980
cgatagctag actgggcggt tttatggaca gcaagcgaac cggaattgcc agctggggcg 8040
ccctctggta aggttgggaa gccctgcaaa gtaaactgga tggctttctt gccgccaagg 8100

-continued atctgatggc gcaggggatc aagatctgat caagagacag gatgaggatc gtttcgcatg 8160
attgaacaag atggattgca cgcaggttct ccggccgctt gggtggagag gctattcggc 8220
tatgactggg cacaacagac aatcggctgc tctgatgccg ccgtgttccg gctgtcagcg 8280
caggggcgcc cggttctttt tgtcaagacc gacctgtccg gtgccctgaa tgaactccaa 8340
gacgaggcag cgcggctatc gtggctggcc acgacgggcg ttccttgcgc agctgtgctc 8400
gacgttgtca ctgaagcggg aagggactgg ctgctattgg gcgaagtgcc ggggcaggat 8460
ctcctgtcat ctcaccttgc tcctgccgag aaagtatcca tcatggctga tgcaatgcgg 8520
cggctgcata cgcttgatcc ggctacctgc ccattcgacc accaagcgaa acatcgcatc 8580
gagcgagcac gtactcggat ggaagccggt cttgtcgatc aggatgatct ggacgaagag 8640
catcaggggc tcgcgccagc cgaactgttc gccaggctca aggcgcggat gcccgacggc 8700
gaggatctcg tcgtgaccca tggcgatgcc tgcttgccga atatcatggt ggaaaatggc 8760
cgcttttctg gattcatcga ctgtggccgg ctgggtgtgg cggaccgcta tcaggacata 8820
gcgttggcta cccgtgatat tgctgaagag cttggcggcg aatgggctga ccgcttcctc 8880
gtgctttacg gtatcgccgc tcccgattcg cagcgcatcg ccttctatcg ccttcttgac 8940
gagttcttct gagcgggact ctggggttcg cggaatcatg accaaaatcc cttaacgtga 9000
gttttcgttc cactgagcgt cagaccccgt agaaaagatc aaaggatctt cttgagatcc 9060
tttttttctg cgcgtaatct gctgcttgca aacaaaaaaa ccaccgctac cagcggtggt 9120
ttgtttgccg gatcaagagc taccaactct ttttccgaag gtaactggct tcagcagagc 9180
gcagatacca aatactgtcc ttctagtgta gccgtagtta ggccaccact tcaagaactc 9240
tgtagcaccg cctacatacc tcgctctgct aatcctgtta ccagtggctg ctgccagtgg 9300
cgataagtcg tgtcttaccg ggttggactc aagacgatag ttaccggata aggcgcagcg 9360
gtcgggctga acggggggtt cgtgcacaca gcccagcttg gagcgaacga cctacaccga 9420
actgagatac ctacagcgtg agctatgaga aagcgccacg cttcccgaag ggagaaaggc 9480
ggacaggtat ccggtaagcg gcagggtcgg aacaggagag cgcacgaggg agcttccagg 9540
gggaaacgcc tggtatcttt atagtcctgt cgggtttcgc cacctctgac ttgagcgtcg 9600
atttttgtga tgctcgtcag gggggcggag cctatggaaa aacgccagca acgcggcctt 9660
tttacggttc ctggcctttt gctggccttt tgctcacatg ttctttcctg cgttatcccc 9720
tgattctgtg gataaccgta ttaccgcctt tgagtgagct gataccgctc gccgcagccg 9780
aacgaccgag cgcagcgagt cagtgagcga ggaagcggaa gagcgcctga tgcggtattt 9840
tctccttacg catctgtgcg gtatttcaca ccgcatatgg tgcactctca gtacaatctg 9900
ctctgatgcc gcatagttaa gccagtatac actccgctat cgctacgtga ctgggtcatg 9960
gctgcgcccc gacacccgcc aacacccgct gacgcgccct gacgggcttg tctgctcccg 10020
gcatccgctt acagacaagc tgtgaccgtc tccgggagct gcatgtgtca gaggttttca 10080
ccgtcatcac cgaaacgcgc gaggcagcag atcaattcgc gcgcgaaggc gaagcggcat 10140
gcatttacgt tgacaccatc gaatggtgca aaacctttcg cggtatggca tgatagcgcc 10200
cggaagagag tcaattcagg gtggtgaatg tgaaaccagt aacgttatac gatgtcgcag 10260
agtatgccgg tgtctcttat cagaccgttt cccgcgtggt gaaccaggcc agccacgttt 10320
ctgcgaaaac gcgggaaaaa gtggaagcgg cgatggcgga gctgaattac attcccaacc 10380
gcgtggcaca acaactggcg ggcaaacagt cgttgctgat tggcgttgcc acctccagtc 10440
tggccctgca cgcgccgtcg caaattgtcg cggcgattaa atctcgcgcc gatcaactgg 10500

-continued

```
gtgccagcgt ggtggtgtcg atggtagaac gaagcggcgt cgaagcctgt aaagcggcgg  10560

tgcacaatct tctcgcgcaa cgcgtcagtg ggctgatcat taactatccg ctggatgacc  10620

aggatgccat tgctgtggaa gctgcctgca ctaatgttcc ggcgttattt cttgatgtct  10680

ctgaccagac acccatcaac agtattattt tctcccatga agacggtacg cgactgggcg  10740

tggagcatct ggtcgcattg ggtcaccagc aaatcgcgct gttagcgggc ccattaagtt  10800

ctgtctcggc gcgtctgcgt ctggctggct ggcataaata tctcactcgc aatcaaattc  10860

agccgatagc ggaacgggaa ggcgactgga gtgccatgtc cggttttcaa caaaccatgc  10920

aaatgctgaa tgagggcatc gttcccactg cgatgctggt tgccaacgat cagatggcgc  10980

tgggcgcaat gcgcgccatt accgagtccg ggctgcgcgt tggtgcggat atctcggtag  11040

tgggatacga cgataccgaa gacagctcat gttatatccc gccgtcaacc accatcaaac  11100

aggattttcg cctgctgggg caaaccagcg tggaccgctt gctgcaactc tctcagggcc  11160

aggcggtgaa gggcaatcag ctgttgcccg tctcactggt gaaaagaaaa accaccctgg  11220

cgcccaatac gcaaaccgcc tctccccgcg cgttggccga ttcattaatg cagctggcac  11280

gacaggtttc ccgactggaa agcgggcagt gagcgcaacg caattaatgt gagttagcgc  11340

gaattgatct ggtttgacag cttatcat                                    11368
```

<210> SEQ ID NO 66
<211> LENGTH: 4365
<212> TYPE: DNA
<213> ORGANISM: Artificial Sequence
<220> FEATURE:
<223> OTHER INFORMATION: operon RpBAS-Nt4CL-FjTAL

<400> SEQUENCE: 66

```
ggatctagga gggagatcat atggcaaccg aggagatgaa gaagctcgca accgtgatgg     60

caatcggcac tgctaaccca ccgaactgct attaccaagc tgattttccc gacttctact    120

tccgcgtgac caactccgat catctgatca acctgaagca gaagttcaag cgcctatgcg    180

aaaactctcg catcgagaag cgctacctcc acgtcaccga ggagatcctc aaggaaaacc    240

caaacatcgc agcttacgag gctactagcc tgaacgtgcg ccacaagatg caggtcaagg    300

gcgtcgcaga actgggcaag gaagctgctc tgaaggctat caaggaatgg ggccagccaa    360

agtccaagat cacccacctg atcgtctgct gcctggctgg cgtggatatg ccaggcgcag    420

attaccagct cactaagctc ctcgatctcg acccatccgt taagcgcttc atgttctacc    480

acctgggttg ctacgccggt ggcaccgtgc tccgcctggc taaggatatc gctgaaaaca    540

acaagggcgc acgcgtgctg atcgtgtgct ctgaaatgac caccacctgt ttccgcggcc    600

cttcagaaac ccacctggac tctatgatcg gccaggccat cctcggtgac ggtgccgcag    660

ccgtgatcgt gggcgcggac cctgatctga ccgtggagcg tccaatcttc gagctggtga    720

gcacggctca gaccatcgtg ccggagtccc acggcgccat cgagggccac ctcctggagt    780

ctggcctgag cttccacctg tacaagaccg tgccgaccct gatctccaac aacatcaaga    840

cctgcctctc cgatgctttc accccactga acatctccga ctggaacagc ctcttctgga    900

tcgcacaccc aggcggcccg gccatcctgg atcaggtgac cgctaaggtg ggcctggaaa    960

aggaaaagct gaaggtgacc cgccaggttc tgaaggatta cggcaacatg tcctccgcta   1020

ccgtgttctt catcatggat gaaatgcgta agaagtccct ggaaaacggc caggcaacca   1080

ccggcgaggg cctggaatgg ggcgtgctgt tcggcttcgg cccaggcatc accgtggaaa   1140
```

-continued ccgtggtcct gcgctccgtc ccagtgatct cctaaggatc taggaggatt atgagatgga 1200
gaaagataca aaacaggttg acataatttt ccgatcaaaa ctccctgata tttacatccc 1260
taaccatctt cctttacact cctactgttt cgaaaacatt tccgagttca gttctcgtcc 1320
ttgtttaatc aatggcgcca acaaacaaat ttatacgtat gctgatgttg aactcaattc 1380
aagaaaagtt gctgctggtc ttcacaaaca agggattcaa ccaaaggata caataatgat 1440
cctattgcct aactccccag aatttgtgtt tgctttcatt ggtgcatcgt acctcggagc 1500
tatttctaca atggccaatc ctttgtttac tcctgctgag gttgtgaagc aagccgaggc 1560
ttctagtgct aagatcattg tcacacaagc gtgtcatgtt aacaaagtga aagattatgc 1620
atttgagaat gatgtgaaga tcatatgcat cgactcggcg ccggagggtt gtctccactt 1680
ctccgtgcta actcaggcta atgagcacga tattcctgag gttgaaattc aacctgacga 1740
tgtggtggcg ttgccatact cctccgggac gacgggatta cctaaaggag tgatgttgac 1800
gcacaaggga cttgtgacaa gcgtcgcaca acaagtcgac ggtgaaaatc cgaatttgta 1860
tatccatagc gaggacgtga tgctttgtgt cttgcccttg ttccatatct attcactcaa 1920
ctccgttttg ctttgtggat taagggtggg agcagcgatt ttgattatgc agaaatttga 1980
tattgtttct ttcttggagt tgatacaaag ttacaaggtg acaatagggc cgtttgtacc 2040
acctattgtt ttggycattg ctaagagtcc tatggttgat gattatgatc tttcatcagt 2100
aagaaccgtc atgtctgggg ctgcaccatt aggaaaggag cttgaagata ctgttcgagc 2160
caaatttcct aatgctaaac ttggtcaggg ttatggtatg acagaagctg gaccagtgtt 2220
ggctatgtgc ttggcatttg caaaagaacc ctttgaaata aaatcagggg catgtggaac 2280
agttgtgaga aatgctgaaa tgaaaattgt ggatcctaaa actggtaatt ctcttcccag 2340
aaatcaatct ggagaaattt gcattagagg agaccagatc atgaaaggct acctgaatga 2400
tccagaggcc acagcaagaa caatagacaa agaagggtgg ttatatactg gtgacattgg 2460
ctacattgat gatgacgacg agcttttcat tgttgatcga ttaaaggaac tgatcaaata 2520
caaaggattt caagtcgcac ctgctgagct cgaagctctc cttctcaacc atcccaacat 2580
ttctgatgct gctgttgtcc ccatgaagga cgagcaagca ggagaagttc cagtggcttt 2640
tgttgttaga tccaacggat ccaccattac tgaagatgaa gtcaaagatt ttatttcaaa 2700
gcaggtgata ttttataaga ggataaagcg ggtatttttc gtggatgcta ttcctaaatc 2760
tccatctggc aaaatccttc gaaaagattt gagagctaaa ctggctgctg ggcttccaaa 2820
ttaaggatct aggaggataa agaaatgaac accatcaacg aatacctgtc cctggaagag 2880
ttcgaagcga tcatcttcgg taaccagaag gttaccatct ccgatgtggt tgtgaaccgt 2940
gttaacgagt ccttcaactt cctcaaggag ttctccggca acaaggtcat ctacggtgtg 3000
aacaccggct tcggcccaat ggcacaatac cgtattaagg aatccgatca gatccagctt 3060
cagtacaatc tgatccgttc ccactcttcg ggcaccggaa aaccactctc cccagtttgt 3120
gctaaggcag caatcttggc tcgcctgaac accctgtccc tcggtaactc cggcgtgcat 3180
ccatctgtca tcaacctgat gtcggaactg atcaacaaag acattacccc actcatcttc 3240
gagcacggtg gcgtcggagc atccggtgac ctggttcagc tttctcacct ggctttggtt 3300
ctcatcggcg aaggcgaagt gttctacaag ggtgaacgcc gcccaactcc agaagttttc 3360
gaaattgagg gcttgaagcc aatccaggtt gagatccgtg agggcctcgc cttgattaac 3420
ggtactagcg tgatgaccgg tattggagtg gtcaacgtgt accacgcaaa gaagctgctg 3480
gactggtccc tgaagtcctc ctgcgccatc aatgaacttg ttcaggctta cgatgatcac 3540
ttcagcgcag agctgaacca gacgaagcgc cacaagggcc agcaggaaat cgctctgaag 3600
atgcgtcaga acctctctga cagcaccctg atccgcaagc gcgaggacca cctgtattcc 3660
ggcgaaaaca ccgaggagat tttcaaggag aaggtgcagg agtactactc cctgcgctgc 3720
gttccacaga ttctcggccc ggtcctcgaa actatcaata acgtcgcctc catcctggaa 3780
gatgagttca actccgctaa cgataaccca atcatcgacg tgaagaacca gcacgtgtac 3840
catggcggca acttccacgg tgactacatc tctctggaaa tggacaagtt gaaaatcgtt 3900
atcaccaaac tgaccatgct tgcagaacgc cagcttaact atcttctcaa ctccaagatc 3960
aacgaacttc tgccaccatt cgtgaacctc ggcaccctgg gtttcaactt cggcatgcag 4020
ggcgttcagt tcaccgcgac ctccaccacc gcagaatctc agatgctgtc caaccctatg 4080
tacgttcact ccattccaaa caacaacgat aaccaggaca tcgtctccat gggcaccaac 4140
tccgcagtga tcacgtccaa ggttatcgag aacgctttcg aagtcctggc tatcgaaatg 4200
atcaccatcg ttcaggccat cgattacctc ggccagaagg ataagatctc ctccgtttcc 4260
aagaagtggt acgatgaaat ccgcaacatt atccctacct tcaaggagga tcaggttatg 4320
tacccattcg tgcagaaggt taaggatcac ctcatcaaca actaa 4365

<210> SEQ ID NO 67
<211> LENGTH: 11380
<212> TYPE: DNA
<213> ORGANISM: Artificial Sequence
<220> FEATURE:
<223> OTHER INFORMATION: plasmid RpBAS-Nt4CL-SeSam8-pECXK (pECXK_X)

<400> SEQUENCE: 67
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360
agctgatttt cccgacttct acttccgcgt gaccaactcc gatcatctga tcaacctgaa 420
gcagaagttc aagcgcctat gcgaaaactc tcgcatcgag aagcgctacc tccacgtcac 480
cgaggagatc ctcaaggaaa acccaaacat cgcagcttac gaggctacta gcctgaacgt 540
gcgccacaag atgcaggtca agggcgtcgc agaactgggc aaggaagctg ctctgaaggc 600
tatcaaggaa tggggccagc caaagtccaa gatcacccac ctgatcgtct gctgcctggc 660
tggcgtggat atgccaggcg cagattacca gctcactaag ctcctcgatc tcgacccatc 720
cgttaagcgc ttcatgttct accacctggg ttgctacgcc ggtggcaccg tgctccgcct 780
ggctaaggat atcgctgaaa acaacaaggg cgcacgcgtg ctgatcgtgt gctctgaaat 840
gaccaccacc tgtttccgcg gcccttcaga aacccacctg gactctatga tcggccaggc 900
catcctcggt gacggtgccg cagccgtgat cgtgggcgcg gaccctgatc tgaccgtgga 960
gcgtccaatc ttcgagctgg tgagcacggc tcagaccatc gtgccggagt cccacggcgc 1020
catcgagggc cacctcctgg agtctggcct gagcttccac ctgtacaaga ccgtgccgac 1080
cctgatctcc aacaacatca agacctgcct ctccgatgct ttcaccccac tgaacatctc 1140
cgactggaac agcctcttct ggatcgcaca cccaggcggc ccggccatcc tggatcaggt 1200
gaccgctaag gtgggcctgg aaaaggaaaa gctgaaggtg acccgccagg ttctgaagga 1260
ttacggcaac atgtcctccg ctaccgtgtt cttcatcatg gatgaaatgc gtaagaagtc 1320
cctggaaaac ggccaggcaa ccaccggcga gggcctggaa tggggcgtgc tgttcggctt 1380
cggcccaggc atcaccgtgg aaaccgtggt cctgcgctcc gtcccagtga tctcctaagg 1440
atctaggagg attatgagat ggagaaagat acaaaacagg ttgacataat tttccgatca 1500
aaactccctg atatttacat ccctaaccat cttcctttac actcctactg tttcgaaaac 1560
atttccgagt tcagttctcg tccttgttta atcaatggcg ccaacaaaca aatttatacg 1620
tatgctgatg ttgaactcaa ttcaagaaaa gttgctgctg gtcttcacaa acaagggatt 1680
caaccaaagg atacaataat gatcctattg cctaactccc cagaatttgt gtttgctttc 1740
attggtgcat cgtacctcgg agctatttct acaatggcca atcctttgtt tactcctgct 1800
gaggttgtga agcaagccga ggcttctagt gctaagatca ttgtcacaca agcgtgtcat 1860
gttaacaaag tgaaagatta tgcatttgag aatgatgtga agatcatatg catcgactcg 1920
gcgccggagg gttgtctcca cttctccgtg ctaactcagg ctaatgagca cgatattcct 1980
gaggttgaaa ttcaacctga cgatgtggtg gcgttgccat actcctccgg gacgacggga 2040
ttacctaaag gagtgatgtt gacgcacaag ggacttgtga caagcgtcgc acaacaagtc 2100
gacggtgaaa atccgaattt gtatatccat agcgaggacg tgatgctttg tgtcttgccc 2160
ttgttccata tctattcact caactccgtt ttgctttgtg gattaagggt gggagcagcg 2220
attttgatta tgcagaaatt tgatattgtt tctttcttgg agttgataca aagttacaag 2280
gtgacaatag ggccgtttgt accacctatt gttttggyca ttgctaagag tcctatggtt 2340
gatgattatg atctttcatc agtaagaacc gtcatgtctg gggctgcacc attaggaaag 2400
gagcttgaag atactgttcg agccaaattt cctaatgcta aacttggtca gggttatggt 2460
atgacagaag ctggaccagt gttggctatg tgcttggcat ttgcaaaaga accctttgaa 2520
ataaaatcag gggcatgtgg aacagttgtg agaaatgctg aaatgaaaat tgtggatcct 2580
aaaactggta attctcttcc cagaaatcaa tctggagaaa tttgcattag aggagaccag 2640
atcatgaaag gctacctgaa tgatccagag gccacagcaa gaacaataga caaagaaggg 2700
tggttatata ctggtgacat tggctacatt gatgatgacg acgagctttt cattgttgat 2760
cgattaaagg aactgatcaa atacaaagga tttcaagtcg cacctgctga gctcgaagct 2820
ctccttctca accatcccaa catttctgat gctgctgttg tccccatgaa ggacgagcaa 2880
gcaggagaag ttccagtggc ttttgttgtt agatccaacg gatccaccat tactgaagat 2940
gaagtcaaag attttatttc aaagcaggtg atattttata agaggataaa gcgggtattt 3000
ttcgtggatg ctattcctaa atctccatct ggcaaaatcc ttcgaaaaga tttgagagct 3060
aaactggctg ctgggcttcc aaattaagga tctaggagga taaagaaatg acccaggtcg 3120
tggagcgcca ggctgatcgt ctgtccagcc gcgagtacct ggcacgcgtt gttcgttccg 3180
caggctggga cgcaggcctc accagctgca ccgatgaaga aatcgtgcgc atgggtgcat 3240
ccgcacgcac cattgaggaa tacctgaagt ctgataagcc gatctacggc ctcacccagg 3300
gcttcggtcc actggtcctg ttcgatgcag attccgaact ggaacagggc ggctctctca 3360
tctcccatct gggcaccggc cagggtgcac cgcttgcacc ggaagtgtcc cgcctgattc 3420
tgtggctccg catccaaaac atgcgcaagg gctattcggc tgtcagtcct gtgttctggc 3480
aaaaactggc cgacctctgg aacaagggct tcacccctgc tatccctcgc cacggcaccg 3540
tgtccgccag cggcgatctc cagcctctgg cacacgctgc cctggctttt accggcgtgg 3600

-continued gcgaggcatg gacccgtgat gcagacggcc gttggtccac cgtgccagcc gtggacgcat 3660
tagcagcact gggtgcagag ccgttcgatt ggccagtgcg cgaggctttg gccttcgtga 3720
acggtacggg cgcatcactc gcggtggcag ttctcaacca cagatccgct ctccgtctcg 3780
tacgagcatg tgcagtcttg tctgcccgtt tggctacctt gctaggagct aatcctgaac 3840
actacgatgt cggccacgga gtcgcaaggg gacaagttgg ccagctgacc gcggcggaat 3900
ggattcggca gggactacca cgcggcatgg tccgagacgg ttcgcgccct cttcaagaac 3960
catacagctt gcgctgtgcc ccccaggtcc ttggcgcggt gctggaccag ctggatggtg 4020
caggcgatgt tctggcccgc gaagtggatg gctgccagga caatcctatc acctacgagg 4080
gcgaactgct gcacggcggt aacttccacg ctatgccagt cggcttcgca tccgaccaga 4140
tcggtctggc gatgcacatg gcagcttatc tggctgaacg ccagctcggc ctgctggtga 4200
gcccggtgac caacggcgac ctgccaccaa tgctgacccc acgcgctgga cgcggtgccg 4260
gcctggcggg cgttcagatc tccgcaacct ccttcgtctc tcgcatccgc cagctggtgt 4320
tcccagctag cctcaccacc ctcccaacca acggctggaa ccaggaccat gtcccaatgg 4380
ctctgaacgg cgcaaacagc gtgttcgaag ctcttgaact gggttggctg accgtgggta 4440
gcctggcagt cggcgtggcc cagctcgctg caatgaccgg ccacgcagct gagggcgtgt 4500
gggccgagtt ggcaggcatc tgcccaccac tggatgctga ccgcccactg ggcgcggagg 4560
tccgcgctgc tcgcgatctc ctctccgcac acgctgacca gctgctcgtt gacgaggctg 4620
atggcaaaga cttcggctaa ctctagagtc gacctgcagg catgcaagct tggctgtttt 4680
ggcggatgag agaagatttt cagcctgata cagattaaat cagaacgcag aagcggtctg 4740
ataaaacaga atttgcctgg cggcagtagc gcggtggtcc cacctgaccc catgccgaac 4800
tcagaagtga aacgccgtag cgccgatggt agtgtggggt ctccccatgc gagagtaggg 4860
aactgccagg catcaaataa aacgaaaggc tcagtcgaaa gactgggcct ttcgttttat 4920
ctgttgtttg tcggtgaacg ctctcctgag taggacaaat ccgccgggag cggatttgaa 4980
cgttgcgaag caacggcccg gagggtggcg ggcaggacgc ccgccataaa ctgccaggca 5040
tcaaattaag cagaaggcca tcctgacgga tggccttttt gcgtttctac aaactctttt 5100
tgtttatttt tctaaataca ttcaaatatg tatccgctca tgaattaatt ccgctagatg 5160
acgtgcggct tcgacctcct gggcgtggcg cttgttggcg cgctcgcggc tggctgcggc 5220
acgacacgcg tctgagcagt attttgcgcg ccgtcctcgt gggtcaggcc ggggtgggat 5280
caggccaccg cagtaggcgc agctgatgcg atcctccact actgcgcgtc ctcctggcgc 5340
tgccgagcac gcagctcgtc ggccagctct tcaaggtcgg ccacaagcgt ttctaggtcg 5400
ctcgcggcac ttgcccagtc gcgtgatgct ggcgcgtctg tcgtatcgag ggcgcggaaa 5460
aatccgatca ccgtttttaa atcgacggcg gcatcgagtg cgtcggactc cagcgcgaca 5520
tcggagagat ccaccgctga tgcttcaggc cagttttggt acttcgtcgt gaaggtcatg 5580
acaccattat aacgaacgtt cgttaaaaat tctagcccca attctgataa tttcttccgg 5640
cactcctgcg aaaacctgcg agacttcttg cccagaaaaa acgccaagcg cagcggttac 5700
cgcacttttt ttccaggtga tttcaccctg accagcgaag cggcacttta gtgcatgagg 5760
tgtgcccctg gtttcccctc tttggagggt tcaacccaaa aaagcacaca agcaaaaatg 5820
aaaatcatca tgagcaagtt ggtgcgaagc agcaacgcgc tagctccaaa aaggtctcca 5880
ggatctcgag gagattttg agggggaggg agtcgaggaa gagccagagc agaaggcggg 5940

-continued

```
gaaccgttct ctgccgacag cgtgagcccc ccttaaaaat caggccgggg aggaaccggg   6000
gagggatcag agctaggagc gagacaccct aaaggggggg aaccgttttc tgctgacggt   6060
gtttcgttta ttagttttca gcccgtggat agcggagggt gagggcaagt gagagccaga   6120
gcaaggacgg gacccctaaa ggggggaacc gttttctgct gacggtgttt cgtttattag   6180
ttttcagccc gtggacggcc gcgtttagct tccattccaa gtgcctttct gacttgttgg   6240
atgcgccttt cactgacacc tagttcgcct gcaagctcac gagtcgaggg atcagcaacc   6300
gattgagaac gggcatccag gatcgcagtt ttgacgcgaa gttcgagcaa ctcgcctgtc   6360
atttctcggc gtttgtttgc ttccgctaat cgctgtcgcg tctcctgcgc atacttactt   6420
tctgggtcag cccatctgcg tgcattcgat gtagctgcgc cccgtcgccc catcgtcgct   6480
agagctttcc gccctcggct gctctgcgtt tccacccgac gagcagggac gactggctgg   6540
cctttagcca cgtagccgcg cacacgacgc gccatcgtca ggcgatcacg catggcggga   6600
agatccggct cccggccgtc tgcaccgacc gcctgggcaa cgttgtacgc cacttcatac   6660
gcgtcgatga tcttggcatc ttttaggcgc tcaccagcag ctttgagctg gtatcccacg   6720
gtcaacgcgt ggcgaaacgc ggtctcgtcg cgcgctcgct ctggatttgt ccagagcact   6780
cgcacgccgt cgatcaggtc gccggacgcg tccagggcgc tcggcaggct cgcgtccaaa   6840
atcgctagcg ccttggcttc tgcggtggcg cgttgtgccg cttcaatgcg ggcgcgtccg   6900
ctggaaaagt cctgctcaat gtactttttc ggcttctgtg atccggtcat cgttcgagca   6960
atctccatta ggtcggccag ccgatccaca cgatcatgct ggcagtgcca tttataggct   7020
gtcggatcgt ctgagacgtg cagcggccac cggctcagcc tatgcgaaaa agcctggtca   7080
gcgccgaaaa cacgagtcat ttcttccgtc gttgcagcca gcaggcgcat atttgggctg   7140
gttttacctg ctgcggcata caccgggtca atgagccaga tgagctggca tttcccgctc   7200
agcggattca cgccgatcca agccggcgct ttttctaggc gtgcccattt ctctaaaatc   7260
gcgtagacct gcgggtttac gtgctcaatc ttcccgccgg cctggtggct gggcacatcg   7320
atgtcaagca cgatcaccgc ggcatgttgc gcgtgcgtca gcgcaacgta ctggcaccgc   7380
gtcagcgctt ttgagccagc ccggtagagc tttggttggg tttcgccggt atccgggttt   7440
ttaatccagg cgctcgcgaa atctcttgtc ttgctgccct ggaagctttc gcgtcccagg   7500
tgagcgagca gttcgcggcg atcttctgcc gtccagccgc gtgagccgca gcgcatagct   7560
tcggggtggg tgtcgaacag atcggcggac aatttccacg cgctagctgt gactgtgtcc   7620
tgcggatcgg ctagagtcat gtcttgagtg ctttctccca gctgatgact gggggttagc   7680
cgacgccctg tgagttcccg ctcacggggc gttcaacttt ttcaggtatt tgtgcagctt   7740
atcgtgtttt cttcgtaaat gaacgcttaa ctaccttgtt aaacgtggca aataggcagg   7800
attgatgggg atctagcttc acgctgccgc aagcactcag ggcgcaaggg ctgctaaagg   7860
aagcggaaca cgtagaaagc cagtccgcag aaacggtgct gaccccggat gaatgtcagc   7920
tactgggcta tctggacaag ggaaaacgca agcgcaaaga gaaagcaggt agcttgcagt   7980
gggcttacat ggcgatagct agactgggcg gttttatgga cagcaagcga accggaattg   8040
ccagctgggg cgccctctgg taaggttggg aagccctgca aagtaaactg gatggctttc   8100
ttgccgccaa ggatctgatg gcgcagggga tcaagatctg atcaagagac aggatgagga   8160
tcgtttcgca tgattgaaca agatggattg cacgcaggtt ctccggccgc ttgggtggag   8220
aggctattcg gctatgactg ggcacaacag acaatcggct gctctgatgc cgccgtgttc   8280
cggctgtcag cgcaggggcg cccggttctt tttgtcaaga ccgacctgtc cggtgccctg   8340
```

aatgaactcc aagacgaggc agcgcggcta tcgtggctgg ccacgacggg cgttccttgc 8400
gcagctgtgc tcgacgttgt cactgaagcg ggaagggact ggctgctatt gggcgaagtg 8460
ccggggcagg atctcctgtc atctcacctt gctcctgccg agaaagtatc catcatggct 8520
gatgcaatgc ggcggctgca tacgcttgat ccggctacct gcccattcga ccaccaagcg 8580
aaacatcgca tcgagcgagc acgtactcgg atggaagccg gtcttgtcga tcaggatgat 8640
ctggacgaag agcatcaggg gctcgcgcca gccgaactgt tcgccaggct caaggcgcgg 8700
atgcccgacg gcgaggatct cgtcgtgacc catggcgatg cctgcttgcc gaatatcatg 8760
gtggaaaatg gccgcttttc tggattcatc gactgtggcc ggctgggtgt ggcggaccgc 8820
tatcaggaca tagcgttggc tacccgtgat attgctgaag agcttggcgg cgaatgggct 8880
gaccgcttcc tcgtgcttta cggtatcgcc gctcccgatt cgcagcgcat cgccttctat 8940
cgccttcttg acgagttctt ctgagcggga ctctggggtt cgcggaatca tgaccaaaat 9000
cccttaacgt gagttttcgt tccactgagc gtcagacccc gtagaaaaga tcaaaggatc 9060
ttcttgagat cctttttttc tgcgcgtaat ctgctgcttg caaacaaaaa aaccaccgct 9120
accagcggtg gtttgtttgc cggatcaaga gctaccaact ctttttccga aggtaactgg 9180
cttcagcaga gcgcagatac caaatactgt ccttctagtg tagccgtagt taggccacca 9240
cttcaagaac tctgtagcac cgcctacata cctcgctctg ctaatcctgt taccagtggc 9300
tgctgccagt ggcgataagt cgtgtcttac cgggttggac tcaagacgat agttaccgga 9360
taaggcgcag cggtcgggct gaacgggggg ttcgtgcaca cagcccagct tggagcgaac 9420
gacctacacc gaactgagat acctacagcg tgagctatga gaaagcgcca cgcttcccga 9480
agggagaaag gcggacaggt atccggtaag cggcagggtc ggaacaggag agcgcacgag 9540
ggagcttcca gggggaaacg cctggtatct ttatagtcct gtcgggtttc gccacctctg 9600
acttgagcgt cgatttttgt gatgctcgtc aggggggcgg agcctatgga aaaacgccag 9660
caacgcggcc tttttacggt tcctggcctt ttgctggcct tttgctcaca tgttctttcc 9720
tgcgttatcc cctgattctg tggataaccg tattaccgcc tttgagtgag ctgataccgc 9780
tcgccgcagc cgaacgaccg agcgcagcga gtcagtgagc gaggaagcgg aagagcgcct 9840
gatgcggtat tttctcctta cgcatctgtg cggtatttca caccgcatat ggtgcactct 9900
cagtacaatc tgctctgatg ccgcatagtt aagccagtat acactccgct atcgctacgt 9960
gactgggtca tggctgcgcc ccgacacccg ccaacacccg ctgacgcgcc ctgacgggct 10020
tgtctgctcc cggcatccgc ttacagacaa gctgtgaccg tctccgggag ctgcatgtgt 10080
cagaggtttt caccgtcatc accgaaacgc gcgaggcagc agatcaattc gcgcgcgaag 10140
gcgaagcggc atgcatttac gttgacacca tcgaatggtg caaaaccttt cgcggtatgg 10200
catgatagcg cccggaagag agtcaattca gggtggtgaa tgtgaaacca gtaacgttat 10260
acgatgtcgc agagtatgcc ggtgtctctt atcagaccgt ttcccgcgtg gtgaaccagg 10320
ccagccacgt ttctgcgaaa acgcgggaaa aagtggaagc ggcgatggcg gagctgaatt 10380
acattcccaa ccgcgtggca caacaactgg cgggcaaaca gtcgttgctg attggcgttg 10440
ccacctccag tctggccctg cacgcgccgt cgcaaattgt cgcggcgatt aaatctcgcg 10500
ccgatcaact gggtgccagc gtggtggtgt cgatggtaga acgaagcggc gtcgaagcct 10560
gtaaagcggc ggtgcacaat cttctcgcgc aacgcgtcag tgggctgatc attaactatc 10620
cgctggatga ccaggatgcc attgctgtgg aagctgcctg cactaatgtt ccggcgttat 10680

-continued ttcttgatgt ctctgaccag acacccatca acagtattat tttctcccat gaagacggta 10740
cgcgactggg cgtggagcat ctggtcgcat tgggtcacca gcaaatcgcg ctgttagcgg 10800
gcccattaag ttctgtctcg gcgcgtctgc gtctggctgg ctggcataaa tatctcactc 10860
gcaatcaaat tcagccgata gcggaacggg aaggcgactg gagtgccatg tccggttttc 10920
aacaaaccat gcaaatgctg aatgagggca tcgttcccac tgcgatgctg gttgccaacg 10980
atcagatggc gctgggcgca atgcgcgcca ttaccgagtc cgggctgcgc gttggtgcgg 11040
atatctcggt agtgggatac gacgataccg aagacagctc atgttatatc ccgccgtcaa 11100
ccaccatcaa acaggatttt cgcctgctgg ggcaaaccag cgtggaccgc ttgctgcaac 11160
tctctcaggg ccaggcggtg aagggcaatc agctgttgcc cgtctcactg gtgaaaagaa 11220
aaaccaccct ggcgcccaat acgcaaaccg cctctccccg cgcgttggcc gattcattaa 11280
tgcagctggc acgacaggtt tcccgactgg aaagcgggca gtgagcgcaa cgcaattaat 11340
gtgagttagc gcgaattgat ctggtttgac agcttatcat 11380

<210> SEQ ID NO 68
<211> LENGTH: 4377
<212> TYPE: DNA
<213> ORGANISM: Artificial Sequence
<220> FEATURE:
<223> OTHER INFORMATION: operon RpBAS-Nt4CL-SeSam8

<400> SEQUENCE: 68
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300
gcgtcgcaga actgggcaag gaagctgctc tgaaggctat caaggaatgg ggccagccaa 360
agtccaagat cacccacctg atcgtctgct gcctggctgg cgtggatatg ccaggcgcag 420
attaccagct cactaagctc ctcgatctcg acccatccgt taagcgcttc atgttctacc 480
acctgggttg ctacgccggt ggcaccgtgc tccgcctggc taaggatatc gctgaaaaca 540
acaagggcgc acgcgtgctg atcgtgtgct ctgaaatgac caccacctgt ttccgcggcc 600
cttcagaaac ccacctggac tctatgatcg gccaggccat cctcggtgac ggtgccgcag 660
ccgtgatcgt gggcgcggac cctgatctga ccgtggagcg tccaatcttc gagctggtga 720
gcacggctca gaccatcgtg ccggagtccc acggcgccat cgagggccac ctcctggagt 780
ctggcctgag cttccacctg tacaagaccg tgccgaccct gatctccaac aacatcaaga 840
cctgcctctc cgatgctttc accccactga acatctccga ctggaacagc ctcttctgga 900
tcgcacaccc aggcggcccg gccatcctgg atcaggtgac cgctaaggtg ggcctggaaa 960
aggaaaagct gaaggtgacc cgccaggttc tgaaggatta cggcaacatg tcctccgcta 1020
ccgtgttctt catcatggat gaaatgcgta agaagtccct ggaaaacggc caggcaacca 1080
ccggcgaggg cctggaatgg ggcgtgctgt tcggcttcgg cccaggcatc accgtggaaa 1140
ccgtggtcct gcgctccgtc ccagtgatct cctaaggatc taggaggatt atgagatgga 1200
gaaagataca aaacaggttg acataatttt ccgatcaaaa ctccctgata tttacatccc 1260
taaccatctt cctttacact cctactgttt cgaaaacatt tccgagttca gttctcgtcc 1320
ttgtttaatc aatggcgcca acaaacaaat ttatacgtat gctgatgttg aactcaattc 1380

-continued

```
aagaaaagtt gctgctggtc ttcacaaaca agggattcaa ccaaaggata caataatgat   1440
cctattgcct aactccccag aatttgtgtt tgctttcatt ggtgcatcgt acctcggagc   1500
tatttctaca atggccaatc ctttgtttac tcctgctgag gttgtgaagc aagccgaggc   1560
ttctagtgct aagatcattg tcacacaagc gtgtcatgtt aacaaagtga aagattatgc   1620
atttgagaat gatgtgaaga tcatatgcat cgactcggcg ccggagggtt gtctccactt   1680
ctccgtgcta actcaggcta atgagcacga tattcctgag gttgaaattc aacctgacga   1740
tgtggtggcg ttgccatact cctccgggac gacgggatta cctaaaggag tgatgttgac   1800
gcacaaggga cttgtgacaa gcgtcgcaca acaagtcgac ggtgaaaatc cgaatttgta   1860
tatccatagc gaggacgtga tgctttgtgt cttgcccttg ttccatatct attcactcaa   1920
ctccgttttg ctttgtggat taagggtggg agcagcgatt ttgattatgc agaaatttga   1980
tattgtttct ttcttggagt tgatacaaag ttacaaggtg acaatagggc cgtttgtacc   2040
acctattgtt ttggycattg ctaagagtcc tatggttgat gattatgatc tttcatcagt   2100
aagaaccgtc atgtctgggg ctgcaccatt aggaaaggag cttgaagata ctgttcgagc   2160
caaatttcct aatgctaaac ttggtcaggg ttatggtatg acagaagctg gaccagtgtt   2220
ggctatgtgc ttggcatttg caaaagaacc ctttgaaata aaatcagggg catgtggaac   2280
agttgtgaga aatgctgaaa tgaaaattgt ggatcctaaa actggtaatt ctcttcccag   2340
aaatcaatct ggagaaattt gcattagagg agaccagatc atgaaaggct acctgaatga   2400
tccagaggcc acagcaagaa caatagacaa agaagggtgg ttatatactg gtgacattgg   2460
ctacattgat gatgacgacg agcttttcat tgttgatcga ttaaaggaac tgatcaaata   2520
caaaggattt caagtcgcac ctgctgagct cgaagctctc cttctcaacc atcccaacat   2580
ttctgatgct gctgttgtcc ccatgaagga cgagcaagca ggagaagttc cagtggcttt   2640
tgttgttaga tccaacggat ccaccattac tgaagatgaa gtcaaagatt ttatttcaaa   2700
gcaggtgata ttttataaga ggataaagcg ggtatttttc gtggatgcta ttcctaaatc   2760
tccatctggc aaaatccttc gaaaagattt gagagctaaa ctggctgctg ggcttccaaa   2820
ttaaggatct aggaggataa agaaatgacc caggtcgtgg agcgccaggc tgatcgtctg   2880
tccagccgcg agtacctggc acgcgttgtt cgttccgcag gctgggacgc aggcctcacc   2940
agctgcaccg atgaagaaat cgtgcgcatg ggtgcatccg cacgcaccat tgaggaatac   3000
ctgaagtctg ataagccgat ctacggcctc acccagggct tcggtccact ggtcctgttc   3060
gatgcagatt ccgaactgga acagggcggc tctctcatct cccatctggg caccggccag   3120
ggtgcaccgc ttgcaccgga agtgtcccgc ctgattctgt ggctccgcat ccaaaacatg   3180
cgcaagggct attcggctgt cagtcctgtg ttctggcaaa aactggccga cctctggaac   3240
aagggcttca cccctgctat ccctcgccac ggcaccgtgt ccgccagcgg cgatctccag   3300
cctctggcac acgctgccct ggcttttacc ggcgtgggcg aggcatggac ccgtgatgca   3360
gacggccgtt ggtccaccgt gccagccgtg gacgcattag cagcactggg tgcagagccg   3420
ttcgattggc cagtgcgcga ggctttggcc ttcgtgaacg gtacgggcgc atcactcgcg   3480
gtggcagttc tcaaccacag atccgctctc cgtctcgtac gagcatgtgc agtcttgtct   3540
gcccgtttgg ctaccttgct aggagctaat cctgaacact acgatgtcgg ccacggagtc   3600
gcaaggggac aagttggcca gctgaccgcg gcggaatgga ttcggcaggg actaccacgc   3660
ggcatggtcc gagacggttc gcgccctctt caagaaccat acagcttgcg ctgtgccccc   3720
```

-continued caggtccttg gcgcggtgct ggaccagctg gatggtgcag gcgatgttct ggcccgcgaa 3780
gtggatggct gccaggacaa tcctatcacc tacgagggcg aactgctgca cggcggtaac 3840
ttccacgcta tgccagtcgg cttcgcatcc gaccagatcg gtctggcgat gcacatggca 3900
gcttatctgg ctgaacgcca gctcggcctg ctggtgagcc cggtgaccaa cggcgacctg 3960
ccaccaatgc tgaccccacg cgctggacgc ggtgccggcc tggcgggcgt tcagatctcc 4020
gcaacctcct tcgtctctcg catccgccag ctggtgttcc cagctagcct caccaccctc 4080
ccaaccaacg gctggaacca ggaccatgtc ccaatggctc tgaacggcgc aaacagcgtg 4140
ttcgaagctc ttgaactggg ttggctgacc gtgggtagcc tggcagtcgg cgtggcccag 4200
ctcgctgcaa tgaccggcca cgcagctgag ggcgtgtggg ccgagttggc aggcatctgc 4260
ccaccactgg atgctgaccg cccactgggc gcggaggtcc gcgctgctcg cgatctcctc 4320
tccgcacacg ctgaccagct gctcgttgac gaggctgatg gcaaagactt cggctaa 4377

<210> SEQ ID NO 69
<211> LENGTH: 12633
<212> TYPE: DNA
<213> ORGANISM: Artificial Sequence
<220> FEATURE:
<223> OTHER INFORMATION: plasmid RpBAS-Pp4CL-RcTAL-RiBAR-pECXK
(pECXK_PB)

<400> SEQUENCE: 69
cgactgcacg gtgcaccaat gcttctggcg tcaggcagcc atcggaagct gtggtatggc 60
tgtgcaggtc gtaaatcact gcataattcg tgtcgctcaa ggcgcactcc cgttctggat 120
aatgtttttt gcgccgacat cataacggtt ctggcaaata ttctgaaatg agctgttgac 180
aattaatcat ccggctcgta taatgtgtgg aattgtgagc ggataacaat ttcacacagg 240
aaacagacca tggaattcga gctggatcta ggagggagat catatggcaa ccgaggagat 300
gaagaagctc gcaaccgtga tggcaatcgg cactgctaac ccaccgaact gctattacca 360
agctgatttt cccgacttct acttccgcgt gaccaactcc gatcatctga tcaacctgaa 420
gcagaagttc aagcgcctat gcgaaaactc tcgcatcgag aagcgctacc tccacgtcac 480
cgaggagatc ctcaaggaaa acccaaacat cgcagcttac gaggctacta gcctgaacgt 540
gcgccacaag atgcaggtca agggcgtcgc agaactgggc aaggaagctg ctctgaaggc 600
tatcaaggaa tggggccagc caaagtccaa gatcacccac ctgatcgtct gctgcctggc 660
tggcgtggat atgccaggcg cagattacca gctcactaag ctcctcgatc tcgacccatc 720
cgttaagcgc ttcatgttct accacctggg ttgctacgcc ggtggcaccg tgctccgcct 780
ggctaaggat atcgctgaaa acaacaaggg cgcacgcgtg ctgatcgtgt gctctgaaat 840
gaccaccacc tgtttccgcg gcccttcaga aacccacctg gactctatga tcggccaggc 900
catcctcggt gacggtgccg cagccgtgat cgtgggcgcg gaccctgatc tgaccgtgga 960
gcgtccaatc ttcgagctgg tgagcacggc tcagaccatc gtgccggagt cccacggcgc 1020
catcgagggc cacctcctgg agtctggcct gagcttccac ctgtacaaga ccgtgccgac 1080
cctgatctcc aacaacatca agacctgcct ctccgatgct ttcaccccac tgaacatctc 1140
cgactggaac agcctcttct ggatcgcaca cccaggcggc ccggccatcc tggatcaggt 1200
gaccgctaag gtgggcctgg aaaaggaaaa gctgaaggtg acccgccagg ttctgaagga 1260
ttacggcaac atgtcctccg ctaccgtgtt cttcatcatg gatgaaatgc gtaagaagtc 1320
cctggaaaac ggccaggcaa ccaccggcga gggcctggaa tggggcgtgc tgttcggctt 1380

-continued

```
cggcccaggc atcaccgtgg aaaccgtggt cctgcgctcc gtcccagtga tctcctaagg   1440
atctaggagg attatgagat gtcaccatcg ctccttcccc agccaatcgt gtccgaatcc   1500
accggtgaat ccgtgatgaa gatgtccctc cagtccgaag tgcgcgaagc atccctggca   1560
accggtgaaa accctgaacc attcctgctg gaaaccgatg ctgaatccca gatcatggaa   1620
cctgtgcacg ctgaagttca cgatttcatc taccgttcta agctgcctga tatcgatatc   1680
ccaaaccaca tgcctctggc tgattactgc ctggagaagt cctcccagtg gcctgataag   1740
gtgtgcctga tcgatggtgt gaccggtcgc gaacaccgct acggcgaaat tgagctgtcc   1800
tcccgccgcg tggcagcagg ccttgataag atcggcgtga agcagggcga tgtcatcgca   1860
ctgctcttgc ctaactgcgc tgagttcgtc ctggtgttcc tgggcgcagc gaagcgcggc   1920
gccgttgtca ccaccgctaa cccattctac accgccgccg agttggagaa gcaaatcgag   1980
gcctccggtg cgggcattgt tatcactcag agcagctaca tcgagaagct cgcaggcctt   2040
aacgtccaga tcatcaccgt tgatcagcac gtggctaatt gcatgcacat ctccgtgctg   2100
ctgaacgcat gcgaagatga atgccctcag gtgcgtatcc accctgacga tctggtctgc   2160
ctgccatact cctccggcac caccggcttg ccaaagggcg tgatgctgac ccacaagtcc   2220
cttgtgtcat ccgtgtccca acaggtggac ggcgaagcac caaacttcaa catcactgtc   2280
gaggacaccc tgatgtgcgt gctgcccatg ttccacatct attccctcaa ctccatcctg   2340
ctgtgcggcc tccgtgtggg cgccaccctc gttattatgc cgaagttcga actgccaaag   2400
ctgttggacc tgatccagcg tcacaaggtg accatgggcc cattcgtgcc gccaatcgtc   2460
ctggccatcg caaagaaccc aatcgtcgag aattacgatc tctcctccat gcgcatggtt   2520
atgtccggcg ctgcacctct gggtcgggag ctggaggacg ctttccgtgc ccgcttgcca   2580
aacgccgttc tgggccaggg ctacgggatg actgaagccg gcccagtcct ggctatgtgc   2640
ctcgcattcg caaagacccc attctccgtg aagccaggct cctgcggcac cgtggtgcgc   2700
aacgctgaag tgaaaatcgt cgataccgaa accggcatgt ccctgccata caaccagcca   2760
ggcgagatct gcatccgcgg cccacagatc atgaagggct acctgaagaa cccagaagct   2820
accgctaaca ccatcgataa ggatggcttc ctgcacaccg gcgatgtcgc attcatcgat   2880
gaggatgagg agatgttcat cgttgatcgc gtcaaggaga tcatcaagtt caagggcttc   2940
caggtgcctc ctgcggagct ggaagctctc ctgctgtccc acaaggagat ccaggacgct   3000
gctgtcgtgt cccgtaagga tgacgtggcg ggcgaagttc cagtggcatt cgtggtccgc   3060
gctaccagct ccaccatcac cgaggatgaa gtcaaggatt acatcgcaaa gcaggtcgtt   3120
ttctacaaga agatccacaa cgtatacttc gtggattccg tgccaaagtc tccatccggc   3180
aagatcctgc gtaaggatct ccgtaacaag gtgtaaggat ctaggaggat aaagaaatga   3240
ccctgcaatc ccagactgca aaggactgcc tggcgctgga tggtgcactg acactggttc   3300
agtgcgaagc aattgccact caccgctcac ggatctccgt cacaccagca ttgcgggaac   3360
gctgcgcccg cgcgcacgca cgtctggagc acgctatcgc agaacagcgt cacatctatg   3420
gtatcaccac cggcttcgga ccactggcta atcgcctgat cggtgcagat cagggcgccg   3480
aactccagca gaacctcatc taccaccttg ctactggcgt gggcccaaaa ctctcctggg   3540
ctgaagcacg tgcactcatg ctggctcgtc tcaactccat ccttcagggc gcatctggtg   3600
catcaccaga aaccatcgac cgtatcgttg ccgttctgaa cgctggcttc gccccagaag   3660
tcccagctca gggcaccgtt ggtgcatctg gcgatctgac ccactggct cacatggtgc    3720
tggcgcttca gggtcgaggt cgtatgatcg atccatccgg ccgtgttcag gaagccggcg   3780
```

cagtgatgga tcgcctgtgc ggtggcccac tgaccttggc agcccgtgac ggtctggctc 3840
tggtcaacgg tacttccgct atgaccgcaa tcgctgcttt gaccggtgtg gaggctgcgc 3900
gcgcaatcga cgccgcattg cgccactccg ctgtgctcat ggaggttctc tccggccacg 3960
ctgaggcttg gcaccctgca tttgctgaac tccgcccaca cccaggccag ctgcgcgcaa 4020
ccgaacgtct ggcccaggct ctcgatggcg ccggtcgcgt ttgccgcacc ttgaccgcgg 4080
cccgtcgcct gaccgcagct gatctgcgcc ctgaggatca cccagcccag gacgcctact 4140
ccctgcgcgt ggtgccacag ctggttggcg ctgtctggga caccctcgat tggcacgatc 4200
gcgtcgtgac ctgcgaactc aactctgtga ccgacaaccc aatcttcccg gaaggctgcg 4260
ctgttccagc actgcacggc ggcaacttca tgggcgtgca cgtcgcactg gcgtcggacg 4320
ccctgaacgc tgcattggtt accctggcag gtctggtgga gcgccagatc gcacgcctta 4380
ctgatgagaa gctgaacaag ggacttccgg cattccttca cggtggtcag gctggccttc 4440
agtccggctt catgggcgcg caggtcaccg caaccgcgct ccttgctgaa atgcgcgcaa 4500
acgcaacccc ggtgtctgtt cagtcactgt ctaccaacgg cgctaaccag gatgttgtca 4560
gcatgggcac catcgctgca cgccgcgctc gcgcacagct gctcccactg tcccagattc 4620
aggcaatcct ggctctcgct ctcgcccagg caatggatct gctggatgat ccagagggcc 4680
aggctggctg gtcccttacc gcacgcgacc tgcgcgatcg catccgcgct gtctcgccgg 4740
gcctgcgcgc agatcgccca ctggccggcc acatcgaggc agtcgctcag ggtctgcgcc 4800
acccttccgc agcagctgat ccaccagcat aaggatctag gaggaaataa ccatggcatc 4860
cggcggtgaa atgcaggttt ccaacaagca ggttatcttc cgtgattacg ttaccggctt 4920
cccaaaggaa tccgatatgg aactcactac ccgctctatc acccttaagt taccacaagg 4980
ttctaccggc ctgctcctga agaacctgta cctttcctgc gatccatata tgcgcgcccg 5040
catgaccaac caccatcgtc tgtcctacgt tgattccttc aagccaggta gcccaatcat 5100
tggttacggt gtagcacgcg ttctggaatc cggtaatcct aagtttaacc caggcgatct 5160
tgtttggggt ttcaccggtt gggaagaata ctctgtgatc accgctactg aatccctgtt 5220
caagatccat aacaccgatg tgccgctgtc ctactacacc ggcctcctgg ggatgccagg 5280
catgaccgca tacgctggct tctacgagat ctgtagccct aagaagggcg aaaccgtcta 5340
cgtgtccgct gcctccggcg cggttggcca gcttgtgggc cagttcgcta agctcaccgg 5400
ctgctacgtg gtgggctctg ccggctccaa ggaaaaggtg gacctgctga agaacaagtt 5460
cggcttcgac gaagcattca actacaagga ggaagcggac ctggacgctg cgctgcgtcg 5520
gtacttcccc gatggaattg atatttactt cgaaaacgtg ggtggcaaga tgctggacgc 5580
tgtcctcccc aacatgcgcc ccaagggccg catcgccgtc tgcggcatga tctcccaata 5640
caaccttgag cagccagagg gcgtccgcaa cctgatggcc ctgatcgtca agcaggtccg 5700
catggaaggc tttatggtgt tctcctacta ccacctgtac ggcaagttcc tggaaaccgt 5760
gctcccatac atcaagcagg gcaagatcac ctacgtggaa gatgtggtgg atggcctgga 5820
caacgcacca gcagccctga tcggcctgta ctccggccgc aacgtgggca agcaggtcgt 5880
cgtggtgtcc cgcgagtaaa gtcgacctgc aggcatgcaa gcttggctgt tttggcggat 5940
gagagaagat tttcagcctg atacagatta aatcagaacg cagaagcggt ctgataaaac 6000
agaatttgcc tggcggcagt agcgcggtgg tcccacctga ccccatgccg aactcagaag 6060
tgaaacgccg tagcgccgat ggtagtgtgg ggtctcccca tgcgagagta gggaactgcc 6120

-continued

```
aggcatcaaa taaaacgaaa ggctcagtcg aaagactggg cctttcgttt tatctgttgt   6180
ttgtcggtga acgctctcct gagtaggaca aatccgccgg gagcggattt gaacgttgcg   6240
aagcaacggc ccggagggtg gcgggcagga cgcccgccat aaactgccag gcatcaaatt   6300
aagcagaagg ccatcctgac ggatggcctt tttgcgtttc tacaaactct ttttgtttat   6360
ttttctaaat acattcaaat atgtatccgc tcatgaatta attccgctag atgacgtgcg   6420
gcttcgacct cctgggcgtg gcgcttgttg gcgcgctcgc ggctggctgc ggcacgacac   6480
gcgtctgagc agtattttgc gcgccgtcct cgtgggtcag gccggggtgg gatcaggcca   6540
ccgcagtagg cgcagctgat gcgatcctcc actactgcgc gtcctcctgg cgctgccgag   6600
cacgcagctc gtcggccagc tcttcaaggt cggccacaag cgtttctagg tcgctcgcgg   6660
cacttgccca gtcgcgtgat gctggcgcgt ctgtcgtatc gagggcgcgg aaaaatccga   6720
tcaccgtttt taaatcgacg gcggcatcga gtgcgtcgga ctccagcgcg acatcggaga   6780
gatccaccgc tgatgcttca ggccagtttt ggtacttcgt cgtgaaggtc atgacaccat   6840
tataacgaac gttcgttaaa aattctagcc ccaattctga taatttcttc cggcactcct   6900
gcgaaaacct gcgagacttc ttgcccagaa aaaacgccaa gcgcagcggt taccgcactt   6960
tttttccagg tgatttcacc ctgaccagcg aagcggcact ttagtgcatg aggtgtgccc   7020
ctggtttccc ctctttggag ggttcaaccc aaaaaagcac acaagcaaaa atgaaaatca   7080
tcatgagcaa gttggtgcga agcagcaacg cgctagctcc aaaaaggtct ccaggatctc   7140
gaggagattt ttgaggggga gggagtcgag gaagagccag agcagaaggc ggggaaccgt   7200
tctctgccga cagcgtgagc ccccttaaa aatcaggccg gggaggaacc ggggagggat   7260
cagagctagg agcgagacac cctaaagggg gggaaccgtt ttctgctgac ggtgtttcgt   7320
ttattagttt tcagcccgtg gatagcggag ggtgagggca agtgagagcc agagcaagga   7380
cgggacccct aaagggggga accgttttct gctgacggtg tttcgtttat tagttttcag   7440
cccgtggacg gccgcgttta gcttccattc caagtgcctt tctgacttgt tggatgcgcc   7500
tttcactgac acctagttcg cctgcaagct cacgagtcga gggatcagca accgattgag   7560
aacgggcatc caggatcgca gttttgacgc gaagttcgag caactcgcct gtcatttctc   7620
ggcgtttgtt tgcttccgct aatcgctgtc gcgtctcctg cgcatactta ctttctgggt   7680
cagcccatct gcgtgcattc gatgtagctg cgccccgtcg ccccatcgtc gctagagctt   7740
tccgccctcg gctgctctgc gtttccaccc gacgagcagg gacgactggc tggcctttag   7800
ccacgtagcc gcgcacacga cgcgccatcg tcaggcgatc acgcatggcg ggaagatccg   7860
gctcccggcc gtctgcaccg accgcctggg caacgttgta cgccacttca tacgcgtcga   7920
tgatcttggc atcttttagg cgctcaccag cagctttgag ctggtatccc acggtcaacg   7980
cgtggcgaaa cgcggtctcg tcgcgcgctc gctctggatt tgtccagagc actcgcacgc   8040
cgtcgatcag gtcgccggac gcgtccaggg cgctcggcag gctcgcgtcc aaaatcgcta   8100
gcgccttggc ttctgcggtg gcgcgttgtg ccgcttcaat gcgggcgcgt ccgctggaaa   8160
agtcctgctc aatgtacttt ttcggcttct gtgatccggt catcgttcga gcaatctcca   8220
ttaggtcggc cagccgatcc acacgatcat gctggcagtg ccatttatag gctgtcggat   8280
cgtctgagac gtgcagcggc caccggctca gcctatgcga aaaagcctgg tcagcgccga   8340
aaacacgagt catttcttcc gtcgttgcag ccagcaggcg catatttggg ctggttttac   8400
ctgctgcggc atacaccggg tcaatgagcc agatgagctg gcatttcccg ctcagcggat   8460
tcacgccgat ccaagccggc gctttttcta ggcgtgccca tttctctaaa atcgcgtaga   8520
```

```
cctgcgggtt tacgtgctca atcttcccgc cggcctggtg gctgggcaca tcgatgtcaa   8580
gcacgatcac cgcggcatgt tgcgcgtgcg tcagcgcaac gtactggcac cgcgtcagcg   8640
cttttgagcc agcccggtag agctttggtt gggtttcgcc ggtatccggg tttttaatcc   8700
aggcgctcgc gaaatctctt gtcttgctgc cctggaagct ttcgcgtccc aggtgagcga   8760
gcagttcgcg gcgatcttct gccgtccagc cgcgtgagcc gcagcgcata gcttcggggt   8820
gggtgtcgaa cagatcggcg gacaatttcc acgcgctagc tgtgactgtg tcctgcggat   8880
cggctagagt catgtcttga gtgctttctc ccagctgatg actgggggtt agccgacgcc   8940
ctgtgagttc ccgctcacgg ggcgttcaac tttttcaggt atttgtgcag cttatcgtgt   9000
tttcttcgta aatgaacgct taactacctt gttaaacgtg gcaaataggc aggattgatg   9060
gggatctagc ttcacgctgc cgcaagcact cagggcgcaa gggctgctaa aggaagcgga   9120
acacgtagaa agccagtccg cagaaacggt gctgaccccg gatgaatgtc agctactggg   9180
ctatctggac aagggaaaac gcaagcgcaa agagaaagca ggtagcttgc agtgggctta   9240
catggcgata gctagactgg gcggttttat ggacagcaag cgaaccggaa ttgccagctg   9300
gggcgccctc tggtaaggtt gggaagccct gcaaagtaaa ctggatggct ttcttgccgc   9360
caaggatctg atggcgcagg ggatcaagat ctgatcaaga gacaggatga ggatcgtttc   9420
gcatgattga acaagatgga ttgcacgcag gttctccggc cgcttgggtg gagaggctat   9480
tcggctatga ctgggcacaa cagacaatcg gctgctctga tgccgccgtg ttccggctgt   9540
cagcgcaggg gcgcccggtt ctttttgtca agaccgacct gtccggtgcc ctgaatgaac   9600
tccaagacga ggcagcgcgg ctatcgtggc tggccacgac gggcgttcct tgcgcagctg   9660
tgctcgacgt tgtcactgaa gcgggaaggg actggctgct attgggcgaa gtgccggggc   9720
aggatctcct gtcatctcac cttgctcctg ccgagaaagt atccatcatg gctgatgcaa   9780
tgcggcggct gcatacgctt gatccggcta cctgcccatt cgaccaccaa gcgaaacatc   9840
gcatcgagcg agcacgtact cggatggaag ccggtcttgt cgatcaggat gatctggacg   9900
aagagcatca ggggctcgcg ccagccgaac tgttcgccag gctcaaggcg cggatgcccg   9960
acggcgagga tctcgtcgtg acccatggcg atgcctgctt gccgaatatc atggtggaaa  10020
atggccgctt ttctggattc atcgactgtg gccggctggg tgtggcggac cgctatcagg  10080
acatagcgtt ggctacccgt gatattgctg aagagcttgg cggcgaatgg gctgaccgct  10140
tcctcgtgct ttacggtatc gccgctcccg attcgcagcg catcgccttc tatcgccttc  10200
ttgacgagtt cttctgagcg ggactctggg gttcgcggaa tcatgaccaa aatcccttaa  10260
cgtgagtttt cgttccactg agcgtcagac cccgtagaaa agatcaaagg atcttcttga  10320
gatccttttt ttctgcgcgt aatctgctgc ttgcaaacaa aaaaaccacc gctaccagcg  10380
gtggtttgtt tgccggatca agagctacca actctttttc cgaaggtaac tggcttcagc  10440
agagcgcaga taccaaatac tgtccttcta gtgtagccgt agttaggcca ccacttcaag  10500
aactctgtag caccgcctac atacctcgct ctgctaatcc tgttaccagt ggctgctgcc  10560
agtggcgata agtcgtgtct taccgggttg gactcaagac gatagttacc ggataaggcg  10620
cagcggtcgg gctgaacggg gggttcgtgc acacagccca gcttggagcg aacgacctac  10680
accgaactga gatacctaca gcgtgagcta tgagaaagcg ccacgcttcc cgaagggaga  10740
aaggcggaca ggtatccggt aagcggcagg gtcggaacag gagagcgcac gagggagctt  10800
ccagggggaa acgcctggta tctttatagt cctgtcgggt ttcgccacct ctgacttgag  10860
```

cgtcgatttt tgtgatgctc gtcagggggg cggagcctat ggaaaaacgc cagcaacgcg 10920
gcctttttac ggttcctggc cttttgctgg ccttttgctc acatgttctt tcctgcgtta 10980
tcccctgatt ctgtggataa ccgtattacc gcctttgagt gagctgatac cgctcgccgc 11040
agccgaacga ccgagcgcag cgagtcagtg agcgaggaag cggaagagcg cctgatgcgg 11100
tattttctcc ttacgcatct gtgcggtatt tcacaccgca tatggtgcac tctcagtaca 11160
atctgctctg atgccgcata gttaagccag tatacactcc gctatcgcta cgtgactggg 11220
tcatggctgc gccccgacac ccgccaacac ccgctgacgc gccctgacgg gcttgtctgc 11280
tcccggcatc cgcttacaga caagctgtga ccgtctccgg gagctgcatg tgtcagaggt 11340
tttcaccgtc atcaccgaaa cgcgcgaggc agcagatcaa ttcgcgcgcg aaggcgaagc 11400
ggcatgcatt tacgttgaca ccatcgaatg gtgcaaaacc tttcgcggta tggcatgata 11460
gcgcccggaa gagagtcaat tcagggtggt gaatgtgaaa ccagtaacgt tatacgatgt 11520
cgcagagtat gccggtgtct cttatcagac cgtttcccgc gtggtgaacc aggccagcca 11580
cgtttctgcg aaaacgcggg aaaaagtgga agcggcgatg gcggagctga attacattcc 11640
caaccgcgtg gcacaacaac tggcgggcaa acagtcgttg ctgattggcg ttgccacctc 11700
cagtctggcc ctgcacgcgc cgtcgcaaat tgtcgcggcg attaaatctc gcgccgatca 11760
actgggtgcc agcgtggtgg tgtcgatggt agaacgaagc ggcgtcgaag cctgtaaagc 11820
ggcggtgcac aatcttctcg cgcaacgcgt cagtgggctg atcattaact atccgctgga 11880
tgaccaggat gccattgctg tggaagctgc ctgcactaat gttccggcgt tatttcttga 11940
tgtctctgac cagacaccca tcaacagtat tattttctcc catgaagacg gtacgcgact 12000
gggcgtggag catctggtcg cattgggtca ccagcaaatc gcgctgttag cgggcccatt 12060
aagttctgtc tcggcgcgtc tgcgtctggc tggctggcat aaatatctca ctcgcaatca 12120
aattcagccg atagcggaac gggaaggcga ctggagtgcc atgtccggtt ttcaacaaac 12180
catgcaaatg ctgaatgagg gcatcgttcc cactgcgatg ctggttgcca acgatcagat 12240
ggcgctgggc gcaatgcgcg ccattaccga gtccgggctg cgcgttggtg cggatatctc 12300
ggtagtggga tacgacgata ccgaagacag ctcatgttat atcccgccgt caaccaccat 12360
caaacaggat tttcgcctgc tggggcaaac cagcgtggac cgcttgctgc aactctctca 12420
gggccaggcg gtgaagggca atcagctgtt gcccgtctca ctggtgaaaa gaaaaaccac 12480
cctggcgccc aatacgcaaa ccgcctctcc ccgcgcgttg gccgattcat taatgcagct 12540
ggcacgacag gtttcccgac tggaaagcgg gcagtgagcg caacgcaatt aatgtgagtt 12600
agcgcgaatt gatctggttt gacagcttat cat 12633

<210> SEQ ID NO 70
<211> LENGTH: 5636
<212> TYPE: DNA
<213> ORGANISM: Artificial Sequence
<220> FEATURE:
<223> OTHER INFORMATION: operon RpBAS-Pp4CL-RcTAL-RiBAR

<400> SEQUENCE: 70
ggatctagga gggagatcat atggcaaccg aggagatgaa gaagctcgca accgtgatgg 60
caatcggcac tgctaaccca ccgaactgct attaccaagc tgattttccc gacttctact 120
tccgcgtgac caactccgat catctgatca acctgaagca gaagttcaag cgcctatgcg 180
aaaactctcg catcgagaag cgctacctcc acgtcaccga ggagatcctc aaggaaaacc 240
caaacatcgc agcttacgag gctactagcc tgaacgtgcg ccacaagatg caggtcaagg 300
gcgtcgcaga actgggcaag gaagctgctc tgaaggctat caaggaatgg ggccagccaa 360
agtccaagat cacccacctg atcgtctgct gcctggctgg cgtggatatg ccaggcgcag 420
attaccagct cactaagctc ctcgatctcg acccatccgt taagcgcttc atgttctacc 480
acctgggttg ctacgccggt ggcaccgtgc tccgcctggc taaggatatc gctgaaaaca 540
acaagggcgc acgcgtgctg atcgtgtgct ctgaaatgac caccacctgt ttccgcggcc 600
cttcagaaac ccacctggac tctatgatcg gccaggccat cctcggtgac ggtgccgcag 660
ccgtgatcgt gggcgcggac cctgatctga ccgtggagcg tccaatcttc gagctggtga 720
gcacggctca gaccatcgtg ccggagtccc acggcgccat cgagggccac ctcctggagt 780
ctggcctgag cttccacctg tacaagaccg tgccgaccct gatctccaac aacatcaaga 840
cctgcctctc cgatgctttc accccactga acatctccga ctggaacagc ctcttctgga 900
tcgcacaccc aggcggcccg gccatcctgg atcaggtgac cgctaaggtg ggcctggaaa 960
aggaaaagct gaaggtgacc cgccaggttc tgaaggatta cggcaacatg tcctccgcta 1020
ccgtgttctt catcatggat gaaatgcgta agaagtccct ggaaaacggc caggcaacca 1080
ccggcgaggg cctggaatgg ggcgtgctgt tcggcttcgg cccaggcatc accgtggaaa 1140
ccgtggtcct gcgctccgtc ccagtgatct cctaaggatc taggaggatt atgagatgtc 1200
accatcgctc cttccccagc caatcgtgtc cgaatccacc ggtgaatccg tgatgaagat 1260
gtccctccag tccgaagtgc gcgaagcatc cctggcaacc ggtgaaaacc ctgaaccatt 1320
cctgctggaa accgatgctg aatcccagat catggaacct gtgcacgctg aagttcacga 1380
tttcatctac cgttctaagc tgcctgatat cgatatccca aaccacatgc ctctggctga 1440
ttactgcctg gagaagtcct cccagtggcc tgataaggtg tgcctgatcg atggtgtgac 1500
cggtcgcgaa caccgctacg gcgaaattga gctgtcctcc cgccgcgtgg cagcaggcct 1560
tgataagatc ggcgtgaagc agggcgatgt catcgcactg ctcttgccta actgcgctga 1620
gttcgtcctg gtgttcctgg gcgcagcgaa gcgcggcgcc gttgtcacca ccgctaaccc 1680
attctacacc gccgccgagt tggagaagca aatcgaggcc tccggtgcgg gcattgttat 1740
cactcagagc agctacatcg agaagctcgc aggccttaac gtccagatca tcaccgttga 1800
tcagcacgtg gctaattgca tgcacatctc cgtgctgctg aacgcatgcg aagatgaatg 1860
ccctcaggtg cgtatccacc ctgacgatct ggtctgcctg ccatactcct ccggcaccac 1920
cggcttgcca aagggcgtga tgctgaccca caagtccctt gtgtcatccg tgtcccaaca 1980
ggtggacggc gaagcaccaa acttcaacat cactgtcgag gacaccctga tgtgcgtgct 2040
gcccatgttc cacatctatt ccctcaactc catcctgctg tgcggcctcc gtgtgggcgc 2100
caccctcgtt attatgccga agttcgaact gccaaagctg ttggacctga tccagcgtca 2160
caaggtgacc atgggcccat tcgtgccgcc aatcgtcctg gccatcgcaa agaacccaat 2220
cgtcgagaat tacgatctct cctccatgcg catggttatg tccggcgctg cacctctggg 2280
tcgggagctg gaggacgctt tccgtgcccg cttgccaaac gccgttctgg gccagggcta 2340
cgggatgact gaagccggcc cagtcctggc tatgtgcctc gcattcgcaa agaccccatt 2400
ctccgtgaag ccaggctcct gcggcaccgt ggtgcgcaac gctgaagtga aaatcgtcga 2460
taccgaaacc ggcatgtccc tgccatacaa ccagccaggc gagatctgca tccgcggccc 2520
acagatcatg aagggctacc tgaagaaccc agaagctacc gctaacacca tcgataagga 2580
tggcttcctg cacaccggcg atgtcgcatt catcgatgag gatgaggaga tgttcatcgt 2640

-continued

```
tgatcgcgtc aaggagatca tcaagttcaa gggcttccag gtgcctcctg cggagctgga   2700
agctctcctg ctgtcccaca aggagatcca ggacgctgct gtcgtgtccc gtaaggatga   2760
cgtggcgggc gaagttccag tggcattcgt ggtccgcgct accagctcca ccatcaccga   2820
ggatgaagtc aaggattaca tcgcaaagca ggtcgttttc tacaagaaga tccacaacgt   2880
atacttcgtg gattccgtgc caaagtctcc atccggcaag atcctgcgta aggatctccg   2940
taacaaggtg taaggatcta ggaggataaa gaaatgaccc tgcaatccca gactgcaaag   3000
gactgcctgg cgctggatgg tgcactgaca ctggttcagt gcgaagcaat tgccactcac   3060
cgctcacgga tctccgtcac accagcattg cgggaacgct gcgcccgcgc gcacgcacgt   3120
ctggagcacg ctatcgcaga acagcgtcac atctatggta tcaccaccgg cttcggacca   3180
ctggctaatc gcctgatcgg tgcagatcag ggcgccgaac tccagcagaa cctcatctac   3240
caccttgcta ctggcgtggg cccaaaactc tcctgggctg aagcacgtgc actcatgctg   3300
gctcgtctca actccatcct tcagggcgca tctggtgcat caccagaaac catcgaccgt   3360
atcgttgccg ttctgaacgc tggcttcgcc ccagaagtcc cagctcaggg caccgttggt   3420
gcatctggcg atctgacccc actggctcac atggtgctgg cgcttcaggg tcgaggtcgt   3480
atgatcgatc catccggccg tgttcaggaa gccggcgcag tgatggatcg cctgtgcggt   3540
ggcccactga ccttggcagc ccgtgacggt ctggctctgg tcaacggtac ttccgctatg   3600
accgcaatcg ctgctttgac cggtgtggag gctgcgcgcg caatcgacgc cgcattgcgc   3660
cactccgctg tgctcatgga ggttctctcc ggccacgctg aggcttggca ccctgcattt   3720
gctgaactcc gcccacaccc aggccagctg cgcgcaaccg aacgtctggc ccaggctctc   3780
gatggcgccg gtcgcgtttg ccgcaccttg accgcggccc gtcgcctgac cgcagctgat   3840
ctgcgccctg aggatcaccc agcccaggac gcctactccc tgcgcgtggt gccacagctg   3900
gttggcgctg tctgggacac cctcgattgg cacgatcgcg tcgtgacctg cgaactcaac   3960
tctgtgaccg acaacccaat cttcccggaa ggctgcgctg ttccagcact gcacggcggc   4020
aacttcatgg gcgtgcacgt cgcactggcg tcggacgccc tgaacgctgc attggttacc   4080
ctggcaggtc tggtggagcg ccagatcgca cgccttactg atgagaagct gaacaaggga   4140
cttccggcat tccttcacgg tggtcaggct ggccttcagt ccggcttcat gggcgcgcag   4200
gtcaccgcaa ccgcgctcct tgctgaaatg cgcgcaaacg caaccccggt gtctgttcag   4260
tcactgtcta ccaacggcgc taaccaggat gttgtcagca tgggcaccat cgctgcacgc   4320
cgcgctcgcg cacagctgct cccactgtcc cagattcagg caatcctggc tctcgctctc   4380
gcccaggcaa tggatctgct ggatgatcca gagggccagg ctggctggtc ccttaccgca   4440
cgcgacctgc gcgatcgcat ccgcgctgtc tcgccgggcc tgcgcgcaga tcgcccactg   4500
gccggccaca tcgaggcagt cgctcagggt ctgcgccacc cttccgcagc agctgatcca   4560
ccagcataag gatctaggag gaaataacca tggcatccgg cggtgaaatg caggtttcca   4620
acaagcaggt tatcttccgt gattacgtta ccggcttccc aaaggaatcc gatatggaac   4680
tcactacccg ctctatcacc cttaagttac cacaaggttc taccggcctg ctcctgaaga   4740
acctgtacct ttcctgcgat ccatatatgc gcgcccgcat gaccaaccac catcgtctgt   4800
cctacgttga ttccttcaag ccaggtagcc caatcattgg ttacggtgta gcacgcgttc   4860
tggaatccgg taatcctaag tttaacccag gcgatcttgt ttggggtttc accggttggg   4920
aagaatactc tgtgatcacc gctactgaat ccctgttcaa gatccataac accgatgtgc   4980
cgctgtccta ctacaccggc ctcctgggga tgccaggcat gaccgcatac gctggcttct   5040
```

acgagatctg tagccctaag aagggcgaaa ccgtctacgt gtccgctgcc tccggcgcgg 5100
ttggccagct tgtgggccag ttcgctaagc tcaccggctg ctacgtggtg ggctctgccg 5160
gctccaagga aaaggtggac ctgctgaaga acaagttcgg cttcgacgaa gcattcaact 5220
acaaggagga agcggacctg gacgctgcgc tgcgtcggta cttccccgat ggaattgata 5280
tttacttcga aaacgtgggt ggcaagatgc tggacgctgt cctccccaac atgcgcccca 5340
agggccgcat cgccgtctgc ggcatgatct cccaatacaa ccttgagcag ccagagggcg 5400
tccgcaacct gatggccctg atcgtcaagc aggtccgcat ggaaggcttt atggtgttct 5460
cctactacca cctgtacggc aagttcctgg aaaccgtgct cccatacatc aagcagggca 5520
agatcaccta cgtggaagat gtggtggatg gcctggacaa cgcaccagca gccctgatcg 5580
gcctgtactc cggccgcaac gtgggcaagc aggtcgtcgt ggtgtcccgc gagtaa 5636

<210> SEQ ID NO 71
<211> LENGTH: 54
<212> TYPE: DNA
<213> ORGANISM: Artificial Sequence
<220> FEATURE:
<223> OTHER INFORMATION: Primer sequence pECXK_RiPKS_F

<400> SEQUENCE: 71
cagaccatgg aattcgagct ggatctagga gggagatcat atggttaccg ttga 54

<210> SEQ ID NO 72
<211> LENGTH: 52
<212> TYPE: DNA
<213> ORGANISM: Artificial Sequence
<220> FEATURE:
<223> OTHER INFORMATION: Primer sequence At4Cl_RiPKS_R

<400> SEQUENCE: 72
ctgtggtgcc atctcataat cctcctagat ccttacacca gggagaagag ga 52

<210> SEQ ID NO 73
<211> LENGTH: 52
<212> TYPE: DNA
<213> ORGANISM: Artificial Sequence
<220> FEATURE:
<223> OTHER INFORMATION: Primer sequence Pp4Cl_RiPKS_R

<400> SEQUENCE: 73
cgatggtgac atctcataat cctcctagat ccttacacca gggagaagag ga 52

<210> SEQ ID NO 74
<211> LENGTH: 52
<212> TYPE: DNA
<213> ORGANISM: Artificial Sequence
<220> FEATURE:
<223> OTHER INFORMATION: Primer sequence Sc4Cl_RiPKS_R

<400> SEQUENCE: 74
ggaacggaac atctcataat cctcctagat ccttacacca gggagaagag ga 52

<210> SEQ ID NO 75
<211> LENGTH: 52
<212> TYPE: DNA
<213> ORGANISM: Artificial Sequence
<220> FEATURE:
<223> OTHER INFORMATION: Primer sequence Nt4Cl_RiPKS_R

<400> SEQUENCE: 75
atctttctcc atctcataat cctcctagat ccttacacca gggagaagag ga 52

<210> SEQ ID NO 76
<211> LENGTH: 52
<212> TYPE: DNA
<213> ORGANISM: Artificial Sequence
<220> FEATURE:
<223> OTHER INFORMATION: Primer sequence pECXK_RpBAS_F

<400> SEQUENCE: 76
cagaccatgg aattcgagct ggatctagga gggagatcat atggcaaccg ag 52

<210> SEQ ID NO 77
<211> LENGTH: 51
<212> TYPE: DNA
<213> ORGANISM: Artificial Sequence
<220> FEATURE:
<223> OTHER INFORMATION: Primer sequence At4Cl_RpBAS_R

<400> SEQUENCE: 77
ctgtggtgcc atctcataat cctcctagat ccttaggaga tcactgggac g 51

<210> SEQ ID NO 78
<211> LENGTH: 51
<212> TYPE: DNA
<213> ORGANISM: Artificial Sequence
<220> FEATURE:
<223> OTHER INFORMATION: Primer sequence Pp4Cl_RpBAS_R

<400> SEQUENCE: 78
cgatggtgac atctcataat cctcctagat ccttaggaga tcactgggac g 51

<210> SEQ ID NO 79
<211> LENGTH: 51
<212> TYPE: DNA
<213> ORGANISM: Artificial Sequence
<220> FEATURE:
<223> OTHER INFORMATION: Primer sequence Sc4Cl_RpBAS_R

<400> SEQUENCE: 79
ggaacggaac atctcataat cctcctagat ccttaggaga tcactgggac g 51

<210> SEQ ID NO 80
<211> LENGTH: 51
<212> TYPE: DNA
<213> ORGANISM: Artificial Sequence
<220> FEATURE:
<223> OTHER INFORMATION: Primer sequence Nt4Cl_RpBAS_R

<400> SEQUENCE: 80
atctttctcc atctcataat cctcctagat ccttaggaga tcactgggac g 51

<210> SEQ ID NO 81
<211> LENGTH: 52
<212> TYPE: DNA
<213> ORGANISM: Artificial Sequence
<220> FEATURE:
<223> OTHER INFORMATION: Primer sequence RiPKS_At4Cl_F

<400> SEQUENCE: 81
tcctcttctc cctggtgtaa ggatctagga ggattatgag atggcaccac ag 52

<210> SEQ ID NO 82
<211> LENGTH: 52
<212> TYPE: DNA
<213> ORGANISM: Artificial Sequence
<220> FEATURE:
<223> OTHER INFORMATION: Primer sequence RpBAS_At4Cl_F

<400> SEQUENCE: 82
ccgtcccagt gatctcctaa ggatctagga ggattatgag atggcaccac ag 52

<210> SEQ ID NO 83
<211> LENGTH: 50
<212> TYPE: DNA
<213> ORGANISM: Artificial Sequence
<220> FEATURE:
<223> OTHER INFORMATION: Primer sequence RcTAL1_At4Cl_R

<400> SEQUENCE: 83
ttgcagggtc atttctttat cctcctagat ccttacaggc cgttagccag 50

<210> SEQ ID NO 84
<211> LENGTH: 50
<212> TYPE: DNA
<213> ORGANISM: Artificial Sequence
<220> FEATURE:
<223> OTHER INFORMATION: Primer sequence FjTAL_At4Cl_R

<400> SEQUENCE: 84
gatggtgttc atttctttat cctcctagat ccttacaggc cgttagccag 50

<210> SEQ ID NO 85
<211> LENGTH: 50
<212> TYPE: DNA
<213> ORGANISM: Artificial Sequence
<220> FEATURE:
<223> OTHER INFORMATION: Primer sequence SeSam8_At4Cl_R

<400> SEQUENCE: 85
gacctgggtc atttctttat cctcctagat ccttacaggc cgttagccag 50

<210> SEQ ID NO 86
<211> LENGTH: 52
<212> TYPE: DNA
<213> ORGANISM: Artificial Sequence
<220> FEATURE:
<223> OTHER INFORMATION: Primer sequence RiPKS_Pp4Cl_F

<400> SEQUENCE: 86
tcctcttctc cctggtgtaa ggatctagga ggattatgag atgtcaccat cg 52

<210> SEQ ID NO 87
<211> LENGTH: 52
<212> TYPE: DNA
<213> ORGANISM: Artificial Sequence
<220> FEATURE:
<223> OTHER INFORMATION: Primer sequence RpBAS _Pp4Cl_F

<400> SEQUENCE: 87
ccgtcccagt gatctcctaa ggatctagga ggattatgag atgtcaccat cg 52

<210> SEQ ID NO 88
<211> LENGTH: 52
<212> TYPE: DNA
<213> ORGANISM: Artificial Sequence
<220> FEATURE:
<223> OTHER INFORMATION: Primer sequence RcTAL1_Pp4Cl_R

<400> SEQUENCE: 88
ttgcagggtc atttctttat cctcctagat ccttacacct tgttacggag at 52

<210> SEQ ID NO 89
<211> LENGTH: 52
<212> TYPE: DNA
<213> ORGANISM: Artificial Sequence
<220> FEATURE:
<223> OTHER INFORMATION: Primer sequence FjTAL_Pp4Cl_R

<400> SEQUENCE: 89
gatggtgttc atttctttat cctcctagat ccttacacct tgttacggag at 52

<210> SEQ ID NO 90
<211> LENGTH: 52
<212> TYPE: DNA
<213> ORGANISM: Artificial Sequence
<220> FEATURE:
<223> OTHER INFORMATION: Primer sequence SeSam8_Pp4Cl_R

<400> SEQUENCE: 90
gacctgggtc atttctttat cctcctagat ccttacacct tgttacggag at 52

<210> SEQ ID NO 91
<211> LENGTH: 52
<212> TYPE: DNA
<213> ORGANISM: Artificial Sequence
<220> FEATURE:
<223> OTHER INFORMATION: Primer sequence RiPKS_Sc4Cl_F

<400> SEQUENCE: 91
tcctcttctc cctggtgtaa ggatctagga ggattatgag atgttccgtt cc 52

<210> SEQ ID NO 92
<211> LENGTH: 52
<212> TYPE: DNA
<213> ORGANISM: Artificial Sequence
<220> FEATURE:
<223> OTHER INFORMATION: Primer sequence RpBAS_Sc4Cl_F

<400> SEQUENCE: 92
ccgtcccagt gatctcctaa ggatctagga ggattatgag atgttccgtt cc 52

<210> SEQ ID NO 93
<211> LENGTH: 52
<212> TYPE: DNA
<213> ORGANISM: Artificial Sequence
<220> FEATURE:
<223> OTHER INFORMATION: Primer sequence RcTAL1_Sc4Cl_R

<400> SEQUENCE: 93
ttgcagggtc atttctttat cctcctagat ccttagcgtg gctcgcgcag ct 52

<210> SEQ ID NO 94
<211> LENGTH: 52
<212> TYPE: DNA
<213> ORGANISM: Artificial Sequence
<220> FEATURE:
<223> OTHER INFORMATION: Primer sequence FjTAL_Sc4Cl_R

<400> SEQUENCE: 94
gatggtgttc atttctttat cctcctagat ccttagcgtg gctcgcgcag ct 52

<210> SEQ ID NO 95
<211> LENGTH: 52
<212> TYPE: DNA
<213> ORGANISM: Artificial Sequence
<220> FEATURE:
<223> OTHER INFORMATION: Primer sequence SeSam8_Sc4Cl_R

<400> SEQUENCE: 95
gacctgggtc atttctttat cctcctagat ccttagcgtg gctcgcgcag ct 52

<210> SEQ ID NO 96
<211> LENGTH: 59
<212> TYPE: DNA
<213> ORGANISM: Artificial Sequence
<220> FEATURE:
<223> OTHER INFORMATION: Primer sequence RiPKS_Nt4Cl_F

<400> SEQUENCE: 96
tcctcttctc cctggtgtaa ggatctagga ggattatgag atggagaaag atacaaaac 59

<210> SEQ ID NO 97
<211> LENGTH: 59
<212> TYPE: DNA
<213> ORGANISM: Artificial Sequence
<220> FEATURE:
<223> OTHER INFORMATION: Primer sequence RpBAS_Nt4Cl_F

<400> SEQUENCE: 97
ccgtcccagt gatctcctaa ggatctagga ggattatgag atggagaaag atacaaaac 59

<210> SEQ ID NO 98
<211> LENGTH: 50
<212> TYPE: DNA
<213> ORGANISM: Artificial Sequence
<220> FEATURE:
<223> OTHER INFORMATION: Primer sequence RcTAL1_Nt4Cl_R

<400> SEQUENCE: 98
ttgcagggtc atttctttat cctcctagat ccttaatttg gaagcccagc 50

<210> SEQ ID NO 99
<211> LENGTH: 50
<212> TYPE: DNA
<213> ORGANISM: Artificial Sequence
<220> FEATURE:
<223> OTHER INFORMATION: Primer sequence FjTAL_Nt4Cl_R

<400> SEQUENCE: 99
gatggtgttc atttctttat cctcctagat ccttaatttg gaagcccagc 50

<210> SEQ ID NO 100
<211> LENGTH: 50
<212> TYPE: DNA
<213> ORGANISM: Artificial Sequence
<220> FEATURE:
<223> OTHER INFORMATION: Primer sequence SeSam8_Nt4Cl_R

<400> SEQUENCE: 100
gacctgggtc atttctttat cctcctagat ccttaatttg gaagcccagc 50

<210> SEQ ID NO 101
<211> LENGTH: 53
<212> TYPE: DNA
<213> ORGANISM: Artificial Sequence
<220> FEATURE:
<223> OTHER INFORMATION: Primer sequence At4Cl_ RcTAL1_F

<400> SEQUENCE: 101
agctggctaa cggcctgtaa ggatctagga ggataaagaa atgaccctgc aat 53

<210> SEQ ID NO 102

<211> LENGTH: 52
<212> TYPE: DNA
<213> ORGANISM: Artificial Sequence
<220> FEATURE:
<223> OTHER INFORMATION: Primer sequence Pp4Cl_ RcTAL1_F

<400> SEQUENCE: 102
atctccgtaa caaggtgtaa ggatctagga ggataaagaa atgaccctgc aa 52

<210> SEQ ID NO 103
<211> LENGTH: 52
<212> TYPE: DNA
<213> ORGANISM: Artificial Sequence
<220> FEATURE:
<223> OTHER INFORMATION: Primer sequence Sc4Cl_ RcTAL1_F

<400> SEQUENCE: 103
agctgcgcga gccacgctaa ggatctagga ggataaagaa atgaccctgc aa 52

<210> SEQ ID NO 104
<211> LENGTH: 52
<212> TYPE: DNA
<213> ORGANISM: Artificial Sequence
<220> FEATURE:
<223> OTHER INFORMATION: Primer sequence Nt4Cl_ RcTAL1_F

<400> SEQUENCE: 104
ctgctgggct tccaaattaa ggatctagga ggataaagaa atgaccctgc aa 52

<210> SEQ ID NO 105
<211> LENGTH: 39
<212> TYPE: DNA
<213> ORGANISM: Artificial Sequence
<220> FEATURE:
<223> OTHER INFORMATION: Primer sequence pECXK_RcTAL1_R

<400> SEQUENCE: 105
cctgcaggtc gactctagag ttatgctggt ggatcagct 39

<210> SEQ ID NO 106
<211> LENGTH: 55
<212> TYPE: DNA
<213> ORGANISM: Artificial Sequence
<220> FEATURE:
<223> OTHER INFORMATION: Primer sequence At4Cl_ FjTAL_F

<400> SEQUENCE: 106
agctggctaa cggcctgtaa ggatctagga ggataaagaa atgaacacca tcaac 55

<210> SEQ ID NO 107
<211> LENGTH: 55
<212> TYPE: DNA
<213> ORGANISM: Artificial Sequence
<220> FEATURE:
<223> OTHER INFORMATION: Primer sequence Pp4Cl_ FjTAL_F

<400> SEQUENCE: 107
atctccgtaa caaggtgtaa ggatctagga ggataaagaa atgaacacca tcaac 55

<210> SEQ ID NO 108
<211> LENGTH: 55
<212> TYPE: DNA
<213> ORGANISM: Artificial Sequence
<220> FEATURE:
<223> OTHER INFORMATION: Primer sequence Sc4Cl_ FjTAL_F

<400> SEQUENCE: 108
agctgcgcga gccacgctaa ggatctagga ggataaagaa atgaacacca tcaac 55

<210> SEQ ID NO 109
<211> LENGTH: 55
<212> TYPE: DNA
<213> ORGANISM: Artificial Sequence
<220> FEATURE:
<223> OTHER INFORMATION: Primer sequence Nt4Cl_ FjTAL_F

<400> SEQUENCE: 109
ctgctgggct tccaaattaa ggatctagga ggataaagaa atgaacacca tcaac 55

<210> SEQ ID NO 110
<211> LENGTH: 42
<212> TYPE: DNA
<213> ORGANISM: Artificial Sequence
<220> FEATURE:
<223> OTHER INFORMATION: Primer sequence pECXK _FjTAL_R

<400> SEQUENCE: 110
cctgcaggtc gactctagag ttagttgttg atgaggtgat cc 42

<210> SEQ ID NO 111
<211> LENGTH: 52
<212> TYPE: DNA
<213> ORGANISM: Artificial Sequence
<220> FEATURE:
<223> OTHER INFORMATION: Primer sequence At4Cl_ SeSam8_F

<400> SEQUENCE: 111
agctggctaa cggcctgtaa ggatctagga ggataaagaa atgacccagg tc 52

<210> SEQ ID NO 112
<211> LENGTH: 52
<212> TYPE: DNA
<213> ORGANISM: Artificial Sequence
<220> FEATURE:
<223> OTHER INFORMATION: Primer sequence Pp4Cl_SeSam8_F

<400> SEQUENCE: 112
atctccgtaa caaggtgtaa ggatctagga ggataaagaa atgacccagg tc 52

<210> SEQ ID NO 113
<211> LENGTH: 52
<212> TYPE: DNA
<213> ORGANISM: Artificial Sequence
<220> FEATURE:
<223> OTHER INFORMATION: Primer sequence Sc4Cl_ SeSam8_F

<400> SEQUENCE: 113
agctgcgcga gccacgctaa ggatctagga ggataaagaa atgacccagg tc 52

<210> SEQ ID NO 114
<211> LENGTH: 52
<212> TYPE: DNA
<213> ORGANISM: Artificial Sequence
<220> FEATURE:
<223> OTHER INFORMATION: Primer sequence Nt4Cl_ SeSam8_F

<400> SEQUENCE: 114
ctgctgggct tccaaattaa ggatctagga ggataaagaa atgacccagg tc 52

<210> SEQ ID NO 115
<211> LENGTH: 38
<212> TYPE: DNA

-continued

<213> ORGANISM: Artificial Sequence
<220> FEATURE:
<223> OTHER INFORMATION: Primer sequence pECXK _ SeSam8_R

<400> SEQUENCE: 115
cctgcaggtc gactctagag ttagccgaag tctttgcc 38

<210> SEQ ID NO 116
<211> LENGTH: 53
<212> TYPE: DNA
<213> ORGANISM: Artificial Sequence
<220> FEATURE:
<223> OTHER INFORMATION: Primer sequence RcTAL_RiBAR_F

<400> SEQUENCE: 116
gctgatccac cagcataact ggatctagga ggaaataacc atggcatccg gcg 53

<210> SEQ ID NO 117
<211> LENGTH: 41
<212> TYPE: DNA
<213> ORGANISM: Artificial Sequence
<220> FEATURE:
<223> OTHER INFORMATION: Primer sequence pECXK_RiBAR_R

<400> SEQUENCE: 117
ccaagcttgc atgcctgcag gttctgcggg acaccacgac g 41

PRODUCTION OF A FLAVOUR COMPOUND IN A HOST CELL

FIELD OF THE INVENTION

The present invention relates to the field of biotechnology; specifically the production of a flavor compound (raspberry ketone) in a host cell.

BACKGROUND OF THE INVENTION

Raspberry ketone is one of key flavour compounds with typical raspberry characteristics and a low odour threshold. It is an expensive flavour compound which is extensively used in the food industry. Raspberry ketone is naturally found in, of course, raspberry (*Rubus idaeus*), but also in other fruits, such as peaches, grapes, apples, several species of berries, in vegetables such as rhubarb and in the bark of some trees, such as yew, maple and pine.

Raspberry ketone is used for various purposes such as in the formulation of multiple aroma's, such as strawberry-, kiwi- and cherry-aroma as well as in cosmetics and as an anti-obesity agent.

It is not straightforward to obtain raspberry ketone in a commercially relevant way from its natural sources since the low content of the raspberry ketone containing fruits and other sources render the extraction and purification process non-profitable (less than 4 mg of raspberry ketone can be obtained per kg of raspberries). To date, raspberry ketone is produced chemically via the condensation of p-hydroxybenzaldehyde with acetone, an environmentally unfriendly process. In addition, the chemical synthesis of flavour compounds often leads to non-desirable racemic-variants and mixtures (Vandamme and Soetaert 2002; J Chem Techno Biotechnol 77:1323-1332). In raspberries, the synthesis of raspberry ketone is a two-enzyme part of the phenylpropanoid pathway. This pathway has been described by Borejsza-Wysocki and Hrazdina (1994). In the first step, coumaroyl-CoA (which is present in many plant tissues) is condensed with one malonyl CoA into benzalacetone (p-hydroxyphenylbut-3-ene-2-one). The enzyme catalysing this step is called benzalacetone synthase (BAS). In the second step, the double bond in benzalacetone is reduced, resulting in raspberry ketone (p-hydroxyphenyl-2-butanone). The enzyme catalysing this step is called benzalacetone reductase (BAR), this enzyme requires the presence of NADPH.

Benzalacetone synthase (BAS), EC 2.3.1.-., is a member of the polyketide synthase family. Benzalacetone synthase condenses one acetone unit of malonyl-CoA with one p-coumaric acid to form benzalacetone. The polyketide synthase family is described in detail in Schroder (1999). Abe et al (2001) teach the cloning of a BAS gene from rhubarb. Koeduka et al (2011) teach the characterization of raspberry BAS.

Soluble enzymes catalysing the reduction of a double bond using NADPH, for example benzalacetone reductase (BAR), are classified by the International Union of Biochemistry and Molecular Biology as belonging to enzymatic class EC 1.3.1.X. For instance, an enzyme annotated as EC 1.3.1.11 from *Arthrobacter* sp. was reported to remove a double bond from coumarate (Levi and Weinstein, 1964), but no gene has been identified in connection to this enzymatic activity. Other enzymes in the enzymatic class EC 1.3.1.X are orotate reductase, 2-hexadecenal reductase, cholestenone 5 alpha-reductase etc. for which genes are known. However, none of these enzymes was reported to have benzalacetone reductase (BAR) activity. It is known from literature that 4-hydroxybenzalacetone can be transformed to raspberry ketone by fungi or yeasts like *Pichia, Saccharomyces, Beauveria, Kloeckera, Aureobasidium, Cladosporium, Geotrichum, Mucor,* and *Candida* spp. (Fuganti and Zucchi, 1998). Beekwilder et al. (2007) report that BAR activity is present in *E. coli.* However, no gene has been identified in connection to this enzymatic activity.

Attempts to biosynthesise raspberry ketone have been described. Hugueny et al (1995, Bioflavour 95 pp 269-273) teach a biotechnological method for producing raspberry ketone. This method comprises culturing a microorganism which has a secondary alcoholdehydrogenase (ADH), such as *Candida boidinii,* and adding the precursor betuloside to the culture medium. In this cellular environment the secondary ADH dehydrogenates betuligenol into raspberry ketone. Abe et al (2001) teach the cloning of rhubarb BAS, expression of the gene in *E. coli,* purification of the recombinant BAS protein and the in vitro synthesis of benzalacetone. However, this study does not teach the in vivo synthesis of benzalacetone or raspberry ketone.

EP1226265 teaches the bioproduction of para hydroxycinnamic acid, also known as p-coumaric acid, which can be used as precursor for raspberry ketone. EP1226265 describes a phenyl-ammonia-lyase enzyme (PAL) (EC4.3.1.5); it does not teach the in vivo synthesis of raspberry ketone. GB2416769 and GB2416770 describe the bioproduction of raspberry ketone in *E. coli* from the precursor p-coumaric acid that is added to the fermentation. Likewise in Beekwilder et al (2007), raspberry ketone is produced in *E. coli* from the precursor p-coumaric acid that is added to the fermentation. In 2016, Lee et al published their results of production of raspberry ketone in *Saccharomyces cerevisiae* from the precursor p-coumaric acid that is added to the fermentation. In addition, they produced tiny amounts of raspberry ketone (0.49mg/L) by *Saccharomyces cerevisiae* using anaerobic fermentation. The addition of a precursor to be able to produce raspberry ketone in a microbial host cell is not efficient. In addition, the use of eukaryotic cells in anaerobic fermentation is laborious and inefficient, certainly at industrial scale. Hence there is a need for the de novo bioproduction of raspberry ketone in a prokaryotic microbial host cell using straightforward fermentation conditions. To date, no de novo bioproduction of raspberry ketone by such prokaryotic host cells using such straightforward aerobic fermentation has been presented.

SUMMARY OF THE INVENTION

The invention relates to a cell capable of producing raspberry ketone, and to methods wherein such a cell is used. In a first aspect the invention provides a prokaryotic microbial cell capable of expressing, preferably expressing, a functional heterologous enzyme with tyrosine ammonium lyase (TAL) activity and further capable of expressing, preferably expressing, at least one functional enzyme selected from the group consisting of a 4-coumarate-CoA ligase (4CL) and a benzalacetone synthase (BAS) and optionally further capable of expressing, preferably expressing, a heterologous benzalacetone reductase (BAR). In embodiments of this aspect the cell is provided wherein the functional heterologous enzyme with TAL activity is from *Rhodobacter capsulatus, Saccharothrix espanaensis,* or *Flavobacterium johnsoniae;* wherein the 4CL is from *Nicotiana tabacum, Arabidopsis thaliana, Physcomitrella patens* or *Streptomyces coelicolor;* wherein the BAS is from *Rubus idaeus* or *Rheum palmatum;* and wherein the optional BAR is from *Rubus idaeus*. In particular embodiments this aspect provides the cell, wherein the polynucleotide sequence of at least one of said enzymes is codon optimized. In further embodiments, this aspect provides the cell, wherein the cell is a Gram positive prokaryotic microbial cell, preferably a *Corynebacterium*, more preferably a *Corynebacterium glutamicum*, even more preferably *Corynebacterium glutamicum* ATCC13032, even more preferably a *Corynebacterium* capable of producing at least twice as much L-Tyrosine as compared to *Corynebacterium glutamicum* ATCC13032. In preferred embodiments of this aspect is provided the cell, wherein at least two of the enzymes are encoded by a single recombinant polynucleotide construct. In further preferred embodiments of this aspect is provided the cell, capable of producing at least 5mg/l raspberry ketone.

In a second aspect, the invention provides a method for the production of a cell according to the first aspect, the method comprising contacting a prokaryotic cell with an expression construct encoding a functional heterologous enzyme with tyrosine ammonium lyase (TAL) activity, and contacting that prokaryotic cell with an expression construct encoding at least one functional enzyme selected from the group consisting of a 4-coumarate-CoA ligase (4CL) and a benzalacetone synthase (BAS), and optionally contacting that prokaryotic cell with an expression construct encoding a heterologous benzalacetone reductase (BAR).

In a third aspect, the invention provides a method for the production of raspberry ketone, comprising culturing a cell according to the first aspect of the invention under conditions conducive to the production of raspberry ketone, and, optionally, isolating and/or purifying the raspberry ketone from the cell and/or the culture medium.

In a fourth aspect, the invention provides the use of a functional heterologous enzyme with tyrosine ammonium lyase (TAL) activity as described in the first aspect of the invention, for the production of raspberry ketone in a prokaryotic host cell, preferably a Gram positive prokaryotic host cell.

In a fifth aspect, the invention provides an expression vector comprising particular operon sequences. In a sixth aspect, the invention provides a polypeptide product expressed from the expression vector according to the fifth aspect.

DESCRIPTION OF THE INVENTION

Figure 1:
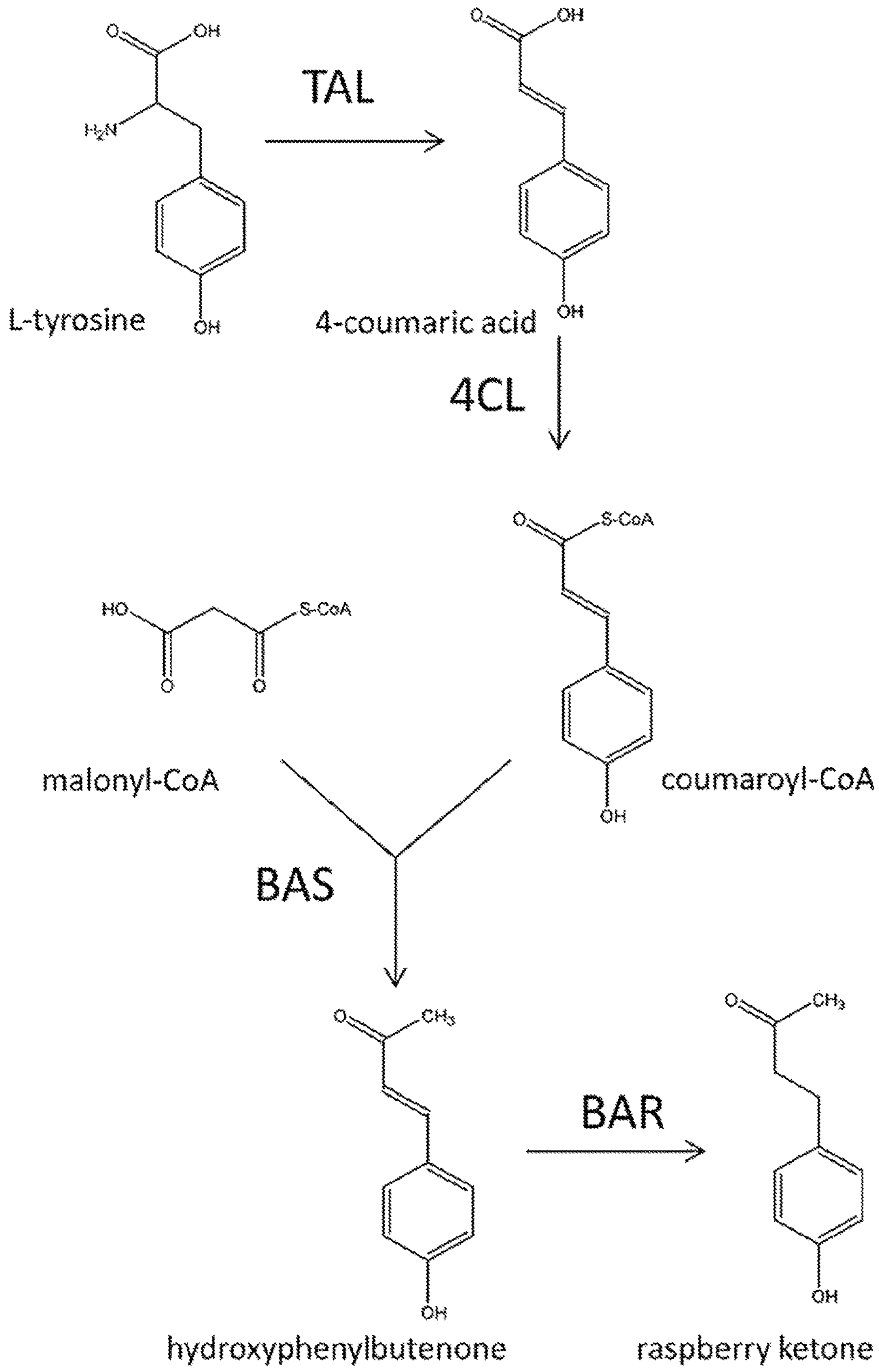
FIG. 1—Biosynthetic pathway for the production of raspberry ketone from L-tyrosine; TAL=tyrosine ammonia lyase; 4CL=4-coumarate-CoA ligase; BAS=benzalacetone synthase; BAR=benzalacetone reductase.

It has been established by the inventors that, surprisingly, raspberry ketone can be synthesized de novo from glucose by a recombinant prokaryotic microbial host cell using straightforward aerobic fermentation conditions.

Accordingly, in a first aspect the invention provides for a prokaryotic microbial cell capable of expressing, preferably expressing, a functional heterologous enzyme with tyrosine ammonium lyase (TAL) activity and further capable of expressing, preferably expressing, at least one functional enzyme selected from the group consisting of a 4-coumarate-CoA ligase (4CL) and a benzalacetone synthase (BAS) and optionally further capable of expressing, preferably expressing, a heterologous benzalacetone reductase (BAR). Such a prokaryotic microbial cell is referred to hereinafter as a cell according to the invention.

In preferred embodiments, this aspect provides for a prokaryotic microbial cell expressing a functional heterologous enzyme with tyrosine ammonium lyase (TAL) activity and further expressing at least one functional enzyme selected from the group consisting of a 4-coumarate-CoA ligase (4CL) and a benzalacetone synthase (BAS) and optionally further expressing a heterologous benzalacetone reductase (BAR).

In particular embodiments, this aspect provides a prokaryotic microbial cell expressing a functional heterologous enzyme with tyrosine ammonium lyase (TAL) activity and further expressing a functional 4-coumarate-CoA ligase (4CL) enzyme and optionally further expressing a heterologous benzalacetone reductase (BAR).

In particular embodiments, this aspect provides a prokaryotic microbial cell expressing a functional heterologous enzyme with tyrosine ammonium lyase (TAL) activity and further expressing a functional benzalacetone synthase (BAS) enzyme and optionally further expressing a heterologous benzalacetone reductase (BAR).

In particular embodiments, this aspect provides a prokaryotic microbial cell expressing a functional heterologous enzyme with tyrosine ammonium lyase (TAL) activity and further expressing a functional 4-coumarate-CoA ligase (4CL) enzyme and a functional benzalacetone synthase (BAS) enzyme and optionally further expressing a heterologous benzalacetone reductase (BAR).

In particular embodiments, this aspect provides a prokaryotic microbial cell expressing a functional heterologous enzyme with tyrosine ammonium lyase (TAL) activity and further expressing a functional 4-coumarate-CoA ligase (4CL) enzyme and a functional benzalacetone synthase (BAS) enzyme and further expressing a heterologous benzalacetone reductase (BAR).

Prokaryotic microbial cells are well known in the art. A prokaryote is a unicellular organism that lacks a membrane-bound nucleus, mitochondria, and other membrane-bound organelles. Examples of prokaryotes are bacteria and archaea. Preferred prokaryotic cells are bacteria such as *Escherichia coli,* or preferably Gram positive bacteria such as *Corynebacterium,* more preferably such as *Corynebacterium glutamicum,* because their culturing is well-established. In preferred embodiments, this aspect provides a cell according to the invention, wherein the cell is a Gram positive prokaryotic microbial cell, preferably a *Corynebacterium,* more preferably a *Corynebacterium glutamicum,* even more preferably *Corynebacterium glutamicum* ATCC13032, even more preferably a *Corynebacterium* capable of producing at least twice as much L-Tyrosine as compared to *Corynebacterium glutamicum* ATCC13032. Strain ATCC13032 is known to the person skilled in art; this strain is also known as DSM 20300, JCM 1318, LMG 3730 and NCIMB 10025.

Throughout this application, expression is considered to be the transcription of a gene into functional mRNA, leading to a functional polypeptide such as an enzyme. An enzyme is a polypeptide that can catalyse a reaction. In this context, increased expression of an enzyme can be considered an increased level of mRNA encoding said enzyme, an increased level of enzyme polypeptide, or an increased total activity of said enzyme. Preferably, an increased expression of an enzyme results in an increased activity of said enzyme, which can be caused by increased levels of enzyme polypeptide. An enzyme that shows activity in catalysing its associated reaction is a functional enzyme. Associated reactions for TAL, 4CL, BAS, and BAR are described elsewhere herein. Activity can be determined by monitoring for the increase of product concentration using chromatographic techniques, such as gas chromatography (GC), high performance liquid chromatography (HPLC), or GC or liquid chromatography with advantageously coupled mass spectrometric methods, such as LCMS or GCMS. A preferred method for detection of intermediates is GCMS. A preferred method for the detection of raspberry ketone is GCMS.

In the context of this application, a cell capable of expressing an enzyme is a cell that comprises the genetic information required for expressing said enzyme, preferably a nucleic acid encoding said enzyme. This does not mean that the enzyme is necessarily expressed. As a non-limiting example, a cell comprising a nucleic acid encoding an enzyme wherein the nucleic acid is under the control of a promotor that responds to a particular induction, the promotor is not necessarily induced and thus the enzyme is not necessarily expressed, whereas the cell is in fact capable of such expression. In preferred embodiments of the invention, a preferred cell capable of expressing a functional enzyme is a cell that expresses said functional enzyme.

A heterologous enzyme is an enzyme derived from a different organism. A heterologous polynucleotide is a polynucleotide derived from a different organism. A heterologous polynucleotide can be a synthetic polynucleotide. In preferred embodiments, the cell according to the invention is provided, wherein the polynucleotide sequence encoding at least one of said enzymes is codon optimized. A codon optimized polynucleotide sequence is a sequence wherein the codon usage bias has been mitigated through selection of alternative codons without altering the encoded polypeptide. For example, rare codons can be replaced by more common codons, or regions comprising many identical codons can be interrupted by substitution of synonymic codons to reduce demand for the many identical codons. Codon optimization is known in the art, and bioinformatics tools for codon optimization are freely available on the internet from various providers.

Tyrosine ammonium lyase, referred to hereinafter as TAL, is also known as tyrosine ammonia lyase, L-tyrosine ammonia-lyase, and tyrase. It is an enzyme (EC 4.3.1.23) in the natural phenols biosynthesis pathway, which transforms L-tyrosine into p-coumaric acid, releasing ammonium. P-coumaric acid is also known as para coumaric acid, 4-coumaric acid, 4-hydroxycinnamic acid, and (E)-3-(4-hydroxyphenyl)-2-propenoic acid. A preferred TAL or a preferred enzyme with TAL activity is a heterologous TAL or is a heterologous enzyme with TAL activity, which is a TAL or an enzyme with TAL activity that is derived from a different organism than the cell according to the invention. Preferred organisms from which TAL or enzymes with TAL activity can be derived are *Rhodobacter capsulatus* (for example RcTAL, represented by SEQ ID NO: 1 and encoded by SEQ ID NO: 2, see Kyndt et al. 2002 FEBS Lett. 512: 240-244), *Saccharothrix espanaensis* (for example SeSam8, represented by SEQ ID NO: 3 and encoded by SEQ ID NO: 4, see Berner el al. 2006 J Bacteriol 188: 2666-2673), and *Flavobacterium johnsoniae* (for example FjTAL, represented by SEQ ID NO: 5 and encoded by SEQ ID NO: 6, see Jendersen et al. 2015 Appl Environ Microbiol 81:4458-4476). A preferred TAL or enzyme with TAL activity has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 1, SEQ ID NO:3, or SEQ ID NO: 5, preferably with SEQ ID NO: 1, or is encoded by a polynucleotide that has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 2, SEQ ID NO: 4, or SEQ ID NO: 6, preferably with SEQ ID NO: 2. Preferred polynucleotides that encode TAL or that encode enzymes with TAL activity are codon optimized. TAL activity of an enzyme can be assayed by chromatographic monitoring of p-coumaric acid production or of ammonia evolution when an enzyme that is to be tested for TAL activity is brought into contact with L-tyrosine in a suitable buffer.

4-coumarate-CoA ligase, hereinafter referred to as 4CL, is also known as 4CL, 4-coumaroyl-CoA synthetase, p-coumaroyl CoA ligase, p-coumaryl coenzyme A synthetase, p-coumaryl-CoA synthetase, p-coumaryl-CoA ligase, feruloyl CoA ligase, hydroxycinnamoyl CoA synthetase, and various other names. It is an enzyme (EC 6.2.1.12) that catalyzes the conjugation of coenzyme A (CoA) to 4-coumarate, forming 4-coumaroyl-CoA under consumption of ATP. 4-coumaroyl-CoA is also known as coumaroyl-CoA. A preferred 4CL is a heterologous 4CL, which is a 4CL that is derived from a different organism than the cell according to the invention. Preferred organisms from which 4CL can be derived are *Nicotiana tabacum* (for example Nt4CL, represented by SEQ ID NO: 7 and encoded by SEQ ID NO: 8, see Lee & Douglas. 1996 Plant Physiol. 112: 193-205), *Arabidopsis thaliana* (for example At4CL, represented by SEQ ID NO: 9 and encoded by SEQ ID NO: 10, see Ehlting et al. 1999 Plant. J. 19: 9-20), *Physcomitrella patens* (for example Pp4CL, represented by SEQ ID NO: 11 and encoded by SEQ ID NO: 12, see Silber et al. 2008 Phytochem. 69: 2449 -2456), and *Streptomyces coelicolor* (for example Sc4CL, represented by SEQ ID NO: 13 and encoded by SEQ ID NO: 14). A preferred 4CL has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 7, SEQ ID NO:9, SEQ ID NO: 11, or SEQ ID NO: 13, preferably with SEQ ID NO: 11, or is encoded by a polynucleotide that has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 8, SEQ ID NO: 10, SEQ ID NO: 12, or SEQ ID NO: 14, preferably with SEQ ID NO 12. Preferred polynucleotides that encode 4CL are codon optimized.

Benzalacetone synthase, hereinafter referred to as BAS, is a plant-specific type III polyketide synthase (PKS). It is an enzyme (EC 2.3.1.212) that catalyses the conversion of 4-coumaroyl-CoA into 4-hydroxybenzalacetone. 4-hydroxybenzalacetone is also known as hydroxyphenylbutenone, p-hydroxybenzalacetone, 1-(4-Hydroxybenzylidene)acetone, and (3E)-4-(4-Hydroxyphenyl)-3-buten-2-one. A preferred BAS is a heterologous BAS, which is a BAS that is derived from a different organism than the cell according to the invention. Preferred organisms from which BAS can be derived are *Rubus idaeus* (for example RiPKS, represented by SEQ ID NO: 15 and encoded by SEQ ID NO: 16, see Zheng & Hrazdina 2008 Arch Biochem Biophys 470: 139-145), and *Rheum palmatum* (for example RpBAS, represented by SEQ ID NO: 17 and encoded by SEQ ID NO: 18, see Abe et al. 2001 Eur J Biochem 268: 3354-3359). A preferred BAS has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 15 or with SEQ ID NO: 17. Preferably with SEQ ID NO: 17, or is encoded by a polynucleotide that has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 16 or with SEQ ID NO: 18, preferably with SEQ ID NO: 18. Preferred polynucleotides that encode BAS are codon optimized.

Benzalacetone reductase is hereinafter referred to as BAR. It is an enzyme (EC 1.3.1.-) that catalyses the conversion of 4-hydroxybenzalacetone into raspberry ketone. Raspberry ketone is also known as 4-(4-hydroxyphenyl) butan-2-one, p-hydroxybenzyl acetone, 4-(p-hydroxyphenyl)-2-butanone, frambinone, oxyphenylon, rheosmin, and rasketone. A preferred BAR is a heterologous BAR, which is a BAR that is derived from a different organism than the cell according to the invention. A preferred organism from which BAR can be derived is *Rubus idaeus* (for example RiBAR, represented by SEQ ID NO: 19 and encoded by SEQ ID NO: 20, see Koeduka et al. 2011 Biochem Biophys Res Commun 412: 104-108). A preferred BAR has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 19, or is encoded by a polynucleotide that has at least 60%, 65%, 70%, 75%, 80%, 85%, 90%, 91%, 92%, 93%, 94%, 95%, 96%, 97%, 98%, 99%, or 100%, preferably at least 80%, 85%, 90%, 91%, 92%, 93%, 94%, 95%, 96%, 97%, 98%, 99%, or 100%, more preferably at least 90%, most preferably 100% sequence identity with SEQ ID NO: 20. Preferred polynucleotides that encode BAR are codon optimized.

Within this aspect, a preferred cell according to the invention is provided wherein

- the functional heterologous enzyme with TAL activity is from *Rhodobacter capsulatus, Saccharothrix espanaensis,* or *Flavobacterium johnsoniae;* preferably, it is from *Rhodobacter capsulatus;*
- the at least one functional enzyme selected from the group consisting of a 4CL and a BAS is 4CL from *Nicotiana tabacum, Arabidopsis thaliana, Physcomitrella patens* or *Streptomyces coelicolor,* or is BAS from *Rubus idaeus* or *Rheum palmatum;* preferably, BAS is from *Rheum palmatum;* preferably, 4CL is from *Physcomitrella patens;* and
- the optional BAR is from *Rubus idaeus.*

In more preferred embodiments, a cell according to the invention is provided wherein

- the functional heterologous enzyme with TAL activity is from *Rhodobacter capsulatus, Saccharothrix espanaensis,* or *Flavobacterium johnsoniae;* preferably, it is from *Rhodobacter capsulatus;*
- the at least one functional enzyme selected from the group consisting of a 4CL and a BAS is 4CL from *Nicotiana tabacum, Arabidopsis thaliana, Physcomitrella patens* or *Streptomyces coelicolor,* or is BAS from *Rubus idaeus* or *Rheum palmatum;* preferably, BAS is from *Rheum palmatum;* preferably, 4CL is from *Physcomitrella patens;* and
- the BAR is from *Rubus idaeus.*

In even more preferred embodiments, a cell according to the invention is provided wherein:

- the functional heterologous enzyme with TAL activity is from *Rhodobacter capsulatus;*
- the at least one functional enzyme selected from the group consisting of a 4CL and a BAS is selected from the group consisting of a 4CL from *Physcomitrella patens* and a BAS from *Rheum palmatum;* and
- the optional BAR is from *Rubus idaeus.*

In particular embodiments, both a BAS and a 4CL are expressed in the cell according to the invention. In such embodiments, a cell according to the invention is provided wherein:

- the functional heterologous enzyme with TAL activity is from *Rhodobacter capsulatus, Saccharothrix espanaensis,* or *Flavobacterium johnsoniae;*
- the 4CL is from *Nicotiana tabacum, Arabidopsis thaliana, Physcomitrella patens* or *Streptomyces coelicolor;*
- the BAS is from *Rubus idaeus* or *Rheum palmatum;* and
- the optional BAR is from *Rubus idaeus.*

In more preferred such embodiments, a cell according to the invention is provided wherein:

the functional heterologous enzyme with TAL activity is from *Rhodobacter capsulatus;* the 4CL is from *Physcomitrella patens;* the BAS is from *Rheum palmatum;* and the optional BAR is from *Rubus idaeus.*

In preferred embodiments within this aspect, the invention provides a cell according to the invention, wherein:

the functional heterologous enzyme with TAL activity has at least 60%, preferably at least 80%, more preferably at least 90%, most preferably 100% sequence identity with SEQ ID NO: 1, SEQ ID NO: 3, or SEQ ID NO: 5, preferably with SEQ ID NO: 1, or is encoded by a polynucleotide which has at least 60%, preferably at least 80%, more preferably at least 90%, most preferably 100% sequence identity with SEQ ID NO: 2, SEQ ID NO: 4, or SEQ ID NO: 6, preferably with SEQ ID NO: 2;

the 4CL has at least 60%, preferably at least 80%, more preferably at least 90%, most preferably 100% sequence identity with SEQ ID NO: 7, SEQ ID NO: 9, SEQ ID NO: 11, or SEQ ID NO: 13, preferably with SEQ ID NO: 11, or is encoded by a polynucleotide which has at least 60%, preferably at least 80%, more preferably at least 90%, most preferably 100% sequence identity with SEQ ID NO: 8, SEQ ID NO: 10, SEQ ID NO: 12, or SEQ ID NO: 14, preferably with SEQ ID NO 12;

the BAS has at least 60%, preferably at least 80%, more preferably at least 90%, most preferably 100% sequence identity with SEQ ID NO: 15 or SEQ ID NO: 17, preferably with SEQ ID NO: 17, or is encoded by a polynucleotide which has at least 60%, preferably at least 80%, more preferably at least 90%, most preferably 100% sequence identity with SEQ ID NO 16 or SEQ ID NO: 18, preferably with SEQ ID NO: 18;

the BAR has at least 60%, preferably at least 80%, more preferably at least 90%, most preferably 100% sequence identity with SEQ ID NO: 19 or is encoded by a polynucleotide which has at least 60%, preferably at least 80%, more preferably at least 90%, most preferably 100% sequence identity with SEQ ID NO: 20.

In this aspect, it can be advantageous to use polynucleotide constructs that encode more than one enzyme. For example, a polycistronic construct can be used, or an operon wherein more than one enzyme is under the control of a single promotor. Such constructs can be created using recombinant DNA techniques that are well known in the art.

Accordingly in preferred embodiments this aspect provides a cell according to the invention, wherein at least two of the enzymes are encoded by a single recombinant polynucleotide construct. Such constructs can be comprised in an expression vector, which may be a plasmid. The two enzymes may also be a single fusion polypeptide.

Raspberry ketone is 4-(4-hydroxyphenyl)butan-2-one, and is also known as p-hydroxybenzyl acetone, 4-(p-hydroxyphenyl)-2-butanone, frambinone, oxyphenylon, rheosmin, and rasketone. It is a natural phenolic compound that is the primary aroma compound of red raspberries. It occurs in a variety of fruits, also including cranberries and blackberries. Cells according to the invention are capable of producing raspberry ketone and produce raspberry ketone when cultured. Preferred cells according to the invention are capable of producing, preferably producing, at least 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 25, 30, 35, 40, 45, or 50 mg/L raspberry ketone, preferably at least 5 mg/L. More preferably, cells according to the invention are capable of producing, preferably producing, at least 100mg/L, 200mg/L, 300mg/L, 400mg/L, 500mg/L, 600mg/L, 700mg/L, 800mg/L, 900mg/L, 1g/L, 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L,18 g/L, 19 g/L, 20 g/L, 21 g/L, 22 g/L, 23 g/L, 24 g/L, or 25g/L raspberry ketone. Preferably, the raspberry ketone is detected in a cell according to the invention and/or in its culture broth or headspace wherein said cell is cultured.

Accordingly, this aspect provides a cell according to the invention, capable of producing at least 5 mg/L raspberry ketone. Preferred embodiments provide a cell according to the invention, capable of producing at least 1 g/L raspberry ketone. More Preferred embodiments provide a cell according to the invention, capable of producing at least 5 g/L raspberry ketone. Still more preferred embodiments provide a cell according to the invention, capable of producing at least 10 g/L raspberry ketone, most preferably at least 20 g/L raspberry ketone. The production of raspberry ketone can be monitored using chromatographic techniques on samples obtained from the production medium. Such amount is preferably obtained in at most 2 weeks, 1 week, 6 days, 5 days, 4 days, 3 days, 2 days, 1 day, 15 hours, 10 hours, 5 hours, 4 hours, 3 hours, 2 hours or 1 hour of culture, preferably after 24 hours of culture.

Production of a Cell

In a second aspect, the invention provides a method for the production of a cell according to the invention. The features of this aspect are preferably those of the first aspect of the invention. In embodiments of this aspect is provided a method for the production of a cell according to the invention, comprising contacting a prokaryotic cell with an expression construct encoding a functional heterologous enzyme with tyrosine ammonium lyase (TAL) activity, and contacting that prokaryotic cell with an expression construct encoding at least one functional enzyme selected from the group consisting of a 4-coumarate-CoA ligase (4CL) and a benzalacetone synthase (BAS), and optionally contacting that prokaryotic cell with an expression construct encoding a heterologous benzalacetone reductase (BAR).

In preferred embodiments of this aspect the invention provides a method for the production of a cell according to the invention, comprising contacting a prokaryotic cell with an expression construct encoding a functional heterologous enzyme with tyrosine ammonium lyase (TAL) activity, and contacting that prokaryotic cell with an expression construct encoding a functional 4-coumarate-CoA ligase (4CL) and a functional benzalacetone synthase (BAS), and optionally contacting that prokaryotic cell with an expression construct encoding a heterologous benzalacetone reductase (BAR).

In preferred embodiments of this aspect the invention provides a method for the production of a cell according to the invention, comprising contacting a prokaryotic cell with an expression construct encoding a functional heterologous enzyme with tyrosine ammonium lyase (TAL) activity, and contacting that prokaryotic cell with an expression construct encoding a functional 4-coumarate-CoA ligase (4CL), and optionally contacting that prokaryotic cell with an expression construct encoding a heterologous benzalacetone reductase (BAR).

In preferred embodiments of this aspect the invention provides a method for the production of a cell according to the invention, comprising contacting a prokaryotic cell with an expression construct encoding a functional heterologous enzyme with tyrosine ammonium lyase (TAL) activity, and contacting that prokaryotic cell with an expression construct encoding a functional benzalacetone synthase (BAS), and optionally contacting that prokaryotic cell with an expression construct encoding a heterologous benzalacetone reductase (BAR).

*Corynebacterium,* more preferably a *Corynebacterium glutamicum*

Suitable cell types were defined earlier herein. A preferred prokaryotic cell is a Gram positive cell, more preferably a *Corynebacterium,* even more preferably a *Corynebacterium glutamicum.*

Accordingly, in preferred embodiments of this aspect the invention provides a method for the production of a cell according to the invention, comprising contacting a *Corynebacterium* cell, preferably a *Corynebacterium glutamicum* cell, with an expression construct encoding a functional heterologous enzyme with tyrosine ammonium lyase (TAL) activity, and contacting that *Corynebacterium* cell with an expression construct encoding at least one functional enzyme selected from the group consisting of a 4-coumarate-CoA ligase (4CL) and a benzalacetone synthase (BAS), and optionally contacting that *Corynebacterium* cell with an expression construct encoding a heterologous benzalacetone reductase (BAR).

For expression of an enzyme in a prokaryotic cell according to the inventions, as well as for additional genetic modification of a prokaryotic cell according to the invention, the cell can be transformed with a nucleic acid or nucleic acid construct described herein by any method known to the person skilled in the art. Such methods are e.g. known from standard handbooks, such as Sambrook and Russel (2001) "Molecular Cloning: A Laboratory Manual (3rd edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of bacterial cells are known from e.g. U.S. Pat. No. 6,699,696 or U.S. Pat. No. 4,778,759. For *Corynebacteria,* reference is made to Eggeling & Reyes 2005 Experiments. In: Eggeling, L., Bott, M. (Eds.), Handbook of *Corynebacterium glutamicum.* CRC Press, Boca Raton, Fla., pp. 3535-3566. Examples are transformation using competent or supercompetent cells, electroporation, use of transfection lipids, use of transfection polymers, or gymnotic transformation. A preferred method is electroporation.

When a nucleic acid construct is used for expression of an enzyme in a prokaryotic cell according to the invention, a selectable marker may be present in the nucleic acid construct comprising a polynucleotide encoding the enzyme. The term "marker" refers herein to a gene encoding a trait or a phenotype which permits the selection of, or the screening for, a cell containing the marker. A marker gene may be an antibiotic resistance gene whereby the appropriate antibiotic can be used to select for transformed cells from among cells that are not transformed. A preferred selection marker is kanamycin and its corresponding resistance gene. Preferably however, a non-antibiotic resistance marker is used, such as an auxotrophic marker (URA3, TRP1, LEU2). A preferred cell according to the invention, e.g. transformed with a nucleic acid construct, is marker gene free. Methods for constructing recombinant marker gene free microbial host cells are described in (Cheah et al., 2013) and are based on the use of bidirectional markers. Alternatively, a screenable marker such as Green Fluorescent Protein, lacZ, luciferase, chloramphenicol acetyltransferase, beta-glucuronidase may be incorporated into a nucleic acid construct according to the invention allowing to screen for transformed cells.

Method for Production of Raspberry Ketone

The prokaryotic cells according to the invention are useful for de novo bioproduction of raspberry ketone using straightforward aerobic fermentation methods. Accordingly, in a third aspect the invention provides a method for the production of raspberry ketone, comprising:

culturing a cell according to the invention under conditions conducive to the production of raspberry ketone, and, optionally, isolating and/or purifying the raspberry ketone from the cell and/or the culture medium.

In preferred embodiment, this aspect provides a method for the production of raspberry ketone, comprising:

culturing a cell according to the invention under conditions conducive to the production of raspberry ketone, and isolating and/or purifying the raspberry ketone from the cell and/or the culture medium.

The features of this aspect are preferably those of the first and second aspect of the invention.

This method is referred to hereinafter as a process according to the invention. Preferably, a process according to the present invention for producing raspberry ketone comprises culturing a cell according to the present invention, preferably a Gram positive cell as defined in the first aspect of the present invention and more preferably a *Corynebacterium* cell as defined om the first aspect, wherein the culture conditions comprise culturing the cells at about 30° C. in LB medium or YT medium or CgXII medium, preferably in CgXII medium, wherein the medium is preferably supplemented with about 20 g/L D-glucose, optionally supplemented with kanamycin (preferably about 50 μg/mL). A culture is preferably shaken or agitated at about 250 rpm. Culturing can involve induction using Isopropyl β-D-1-thiogalactopyranoside (IPTG) or arabinose or another suitable inductor, as will be apparent to the skilled person. Culturing can entail use of a starting culture.

Further examples of conducive conditions are provided in the examples.

Usually, a single colony is inoculated in 5 mL LB medium supplemented with 50 μg/ml kanamycin and 1% glucose. The starter culture can be grown overnight at 37° C. and 230 rpm. About 200 μl of the starting culture can be used to inoculate about 20 ml of 2×YT medium (16 g/L tryptone, 10 g/L yeast extract, 10 g/L NaCl) supplemented with about 50 μg/ml kanamycin in a 100 mL erlenmeyer flask and incubated at 37° C., 230 rpm until the optical density at 600 nm (0D600 or A600) of 0.4-0.6. Subsequently, 1 mM IPTG can be added to the medium and cultures can be incubated at 30°

C. at 250 rpm. Optionally, cultures can be supplemented with 4-coumaric acid, preferably with about 3 mM 4-coumaric acid. Total bacterial culture is preferably collected 24 h after induction by IPTG and can be stored at −20° C. This method is especially suitable for *E. coli.*

Alternately, starting cultures can be grown for 48 h in 25 mL LB medium supplemented with 50 μg/ml kanamycin and 1% glucose at 250 rpm and 30° C. Starter cultures can then be centrifuged for about 10 min at about 5000 rpm and the bacterial pellet can be resuspended in about 1.5 ml CgXII minimal medium. Subsequently, the cultures can be transferred to about 100 mL Erlenmeyer flasks containing about 25 mL of CgXII minimal medium supplemented with about 50 μg/ml kanamycin and about 20 g/L D-glucose and can then directly be induced with about 1 mM of IPTG. Bacterial cultures can be cultivated at about 30° C. and about 250 rpm for about 30 hours, up to about 4 days.

Optionally, cultures can be supplemented with 4-coumaric acid, preferably with about 3 mM 4-coumaric acid. After fermentation the total bacterial culture can be collected and stored at −20° C. This method is especially suitable for *C. glutamicum.*

In a preferred process, the raspberry ketone is separated from the culture broth. This may be realized continuously with the production process or subsequently to it. Separation may be based on any separation method known to the person skilled in the art. Chromatography or liquid/liquid extraction are attractive techniques.

The raspberry ketone produced by a cell according to the invention and by a process according to the invention has specific properties, such as being free of trace impurities that remain after chemical synthesis. Accordingly, there is provided for a raspberry ketone obtainable by a process according to the invention.

A raspberry ketone obtained using a process according to the invention can conveniently be used in a product. Accordingly, there is provided for a pharmaceutical composition, a flavor composition, a fragrance composition, a cosmetic composition, or a food composition comprising a raspberry ketone obtainable by a process according to the invention.

A process according to the invention is preferably a de novo process, i.e. a method for the de novo production of raspberry ketone. In a de novo process, no dedicated precursor is added to a culture, which is then to be converted via fermentation. In other words, in a de novo process the intended product is formed from metabolites that are conventionally present in a culture broth. As a non-limiting example, the addition of 4-coumaric acid to a culture broth in a process for obtaining raspberry ketone could be seen as not being a de novo process, as the raspberry ketone will be formed, at least in part, from the exogenously added 4-coumaric acid, and 4-coumaric acid is not a conventional ingredient for a culture broth. As a non-limiting example, the formation of raspberry ketone out of L-tyrosine can be seen as a de novo production, as L-tyrosine is routinely present in culture broths.

Use of TAL

The functionality of TAL is an important feature of the present invention. Accordingly, in a fourth aspect the invention provides the use of a functional enzyme with tyrosine ammonium lyase (TAL) activity as defined earlier herein, for the production of raspberry ketone in a prokaryotic host cell, preferably a Gram positive prokaryotic host cell. The features of this aspect are preferably those of the first, second and third aspect of the invention. In preferred embodiments of this aspect, the invention provides the use of a functional heterologous enzyme with tyrosine ammonium lyase (TAL) activity as defined earlier herein, for the production of raspberry ketone in a prokaryotic host cell, preferably a Gram positive prokaryotic host cell. In more preferred embodiments of this aspect, the invention provides the use of a functional heterologous enzyme with tyrosine ammonium lyase (TAL) activity as defined earlier herein, for the production of raspberry ketone in a Gram positive prokaryotic host cell, preferably a *Corynebacterium* host cell, more preferably a *Corynebacterium glutamicum* host cell. Features and definitions are provided elsewhere herein.

Expression Vectors

In a fifth aspect of the invention operons and expression vectors as defined earlier herein are provided. The features of this aspect are preferably those of the first, second, third and fourth aspect of the invention. Such expression vectors are referred to herein as expression vectors according to the invention. Such operons are referred to herein as operons according to the invention. Accordingly, preferred embodiments of this fifth aspect provide an expression vector comprising a first polynucleotide that has at least 60%, 65%, 70%, 75%, 80%, 85%, 90%, 95%, 96%, 97%, 98%, 99%, or 100% sequence identity with SEQ ID NO: 22, 24, 26, 28, 30, 32, 34, 36, 38, 40, 42, 44, 46, 48, 50, 52, 54, 56, 58, 60, 62, 64, 66, 68, or 70, more preferably with SEQ ID NO: 52 or with SEQ ID NO: 70, most preferably with SEQ ID NO: 70, or wherein the expression vector consists of a polynucleotide that has at least 60%, 65%, 70%, 75%, 80%, 85%, 90%, 95%, 96%, 97%, 98%, 99%, or 100% sequence identity with SEQ ID NO: 21, 23, 25, 27, 29, 31, 33, 35, 37, 39, 41, 43, 45, 47, 49, 51, 53, 55, 57, 59, 61, 63, 65, 67, or 69, more preferably with SEQ ID NO: 51 or with SEQ ID NO: 69, most preferably with SEQ ID NO: 69.

More preferred embodiments of this fifth aspect provide an expression vector comprising a first polynucleotide that has at least 85%, 90%, 95%, 96%, 97%, 98%, 99%, or 100% sequence identity, preferably at least 90% sequence identity with SEQ ID NO: 52 or with SEQ ID NO: 70, most preferably with SEQ ID NO: 70, or wherein the expression vector consists of a polynucleotide that has at least 85%, 90%, 95%, 96%, 97%, 98%, 99%, or 100% sequence identity, preferably at least 90% sequence identity with SEQ ID NO: 51 or with SEQ ID NO: 69, most preferably with SEQ ID NO: 69.

Further preferred embodiments of this fifth aspect provide an expression vector comprising a first polynucleotide that has at least 85%, 90%, 95%, 96%, 97%, 98%, 99%, or 100% sequence identity, preferably at least 90% sequence identity with SEQ ID NOs: 46, 48, 52, 54, or 70 most preferably with SEQ ID NOs: 46, 48, 52, or 54, or wherein the expression vector consists of a polynucleotide that has at least 85%, 90%, 95%, 96%, 97%, 98%, 99%, or 100% sequence identity, preferably at least 90% sequence identity with SEQ ID NOs: 45, 47, 51, 53, or 69, most preferably with SEQ ID NOs: 45, 47, 51, or 53.

A polynucleotide is represented by a nucleotide sequence. A polypeptide is represented by an amino acid sequence. A nucleic acid construct is defined as a polynucleotide which is isolated from a naturally occurring gene or which has been modified to contain segments of polynucleotides which are combined or juxtaposed in a manner which would not otherwise exist in nature. Optionally, a polynucleotide present in a nucleic acid construct is operably linked to one or more control sequences, which direct the production or expression of said peptide or polypeptide in a cell or in a subject.

Polynucleotides described herein may be native or may be codon optimized. Codon optimization adapts the codon usage for an encoded polypeptide towards the codon bias of the organism where the polypeptide is to be produced in. Codon optimization generally helps to increase the production level of the encoded polypeptide in the host cell, such as in the preferred host herein: *Corynebacterium*. Many algorithms are available to the person skilled in the art for codon optimization. A preferred method is the "guided random method based on a Monte Carlo alogorithm available via the internet at genomes.urv.es/OPTIMIZER/(P. Puigbò, E. Guzmán, A. Romeu, and S. Garcia-Vallve. Nucleic Acids Res. 2007 July; 35(Web Server issue): W126W131).

As used herein the term "heterologous sequence" or "heterologous nucleic acid" is one that is not naturally found operably linked as neighboring sequence of said first nucleotide sequence. As used herein, the term "heterologous" may mean "recombinant". "Recombinant" refers to a genetic entity distinct from that generally found in nature. As applied to a nucleotide sequence or nucleic acid molecule, this means that said nucleotide sequence or nucleic acid molecule is the product of various combinations of cloning, restriction and/or ligation steps, and other procedures that result in the production of a construct that is distinct from a sequence or molecule found in nature. A recombinant oligonucleotide can be an oligonucleotide that comprises sequences from more than one single source.

"Operably linked" is defined herein as a configuration in which a control sequence is appropriately placed at a position relative to the nucleotide sequence coding for the polypeptide of the invention such that the control sequence directs the production/expression of the peptide or polypeptide of the invention in a cell and/or in a subject.

"Operably linked" may also be used for defining a configuration in which a sequence is appropriately placed at a position relative to another sequence coding for a functional domain such that a chimeric polypeptide is encoded in a cell and/or in a subject. Throughout this application, any nucleic acid sequence coding for an enzyme is preferably operably linked to another such sequence, or to a promoter.

As used herein, the term "promoter" refers to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

Optional further elements that may be present in a nucleic acid construct according to the invention include, but are not limited to, one or more leader sequences, enhancers, integration factors, and/or reporter genes, intron sequences, centromers, telomers and/or matrix attachment (MAR) sequences. A nucleic acid construct according to the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual (3rd edition), Cold Spring Harbor Laboratory, Cold Spring Harbor Laboratory Press.

Polypeptides

In a sixth aspect, the invention provides a polypeptide product expressed from the expression vector according to the invention. Features and definitions are provided elsewhere herein and are preferably those of the first, second, third, fourth and fifth aspect of the invention.

Definitions

"Sequence identity" or "identity" in the context of amino acid- or nucleic acid-sequence is herein defined as a relationship between two or more amino acid (peptide, polypeptide, or protein) sequences or two or more nucleic acid (nucleotide, polynucleotide) sequences, as determined by comparing the sequences. In the art, "identity" also means the degree of sequence relatedness between amino acid or nucleotide sequences, as the case may be, as determined by the match between strings of such sequences. Within the present invention, sequence identity with a particular sequence preferably means sequence identity over the entire length of said particular polypeptide or polynucleotide sequence. The sequence information as provided herein should not be so narrowly construed as to require inclusion of erroneously identified bases. The skilled person is capable of identifying such erroneously identified bases and knows how to correct for such errors. Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons. Moderate conditions are herein defined as conditions that allow a nucleic acid sequences of at least 50 nucleotides, preferably of about 200 or more nucleotides, to hybridize at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridization is performed overnight, i.e. at least for 10 hours, and preferably washing is performed for at least one hour with at least two changes of the washing solution. These conditions will usually allow the specific hybridization of sequences having up to 50% sequence identity. The person skilled in the art will be able to modify these hybridization conditions in order to specifically identify sequences varying in identity between 50% and 90%.

Expression will be understood to include any step involved in the production of the peptide or polypeptide including, but not limited to, transcription, post-transcriptional modification, translation, post-translational modification, and secretion.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 10% of the value. The sequence information as provided herein should not be so narrowly construed as to require inclusion of erroneously identified bases. The skilled person is capable of identifying such erroneously identified bases and knows how to correct for such errors. In case of sequence errors, the sequence of the enzymes obtainable by expression of the genes as represented by SEQ ID NO's 1, 3, 5, 7, 9, 11, 13, 15, 17, and 19 containing the enzyme encoding polynucleotide sequences should prevail.

All patent and literature references cited in the present specification are hereby incorporated by reference in their entirety.

EXAMPLES

Example 1—Enzymes and Synthetic Operons for the Production of Raspberry Ketone The inventors have introduced a specific four-enzyme pathway into *Escherichia coli* and *Corynebacterium glutamicum* to produce raspberry ketone. A biosynthetic pathway was designed to produce raspberry ketone (4-(4-Hydroxyphenyl)-2-butanone) from L-tyrosine in four steps (FIG. 1). The first dedicated step to the biosynthesis of raspberry ketone is the conversion of L-tyrosine to 4-coumaric acid (4-hydroxycinnamic acid) by the tyrosine amonia lyase (TAL). In a second step the 4-coumarate-CoA ligase (4CL) catalyses activation of 4-coumaric acid to its CoA ester, 4-coumaroyl-CoA. In a third step a benzalacetone synthase (BAS) catalyses one-step decarboxylative condensation of 4-coumaroyl-CoA and malonyl-CoA to produce hydroxyphenylbutenone ((E)-4-(4-Hydroxyphenyl)-3-buten-2-one). In a final step for raspberry ketone biosynthesis an enzyme with benzalacetone reductase enzyme activity (BAR) activity produces raspberry ketone from hydroxyphenylbutenone.

To produce 4-coumaric acid in *E. coli* or in *C. glutamicum* the following three TAL enzymes were used: TAL from *Rhodobacter capsulatus* (RcTAL; SEQ ID NO: 1, 2), TAL from *Saccharothrix espanaensis* (SeSam8, SEQ ID NO: 3, 4), or TAL from *Flavobacterium johnsoniae* (FjTAL; SEQ ID NO: 5, 6). The following 4CL enzymes were used to produce 4-coumaroyl-CoA in *E. coli* or *C. glutamicum:* 4CL from *N. tabacum* (Nt4CL; SEQ ID NO: 7, 8), 4CL from *Arabidopsis thaliana* (At4CL; SEQ ID NO: 9, 10), 4CL from *Physcomitrella patens* (Pp4CL; SEQ ID NO: 11, 12) or 4CL from *Streptomyces coelicolor* (Sc4CL; SEQ ID NO: 13, 14). Two benzalacetone synthases were used to produce hydroxyphenylbutenone in *E. coli* or *C. glutamicum:* BAS from *Rubus idaeus* (RiPKS; SEQ ID NO: 15, 16) or BAS from *Rheum palmatum* (RpBAS; SEQ ID NO: 17, 18). The benzalacetone reductase (BAR) enzyme from *Rubus idaeus* was used (RiBAR; SEQ ID NO: 19, 20). All genes except Nt4CL were codon optimised for expression in *C. glutamicum* and obtained through chemical synthesis. Nt4CL gene was obtained in plasmid pAC-4CL-STS (see Beekwilder et al. 2006 Appl Environ Microbiol 72: 5670-5672) and was not codon optimised.

Subsequently, biosynthetic genes were assembled into 3-gene operons containing a BAS gene, a 4CL gene, and a TAL gene, in this respective order, using the Gibson assembly method. A combinatorial scheme was followed where the two BAS genes, four 4CL genes and three TAL genes were combined in a total of 24 possible combinations (Table 1).

Each of the biosynthetic genes was amplified by PCR. The amplification primers were designed to span the junction region between the vector and the insert or to span the junction between two adjacent genes. By this design overlapping regions were created in the PCR products that allow the plasmid assembly to proceed. Additionally, an intergenic spacer of 20 nucleotides was added containing a ribosomal binding site AGGAGG. The primers for the amplification of the genes are listed in the sequence table (RiPKS: SEQ ID NOs: 71, 72, 73, 74, 75; RpBAS: SEQ ID NOs: 76, 77, 78, 79, 80; At4CL: SEQ ID NOs: 81, 82, 83, 84, 85; Pp4CL: SEQ ID NOs: 86, 87, 88, 89, 90; Sc4CL: SEQ ID NOs: 91, 92, 93, 94, 95; Nt4CL: SEQ ID NOs: 96, 97, 98, 99, 100; RcTAL: SEQ ID NOs: 101, 102, 103, 104, 105; FjTAL: SEQ ID NOs: 106, 107, 108, 109, 110; SeSam8: SEQ ID NOs: 111, 112, 113, 114, 115). This resulted in the generation of four different PCR products for each BAS gene, 6 different PCR products for each 4CL gene and 4 different PCR products for each TAL gene.

The genes were amplified with a proof-reading Q5 High-Fidelity DNA Polymerase (from New England Biolabs, (NEB)). The PCR conditions were as follows: initial denaturation of 30 s at 98° C. was followed by thirty-five PCR cycles of 10 s at 98° C., 20 s at 52° C. and 1 min at 72° C. and a final extension of 2 minutes at 72° C. The final concentration of PCR reagents was 1×Q5 reaction buffer (NEB), 400 μM dNTPs, 400 nM primers and 0.5 μL Q5 DNA polymerase (NEB) in a total reaction volume of 50 μL. The obtained PCR fragment was electrophoresed and subsequently purified from the agarose gel.

The *Escherichia coli-Corynebacterium glutamicum* shuttle vector pEC-XK99E (see Kirchner & Tauch 2003 J Biotechnol 104:287-299) carrying the pGA1 origin of replication and the kanamycin resistance marker (GenBank accession number: AY219683.1) was linearized by restriction with Sac! and BamHI restriction enzymes (NEB). The linearized vector was electrophoresed and subsequently purified from the agarose gel. To create a circular plasmid containing the BAS-4CL-TAL operon 100 ng of the linearized vector was added to a reaction mix containing purified PCR products of BAS, 4CL, and TAL synthetic genes, in 24 possible combinations, with a vector-insert ratio maintained at 1:3. Next, 1× Gibson assembly mix (NEB) was added to the reactions and the total reaction volume was maintained at 20 pl. The reactions were incubated for 4 hours at 50° C. and subsequently transformed into chemically competent *E. coli* DH5α cells. Recombinant bacteria were selected on LB plates supplemented with 50 μg/ml kanamycin and 1% glucose. The recombinant cells containing a BAS-4CL-TAL operon assembly of correct size were identified by colony PCR. A single bacterial colony was inoculated into 5 ml liquid LB medium supplemented by 50 μg/ml kanamycin and 1% glucose and grown overnight at 37° C. at 250 rpm. Plasmid DNA was isolated and the junction sites between the operon and the vector and the junction sites between the genes within the operon were sequenced by Sanger sequencing using a selection of vector and gene specific primers. Strains of *E. coli* DH5a obtained by this procedure (Table 1) were maintained as glycerol stocks and were stored at −80° C. Additionally, a strain of *E. coli* DH5α was generated containing the empty plasmid pEC-XK99E. This strain was named Ec_RK_EV.

Figure 2:
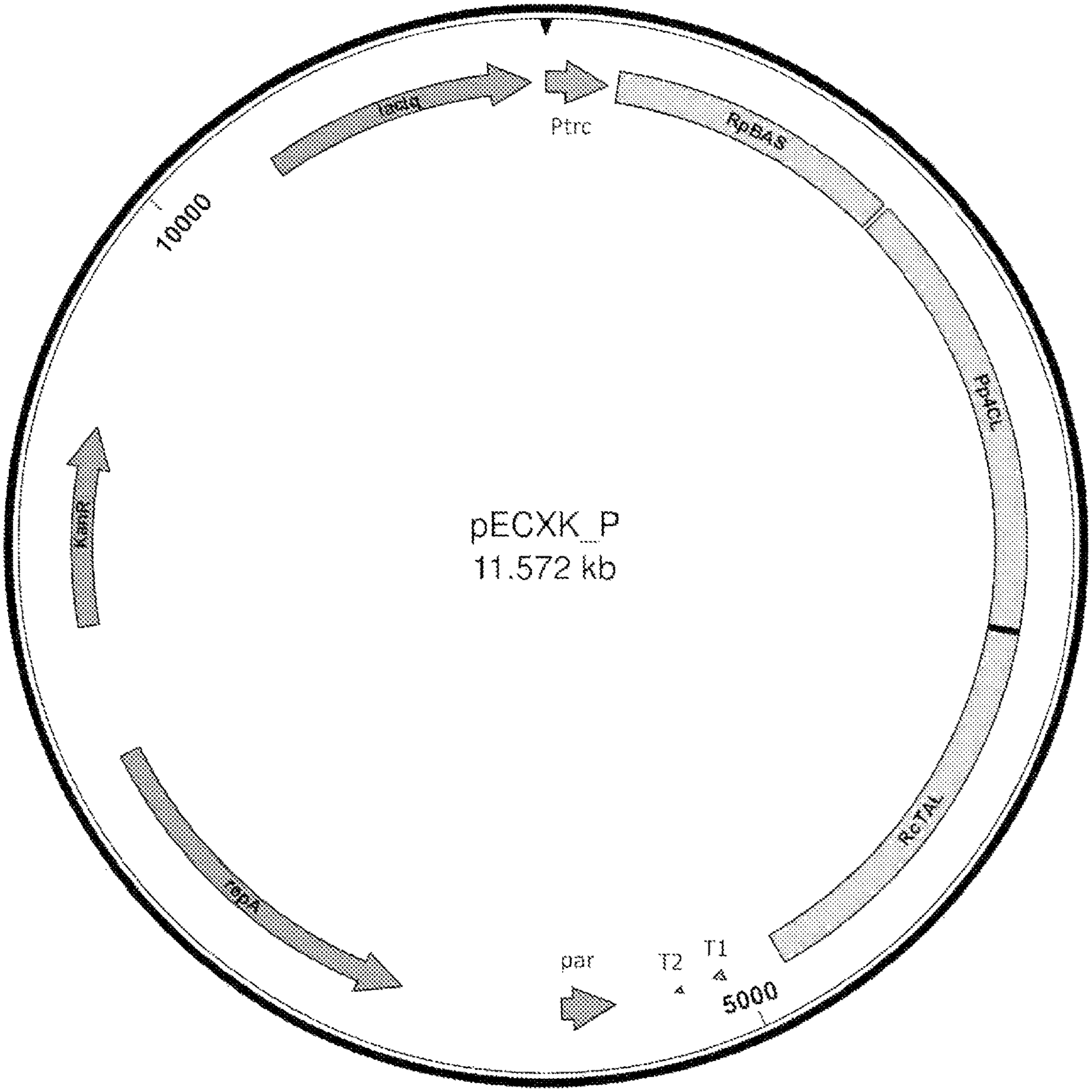
FIG. 2—Plasmid map of plasmid pECXK_P; RpBAS=*Rheum palmatum* benzalacetone synthase, Pp4CL=*Physcomitrella patens* 4-coumarate-CoA ligase, RcTAL=*Rhodobacter capsulatus* tyrosine ammonia lyase, Laclq=repressor gene, Ptrc=IPTG-inducible Ptrc promoter; T1 & T2=rrnB transcriptional terminators T1 and T2; KanR=kanamycine resistance; repA=replication origin pGA1; per=positive effector of plasmid replication.
Figure 3:
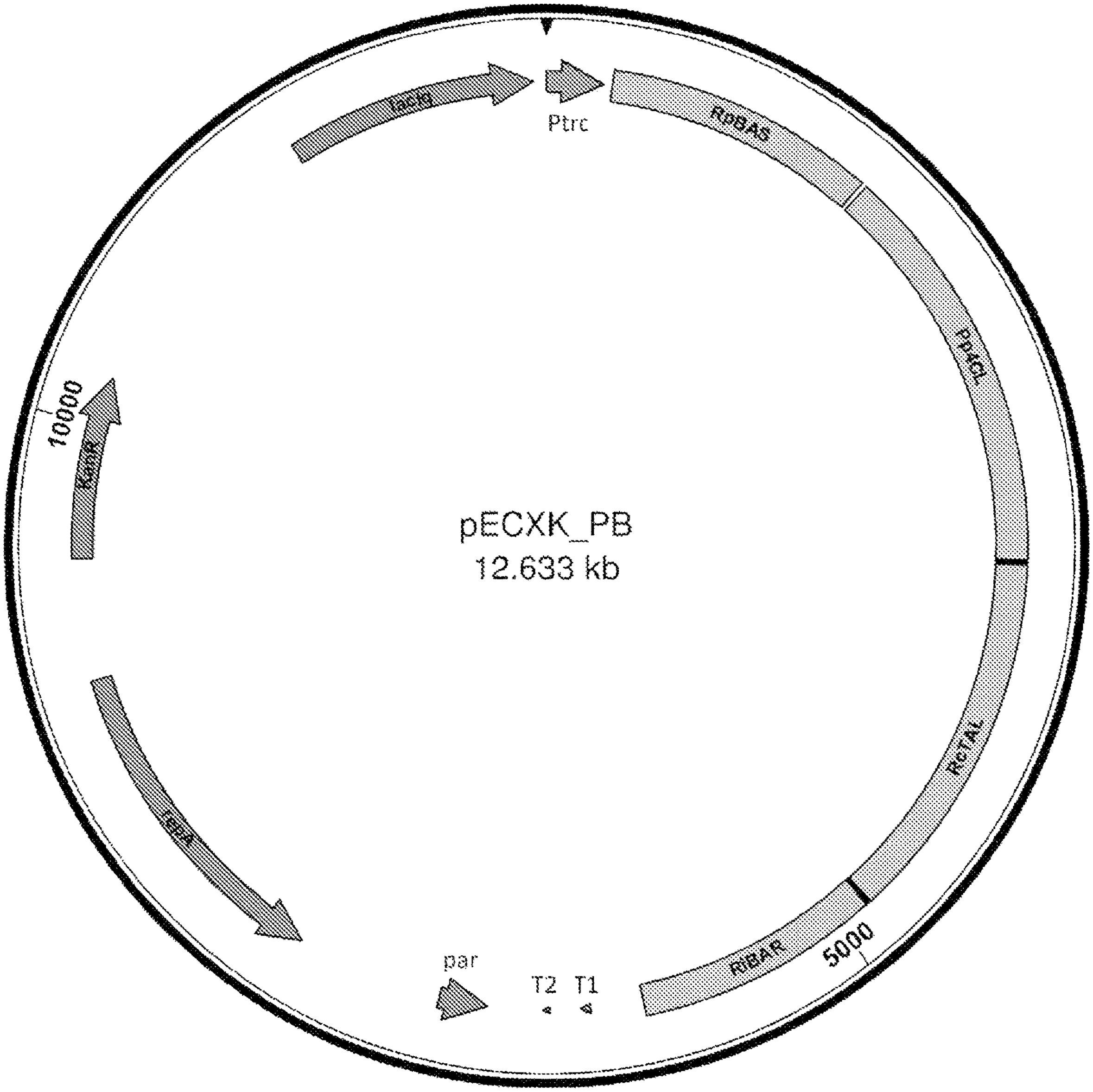
FIG. 3—Plasmid map of plasmid pECXK_PB; RpBAS=*Rheum palmatum* benzalacetone synthase; Pp4CL=*Physcomitrella patens* 4-coumarate-CoA ligase; RcTAL=*Rhodobacter capsulatus* tyrosine ammonia lyase; RiBAR=*Rubus idaeus* benzalacetone reductase; Laclq=repressor gene; Ptrc=IPTG-inducible Ptrc promoter; T1 & T2=rrnB transcriptional terminators T1 and T2; KanR=kanamycine resistance; repA=replication origin pGA1; per=positive effector of plasmid replication.
Figure 4A:
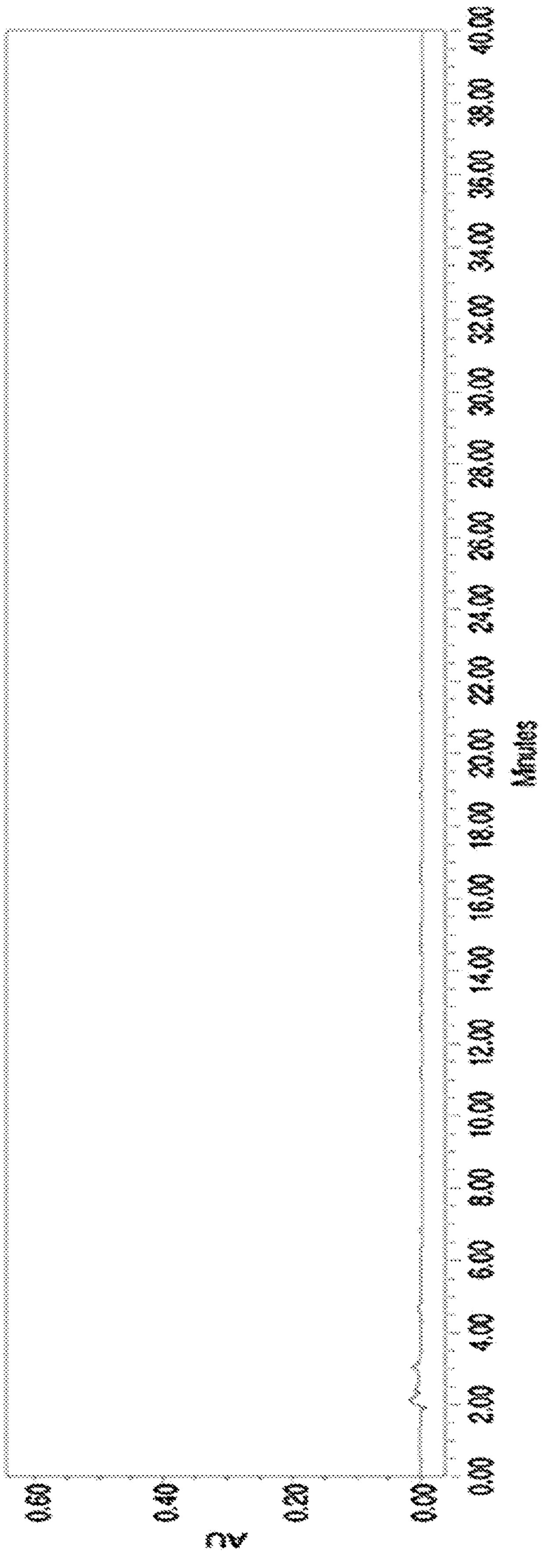
FIG. 4—De novo production of 4-coumaric acid in *E. coli* HPLC chromatograms are shown for strains A.) Ec_RK_EV, B.) Ec_RK_P and C.) Ec_RK_PB and the D.) 4-coumaric acid standard. The peak of 4-coumaric acid is observed at the retention time of 17.9 min FIG. 5—De novo production of hydroxyphenylbutenone in *E. coli* HPLC chromatograms are shown for strains A.) Ec_RK_EV, B.) Ec_RK_P and C.) Ec_RK_PB and the D.) hydroxyphenylbutenone standard. The peak of hydroxyphenylbutenone is observed at the retention time of 23.1 min and is indicated by an arrow.
Figure 4B:
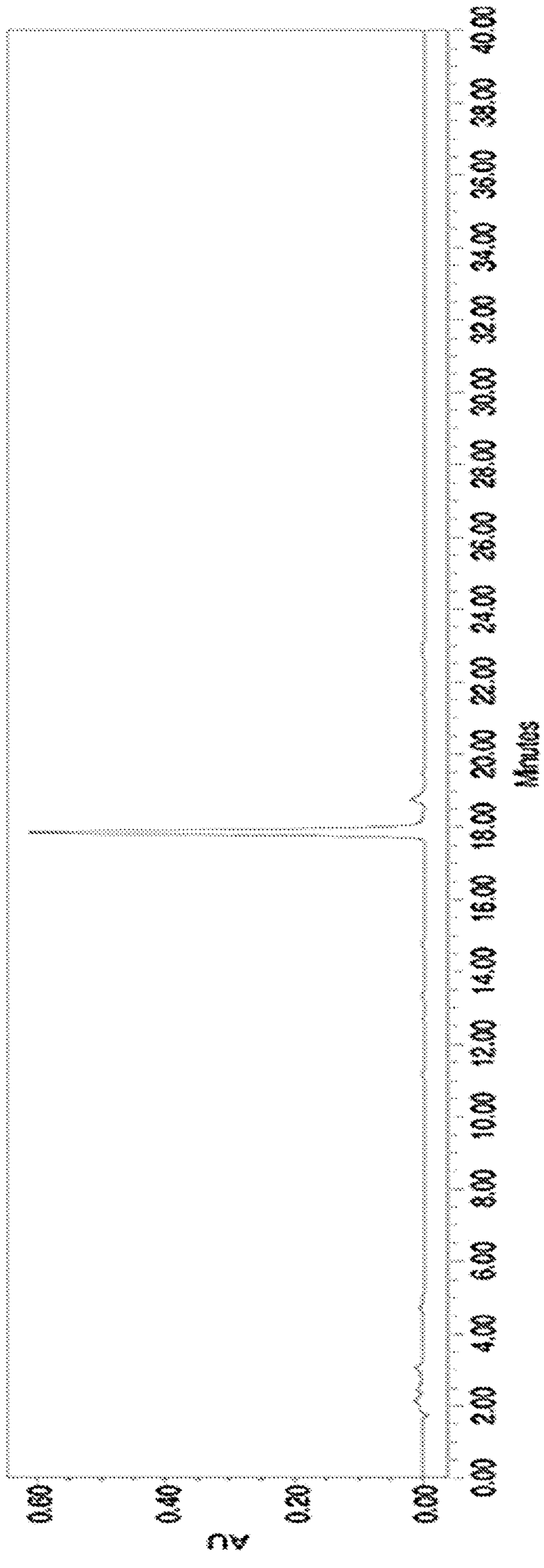
Figure 4C:
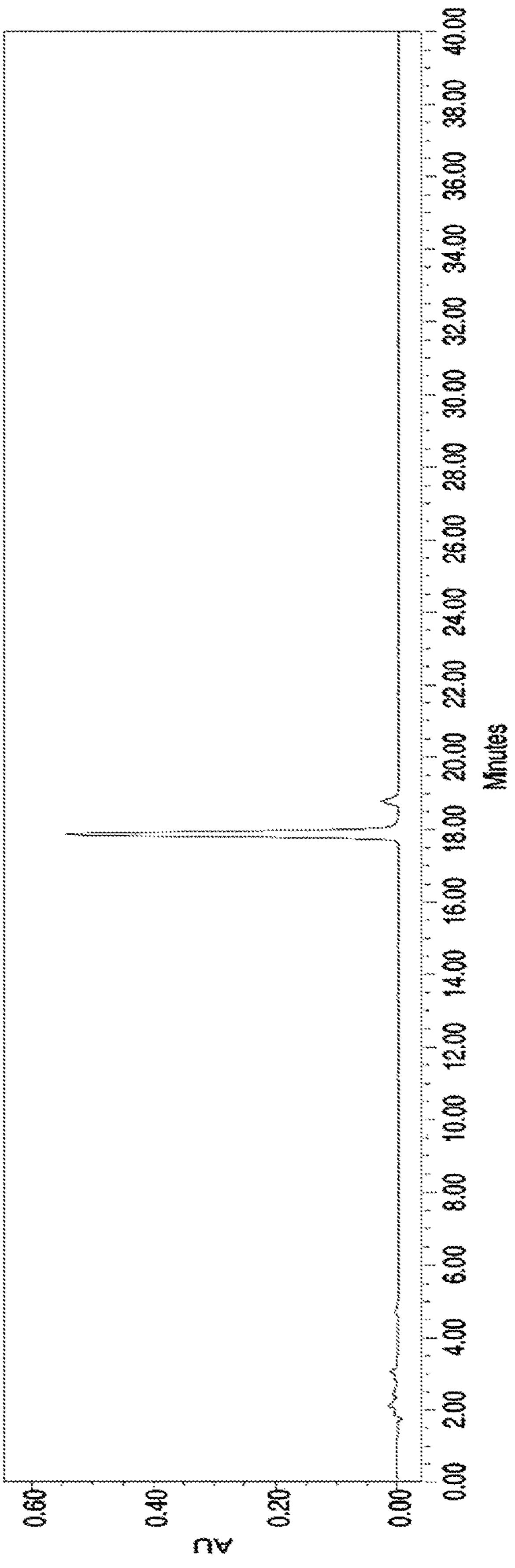
Figure 4D:
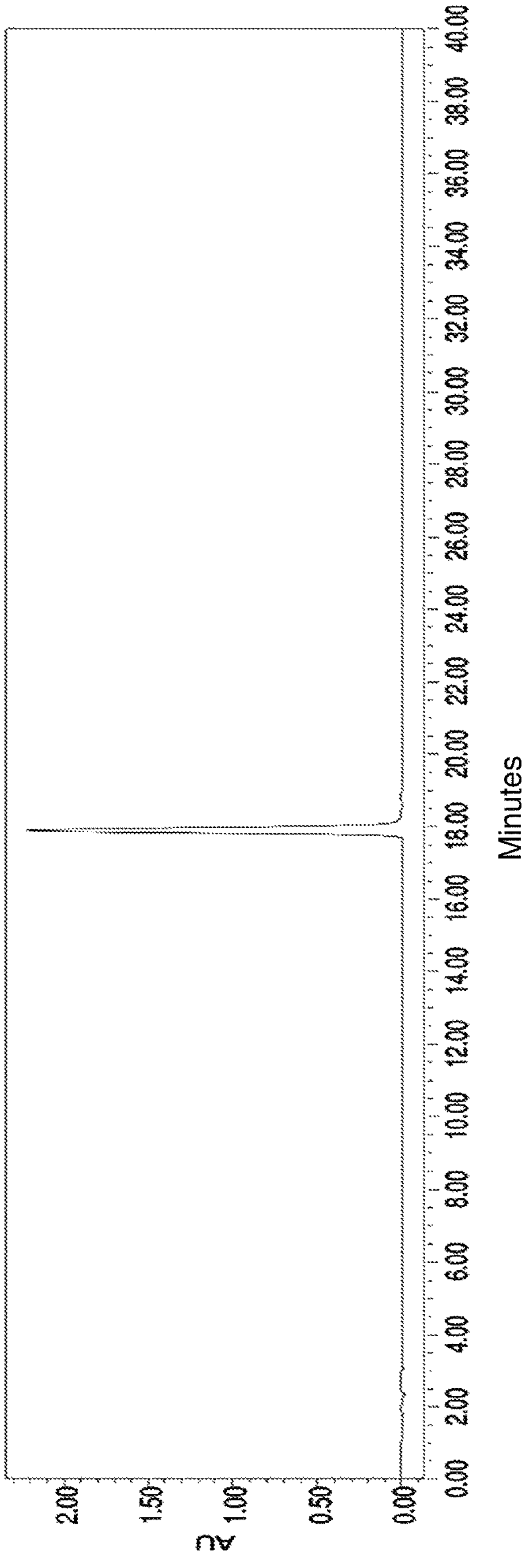
Figure 5A:
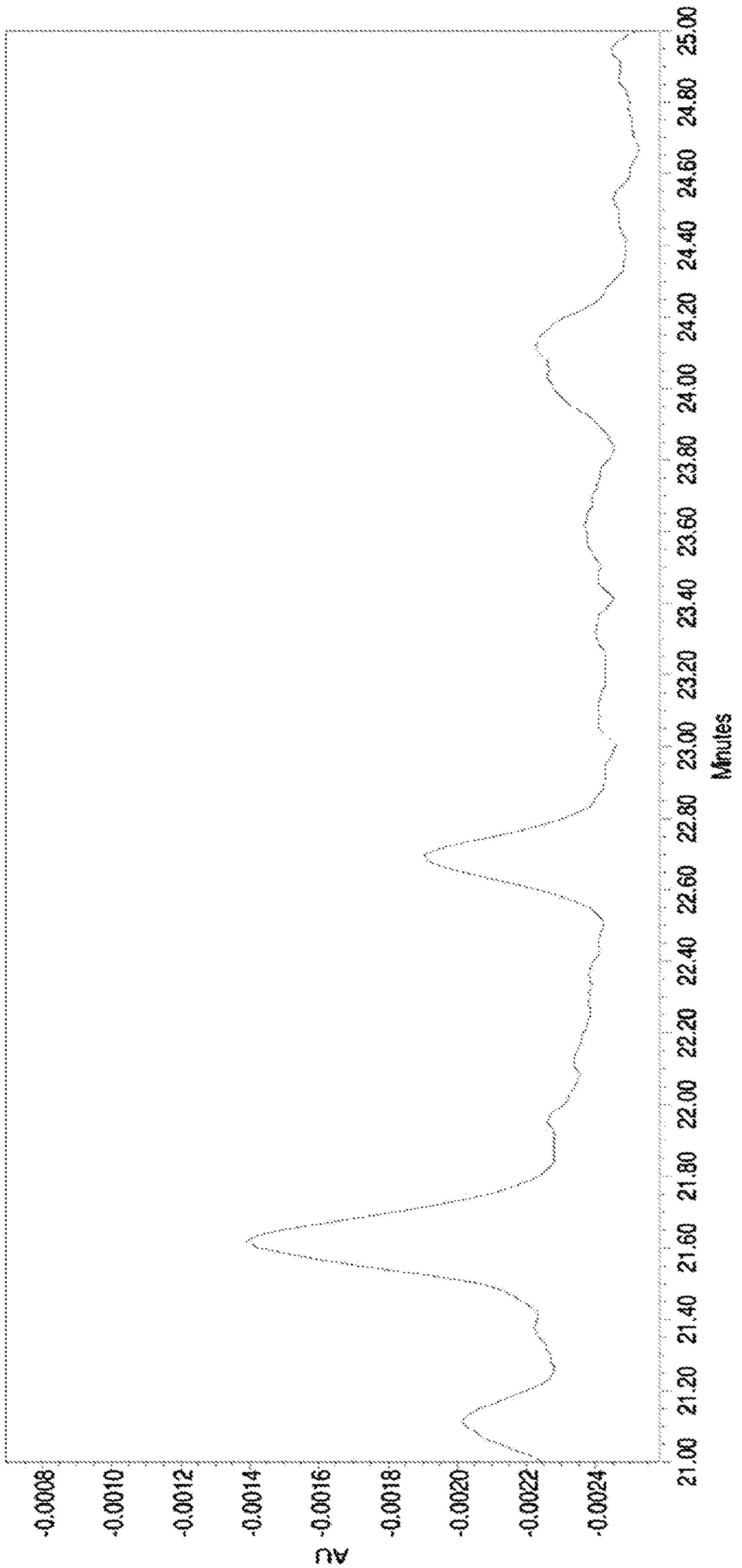
Figure 5B:
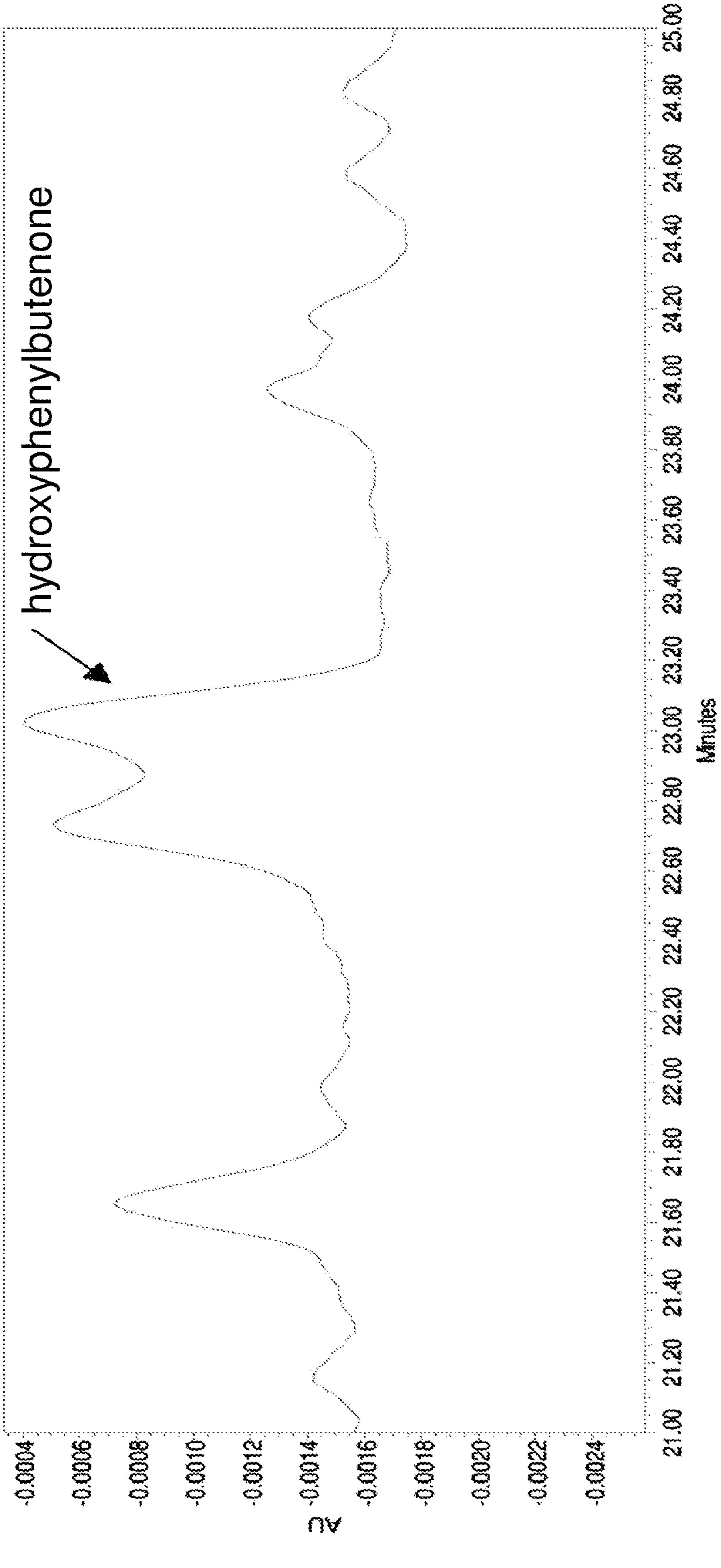
Figure 5C:
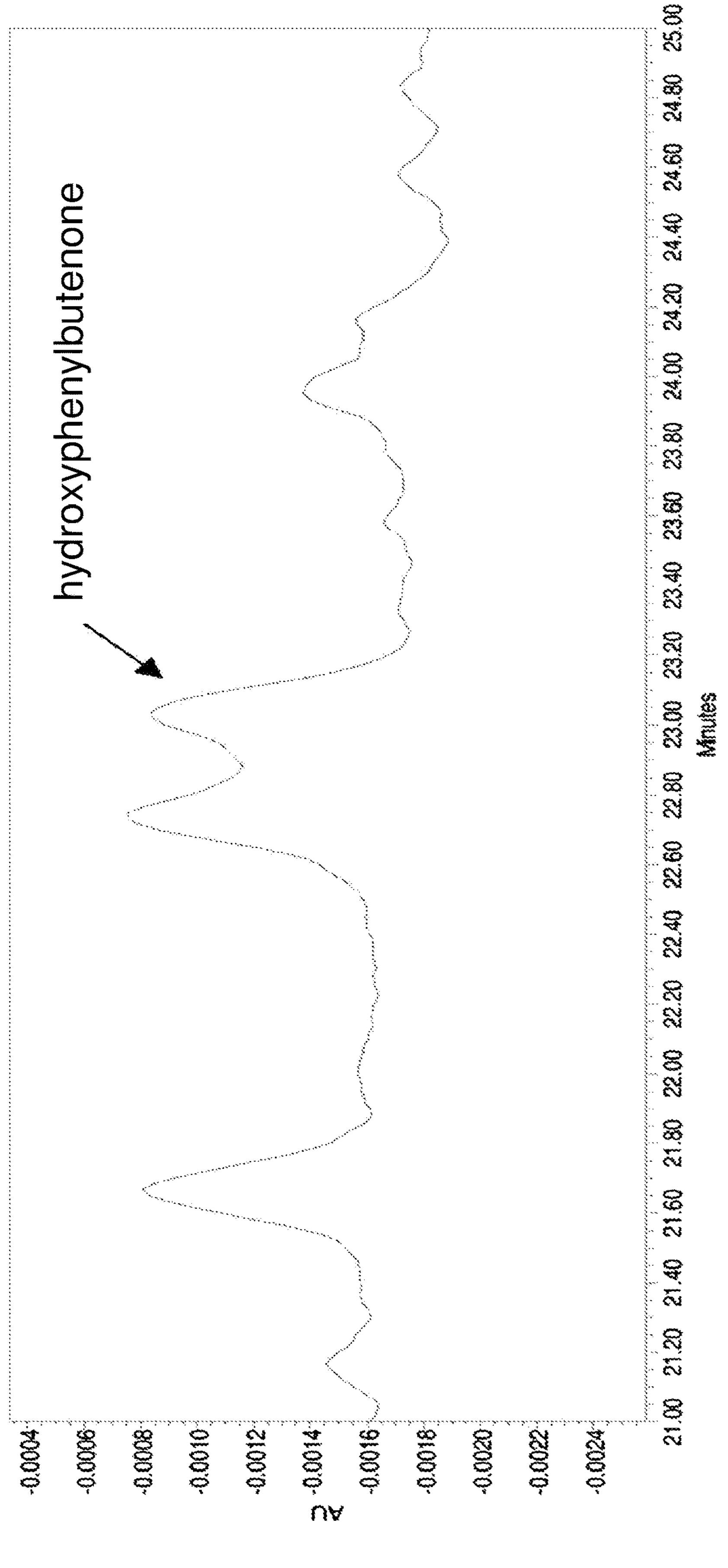
Figure 5D:
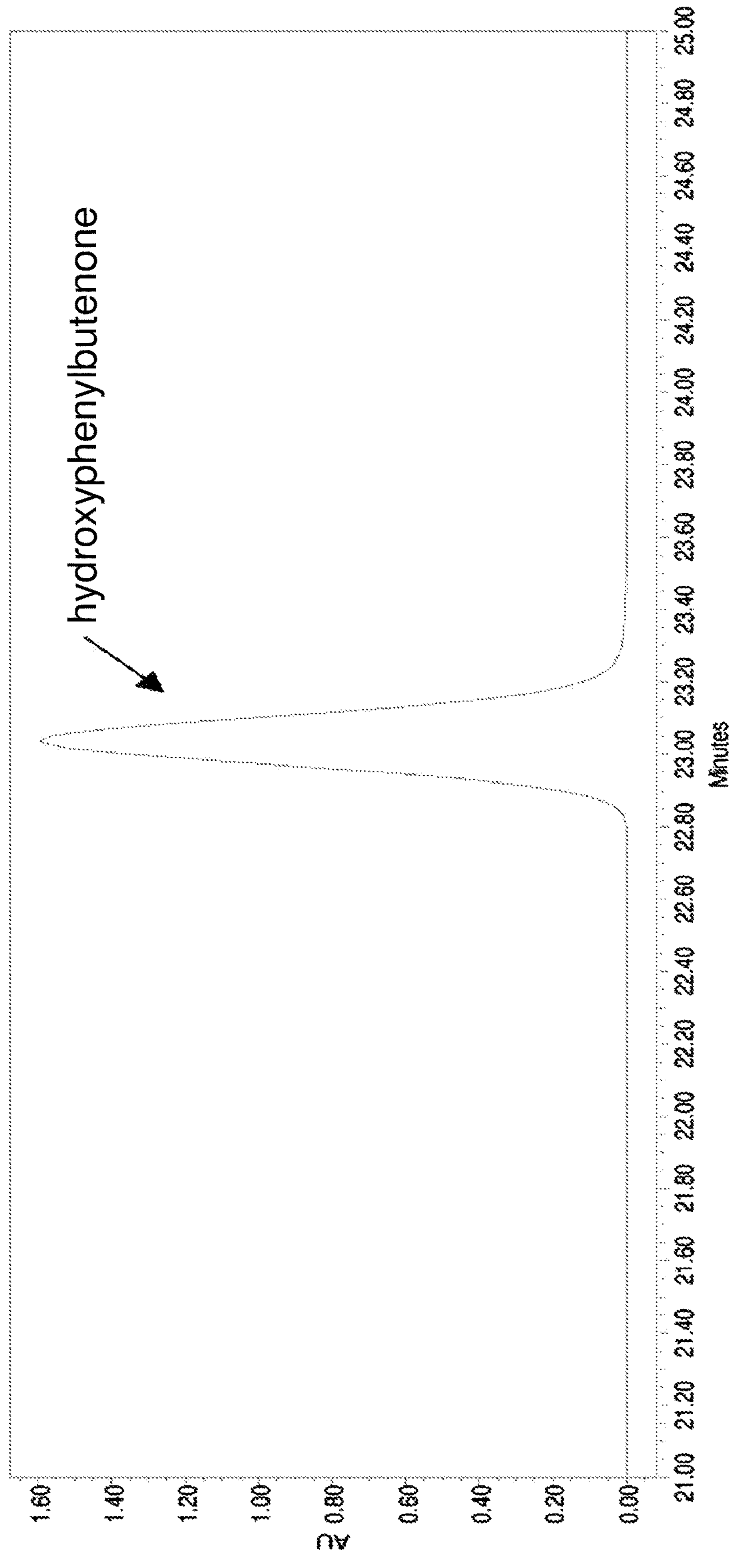
Figure 6A:
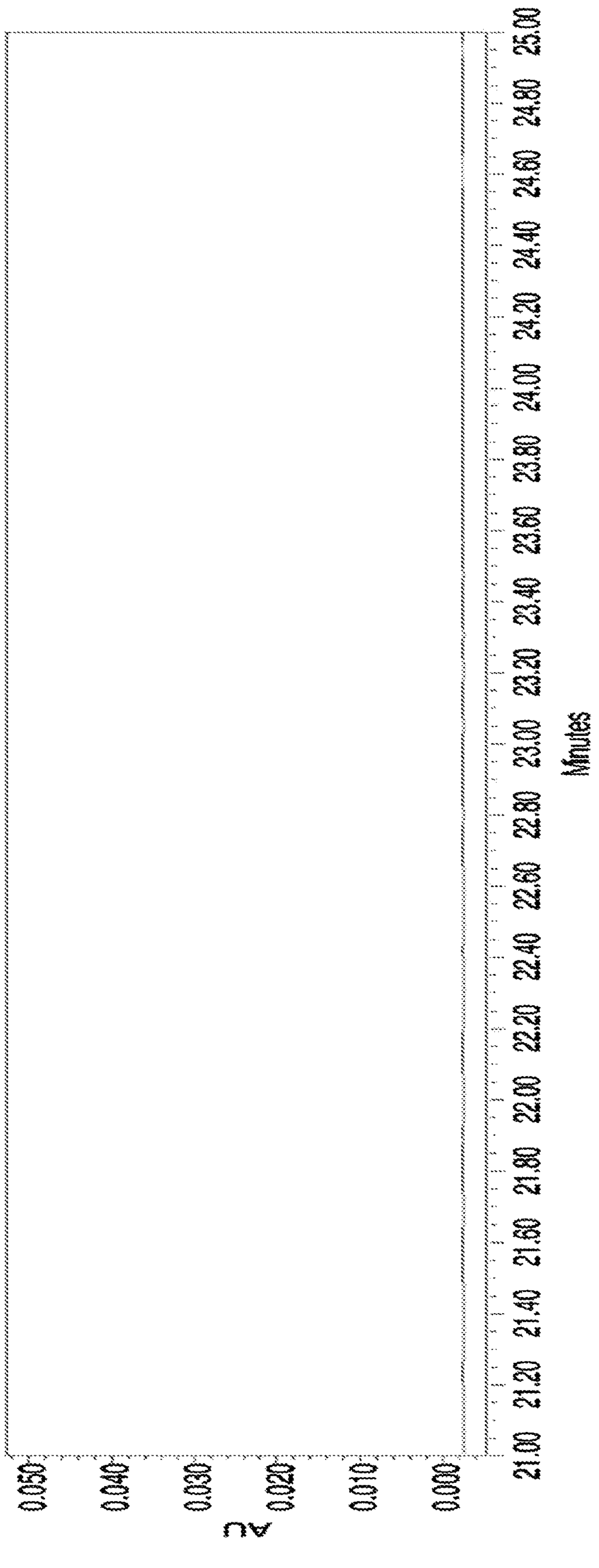
FIG. 6—HPLC analysis of de novo production of hydroxyphenylbutenone in *C.glutamicum*. HPLC chromatograms are shown for strains A.) Cg_RK_EV, B.) Cg_RK_P and C.) Cg_RK_PB and the D.) hydroxyphenylbutenone standard. The peak of hydroxyphenylbutenone is observed at the retention time of 23.1 min and is indicated by an arrow.
Figure 6B:
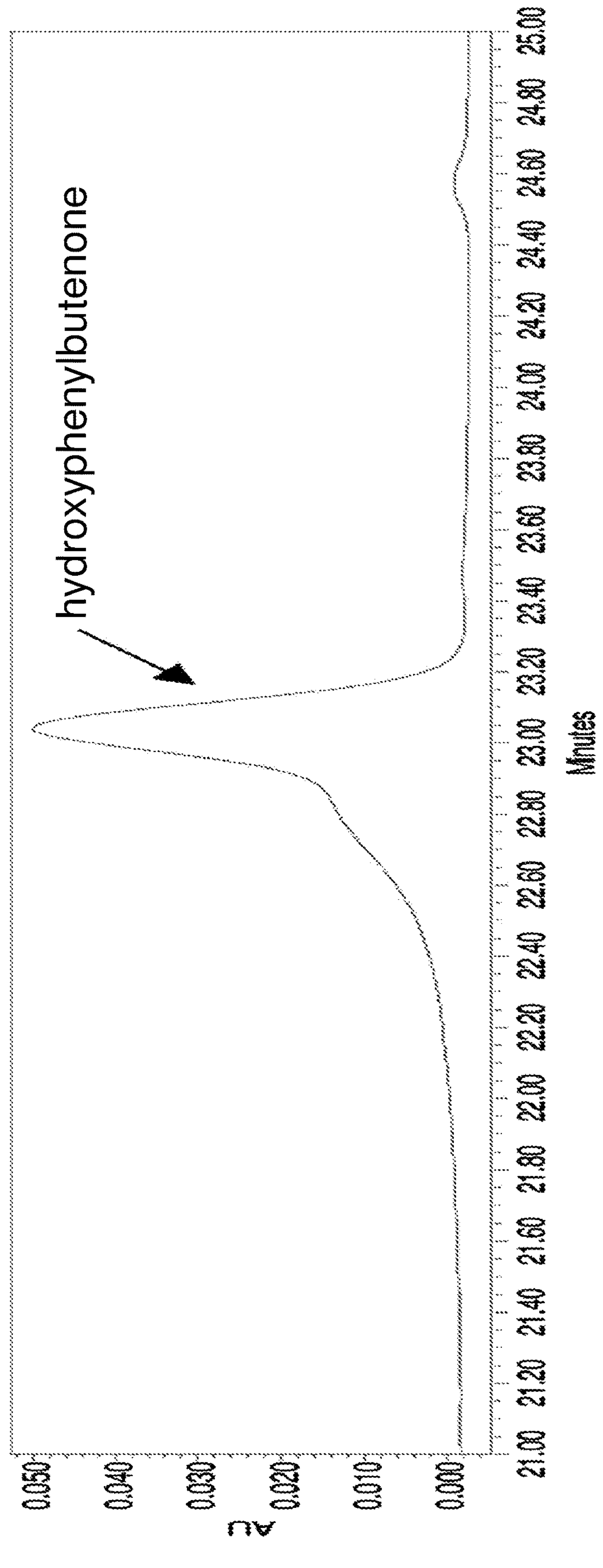
Figure 6C:
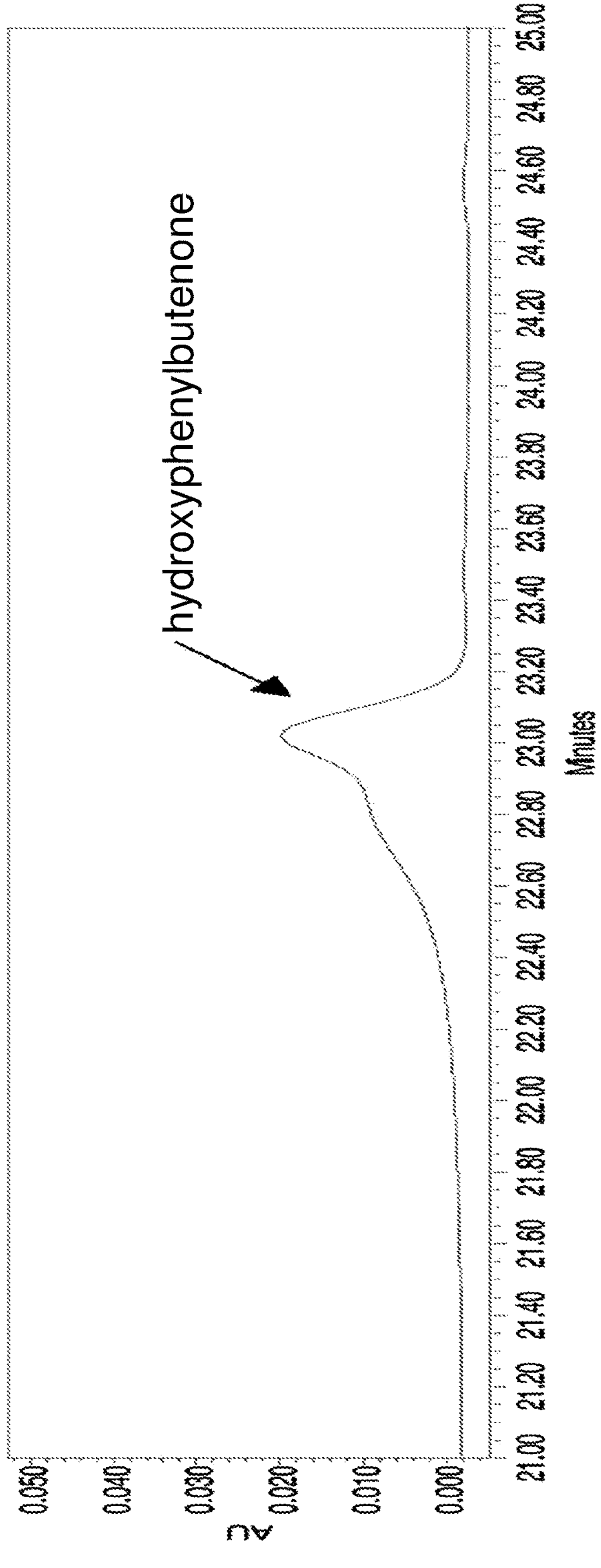
Figure 6D:
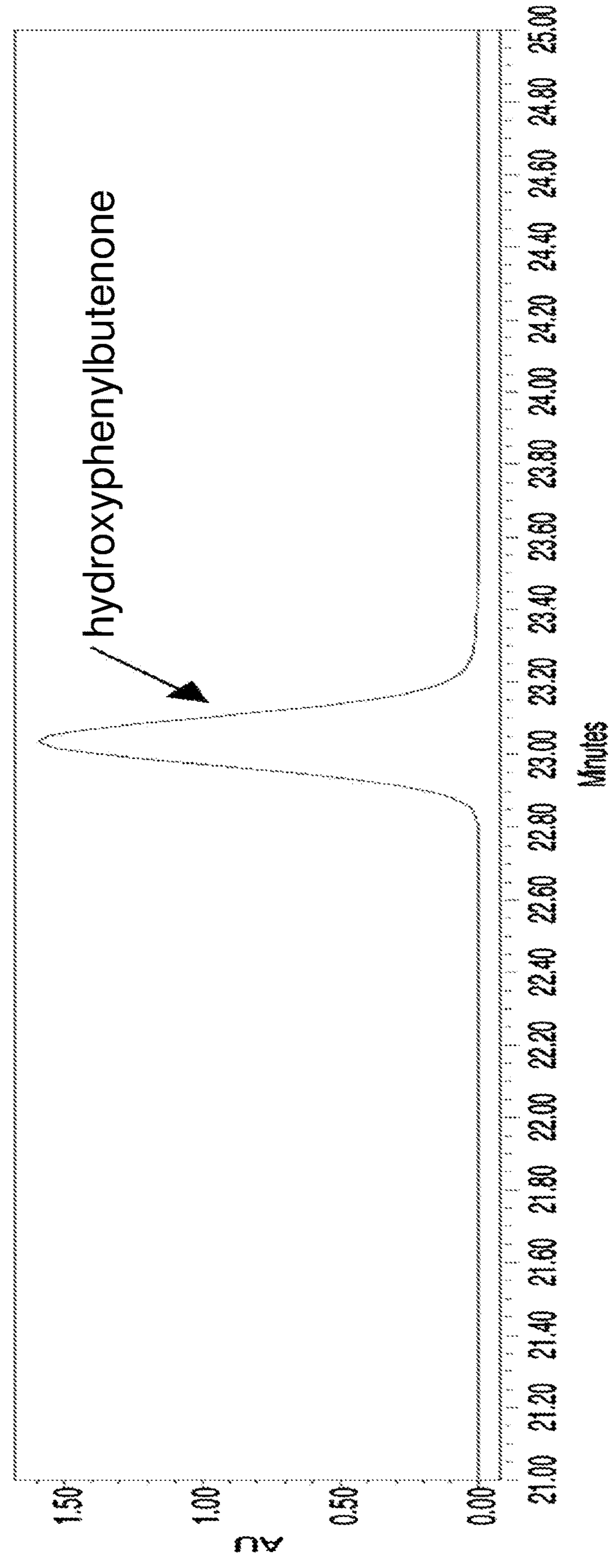

Subsequently, the benzalacetone reductase from *R. ideaus* (RiBAR) was added to the operon. For this purpose, plasmid pECXK_P (containing the RpBAS-Pp4CL-RcTAL operon, see FIG. 2) was linearized using SalI restriction enzyme (NEB). The linearized vector was electrophoresed and subsequently purified from the agarose gel. The RiBAR synthetic gene was amplified with a proof-reading Q5 High-Fidelity DNA Polymerase (NEB). The PCR conditions were as follows: initial denaturation of 30 s at 98° C. was followed by thirty-five PCR cycles of 10 s at 98° C., 20 s at 52° C. and 1 min at 72° C. and a final extension of 2 minutes at 72° C. The final concentration of PCR reagents was 1×Q5 reaction buffer (NEB), 400 μM dNTPs, 400 nM primers and 0.5 μL Q5 DNA polymerase (NEB) in a total reaction volume of 50 μL. The obtained PCR fragment was electrophoresed and subsequently purified from the agarose gel. The amplification primers were designed to overlap with the adjacent RcTAL gene and the pEC-XK99E plasmid (RiBAR: SEQ ID NO: 116, SEQ ID NO: 117). Additionally, a 20 bp intergenic region with a ribosomal binding site AGGAGG was added to the forward primer (SEQ ID NO: 116). To create a circular plasmid, 100 ng of the linearized plasmid pECXK_P was added to a reaction containing the purified RiBAR PCR product. Next, 1× Gibson assembly mix (NEB) was added to the reaction and the total reaction volume was set at 20 μl. The reaction was incubated for 4 hours at 50° C. and subsequently transformed into chemically competent *E. coli* DH5α cells. Recombinant bacteria were selected on LB plates supplemented with 50 μg/ml kanamycin and 1% glucose. The recombinant cells containing a plasmid comprising the RpBAS-Pp4CL-RcTAL-RiBAR operon assembly of correct size were identified by colony PCR. A single colony of transformed bacteria was inoculated into 5 ml liquid LB medium containing 50 μg/ml kanamycine and 1% glucose and grown overnight at 37° C. at 250 rpm, and plasmid was isolated. The junction sites between the RiBAR gene and the RcTAL gene and the RiBAR gene and the pEC-XK99E vector were confirmed by Sanger sequencing using vector and gene specific primers. The construct obtained by this procedure was named plasmid pECXK_PB (RpBAS-Pp4CL-RcTAL-RiBAR-pECXK; SEQ ID NO: 69, 70), see FIG. 3. The strain of *E. coli* DH5α obtained by this procedure was named Ec_RK_PB and was maintained as glycerol stock and stored at −80° C.

TABLE 1 operons and vectors and strains for the production of raspberry ketone

| Vector name (SEQ ID NO)[a] | Operon (SEQ ID NO)[a] | Corresponding strains *E. coli* | Corresponding strains *C. glutamicum* |
|---|---|---|---|
| pECXK_A (21) | RiPKS-At4CL-RcTAL (22) | Ec_RK_A | Cg_RK_A |
| pECXK_B (23) | RiPKS-At4CL-FjTAL (24) | Ec_RK_B | Cg_RK_B |
| pECXK_C (25) | RiPKS-At4CL-SeSam8 (26) | Ec_RK_C | Cg_RK_C |
| pECXK_D (27) | RiPKS-Pp4CL-RcTAL (28) | Ec_RK_D | Cg_RK_D |
| pECXK_E (29) | RiPKS-Pp4CL-FjTAL (30) | Ec_RK_E | Cg_RK_E |
| pECXK_F (31) | RiPKS-Pp4CL-SeSam8 (32) | Ec_RK_F | Cg_RK_F |
| pECXK_G (33) | RiPKS-Sc4CL-RcTAL (34) | Ec_RK_G | Cg_RK_G |
| pECXK_H (35) | RiPKS-Sc4CL-FjTAL (36) | Ec_RK_H | Cg_RK_H |
| pECXK_I (37) | RiPKS-Sc4CL-SeSam8 (38) | Ec_RK_I | Cg_RK_I |
| pECXK_J (39) | RiPKS-Nt4CL-RcTAL (40) | Ec_RK_3 | Cg_RK_3 |
| pECXK_K (41) | RiPKS-Nt4CL-FjTAL (42) | Ec_RK_K | Cg_RK_K |
| pECXK_L (43) | RiPKS-Nt4CL-SeSam8 (44) | Ec_RK_L | Cg_RK_L |
| pECXK_M (45) | RpBAS-At4CL-RcTAL (46) | Ec_RK_M | Cg_RK_M |
| pECXK_N (47) | RpBAS-At4CL-FjTAL (48) | Ec_RK_N | Cg_RK_N |
| pECXK_O (49) | RpBAS-At4CL-SeSam8 (50) | Ec_RK_O | Cg_RK_O |
| pECXK_P (51) | RpBAS-Pp4CL-RcTAL (52) | Ec_RK_P | Cg_RK_P |
| pECXK_Q (53) | RpBAS-Pp4CL-FjTAL (54) | Ec_RK_Q | Cg_RK_Q |
| pECXK_R (55) | RpBAS-Pp4CL-SeSam8 (56) | Ec_RK_R | Cg_RK_R |
| pECXK_S (57) | RpBAS-Sc4CL-RcTAL (58) | Ec_RK_S | Cg_RK_S |
| pECXK_T (59) | RpBAS-Sc4CL-FjTAL (60) | Ec_RK_T | Cg_RK_T |
| pECXK_U (61) | RpBAS-Sc4CL-SeSam8 (62) | Ec_RK_U | Cg_RK_U |
| pECXK_V (63) | RpBAS-Nt4CL-RcTAL (64) | Ec_RK_V | Cg_RK_V |
| pECXK_W (65) | RpBAS-Nt4CL-FjTAL (66) | Ec_RK_W | Cg_RK_W |
| pECXK_X (67) | RpBAS-Nt4CL-SeSam8 (68) | Ec_RK_X | Cg_RK_X |
| pECXK_PB (69) | RpBAS-Pp4CL-RcTAL-RiBAR (70) | Ec_RK_PB | Cg_RK_PB |

[a]the number in parentheses refers to the SEQ ID NO representing the vector or the operon Example 2—Production of Hydroxyphenylbutenone and Raspberry Ketone in *E. coli*

A single colony of strains Ec_RK_P and Ec_RK_PB was inoculated in 5 mL LB medium supplemented with 50 μg/ml kanamycin and 1% glucose. The starter culture was grown overnight at 37° C. and 230 rpm. 200 μl of the starting culture was used to inoculate 20 ml of 2×YT medium (16 g/L tryptone, 10 g/L yeast extract, 10 g/L NaCl) supplemented with 50 μg/ml kanamycin in a 100 mL erlenmeyer flask and incubated at 37° C. and 230 rpm until the optical density at 600 nm (0D600 or A600) of 0.4-0.6 was reached. Subsequently, 1 mM IPTG was added to the medium and cultures were incubated at 30° C. at 250 rpm. Four fermentation flasks were set up in parallel for each bacterial strain, from which two were supplemented with 3 mM 4-coumaric acid and, thus, in two no 4-coumaric acid was added. A fermentation experiment with a control strain Ec_RK_EV was set up in the same manner. Total bacterial culture was collected 24 h after induction (IPTG) and stored at −20° C.

For the HPLC analysis 500 μl of 100% methanol was added to 500 μl of the bacterial culture. The mixture was mixed by vortexing for 20 s and subsequently sonicated for 10 min. Next, the extract was centrifuged for 15 min at 13.000 rpm in a table top centrifuge and the supernatant was filtered using a Minisart SRP4 syringe filter (Sartorius). 5 μl of the extract was used for HLPC analysis.

The HPLC system comprised a Waters e2695 HPLC, a Waters 2996 photodiodearray (PDA) detector, and a column incubator at 40° C. The HPLC column used was a Luna 3u C18 (2) 100 A 150×2 mm (Phenomenex, Calif.). The eluents used were 0.1% formic acid in MQ water and 0.1% formic acid in acetonitrile. Separation of compounds in the extracts was conducted in a 40 min run during which a linear acetonitrile gradient was applied from 5 to 35% with a flow of 0.19 mL/min. Compounds eluting from the column passed through a PDA detector (set at an absorbance range of 240-600 nm). The retention time and the maximum absorbance wavelength of the peaks in the fermentation samples was compared to authentic standards of 4-coumaric acid (Sigma), hydroxyphenylbutenone (Pfaltz & Bauer) and raspberry ketone (Apin Chemical Limited). The peak intensity of eluted compounds was analysed at the wavelengths of 280 nm for the detection of raspberry ketone at the retention time of 21.9 min. The peak intensity of eluted compounds was also analysed at the wavelength of 312 nm for the detection of hydroxyphenylbutenone at retention time of 23.1 min and 4-coumaric acid at the retention time of 17.9 min.

In the cultures of strain Ec_RK_P where no 4-coumaric acid was added to the medium, de novo production of 4-coumaric acid was observed (FIG. 4). 4-Coumaric acid was accumulated at the 54±3 mg/L culture. Additionally, production of hydroxyphenylbutenone was observed at the concentration of 0.2±0.0 mg/L bacterial culture (FIG. 5). No raspberry ketone was observed in the HPLC chromatogram of the Ec_RK_P strain. For strain Ec_RK_PB accumulation of 4-coumaric acid at 49±1 mg/L culture and hydroxyphenylbutenone at 0.1±0.0 mg/L was observed. No raspberry ketone was detected by HPLC for strain Ec_RK_PB. For strain Ec_RK_EV, transformed with the empty pEC-XK99E plasmid, no 4-coumaric acid, hydroxyphenylbutenone or raspberry ketone accumulation was observed, as expected.

In the *E. coli* cultures supplemented with 3 mM 4-coumaric acid accumulation of 4-coumaric acid was observed for cultures Ec_RK_P, Ec_RK_PB and Ec_RK_EV at 328±16 mg/L, 345±26 mg/L and 303±3 mg/L bacterial culture, respectively. Production of hydroxyphenylbutenone of 4.0±0.1 mg/L and 3.9±0.1 mg/L was observed for bacterial strains Ec_RK_P and Ec_RK_PB supplemented with 3 mM 4-coumaric acid, respectively. No raspberry ketone production was observed for strains Ec_RK_P and Ec_RK_PB. No hydroxyphenylbutenone or raspberry ketone production was observed for strain Ec_RK_EV when supplemented with 4-coumaric acid, as expected.

From this experiment it was concluded that 4-coumaric acid accumulates in *E. coli* fermentation. The production of hydroxyphenylbutenone in *E. coli* was successful. To further investigate raspberry ketone production a more sensitive GC-MS analysis was employed.

For the GC-MS analysis 16 ml of bacterial culture of strains Ec_RK_P, Ec_RK_PB and Ec_RK_EV (not supplemented with 4-coumaric acid) was extracted with 4 ml ethyl acetate. The cultures and the solvent were mixed by vortexing for 20 s and were subsequently sonicated for 10 minutes. The cultures were centrifuged at 1200 rpm for 10 min and EtAc was collected in a new glass vial. The samples were dried using a $Na_2SO_4$ column. Analytes from 1 μL samples were separated using a gas chromatograph (5890 series II, Hewlett-Packard) equipped with a 30 m×0.25 mm, 0.25 mm film thickness column (ZB-5, Phenomenex) using helium as carrier gas at flow rate of 1 ml/min. The injector was used in splitless mode with the inlet temperature set to 250° C. The initial oven temperature of 45° C. was increased after 1 min to 300° C. at a rate of 10° C./min and held for 5 min at 300° C. The GC was coupled to a mass-selective detector (model 5972A, Hewlett-Packard). Raspberry ketone was identified by comparison of mass spectra and retention times (rt) with those of the authentic standard of raspberry ketone (Apin Chemical Limited). A trace amount of raspberry ketone was observed in the extract of strains Ec_RK_P and Ec_RK_PB. No raspberry ketone production was observed for strain Ec_RK_EV.

Example 3—*C. glutamicum* Strains for the Production of Raspberry Ketone

Plasmids for raspberry ketone production were next transformed into electrocompetent cells of wild-type *C. glutamicum* strain ATCC13032. By this procedure 25 bacterial strains were created, which are listed in Table 1. Recombinant bacteria were selected on LB plates supplemented with 50 μg/ml kanamycin and 1% glucose after an incubation at 30° C. for two days. Additionally, the empty pEC-XK99E vector was transformed into *C. glutamicum* ATCC13032 and the obtained strain was named Cg_RK_EV. Glycerol stocks of strains obtained by this procedure were maintained at −80° C.

Example 4—Production of Raspberry Ketone in *C. glutamicum*

Starting cultures of *C. glutamicum* strains Cg_RK_P, Cg_RK_PB and Cg_RK_EV were grown for 48 h in 25 mL LB medium supplemented with 50 μg/ml kanamycin and 1% glucose at 250 rpm and 30° C. Starter cultures were centrifuged for 10 min at 5000 rpm and the bacterial pellet was resuspended in 1.5 ml CgXII minimal medium (see Eggeling & Reyes 2005). Subsequently, the cultures were transferred to 100 mL Erlenmeyer flasks containing 25 mL of CgXII minimal medium supplemented with 50 μg/ml kanamycin and 20 g/L D-glucose and were directly induced with 1mM of IPTG. Four fermentation flasks were set up in parallel for each bacterial strain, from which two were supplemented with 3mM 4-coumaric acid and in two no 4-coumaric acid was added. Bacterial cultures were cultivated at 30° C. and 250 rpm for 30 hours. After the fermentation the total bacterial culture was collected and stored at −20° C. until analysis.

Extraction of metabolites and HPLC analysis was conducted as described in Example 2. No accumulation of 4-coumaric acid was observed for *C. glutamicum* extracts for strains Cg_RK_P, Cg_RK_PB and Cg_RK_EV, both in cultures that were supplemented with 3 mM 4-coumaric acid and cultures where no 4-coumaric acid was added. This indicates that 4-coumaric acid was metabolised by *C. glutamicum*. For strain Cg_RK_P de novo production of hydroxyphenylbutenone was observed at 13.2±0.0 mg/L when no 4-coumaric acid was added to the fermentation (FIG. 6). Production of hydroxyphenylbutenone at 3.7±0.3 mg/L was observed for Cg_RK_P cultures supplemented with 3mM 4-coumaric acid. No hydroxyphenylbutenone was observed in C. glutamicum cultures of strain Cg_RK_EV. No raspberry ketone production was detected by HPLC for bacterial strains Cg_RK_P and Cg_RK_EV, neither for cultures supplemented with 3 mM 4-coumaric acid nor cultures with no added substrate.

For strain Cg_RK_PB, the production of hydroxyphenylbutenone was 7.1±0.3 and 2.5±0.2 mg/L for cultures with no added substrate and cultures supplemented with 4-coumaric acid, respectively. This corresponds to a reduction of hydroxyphenylbutenone production of 46% and 33% compared to strain Cg_RK_P. In addition, a clear peak of raspberry ketone was observed in HPLC for strain Cg_RK_PB. This indicates that addition of the BAR gene significantly increased the conversion of hydroxyphenylbutenone to raspberry ketone in *C. glutamicum*. The raspberry ketone production was further analysed by GC-MS using the protocol described in Example 2.

Figure 7A:
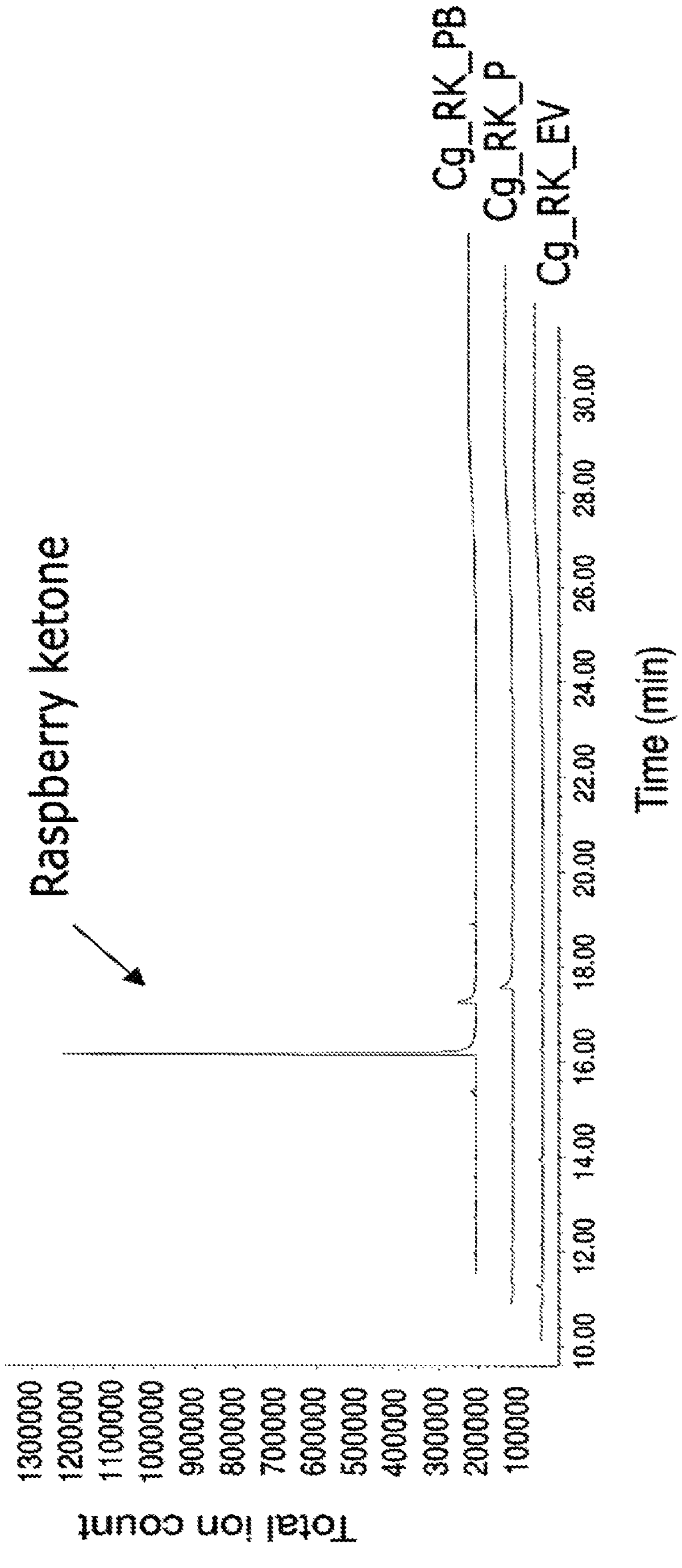
FIG. 7—GC-MS analysis of raspberry ketone production in *C. glutamicum*. The GC-MS chromatograms in panel A are shown for strains Cg_RK_EV, Cg_RK_P and Cg_RK_PB. The raspberry ketone peak is observed at the retention time of 14.2 min. In panel B the mass spectrum of raspberry ketone produced by strain Cg_RK_PB is shown. In panel C the mass spectrum of the authentic raspberry ketone standard is shown.
Figure 7B:
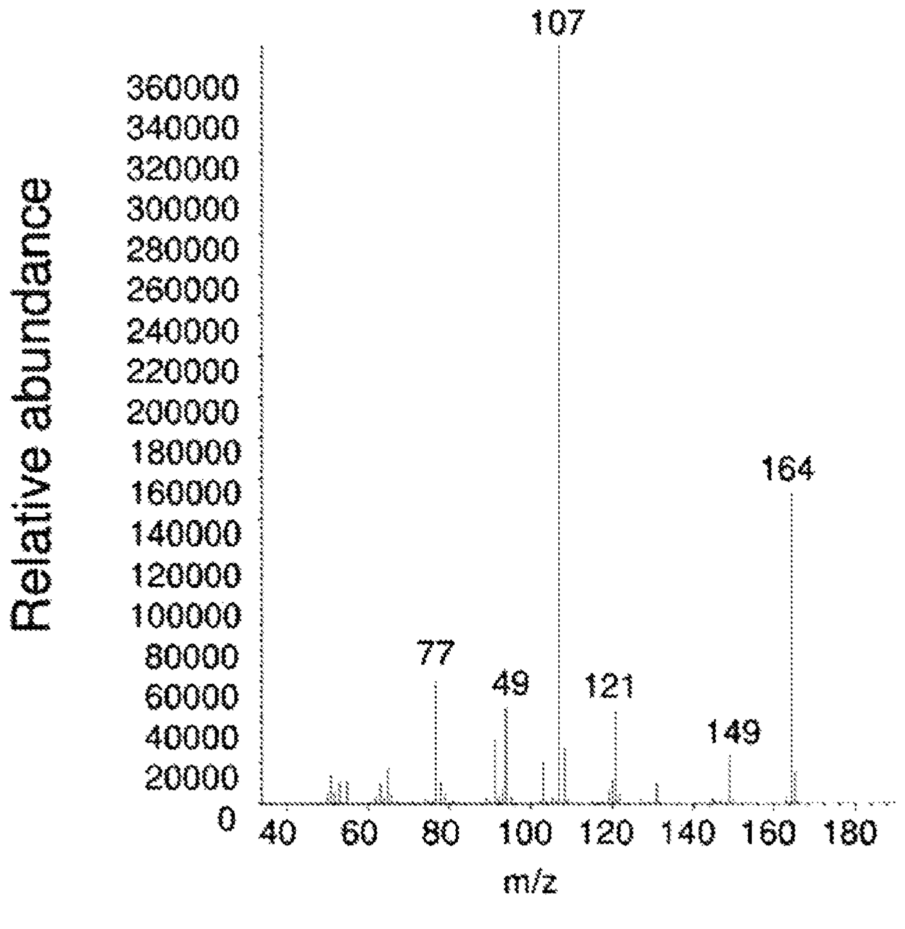
Figure 7C:
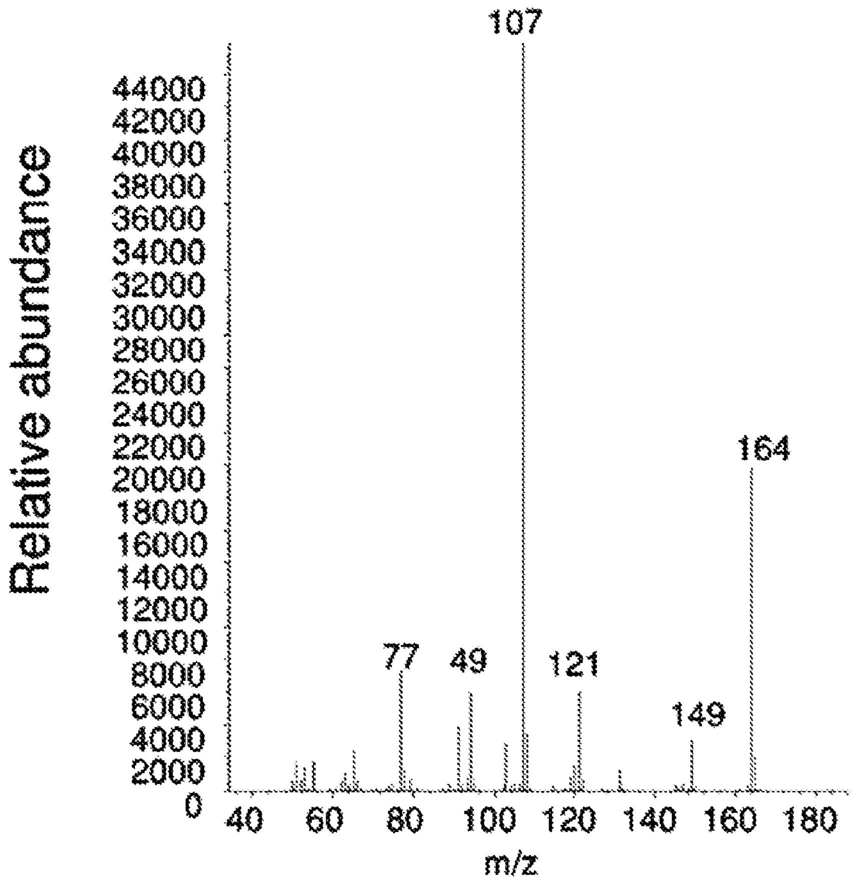

In the GC-MS analysis a predominant peak of raspberry ketone was observed in the extracts of Cg_RK_PB strains (FIG. 7). The production was quantified at 19 mg/L. No raspberry ketone was observed in the GC-MS analysis of strains Cg_RK_P and the strain Cg_RK_EV.

REFERENCES

Kyndt et al. 2002 FEBS Lett. 512: 240-244

Berner el al. 2006 J Bacteriol 188: 2666-2673

Jendersen et al. 2015 Appl Environ Microbiol 81:4458-4476

Lee & Douglas. 1996 Plant Physiol. 112: 193-205

Ehlting et al. 1999 Plant. J. 19: 9-20

Silber et al. 2008 Phytochem. 69: 2449 -2456

Zheng & Hrazdina 2008 Arch Biochem Biophys 470: 139-145

Abe et al. 2001 Eur J Biochem 268: 3354-3359

Koeduka et al. 2011 Biochem Biophys Res Commun 412: 104-108

Beekwilder et al. 2006 Appl Environ Microbiol 72: 5670-5672

Gibson et al. 2009 Nature Methods 6: 343-345

Vandamme and Soetaert 2002; J Chem Techno Biotechnol 77:1323-1332

Kirchner & Tauch 2003 J Biotechnol 104:287-299

Borejsza-Wysocki and Hrazdina (1994) Plant Physiol. 1996 Mar;110(3):791-799.

Schroder 1999 (Comprehensive natural products chemistry vol 1: polyketides and other secondary metabolites including fatty acids and their derivatives [U. Sankawa Ed] pp 749-771)

Eggeling & Reyes 2005 Experiments. In: Eggeling, L., Bott, M. (Eds.), Handbook of *Corynebacterium glutamicum*. CRC Press, Boca Raton, Fla., pp. 3535-3566

Levi and Weinstein, 1964 Biochemistry, 1964, 3 (12), pp 1944-1947

Fuganti and Zucchi, 1998 Journal of Molecular Catalysis B: Enzymatic 4, 289-293

Hugueny et al (1995, Bioflavour 95 pp 269-273

EP1226265; GB2416769 GB2416770

Beekwilder et al (2007) Biotechnol. J. 2007, 2, 1270-1279

2016, Lee et al Microb Cell Fact. 15:49.

The invention claimed is:

1. A *Corynebacterium glutarnicum* cell expressing a functional heterologous enzyme with tyrosine ammonium lyase (TAL) activity and further expressing at least one functional enzyme selected from the group consisting of a 4-coumarate-CoA ligase (4CL) and a benzalacetone synthase (BAS) and optionally further expressing a heterologous benzalacetone reductase (BAR), wherein the cell produces at least 5 mg/L raspberry ketone when cultured in the absence of p-coumaric acid.

2. The cell according to claim 1, wherein:
the functional heterologous enzyme with TAL activity is from *Rhodobacter capsulatus, Saccharothrix espanaensis*, or *Flavobacterium johnsoniae;*
the at least one functional enzyme selected from the group consisting of a 4CL and a BAS is 4CL from *Nicotiana tabacum, Arabidopsis thaliana, Physcomitrella patens* or *Streptomyces coelicolor*, or is BAS from *Rubus idaeus* or *Rheum palmatum*; and
the optional BAR is from *Rubus idaeus.*

3. The cell according to claim 1, wherein:
the functional heterologous enzyme with TAL activity is from *Rhodobacter capsulatus;*
the at least one functional enzyme selected from the group consisting of a 4CL and a BAS is selected from the group consisting of a 4CL from *Physcomitrella patens* and a BAS from *Rheum palmaturn*; and
the optional BAR is from *Rubus idaeus.*

4. The cell according to claim 1, wherein:
the functional heterologous enzyme with TAL activity has at least 60% sequence identity with SEQ ID NO: 1, SEQ ID NO: 3, or SEQ ID NO: 5, or is encoded by a polynucleotide which has at least 60% sequence identity with SEQ ID NO: 2, SEQ ID NO: 4, or SEQ ID NO: 6,;
the 4CL has at least 60% sequence identity with SEQ ID NO: 7, SEQ ID NO: 9, SEQ ID NO: 11, or SEQ ID NO: 13, or is encoded by a polynucleotide which has at least 60% sequence identity with SEQ ID NO: 8, SEQ ID NO: 10, SEQ ID NO: 12, or SEQ ID NO: 14;
the BAS has at least 60% sequence identity with SEQ ID NO: 15 or SEQ ID NO: 17, or is encoded by a polynucleotide which has at least 60% sequence identity with SEQ ID NO 16 or SEQ ID NO: 18;
the BAR has at least 60% sequence identity with SEQ ID NO: 19 or is encoded by a polynucleotide which has at least 60% sequence identity with SEQ ID NO: 20.

5. The cell according to claiml, wherein the polynucleotide sequence encoding at least one of said enzymes is codon optimized.

6. The cell according to claim 1, wherein the cell is *Corynebacterium glutamicum* ATCC13032 cell.

7. The cell according to claim 1, wherein at least two of the enzymes are encoded by a single recombinant polynucleotide construct.

8. A method for the production of a cell according to claim 1, comprising
contacting a *Corynebacterium glutamicum* with an expression construct encoding a functional heterologous enzyme with tyrosine ammonium lyase (TAL) activity, and
contacting that *Corynebacterium glutamicum* cell with an expression construct encoding at least one functional enzyme selected from the group consisting of a 4-coumarate-CoA ligase (4CL) and a benzalacetone synthase (BAS), and
optionally contacting that *Corynebacterium glutamicum* cell with an expression construct encoding a heterologous benzalacetone reductase (BAR).

9. A method for the production of raspberry ketone, comprising:
culturing a cell according to claim 1 under conditions conducive to the production of raspberry ketone, and, optionally, isolating and/or purifying the raspberry ketone from the cell and/or the culture medium.

10. The cell according to claim 1, wherein the cell is a *Corynebacterium glutamicum* cell capable of producing at least twice as much L-Tyrosine as compared to *Corynebacterium glutamicum* ATCC13032.

* * * * *